US009957264B2

(12) United States Patent
Childers et al.

(10) Patent No.: US 9,957,264 B2
(45) Date of Patent: May 1, 2018

(54) GEMINALLY SUBSTITUTED CYANOETHYLPYRAZOLO PYRIDONES AS JANUS KINASE INHIBITORS

(71) Applicant: Merck Sharp & Dohme Corp., Rahway, NJ (US)

(72) Inventors: Matthew Lloyd Childers, Medfield, MA (US); Peter Fuller, Ashland, MA (US); David Guerin, Natick, MA (US); Jason David Katz, Newton, MA (US); Qinglin Pu, Needham, MA (US); Mark E. Scott, Andover, MA (US); Christopher F. Thompson, Arlington, MA (US); Michelle Martinez, Watertown, MA (US); Danielle Falcone, Brookline, MA (US); Luis Torres, Norwood, MA (US); Yongqi Deng, Newton, MA (US); Ravi Kurukulasuriya, Niantic, CT (US); Hongbo Zeng, Westford, MA (US); Yunfeng Bai, Beijing (CN); Norman Kong, Beijing (CN); Yumei Liu, Beijing (CN); Zhixiang Zheng, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days. days.

(21) Appl. No.: 14/778,046

(22) PCT Filed: Mar. 19, 2014

(86) PCT No.: PCT/CN2014/000297
§ 371 (c)(1),
(2) Date: Sep. 17, 2015

(87) PCT Pub. No.: WO2014/146491
PCT Pub. Date: Sep. 25, 2014

(65) Prior Publication Data
US 2016/0272632 A1 Sep. 22, 2016

(30) Foreign Application Priority Data

Mar. 19, 2013 (WO) ............... PCT/CN2013/072873

(51) Int. Cl.
C07D 471/04 (2006.01)
C07D 519/00 (2006.01)

(52) U.S. Cl.
CPC ......... C07D 471/04 (2013.01); C07D 519/00 (2013.01)

(58) Field of Classification Search
CPC .................................... C07D 471/04
See application file for complete search history.

(56) References Cited

U.S. PATENT DOCUMENTS

2010/0105661 A1 4/2010 Shirakami

FOREIGN PATENT DOCUMENTS

| EP | 2857400 | 4/2015 | |
|---|---|---|---|
| WO | WO2011130146 | 10/2011 | |
| WO | 2012030924 A1 | 3/2012 | |
| WO | WO2013036611 A1 | 3/2013 | |
| WO | WO 2013040863 A1 * | 3/2013 | .......... C07D 403/12 |
| WO | WO 2013041042 A1 * | 3/2013 | .......... C07D 403/12 |
| WO | 2013180265 A1 | 5/2013 | |
| WO | WO2012066061 A1 | 5/2013 | |

OTHER PUBLICATIONS

International Search Report for PCT/CN2014/000297 dated Jun. 30, 2014.
Smyth, et al., Design and evaluation of 3-aminopyrazolopyridinone kinase inhibitors inspired by the natural product indirubin, Bioorganic & Medicinal Chemistry, 2011, pp. 3569-3578, vol. 19.

* cited by examiner

Primary Examiner — David K O'Dell
(74) Attorney, Agent, or Firm — Patricia A. Shatynski; John C. Todaro

(57) ABSTRACT

The instant invention provides compounds of Formula (I) which are JAK inhibitors, and as such are useful for the treatment of JAK-mediated diseases such as rheumatoid arthritis, asthma, COPD and cancer.

9 Claims, No Drawings

GEMINALLY SUBSTITUTED CYANOETHYLPYRAZOLO PYRIDONES AS JANUS KINASE INHIBITORS

CROSS REFERENCE TO RELATED APPLICATIONS

This application is a U.S. National Phase application under 35 U.S.C. § 371 of PCT Application No. PCT/CN2014/000297, filed Mar. 19, 2014 which claims priority under 35 U.S.C. § 365 from PCT Application No. PCT/CN2013/072873 filed on Mar. 19, 2013.

BACKGROUND OF THE INVENTION

Protein kinases are a group of enzymes that regulate the activity of their target proteins by the addition of phosphate groups to the protein substrate. Kinases play an essential role in many physiological processes including cell division, differentiation, cellular homeostasis and signal transduction. Kinases can be subdivided by their target into Serine/Threonine kinases and Tyrosine kinases. Tyrosine kinases are further subdivided into receptor tyrosine kinases and non-receptor tyrosine kinases. The mammalian Janus kinase (JAK) family members are non-receptor tyrosine kinases.

The JAK family has four members; JAK1, JAK2, JAK3 and TYK2. JAK1, JAK2 and TYK2 are universally expressed, whereas JAK3 expression is limited to hematopoetic cells. The JAK family is involved in intracellular signal transduction from >70 different cytokines Cytokines bind to their cell surface receptors resulting in receptor dimerization and subsequent activation/phosphorylation of JAK tyrosine kinases. The JAKs are either constitutively associated with the receptor or are recruited upon cytokine binding. Specific tyrosine residues on the receptor are then phosphorylated by activated JAKs and serve as docking sites for STAT proteins. STATs are phosphorylated by JAKs, dimerize, then translocate to the nucleus where they bind specific DNA elements and activate gene transcription. JAK1 signals in conjunction with all JAK isoforms in a cytokine dependent manner.

JAKs are essential for multiple physiological functions. This has been demonstrated using genetically engineered mouse models that are deficient in specific JAKs. Jak1$^{-/-}$ mice die perinatally, while Jak2$^{-/-}$ mice have deficiencies in erythropoesis and die around day E12. Jak3$^{-/-}$ mice are viable, but have a SCID phenotype with deficiencies in T cells, B cells and NK cells. TYK2$^{-/-}$ mice exhibit features of hyper IgE syndrome. These phenotypes demonstrate the essential and non-redundant roles of JAK activity in vivo (K. Ghoreschi, A. Laurence, J. J. O'Shea, *Immunol. Rev.* 228, 273 (2009)).

Furthermore, mutations in the JAK enzymes have been associated with diseases in humans. Inactivating mutations in JAK3 (or the cognate common gamma chain cytokine receptor) cause a severe SCID phenotype (J. J. O'Shea, M. Pesu, D. C. Borie, P. S. Changelian, *Nat. Rev. Drug Discov.* 3, 555 (2004)). Deletions of TYK2 result in hyper IgG syndrome and increased infection risk (Y. Minegishi et al., *Immunity.* 25, 745 (2006)). No inactivating mutations have been reported for JAK1 or JAK2, consistent with the data from mice that demonstrates that JAK1 and JAK2 deficient mice are not viable. However, several mutations that result in constitutively active JAK2 have been identified, resulting in myeloproliferative diseases and confirming the central role of JAK2 in hematopoesis (O. bdel-Wahab, *Curr. Opin. Hematol.* 18, 117 (2011)). JAK2 is the sole JAK family member involved in signal transduction of the critical hematopoetic cytokines IL-3, GMCSF, EPO and TPO.

The wealth of mouse and human genetic data demonstrating a central role for JAK kinase activity in autoimmune disease, hematopoesis and oncology has been supported by the use of pan-JAK inhibitors in clinical trials for autoimmune diseases and neoplasms (See K. Ghoreschi, et al, *Immunol. Rev.* 228, 273 (2009), and A. Quintas-Cardama, H. Kantarjian, J. Cortes, S. Verstovsek, *Nat. Rev. Drug Discov.* 10, 127 (2011)).

A considerable body of literature has accumulated that link the Jak/STAT pathway to various diseases and disorders including hyperproliferative disorders and cancer such as leukemia and lymphomas, immunological and inflammatory disorders such as transplant rejection, asthma, chronic obstructive pulmonary disease, allergies, rheumatoid arthritis, type I diabetes, amyotropic lateral sclerosis and multiple sclerosis.

SUMMARY OF THE INVENTION

The present invention provides novel compounds which are inhibitors of JAKs. The invention also provides a method for the treatment and prevention of JAK-mediated diseases and disorders using the novel compounds, as well as pharmaceutical compositions containing the compounds.

DETAILED DESCRIPTION OF THE INVENTION

The present invention provides compounds of formula I or pharmaceutically acceptable salts, or stereoisomers thereof:

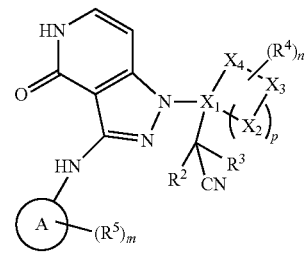

I

A is selected from aryl, heteroaryl, cycloalkylC$_{(0-10)}$alkyl, C$_{1-6}$alkyl;

R$^2$ and R$^3$ are each independently selected from hydrogen, C$_{1-4}$alkyl and hydroxy, wherein R$^2$ and R$^3$ may optionally, join together with the carbon they are attached to form a 3 to 6 membered ring;

X$_1$ is C;

X$_2$, X$_3$, and X$_4$ are each independently selected from O, N, S, and C and provided that the formed ring system contains 0, 1, 2, or 3 atoms selected from O, N and S;

n is 0, 1, 2, 3 or 4;

m is 0, 1, 2, 3 or 4;

p is 0, 1, 2, 3, or 4;

R$^4$ is selected from:
 halogen,
 oxo (=O),
 C$_{1-10}$ alkyl(oxy)$_{0-1}$(carbonyl)$_{0-1}$C$_{0-10}$ alkyl,
 C$_{1-10}$ heteroalkyl(oxy)$_{0-1}$(carbonyl)$_{0-1}$C$_{0-10}$ alkyl,
 C$_{2-10}$ alkenyl(oxy)$_{0-1}$(carbonyl)$_{0-1}$C$_{0-10}$ alkyl,
 aryl C$_{0-10}$ alkyl(oxy)$_{0-1}$(carbonyl)$_{0-1}$C$_{0-10}$ alkyl, $C_{3-12}$ cycloalkyl $C_{0-10}$ alkyl(oxy)$_{0-1}$(carbonyl)$_{0-1}$$C_{0-10}$ alkyl,
heteroaryl $C_{0-10}$ alkyl(oxy)$_{0-1}$(carbonyl)$_{0-1}$$C_{0-10}$ alkyl,
$(C_{3-12})$heterocycloalkyl $C_{0-10}$ alkyl(oxy)$_{0-1}$(carbonyl)$_{0-1}$ $C_{0-10}$ alkyl,
$C_{0-10}$ alkyl(oxy)$_{0-1}$(carbonyl)$_{0-1}$ amino$C_{0-10}$ alkyl,
$C_{1-10}$ alkylamino(carbonyl)$_{0-1}$$C_{0-10}$alkyl,
$(C_{1-10})$heteroalkyl(oxy)$_{0-1}$(carbonyl)$_{0-1}$amino$C_{0-10}$alkyl,
$(C_{1-10})$heteroalkylamino(carbonyl)$_{0-1}$$C_{0-10}$alkyl,
$C_{3-12}$ cycloalkyl $C_{0-10}$ alkylamino$C_{0-10}$ alkyl,
aryl $C_{0-10}$ alkylamino$C_{0-10}$ alkyl,
heteroaryl $C_{0-10}$ alkylamino$C_{0-10}$ alkyl,
$(C_{3-12})$heterocycloalkyl $C_{0-10}$ alkylamino$C_{0-10}$ alkyl,
$C_{1-10}$ alkylsulfonyl,
$C_{1-10}$ heteroalkylsulfonyl,
$(C_{3-12})$cycloalkyl$C_{0-10}$alkylsulfonyl,
$(C_{3-12})$cycloheteroalkyl$C_{0-10}$alkylsulfonyl,
heteroaryl$C_{0-10}$ alkylsulfonyl,
aryl$C_{0-10}$ alkylsulfonyl,
—$SO_2NH_2$,
—$SO_2NH(C_{1-6}$alkyl),
—$SO_2N(C_{1-6}$alkyl)$_2$,
$C_{0-10}$ alkylsulfamoyl,
$C_{1-10}$ heteroalkylsulfamoyl,
$(C_{3-12})$cycloalkyl$C_{0-10}$ alkylsulfamoyl,
$(C_{3-12})$cycloheteroalkyl$C_{0-10}$ alkylsulfamoyl,
heteroaryl$C_{0-10}$ alkylsulfamoyl,
aryl$C_{0-10}$ alkylsulfamoyl,
$C_{0-10}$ alkylsulfonimidoyl$C_{0-10}$ alkyl,
$C_{1-10}$ heteroalkylsulfonimidoyl$C_{0-10}$ alkyl,
$(C_{3-12})$cycloalkyl$C_{0-10}$ alkylsulfonimidoyl$C_{0-10}$ alkyl,
$(C_{3-12})$cycloheteroalkyl$C_{0-10}$alkylsulfonimidoyl$C_{0-10}$ alkyl,
heteroaryl$C_{0-10}$ alkylsulfonimidoyl$C_{0-10}$ alkyl,
aryl$C_{0-10}$ alkylsulfonimidoyl$C_{0-10}$ alkyl,
$(C_{1-10}$ alkyl)$_{1-2}$amino,
—$CO_2(C_{0-10}$ alkyl),
—$(C_{0-10}$ alkyl)$CO_2H$,
—$SO_2CF_3$,
—$SO_2CF_2H$,
—$SO_2CH_2CF_3$,
$C_{1-10}$ alkylsulfinyl,
$C_{1-4}$acylamino$C_{0-10}$ alkyl,
hydroxy,
—$(C_{1-10}$ alkyl)OH,
$C_{1-10}$ alkoxy$C_{0-10}$ alkyl, cyano,
$(C_{1-6}$alkyl)cyano, and
$C_{1-6}$haloalkyl,
wherein two $R^4$ together with the ring atom to which each is attached optionally may form a saturated ring;
$R^5$ is selected from:
halogen,
oxo (=O),
$C_{1-10}$ alkyl(oxy)$_{0-1}$(carbonyl)$_{0-1}$$C_{0-10}$ alkyl,
$C_{1-10}$ heteroalkyl(oxy)$_{0-1}$(carbonyl)$_{0-1}$$C_{0-10}$ alkyl,
$C_{2-10}$ alkenyl(oxy)$_{0-1}$(carbonyl)$_{0-1}$$C_{0-10}$ alkyl,
aryl $C_{0-10}$ alkyl(oxy)$_{0-1}$(carbonyl)$_{0-1}$$C_{0-10}$ alkyl,
$C_{3-12}$ cycloalkyl $C_{0-10}$ alkyl(oxy)$_{0-1}$(carbonyl)$_{0-1}$$C_{0-10}$ alkyl,
heteroaryl $C_{0-10}$ alkyl(oxy)$_{0-1}$(carbonyl)$_{0-1}$$C_{0-10}$ alkyl,
$(C_{3-12})$heterocycloalkyl $C_{0-10}$ alkyl(oxy)$_{0-1}$(carbonyl)$_{0-1}$$C_{0-10}$ alkyl,
$C_{0-10}$ alkylaminocarbonyl$C_{0-10}$alkyl,
$C_{0-10}$ alkyl(oxy)$_{0-1}$(carbonyl)$_{0-1}$ amino$C_{0-10}$ alkyl,
$(C_{1-10})$heteroalkyl(oxy)$_{0-1}$(carbonyl)$_{0-1}$ amino$C_{0-10}$ alkyl,
$C_{3-12}$ cycloalkyl $C_{0-10}$ alkylamino$C_{0-10}$ alkyl,
aryl $C_{0-10}$ alkylamino$C_{0-10}$ alkyl,
heteroaryl $C_{0-10}$ alkylamino$C_{0-10}$ alkyl,
$(C_{3-12})$heterocycloalkyl $C_{0-10}$ alkylamino$C_{0-10}$ alkyl,
$(C_{1-10}$ alkyl)$_{1-2}$ amino,
—$SF_5$,
$C_{0-10}$ alkylsulfonyl,
$C_{1-10}$ heteroalkylsulfonyl,
$(C_{3-12})$cycloalkyl$C_{0-10}$alkylsulfonyl,
$(C_{3-12})$cycloheteroalkyl$C_{0-10}$alkylsulfonyl,
heteroaryl$C_{0-10}$ alkylsulfonyl,
aryl$C_{0-10}$ alkylsulfonyl,
$C_{0-10}$ alkylsulfamoyl,
$C_{1-10}$ heteroalkylsulfamoyl,
$(C_{3-12})$cycloalkyl$C_{0-10}$ alkylsulfamoyl,
$(C_{3-12})$cycloheteroalkyl$C_{0-10}$ alkylsulfamoyl,
heteroaryl$C_{0-10}$ alkylsulfamoyl,
$C_{0-10}$ alkylsulfonimidoyl$C_{0-10}$ alkyl,
$C_{1-10}$ heteroalkylsulfonimidoyl$C_{0-10}$ alkyl,
$(C_{3-12})$cycloalkyl$C_{0-10}$ alkylsulfonimidoyl$C_{0-10}$ alkyl,
$(C_{3-12})$cycloheteroalkyl$C_{0-10}$alkylsulfonimidoyl$C_{0-10}$ alkyl,
heteroaryl$C_{0-10}$ alkylsulfonimidoyl$C_{0-10}$ alkyl,
aryl$C_{0-10}$ alkylsulfonimidoyl$C_{0-10}$ alkyl,
—$SO_2NH_2$,
—$SO_2NH(C_{1-6}$alkyl),
—$SO_2N(C_{1-6}$alkyl)$_2$,
aryl$C_{0-10}$ alkylsulfamoyl,
$(C_{0-10}$ alkyl)$_{1-2}$ amino,
—$CO_2(C_{0-10}$ alkyl),
—$(C_{0-10}$ alkyl)$CO_2H$,
—$SO_2CF_3$,
—$SO_2CF_2H$,
—$SO_2CH_2CF_3$,
$C_{1-10}$ alkylsulfinyl,
$C_{1-4}$acylamino$C_{0-10}$ alkyl, hydroxy,
—$(C_{1-10}$ alkyl)OH,
$C_{1-10}$ alkoxy$C_{0-10}$ alkyl,
cyano,
$(C_{1-6}$alkyl)cyano, and
$C_{1-6}$haloalkyl; and
wherein $R^4$ and $R^5$ are each optionally substituted with 1, 2, 3, or 4 $R^6$ substituents and $R^6$ is independently selected from:
halogen,
$C_{1-10}$ alkyl(oxy)$_{0-1}$(carbonyl)$_{0-1}$$C_{0-10}$ alkyl,
$C_{1-10}$ heteroalkyl(oxy)$_{0-1}$(carbonyl)$_{0-1}$$C_{0-10}$ alkyl,
$C_{2-10}$ alkenyl(oxy)$_{0-1}$(carbonyl)$_{0-1}$$C_{0-10}$ alkyl,
aryl $C_{0-10}$ alkyl(oxy)$_{0-1}$(carbonyl)$_{0-1}$$C_{0-10}$ alkyl,
$C_{3-12}$ cycloalkyl $C_{0-10}$ alkyl(oxy)$_{0-1}$(carbonyl)$_{0-1}$$C_{0-10}$ alkyl,
heteroaryl $C_{0-10}$ alkyl(oxy)$_{0-1}$(carbonyl)$_{0-1}$$C_{0-10}$ alkyl,
$(C_{3-12})$heterocycloalkyl $C_{0-10}$ alkyl(oxy)$_{0-1}$(carbonyl)$_{0-1}$$C_{0-10}$ alkyl,
$C_{1-10}$ alkyl(carbonyl)$_{0-1}$oxy$C_{0-10}$ alkyl,
$C_{2-10}$ alkenyl(carbonyl)$_{0-1}$ oxy$C_{0-10}$ alkyl,
$C_{1-10}$ heteroalkyl(carbonyl)$_{0-1}$ oxy$C_{0-10}$ alkyl,
aryl $C_{0-10}$ alkyl (carbonyl)$_{0-1}$oxy$C_{0-10}$ alkyl,
$(C_{3-12})$cycloalkyl $C_{0-10}$ alkyl(carbonyl)$_{0-1}$ oxy$C_{0-10}$ alkyl,
heteroaryl$C_{0-10}$ alkyl(carbonyl)$_{0-1}$ oxy$C_{0-10}$ alkyl,
$(C_{3-12})$heterocycloalkyl $C_{0-10}$ alkyl(carbonyl)$_{0-1}$ oxy$C_{0-10}$ alkyl,
$((C_{0-10})$alkyl)$_{1-2}$aminocarbonyloxy,
aryl $(C_{0-10})$alkylaminocarbonyloxy,
—$CO_2(C_{0-10}$ alkyl),
—$(C_{0-10}$ alkyl)$CO_2H$,
oxo (=O),
$C_{0-10}$ alkylsulfonyl,
$C_{1-10}$ heteroalkylsulfonyl, ($C_{3-12}$) cycloalkylsulfonyl,
($C_{3-12}$) cycloheteroalkylsulfonyl,
heteroarylsulfonyl,
arylsulfonyl,
aminosulfonyl,
—$SO_2NH_2$,
—$SO_2NH(C_{1-6}alkyl)$,
—$SO_2N(C_{1-6}alkyl)_2$,
—$SO_2CF_3$,
—$SO_2CF_2H$,
$C_{1-10}$ alkylsulfinyl,
amino,
($C_{1-10}$ alkyl)$_{1-2}$amino,
-(oxy)$_{0-1}$(carbonyl)$_{0-1}$N($C_{0-10}$ alkyl)$_{1-2}$
$C_{1-4}$acylamino$C_{0-10}$ alkyl,
hydroxy,
($C_{1-10}$ alkyl)OH,
$C_{1-10}$ alkoxy$C_{0-10}$ alkyl,
($C_{1-10}$ alkyl)cyano,
cyano, and
$C_{1-6}$haloalkyl; and
$R^6$ is optionally substituted with 1, 2, or 3 $R^7$ substituents selected from hydrogen, hydroxy, ($C_{1-6}$)alkyl, $C_{1-10}$ alkoxy$C_{0-10}$ alkyl, ($C_{1-10}$ alkyl)OH, halogen, $CO_2H$, —($C_{0-6}$)alkylCN, —O(C═O)$C_1$-$C_6$ alkyl, $NO_2$, trifluoromethoxy, trifluoroethoxy, trifluoromethyl, trifluoroethyl, —N═C(O)O($C_{0-6}$)alkyl, $C_{1-10}$ alkylsulfonyl, oxo (O═), aminosulfonyl, —$SO_2C_{1-6}$alkyl, —$SO_2CF_3$, —$SO_2CF_2H$, —$C_{1-10}$ alkylsulfinyl, —$O_{(0-1)}$($C_{1-10}$)halo, —$SO_2NH_2$, —$SO_2NH(C_{1-6}alkyl)$, —$SO_2N(C_{1-6}alkyl)_2$, alkyl, amino($C_{1-6}$alkyl)$_{0-2}$ and $NH_2$ Representative compounds of the instant invention include, but are not limited to the following compounds and their pharmaceutically acceptable salts and stereoisomers thereof:

tert-butyl 3-(cyanomethyl)-3-(4-oxo-3-(phenylamino)-4,5-dihydro-1H-pyrazolo[4,3-c]pyridin-1-yl)azetidine-1-carboxylate;

tert-butyl 4-(cyanomethyl)-4-(4-oxo-3-(phenylamino)-4,5-dihydro-1H-pyrazolo[4,3-c]pyridin-1-yl)piperidine-1-carboxylate;

tert-butyl 4-(cyanomethyl)-4-[3-(ethylamino)-4-oxo-4,5-dihydro-1H-pyrazolo[4,3-c]pyridin-1-yl]piperidine-1-carboxylate;

tert-butyl 4-(cyanomethyl)-4-{3-[(cyclopropylmethyl)amino]-4-oxo-4,5-dihydro-1H-pyrazolo[4,3-c]pyridin-1-yl}piperidine-1-carboxylate;

tert-butyl 4-(cyanomethyl)-4-[3-(cyclobutylamino)-4-oxo-4,5-dihydro-1H-pyrazolo[4,3-c]pyridin-1-yl]piperidine-1-carboxylate;

tert-butyl 3-(cyanomethyl)-3-[3-(ethylamino)-4-oxo-4,5-dihydro-1H-pyrazolo[4,3-c]pyridin-1-yl]azetidine-1-carboxylate;

tert-butyl 4-(cyanomethyl)-4-[3-(methylamino)-4-oxo-4,5-dihydro-1H-pyrazolo[4,3-c]pyridin-1-yl]piperidine-1-carboxylate;

tert-butyl 3-(cyanomethyl)-3-[3-(cyclopropylamino)-4-oxo-4,5-dihydro-1H-pyrazolo[4,3-c]pyridin-1-yl]azetidine-1-carboxylate;

tert-butyl 3-(cyanomethyl)-3-(4-oxo-3-((2-(trifluoromethyl)pyridin-4-yl)amino)-4,5-dihydro-1H-pyrazolo[4,3-c]pyridin-1-yl)azetidine-1-carboxylate;

tert-butyl 3-(cyanomethyl)-3-(3((4(methoxycarbonyl)phenyl)amino)-4-oxo-4,5-dihydro-1H-pyrazolo[4,3-c]pyridin-1-yl)azetidine-1-carboxylate;

tert-butyl 3-(cyanomethyl)-3-(3-((4-fluorophenyl)amino)-4-oxo-4,5-dihydro-1H-pyrazolo[4,3-c]pyridin-1-yl)azetidine-1-carboxylate;

tert-butyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

tert-butyl 4-(cyanomethyl)-4-[4-oxo-3-({4-[2,2,2-trifluoro-hydroxyethyl]phenyl}amino)-4,5-dihydro-1H-pyrazolo[4,3-c]pyridin-1-yl]piperidine-1-carboxylate;

tert-butyl 4-(cyanomethyl)-4-{4-oxo-3-[(4-sulfamoylphenyl)amino]-4,5-dihydro-1H-pyrazolo[4,3-c]pyridin-1-yl}piperidine-1-carboxylate;

tert-butyl 4-(cyanomethyl)-4-(4-oxo-3-{[1-oxo-2-(2,2,2-trifluoroethyl)-2,3-dihydro-1H-isoindol-5-yl]amino}-4,5-dihydro-1H-pyrazolo[4,3-c]pyridin-1-yl)piperidine-1-carboxylate;

tert-butyl 4-(cyanomethyl)-3-fluoro-4-(3-{[4-(methylsulfonyl)phenyl]amino}-4-oxo-4,5-dihydro-1H-pyrazolo[4,3-c]pyridin-1-yl)piperidine-1-carboxylate;

tert-butyl 4-(cyanomethyl)-4-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}piperidine-1-carboxylate;

tert-butyl 4-(cyanomethyl)-4-(4-oxo-3-{[4-(pentafluorosulfanyl)phenyl]amino}-4,5-dihydro-1H-pyrazolo[4,3-c]pyridin-1-yl)piperidine-1-carboxylate;

tert-butyl 4-(cyanomethyl)-4-(4-oxo-3-{[4-(trifluoromethyl)phenyl]amino}-4,5-dihydro-1H-pyrazolo[4,3-c]pyridin-1-yl)piperidine-1-carboxylate;

tert-butyl 4-(cyanomethyl)-3-fluoro-4-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}piperidine-1-carboxylate;

tert-butyl 4-(cyanomethyl)-3-methyl-4-(3-{[4-(methylsulfonyl)phenyl]amino}-4-oxo-4,5-dihydro-1H-pyrazolo[4,3-c]pyridin-1-yl)piperidine-1-carboxylate;

tert-butyl 4-(cyanomethyl)-4-(4-oxo-3-((1-oxo-2,3-dihydro-1H-inden-5-yl)amino)-4,5-dihydro-1H-pyrazolo[4,3-c]pyridin-1-yl)piperidine-1- carboxylate;

tert-butyl 4-(cyanomethyl)-4-(3-{[3-(methylsulfonyl)phenyl]amino}-4-oxo-4,5-dihydro-1H-pyrazolo[4,3-c]pyridin-1-yl)piperidine-1-carboxylate;

tert-butyl 4-(cyanomethyl)-3-fluoro-4-(3-{[4-(methylsulfonyl)phenyl]amino}-4-oxo-4,5-dihydro-1H-pyrazolo[4,3-c]pyridin-1-yl)piperidine-1-carboxylate;

tert-butyl 4-(cyanomethyl)-4-(3-{[4-(dimethylsulfamoyl)phenyl]amino}-4-oxo-4,5-dihydro-1H-pyrazolo[4,3-c]pyridin-1-yl)-3-fluoropiperidine-1-carboxylate;

tert-butyl 4-(cyanomethyl)-3-fluoro-4-[4-oxo-3-(phenylamino)-4,5-dihydro-1H-pyrazolo[4,3-c]pyridin-1-yl]piperidine-1-carboxylate;

tert-butyl 4-(cyanomethyl)-3-fluoro-4-[4-oxo-3-({4-[2,2,2-trifluoro-1-hydroxyethyl]phenyl}amino)-4,5-dihydro-1H-pyrazolo[4,3-c]pyridin-1-yl]piperidine-1-carboxylate;

tert-butyl 4-{3-[(2-tert-butyl-1,12-dioxido-2,3-dihydro-1,2-benzisothiazol-5-yl)amino]-4-oxo-4,5-dihydro-1H-pyrazolo[4,3-c]pyridin-1-yl}-4-(cyanomethyl)-3-fluoropiperidine-1-carboxylate;

tert-butyl 4-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}-4-(cyanomethyl)piperidine-1-carboxylate;

tert-butyl 4-(cyanomethyl)-4-(3-{[1,1-dioxido-2-(2,2,2-trifluoroethyl)-2,3-dihydro-1,2-benzisothiazol-5-yl]amino}-4-oxo-4,5-dihydro-1H-pyrazolo[4,3-c]pyridin-1-yl)-3-fluoropiperidine-1-carboxylate;

tert-butyl 4-(cyanomethyl)-4-(3-((1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)piperidine-1-carboxylate;

2-(4-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-1-(2,2-difluoropropanoyl)piperidin-4-yl)acetonitrile;

2-(3-(4-oxo-3-(phenylamino)-4,5-dihydro-1H-pyrazolo[4,3-c]pyridin-1-yl)tetrahydro-2H-pyran-3-yl)acetonitrile;

4-((1-(3-(cyanomethyl)tetrahydro-2H-pyran-3-yl)-4-oxo-4,5-dihydro-1H-pyrazolo[4,3-c]pyridin-3-yl)amino)-N,N-dimethylbenzenesulfonamide;

2-(3-(3-((4-(methylsulfonyl)phenyl)amino)-4-oxo-4,5-dihydro-1H-pyrazolo[4,3-c]pyridin-1-yl)tetrahydro-2H-pyran-3-yl)acetonitrile;

methyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate;

tert-butyl 5-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-5-(cyanomethyl)tetrahydro-2H-pyran-2-carboxylate;

tert-butyl 5-(cyanomethyl)-5-(3-((4-(N,N-dimethylsulfamoyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)tetrahydro-2H-pyran-2-carboxylate;

tert-butyl 3-(cyanomethyl)-3-(3-{[4-(methylsulfonyl)phenyl]amino}-4-oxo-4,5-dihydro-1H-pyrazolo[4,3-c]pyridin-1-yl)azetidine-1-carboxylate;

tert-butyl 3-(cyanomethyl)-3-{3-[(2-fluoropyridin-4-yl)amino]-4-oxo-4,5-dihydro-1H-pyrazolo[4,3-c]pyridin-1-yl}azetidine-1-carboxylate;

tert-butyl 3-(cyanomethyl)-3-[4-oxo-3-({4-[(trifluoromethyl)sulfonyl]phenyl}amino)-4,5-dihydro-1H-pyrazolo[4,3-c]pyridin-1-yl]azetidine-1-carboxylate;

tert-butyl 4-(cyanomethyl)-4-{3-[(4-fluorophenyl)amino]-4-oxo-4,5-dihydro-1H-pyrazolo[4,3-c]pyridin-1-yl}piperidine-1-carboxylate;

tert-butyl 4-(cyanomethyl)-4-(3-((4-(N,N-dimethylsulfamoyl)-3-methylphenyl)amino)-4-oxo-4,5-dihydro-1H-pyrazolo[4,3-c]pyridin-1-yl)piperidine-1-carboxylate;

tert-butyl 5-(3-((4-1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate;

tert-butyl 5-(cyanomethyl)-5-(4-oxo-3-(phenylamino)-4,5-dihydro-1H-pyrazolo[4,3-c]pyridin-1-yl)tetrahydro-2H-pyran-2-carboxylate;

tert-butyl 5-(cyanomethyl)-5-(3-((2-methyl-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-2-carboxylate;

N-(tert-butyl)-4-((1-(4-(cyanomethyl)-1-(2,2-difluoropropanoyl)piperidin-4-yl)-4-oxo-4,5-dihydro-1H-pyrazolo[4,3-c]pyridin-3-yl)amino)benzenesulfonamide;

2-(1-(2,2-difluoropropanoyl)-4-(3-((4-(isopropylsulfonyl)phenyl)amino)-4-oxo-4,5-dihydro-1H-pyrazolo[4,3-c]pyridin-1-yl)piperidin-4-yl)acetonitrile;

N-(tert-butyl)-4-((1-(4-(cyanomethyl)-1-(2,2-difluoropropanoyl)piperidin-4-yl)-4-oxo-4,5-dihydro-1H-pyrazolo[4,3-c]pyridin-3-yl)amino)-N-methylbenzenesulfonamide;

2-(4-(3-((4-(tert-butylsulfonyl)phenyl)amino)-4-oxo-4,5-dihydro-1H-pyrazolo[4,3-c]pyridin-1-yl)-1-(2,2-difluoropropanoyl)piperidin-4-yl)acetonitrile;

tert-butyl 4-(3-(3,5-bis((1H-pyrazol-1-yl)methyl)phenylamino)-4-oxo-4,5-dihydropyrazolo[4,3-c]pyridin-1-yl)-4-(cyanomethyl)piperidine-1-carboxylate;

tert-butyl 4-(cyanomethyl)-4-(3-(3,5-dimethylphenylamino)-4-oxo-4,5-dihydropyrazolo[4,3-c]pyridin-1-yl)piperidine-1-carboxylate;

tert-butyl 4-(3-(3,5-bis((1H-1,2,3-triazol-1-yl)methyl)phenylamino)-4-oxo-4,5-dihydropyrazolo[4,3-c]pyridin-1-yl)-4-(cyanomethyl)piperidine-1-carboxylate;

tert-butyl 4-(3-(3,5-bis((2H-1,2,3-triazol-2-yl)methyl)phenylamino)-4-oxo-4,5-dihydropyrazolo[4,3-c]pyridin-1-yl)-4-(cyanomethyl)piperidine-1-carboxylate;

tert-butyl 4-(3-(3-((1H-1,2,3-triazol-1-yl)methyl)-5-((2H-1,2,3-triazol-2-yl)methyl)phenylamino)-4-oxo-4,5-dihydropyrazolo[4,3-c]pyridin-1-yl)-4-(cyanomethyl)piperidine-1-carboxylate;

tert-butyl 4-(3-(m-toluidino)-4-oxo-4,5-dihydropyrazolo[4,3-c]pyridin-1-yl)-4-(cyanomethyl)piperidine-1-carboxylate;

tert-butyl 4-(cyanomethyl)-4-(3-(isoindolin-5-ylamino)-4-oxo-4,5-dihydropyrazolo[4,3-c]pyridin-1-yl)piperidine-1-carboxylate;

1,1-dioxo-2,3-dihydro-1,2-benzothiazol-5-yl]amino}-4-oxo-1H,4H,5H-pyrazolo[4,3-c]pyridin-1-yl)piperidine-1-carboxylate;

tert-butyl 4-(cyanomethyl)-4-(3-{[2-(cyclopropylmethyl)-1,1-dioxo-2,3-dihydro-1,2-benzothiazol-5-yl]amino}-4-oxo-1H,4H,5H-pyrazolo[4,3-c]pyridin-1-yl)piperidine-1-carboxylate;

tert-butyl 4-(cyanomethyl)-4-{3-[(2-ethyl-1,1-dioxo-2,3-dihydro-1,2-benzothiazol-5-yl)amino]-4-oxo-1H,4H,5H-pyrazolo[4,3-c]pyridin-1-yl}piperidine-1-carboxylate;

methyl 4-(cyanomethyl)-4-[3-[(2-methyl-1,1-dioxo-2,3-dihydro-1,2-benzothiazol-5-yl)amino]-4-oxo-1H,4H,5H-pyrazolo[4,3-c]pyridin-1-yl]piperidine-1-carboxylate;

methyl 4-{3-[(2-tert-butyl-1,1-dioxo-2,3-dihydro-1,2-benzothiazol-5-yl)amino]-4-oxo-1H,4H,5H-pyrazolo[4,3-c]pyridin-1-yl}-4-(cyanomethyl)piperidine-1-carboxylate;

methyl 4-{3-[(2-ethyl-1,1-dioxo-2,3-dihydro-1,2-benzothiazol-5-yl)amino]-4-oxo-1H,4H,5H-pyrazolo[4,3-c]pyridin-1-yl}-4-(cyanomethyl)piperidine-1-carboxylate;

methyl 4-(cyanomethyl)-4-(3-{[2-(2-methylpropyl)-1,1-dioxo-2,3-dihydro-1,2-benzothiazol-5-yl]amino}-4-oxo-1H,4H,5H-pyrazolo[4,3-c]pyridin-1-yl)piperidine-1-carboxylate;

methyl 4-(cyanomethyl)-4-(3-{[2-(cyclopropylmethyl)-1,1-dioxo-2,3-dihydro-1,2-benzothiazol-5-yl]amino}-4-oxo-1H,4H,5H-pyrazolo[4,3-c]pyridin-1-yl)piperidine-1-carboxylate;

methyl 4-(cyanomethyl)-4-(3-{[2-(cyclopentylmethyl)-1,1-dioxo-2,3-dihydro-1,2-benzothiazol-5-yl]amino}-4-oxo-1H,4H,5H-pyrazolo[4,3-c]pyridin-1-yl)piperidine-1-carboxylate;

tert-butyl 4-(cyanomethyl)-4-[4-oxo-3-({4-[(trifluoromethyl)sulfonyl]phenyl}amino)-4,5-dihydro-1H-pyrazolo[4,3-c]pyridin-1-yl]piperidine-1-carboxylate;

tert-butyl 4-(cyanomethyl)-4-(3-{[4-(methylsulfonyl)phenyl]amino}-4-oxo-4,5-dihydro-1H-pyrazolo[4,3-c]pyridin-1-yl)piperidine-1-carboxylate;

tert-butyl 4-(cyanomethyl)-4-{3-[(2-fluoropyridin-4-yl)amino]-4-oxo-4,5-dihydro-1H-pyrazolo[4,3-c]pyridin-1-yl}piperidine-1-carboxylate;

4-(1-(1-(cyanomethyl)cyclohexyl)-4-oxo-4,5-dihydro-1H-pyrazolo[4,3-c]pyridin-3-ylamino)-N,N-dimethylbenzenesulfonamide;

2-(1-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)cyclohexyl)acetonitrile;

2-(1-(3-((2-methyl-1,1-dioxido-2,3-dihydrobenzo[d]isothiazol-5-yl)amino)-4-oxo-4,5-dihydro-1H-pyrazolo[4,3-c]pyridin-1- yl)cyclohexyl)acetonitrile;

tert-butyl 4-(cyanomethyl)-4-(3-((1,1-dioxido-2,3-dihydrobenzo[b]thiophen-5-yl)amino)-4-oxo-4,5-dihydro-1H-pyrazolo[4,3-c]pyridin-1-yl)piperidine-1-carboxylate;

2-(8-(4-oxo-3-((4-(trifluoromethyl)phenyl)amino)-4,5-dihydro-1H-pyrazolo[4,3-c]pyridin-1-yl)-1,4-dioxaspiro[4.5]decan-8-yl)acetonitrile;

4-({-[1-(cyanomethyl)-2-fluorocyclohexyl]-4-oxo-4,5-dihydro-1H-pyrazolo[4,3-c]pyridin-3-yl}amino)-N,N-dimethylbenzenesulfonamide;

{2-fluoro-1-[4-oxo-3-({4-[2,2,2-trifluoro-1-hydroxy-1-methylethyl]phenyl}amino)-4,5-dihydro-1H-pyrazolo[4,3-c]pyridin-1-yl]cyclohexyl}acetonitrile {2-fluoro-1-[3-({4-[(1-methylethyl)sulfonyl]phenyl}amino)-4-oxo-4,5-dihydro-1H-pyrazolo[4,3-c]pyridin-1-yl]cyclohexyl}acetonitrile;

2-(1-(3-((4-(1-amino-2,2,2-trifluoroethyl)phenyl)amino)-4-oxo-4,5-dihydro-1H-pyrazolo[4,3-c]pyridin-1-yl)cyclopentyl)acetonitrile;

tert-butyl 5-(3-((4-(N-(tert-butyl)-N-methylsulfamoyl)phenyl)amino)-4-oxo-4,5-dihydro-1H-pyrazolo[4,3-c]pyridin-1-yl)-5-(cyanomethyl)tetrahydro-2H-pyran-2-carboxylate;

tert-butyl 5-(cyanomethyl)-5-(3-((4-(N-isopropyl-N-methylsulfamoyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(N-ethyl-N-methylsulfamoyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(N-methylsulfamoyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((1-oxo-2-(2,2,2-trifluoroethyl)isoindolin-5-yl)amino)-4,5-dihydro-1H-pyrazolo[4,3-c]pyridin-1-yl)tetrahydro-2H-pyran-2-carboxylate;

tert-butyl 5-(3-((4-((1H-1,2,3-triazol-1-yl)methyl)phenyl)amino)-4-oxo-4,5-dihydro-1H-pyrazolo[4,3-c]pyridin-1-yl)-5-(cyanomethyl)tetrahydro-2H-pyran-2-carboxylate;

tert-butyl 5-(3-((4-((2H-1,2,3-triazol-2-yl)methyl)phenyl)amino)-4-oxo-4,5-dihydro-1H-pyrazolo[4,3-c]pyridin-1-yl)-5-(cyanomethyl)tetrahydro-2H-pyran-2-carboxylate;

tert-butyl 5-(cyanomethyl)-5-(3-((4-(isopropylsulfonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(cyclopropylsulfonyl)phenyl)amino)-4-oxo-4,5-dihydro-1H-pyrazolo[4,3-c]pyridin-1-yl)tetrahydro-2H-pyran-2-carboxylate;

tert-butyl 5-(3-((2-(tert-butyl)-1-oxoisoindolin-5-yl)amino)-4-oxo-4,5-dihydro-1H-pyrazolo[4,3-c]pyridin-1-yl)-5-(cyanomethyl)tetrahydro-2H-pyran-2-carboxylate;

tert-butyl 5-(cyanomethyl)-5-(3-((2-cyclohexyl-1-oxoisoindolin-5-yl)amino)-4-oxo-4,5-dihydro-1H-pyrazolo[4,3-c]pyridin-1-yl)tetrahydro-2H- pyran-2-carboxylate;

tert-butyl 5-(cyanomethyl)-5-(3-((2-cyclopentyl-1-oxoisoindolin-5-yl)amino)-4-oxo-4,5-dihydro-1H-pyrazolo[4,3-c]pyridin-1-yl)tetrahydro-2H-pyran-2-carboxylate;

tert-butyl 5-(3-((4-(1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate;

[3-(3-{[4-(azetidin-1-ylsulfonyl)phenyl]amino}-4-oxo-4,5-dihydro-1H-pyrazolo[4,3-c]pyridin-1-yl)tetrahydro-2H-pyran-3-yl]acetonitrile;

{3-[3-({4-[(3-methylazetidin-1-yl)sulfonyl]phenyl}amino)-4-oxo-4,5-dihydro-1H-pyrazolo[4,3-c]pyridin-1-yl]tetrahydro-2H-pyran-3-yl}acetonitrile;

{3-[3-({4-[(2,2-dimethylpyrrolidin-1-yl)sulfonyl]phenyl}amino)-4-oxo-4,5-dihydro-1H-pyrazolo[4,3-c]pyridin-1-yl]tetrahydro-2H-pyran-3-yl}acetonitrile;

[3-{3-[(4-{[2-methylazetidin-1-yl]sulfonyl}phenyl)amino]-4-oxo-4,5-dihydro-1H-pyrazolo[4,3-c]pyridin-1-yl}tetrahydro-2H-pyran-3-yl]acetonitrile;

{3-[4-oxo-3-({4-[2,2,2-trifluoro-1-hydroxy-1-methylethyl]phenyl}amino)-4,5-dihydro-1H-pyrazolo[4,3-c]pyridin-1-yl]tetrahydro-2H-pyran-3-yl}acetonitrile;

ethyl 3-(4-((1-(3-(cyanomethyl)tetrahydro-2H-pyran-3-yl)-4-oxo-4,5-dihydro-1H-pyrazolo[4,3-c]pyridin-3-yl)amino)phenyl)-4,4,4-trifluoro-3-hydroxy-2,2-dimethylbutanoate;

2-(3-(3-((4-(3-hydroxy-3-(trifluoromethyl)pyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;

2-(3-(3-((4-(3-fluoropyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;

2-(3-(3-((4-(3-methoxypyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;

2-(3-(3-((4-(3-methoxypyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;

2-(3-(3-((3-methyl-4-(morpholine-4-carbonyl)phenyl)amino)-4-oxo-4,5-dihydro-1H-pyrazolo[4,3-c]pyridin-1-yl)tetrahydro-2H-pyran-3-yl)acetonitrile;

2-(3-(3-((1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)tetrahydro-2H-pyran-3-yl)acetonitrile;

2-(1-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)cyclopentyl)acetonitrile;

2-(1-(3-((4-(tert-butylsulfonyl)phenyl)amino)-4-oxo-4,5-dihydro-1H-pyrazolo[4,3-c]pyridin-1-yl)cyclopentyl)acetonitrile;

4-((1-(1-(cyanomethyl)cyclopentyl)-4-oxo-4,5-dihydro-1H-pyrazolo[4,3-c]pyridin-3-yl)amino)-N,N-dimethylbenzenesulfonamide;

4-((1-(1-(cyanomethyl)cyclopentyl)-4-oxo-4,5-dihydro-1H-pyrazolo[4,3-c]pyridin-3-yl)amino)benzonitrile;

2-(1-(4-oxo-3-((1-oxo-1,3-dihydroisobenzofuran-5-yl)amino)-4,5-dihydro-1H-pyrazolo[4,3-c]pyridin-1-yl)cyclopentyl)acetonitrile;

(1-{3-[(3,3-dimethyl-1-oxo-1,3-dihydro-2-benzofuran-5-yl)amino]-4-oxo-4,5-dihydro-1H-pyrazolo[4,3-c]pyridin-1-yl}cyclopentyl)acetonitrile;

tert-butyl 4-((1-(1-(cyanomethyl)cyclopentyl)-4-oxo-4,5-dihydro-1H-pyrazolo[4,3-c]pyridin-3-yl)amino)benzoate;

4-((1-(1-(cyanomethyl)cyclopentyl)-4-oxo-4,5-dihydro-1H-pyrazolo[4,3-c]pyridin-3-yl)amino)-N-methylbenzamide;

2-(1-(3-((2-isopropyl-1-oxoisoindolin-5-yl)amino)-4-oxo-4,5-dihydro-1H-pyrazolo[4,3-c]pyridin-1-yl)cyclopentyl)acetonitrile;

4-((1-(1-(cyanomethyl)cyclopentyl)-4-oxo-4,5-dihydro-1H-pyrazolo[4,3-c]pyridin-3-yl)amino)-N-isopropylbenzenesulfonamide;

4-((1-(1-(cyanomethyl)cyclopentyl)-4-oxo-4,5-dihydro-1H-pyrazolo[4,3-c]pyridin-3-yl)amino)-N-methylbenzenesulfonamide;

2-(1-(3-((4-(azetidin-1-ylsulfonyl)phenyl)amino)-4-oxo-4,5-dihydro-1H-pyrazolo[4,3-c]pyridin-1-yl)cyclopentyl)acetonitrile;

2-(1-(3-((4-(ethylsulfonyl)phenyl)amino)-4-oxo-4,5-dihydro-1H-pyrazolo[4,3-c]pyridin-1-yl)cyclopentyl)acetonitrile;

N-(tert-butyl)-4-((1-(1-(cyanomethyl)cyclopentyl)-4-oxo-4,5-dihydro-1H-pyrazolo[4,3-c]pyridin-3-yl)amino)-N-methylbenzenesulfonamide;

N-(tert-butyl)-4-((1-(1-(cyanomethyl)cyclopentyl)-4-oxo-4,5-dihydro-1H-pyrazolo[4,3-c]pyridin-3-yl)amino)-N-ethylbenzenesulfonamide;

4-((1-(1-(cyanomethyl)cyclopentyl)-4-oxo-4,5-dihydro-1H-pyrazolo[4,3-c]pyridin-3-yl)amino)-N,N-diethylbenzenesulfonamide;

tert-butyl 2-(4-((1-(1-(cyanomethyl)cyclopentyl)-4-oxo-4,5-dihydro-1H-pyrazolo[4,3-c]pyridin-3-yl)amino)-N-methylphenylsulfonamido)-2-methylpropanoate;

2-(1-(4-oxo-3-((1-oxo-2-(2,2,2-trifluoroethyl)isoindolin-5-yl)amino)-4,5-dihydro-1H-pyrazolo[4,3-c]pyridin-1-yl)cyclopentyl)acetonitrile;

ethyl 2-(4-((1-(1-(cyanomethyl)cyclopentyl)-4-oxo-4,5-dihydro-1H-pyrazolo[4,3-c]pyridin-3-yl)amino)-N-methylphenylsulfonamido)-2-methylpropanoate;

tert-butyl 2-(5-((1-(1-(cyanomethyl)cyclopentyl)-4-oxo-4,5-dihydro-1H-pyrazolo[4,3-c]pyridin-3-yl)amino)-1-oxoisoindolin-2-yl)-2-methylpropanoate;

methyl 4-(cyanomethyl)-4-(4-oxo-3-((4-(1,1,1-trifluoro-2-hydroxypropan-2-yl)phenyl)amino)-4,5-dihydro-1H-pyrazolo[4,3-c]pyridin-1-yl)piperidine-1-carboxylate;

methyl 4-(cyanomethyl)-4-(3-((1-hydroxy-1-(trifluoromethyl)-2,3-dihydro-1H-inden-5-yl)amino)-4-oxo-4,5-dihydro-1H-pyrazolo[4,3-c]pyridin-1-yl)piperidine-1-carboxylate;

methyl 4-(cyanomethyl)-4-(3-((4-cyanophenyl)amino)-4-oxo-4,5-dihydro-1H-pyrazolo[4,3-c]pyridin-1-yl)piperidine-1-carboxylate;

methyl 4-(cyanomethyl)-4-(3-((4-fluorophenyl)amino)-4-oxo-4,5-dihydro-1H-pyrazolo[4,3-c]pyridin-1-yl)piperidine-1-carboxylate;

methyl 4-(cyanomethyl)-4-(4-oxo-3-((4-(trifluoromethyl)phenyl)amino)-4,5-dihydro-1H-pyrazolo[4,3-c]pyridin-1-yl)piperidine-1-carboxylate;

methyl 4-(cyanomethyl)-4-(4-oxo-3-(quinolin-6-ylamino)-4,5-dihydro-1H-pyrazolo[4,3-c]pyridin-1-yl)piperidine-1-carboxylate;

methyl 4-(cyanomethyl)-4-(3-((4-(isopropylsulfonyl)phenyl)amino)-4-oxo-4,5-dihydro-1H-pyrazolo[4,3-c]pyridin-1-yl)piperidine-1-carboxylate;

methyl 4-(3-((4-(tert-butylsulfonyl)phenyl)amino)-4-oxo-4,5-dihydro-1H-pyrazolo[4,3-c]pyridin-1-yl)-4-(cyanomethyl)piperidine-1-carboxylate;

2-(2-fluoro-1-(3-((3-methyl-4-(morpholine-4-carbonyl)phenyl)amino)-4-oxo-4,5-dihydro-1H-pyrazolo[4,3-c]pyridin-1-yl)cyclohexyl)acetonitrile;

2-(2-fluoro-1-(3-((2-fluoropyridin-4-yl)amino)-4-oxo-4,5-dihydro-1H-pyrazolo[4,3-c]pyridin-1-yl)cyclohexyl)acetonitrile;

2-(1-(3-((4-(4,4-difluoropiperidine-1-carbonyl)-3-methylphenyl)amino)-4-oxo-4,5-dihydro-1H-pyrazolo[4,3-c]pyridin-1-yl)-2-fluorocyclohexyl)acetonitrile;

2-(2-fluoro-1-(3-((3-methyl-4-(thiomorpholine-4-carbonyl)phenyl)amino)-4-oxo-4,5-dihydro-1H-pyrazolo[4,3-c]pyridin-1- yl)cyclohexyl)acetonitrile;

tert-butyl 5-(cyanomethyl)-5-(3-((3-methyl-4-(thiazolidine-3-carbonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((3-methyl-4-(2-methylthiazolidine-3-carbonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((3-methyl-4-(2-methylthiomorpholine-4-carbonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(3-hydroxy-3-(trifluoromethyl)pyrrolidine-1-carbonyl)-3-methylphenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(1,1,1-trifluoro-2-hydroxy-4-isopropoxy-3,3-dimethyl-4-oxobutan-2-yl)phenyl)amino)-4,5-dihydro-1H-pyrazolo[4,3-c]pyridin-1-yl)tetrahydro-2H-pyran-2-carboxylate;

tert-butyl 5-(cyanomethyl)-5-(3-((1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(1,1,1-trifluoro-2-hydroxy-3,3-dimethylbutan-2-yl)phenyl)amino)-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(2,2,2-trifluoro-1-hydroxyethyl)phenyl)amino)-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(1,1,1-trifluoro-2-hydroxypropan-2-yl)phenyl)amino)-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(1,1,1-trifluoro-2-methoxypropan-2-yl)phenyl)amino)-4,5-dihydro-1H-pyrazolo[4,3-c]pyridin-1-yl)tetrahydro-2H-pyran-2-carboxylate;

{1-[3-({4-[1-(ethylamino)-2,2,2-trifluoroethyl]phenyl}amino)-4-oxo-4,5-dihydro-1H-pyrazolo[4,3-c]pyridin-1-yl]-2-fluorocyclohexyl}acetonitrile;

[2-fluoro-1-{3-[(4-{1-methyl-1-[(1-methylethyl)amino]ethyl}phenyl)amino]-4-oxo-4,5-dihydro-1H-pyrazolo[4,3-c]pyridin-1- yl}cyclohexyl]acetonitrile;

{1-[3-({4-[1-amino-2,2,2-trifluoroethyl]phenyl}amino)-4-oxo-4,5-dihydro-1H-pyrazolo[4,3-c]pyridin-1-yl]-2-fluorocyclohexyl}acetonitrile;

[3-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}tetrahydro-2H-pyran-3-yl]acetonitrile;

{3-[3-({4-[(1-methylethyl)sulfonyl]phenyl}amino)-4-oxo-4,5-dihydro-1H-pyrazolo[4,3-c]pyridin-1-yl]tetrahydro-2H-pyran-3-yl}acetonitrile;

4-({1-[3-(cyanomethyl)-4-fluorotetrahydro-2H-pyran-3-yl]-4-oxo-4,5-dihydro-1H-pyrazolo[4,3-c]pyridin-3-yl}amino)-N,N-dimethylbenzenesulfonamide;

N-tert-butyl-4-({1-[3-(cyanomethyl)tetrahydro-2H-pyran-3-yl]-4-oxo-4,5-dihydro-1H-pyrazolo[4,3-c]pyridin-3-yl}amino)-N-methylbenzenesulfonamide;

[3-(3-{[4-(tert-butylsulfonyl)phenyl]amino}-4-oxo-4,5-dihydro-1H-pyrazolo[4,3-c]pyridin-1-yl)tetrahydro-2H-pyran-3-yl]acetonitrile;

N-tert-butyl-4-({1-[3-(cyanomethyl)tetrahydro-2H-pyran-3-yl]-4-oxo-4,5-dihydro-1H-pyrazolo[4,3-c]pyridin-3-yl}amino)benzenesulfonamide;

tert-butyl[5-({1-[3-(cyanomethyl)tetrahydro-2H-pyran-3-yl]-4-oxo-4,5-dihydro-1H-pyrazolo[4,3-c]pyridin-3-yl}amino)-1,1-dioxido-1,2-benzisothiazol-2(3H)-yl]acetate;

tert-butyl 3-{[4-({1-[3-(cyanomethyl)tetrahydro-2H-pyran-3-yl]-4-oxo-4,5-dihydro-1H-pyrazolo[4,3-c]pyridin-3-yl}amino)phenyl]sulfonyl}-3-methylbutanoate;

{3-[3-({4-[1-amino-2,2,2-trifluoroethyl]phenyl}amino)-4-oxo-4,5-dihydro-1H-pyrazolo[4,3-c]pyridin-1-yl]tetrahydro-2H-pyran-3-yl}acetonitrile;

{3-[3-({4-[1-(tert-butylamino)-2,2,2-trifluoroethyl]phenyl}amino)-4-oxo-4,5-dihydro-1H-pyrazolo[4,3-c]pyridin-1-yl]tetrahydro-2H-pyran-3-yl}acetonitrile;

[3-(3-{[4-(cyclopentylsulfonyl)phenyl]amino}-4-oxo-4,5-dihydro-1H-pyrazolo[4,3-c]pyridin-1-yl)tetrahydro-2H-pyran-3-yl]acetonitrile;

{3-[4-oxo-3-({4-[(1,1,2-trimethylpropyl)sulfonyl]phenyl}amino)-4,5-dihydro-1H-pyrazolo[4,3-c]pyridin-1-yl]tetrahydro-2H-pyran-3-yl}acetonitrile;

[3-(3-{[4-(cyclohexylsulfonyl)phenyl]amino}-4-oxo-4,5-dihydro-1H-pyrazolo[4,3-c]pyridin-1-yl)tetrahydro-2H-pyran-3-yl]acetonitrile;

tert-butyl 5-(3-((4-(1-(tert-butylamino)-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate;

{3-[3-({4-[(1,1-dimethylpropyl)sulfonyl]phenyl}amino)-4-oxo-4,5-dihydro-1H-pyrazolo[4,3-c]pyridin-1-yl]tetrahydro-2H-pyran-3-yl}acetonitrile;

[3-{3-[(2-cyclopentyl-1-oxo-2,3-dihydro-1H-isoindol-5-yl)amino]-4-oxo-4,5-dihydro-1H-pyrazolo[4,3-c]pyridin-1-yl}tetrahydro-2H-pyran-3-yl]acetonitrile;

{3-[4-oxo-3-({4-[2,2,2-trifluoro-1-pyrrolidin-1-ylethyl]phenyl}amino)-4,5-dihydro-1H-pyrazolo[4,3-c]pyridin-1-yl]tetrahydro-2H-pyran-3-yl}acetonitrile;

{3-[4-oxo-3-({4-[1-pyrrolidin-1-ylethyl]phenyl}amino)-4,5-dihydro-1H-pyrazolo[4,3-c]pyridin-1-yl]tetrahydro-2H-pyran-3-yl}acetonitrile;

{3-[3-({4-[(2,2-dimethylcyclopentyl)sulfonyl]phenyl}amino)-4-oxo-4,5-dihydro-1H-pyrazolo[4,3-c]pyridin-1-yl]tetrahydro-2H-pyran-3-yl}acetonitrile;

tert-butyl 5-(cyanomethyl)-5-(3-((4-(morpholinosulfonyl)phenyl)amino)-4-oxo-4,5-dihydro-1H-pyrazolo[4,3-c]pyridin-1-yl)tetrahydro-2H-pyran-2-carboxylate;

[3-(3-{[4-(morpholin-4-ylsulfonyl)phenyl]amino}-4-oxo-4,5-dihydro-1H-pyrazolo[4,3-c]pyridin-1-yl)tetrahydro-2H-pyran-3-yl]acetonitrile;

[3-{4-oxo-3-[(4-{2,2,2-trifluoro-1-[(1-methylethyl)amino]ethyl}phenyl)amino]-4,5-dihydro-1H-pyrazolo[4,3-c]pyridin-1-yl}tetrahydro-2H-pyran-3-yl]acetonitrile;

tert-butyl 5-(cyanomethyl)-5-(3-((4-(1-(ethylamino)-2,2,2-trifluoroethyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(2,2,2-trifluoro-1-(isopropylamino)ethyl)phenyl)amino)-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(1-(pyrrolidin-1-yl)ethyl)phenyl)amino)-4,5-dihydro-1H-pyrazolo[4,3-c]pyridin-1-yl)tetrahydro-2H- pyran-2-carboxylate;

tert-butyl 5-(cyanomethyl)-5-(3-((4-(1-(dimethylamino)-2,2,2-trifluoroethyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(4-oxo-3-(quinolin-6-ylamino)-4,5-dihydro-1H-pyrazolo[4,3-c]pyridin-1-yl)tetrahydro-2H-pyran-2-carboxylate;

tert-butyl 5-(cyanomethyl)-5-(3-((2-cyanoquinolin-6-yl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((2-methylquinolin-6-yl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(3,5-dimethyl-1H-pyrazol-1-yl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((3-methyl-4-(1H-pyrazol-1-yl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(2,2-dimethylmorpholine-4-carbonyl)-3-methylphenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(4-oxo-3-(quinolin-3-ylamino)-4,5-dihydro-1H-pyrazolo[4,3-c]pyridin-1-yl)tetrahydro-2H-pyran-2-carboxylate;

tert-butyl 5-(cyanomethyl)-5-(3-((2-(dimethylamino)quinolin-6-yl)amino)-4-oxo-4,5-dihydro-1H-pyrazolo[4,3-c]pyridin-1-yl)tetrahydro-2H-pyran-2-carboxylate;

tert-butyl 5-(3-((2-carbamoylquinolin-6-yl)amino)-4-oxo-4,5-dihydro-1H-pyrazolo[4,3-c]pyridin-1-yl)-5-(cyanomethyl)tetrahydro-2H-pyran-2-carboxylate;

2-(3-(4-oxo-3-((4-(1-(trifluoromethyl)cyclopropyl)phenyl)amino)-4,5-dihydro-1H-pyrazolo[4,3-c]pyridin-1-yl)tetrahydro-2H-pyran-3-yl)acetonitrile;

2-(3-(3-((2-(dimethylamino)quinolin-6-yl)amino)-4-oxo-4,5-dihydro-1H-pyrazolo[4,3-c]pyridin-1-yl)tetrahydro-2H-pyran-3-yl)acetonitrile;

2-(3-(3-((2-methylquinolin-6-yl)amino)-4-oxo-4,5-dihydro-1H-pyrazolo[4,3-c]pyridin-1-yl)tetrahydro-2H-pyran-3-yl)acetonitrile;

tert-butyl 5-(cyanomethyl)-5-(3-((2-morpholinoquinolin-6-yl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((2-(2-methylmorpholino)quinolin-6-yl)amino)-4-oxo-4,5-dihydro-1H-pyrazolo[4,3-c]pyridin-1-yl)tetrahydro-2H-pyran-2-carboxylate;

tert-butyl 5-(3-((2-(8-oxa-3-azabicyclo[3.2.1]octan-3-yl)quinolin-6-yl)amino)-4-oxo-4,5-dihydro-1H-pyrazolo[4,3-c]pyridin-1-yl)-5-(cyanomethyl)tetrahydro-2H-pyran-2-carboxylate;

tert-butyl 5-(cyanomethyl)-5-(4-oxo-3-((4-(propan-2-yl-(S or R)-sulfonimidoyl)phenyl)amino)-4,5-dihydro-1H-pyrazolo[4,3-c]pyridin-1-yl)tetrahydro-2H-pyran-2-carboxylate;

2-(3-(4-oxo-3-((4-(propan-2-yl-(S or R)-sulfonimidoyl)phenyl)amino)-4,5-dihydro-1H-pyrazolo[4,3-c]pyridin-1-yl)tetrahydro-2H-pyran-3-yl)acetonitrile;

4-({1-[1-(cyanomethyl)-2-fluorocyclohexyl]-4-oxo-4,5-dihydro-1H-pyrazolo[4,3-c]pyridin-3-yl}amino)-N,N-dimethylbenzenesulfonamide;

tert-butyl 5-(3-((4-(tert-butylsulfonyl)phenyl)amino)-4-oxo-4,5-dihydro-1H-pyrazolo[4,3-c]pyridin-1-yl)-5-(cyanomethyl)tetrahydro-2H-pyran-2-carboxylate;

tert-butyl 5-(cyanomethyl)-5-(3-((4-(cyclopropylsulfonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(isopropylsulfonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((2-(dimethylcarbamoyl)quinolin-6-yl)amino)-4-oxo-4,5-dihydro-1H-pyrazolo[4,3-c]pyridin-1-yl)tetrahydro-2H-pyran-2-carboxylate;

4-({1-[3-(cyanomethyl)tetrahydrofuran-3-yl]-4-oxo-4,5-dihydro-1H-pyrazolo[4,3-c]pyridin-3-yl}amino)benzonitrile;

[3-{3-[(4-chlorophenyl)amino]-4-oxo-4,5-dihydro-1H-pyrazolo[4,3-c]pyridin-1-yl}tetrahydrofuran-3-yl]acetonitrile;

[3-{3-[(4-chloro-8-fluoroquinolin-6-yl)amino]-4-oxo-4,5-dihydro-1H-pyrazolo[4,3-c]pyridin-1-yl}tetrahydrofuran-3-yl]acetonitrile;

[3-{3-[(4-fluoroquinolin-6-yl)amino]-4-oxo-4,5-dihydro-1H-pyrazolo[4,3-c]pyridin-1-yl}tetrahydrofuran-3-yl]acetonitrile;

(3-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)tetrahydrofuran- 3-yl)acetonitrile;

2-(3-(3-((4-(tert-butylsulfonyl)phenyl)amino)-4-oxo-4,5-dihydro-1H-pyrazolo[4,3-c]pyridin-1-yl)tetrahydrofuran-3-yl)acetonitrile;

2-(4-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-4-yl)acetonitrile;

2-(4-(3-((4-(tert-butylsulfonyl)phenyl)amino)-4-oxo-4,5-dihydro-1H-pyrazolo[4,3-c]pyridin-1-yl)tetrahydro-2H-pyran-4-yl)acetonitrile;

N-(tert-butyl)-4-((1-(4-(cyanomethyl)tetrahydro-2H-pyran-4-yl)-4-oxo-4,5-dihydro-1H-pyrazolo[4,3-c]pyridin-3-yl)amino)-N-methylbenzenesulfonamide;

4-((1-(4-(cyanomethyl)tetrahydro-2H-pyran-4-yl)-4-oxo-4,5-dihydro-1H-pyrazolo[4,3-c]pyridin-3-yl)amino)-N,N-dimethylbenzenesulfonamide;

2-(4-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-3-fluorotetrahydro-2H-pyran-4-yl)acetonitrile;

2-(3-fluoro-4-(3-(3-methyl-4-(morpholine-4-carbonyl)phenylamino)-4-oxo-4,5-dihydropyrazolo[4,3-c]pyridin-1-yl)-tetrahydro-2H-pyran-4-yl)acetonitrile;

2-(4-(3-((2-(tert-butyl)-1-oxoisoindolin-5-yl)amino)-4-oxo-4,5-dihydro-1H-pyrazolo[4,3-c]pyridin-1-yl)-3-fluorotetrahydro-2H-pyran-4-yl)acetonitrile;

2-(3-fluoro-4-(3-(3-methyl-4-(thiomorpholine-4-carbonyl)phenylamino)-4-oxo-4,5-dihydropyrazolo[4,3-c]pyridin-1-yl)-tetrahydro-2H-pyran-4-yl)acetonitrile;

2-(3-fluoro-4-(4-oxo-3-((4-(2-(trifluoromethyl)piperidin-2-yl)phenyl)amino)-4,5-dihydro-1H-pyrazolo[4,3-c]pyridin-1-yl)tetrahydro-2H-pyran-4-yl)acetonitrile;

2-(4-(3-((4-(1-(tert-butylamino)-2,2,2-trifluoroethyl)phenyl)amino)-4-oxo-4,5-dihydro-1H-pyrazolo[4,3-c]pyridin-1-yl)-3-fluorotetrahydro-2H-pyran-4-yl)acetonitrile;

2-[4-(3-{[1,1-dioxo-2-(piperidin-4-yl)-3H-1,2-benzothiazol-5-yl]amino}-4-oxo-5H-pyrazolo[4,3-c]pyridin-1-yl)-3-fluorooxan-4-yl]acetonitrile;

tert-butyl-4-(cyanomethyl)-3-fluoro-4-{3-[(4-{1-methyl-1-[(1-methylethyl)amino]ethyl}phenyl)amino]-4-oxo-4,5-dihydro-1H-pyrazolo[4,3-c]pyridin-1-yl}piperidine-1-carboxylate;

tert-butyl 5-(cyanomethyl)-5-(3-((4-(2-(isopropylamino)propan-2-yl)phenyl)amino)-4-oxo-4,5-dihydro-1H-pyrazolo[4,3-c]pyridin-1-yl)tetrahydro-2H-pyran-2-carboxylate;

tert-butyl-4-(cyanomethyl)-3-fluoro-4-(3-{[4-(1-methoxyethyl)phenyl]amino}-4-oxo-4,5-dihydro-1H-pyrazolo[4,3-c]pyridin-1-yl)piperidine-1-carboxylate;

tert-butyl 4-(cyanomethyl)-4-{3-[(4-{1-methyl-1-[(1-methylethyl)amino]ethyl}phenyl)amino]-4-oxo-4,5-dihydro-1H-pyrazolo[4,3-c]pyridin-1-yl}piperidine-1-carboxylate;

2-(4-(3-((1,1-dioxido-2-(1-(2,2,2-trifluoroethyl)piperidin-4-yl)-2,3-dihydrobenzo[d]isothiazol-5-yl)amino)-4-oxo-4,5-dihydro-1H-pyrazolo[4,3-c]pyridin-1-yl)-3-fluorotetrahydro-2H-pyran-4-yl)acetonitrile;

tert-butyl 4-(cyanomethyl)-3-fluoro-4-(3-((3-methyl-4-(thiomorpholine-4-carbonyl)phenyl)amino)-4-oxo-4,5-dihydro-1H-pyrazolo[4,3-c]pyridin-1-yl)piperidine-1-carboxylate;

tert-butyl 4-(3-((4-(1-benzyl-3-(trifluoromethyl)pyrrolidin-3-yl)phenyl)amino)-4-oxo-4,5-dihydro-1H-pyrazolo[4,3-c]pyridin-1-yl)-4-(cyanomethyl)piperidine-1-carboxylate;

tert-butyl 4-(cyanomethyl)-4-(4-oxo-3-((4-(3-(trifluoromethyl)pyrrolidin-3-yl)phenyl)amino)-4,5-dihydro-1H-pyrazolo[4,3-c]pyridin-1-yl)piperidine-1-carboxylate;

tert-butyl 5-(cyanomethyl)-5-(4-oxo-3-((4-(3-(trifluoromethyl)pyrrolidin-3-yl)phenyl)amino)-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-((S or R)-2-(trifluoromethyl)piperidin-2-yl)phenyl)amino)-4,5-dihydro-1H-pyrazolo[4,3-c]pyridin-1-yl)tetrahydro-2H-pyran-2-carboxylate;

tert-butyl 4-(cyanomethyl)-4-(4-oxo-3-((4-(((2,2,2-trifluoroethyl)amino)methyl)phenyl)amino)-4,5-dihydro-1H-pyrazolo[4,3-c]pyridin-1-yl)piperidine-1-carboxylate;

tert-butyl 4-(cyanomethyl)-4-(3-((4-(N-isopropylsulfamoyl)phenyl)amino)-4-oxo-4,5-dihydro-1H-pyrazolo[4,3-c]pyridin-1-yl)piperidine-1-carboxylate;

tert-butyl 4-(3-((4-(N-benzylsulfamoyl)phenyl)amino)-4-oxo-4,5-dihydro-1H-pyrazolo[4,3-c]pyridin-1-yl)-4-(cyanomethyl)piperidine-1-carboxylate;

tert-butyl 4-(cyanomethyl)-4-(3-((4-(N-(cyclopropylmethyl) sulfamoyl)phenyl)amino)-4-oxo-4,5-dihydro-1H-pyrazolo[4,3-c]pyridin-1-yl)piperidine-1-carboxylate;

tert-butyl 4-(cyanomethyl)-4-(3-((4-(N-(2-methoxyethyl)sulfamoyl)phenyl)amino)-4-oxo-4,5-dihydro-1H-pyrazolo[4,3-c]pyridin-1-yl)piperidine-1-carboxylate;

tert-butyl 4-(cyanomethyl)-4-(3-((4-(N-cyclohexylsulfamoyl)phenyl)amino)-4-oxo-4,5-dihydro-1H-pyrazolo[4,3-c]pyridin-1-yl)piperidine-1-carboxylate;

tert-butyl 4-(cyanomethyl)-4-(4-oxo-3-((4-(piperidin-1-ylsulfonyl)phenyl)amino)-4,5-dihydro-1H-pyrazolo[4,3-c]pyridin-1-yl)piperidine-1- carboxylate;

tert-butyl 4-(cyanomethyl)-4-(3-((4-(morpholinosulfonyl) phenyl)amino)-4-oxo-4,5-dihydro-1H-pyrazolo[4,3-c] pyridin-1-yl)piperidine-1-carboxylate;

tert-butyl 4-(cyanomethyl)-4-(3-((3-fluoro-4-(N-isopropyl-sulfamoyl)phenyl)amino)-4-oxo-4,5-dihydro-1H-pyrazolo[4,3-c]pyridin-1-yl)piperidine-1-carboxylate;

tert-butyl 4-(cyanomethyl)-4-(3-((4-(N-(cyclopropylmethyl)sulfamoyl)-3-fluorophenyl)amino)-4-oxo-4,5-dihydro-1H-pyrazolo[4,3-c]pyridin-1-yl)piperidine-1-carboxylate;

(4-{3-[(4-fluorophenyl)amino]-4-oxo-4,5-dihydro-1H-pyrazolo[4,3-c]pyridin-1-yl}piperidin-4-yl)acetonitrile;

[1-(cyclopropylcarbonyl)-4-{3-[(4-fluorophenyl)amino]-4-oxo-4,5-dihydro-1H-pyrazolo[4,3-c]pyridin-1-yl}piperidin-4-yl]acetonitrile;

4-({1-[1-benzyl-4-(cyanomethyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(4-methylbenzyl)piperidin-4-yl]-4-oxo-4,5-dihydro-1H-pyrazolo[4,3-c]pyridin-3-yl}amino)-N,N-dimethylbenzenesulfonamide;

4-[(1-{4-(cyanomethyl)-1-[4-(trifluoromethyl)benzyl]piperidin-4-yl}-4-oxo-4,5-dihydro-1H-pyrazolo[4,3-c]pyridin-3-yl)amino]-N,N-dimethylbenzenesulfonamide;

4-[(1-{4-(cyanomethyl)-1-[4-(1-methylethyl)benzyl]piperidin-4-yl}-4-oxo-4,5-dihydro-1H-pyrazolo[4,3-c]pyridin-3-yl)amino]-N,N-dimethylbenzenesulfonamide;

4-[(1-{4-(cyanomethyl)-1-[4-(1-methylethyl)benzyl]piperidin-4-yl}-4-oxo-4,5-dihydro-1H-pyrazolo[4,3-c]pyridin-3-yl)amino]-N,N-dimethylbenzene sulfonamide;

4-[(1-{4-(cyanomethyl)-1-[4-(1methylethoxy)benzyl]piperidin-4-yl}-4-oxo-4,5-dihydro-1H-pyrazolo[4,3-c]pyridin-3-yl)amino]-N,N-dimethylbenzene sulfonamide;

4-({1-[4-(cyanomethyl)-1-(4-fluorobenzyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(3-fluorobenzyl)piperidin-4-yl]-4-oxo-4,5-dihydro-1H-pyrazolo[4,3-c]pyridin-3-yl}amino)-N,N-dimethylbenzene sulfonamide;

4-({1-[4-(cyanomethyl)-1-(2-fluorobenzyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(2,6-difluorobenzyl)piperidin-4-yl]-4-oxo-4,5-dihydro-1H-pyrazolo[4,3-c]pyridin-3-yl}amino)-N,N-dimethylbenzene sulfonamide;

4-({1-[4-(cyanomethyl)-1-(2,3,6-trifluorobenzyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(1,3-oxazol-2-ylmethyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(4-isoxazol-3-ylbenzyl)piperidin-4-yl]-4-oxo-4,5-dihydro-1H-pyrazolo[4,3-c]pyridin-3-yl}amino)-N,N-dimethylbenzenesulfonamide;

4-[(1-{4-(cyanomethyl)-1-[4-(2-oxopyrrolidin-1-yl)benzyl]piperidin-4-yl}-4-oxo-4,5-dihydro-1H-pyrazolo[4,3-c]pyridin-3- yl)amino]-N,N-dimethylbenzenesulfonamide;

4-({1-[4-(cyanomethyl)-1-(3-phenylpropyl)piperidin-4-yl]-4-oxo-4,5-dihydro-1H-pyrazolo[4,3-c]pyridin-3-yl}amino)-N,N-dimethylbenzene sulfonamide;

4-({1-[4-(cyanomethyl)-1-(1H-indol-4-ylmethyl)piperidin-4-yl]-4-oxo-4,5-dihydro-1H-pyrazolo[4,3-c]pyridin-3-yl}amino)-N,N-dimethylbenzenesulfonamide;

4-(((1-(4-(cyanomethyl)-1-(1-(2,6-difluorophenyl)ethyl)piperidin-4-yl)-4-oxo-4,5-dihydro-1H-pyrazolo[4,3-c]pyridin-3-yl)amino)-N,N-dimethylbenzenesulfonamide;

4-(((1-(4-(cyanomethyl)-1-phenethylpiperidin-4-yl)-4-oxo-4,5-dihydro-1H-pyrazolo[4,3-c]pyridin-3-yl)amino)-N,N-dimethylbenzenesulfonamide;

3-({1-[4-(cyanomethyl)-1-(pyridin-3-ylmethyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-propanoylpiperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(3,3,3-trifluoropropanoyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(methoxyacetyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(N,N-dimethylglycyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(2,2-dimethylpropanoyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(cyclopropylcarbonyl)piperidin-4-yl]-4-oxo-4,5-dihydro-1H-pyrazolo[4,3-c]pyridin-3-yl}amino)-N,N-dimethylbenzenesulfonamide;

4-[(1-{4-(cyanomethyl)-1-[(3,3-difluorocyclobutyl)carbonyl]piperidin-4-yl}-4-oxo-4,5-dihydro-1H-pyrazolo[4,3-c]pyridin-3-yl)amino]- N,N-dimethylbenzenesulfonamide;

4-({1-[4-(cyanomethyl)-1-(cyclohexylcarbonyl)piperidin-4-yl]-4-oxo-4,5-dihydro-1H-pyrazolo[4,3-c]pyridin-3-yl}amino)-N,N-dimethylbenzenesulfonamide;

4-[(1-{4-(cyanomethyl)-1-[tricyclo[3.3.1.13,7]dec-1-ylcarbonyl]piperidin-4-yl}-4-oxo-4,5-dihydro-1H-pyrazolo[4,3-c]pyridin-3-yl)amino]-N,N-dimethylbenzenesulfonamide;

4-({1-[4-(cyanomethyl)-1-(cyclopropylacetyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(3-cyclopropylpropanoyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(phenylcarbonyl)piperidin-4-yl]-4-oxo-4,5-dihydro-1H-pyrazolo[4,3-c]pyridin-3-yl}amino)-N,N-dimethylbenzenesulfonamide;

4-[(1-{1-[(4-chlorophenyl)carbonyl]-4-(cyanomethyl)piperidin-4-yl}-4-oxo-4,5-dihydro-1H-pyrazolo[4,3-c]pyridin-3-yl)amino]-N,N-dimethylbenzenesulfonamide;

4-[(1-{1-[(3-chlorophenyl)carbonyl]-4-(cyanomethyl)piperidin-4-yl}-4-oxo-4,5-dihydro-1H-pyrazolo[4,3-c]pyridin-3-yl)amino]-N,N-dimethylbenzenesulfonamide;

4-[(1-{1-[(2-chlorophenyl)carbonyl]-4-(cyanomethyl)piperidin-4-yl}-4-oxo-4,5-dihydro-1H-pyrazolo[4,3-c]pyridin-3-yl)amino]-N,N-dimethylbenzenesulfonamide;

4-({1-[4-(cyanomethyl)-1-{[4-(trifluoromethyl)phenyl]acetyl}piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(3-phenylpropanoyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(2,3-dihydro-1H-inden-2-ylcarbonyl)piperidin-4-yl]-4-oxo-4,5-dihydro-1H-pyrazolo[4,3-c]pyridin-3-yl}amino)-N,N-dimethylbenzenesulfonamide;

4-[(1-{4-(cyanomethyl)-1-[(2-oxopyrrolidin-1-yl)acetyl]piperidin-4-yl}-4-oxo-4,5-dihydro-1H-pyrazolo[4,3-c]pyridin-3-yl)amino]-N,N-dimethylbenzenesulfonamide;

4-({1-[4-(cyanomethyl)-1-(tetrahydro-2H-pyran-4-ylcarbonyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(4,4,4-trifluorobutanoyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(3-cyanopropanoyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(3,3-dimethylbutanoyl)piperidin-4-yl]-4-oxo-4,5-dihydro-1H-pyrazolo[4,3-c]pyridin-3-yl}amino)-N,N-dimethylbenzenesulfonamide;

4-((1-(4-(cyanomethyl)-1-(2-(methylthio)propanoyl)piperidin-4-yl)-4-oxo-4,5-dihydro-1H-pyrazolo[4,3-c]pyridin-3-yl)amino)-N,N-dimethylbenzenesulfonamide;

4-((1-(1-(2-cyanoacetyl)-4-(cyanomethyl)piperidin-4-yl)-4-oxo-4,5-dihydro-1H-pyrazolo[4,3-c]pyridin-3-yl)amino)-N,N-dimethylbenzenesulfonamide;

methyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

phenyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

4-fluorophenyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

neopentyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

ethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

isopropyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

methyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

2-methylcyclopentyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

2-(methylthio)ethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

tetrahydro-2H-thiopyran-4-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

1-methoxypropan-2-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

tetrahydrofuran-3-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

tetrahydro-2H-pyran-4-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

1,1,1-trifluoropropan-2-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

1-(pyridin-2-yl)ethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

1-cyanoethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

tetrahydrofuran-3-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

2,2,2-trifluoroethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

isopropyl-4-(cyanomethyl)-4-(3-(2-fluoropyridin-4-ylamino)-4-oxo-4,5-dihydropyrazolo[4,3-c]pyridin-1-yl)piperidine-1-carboxylate;

methyl 4-(cyanomethyl)-4-(3-(2-fluoropyridin-4-ylamino)-4-oxo-4,5-dihydropyrazolo[4,3-c]pyridin-1-yl)piperidine-1-carboxylate;

4-((1-(4-(cyanomethyl)-1-((2,2,2-trifluoroethyl)sulfonyl)piperidin-4-yl)-4-oxo-4,5-dihydro-1H-pyrazolo[4,3-c]pyridin-3-yl)amino)-N,N-dimethylbenzenesulfonamide;

4-((1-(4-(cyanomethyl)-1-(cyclopropylsulfonyl)piperidin-4-yl)-4-oxo-4,5-dihydro-1H-pyrazolo[4,3-c]pyridin-3-yl)amino)-N,N-dimethylbenzenesulfonamide;

2-(4-(3-((4-(methylsulfonyl)phenyl)amino)-4-oxo-4,5-dihydro-1H-pyrazolo[4,3-c]pyridin-1-yl)-1-(4-(trifluoromethyl)pyridin-2-yl)piperidin-4-yl)acetonitrile;

6-(4-(cyanomethyl)-4-(3-((4(methylsulfonyl)phenyl)amino)-4-oxo-4,5-dihydro-1H-pyrazolo[4,3-c]pyridin-1-yl)piperidin-1-yl)nicotinonitrile;

6-(4-(cyanomethyl)-4-(3-((4((difluoromethyl)sulfonyl)phenyl)amino)-4-oxo-4,5-dihydro-1H-pyrazolo[4,3-c]pyridin-1-yl)piperidin-1-yl)nicotinonitrile;

2-(4-(3-((4-(methylsulfonyl)phenyl)amino)-4-oxo-4,5-dihydro-1H-pyrazolo[4,3-c]pyridin-1-yl)-1-(5 (trifluoromethyl)pyridin-2-yl)piperidin-4-yl)acetonitrile;

6-(4-(cyanomethyl)-4-(3-((3-methyl-4-(thiomorpholine-4-carbonyl)phenyl)amino)-4-oxo-4,5-dihydro-1H-pyrazolo[4,3-c]pyridin-1-yl)piperidin-1-yl)nicotinonitrile;

6-((3R,4R)-4-(cyanomethyl)-3-fluoro-4-(3-((3-methyl-4-(thiomorpholine-4-carbonyl)phenyl)amino)-4-oxo-4,5-dihydro-1H-pyrazolo[4,3-c]pyridin-1-yl)piperidin-1-yl)nicotinonitrile;

2-(1-(5-iodopyridin-2-yl)-4-(3-((4-(methylsulfonyl)phenyl)amino)-4-oxo-4,5-dihydro-1H-pyrazolo[4,3-c]pyridin-1-yl)piperidin-4-yl)acetonitrile;

2-(1-(5-bromopyridin-2-yl)-4-(3-((4-(methylsulfonyl)phenyl)amino)-4-oxo-4,5-dihydro-1H-pyrazolo[4,3-c]pyridin-1-yl)piperidin-4-yl)acetonitrile;

2-(4-(3-(3-methyl-4-(thiomorpholine-4-carbonyl)phenylamino)-4-oxo-4,5-dihydropyrazolo[4,3-c]pyridin-1-yl)-1-(4-(trifluoromethyl)pyridin-2-yl)piperidin-4-yl)acetonitrile;

2-(4-(4-oxo-3-(4-(2,2,2-trifluoro-1-hydroxyethyl)phenylamino)-4,5-dihydropyrazolo[4,3-c]pyridin-1-yl)-1-(4-(trifluoromethyl)pyridin-2-yl)piperidin-4-yl)acetonitrile;

2-(4-(3-(4-(4,4-difluoropiperidine-1-carbonyl)-3-methylphenylamino)-4-oxo-4,5-dihydropyrazolo[4,3-c]pyridin-1-yl)-1-(4-(trifluoromethyl)pyridin-2-yl)piperidin-4-yl)acetonitrile;

2-(1-(2,2-difluoropropanoyl)-4-(3-((4-(methylsulfonyl)phenyl)amino)-4-oxo-4,5-dihydro-1H-pyrazolo[4,3-c]pyridin-1-yl)piperidin-4-yl)acetonitrile;

2-(4-(3-fluoroazetidin-1-yl)-1-(4-oxo-3-((4-(trifluoromethyl)phenyl)amino)-4,5-dihydro-1H-pyrazolo[4,3-c]pyridin-1-yl)cyclohexyl)acetonitrile;

2-(1-(4-oxo-3-((4-(trifluoromethyl)phenyl)amino)-4,5-dihydro-1H-pyrazolo[4,3-c]pyridin-1-yl)-4-(phenylamino)cyclohexyl)acetonitrile;

2-(4-hydroxy-1-(4-oxo-3-((4-(trifluoromethyl)phenyl)
  amino)-4,5-dihydro-1H-pyrazolo[4,3-c]pyridin-1-yl)cy-
  clohexyl)acetonitrile;
2-(1-(3-((4-chlorophenyl)amino)-4-oxo-4,5-dihydro-1H-
  pyrazolo[4,3-c]pyridin-1-yl)-4-(3-fluoroazetidin-1-yl)cy-
  clohexyl)acetonitrile;
2-(1-(3-((4-chlorophenyl)amino)-4-oxo-4,5-dihydro-1H-
  pyrazolo[4,3-c]pyridin-1-yl)-4-(3-methoxyazetidin-1-yl)
  cyclohexyl)acetonitrile;
2-(1-(3-((4-chlorophenyl)amino)-4-oxo-4,5-dihydro-1H-
  pyrazolo[4,3-c]pyridin-1-yl)-4-((2,2,2-trifluoroethyl)
  amino)cyclohexyl)acetonitrile;
2-(1-(3-((4-chlorophenyl)amino)-4-oxo-4,5-dihydro-1H-
  pyrazolo[4,3-c]pyridin-1-yl)-4-hydroxycyclohexyl)ac-
  etonitrile;
2-(1-(3-((4-chlorophenyl)amino)-4-oxo-4,5-dihydro-1H-
  pyrazolo[4,3-c]pyridin-1-yl)-4-(phenylamino)cyclo-
  hexyl)acetonitrile;
2-(4-(3-methoxyazetidin-1-yl)-1-(4-oxo-3-((4-(trifluo-
  romethoxy)phenyl)amino)-4,5-dihydro-1H-pyrazolo[4,3-
  c]pyridin-1-yl)cyclohexyl)acetonitrile;
2-(1-(4-oxo-3-((4-(trifluoromethoxy)phenyl)amino)-4,5-di-
  hydro-1H-pyrazolo[4,3-c]pyridin-1-yl)-4-(phenylamino)
  cyclohexyl)acetonitrile;
2-(4-(cyclohexylamino)-1-(4-oxo-3-((4-(trifluoromethoxy)
  phenyl)amino)-4,5-dihydro-1H-pyrazolo[4,3-c]pyridin-
  1-yl)cyclohexyl)acetonitrile;
2-(1-(3-((4-chloro-3-fluorophenyl)amino)-4-oxo-4,5-di-
  hydro-1H-pyrazolo[4,3-c]pyridin-1-yl)-4-(cyclohexy-
  lamino)cyclohexyl)acetonitrile;
2-(1-(3-((4-chloro-3-fluorophenyl)amino)-4-oxo-4,5-di-
  hydro-1H-pyrazolo[4,3-c]pyridin-1-yl)-4-(3-
  methoxyazetidin-1-yl)cyclohexyl)acetonitrile;
2-(1-(3-((4-chloro-3-fluorophenyl)amino)-4-oxo-4,5-di-
  hydro-1H-pyrazolo[4,3-c]pyridin-1-yl)-4-(phenylamino)
  cyclohexyl)acetonitrile;
2-(1-(3-((4-((difluoromethyl)sulfonyl)phenyl)amino)-4-
  oxo-4,5-dihydro-1H-pyrazolo[4,3-c]pyridin-1-yl)-4-(3-
  fluoroazetidin-1-yl)cyclohexyl)acetonitrile;
4-((1-(1-(cyanomethyl)-4-(3-fluoroazetidin-1-yl)cyclo-
  hexyl)-4-oxo-4,5-dihydro-1H-pyrazolo[4,3-c]pyridin-3-
  yl)amino)-N,N-dimethylbenzenesulfonamide;
2-(4-(3-fluoroazetidin-1-yl)-1-(3-((2-methyl-1,1-dioxido-2,
  3-dihydrobenzo[d]isothiazol-6-yl)amino)-4-oxo-4,5-di-
  hydro-1H-pyrazolo[4,3-c]pyridin-1-yl)cyclohexyl)ac-
  etonitrile;
2-(4-(dimethylamino)-1-(3-((2-methyl-1,1-dioxido-2,3-di-
  hydrobenzo-[d]isothiazol-6-yl)amino)-4-oxo-4,5-di-
  hydro-1H-pyrazolo[4,3-c]pyridin-1-yl)cyclohexyl)ac-
  etonitrile;
2-(4-(3-fluoroazetidin-1-yl)-1-(3-((2-methyl-1,1-dioxido-2,
  3-dihy-drobenzo[d]isothiazol-6-yl)amino)-4-oxo-4,5-di-
  hydro-1H-pyrazolo[4,3-c]pyridin-1-yl)cyclohexyl)ac-
  etonitrile;
2-(1-(3-((2-(tert-butyl)-1, 1-dioxido-2,3-dihydrobenzo[d]
  isothiazol-5-yl)amino)-4-oxo-4,5-dihydro-1H-pyrazolo
  [4,3-c]pyridin-1-yl)-4-(dimethylamino)cyclohexyl)ac-
  etonitrile;
4-((1-(1-(cyanomethyl)-4-oxocyclohexyl)-4-oxo-4,5-di-
  hydro-1H-pyrazolo[4,3-c]pyridin-3-yl)amino)-N,N-dim-
  ethylbenzenesulfonamide;
N-(tert-butyl)-5-(3-((2-(tert-butyl)-1,1-dioxido-2,3-dihyd-
  robenzo[d]isothiazol-5-yl)amino)-4-oxo-4,5-dihydro-1H-
  pyrazolo[4,3-c]pyridin-1-yl)-5-(cyanomethyl)tetrahydro-
  2H-pyran-2-carboxamide;
N-tert-butyl-5-{3-[(2-tert-butyl-1,1-dioxido-2,3-dihydro-1,
  2-benzisothiazol-5-yl)amino]-4-oxo-4,5-dihydro-1H-
  pyrazolo[4,3-c]pyridin-1-yl}-5-(cyanomethyl)-N-methyl-
  tetrahydro-2H-pyran-2-carboxamide;
isopropyl 5-(3-((2-(tert-butyl)-1,1-dioxido-2,3-dihyd-
  robenzo[d]isothiazol-5-yl)amino)-4-oxo-4,5-dihydro-1H-
  pyrazolo[4,3-c]pyridin-1-yl)-5-(cyanomethyl)tetrahydro-
  2H-pyran-2-carboxylate;
2-(3-(3-((4-(4,4-difluoropiperidine-1-carbonyl)-3-methyl-
  phenyl)amino)-4-oxo-4,5-dihydro-1H-pyrazolo[4,3-c]
  pyridin-1-yl)tetrahydro-2H-pyran-3-yl)acetonitrile;
2-(3-(3-((3-methyl-4-(2-methylpiperidine-1-carbonyl)phe-
  nyl)amino)-4-oxo-4,5-dihydro-1H-pyrazolo[4,3-c]pyri-
  din-1-yl)tetrahydro-2H-pyran-3-yl)acetonitrile;
2-(3-(3-((3-methyl-4-(2-methylpiperidine-1-carbonyl)phe-
  nyl)amino)-4-oxo-4,5-dihydro-1H-pyrazolo[4,3-c]pyri-
  din-1-yl)tetrahydro-2H-pyran-3-yl)acetonitrile;
2-(3-(3-((4-(4-hydroxy-4-methylpiperidine-1-carbonyl)-3-
  methylphenyl)amino)-4-oxo-4,5-dihydro-1H-pyrazolo[4,
  3-c]pyridin-1-yl)tetrahydro-2H-pyran-3-yl)acetonitrile;
tert-butyl 5-(cyanomethyl)-5-(3-((3-methyl-4-(morpholine-
  4-carbonyl)phenyl)amino)-4-oxo-4,5-dihydro-1H-pyra-
  zolo[4,3-c]pyridin-1-yl)tetrahydro-2H-pyran-2-carboxy-
  late;
tert-butyl 5-(cyanomethyl)-5-(3-((3-methyl-4-(thiomorpho-
  line-4-carbonyl)phenyl)amino)-4-oxo-4,5-dihydro-1H-
  pyrazolo[4,3-c]pyridin-1-yl)tetrahydro-2H-pyran-2-car-
  boxylate;
tert-butyl 5-(cyanomethyl)-5-(3-((3-methyl-4-(pyrrolidine-
  1-carbonyl)phenyl)amino)-4-oxo-4,5-dihydro-1H-pyra-
  zolo[4,3-c]pyridin-1-yl)tetrahydro-2H-pyran-2-carboxy-
  late;
tert-butyl 5-(cyanomethyl)-5-(3-((3-methyl-4-(3-methyl-
  morpholine-4-carbonyl)phenyl)amino)-4-oxo-4,5-di-
  hydro-1H-pyrazolo[4,3-c]pyridin-1-yl)tetrahydro-2H-
  pyran-2-carboxylate;
tert-butyl 5-(cyanomethyl)-5-(3-((3-methyl-4-(2-methyl-
  morpholine-4-carbonyl)phenyl)amino)-4-oxo-4,5-di-
  hydro-1H-pyrazolo[4,3-c]pyridin-1-yl)tetrahydro-2H-
  pyran-2-carboxylate;
tert-butyl 5-(cyanomethyl)-5-(3-((4-(2,6-dimethylmorpho-
  line-4-carbonyl)-3-methylphenyl)amino)-4-oxo-4,5-di-
  hydro-1H-pyrazolo[4,3-c]pyridin-1-yl)tetrahydro-2H-
  pyran-2-carboxylate;
tert-butyl 5-(cyanomethyl)-5-(3-((4-(ethyl(2,2,2-trifluoro-
  ethyl)carbamoyl)-3-methylphenyl)amino)-4-oxo-4,5-di-
  hydro-1H-pyrazolo[4,3-c]pyridin-1-yl)tetrahydro-2H-
  pyran-2-carboxylate;
tert-butyl 5-(cyanomethyl)-5-(3-((3-methyl-4-(methyl(2,2,
  2-trifluoroethyl)carbamoyl)phenyl)amino)-4-oxo-4,5-di-
  hydro-1H-pyrazolo[4,3-c]pyridin-1-yl)tetrahydro-2H-
  pyran-2-carboxylate;
tert-butyl 5-(3-((4-(2-oxa-5-azabicyclo[2.2.1]heptane-5-car-
  bonyl)-3-methylphenyl)amino)-4-oxo-4,5-dihydro-1H-
  pyrazolo[4,3-c]pyridin-1-yl)-5-(cyanomethyl)tetrahydro-
  2H-pyran-2-carboxylate;
tert-butyl 5-(cyanomethyl)-5-(3-((2-methylbenzo[d]thiazol-
  6-yl)amino)-4-oxo-4,5-dihydro-1H-pyrazolo[4,3-c]pyri-
  din-1-yl)tetrahydro-2H-pyran-2-carboxylate;
[1-{3-[(3,3-dimethyl-2-oxo-2,3-dihydro-1H-indol-6-yl)
  amino]-4-oxo-4,5-dihydro-1H-pyrazolo[4,3-c]pyridin-1-
  yl}-2-fluorocyclohexyl]acetonitrile;
(tert-butyl 5-(cyanomethyl)-5-(3-((3,3-dimethyl-2-oxoindo-
  lin-6-yl)amino)-4-oxo-4,5-dihydro-1H-pyrazolo[4,3-c]
  pyridin-1-yl)tetrahydro-2H- pyran-2-carboxylate;
[3-{3-[(3,3-dimethyl-2-oxo-2,3-dihydro-1H-indol-6-yl)
  amino]-4-oxo-4,5-dihydro-1H-pyrazolo[4,3-c]pyridin-1-
  yl}tetrahydro-2H-pyran-3-yl]acetonitrile;

[3-{3-[(2-methyl-1,3-benzothiazol-6-yl)amino]-4-oxo-4,5-dihydro-1H-pyrazolo[4,3-c]pyridin-1-yl}tetrahydro-2H-pyran-3-yl]acetonitrile;
tert-butyl 5-(cyanomethyl)-5-(3-((2-fluoropyridin-4-yl)amino)-4-oxo-4,5-dihydro-1H-pyrazolo[4,3-c]pyridin-1-yl)tetrahydro-2H-pyran-2-carboxylate;
tert-butyl 5-(cyanomethyl)-5-(4-oxo-3-((4-(2,2,2-trifluoro-1-methoxyethyl)phenyl)amino)-4,5-dihydro-1H-pyrazolo[4,3-c]pyridin-1-yl)tetrahydro-2H-pyran-2-carboxylate;
tert-butyl 5-(cyanomethyl)-5-(4-oxo-3-((4-(2,2,2-trifluoro-1-methoxyethyl)phenyl)amino)-4,5-dihydro-1H-pyrazolo[4,3-c]pyridin-1-yl)tetrahydro-2H-pyran-2-carboxylate;
tert-butyl 4-(cyanomethyl)-4-(3-((4-(4,4-difluoropiperidine-1-carbonyl)-3-methylphenyl)amino)-4-oxo-4,5-dihydro-1H-pyrazolo[4,3-c]pyridin-1-yl)piperidine-1-carboxylate;
tert-butyl-4-(3-((4-(8-oxa-3-azabicyclo[3.2.1]octane-3-carbonyl)-3-methylphenyl)amino)-4-oxo-4,5-dihydro-1H-pyrazolo[4,3-c]pyridin-1-yl)-4-(cyanomethyl)piperidine-1-carboxylate;
tert-butyl 4-(cyanomethyl)-4-{3-[(5-methyl-4-{3-oxa-8-azabicyclo[3.2.1]octan-8-ylcarbonyl}cyclohexa-1,3,5-trien-1-yl)amino]-4-oxo-5H-pyrazolo[4,3-c]pyridin-1-yl}piperidine-1-carboxylate;
tert-butyl-4-(cyanomethyl)-4-(3-(3-methyl-4-(thiomorpholine-4-carbonyl)phenylamino)-4-oxo-4,5-dihydropyrazolo[4,3-c]pyridin-1-yl)piperidine-1-carboxylate;
tert-butyl-4-(cyanomethyl)-4-(3-((1,1-dioxido-2-(1-(2,2,2-trifluoroethyl)piperidin-4-yl)-2,3-dihydrobenzo[d]isothiazol-5-yl)amino)-4-oxo-4,5-dihydro-1H-pyrazolo[4,3-c]pyridin-1-yl)piperidine-1-carboxylate;
tert-butyl 4-(cyanomethyl)-4-(4-oxo-3-(4-(2-(trifluoromethyl)piperidin-2-yl)phenylamino)-4,5-dihydropyrazolo[4,3-c]pyridin-1-yl)piperidine-1-carboxylate;
tert-butyl 4-(cyanomethyl)-4-(4-oxo-3-(4-(2-(trifluoromethyl)pyrrolidin-2-yl)phenylamino)-4,5-dihydropyrazolo[4,3-c]pyridin-1-yl)piperidine-1-carboxylate;
tert-butyl 4-(cyanomethyl)-4-(3-(3-methyl-4-(morpholine-4-carbonyl)phenylamino)-4-oxo-4,5-dihydropyrazolo[4,3-c]pyridin-1-yl)piperidine-1-carboxylate;
5-(3-((4-chlorophenyl)amino)-4-oxo-4,5-dihydro-1H-pyrazolo[4,3-c]pyridin-1-yl)-5-(cyanomethyl)-N-(methylsulfonyl)tetrahydro-2H-pyran-2-carboxamide;
5-(3-((4-chlorophenyl)amino)-4-oxo-4,5-dihydro-1H-pyrazolo[4,3-c]pyridin-1-yl)-5-(cyanomethyl)-N,N-dimethyltetrahydro-2H-pyran-2-carboxamide; and
2-(3-(3-((4-chlorophenyl)amino)-4-oxo-4,5-dihydro-1H-pyrazolo[4,3-c]pyridin-1-yl)-6-(2-hydroxypropan-2-yl)tetrahydro-2H-pyran-3-yl)acetonitrile.

The invention also encompasses pharmaceutical compositions containing a compound of Formula I, and methods for treatment or prevention of JAK mediated diseases using compounds of Formula I.

The invention is described using the following definitions unless otherwise indicated.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or $CH_3$, ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-6}$ alkyl" (or "$C_1$-$C_6$ alkyl") for example, means linear or branched chain alkyl groups, including all isomers, having the specified number of carbon atoms. $C_{1-6}$ alkyl includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl.

The term "alkylene" refers to both branched- and straight-chain saturated aliphatic hydrocarbon groups, including all isomers, having the specified number of carbons, and having two terminal end chain attachments. For illustration, the term "unsubstituted A-$C_4$alkylene-B" represents A-$CH_2$—$CH_2$—$CH_2$—$CH_2$—B.

The term "alkoxy" represents a linear or branched alkyl group of indicated number of carbon atoms attached through an oxygen bridge.

"Acyl" means a —C(O)R radical where R is optionally substituted alkyl, alkenyl, cycloalkyl, heterocycloalkyl, aryl heteroaryl, etc.

"Acylamino" means a —NRR' radical where R is H, OH, or alkoxy and R' is acyl, as defined herein.

The term "alkyl" refers to an aliphatic hydrocarbon group which may be straight or branched and having the indicated number of carbon atoms. Non-limiting examples of alkyl groups include methyl, ethyl, propyl, isopropyl, butyl, s- and t-butyl, pentyl, hexyl, and the like.

The term "heteroalkyl" refers to an alkyl group where 1, 2, or 3 of the carbon atoms is substituted by a heteroatom independently chosen from N, O, or S.

"Alkenyl" refers to an aliphatic hydrocarbon group containing at least one carbon-carbon double bond and which may be straight or branched and having the indicated number of carbon atoms. Preferably alkenyl contains one carbon to carbon double bond, and up to four nonaromatic carbon-carbon double bonds may be present. Examples of alkenyl groups include ethenyl, propenyl, n-butenyl, 2-methyl-1-butenyl, 3-methylbut-2-enyl, n-pentenyl, octenyl and decenyl.

"Alkynyl" refers to an aliphatic hydrocarbon group containing at least one carbon-carbon triple bond and which may be straight or branched and having the indicated number of carbon atoms. Non-limiting examples of suitable alkynyl groups include ethynyl, propynyl, 2-butynyl and 3-methylbutynyl.

"Alkoxy" refers to an alkyl-O— group in which the alkyl group is as described above. $C_{1-6}$alkoxy, for example, includes methoxy, ethoxy, propoxy, isopropoxy, and the like.

"Alkoxyalkyl" refers to an alkyl group as described above in which one or more (in particular 1 to 3) hydrogen atoms have been replaced by alkoxy groups. Examples include $CH_2OCH_3$, $CH_2CH_2OCH_3$ and $CH(OCH_3)CH_3$.

"Aminoalkyl" refers to an alkyl group as described above in which one hydrogen atom has been replaced by an amino, monoalkylamino or dialkylamino group. Examples include $CH_2NH_2$, $CH_2CH_2NHCH_3$ and $CH(N(CH_3)_2)CH_3$.

The term "$C_0$" as employed in expressions such as "$C_{0-6}$ alkyl" means a direct covalent bond; or when the term appears at the terminus of a substituent, $C_{0-6}$ alkyl means hydrogen or $C_{1-6}$alkyl. Similarly, when an integer defining the presence of a certain number of atoms in a group is equal to zero, it means that the atoms adjacent thereto are connected directly by a bond. For example, in the structure

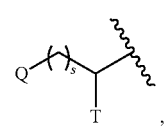

wherein s is an integer equal to zero, 1 or 2, the structure is

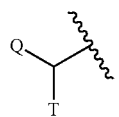

when s is zero.

The term "$C_{3-8}$ cycloalkyl" (or "$C_3$-$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The terms "$C_{3-7}$ cycloalkyl", "$C_{3-6}$ cycloalkyl", "$C_{5-7}$ cycloalkyl" and the like have analogous meanings.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and poly-carbocyclic ring systems, wherein the individual carbocyclic rings in the polyring systems are fused or attached to each other via a single bond. Suitable aryl groups include phenyl, naphthyl, 2,3-dihydro-1H-indenyl, and biphenyl.

The term "carbocycle" (and variations thereof such as "carbocyclic" or "carbocyclyl") as used herein, unless otherwise indicated, refers to (i) a $C_3$ to $C_8$ monocyclic, saturated or unsaturated ring or (ii) a $C_7$ to $C_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a $C_7$ to $C_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. Unless otherwise noted, carbocycle is unsubstituted or substituted with $C_{1-6}$ alkyl, $C_{1-6}$ alkenyl, $C_{1-6}$ alkynyl, aryl, halogen, $NH_2$ or OH. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

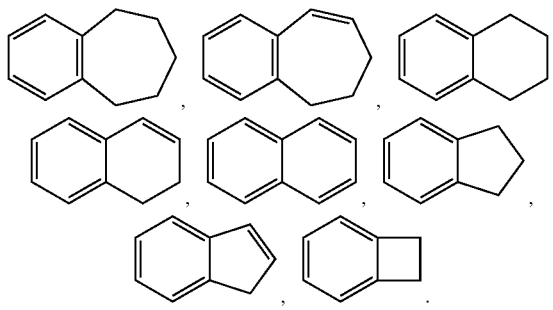

"Cyanoalkyl" refers to an alkyl group as described above in which one hydrogen atom has been replaced by a cyano group. Examples include $CH_2CN$, $CH_2CH_2CN$ and $CH(CN)CH_3$.

"Cycloalkyl" means a carbocyclic ring system having 3 to 12 ring carbon atoms; said ring system may be (a) a monocyclic saturated carbocycle optionally fused to a benzene or a partially unsaturated carbocycle, or (b) a bicyclic saturated carbocycle. For a bicyclic system, within either (a) or (b), the rings are fused across two adjacent ring carbon atoms (e.g., decalin), at one ring carbon atom (e.g., spiro[2.2]pentane), or are bridged groups (e.g., norbornane). Additional examples within the above meaning include, but are not limited to, cyclopropane, cyclobutane, cyclopentane, cyclohexane, perhydroindan, decalin, spiro[4.5]decane, bicyclo[2.2.2]octane, and the like.

"Haloalkyl" refers to an alkyl group as described above wherein one or more (in particular 1 to 5) hydrogen atoms have been replaced by halogen atoms, with up to complete substitution of all hydrogen atoms with halo groups. $C_{1-6}$ haloalkyl, for example, includes $-CF_3$, $-CF_2CF_3$, $CHFCH_3$, and the like.

"Heterocycle", "heterocyclic" or "heterocyclyl" represents a monocyclic or bicyclic 3-12 membered ring system in which at least one ring is non-aromatic (saturated or partially unsaturated) and containing at least one heteroatom selected from O, S and N. In a bicyclic ring system, the second ring may be a heteroaryl, heterocycle or a saturated, partially unsaturated or aromatic carbocycle, and the point(s) of attachment to the rest of the molecule may be on either ring. For a bicyclic system, the rings may be fused across two adjacent ring atoms (e.g., quinoline), at one ring carbon atom (e.g., 1,4-dioxaspiro[4.5]decane), or are bridged groups (e.g. 8-azabicyclo[3.2.1]octanyl,). "Heterocyclyl" therefore includes heteroaryls, as well as dihydro and tetrahydro analogs thereof. Attachment of a heterocyclyl substituent can occur via a carbon atom or via a heteroatom.

Examples of heterocycles (heterocyclyl) include, but are not limited to, azetidinyl, pyrrolidinyl, piperidinyl, piperazinyl, morpholinyl, thiamorpholinyl, tetrahydrofuranyl, dihydrofuranyl, tetrahydrothienyl, tetrahydropyranyl, dihydropyranyl, dihydroimidazolyl, dihydroindolyl, 1,2,3,4-tetrahydroisoquinolinyl, 5,6,7,8-tetrahydroimidazo[1,2-a]pyrazine, 2,3-dihydrobenzofuranyl, benzo-1,4-dioxanyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridinyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

Saturated heterocyclics form a subset of the heterocycles; i.e., the terms "saturated heterocyclic and $(C_{3-12})$heterocycloalkyl" generally refers to a heterocycle as defined above in which the entire ring system (whether mono- or polycyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. For a bicyclic heteroaryl only one of the rings need to be heteroaromatic, the second ring may be a heteroaromatic or an aromatic, saturated, or partially unsatuated carbocycle, and the point(s) of attachment to the rest of the molecule may be on either ring. In the case of substituted heteroaryl rings containing at least one nitrogen atom (e.g., pyridine), such substitutions can be those resulting in N-oxide formation. Examples of heteroaryl include, but are not limited to, furanyl, thienyl (or thiophenyl), pyrrolyl, imidazolyl, pyrazolyl, oxazolyl, thiazolyl, isoxazolyl, isothiazolyl, triazolyl, oxadiazolyl, thiadiazolyl, tetrazolyl, pyridyl, pyrimidinyl, pyrazinyl, pyridazinyl, triazinyl, quinolinyl, isoquinolinyl, naphthyridinyl, benzothienyl, benzofuranyl, benzimidazole, benzpyrazolyl, indolyl, isoindolyl, indolizinyl, indazolyl, purinyl, quinolizinyl, phthalazinyl, quinoxalinyl, quinazolinyl, benzoxazolyl, benzisoxazolyl, 5,6,7,8-tetrahydroquinolinyl, imidazo[1,2-a]pyridinyl, imidazo[1,2-a]-pyrimidinyl, 5,6-dihydropyrrolo[1,2-b]pyrazolyl, pyrrolo[3,2-c]pyridinyl, pyrrolo[2,3-b]pyridinyl, thieno[2,3-b]pyrrolyl, furopyridine and thienopyridine.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

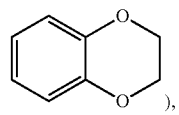

), imidazo(2,1-b)(1,3)thiazole, (i.e.,

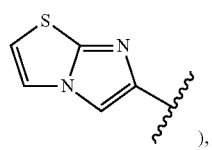 [SMILES: *c1cn2ccsc2n1]

), and benzo-1,3-dioxolyl (i.e.,

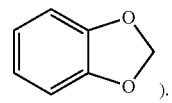

).

In certain contexts herein,

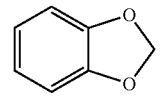

is alternatively referred to as phenyl having as a substituent methylenedioxy attached to two adjacent carbon atoms.

Non-limiting examples of substituted heteroaryls include: isoindolinone, isoindolin-1-one, 2,3-dihydro-1H-pyrazolo[4,3-c]pyridin-4(5H)-one, 2,3,4,5-tetrahydrobenzo[d]isothiazole 1,1-dioxide, and 2,3,4,5-tetrahydrobenzo[b]thiophene 1,1-dioxide.

"Hydroxyalkyl" refers to an alkyl group as described above in which one or more (in particular 1 to 3) hydrogen atoms have been replaced by hydroxy groups. Examples include $CH_2OH$, $CH_2CHOH$ and $CHOHCH_3$.

"Alkylene," "alkenylene," "alkynylene," "cycloalkylene," "arylene," "heteroarylene," and "heterocyclylene" refer to a divalent radical obtained by the removal of one hydrogen atom from an alkyl, alkenyl, alkynyl, cycloalkyl, aryl, heteroaryl, and heterocyclyl group, respectively, each of which is as defined above.

Unless expressly stated to the contrary, an "unsaturated" ring is a partially or fully unsaturated ring. For example, an "unsaturated monocyclic $C_6$ carbocycle" refers to cyclohexene, cyclohexadiene, and benzene.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "sulfamoyl" is a suffix to denote radicals derived from sulfamide such as —$SO_2NH_2$, —$SO_2NHR$ and —$SO_2N(RR^1)$.

The term "sulfonimidoyl" is a suffix to denote the radical

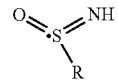

where R is $C_{(1-10)}$ alkyl, aryl, heteroaryl, cycloalkyl, heterocycloalkyl and the like, such as for example methyl, ethyl, isopropy and propyl.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

The term "oxy" means an oxygen (O) atom. The term "thio" means a sulfur (S) atom. The term "oxo" means "=O". The term "carbonyl" means "C=O."

When any variable (e.g., $R^2$, $R^3$, etc.) occurs more than one time in any substituent or in Formula I its definition in each occurrence is independent of its definition at every other occurrence. Also, combinations of substituents and/or variables are permissible only if such combinations result in stable compounds.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to

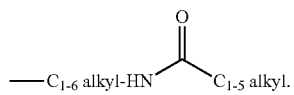

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

Structural representations of compounds having substituents terminating with a methyl group may display the terminal methyl group either using the characters "CH₃", e.g. "—CH₃" or using a straight line representing the presence of the methyl group, e.g. "—", i.e.,

and

have equivalent meanings.

For variable definitions containing terms having repeated terms, e.g., $(CR^iR^j)_r$, where r is the integer 2, $R^i$ is a defined variable, and $R^j$ is a defined variable, the value of $R^i$ may differ in each instance in which it occurs, and the value of $R^j$ may differ in each instance in which it occurs. For example, if $R^i$ and $R^j$ are independently selected from the group consisting of methyl, ethyl, propyl and butyl, then $(CR^iR^j)_2$ can be

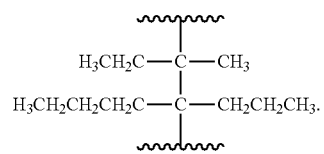

"Patient" includes both human and animals.

"Mammal" means humans and other mammalian animals.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, and pharmaceutically acceptable excipients.

The term "optionally substituted" means "unsubstituted or substituted," and therefore, the generic structural formulas described herein encompasses compounds containing the specified optional substituent as well as compounds that do not contain the optional substituent.

Each variable is independently defined each time it occurs within the generic structural formula definitions. For example, when there is more than one substituent for aryl/heteroaryl, each substituent is independently selected at each occurrence, and each substituent can be the same or different from the other(s). As another example, for the group $—(CR^3R^3)_2—$, each occurrence of the two $R^3$ groups may be the same or different. As used herein, unless explicitly stated to the contrary, each reference to a specific compound of the present invention or a generic formula of compounds of the present invention is intended to include the compound(s) as well as pharmaceutically acceptable salts thereof.

In one embodiment of the invention, A is selected from phenyl, methyl, ethyl, pyridinyl, cyclobutyl, cyclopropyl, cyclopropylmethyl, dihydroisoindolyl, dihydrobenzisothiazolyl, dihydroindenyl, isoindolyl, dihydro[b]thiophenyl, 2,3-dihydrobenzo[d]isothiazole-1,1-dioxide 1-oxo-2,3-dihydro-1H-indene and 1,1-dioxido-2,3-dihydrobenzo[b]thiophene.

In one embodiment of the invention, A is selected from: phenyl, methyl, ethyl, cyclopropylmethyl, cyclopropyl, cyclobutyl, isoindolinyl, benzo[d]thiazolyl,

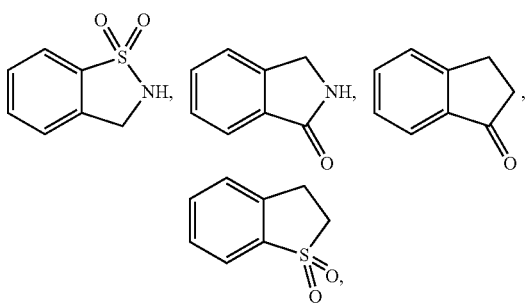

2,3-dihydro-1H-indenyl, quinolinyl, pyridinyl, and indolinyl.

In a variant of this embodiment, A is selected from: methyl, ethyl, cyclopropylmethyl, cyclopropyl, and cyclobutyl, In another variant, A is selected from isoindolinyl, benzo[d]thiazolyl,

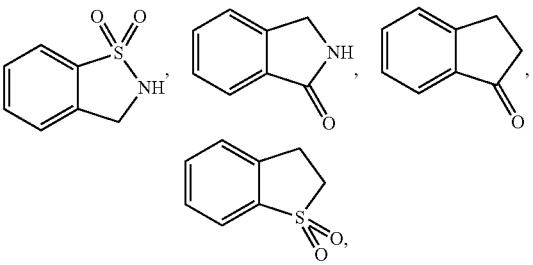

2,3-dihydro-1H-indenyl, quinolinyl, pyridinyl, and indolinyl.

In an embodiment of the invention, $R^2$ and $R^3$ are each independently selected from hydrogen, methyl, ethyl, propyl and hydroxyl. In a variant of this embodiment, $R^2$ and $R^3$ are each a hydrogen.

In another embodiment, $R^2$ and $R^3$ join together with the carbon they are attached to form a 3 to 6 membered ring.

In one embodiment of the invention,

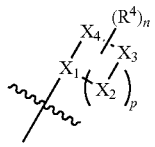

of formula I, where p is 0, 1, 2, 3, or 4; n is 0, 1, 2, 3, or 4; and two R4 together with the ring atom to which each is attached optionally may form a saturated ring, is selected from: piperidinyl, azetidinyl, tetrahydropyranyl, tetrahydro-2H-pyranyl, cyclohexyl, cyclopentyl, tetrahydrofuranyl, and 1,4-dioxaspiro[4.5]decanyl In another embodiment,

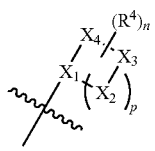

of formula I, where p is 0, 1, 2, 3, or 4; n is 0, 1, 2, 3, or 4 is selected from cyclohexyl, piperidinyl, tetrahydropyranyl, cyclopentyl, tetrahydrofuranyl, and azetidinyl.

In one embodiment of the invention, n is 0, 1, 2, 3, or 4. In one embodiment of the invention, n is 0, 1, 2, or 3. In a variant of this embodiment, n is 0, 1, or 2.

In one embodiment of the invention, m is 0, 1, 2, 3 or 4. In one embodiment of the invention, m is 0, 1, 2, or 3. In a variant of this embodiment, m is 0, 1, or 2.

In one embodiment of the invention, p is 1, 2, 3 or 4.

In one embodiment of the invention, p is 0, 1, 2, or 3. In a variant of this embodiment, p is 1, 2, or 3.

In one embodiment of the invention, $R^4$ is selected from: halogen, oxo (=O), $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, $C_{3-12}$ cycloalkyl $C_{0-10}$ alkyl(oxy)$_{0-1}$(carbonyl)$_{0-1}C_{0-10}$ alkyl, heteroaryl $C_{0-10}$ alkyl(oxy)$_{0-1}$(carbonyl)$_{0-1}C_{0-10}$ alkyl, $(C_{3-12})$heterocycloalkyl $C_{0-10}$ alkyl(oxy)$_{0-1}$(carbonyl)$_{0-1}C_{0-10}$ alkyl, $C_{0-10}$ alkyl(oxy)$_{0-1}$(carbonyl)$_{0-1}$ amino$C_{0-10}$ alkyl, $C_{1-10}$ alkylamino(carbonyl)$_{0-1}C_{0-10}$alkyl, $(C_{1-10})$heteroalkyl(oxy)$_{0-1}$(carbonyl)$_{0-1}$ amino $C_{0-10}$ alkyl, $(C_{1-10})$heteroalkylamino(carbonyl)$_{0-1}C_{0-10}$alkyl, $C_{3-12}$ cycloalkyl $C_{0-10}$ alkylamino$C_{0-10}$ alkyl, aryl $C_{0-10}$ alkylamino$C_{0-10}$ alkyl, heteroaryl $C_{0-10}$ alkylamino$C_{0-10}$ alkyl, $(C_{3-12})$heterocycloalkyl $C_{0-10}$ alkylamino$C_{0-10}$ alkyl, $C_{0-10}$ alkylsulfonyl, $(C_{3-12})$cycloalkyl$C_{0-10}$alkylsulfonyl, $(C_{3-12})$cycloheteroalkyl$C_{0-10}$alkylsulfonyl, —SO$_2$NH$_2$, —SO$_2$NH($C_{1-6}$alkyl), —SO$_2$N($C_{1-6}$alkyl)$_2$, $C_{0-10}$ alkylsulfonimidoyl$C_{0-10}$ alkyl, $C_{1-10}$ heteroalkylsulfonimidoyl$C_{0-10}$ alkyl, $(C_{1-10}$ alkyl)$_{1-2}$amino, —CO$_2$(C$_{0-10}$ alkyl), —SO$_2$CF$_3$, —SO$_2$CF$_2$H, —SO$_2$CH$_2$CF$_3$, hydroxy, —($C_{1-10}$ alkyl)OH, $C_{1-10}$ alkoxy$C_{0-10}$ alkyl, cyano, ($C_{1-6}$alkyl)cyano, and $C_{1-6}$haloalkyl, wherein $R^4$ is optionally substituted with 0, 1, 2, 3, or 4 $R^6$ substituents, and two $R^4$ together with the ring atom to which each is attached optionally may form a saturated ring.

In a variant of this embodiment, $R^4$ is selected from: halogen, oxo (=O), $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, aryl $C_{0-10}$ alkyl(oxy)$_{0-1}$(carbonyl)$_{0-1}C_{0-10}$ alkyl, $C_{3-12}$ cycloalkyl $C_{0-10}$ alkyl(oxy)$_{0-1}$(carbonyl)$_{0-1}C_{0-10}$ alkyl, heteroaryl $C_{0-10}$ alkyl(oxy)$_{0-1}$(carbonyl)$_{0-1}C_{0-10}$ alkyl, $(C_{3-12})$heterocycloalkyl $C_{0-10}$ alkyl(oxy)$_{0-1}$(carbonyl)$_{0-1}C_{0-10}$ alkyl, $C_{0-10}$ alkyl(oxy)$_{0-1}$(carbonyl)$_{0-1}$ amino$C_{0-10}$ alkyl, $C_{1-10}$ alkylamino(carbonyl)$_{0-1}C_{0-10}$alkyl, $C_{3-12}$ cycloalkyl $C_{0-10}$ alkylamino$C_{0-10}$ alkyl, aryl $C_{0-10}$ alkylamino$C_{0-10}$ alkyl, $C_{0-10}$ alkylsulfonyl, $(C_{3-12})$cycloalkyl$C_{0-10}$alkylsulfonyl, $(C_{0-10}$ alkyl) 1-2amino, —SO$_2$CH$_2$CF$_3$, hydroxy, —($C_{1-10}$ alkyl)OH, $C_{1-10}$ alkoxy$C_{0-10}$ alkyl, and $C_{1-6}$haloalkyl, wherein $R^4$ is optionally substituted with 0, 1, 2, 3, or 4 $R^6$ substituents, and two $R^4$ together with the ring atom to which each is attached optionally may form a saturated ring.

In a variant of this embodiment, $R^4$ is selected from tert-butylcarbonyl, methoxycarbonyl, methylcarbonyl, cyclopropylmethyl, cyclopropylmethylcarbonyl, cyclopropylethylcarbonyl, cyclopropylcarbonyl, cyclobutylcarbonyl, cyclopentyloxycarbonyl, isopropyloxycarbonyl, phenylmethyl, phenylpropyl, phenylmethylcarbonyl, phenylethylcarbonyl, phenyloxycarbonyl, phenylcarbonyl, oxazolylmethyl, 1,3-oxazolylmethyl, indolylmethyl, 1-phenylethyl, pyridinylmethyl, cyclohexylcarbonyl, fluoro, 2,2,2-trifluoroethyl, ethyl, 2-hydoxyethyl, neopentylcarbonyl, neopentyloxycarbonyl, ethylcarbonyl, ethyloxycarbonyl, methoxymethylcarbonyl (methylamino)methylcarbonyl, 2,3-dihydro-1H-indenylcarbonyl, pyrrolidinylmethylcarbonyl, tetrahydro-2H-pyranylcarbonyl, tetrahydro-2H-thiopyranyloxycarbonyl, tetrahydro-2H-pyranyloxycarbonyl, 1-(pyridinyl)ethyloxycarbonyl, adamantylcarbonyl, tetrahydrofuranyloxycarbonyl, trifluoroethylsulfonyl, dimethylamino, tert-butyloxycarbonyl, methyl, tert-butylaminocarbonyl, aminocarbonyl, azetidinyl, cyclohexylamino, oxo, hydroxy, methylaminocarbonyl, cyclopropylsulfonyl, methoxy, phenylamino, pyridinyl, hydroxyisopropyl, hydroxyeth-2-yl, trifluoromethyl, 2-(methylthio)eth-2-ylcarbonyl, methylsulfonyl, ethylcarbonyl, methylamino, isopropyloxycarbonyl, and hydroxyisopropyl; wherein $R^4$ is optionally substituted with 0, 1, 2, 3, or 4 $R^6$ substituents, and wherein two $R^4$ together with the ring atom to which each is attached optionally may form a saturated ring.

In one embodiment, $R^5$ is selected from: halogen, oxo (=O), $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, aryl $C_{0-10}$ alkyl (oxy)$_{0-1}$(carbonyl)$_{0-1}C_{0-10}$ alkyl, $C_{3-12}$ cycloalkyl $C_{0-10}$ alkyl (oxy)$_{0-1}$(carbonyl)$_{0-1}C_{0-10}$ alkyl, heteroaryl $C_{0-10}$ alkyl (oxy)$_{0-1}$(carbonyl)$_{0-1}C_{0-10}$ alkyl, $(C_{3-12})$heterocycloalkyl $C_{0-10}$ alkyl(oxy)$_{0-1}$(carbonyl)$_{0-1}C_{0-10}$ alkyl, $C_{0-10}$ alkylaminocarbonyl$C_{0-10}$alkyl, $C_{0-10}$ alkyl(oxy)$_{0-1}$(carbonyl)$_{0-1}$amino$C_{0-10}$ alkyl, $(C_{1-10})$heteroalkyl(oxy)$_{0-1}$(carbonyl)$_{0-1}$amino$C_{0-10}$ alkyl, —$SF_5$, $C_{0-10}$ alkylsulfonyl, $C_{1-10}$ heteroalkylsulfonyl, $(C_{3-12})$cycloalkyl$C_{0-10}$alkylsulfonyl, $(C_{3-12})$cycloheteroalkyl$C_{0-10}$alkylsulfonyl, $C_{0-10}$ alkylsulfamoyl, $(C_{3-12})$cycloalkyl$C_{0-10}$ alkylsulfamoyl, $(C_{3-12})$cycloheteroalkyl$C_{0-10}$ alkylsulfamoyl, heteroaryl$C_{0-10}$ alkylsulfamoyl, $C_{0-10}$ alkylsulfonimidoyl$C_{0-10}$ alkyl, $C_{1-10}$ heteroalkylsulfonimidoyl$C_{0-10}$ alkyl, —$SO_2NH_2$, —$SO_2NH(C_{1-6}alkyl)$, —$SO_2N(C_{1-6}alkyl)_2$, aryl$C_{0-10}$ alkylsulfamoyl, $(C_{1-10}$ alkyl)$_{1-2}$amino, —$SO_2CF_3$, —$SO_2CF_2H$, —$SO_2CH_2CF_3$, hydroxy, —$(C_{1-10}$ alkyl)OH, $C_{1-10}$ alkoxy$C_{0-10}$ alkyl, cyano, $(C_{1-6}alkyl)$cyano, and $C_{1-6}$haloalkyl; wherein $R^5$ is optionally substituted with 0, 1, 2, 3, or 4 $R^6$ substituents.

In another embodiment, $R^5$ is selected from: halogen, oxo (=O), $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, aryl $C_{0-10}$ alkyl (oxy)$_{0-1}$(carbonyl)$_{0-1}C_{0-10}$ alkyl, $C_{3-12}$ cycloalkyl $C_{0-10}$ alkyl (oxy)$_{0-1}$(carbonyl)$_{0-1}C_{0-10}$ alkyl, heteroaryl $C_{0-10}$ alkyl (oxy)$_{0-1}$(carbonyl)$_{0-1}C_{0-10}$ alkyl, $(C_{3-12})$heterocycloalkyl $C_{0-10}$ alkyl(oxy)$_{0-1}$(carbonyl)$_{0-1}C_{0-10}$ alkyl, $C_{0-10}$ alkylaminocarbonyl$C_{0-10}$alkyl, $C_{0-10}$ alkyl(oxy)$_{0-1}$(carbonyl)$_{0-1}$ amino $C_{0-10}$ alkyl, $(C_{1-10})$heteroalkyl(oxy)$_{0-1}$(carbonyl)$_{0-1}$ amino$C_{0-10}$ alkyl, —$SF_5$, $C_{0-10}$ alkylsulfonyl, $C_{1-10}$ heteroalkylsulfonyl, $(C_{3-12})$cycloalkyl$C_{0-10}$ alkylsulfonyl, $(C_{3-12})$cycloheteroalkyl$C_{0-10}$alkylsulfonyl, $C_{0-10}$ alkylsulfamoyl, $(C_{3-12})$cycloalkyl$C_{0-10}$ alkylsulfamoyl, $(C_{3-12})$cycloheteroalkyl$C_{0-10}$ alkylsulfamoyl, heteroaryl$C_{0-10}$ alkylsulfamoyl, $C_{0-10}$ alkylsulfonimidoyl$C_{0-10}$ alkyl, $C_{1-10}$ heteroalkylsulfonimidoyl$C_{0-10}$ alkyl, —$SO_2NH_2$, —$SO_2NH(C_{1-6}alkyl)$, —$SO_2N(C_{1-6}alkyl)_2$, aryl$C_{0-10}$ alkylsulfamoyl, $(C_{1-10}$ alkyl)$_{1-2}$amino, —$SO_2CF_3$, —$SO_2CF_2H$, —$SO_2CH_2CF_3$, hydroxy, —$(C_{1-10}$ alkyl)OH, $C_{1-10}$ alkoxy$C_{0-10}$ alkyl, cyano, $(C_{1-6}alkyl)$cyano, and $C_{1-6}$haloalkyl; and wherein $R^5$ is optionally substituted with 0, 1, 2, 3, or 4 $R^6$ substituents.

In one embodiment, wherein $R^5$ is selected from: oxo, trifluoromethyl, methoxycarbonyl, fluoro, dimethylsulfamoyl, hydroxyethyl, sulfamoyl, trifluoroethyl, methylsulfonyl, methyl, pentafluorosulfanyl, 2,2,2-trifluoroethyl, tert-butyl, (trifluoromethyl)sulfonyl, methylamino, tert-butylsulfamoyl, isopropylsulfonyl, tert-butylsulfamoyl, pyrazolylmethyl, triazolylmethyl, 1,2,3-triazolylmethyl, isobutyl, cyclopropylmethyl, ethyl, cyclopentylmethyl, isopropylsulfamoyl, benzylsulfamoyl, (cyclopropylmethyl)sulfamoyl, (methoxyethyl)sulfamoyl, cyclohexylsulfamoyl, piperidinylsulfonyl, morpholinosulfonyl, difluoromethylsulfonyl, chloro, and methoxy; wherein $R^5$ is optionally substituted with 0, 1, 2, 3, or 4 $R^6$ substituents.

In another embodiment $R^5$ is selected from: methoxycarbonyl, tert-butylsulfonyl, tert-butylsulfamoyl, tert-butyl (methyl)sulfamoyl, tert-butyl(ethyl)sulfamoyl, pentafluorosulfanyl, methoxy, dimethyamino, oxo, amino, fluoro, isobutyl, isopropyl, sulfamoyl, dimethylsulfamoyl, methylsulfonyl, ethylsulfonyl, trifluoromethylsulfonyl, tert-butyloxycarbonyl(1-methyl)ethyl, diethylsulfamoyl, ethylsulfamoyl, pyrrolidinylsulfonyl, methyl, tert-butylaminomethyl, methylaminocarbonyl, methylaminomethyl, ethyl, (1-hydroxy)ethyl, piperidinylsulfonyl, piperidinyl, thiomorpholinylcarbonyl, thiazolidinylcarbonyl, thiomorpholinylmethyl, pyrrolidinylcarbonyl, piperidinylcarbonyl, ethylaminocarbonyl, morpholinylcarbonyl, tert-butyl, cyclopentylmethyl, cyclohexyl, cyclohexylsulfonyl, cyclohexylsulfamoyl, cyclopentyl, cyclopentylsulfonyl, benzyl, hydroxymethyl, 8-oxa-3-azabicyclo[3.2.1]octanyl, 8-oxa-3-azabicyclo[3.2.1]octane-3carbonyl, 3-oxa-8-azabicyclo[3.2.1]octan-8-ylcarbonyl, ethoxycarbonyl(dimethyleth-2-yl), hydroxy, trifluoromethyl, azetidinylsulfonyl, cyclopropylsulfonyl, cyclopropyl, chloro, ethylaminomethyl, pyrrolidinylmethyl, 1-pyrrolidin-1-ylethyl, cyclopropylmethyl, pyrazolylmethyl, morpholinylsulfonyl, isopropylaminomethyl, pyrazolyl, pyrrolidinyl, piperadinyl, methylsulfonyl, isopropylsulfonyl, isopropylsulfamoyl, methylsulfamoyl, benzylsulfamoyl, cyclopropylmethyl, cyclobutyl, tert-butylsulfonyl, tert-butyloxycarbonyl, tert-butyloxycarbonylmethyl, methoxymethyl, 2-oxa-5-azabicyclo[2.2.1]heptane-5-carbonyl, methoxyeth-2-yl, triazolylmethyl, 1,2,3-triazolylmethyl, aminomethyl, ethylaminomethyl, aminocarbonyl, morpholinyl, isopropyl, isopropyl(methy)sulfamoyl, sulfonyl, cyano, 2,2,2-trifluoroethyl, ethylaminocarbonyl, tert-butylaminomethyl, isopropyloxycarbonyl (dimethyleth-2-yl), 1,1,1-trifluoro-3,3-dimethylbut-2-yl, (1,1,2-trimethylpropyl)sulfonyl, (1,1-dimethylpropyl)sulfonyl, isopropylsulfonimidoyl methylsulfonyl, ethylcarbonyl, 2,3-dihydro-1H-indenyl, ethylmethylsulfamoyl, neopentyl, methylaminomethyl dimethylamino, 2-(isopropylamino) propan-2-yl, 2,2-dimethylpropyl, hydroxymethyl, hydroxyeth-2-yl, tert-butyloxycarbonyl(2-methylprop-2-yl), methoxy, ethylaminocarbonyl, methylaminocarbonyl, and methoxymethyl; and wherein $R^5$ is optionally substituted with 0, 1, 2, 3, or 4 $R^6$ substituents.

In one embodiment, $R^6$ is independently selected from: halogen, $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, aryl $C_{0-10}$ alkyl (oxy)$_{0-1}$(carbonyl)$_{0-1}C_{0-10}$ alkyl, $C_{3-12}$ cycloalkyl $C_{0-10}$ alkyl (oxy)$_{0-1}$(carbonyl)$_{0-1}C_{0-10}$ alkyl, heteroaryl $C_{0-10}$ alkyl (oxy)$_{0-1}$(carbonyl)$_{0-1}C_{0-10}$ alkyl, $(C_{3-12})$heterocycloalkyl $C_{0-10}$ alkyl(oxy)$_{0-1}$(carbonyl)$_{0-1}C_{0-10}$ alkyl, $C_{1-10}$ alkyl(carbonyl)$_{0-1}$oxy$C_{0-10}$ alkyl, $((C_{0-10})$alkyl)$_{1-2}$aminocarbonyloxy, $C_{0-10}$alkylsulfonyl, —$CO_2(C_{0-10}$ alkyl), —$(C_{0-10}$ alkyl) $CO_2H$, oxo (=O), —$SO_2NH_2$, —$SO_2NH(C_{1-6}alkyl)$, —$SO_2N(C_{1-6}alkyl)_2$, —$SO_2CF_3$, —$SO_2CF_2H$, amino, $(C_{0-10}$ alkyl)$_{1-2}$ amino, hydroxy, $(C_{1-10}$ alkyl)OH, $C_{1-10}$ alkoxy$C_{0-10}$ alkyl, cyano, and $C_{1-6}$haloalkyl.

In one embodiment, $R^6$ is independently selected from: halogen, $C_{1-10}$ alkyl(oxy)$_{0-1}$(carbonyl)$_{0-1}C_{0-10}$ alkyl, $C_{1-10}$ heteroalkyl(oxy)$_{0-1}$(carbonyl)$_{0-1}C_{0-10}$ alkyl, aryl $C_{0-10}$ alkyl (oxy)$_{0-1}$(carbonyl)$_{0-1}C_{0-10}$ alkyl, $C_{3-12}$ cycloalkyl $C_{0-10}$ alkyl (oxy)$_{0-1}$(carbonyl)$_{0-1}C_{0-10}$ alkyl, heteroaryl $C_{0-10}$ alkyl (oxy)$_{0-1}$(carbonyl)$_{0-1}C_{0-10}$ alkyl, $(C_{3-12})$heterocycloalkyl $C_{0-10}$ alkyl(oxy)$_{0-1}$(carbonyl)$_{0-1}C_{0-10}$ alkyl, oxo (=O), $C_{0-10}$alkylsulfonyl, amino, hydroxy, $C_{1-10}$ alkoxy$C_{0-10}$ alkyl, cyano, and $C_{1-6}$haloalkyl, wherein $R^6$ is optionally substituted with 1, 2, or 3 $R^7$ substituents In another embodiment, $R^6$ is independently selected from: trifluoromethyl, 2,2,2-trifluroethyl, amino, methyl, fluoro, methoxy, tert-butyl, ethyl, tert-butyloxycarbonyl(1-methyl)ethyl, ethoxycarbonyl, tert-butyloxycarbonylmethyl, phenyl, trifluoroethyl, cyclopropyl, oxo, tert-butyloxycarbonyl, isopropyl, cyano, isopropyloxy, isoxazolyl, pyrrolidinyl, chloro, methylthio, methylsulfonyl, iodine, and bromine; wherein $R^6$ is optionally substituted with 1, 2, or 3 $R^7$ substituents.

In one embodiment, $R^7$ selected from hydrogen, hydroxy, $(C_{1-6})$alkyl, halogen, trifluoromethyl, trifluoroethyl, $C_{1-10}$ alkylsulfonyl, oxo (O=), —SO$_2$CF$_3$, —SO$_2$CF$_2$H, and NH$_2$.

In a variant of this embodiment $R^7$ selected from hydrogen, and oxo (O=).

In one embodiment, the section of formula I,

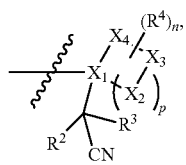

is selected from:

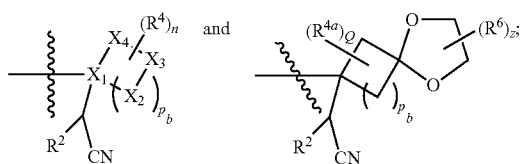

wherein $R^2$ is hydrogen; Q is 0, 1, 2 or 3; $R^{4a}$ is OH, $C_{(1-4)}$ alkyl, oxo, or halogen; $p_b$ is independently 0, 1, 2, 3, or 4; and Z is 0, 1, or 2, provided that the sum of Q and Z is less than or equal to 4; $R^4$ is selected from tert-butylcarbonyl, methoxycarbonyl, methylcarbonyl, cyclopropylmethyl, cyclopropylmethylcarbonyl, cyclopropylethylcarbonyl, cyclopropylcarbonyl, cyclobutylcarbonyl, cyclopentyloxycarbonyl, isopropyloxycarbonyl, phenylmethyl, phenylpropyl, phenylmethylcarbonyl, phenylethylcarbonyl, phenyloxycarbonyl, phenylcarbonyl, oxazolylmethyl, 1,3-oxazolylmethyl, indolylmethyl, 1-phenylethyl, pyridinylmethyl, cyclohexylcarbonyl, fluoro, 2,2,2-trifluoroethyl, ethyl, 2-hydroxyethyl, neopentylcarbonyl, neopentyloxycarbonyl, ethylcarbonyl, ethyloxycarbonyl, methoxymethylcarbonyl (methylamino)methylcarbonyl, 2,3-dihydro-1H-indenylcarbonyl, pyrrolidinylmethylcarbonyl, tetrahydro-2H-pyranylcarbonyl, tetrahydro-2H-thiopyranyloxycarbonyl, tetrahydro-2H-pyranyloxycarbonyl, 1-(pyridinyl)ethyloxycarbonyl, adamantylcarbonyl, tetrahydrofuranyloxycarbonyl, trifluoroethylsulfonyl, dimethylamino, tert-butyloxycarbonyl, methyl, tert-butylaminocarbonyl, aminocarbonyl, azetidinyl, cyclohexylamino, oxo, hydroxy, methylaminocarbonyl, cyclopropylsulfonyl, methoxy, phenylamino, pyridinyl, carbonyl, hydroxyisopropyl, hydroxyeth-2-yl, trifluoromethyl, 2-(methylthio)eth-2-ylcarbonyl, methylsulfonyl, ethylcarbonyl, methylamino, isopropyloxycarbonyl, and hydroxyisopropyl; wherein $R^4$ is optionally substituted with 0, 1, 2, 3, or 4 $R^6$ substituents and $R^6$ is selected from from hydrogen and oxo. In variant of this embodiment, Q is 0, and $R^6$ is oxo.

In another embodiment of the invention, the portion of formula I,

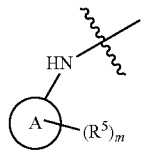

is selected from:

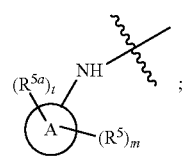

and t is 0, 1, 2 or 3; m is 0, 1, or 2; and $R^{5a}$ is selected from halogen, methyl, ethyl, oxo, $C_{1-10}$ alkyl(oxy)$_{0-1}$(carbonyl)$_{0-1}$ $C_{0-10}$ alkyl, $C_{1-10}$ heteroalkyl(oxy)$_{0-1}$(carbonyl)$_{0-1}$$C_{0-10}$ alkyl, aryl $C_{0-10}$ alkyl(oxy)$_{0-1}$(carbonyl)$_{0-1}$$C_{0-10}$ alkyl, $C_{3-12}$ cycloalkyl $C_{0-10}$ alkyl(oxy)$_{0-1}$(carbonyl)$_{0-1}$$C_{0-10}$ alkyl, heteroaryl $C_{0-10}$ alkyl(oxy)$_{0-1}$(carbonyl)$_{0-1}$$C_{0-10}$ alkyl, and $(C_{3-12})$heterocycloalkyl $C_{0-10}$ alkyl(oxy)$_{0-1}$(carbonyl)$_{0-1}$$C_{0-10}$ alkyl; provided that the sum of t plus m is less than or equal to 4. In a variant of this embodiment, $R^{5a}$ is selected from halogen, methyl, ethyl, oxo, and heteroaryl $C_{0-10}$ alkyl (oxy)$_{0-1}$(carbonyl)$_{0-1}$$C_{0-10}$ alkyl and $R^5$ is selected from: methoxycarbonyl, tert-butylsulfonyl, tert-butylsulfamoyl, tert-butyl(methyl)sulfamoyl, tert-butyl(ethyl)sulfamoyl, pentafluorosulfanyl, methoxy, dimethyamino, oxo, amino, fluoro, isobutyl, isopropyl, sulfamoyl, dimethylsulfamoyl, methylsulfonyl, ethylsulfonyl, trifluoromethylsulfonyl, tert-butyloxycarbonyl(1-methyl)ethyl, diethylsulfamoyl, ethylsulfamoyl, pyrrolidinylsulfonyl, methyl, tert-butylaminomethyl, methylaminocarbonyl, methylaminomethyl, ethyl, (1-hydroxy)ethyl, piperidinylsulfonyl, piperidinyl, thiomorpholinylcarbonyl, thiazolidinylcarbonyl, thiomorpholinylmethyl, pyrrolidinylcarbonyl, piperidinylcarbonyl, ethylaminocarbonyl, morpholinylcarbonyl, tert-butyl, cyclopentylmethyl, cyclohexyl, cyclohexylsulfonyl, cyclohexylsulfamoyl, cyclopentyl, cyclopentylsulfonyl, benzyl, hydroxymethyl, 8-oxa-3-azabicyclo[3.2.1]octanyl, 8-oxa-3-azabicyclo[3.2.1]octane-3carbonyl, 3-oxa-8-azabicyclo[3.2.1]octan-8-ylcarbonyl, ethoxycarbonyl(dimethyleth-2-yl), hydroxy, trifluoromethyl, azetidinylsulfonyl, cyclopropylsulfonyl, cyclopropyl, chloro, ethylaminomethyl, pyrrolidinylmethyl, 1-pyrrolidin-1-ylethyl, cyclopropylmethyl, pyrazolylmethyl, morpholinylsulfonyl, isopropylaminomethyl, pyrazolyl, pyrrolidinyl, piperadinyl, methylsulfonyl, isopropylsulfonyl, isopropylsulfamoyl, methylsulfamoyl, benzylsulfamoyl, cyclopropylmethyl, cyclobutyl, tert-butylsulfonyl, tert-butyloxycarbonyl, tert-butyloxycarbonylmethyl, methoxymethyl, 2-oxa-5-azabicyclo[2.2.1]heptane-5-carbonyl, methoxyeth-2-yl, triazolylmethyl, 1,2,3-triazolylmethyl, aminomethyl, ethylaminomethyl, aminocarbonyl, morpholinyl, isopropyl, isopropyl(methy)sulfamoyl, sulfonyl, cyano, 2,2,2-trifluoroethyl, ethylaminocarbonyl, tert-butylaminomethyl, isopropyloxycarbonyl(dimethyleth-2-yl), 1,1,1-trifluoro-3,3-dimethylbut-2-yl, (1,1,2-trimethylpropyl)sulfonyl, (1,1-dimethylpropyl)sulfonyl, isopropylsulfonimidoyl methylsulfonyl, ethylcarbonyl, 2,3-dihydro-1H-indenyl, ethylmethylsulfamoyl, neopentyl, methylaminomethyl dimethylamino, 2-(isopropylamino)propan-2-yl, 2,2-dimethylpropyl, hydroxymethyl, hydroxyeth-2-yl, tert-butyloxycarbonyl(2-methylprop-2-yl), methoxy, ethylaminocarbonyl, methylaminocarbonyl, and methoxymethyl; and wherein $R^5$ is optionally substituted with 0, 1, 2, 3, or 4 $R^6$ substituents.

In one embodiment of the invention provides compounds of Formula I or pharmaceutically acceptable salts, or stereoisomers thereof:

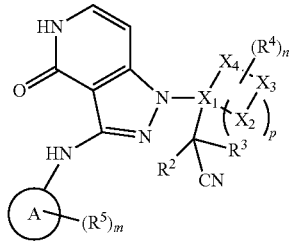

I

A is selected from aryl, heteroaryl, cycloalkyl$C_{(0-10)}$alkyl, $C_{1-6}$alkyl;

$R^2$ and $R^3$ are each independently selected from hydrogen, $C_{1-4}$alkyl and hydroxyl, wherein $R^2$ and $R^3$ may optionally, join together with the carbon they are attached to form a 3 to 6 membered ring;

$X_1$ is C;

$X_2$, $X_3$, and $X_4$ are each independently selected from O, N, S, and C and provided that the formed ring system contains 0, 1, 2, or 3 atoms selected from O, N and S;

n is 0, 1, 2, 3 or 4;

m is 0, 1, 2, 3 or 4;

p is 0, 1, 2, 3, or 4;

$R^4$ is selected from:
halogen,
oxo (=O),
$C_{1-10}$ alkyl(oxy)$_{0-1}$(carbonyl)$_{0-1}$$C_{0-10}$ alkyl,
$C_{1-10}$ heteroalkyl(oxy)$_{0-1}$(carbonyl)$_{0-1}$$C_{0-10}$ alkyl,
$C_{2-10}$ alkenyl(oxy)$_{0-1}$(carbonyl)$_{0-1}$$C_{0-10}$ alkyl,
aryl $C_{0-10}$ alkyl(oxy)$_{0-1}$(carbonyl)$_{0-1}$$C_{0-10}$ alkyl,
$C_{3-12}$ cycloalkyl $C_{0-10}$ alkyl(oxy)$_{0-1}$(carbonyl)$_{0-1}$$C_{0-10}$ alkyl,
heteroaryl $C_{0-10}$ alkyl(oxy)$_{0-1}$(carbonyl)$_{0-1}$$C_{0-10}$ alkyl,
($C_{3-12}$)heterocycloalkyl $C_{0-10}$ alkyl(oxy)$_{0-1}$(carbonyl)$_{0-1}$ $C_{0-10}$ alkyl,
$C_{0-10}$ alkyl(oxy)$_{0-1}$(carbonyl)$_{0-1}$ amino$C_{0-10}$ alkyl,
$C_{0-10}$ alkylamino(oxy)$_{0-1}$(carbonyl)$_{0-1}$$C_{0-10}$ alkyl,
($C_{1-10}$)heteroalkyl(oxy)$_{0-1}$(carbonyl)$_{0-1}$ amino $C_{0-10}$ alkyl,
($C_{1-10}$)heteroalkylamino(oxy)$_{0-1}$(carbonyl)$_{0-1}$$C_{0-10}$ alkyl,
$C_{3-12}$ cycloalkyl $C_{0-10}$ alkylamino$C_{0-10}$ alkyl,
aryl $C_{0-10}$ alkylamino$C_{0-10}$ alkyl,
heteroaryl $C_{0-10}$ alkylamino$C_{0-10}$ alkyl,
($C_{3-12}$)heterocycloalkyl $C_{0-10}$ alkylamino$C_{0-10}$ alkyl,
sulfonyl,
$C_{1-10}$ alkylsulfonyl,
$C_{1-10}$ heteroalkylsulfonyl,
($C_{3-12}$)cycloalkyl$C_{0-10}$alkylsulfonyl,
($C_{3-12}$)cycloheteroalkyl$C_{0-10}$alkylsulfonyl,
heteroaryl$C_{0-10}$ alkylsulfonyl,
aryl$C_{0-10}$ alkylsulfonyl,
$C_{0-10}$ alkylsulfamoyl,
$C_{1-10}$ heteroalkylsulfamoyl,
($C_{3-12}$)cycloalkyl$C_{0-10}$ alkylsulfamoyl,
($C_{3-12}$)cycloheteroalkyl$C_{0-10}$ alkylsulfamoyl,
heteroaryl$C_{0-10}$ alkylsulfamoyl,
aryl$C_{0-10}$ alkylsulfamoyl,
($C_{0-10}$ alkyl)$_{1-2}$ amino,
—$CO_2$($C_{0-10}$ alkyl),
—($C_{0-10}$ alkyl)$CO_2H$,
—$SO_2CF_3$,
—$SO_2CF_2H$,
$C_{1-10}$ alkylsulfinyl,
$C_{1-4}$acylamino$C_{0-10}$ alkyl,
hydroxy,
—($C_{1-10}$ alkyl)OH,
—$C_{0-10}$ alkylalkoxy,
cyano,
($C_{1-6}$alkyl)cyano, and
$C_{1-6}$haloalkyl,
wherein two R4 together with the ring atom to which each is attached optionally may form a saturated ring;

$R^5$ is selected from:
halogen,
oxo (=O),
$C_{1-10}$ alkyl(oxy)$_{0-1}$(carbonyl)$_{0-1}$$C_{0-10}$ alkyl,
$C_{1-10}$ heteroalkyl(oxy)$_{0-1}$(carbonyl)$_{0-1}$$C_{0-10}$ alkyl,
$C_{2-10}$ alkenyl(oxy)$_{0-1}$(carbonyl)$_{0-1}$$C_{0-10}$ alkyl,
aryl $C_{0-10}$ alkyl(oxy)$_{0-1}$(carbonyl)$_{0-1}$$C_{0-10}$ alkyl,
$C_{3-12}$ cycloalkyl $C_{0-10}$ alkyl(oxy)$_{0-1}$(carbonyl)$_{0-1}$$C_{0-10}$ alkyl,
heteroaryl $C_{0-10}$ alkyl(oxy)$_{0-1}$(carbonyl)$_{0-1}$$C_{0-10}$ alkyl,
($C_{3-12}$)heterocycloalkyl $C_{0-10}$ alkyl(oxy)$_{0-1}$(carbonyl)$_{0-1}$$C_{0-10}$ alkyl,
$C_{0-10}$ alkyl(oxy)$_{0-1}$(carbonyl)$_{0-1}$ amino$C_{0-10}$ alkyl,
($C_{1-10}$)heteroalkyl(oxy)$_{0-1}$(carbonyl)$_{0-1}$ amino$C_{0-10}$ alkyl,
$C_{3-12}$ cycloalkyl $C_{0-10}$ alkylamino$C_{0-10}$ alkyl,
aryl $C_{0-10}$ alkylamino$C_{0-10}$ alkyl,
heteroaryl $C_{0-10}$ alkylamino$C_{0-10}$ alkyl,
($C_{3-12}$)heterocycloalkyl $C_{0-10}$ alkylamino$C_{0-10}$ alkyl,
—$SF_5$,
$C_{1-10}$ alkylsulfonyl,
$C_{1-10}$ heteroalkylsulfonyl,
($C_{3-12}$)cycloalkyl$C_{0-10}$alkylsulfonyl,
($C_{3-12}$)cycloheteroalkyl$C_{0-10}$alkylsulfonyl,
heteroaryl$C_{0-10}$ alkylsulfonyl,
aryl$C_{0-10}$ alkylsulfonyl,
$C_{0-10}$ alkylsulfamoyl,
$C_{1-10}$ heteroalkylsulfamoyl,
($C_{3-12}$)cycloalkyl$C_{0-10}$ alkylsulfamoyl,
($C_{3-12}$)cycloheteroalkyl$C_{0-10}$ alkylsulfamoyl,
heteroaryl$C_{0-10}$ alkylsulfamoyl,
aryl$C_{0-10}$ alkylsulfamoyl,
—$SO_2NH_2$,
—$SO_2NH(C_{1-6}alkyl)$,
—$SO_2N(C_{1-6}alkyl)_2$,
aryl$C_{0-10}$ alkylsulfamoyl,
($C_{0-10}$ alkyl)$_{1-2}$ amino,
—$CO_2$($C_{0-10}$ alkyl),
—($C_{0-10}$ alkyl)$CO_2H$,
—$SO_2CF_3$,
—$SO_2CF_2H$,
$C_{1-10}$ alkylsulfinyl,
$C_{1-4}$acylamino$C_{0-10}$ alkyl,
hydroxy,
—($C_{1-10}$ alkyl)OH, $C_{0-10}$ alkylalkoxy,
cyano,
$(C_{1-6}$alkyl)cyano, and
$C_{1-6}$haloalkyl; and
wherein $R^4$ and $R^5$ are each optionally substituted with 1, 2, 3, or 4 $R^6$ substituents and $R^6$ is independently selected from:
halogen,
$C_{1-10}$ alkyl(oxy)$_{0-1}$(carbonyl)$_{0-1}$$C_{0-10}$ alkyl,
$C_{1-10}$ heteroalkyl(oxy)$_{0-1}$(carbonyl)$_{0-1}$$C_{0-10}$ alkyl,
$C_{2-10}$ alkenyl(oxy)$_{0-1}$(carbonyl)$_{0-1}$$C_{0-10}$ alkyl,
aryl $C_{0-10}$ alkyl(oxy)$_{0-1}$(carbonyl)$_{0-1}$$C_{0-10}$ alkyl,
$C_{3-12}$ cycloalkyl $C_{0-10}$ alkyl(oxy)$_{0-1}$(carbonyl)$_{0-1}$$C_{0-10}$ alkyl,
heteroaryl $C_{0-10}$ alkyl(oxy)$_{0-1}$(carbonyl)$_{0-1}$$C_{0-10}$ alkyl,
$(C_{3-12})$heterocycloalkyl $C_{0-10}$ alkyl(oxy)$_{0-1}$(carbonyl)$_{0-1}$ $C_{0-10}$ alkyl,
$C_{1-10}$ alkyl(carbonyl)$_{0-1}$oxy$C_{0-10}$ alkyl,
$C_{2-10}$ alkenyl(carbonyl)$_{0-1}$ oxy$C_{0-10}$ alkyl,
$C_{1-10}$ heteroalkyl(carbonyl)$_{0-1}$ oxy$C_{0-10}$ alkyl,
aryl $C_{0-10}$ alkyl (carbonyl)$_{0-1}$oxy$C_{0-10}$ alkyl,
$(C_{3-12})$cycloalkyl $C_{0-10}$ alkyl(carbonyl)$_{0-1}$ oxy$C_{0-10}$ alkyl,
heteroaryl$C_{0-10}$ alkyl(carbonyl)$_{0-1}$ oxy$C_{0-10}$ alkyl,
$(C_{3-12})$heterocycloalkyl $C_{0-10}$ alkyl(carbonyl)$_{0-1}$ oxy$C_{0-10}$ alkyl,
$((C_{0-10})$alkyl$)_{1-2}$aminocarbonyloxy,
aryl $(C_{0-10})$alkylaminocarbonyloxy,
—$CO_2(C_{0-10}$ alkyl),
—$(C_{0-10}$ alkyl)$CO_2H$,
oxo (=O),
$C_{1-10}$ alkylsulfonyl,
$C_{1-10}$ heteroalkylsulfonyl,
$(C_{3-12})$ cycloalkylsulfonyl,
$(C_{3-12})$ cycloheteroalkylsulfonyl,
heteroarylsulfonyl,
arylsulfonyl,
aminosulfonyl,
—$SO_2NH_2$,
—$SO_2NH(C_{1-6}$alkyl),
—$SO_2N(C_{1-6}$alkyl)$_2$,
—$SO_2CF_3$,
—$SO_2CF_2H$,
$C_{1-10}$ alkylsulfinyl,
amino,
$(C_{0-10}$ alkyl)$_{1-2}$ amino,
-(oxy)$_{0-1}$(carbonyl)$_{0-1}$N$(C_{0-10}$ alkyl)$_{1-2}$
$C_{1-4}$acylamino$C_{0-10}$ alkyl,
hydroxy,
$(C_{1-10}$ alkyl)OH,
$C_{1-10}$ alkoxy,
$(C_{1-10}$ alkyl)cyano,
cyano, and
$C_{1-6}$haloalkyl; and
$R^6$ is optionally substituted with 1, 2, or 3 substituents selected from hydrogen, hydroxy, $(C_{1-6})$alkyl, $(C_{1-6})$alkoxy, $(C_{1-10}$ alkyl)OH, halogen, $CO_2H$, —$(C_{0-6})$alkylCN, —O(C=O)$C_1$-$C_6$ alkyl, $NO_2$, trifluoromethoxy, trifluoroethoxy, trifluoromethyl, trifluoroethyl, —N=C(O)O$(C_{0-6})$alkyl, $C_{1-10}$ alkylsulfonyl, oxo (O=), aminosulfonyl, —$SO_2C_{1-6}$alkyl, —$SO_2CF_3$, —$SO_2CF_2H$, —$C_{1-10}$ alkylsulfinyl, —O$_{(0-1)}$($C_{1-10}$) halo, —$SO_2NH_2$, —$SO_2NH(C_{1-6}$alkyl), —$SO_2N(C_{1-6}$ alkyl)$_2$, alkyl, amino$(C_{1-6}$alkyl)$_{0-2}$ and $NH_2$.

Optical Isomers—Diastereomers—Geometric Isomers—Tautomers

Compounds of Formula I contain one or more asymmetric centers and can thus occur as racemates and racemic mixtures, single enantiomers, diastereomeric mixtures and individual diastereomers. The present invention is meant to comprehend all such isomeric forms of the compounds of Formula I, either as single species or mixtures thereof.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of Formula I.

Specific embodiments of the present invention include a compound which is selected from the group consisting of the subject compounds of the examples herein or a pharmaceutically acceptable salt thereof.

The compounds of the present invention may contain one or more asymmetric centers and can thus occur as "stereoisomers" including racemates and racemic mixtures, enantiomeric mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the scope of this invention. The present invention is meant to comprehend all such isomeric forms of these compounds. When bonds to the chiral carbon are depicted as straight lines in the formulas of the invention, it is understood that both the (R) and (S) configurations of the chiral carbon, and hence both enantiomers and mixtures thereof, are embraced within the formula. For example, Formula I shows the structure of the class of compounds without specific stereochemistry. When the compounds of the present invention contain one chiral center, the term "stereoisomer" includes both enantiomers and mixtures of enantiomers, such as the specific 50:50 mixture referred to as racemic mixtures.

The compounds of formula (I) may contain asymmetric or chiral centers, and, therefore, exist in different stereoisomeric forms. It is intended that all stereoisomeric forms of the compounds of formula (I) as well as mixtures thereof, including racemic mixtures, form part of the present invention. In addition, the present invention embraces all geometric and positional isomers. For example, if a compound of formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of formula (I) may be atropisomers (e.g., substituted biaryls) and are considered as part of this invention. Enantiomers can also be separated by use of chiral HPLC column.

It is also possible that the compounds of formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). For example, if a compound of formula (I) incorporates a double bond or a fused ring, both the cis- and trans-forms, as well as mixtures, are embraced within the scope of the invention. Also, for example, all keto-enol and imine-enamine forms of the compounds are included in the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

In the present application when a particular stereomeric compound is named using an "and" in the stereomeric designation, for example, tert-butyl (3R,4S and 3S,4R)-4-(cyanomethyl)-3-methyl-4-(3-{[4-(methylsulfonyl)phenyl]amino}-4-oxo-4,5-dihydro-1H-pyrazolo[4,3-c]pyridin-1-yl)piperidine-1-carboxylate, the "and" indicates a racemic mixture of the enantiomers. That is, the individual enantiomers were not individually isolated.

When the stereomeric nomenclature includes "or", for example, tert-butyl 4-(cyanomethyl)-4-[4-oxo-3-({4-[(1R or 1S)-2,2,2-trifluoro-1-hydroxyethyl]phenyl}amino)-4,5-dihydro-1H-pyrazolo[4,3-c]pyridin-1-yl]piperidine-1-carboxylate, the "or" indicates that chiral resolution of racemate into individual enantiomers was accomplished but the actual optical activity of the specific enantiomer was not nessissarily determined.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound can be obtained by stereoselective synthesis using optically pure starting materials or reagents of known configuration by methods well known in the art.

Salt

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, 1-hydroxy-2-naphthoic acid (xinafoate) and the like. Particularly preferred are citric, hydrobromic, hydrochloric, maleic, phosphoric, sulfuric, and tartaric acids.

It will be understood that, unless otherwise specified, references to the compound of Formula I subsets thereof, embodiments thereof, as well as specific compounds are meant to also include the pharmaceutically acceptable salts and stereoisomers thereof.

Furthermore, some of the crystalline forms for compounds of the present invention may exist as polymorphs and as such all forms are intended to be included in the present invention. In addition, some of the compounds of the instant invention may form solvates with water (hydrates) or common organic solvents. Such solvates are encompassed within the scope of this invention.

Labelled Compounds

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the schemes and examples herein using appropriate isotopically-enriched reagents and/or intermediates.

Utilities

Compound of Formula I or its pharmaceutically acceptable salts and pharmaceutical compositions can be used to treat or prevent a variety of conditions or diseases mediated by Janus kinases, in particular diseases or conditions that can be ameliorated by the inhibition of a Janus kinase such as JAK1, JAK2, JAK3 or TYK2. Such conditions and diseases include, but are not limited to:

(1) arthritis, including rheumatoid arthritis, juvenile arthritis, and psoriatic arthritis; (2) asthma and other obstructive airways diseases, including chronic asthma, late asthma, airway hyper-responsiveness, bronchitis, bronchial asthma, allergic asthma, intrinsic asthma, extrinsic asthma, dust asthma, recurrent airway obstruction, and chronic obstruction pulmonary disease including emphysema; (3) autoimmune diseases or disorders, including those designated as single organ or single cell-type autoimmune disorders, for example Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those designated as involving systemic autoimmune disorder, for example systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid, and additional autoimmune diseases, which can be B-cell (humoral) based or T-cell based, including Cogan's syndrome, ankylosing spondylitis, Wegener's granulomatosis, autoimmune alopecia, Type I or juvenile onset diabetes, and thyroiditis; (4) cancers or tumors, including alimentary/gastrointestinal tract cancer, colon cancer, liver cancer, skin cancer including mast cell tumor and squamous cell carcinoma, breast and mammary cancer, ovarian cancer, prostate cancer, lymphoma, leukemia, including acute myelogenous leukemia and chronic myelogenous leukemia, kidney cancer, lung cancer, muscle cancer, bone cancer, bladder cancer, brain cancer, melanoma including oral and metastatic melanoma, Kaposi's sarcoma, myelomas including multiple myeloma, myeloproliferative disorders, proliferative diabetic retinopathy, and angiogenic-associated disorders including solid tumors; (5) diabetes, including Type I diabetes and complications from diabetes; (6) eye diseases, disorders or conditions including autoimmune diseases of the eye, keratoconjunctivitis, vernal conjunctivitis, uveitis including uveitis associated with Behcet's disease and lens-induced uveitis, keratitis, herpetic keratitis, conical keratitis, corneal epithelial dystrophy, keratoleukoma, ocular premphigus, Mooren's ulcer, scleritis, Grave's ophthalmopathy, Vogt-Koyanagi-Harada syndrome, keratoconjunctivitis sicca (dry eye), phlyctenule, iridocyclitis, sarcoidosis, endocrine ophthalmopathy, sympathetic ophthalmitis, allergic conjunctivitis, and ocular neovascularization; (7) intestinal inflammations, allergies or conditions including Crohn's disease and/or ulcerative colitis, inflammatory bowel disease, coeliac diseases, proctitis, eosinophilic gastroenteritis, and mastocytosis; (8) neurodegenerative diseases including motor neuron disease, Alzheimer's disease, Parkinson's disease, amyotrophic lateral sclerosis, Huntington's disease, cerebral ischemia, or neurodegenerative disease caused by traumatic injury, strike, glutamate neurotoxicity or hypoxia; ischemic/reperfusion injury in stroke, myocardial ischemica, renal ischemia, heart attacks, cardiac hypertrophy, atherosclerosis and arteriosclerosis, organ hypoxia, and platelet aggregation; (9) skin diseases, conditions or disorders including atopic dermatitis, eczema, psoriasis, scleroderma, pruritus and other pruritic conditions; (10) allergic reactions including anaphylaxis, allergic rhinitis, allergic dermatitis, allergic urticaria, angioedema, allergic asthma, or allergic reaction to insect bites, food, drugs, or pollen; (11) transplant rejection, including pancreas islet transplant rejection, bone marrow transplant rejection, graft-versus-host disease, organ and cell transplant rejection such as bone marrow, cartilage, cornea, heart, intervertebral disc, islet, kidney, limb, liver, lung, muscle, myoblast, nerve, pancreas, skin, small intestine, or trachea, and xeno transplantation.

Accordingly, another aspect of the present invention provides a method for the treatment or prevention of a JAK-mediated disease or disorder comprising administering to a mammal in need thereof a therapeutically effective amount of a compound of Formula I. In one embodiment such diseases include asthma and rheumatoid arthritis.

Another aspect of the present invention provides for the use of a compound of Formula I in the manufacture of a medicament for the treatment or prevention of a JAK-mediated disease or disorder.

One aspect of the invention is the use of a compound of Formula I or a pharmaceutically acceptable salt or a stereoisomer thereof in the manufacture of a medicament for the treatment of a disease or a disorder ameliorated by inhibition of Janus kinases JAK1 and JAK2.

Another aspect of the invention is the use of a compound of Formula I or a pharmaceutically acceptable salt or a stereoisomer thereof and a second active agent in the manufacture of a medicament for the treatment of a disease or a disorder ameliorated by inhibition of Janus kinases JAK1 and JAK2.

Dose Ranges

The magnitude of prophylactic or therapeutic dose of a compound of Formula I will, of course, vary with the nature and the severity of the condition to be treated and with the particular compound of Formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g, of active agent compounded with an appropriate and convenient amount of carrier material which may vary from about 5 to about 99.95 percent of the total composition. In some cases, the dosage unit forms may contain from about 0.05 to about 3 g of active ingredient. Dosage unit forms will generally contain between from about 0.1 mg to about 0.4 g of an active ingredient, typically 0.1 mg, 0.2 mg, 0.3 mg, 0.4 mg, 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of Formula I with a pharmaceutically acceptable carrier. For the treatment of any of the prostanoid mediated diseases compounds of Formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms for inhaled administration may conveniently be formulated as aerosols or dry powders. For compositions suitable and/or adapted for inhaled administration, it is preferred that the active substance is in a particle-size-reduced form, and more preferably the size-reduced form is obtained or obtainable by micronization.

In one embodiment the medicinal preparation is adapted for use with a pressurized metered dose inhaler (pMDI) which releases a metered dose of medicine upon each actuation. The formulation for pMDIs can be in the form of solutions or suspensions in halogenated hydrocarbon propellants. The type of propellant being used in pMDIs is being shifted to hydrofluoroalkanes (HFAs), also known as hydrofluorocarbons (HFCs). In particular, 1,1,1,2-tetrafluoroethane (HFA 134a) and 1,1,1,2,3,3,3-heptafluoropropane (HFA 227) are used in several currently marketed pharmaceutical inhalation products. The composition may include other pharmaceutically acceptable excipients for inhalation use such as ethanol, oleic acid, polyvinylpyrrolidone and the like.

Pressurized MDIs typically have two components. Firstly, there is a canister component in which the drug particles are stored under pressure in a suspension or solution form. Secondly, there is a receptacle component used to hold and actuate the canister. Typically, a canister will contain multiple doses of the formulation, although it is possible to have single dose canisters as well. The canister component typically includes a valve outlet from which the contents of the canister can be discharged. Aerosol medication is dispensed from the pMDI by applying a force on the canister component to push it into the receptacle component thereby opening the valve outlet and causing the medication particles to be conveyed from the valve outlet through the receptacle component and discharged from an outlet of the receptacle. Upon discharge from the canister, the medication particles are "atomized", forming an aerosol. It is intended that the patient coordinate the discharge of aerosolized medication with his or her inhalation, so that the medication particles are entrained in the patient's aspiratory flow and conveyed to the lungs. Typically, pMDIs use propellants to pressurize the contents of the canister and to propel the medication particles out of the outlet of the receptacle component. In pMDIs, the formulation is provided in a liquid or suspension form, and resides within the container along with the propellant. The propellant can take a variety of forms. For example, the propellant can comprise a compressed gas or liquefied gas.

In another embodiment the medicinal preparation is adapted for use with a dry powder inhaler (DPI). The inhalation composition suitable for use in DPIs typically comprises particles of the active ingredient and particles of a pharmaceutically acceptable carrier. The particle size of the active material may vary from about 0.1 µm to about 10 µm; however, for effective delivery to the distal lung, at least 95 percent of the active agent particles are 5 µm or smaller. Each of the active agent can be present in a concentration of 0.01-99%. Typically however, each of the active agents is present in a concentration of about 0.05 to 50%, more typically about 0.2-20% of the total weight of the composition.

As noted above, in addition to the active ingredients, the inhalable powder preferably includes pharmaceutically acceptable carrier, which may be composed of any pharmacologically inert material or combination of materials which is acceptable for inhalation. Advantageously, the carrier particles are composed of one or more crystalline sugars; the carrier particles may be composed of one or more sugar alcohols or polyols. Preferably, the carrier particles are particles of dextrose or lactose, especially lactose. In embodiments of the present invention which utilize conventional dry powder inhalers, such as the Handihaler, Rotohaler, Diskhaler, Twisthaler and Turbohaler, the particle size of the carrier particles may range from about 10 microns to about 1000 microns. In certain of these embodiments, the particle size of the carrier particles may range from about 20 microns to about 120 microns. In certain other embodiments, the size of at least 90% by weight of the carrier particles is less than 1000 microns and preferably lies between 60 microns and 1000 microns. The relatively large size of these carrier particles gives good flow and entrainment characteristics. Where present, the amount of carrier particles will generally be up to 95%, for example, up to 90%, advantageously up to 80% and preferably up to 50% by weight based on the total weight of the powder. The amount of any fine excipient material, if present, may be up to 50% and advantageously up to 30%, especially up to 20%, by weight, based on the total weight of the powder. The powder may optionally contain a performance modifier such as L-leucine or another amino acid, and/or metals salts of stearic acid such as magnesium or calcium stearate.

Compounds of Formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of JAK mediated diseases, compound of Formula I may be co-administered with other therapeutic agents. Thus in another aspect the present invention provides pharmaceutical compositions for treating JAK mediated diseases comprising a therapeutically effective amount of a compound of Formula I and one or more other therapeutic agents. In particular, for the treatment of the inflammatory diseases rheumatoid arthritis, psoriasis, inflammatory bowel disease, COPD, asthma and allergic rhinitis a compound of Formula I may be combined with agents such as: (1) TNF-α inhibitors such as Remicade® and Enbrel®); (2) non-selective COX-I/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin); (3) COX-2 inhibitors (such as meloxicam, celecoxib, rofecoxib, valdecoxib and etoricoxib); (4) other agents for treatment of rheumatoid arthritis including low dose methotrexate, lefunomide, ciclesonide, hydroxychloroquine, d-penicillamine, auranofin or parenteral or oral gold; (5) leukotriene biosynthesis inhibitor, 5-lipoxygenase (5-LO) inhibitor or 5-lipoxygenase activating protein (FLAP) antagonist such as zileuton; (6) LTD4 receptor antagonist such as zafirlukast, montelukast and pranlukast; (7) PDE4 inhibitor such as roflumilast; (8) antihistaminic H1 receptor antagonists such as cetirizine, loratadine, desloratadine, fexofenadine, astemizole, azelastine, and chlorpheniramine; (9) α1- and α2-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (10) anticholinergic agents such as ipratropium bromide, tiotropium bromide, oxitropium bromide, aclindinium bromide, glycopyrrolate, pirenzepine, and telenzepine; (11) β-adrenoceptor agonists such as metaproterenol, isoproterenol, isoprenaline, albuterol, salbutamol, formoterol, salmeterol, terbutaline, orciprenaline, bitolterol mesylate, and pirbuterol, or methylxanthanines including theophylline and aminophylline, sodium cromoglycate; (12) insulin-like growth factor type I (IGF-1) mimetic; (13) inhaled glucocorticoid with reduced systemic side effects, such as prednisone, prednisolone, flunisolide, triamcinolone acetonide, beclomethasone dipropionate, budesonide, fluticasone propionate, ciclesonide and mometasone furoate.

SCHEMES AND EXAMPLES

The abbreviations used herein have the following tabulated meanings. Abbreviations not tabulated below have their meanings as commonly used unless specifically stated otherwise.

| | |
|---|---|
| AD | adamantyl |
| ACN, MeCN | acetonitrile |
| BAST | bis(2-methoxyethyl)aminosulfur trifluoride |
| t-Bu XPhos | 2-di tert-butylphosphino-2',4',6'-triisopropylbiphenyl |
| Chiral SFC | chiral super critical fluid chromatography |
| $CO_2$ | carbon dioxide |
| $Cs_2CO_3$ | cesium carbonate |
| dba | dibenzylideneacetone |
| DBU | 1,8-diazabicyclo[5.4.0]undec-7-ene |
| DCE | 1,2-dichloroethane |
| DCM | dichloromethane |
| DEA | diethylamine |
| DIPEA | N,N-diisopropylethylamine |
| DMEA | dimethylethylamine |
| DMF | N,N-dimethylformamide |
| DMSO | dimethyl sulfoxide |
| DSC | N,N-disuccinimidyl carbonate |
| EDC | 3-(ethyliminomethyleneamino)-N,N-dimethyl-propan-1-amine |
| EtOAc | ethyl acetate |
| ESI | electro spray ionization |
| GCMS | gas chromatography/mass spectrometry |
| HATU | O-(7-aza-1H-benzotriazol-1-yl)-N,N,N',N'-tetramethyluronium hexafluorophosphate |
| HCl | hydrogen chloride |
| HOBt | 1-hydroxybenzotriazole |
| HPLC | high pressure liquid chromatography |
| IPA | 2-propanol |
| LDA | lithium diisopropylamide |
| m-CPBA | meta-chloroperoxybenzoic acid |
| LR | low resolution |
| LRMS | low resolution mass spectrometry |
| MeI | iodomethane |
| Me-THF | 2-methyltetrahydrofuran |
| $Me_4$-t-Bu-X-Phos | di-tert-butyl[3,4,5,6-tetramethyl-2',4',6'-tri(propan-2-yl)biphenyl-2-yl]phosphane |
| $MgSO_4$ | magnesium sulfate |
| MP-$(OAc)_3$BH | solid supported (macro porous) triacetoxyborohydride |
| MPLC | medium pressure liquid chromatography |
| NaH | sodium hydride |
| $Na_2SO_4$ | sodium sulfate |
| $NaBH_4$ | sodium borohydride |
| $NaHCO_3$ | sodium bicarbonate |
| NaOMe | sodium methoxide |
| NMO | 4-methylmorpholine N-oxide |
| $Pd_2(dba)_3$ | tris(dibenzylideneacetone)dipalladium(0) |
| $POCl_3$ | phosphorus (V) oxychloride |
| PS-CDI | polystyrene bound carbonyldiimidazole |
| PyBOP | (7-azabenzotriazol-1-yloxy)tripyrrolidinophosphonium hexafluorophosphate |
| SEM-Cl | 2-(trimethylsilyl)ethoxymethyl chloride |
| SFC | Supercritical fluid chromatography |
| SiliaCat ® DPP-Pd | silica bound diphenylphosphine palladium (II) |
| TBAF | tetra-n-butylammonium fluoride |
| TBS-Cl | tert-butyldimethylsilyl chloride |
| t-BuOH | tert-butanol |
| t-Bu Xphos | 2-di-tert-butylphosphino-2',4',6'-triisopropylbiphenyl |
| TEA | triethylamine |
| TFA | trifluoroacetic acid |
| THF | tetrahydrofuran |
| TPAP | tetra-n-propylammonium perruthenate (VII) |
| Tr | retention time |
| X-Phos | 2-dicyclohexylphosphino-2',4',6'-triisopropylbiphenyl |
| HCOOH | formic acid |
| Kt-OBu | potassium tert-butoxide |
| $Na_2S_2O_5$ | sodium metabisulfite |
| NMR | nuclear magnetic resonance |
| TLC | thin layer chromatography |
| $(EtO)_2P(O)CH_2CN$ | diethyl (cyanomethyl)phosphonate |
| MsCl | methanesulfonyl chloride |
| TsOH | p-toluenesulfonic acid |
| KCN | potassium cyanide |
| Si-DMT | silica supported dimercaptotriazine |
| TMS | trimethylsilane |
| $CF_3TMS$ | (trifluoromethyl)trimethylsilane |

Alkyl Group Abbreviations

| | |
|---|---|
| Me | methyl |
| Et | ethyl |
| n-Pr | normal propyl |
| i-Pr | isopropyl |
| n-Bu | normal butyl |
| i-Bu | isobutyl |
| s-Bu | secondary butyl |
| t-Bu | tertiary butyl |
| c-Pr | cyclopropyl |
| c-Bu | cyclobutyl |
| c-Pen | cyclopentyl |
| c-Hex | cyclohexyl |

Methods of Synthesis

The compounds of the present invention can be prepared according to the following general schemes using appropriate materials, and are further exemplified by the subsequent specific examples. The compounds illustrated in the examples are not to be construed as forming the only genus that is considered as the invention. The illustrative Examples below, therefore, are not limited by the compounds listed or by any particular substituents employed for illustrative purposes. Substituent numbering as shown in the schemes does not necessarily correlate to that used in the claims and often, for clarity, a single substituent is shown attached to the compound where multiple substituents are allowed under the definitions of the instant invention herein above.

Those skilled in the art will readily understand that known variations of the conditions and processes of the following preparative procedures can be used to prepare these compounds. The invention will now be illustrated in the following non-limiting Examples in which, unless otherwise stated:

All reactions were stirred (mechanically, stir bar/stir plate, or shaken) and conducted under an inert atmosphere of nitrogen or argon unless specifically stated otherwise.

All starting materials used to prepare the intermediates and final compounds described herein were obtained from commercial vendors, and were used as is upon receipt.

All temperatures are degrees Celsius (° C.) unless otherwise noted.

Ambient temperature is 15-25° C.

Most compounds were purified by reverse-phase preparative HPLC, MPLC on silica gel, SFC, recrystallization and/or swish (suspension in a solvent followed by filtration of the solid).

The course of the reactions was followed by thin layer chromatography (TLC) and/or LCMS and/or NMR and reaction times are given for illustration only.

All end products were analyzed by NMR and LCMS.

Intermediates were analyzed by NMR and/or TLC and/or LCMS.

Method 1

General procedures to prepare intermediates of the instant invention are described in Scheme 1. Optionally substituted alkyl aldehydes or ketones I are condensed with diethyl (cyanomethyl)phosphonate in the presence of a suitable base, such as potassium tert-butoxide, potassium hydroxide, sodium hydride, or triethylamine/LiBr to yield substituted acrylonitriles II used as intermediates in the synthesis of examples of the instant invention.

SCHEME 1

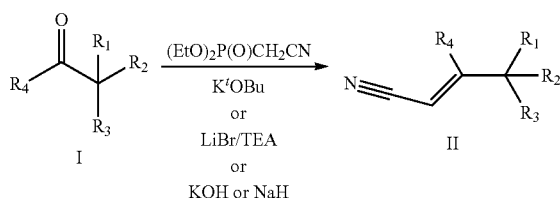

Method 2

General procedures to prepare intermediates of the instant invention are described in Scheme 2. In Scheme 2, The sum of n+m can be 1, 2, 3, or 4. Optionally substituted carbamate protected heterocyclic ketones III are condensed with diethyl (cyanomethyl)phosphonate or another suitable cyanoalkylphosphonate in the presence of a suitable base, such as potassium tert-butoxide or TEA/LiBr, to yield optionally substituted acrylonitriles IV used as intermediates in the synthesis of examples of the instant invention.

SCHEME 2

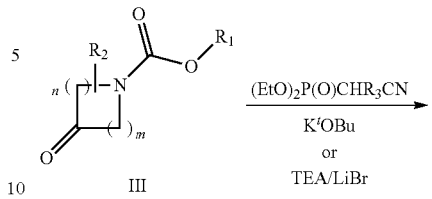

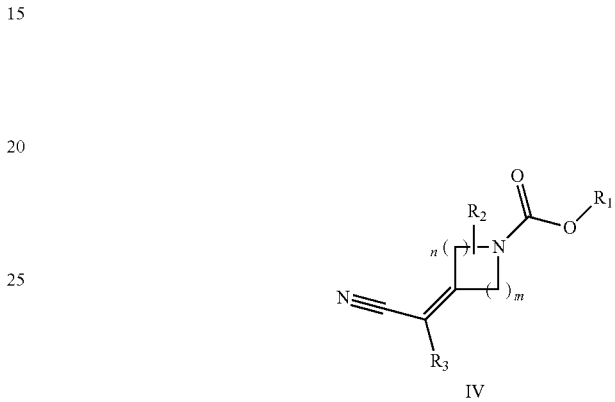

Method 3

General procedures to prepare intermediates of the instant invention are described in Scheme 3. Carbamate protected optionally substituted acrylonitriles IV are deprotected in the presence of a suitable acid, such as TFA or HCl, to form amino intermediates V that are further derivatized to form sulfonamides VI, carbamates VII, N-arylated intermediates VIII, or amides IX. Sulfonamide derivatives VI are formed by reacting deprotected optionally substituted acrylonitriles with optionally substituted sulfonyl chlorides in a suitable solvent, such as DCM, using an appropriate base, such as DIPEA. Carbamate derivatives VII are formed by reacting deprotected optionally substituted acrylonitriles with a doubly activated carbonyl equivalent, such as DSC or triphosgene, and optionally substituted alcohols in the presence of a suitable base, such as TEA. Alternatively, carbamate derivatives VII may be prepared via reaction of the amine and an activated carbamoyl moiety such as an alkyl chloroformate in the presence of a suitable base, such as 2,6-lutidine, DIPEA or TEA, in a suitable solvent such as DCM. N-arylated derivatives VIII are formed by reacting deprotected optionally substituted acrylonitriles with optionally substituted electronically-deficient aryl halides using an appropriate base, such as TEA, in a solvent, such as DMF or NMP, at or around 120° C. Amide derivatives IX are formed by reacting deprotected optionally substituted acrylonitriles with optionally substituted carboxylic acids in the presence of a suitable coupling agent such as EDC, CDI or HATU, in the presence of a suitable base such as TEA or Hunig's base. Alternatively, amide derivatives IX can be prepared in certain instances using an activated acylating reagent such as the acid chloride in place of the carboxylic acid.

SCHEME 3

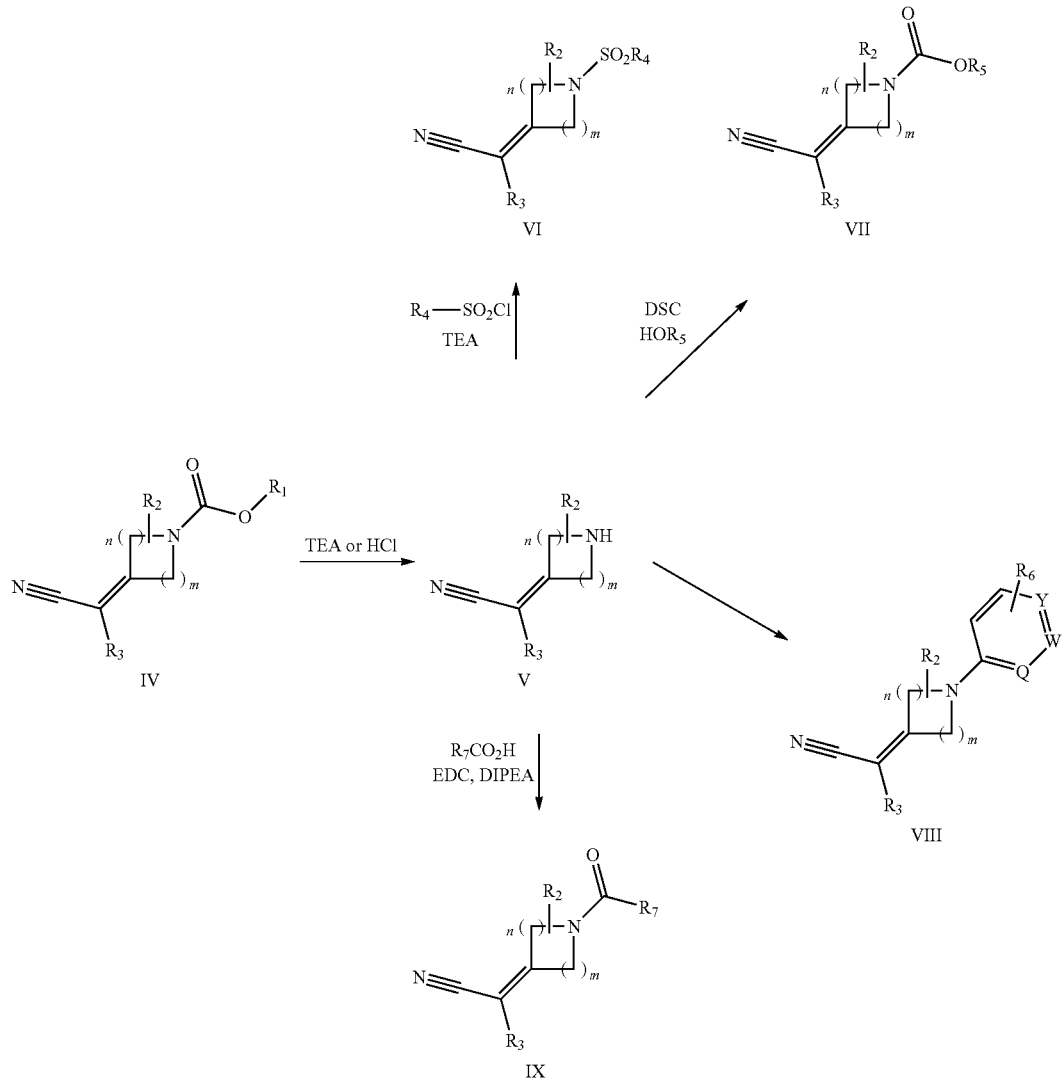

Method 4

General procedures to prepare intermediates of the instant invention are described in Scheme 4. Using an appropriate base, such as DBU, in a suitable solvent, such as MeCN, EtOH, n-BuOH or tert-BuOH, at a temperature between 25-110° C. either the unprotected pyrazolopyridone X or protected pyrazolopyridone XI can undergo conjugate addition to optionally substituted acrylonitriles to yield alkylated unprotected pyrazolopyridones XII or protected pyrazolopyridones XIII, an intermediate in the synthesis of examples of the instant invention. Deprotection of XIII to the free alkylated pyridone XII can then be effected either using a suitable acid, such as TFA, or under hydrogenolysis conditions using Pd on carbon at approximately 1 atmosphere of hydrogen, in a suitable solvent such as EtOAc, EtOH, MeOH, or using combinations of solvents thereof.

SCHEME 4

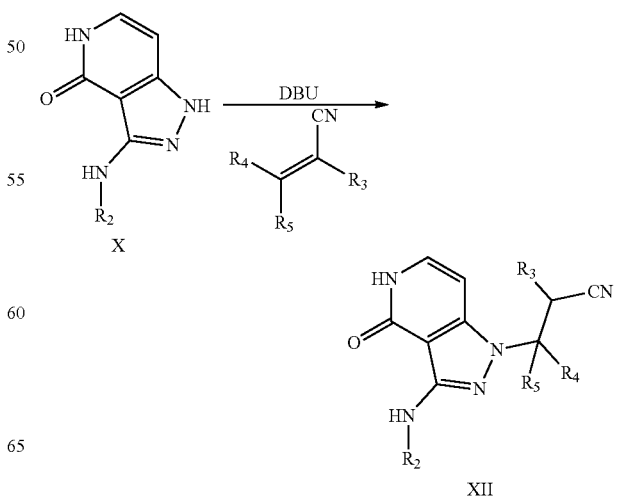

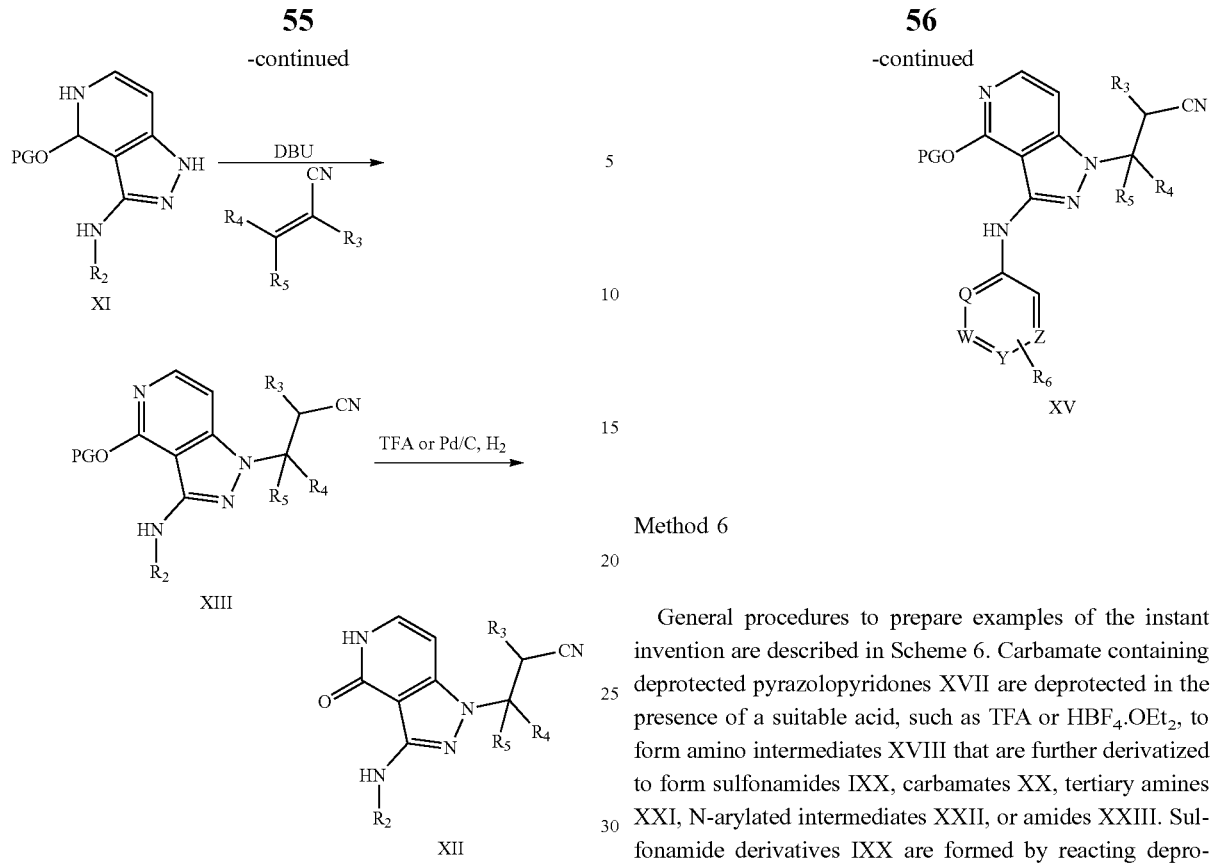

Method 5

General procedures to prepare examples of the instant invention are described in Scheme 5. Alkylated 3-amino pyrazolopyrimidines XIII (R$_2$=H) are cross coupled to aryl and heteroaryl halides XIV using an appropriate catalytic palladium-ligand system, such as Pd$_2$(dba)$_3$ or Pd$_2$(dba)$_3$·CHCl$_3$, and 2-di-tert-butylphosphino-2',4',6'-triisopropylbiphenyl (t-Bu XPhos) or di-tert-butyl[3,4,5,6-tetramethyl-2', 4',6'-tri(propan-2-yl)biphenyl-2-yl]phosphane (Me$_4$ $^t$Bu-XPhos), or 2-dicyclohexylphosphino-2',4',6'-triisopropylbiphenyl (XPhos). Typical conditions employ 1-2 equivalents of the aryl/heteroaryl halide relative to the pyrazolopyrimidine with 10-25% Pd precatalyst loading, using an approximate Pd:ligand ratio of 1:2 to 1:2.5. Typically, the cross coupling is carried out using either 2-propanol or t-amyl alcohol solvents, and between 1-3.1 equivalents of KOAc or K$_3$PO$_4$ base. Reactions were typically carried out between 65-90° C., to yield intermediates XV of the instant invention.

SCHEME 5

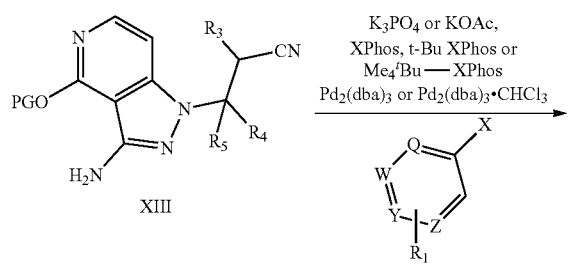

Method 6

General procedures to prepare examples of the instant invention are described in Scheme 6. Carbamate containing deprotected pyrazolopyridones XVII are deprotected in the presence of a suitable acid, such as TFA or HBF$_4$.OEt$_2$, to form amino intermediates XVIII that are further derivatized to form sulfonamides IXX, carbamates XX, tertiary amines XXI, N-arylated intermediates XXII, or amides XXIII. Sulfonamide derivatives IXX are formed by reacting deprotected optionally substituted acrylonitriles with optionally substituted sulfonyl chlorides in a suitable solvent, such as DCM, using an appropriate base, such as DIPEA or TEA. Carbamate derivatives XX are formed by reacting deprotected optionally substituted acrylonitriles with a doubly activated carbonyl equivalent, such as DSC or triphosgene, and optionally substituted alcohols in the presence of a suitable base, such as DIPEA or TEA. Alternatively, carbamate derivatives XX may be prepared via reaction of the amine and an activated carbamoyl moiety such as an alkyl chloroformate in the presence of a suitable base, such as 2,6-lutidine, DIPEA or TEA, in a suitable solvent such as DCM. Tertiary amine derivatives XXI may be prepared via reaction of the amine an an appropriate carbonyl containing compound, such as an aldehyde or ketone, in the presence of a suitable acid catalyst such as TFA and a suitable reducing agent, such as sodium triacetoxyborohydride. N-arylated derivatives XXII are formed by reacting deprotected optionally substituted acrylonitriles with optionally substituted electronically-deficient aryl halides using an appropriate base, such as TEA, in a solvent, such as DMF or NMP, at or around 120° C. Amide derivatives XXIII are formed by reacting deprotected optionally substituted acrylonitriles with optionally substituted carboxylic acids in the presence of a suitable coupling agent such as EDC, CDI or HATU, in the presence of a suitable base such as TEA or DIPEA. Alternatively, amide derivatives XXIII can be prepared in certain instances using an activated acylating reagent such as the acid chloride in place of the carboxylic acid.

SCHEME 6
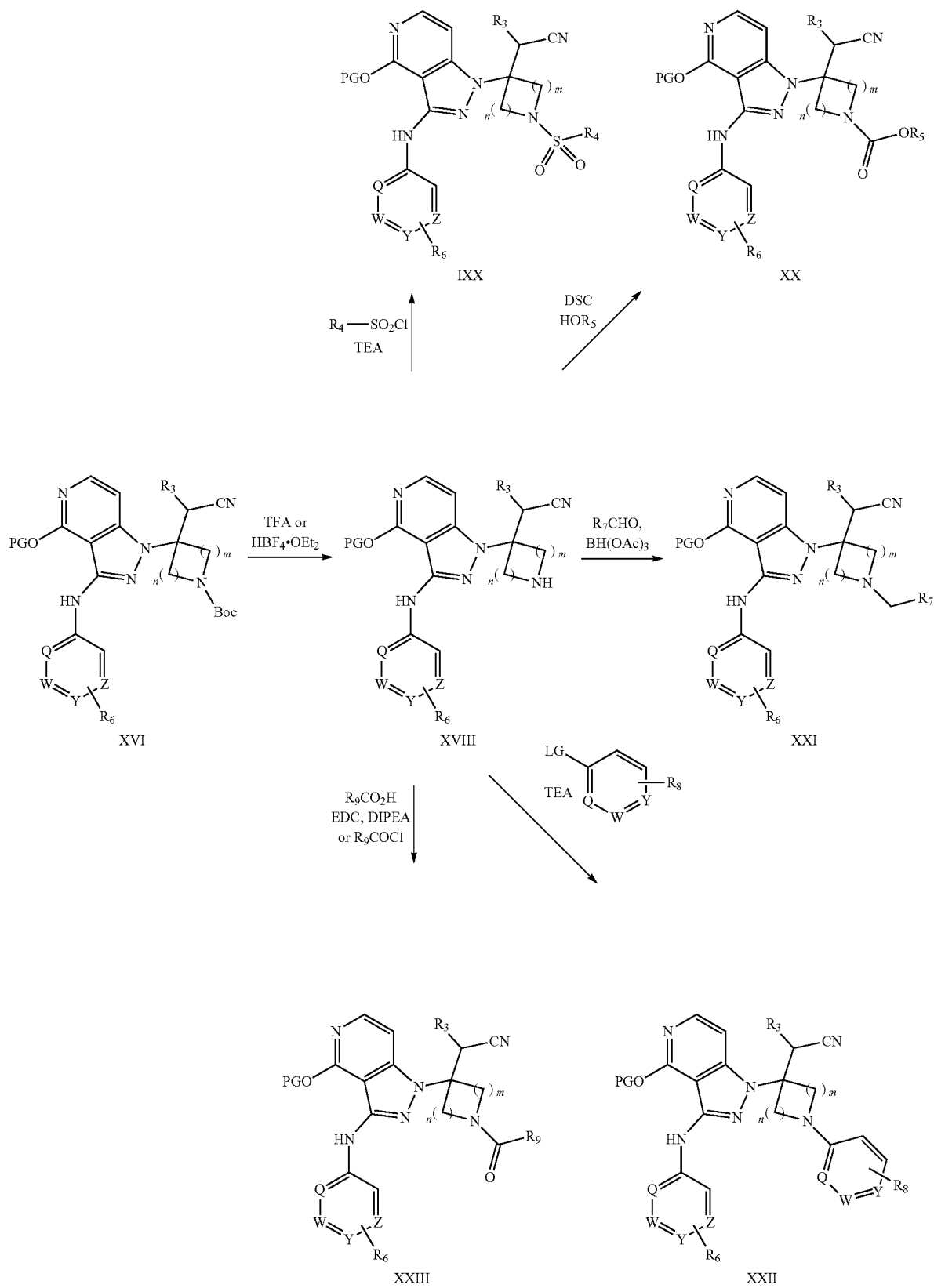

Method 7

General procedures to prepare examples of the instant invention are described in Scheme 7. Protected pyrazolopyrimidines XV are deprotected in the presence of acid, such as TFA or HCl, to afford the deprotected pyrazolopyridones XVI. Alternatively, in the case of hydrolytically unstable pyridone protecting groups (e.g. PG=Bn), deprotection could be achieved under hydrogenolysis conditions using Pd on Carbon in the presence of hydrogen in a suitable solvent such as EtOAc, EtOH, MeOH, or combinations of solvents thereof.

SCHEME 7

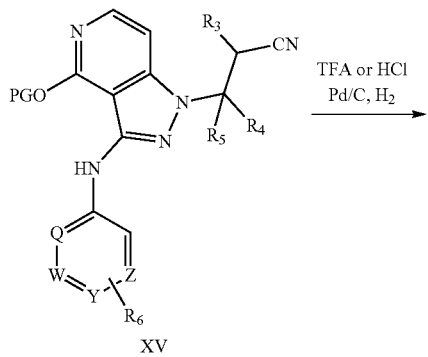

INTERMEDIATES

The following experimental procedures detail the preparation of chemical materials used in the synthesis of examples of the instant invention. The exemplified procedures are for illustrative purposes only, and are not intended to limit the scope of the instant invention in any way.

Intermediate 1

4-(benzyloxy)-1H-pyrazolo[4,3-c]pyridin-3-amine

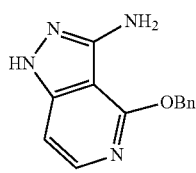

Step 1: 2-(benzyloxy)-4-methoxynicotinonitrile

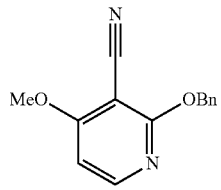 [SMILES: COc1ccnc(OCc2ccccc2)c1C#N]

To a solution of 2-hydroxy-4-methoxynicotinonitrile (60 g, 0.4 mol) in toluene (0.60 L) was added $Ag_2CO_3$ (0.14 kg, 0.51 mol) and BnBr (87 g, 0.51 mol) at room temperature. The mixture was stirred at 50° C. for 3 hours. The mixture was filtered and the cake washed with DCM. The filtrate was concentrated in vacuo and petroleum ether (100 mL) was added to the residue and the solid was filtered to give 2-(benzyloxy)-4-methoxynicotinonitrile as a solid. LRMS (ESI) calc'd for $C_{14}H_{13}N_2O_2$ [M+H]$^+$: 241, found 241. $^1$H NMR (600 MHz CDCl$_3$): δ 8.21 (d, J=6.6 Hz, 1H), 7.48 (d, J=7.8 Hz, 2H), 7.38 (m, 2H), 7.32 (m, 1H), 6.58 (d, J=6.0 Hz, 1H), 5.51 (s, 2H), 3.99 (s, 3H).

Step 2: 4-(benzyloxy)-1H-pyrazolo[4,3-c]pyridin-3-amine

A suspension of 2-(benzyloxy)-4-methoxynicotinonitrile (100 g, 410 mmol) in hydrazine hydrate (0.20 kg, 4.1 mol) and n-BuOH (600 mL) was heated to reflux overnight. The mixture was concentrated in vacuo and purified by silica chromatography, eluting with 25% ethyl acetate in hexanes. Concentration of the desired fraction in vacuo afforded compound I-1. $^1$H NMR (400 MHz CDCl$_3$) δ 9.97 (s, 1H), 7.75 (d, J=6.4 Hz, 1H), 7.40 (d, J=7.2 Hz, 2H), 7.24-7.33 (m, 3H), 6.69 (d, J=6.4 Hz, 1H), 5.46 (s, 2H), 4.50 (s, 2H).

Intermediate 2

3-amino-1H-pyrazolo[4,3-c]pyridin-4-ol

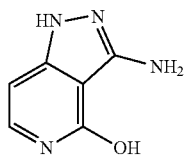

3-Cyano-2-hydroxy-4-methoxypyridine (1.00 g, 6.66 mmol) was dissolved in hydrazine hydrate (24.8 mL, 260 mmol) in a pressure vessel. The reaction mixture was heated to 140° C. for 21 hours, then cooled to ambient temperature and allowed to stir for an additional 48 hours. The reaction mixture was concentrated to give a solid that was slurried in diethyl ether, filtered, and washed with diethyl ether. The solid was dried under vacuo to give I-2. LRMS (ESI) calc'd for $C_6H_7N_4O$ [M+H]$^+$: 151, found 151.

Intermediate 3

3-(phenylamino)-1H-pyrazolo[4,3-c]pyridin-4(5H)-one

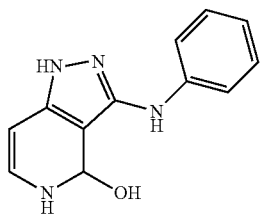

I-3

3-Amino-1H-pyrazolo[4,3-c]pyridin-4-ol (50.0 mg, 0.333 mmol), 2-di-t-butylphosphino-3,4,5,6-tetramethyl-2',4',6'-tri-i-propylbiphenyl (4.0 mg, 8.3 gmol), Pd$_2$dba$_3$ (30.5 mg, 0.033 mmol), potassium phosphate tribasic (141 mg, 0.666 mmol), and bromobenzene (26 μL, 0.25 mmol) were suspended in 2-propanol (3.0 mL). The reaction mixture was sparged with argon for 10 minutes, then heated to 75° C. for 2 hours. The reaction mixture was diluted in 3:1 chloroform/isopropanol, washed with water and brine, dried over Na$_2$SO$_4$, filtered and concentrated in vacuo. The residue was purified by preparative reverse phase chromatography, eluting with acetonitrile/water with 0.1% TFA modifier. The fractions containing the desired product were combined and diluted in 3:1 chloroform/isopropanol, washed with aqueous sodium bicarbonate and brine. The combined aqueous layers were back extracted with 3:1 chloroform/isopropanol (×1) and the combined organic layers were dried over Na$_2$SO$_4$, filtered and concentrated in vacuo to give the desired product I-3 as a solid. LRMS (ESI) calc'd for C$_{12}$H$_{11}$N$_4$O [M+H]$^+$: 227, found 227.

Intermediate I-4

4-fluorodihydro-2H-pyran-3(4H)-one

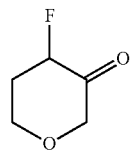

I-4

Step 1: ((5,6-dihydro-2H-pyran-3-yl)oxy)trimethylsilane

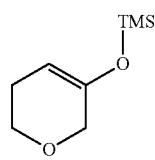 [SMILES: C[Si](C)(C)OC1=CCCOC1]

Dihydro-2H-pyran-3(4H)-one (4.00 g, 40.0 mmol) was dissolved in THF (32.0 mL) and chlorotrimethylsilane (12.8 mL, 100 mmol) was added. The reaction was stirred at room temperature for 10 minutes. Triethylamine (15.0 mL, 108 mmol) was then added dropwise under nitrogen. A white precipitate formed and the resulting suspension was heated to 70° C. over the weekend. The reaction mixture was cooled to room temperature and concentrated in vacuo. Pentane (80 mL) was added, the suspension was filtered, and the solid was washed with pentane (40 mL). The filtrate was concentrated in vacuo to give the title compound as a liquid that was used as is in the next step without further purification. $^1$H NMR (500 MHz, CDCl$_3$) δ 4.98-4.92 (m, 1H), 3.88 (m, 2H), 3.69 (t, J=5.5 Hz, 2H), 2.16 (m, 2H), 0.19 (s, 9H).

Step 2: 4-fluorodihydro-2H-pyran-3(4H)-one (I-4)

To a solution of ((5,6-dihydro-2H-pyran-3-yl)oxy)trimethylsilane (5.1 g, 30 mmol) in acetonitrile (75.0 mL) at 0° C., was added Selectfluor® (15.8 g, 44.5 mmol). The reaction was then stirred to room temperature overnight, diluted with ethyl acetate, washed with brine, and the aqueous layer was extracted with ethyl acetate (×2). The combined organic layers were dried over Na$_2$SO$_4$, filtered, and concentrated in vacuo to afford a solid. The solid was taken up in DCM, filtered, and concentrated in vacuo to afford I-4 as a liquid that was used without further purification. $^1$H NMR (500 MHz, CDCl$_3$) δ 5.06 (ddd, J=6.9, 11.1, 48.0 Hz, 1H), 4.21 (dd, J=4.5, 14.9 Hz, 1H), 4.11 (dt, J=4.1, 12.7 Hz, 1H), 3.84 (m, 2H), 2.50 (m, 1H), 2.37-2.24 (m, 1H).

Intermediate 5-1 tert-butyl 4-(cyanomethylene)-3-fluoropiperidine-1-carboxylate

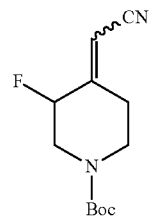

I-5-1

To a solution of diethyl (cyanomethyl)phosphonate (67 g, 0.38 mol) in THF (0.70 L) was added TEA (70 g, 0.69 mol) and LiBr (36 g, 0.42 mol) at room temperature. The reaction was stirred at room temperature for 30 minutes before tert-butyl-3-fluoro-4-oxopiperidine-1-carboxylate (75 g, 0.35 mol) was added. The reaction was stirred for another 3 hours, then H$_2$O (1.0 L) was added, and the mixture was extracted with EtOAc (×3). The organic layers were washed with brine, dried over Na$_2$SO$_4$, filtered and concentrated in vacuo. The residue was purified by silica chromatography, eluting with 10% ethyl acetate in hexanes. Concentration in vacuo of the desired fractions afforded the desired product as a solid, I-5-1. $^1$H NMR (600 MHz DMSO-d6): δ 5.88 (s, 1H), 5.27 (m, 0.5H), 5.19 (m, 0.5H), 3.86-3.40 (br m, 4H), 2.65 (m, 1H), 2.51 (m, 1H), 1.45 (s, 9H).

Following analogous procedure as described above for Intermediate 5-1, the following acrylonitrile intermediates shown in Table 1 were prepared:

TABLE 1

| Intermediate # | Structure | Compound Name | $^1$H NMR/MS |
|---|---|---|---|
| 1-5-2 | ![structure] | tert-butyl 4-(cyanomethylene)-3-methylpiperidine-1-carboxylate | LRMS (ESI) calc'd for $C_8H_{13}N_2$ [M – Boc + H]$^+$: 137, found 137. |
| 1-5-3 | ![structure] | 2-(4-fluorodihydro-2H-pyran-3(4H)-ylidene)acetonitrile | $^1$H NMR (500 MHz, CDCl$_3$) δ 5.66-5.50 (m, 1H), 5.55 (s, 1H), 5.26-5.08 (m, 1H), 4.75 (dd, J = 4.1, 13.6 Hz, 1H), 4.33 (m, 1H), 3.62 (dddd, J = 1.3, 2.6, 10.7, 12.0 Hz, 1H), 2.30-2.14 (m, 1H), 2.12-1.96 (m, 1H). |

Intermediate 6-1 tert-butyl 4-(cyanomethylidene)piperidine-1-carboxylate

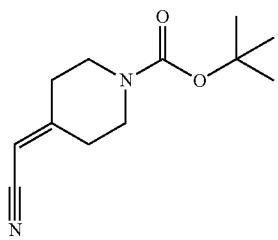

I-6-1

To a cooled, 0° C. solution of potassium tert-butoxide (263 mL, 263 mmol, 1.0 M in THF) and THF (200 mL), was slowly added diethyl (cyanomethyl)phosphonate (43.7 mL, 276 mmol). The reaction mixture was maintained at 0° V for 10 minutes, then warmed to ambient temperature and maintained for 1 hour. The mixture was cooled to 0° C. and treated with the dropwise addition of tert-butyl 4-oxopiperidine-1-carboxylate (50.0 g, 251 mmol) in THF (150 mL) over 30 minutes. After addition, the mixture was maintained at 0° C. for 20 minutes, then warmed to ambient temperature and maintained for 18 hours. The reaction mixture was then diluted with water (800 mL) and extracted with EtOAc (×2). The combined organic extracts were washed with water, brine, dried over anhydrous Na$_2$SO$_4$, filtered, and concentrated in vacuo to afford the title compound as a solid, I-6-1. $^1$H NMR (600 MHz, CDCl$_3$): δ 5.19 (s, 1H), 3.48-3.53 (m, 4H), 2.56 (t, J=5.4 Hz, 2H), 2.33 (t, J=5.4 Hz, 2H), 1.47 (s, 9H).

Following an analogous procedure to that used for Intermediate I-6-1, the following acrylonitrile intermediates in Table 2 were prepared:

TABLE 2

| Intermediate # | Structure | Compound Name | $^1$H NMR/LRMS |
|---|---|---|---|
| 1-6-2 | ![structure] | 2 (dihydro-2H-pyran-3(4H)-ylidene)acetonitrile | LRMS (ESI) calc'd for $C_7H_{10}NO$ [M + H]$^+$: 124, found 124. |
| 1-6-3 | ![structure] | tert-butyl 3-(cyanomethylidene)azetidine-1-carboxylate | $^1$H NMR (600 MHz, CDCl$_3$): δ 5.38-5.35 (m, 1H), 4.69 (m, 2H), 4.61-4.58 (m, 2H), 1.44 (s, 9H). |
| 1-6-4 | ![structure] | 2-(1,4-dioxaspiro[4.5]decan-8-ylidene)acetonitrile | $^1$H NMR (600 MHz, CDCl$_3$): δ 5.11 (s, 1H), 3.97 (m, 4H), 2.65 (t, J = 7.1 Hz, 2H), 2.42 (t, J = 7.1 Hz, 2H), 1.78 (t, J = 7.1 Hz, 2H), 1.75 (t, J = 7.1 Hz, 2H). |

TABLE 2-continued

| Intermediate # | Structure | Compound Name | ¹H NMR/LRMS |
|---|---|---|---|
| 1-6-5 | 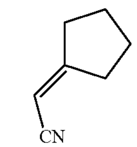 | 2-cyclopentylideneacetonitrile | ¹HNMR (CDCl$_3$, 500 MHz): δ 5.22 (m, 1H), 2.60-2.56 (m, 2H), 2.45-2.41 (m, 2H), 1.30-1.20 (m, 4H). |

Intermediates 7-1 and 7-2

(3R,4S and 3S,4R)-tert-butyl 4-(3-amino-4-(benzyloxy)-1H-pyrazolo[4,3-c]pyridin-1-yl)-4-(cyanomethyl)-3-fluoropiperidine-1-carboxylate (I-7-1), and (3S,4S and 3R,4R)-tert-butyl 4-(3-amino-4-(benzyloxy)-1H-pyrazolo[4,3-c]pyridin-1-yl)-4-(cyanomethyl)-3-fluoropiperidine-1-carboxylate (I-7-2)

I-7-1

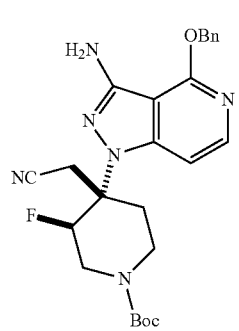

I-7-2

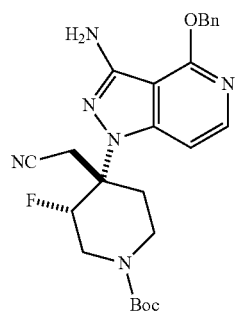

To a solution of tert-butyl 4-(cyanomethylene)-3-fluoropiperidine-1-carboxylate (50 g, 208 mmol) and 4-(benzyloxy)-1H-pyrazolo[4,3-c]pyridin-3-amine (25 g, 104 mmol) in CH$_3$CN (200 mL) at room temperature, was added DBU (17.4 g, 115 mmol). The mixture was stirred at 50° C. for 48 hours before being concentrated in vacuo. Water (200 mL) was then added and the reaction was extracted with EtOAc (×3). The organic layer was washed with brine (500 mL), dried over Na$_2$SO$_4$, filtered and concentrated in vacuo. The residue was purified by silica chromatography, eluting with 9-33% EtOAc in hexanes to afford the two diastereomers as solids.

Major isomer I-7-1: LRMS (ESI) calc'd for C$_{25}$H$_{30}$N$_6$O$_3$F [M+H]$^+$: 481, found 481. ¹H NMR (600 MHz, DMSO-d6): δ 7.77 (d, J=6.1 Hz, 1H), 7.48 (d, J=6.5 Hz, 2H), 7.35 (t, J=7.6 Hz, 2H), 7.29 (t, J=7.2 Hz, 1H), 7.17 (d, J=6.1 Hz, 1H), 5.51 (s, 2H), 5.47 (m, 1H), 5.30 (s, 2H), 4.13 (t, J=13.1 Hz, 1H), 3.91 (d, J=13.1 Hz, 1H), 3.17 (m, 2H), 3.15 (m, 1H), 2.91 (br m, 1H), 2.75 (d, J=15.5 Hz, 1H), 2.05 (t, J=13.0 Hz, 1H), 1.37 (s, 9H). SFC separation was achieved using a ChiralPak OJ-H, with 30% methanol modifier in CO$_2$: retention times=3.7 (I-7-1A) & 5.7 (I-7-1B) minutes.

Minor isomer I-7-2: LRMS (ESI) calc'd for C$_{25}$H$_{30}$N$_6$O$_3$F [M+H]$^+$: 481, found 481. ¹H NMR (600 MHz, DMSO-d6): δ 7.77 (d, J=7.0 Hz, 1H), 7.55 (d, J=7.0 Hz, 2H), 7.43 (t, J=8.2 Hz, 2H), 7.36 (t, J=7.3 Hz, 1H), 7.25 (d, J=6.7 Hz, 1H), 5.56 (s, 2H), 5.49 (s, 2H), 5.23 (d, J=46.8 Hz, 1H), 4.18 (m, 2H), 3.57 (d, J=17.2 Hz, 1H), 3.46 (d, J=17.3 Hz, 1H), 3.35-3.14 (m, 2H), 2.67 (m, 1H), 2.44 (m, 1H), 1.38 (s, 9H). SFC separation was achieved using a ChiralPak AD-3, with 5-40% ethanol modifier (0.05% DEA in ethanol) in CO$_2$: retention times=5.4 (I-7-2A) & 6.1 (I-7-2B) minutes.

Following analogous procedure as described above for Intermediate 7-1 and 7-2, the following intermediates shown in Table 3 were prepared. In select cases, the general procedure was modified to alternatively utilize between 1.0-1.5 equivalents DBU, at 25-50° C.

TABLE 3

| Intermediate # | Structure | Compound Name | LRMS |
|---|---|---|---|
| I-7-3A | 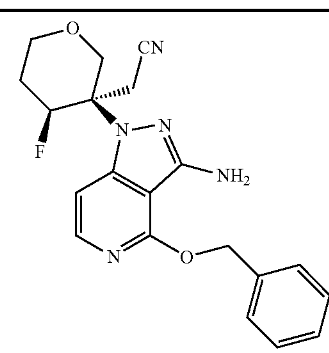 | 2-((3R,4S or 3S, 4R)-3-(3-amino-4-(benzyloxy)-1H-pyrazolo[4,3-c]pyridin-1-yl)-4-fluorotetrahydro-2H-pyran-3-yl)acetonitrile (Derived from Peak A via SFC: AD-H, 25% MeOH in CO$_2$, Tr = 4.8 minutes) | LRMS (ESI) calc'd for C$_{20}$H$_{21}$FN$_5$O$_2$ [M + H]$^+$: 382, found 382. |

| Intermediate # | Structure | Compound Name | LRMS |
|---|---|---|---|
| I-7-3B | 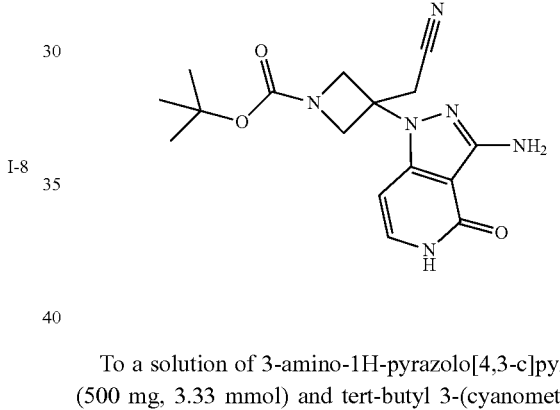 | 2-((3R,4S or 3A,4R)-3-(3-amino-4-(benzyloxy)-1H-pyrazolo[4,3-c]pyridin-1-yl)-4-fluorotetrahydro-2H-pyran-3-yl)acetonitrile (Derived from Peak B via SFC, AD-H, 25% MeOH in $CO_2$, Tr = 5.9 minutes) | LRMS (ESI) calc'd for $C_{20}H_{21}FN_5O_2$ $[M + H]^+$: 382, found 382. |

Intermediate 8 tert-butyl 4-(3-amino-4-(benzyloxy)-1H-pyrazolo[4,3-c]pyridin-1-yl)-4-(cyanomethyl)piperidine-1-carboxylate

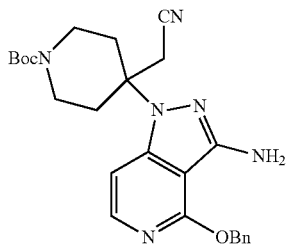

To a solution of 4-(benzyloxy)-1H-pyrazolo[4,3-c]pyridin-3-amine (155 g, 645 mmol) in $CH_3CN$ (2.50 L), was added (batchwise) tert-butyl 4-(cyanomethylene)piperidine-1-carboxylate (286 g, 1.29 mol) followed by dropwise addition of DBU (99.0 g, 650 mmol) at 20° C. over 20 minutes. The resulting solution was stirred for 3 days at 20° C., concentrated in vacuo at 40-45° C., and then purified by silica chromatography, eluting with 0-50% ethyl acetate/petroleum ether. Concentration of the desired fraction in vacuo afforded compound I-8. LRMS (ESI) calc'd for $C_{25}H_{31}N_6O_3$ $[M+H]^+$: 463, found 463. $^1$H NMR (300 MHz, $CDCl_3$): δ 7.82 (d, 1H), 7.34-7.50 (m, 5H), 6.84 (d, 1H), 5.54 (s, 2H), 4.51 (br s, 2H), 3.94-3.97 (d, 2H), 3.05 (br s, 2H), 2.85-2.90 (m, 2H), 2.79 (s, 2H), 1.92-2.04 (m, 2H), 1.45 (s, 9H).

Intermediate 9 tert-butyl 3-(3-amino-4-oxo-4,5-dihydro-1H-pyrazolo[4,3-c]pyridin-1-yl)-3-(cyanomethyl)azetidine-1-carboxylate To a solution of 3-amino-1H-pyrazolo[4,3-c]pyridin-4-ol (500 mg, 3.33 mmol) and tert-butyl 3-(cyanomethylidene)azetidine-1-carboxylate (356 mg, 1.83 mmol) in DMF (22.2 mL) was added DBU (0.602 mL, 4.00 mmol). The reaction was heated to 50° C. and allowed to stir for 1 hour, after which a second portion of tert-butyl 3-(cyanomethylidene)azetidine-1-carboxylate (356 mg, 1.83 mmol) was added to the reaction mixture. After an additional 2 hours at 50° C. the reaction was cooled, diluted with water (100 mL) and extracted with 3:1 $CHCl_3$:IPA (×3). The combined organic layers were washed once with brine (50 mL). The resulting organic layer was dried with $Na_2SO_4$, filtered and concentrated in vacuo. The residue was purified by reverse phase chromatography, eluting with acetonitrile/water with 0.1% TFA modifier. Fractions containing desired product were diluted with EtOAc, washed with saturated $NaHCO_3$, dried over $Na_2SO_4$, filtered, and concentrated in vacuo to afford compound I-9. LRMS (ESI) calc'd for $C_{16}H_{21}N_6O_3$ $[M+H]^+$: 345, found 345. $^1$H NMR (600 MHz, DMSO-d6): δ 10.92 (s, 1H), 7.07 (t, J=5.7 Hz, 1H), 6.20 (d, J=7.2 Hz, 1H), 5.46 (s, 2H), 4.35 (m, 2H), 4.15 (m, 2H), 3.28 (s, 2H) 1.34 (s, 9H).

Intermediate 10 tert-butyl 3-[3-amino-4-(benzyloxy)-1H-pyrazolo[4,3-c]pyridin-1-yl]-3-(cyanomethyl)azetidine-1-carboxylate

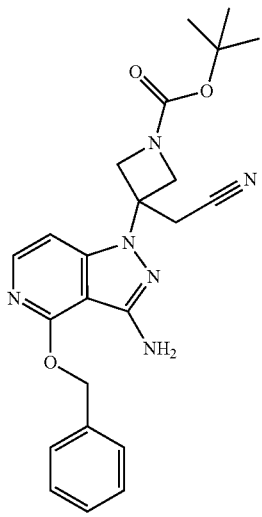

I-10

4-(Benzyloxy)-1H-pyrazolo[4,3-c]pyridin-3-amine (8.0 g, 33 mmol) and tert-butyl 3-(cyanomethylidene)azetidine-1-carboxylate (9.7 g, 50 mmol) were dissolved in acetonitrile (200 mL) and DBU (7.6 g, 50 mmol) was added. The resulting mixture was stirred for 2 hours at room temperature, then concentrated in vacuo and purified by silica chromatrography, eluting with 17-67% EtOAc in hexanes. Concentration of the desired fractions afforded compound 1-10, as a solid. LRMS (ESI) calc'd for $C_{23}H_{27}N_6O_3$ [M+H]$^+$: 435. found 435. $^1$H NMR (400 MHz, CDCl$_3$): δ 7.85 (d, J=6.4 Hz, 1H), 7.45 (d, J=7.2 Hz, 2H), 7.30-7.39 (m, 3H), 6.65 (d, J=6.4 Hz, 1H), 5.51 (s, 2H), 4.60 (d, J=9.2 Hz, 2H), 4.52 (s, 2H), 4.22 (d, J=9.6 Hz, 2H), 3.04 (s, 2H), 1.44 (s, 9H).

Intermediate 11

2-(4-(3-amino-4-(benzyloxy)-1H-pyrazolo[4,3-c]pyridin-1-yl)-1-(2,2-difluoropropanoyl)piperidin-4-yl)acetonitrile

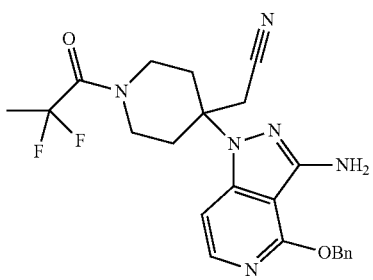

I-11

Step 1: 2-(piperidin-4-ylidene)acetonitrile HCl salt

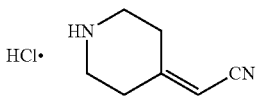

To tert-butyl 4-(cyanomethylene)piperidine-1-carboxylate (2.03 g, 9.15 mmol) was added HCl in dioxane (21 mL, 84 mmol, 4M) and the resulting slurry was stirred at room temperature for 30 minutes, then concentrated in vacuo to afford a crude product that was used as is without further purification. $^1$H NMR (600 MHz, DMSO-d6): δ 9.30 (br s, 1H), 5.66 (s, 1H), 3.20-3.10 (m, 4H), 2.67 (t, J=6.1 Hz, 2H), 2.56 (t, J=6.1 Hz, 2H).

Step 2: 2-(1-(2,2-difluoropropanoyl)piperidin-4-ylidene)acetonitrile

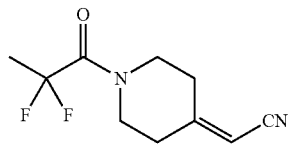

To the mixture of 2-(piperidin-4-ylidene)acetonitrile (1.12 g, 9.15 mmol), HATU (5.22 g, 13.7 mmol) in DCM (36.6 mL), was added DIPEA (8.0 mL, 46 mmol) and 2,2-difluoropropanoic acid (2.00 g, 18.3 mmol). The reaction mixture was stirred at room temperature for 2 hours and then concentrated in vacuo to afford a residue that was purified by silica chromatography, eluting with 3% EtOAc in hexanes. Concentration of the desired fraction afforded 2-(1-(2,2-difluoropropanoyl)piperidin-4-ylidene)acetonitrile as a solid. LRMS (ESI) calc'd for $C_{10}H_{13}F_2N_2O$ [M+H]$^+$: 215, found 215. $^1$H NMR (600 MHz, CDCl$_3$): δ 5.23 (s, 1H), 3.73-3.75 (m, 4H), 2.62-2.63 (m, 2H), 2.41 (q, J=6.2 Hz, 2H), 1.84 (t, J=19.9 Hz, 3H).

Step 3: 2-(4-(3-amino-4-(benzyloxy)-1H-pyrazolo[4,3-c]pyridin-1-yl)-1-(2,2-difluoropropanoyl)piperidin-4-yl)acetonitrile To a solution of 4-(benzyloxy)-1H-pyrazolo[4,3-c]pyridin-3-amine (4.76 g, 19.8 mmol) in acetonitrile (45 mL) was added 2-(1-(2,2-difluoropropanoyl)piperidin-4-ylidene)acetonitrile (2.12 g, 9.90 mmol) and DBU (1.49 mL, 9.90 mmol). The reaction mixture was stirred at 40° C. for 72 hours, then concentrated in vacuo to afford a residue that was purified by silica chromatography, eluting with 43% EtOAc in hexanes. LRMS (ESI) calc'd for $C_{23}H_{25}F_2N_6O_2$ [M+H]$^+$: 455, found 455. $^1$H NMR (600 MHz, DMSO-d6): δ 7.76 (d, J=6.4 Hz, 1H), 7.52 (d, J=7.5 Hz, 2H), 7.39 (t, J=7.9 Hz, 2H), 7.32 (t, J=7.3 Hz, 1H), 7.20 (d, J=6.3 Hz, 1H), 5.52 (s, 2H), 5.46 (s, 2H), 4.12 (m, 1H), 4.01 (m, 1H), 3.31 (m, 1H), 3.17 (s, 2H), 3.01 (m, 1H), 2.83-2.77 (m, 2H), 2.04-1.94 (m, 2H), 1.79 (t, J=20.1 Hz, 3H).

Intermediate 12 methyl 4-(3-amino-4-(benzyloxy)-1H-pyrazolo[4,3-c]pyridin-1-yl)-4-(cyanomethyl)piperidine-1-carboxylate

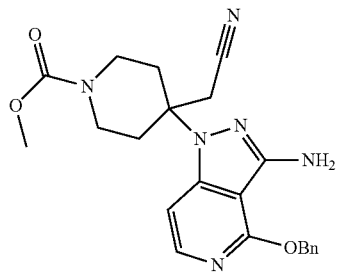

I-12

Step 1: 2-(piperidin-4-ylidene)acetonitrile TFA salt

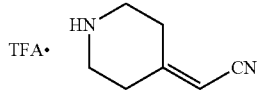

To a solution of tert-butyl 4-(cyanomethylidene)piperidine-1-carboxylate (3.00 g, 13.5 mmol) in dichloromethane (30 mL) at 20° C., was added trifluoroacetic acid (13.0 g, 115 mmol). The resulting solution was stirred for 1 hour at 20° C. and then concentrated in vacuo to afford an oil that was used as is.

Step 2: methyl 4-(cyanomethylene)piperidine-1-carboxylate

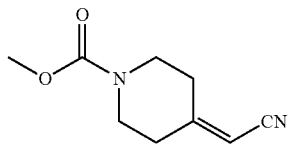

To a solution of crude 2-(piperidin-4-ylidene)acetonitrile TFA salt (3.00 g, 13.7 mmol) in dichloromethane (30 mL), was added triethylamine (7.50 g, 74.1 mmol) and chloro(methoxy)methanone (2.80 g, 29.6 mmol). The resulting solution was stirred for 30 minutes at 20° C. and then concentrated in vacuo. The residue was purified by silica chromatography, eluting with 25% EtOAc in hexanes. Concentration of the desired fractions afforded methyl 4-(cyanomethylidene)piperidine-1-carboxylate as a solid. $^1$H NMR (400 MHz, CDCl$_3$): δ 5.22 (s, 1H), 3.74 (s, 3H), 3.57 (m, 4H), 2.59 (t, J=2.8 Hz, 2H), 2.36 (t, J=2.8 Hz, 2H).

Step 3: methyl 4-(3-amino-4-(benzyloxy)-1H-pyrazolo[4,3-c]pyridin-1-yl)-4-(cyanomethyl)piperidine-1-carboxylate (I-12)

To a solution of 4-(benzyloxy)-1H-pyrazolo[4,3-c]pyridin-3-amine (1.00 g, 4.16 mmol) in ethanol (10 mL), was added methyl 4-(cyanomethylidene)piperidine-1-carboxylate (750 mg, 4.16 mmol) and DBU (630 mg, 4.14 mmol). The resulting solution was stirred for 8 hours at 78° C. The reaction mixture was concentrated in vacuo and purified by silica chromatrography, eluting with 50% EtOAc in hexanes and then the desired fractions were concentrated in vacuo and repurified by preparative TLC using DCM/MeOH=10:1 to afford compound I-12 as a solid. $^1$H NMR (400 MHz, CDCl$_3$): δ 7.86 (d, J=6.4 Hz, 1H), 7.50 (d, J=7.2 Hz, 2H), 7.36-7.44 (m, 3H), 6.86 (d, J=6.4 Hz, 1H), 5.57 (s, 2H), 4.53 (m, 2H), 4.12 (m, 2H), 3.72 (s, 3H), 3.05-3.17 (m, 2H), 2.90-2.98 (m, 2H), 2.82 (s, 2H), 1.96-2.05 (m, 2H).

Intermediate 13 methyl 5-(3-amino-4-(benzyloxy)-1H-pyrazolo[4,3-c]pyridin-1-yl)-5-(cyanomethyl)tetrahydro-2H-pyran-2-carboxylate

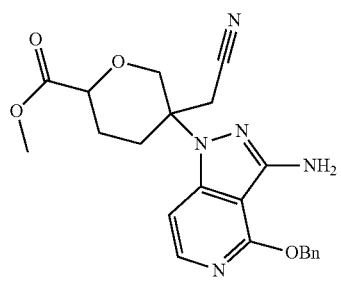

I-13

Step 1: methyl 5-oxotetrahydro-2H-pyran-2-carboxylate

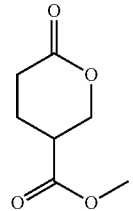

To a solution of methyl 5-hydroxy-tetrahydro-2H-pyran-2-carboxylate (487 mg, 3.04 mmol) in CH$_2$Cl$_2$ (10 mL), was added Dess-Martin periodinane (1.60 g, 3.80 mmol). The reaction was stirred at room temperature for 2 hours, then diluted with saturated sodium thiosulfate solution and saturated sodium bicarbonate solution and filtered through Celite. The aqueous layer was extracted with CH$_2$Cl$_2$ (×2) and the combined organic layers were washed with brine, dried over sodium sulfate, filtered and concentrated in vacuo to afford a residue that was purified by silica chromatography, eluting with 33% EtOAc in hexanes. Concentration of the desired fractions afforded methyl 5-oxotetrahydro-2H-pyran-2-carboxylate as an oil. $^1$H NMR (600 MHz, CDCl$_3$): δ 4.40 (dd, J=9.2, 4.9 Hz, 1H), 4.32 (d, J=16.9 Hz, 1H), 4.05 (d, J=16.9 Hz, 1H), 3.79 (s, 3H), 2.56 (m, 2H), 2.39 (m, 1H), 2.21 (m, 1H).

Step 2: methyl 5-(cyanomethylene)tetrahydro-2H-pyran-2-carboxylate

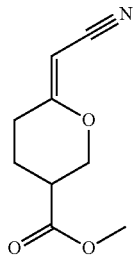

A mixture of triethylamine (594 µL, 4.26 mmol), lithium bromide (341 mg, 3.93 mmol) and diethyl (cyanomethyl) phosphonate (379 µL, 2.34 mmol) in THF (5 mL) was stirred for 30 minutes at room temperature. Methyl 5-oxotetrahydro-2H-pyran-2-carboxylate (337 mg, 2.13 mmol) in THF (1 mL) was then added and the reaction mixture was stirred for 12 hours before being quenched with water (5 mL) and extracted with ethyl acetate (×4). The combined organic layers were dried over sodium sulfate, filtered, and concentrated in vacuo to afford a residue that was purified by silica chromatography, eluting with 38% EtOAc in hexanes. Concentration of the desired fractions afforded the title compound (E and Z=5:3) as an oil. LRMS (ESI) calc'd for $C_9H_{12}NO_3$ [M+H]$^+$: 182, found 182. $^1$H NMR (600 MHz, DMSO-d6): δ 5.62 (d, J=16.7 Hz, 1H), 4.46 (d, J=13.7 Hz, 0.5H), 4.29 (m, 1.5H), 4.16 (d, J=13.7 Hz, 0.5H), 4.09 (d, J=13.4 Hz, 0.5H), 3.63 (d, J=1.4 Hz, 3H), 2.68 (dt, J=14.7, 4.5 Hz, 0.5H), 2.52 (m, 1.5H), 2.02 (m, 1H), 1.69 (m, 1H).

Step 3: 5-(3-amino-4-(benzyloxy)-1H-pyrazolo[4,3-c]pyridin-1-yl)-5-(cyanomethyl)tetrahydro-2H-pyran-2-carboxylate To 4-(benzyloxy)-1H-pyrazolo[4,3-c]pyridin-3-amine (1.56 g, 6.46 mmol) in acetonitrile (4.3 mL) was added methyl 5-(cyanomethylene)tetrahydro-2H-pyran-2-carboxylate (234 mg, 1.29 mmol) and DBU (195 µL, 1.29 mmol). The reaction mixture was stirred at 40° C. for 72 hours, then concentrated in vacuo to afford a residue that was purified by silica chromatography, eluting with 33% EtOAc in hexanes. Concentration of the desired fractions afforded compound 1-13 as a solid. LRMS (ESI) calc'd for $C_{22}H_{24}N_5O_4$ [M+H]$^+$: 422, found 422. $^1$H NMR (600 MHz, DMSO-d6): δ 7.70 (d, J=6.4 Hz, 1H), 7.46 (d, J=7.6 Hz, 2H), 7.35 (t, J=7.5 Hz, 2H), 7.29 (d, J=7.3 Hz, 1H), 7.17 (d, J=6.4 Hz, 1H), 5.48 (s, 2H), 5.40 (s, 2H), 4.29 (dd, J=9.4, 3.9 Hz, 1H), 4.19 (d, J=12.0 Hz, 1H), 4.05 (d, J=11.7 Hz, 1H), 3.66 (s, 3H), 3.32 (m, 1H), 3.28 (d, J=9.1 Hz, 2H), 2.55 (m, 1H), 2.49-2.44 (m, 1H), 1.94-1.78 (m, 2H).

Intermediate 14 tert-butyl 5-(3-amino-4-(benzyloxy)-1H-pyrazolo[4,3-c]pyridin-1-yl)-5-(cyanomethyl)tetrahydro-2H-pyran-2-carboxylate

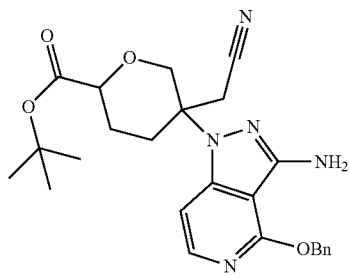

I-14

Step 1: (2S,5R)-methyl 5-((tert-butyldimethylsilyl)oxy)tetrahydro-2H-pyran-2-carboxylate

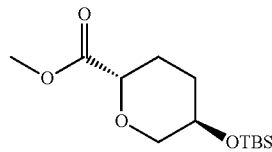 [SMILES: COC(=O)[C@@H]1CC[C@@H](O[Si](C)(C)C(C)(C)C)CO1]

To a solution of (2S,5R)-methyl 5-hydroxytetrahydro-2H-pyran-2-carboxylate (3.48 g, 21.7 mmol) in $CH_2Cl_2$ (90 mL) was added imidazole (2.22 g, 32.6 mmol) and tert-butyldimethylsilyl chloride (3.93 g, 26.1 mmol). The reaction mixture was stirred at room temperature overnight, then quenched with water (50 mL) and extracted with $CH_2Cl_2$ (×3). The combined organic layers were concentrated in vacuo to afford a residue that was purified by silica chromatography, eluting with 10% EtOAc in hexanes. Concentration of the desired fractions afforded (2S,5R)-methyl 5-((tert-butyldimethylsilyl)oxy)tetrahydro-2H-pyran-2-carboxylate as an oil. $^1$H NMR (600 MHz, CDCl$_3$): δ 3.97 (ddd, J=11.0, 4.9, 1.9 Hz, 1H), 3.90 (dd, J=11.6, 2.2 Hz, 1H), 3.74 (s, 3H), 3.61 (m, 1H), 3.13 (dd, J=11.0, 9.8 Hz, 1H), 2.06 (m, 2H), 1.68-1.60 (m, 1H), 1.51-1.45 (m, 1H), 0.85 (s, 9H), 0.03 (d, J=6.45 Hz, 6H).

Step 2: (2S,5R)-5-((tert-butyldimethylsilyl)oxy)tetrahydro-2H-pyran-2-carboxylic acid

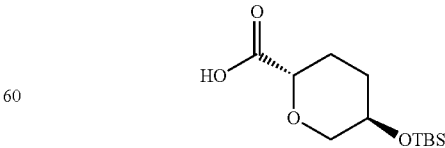

To the solution of (2S,5R)-methyl 5-((tert-butyldimethylsilyl)oxy)tetrahydro-2H-pyran-2-carboxylate (5.40 g, 19.7 mmol) in methanol (55 mL) was added 4N aqueous potassium hydroxide (24.6 mL, 98.4 mmol). The reaction mixture was stirred at room temperature for 2 hours and then the solvent was removed in vacuo. The aqueous residue was acidified to pH-2 using 1N HCl and extracted with chloroform/isopropanol (3:1, ×3). The combined organic layers were dried over sodium sulfate, filtered, and concentrated in vacuo to afford (2S,5R)-5-((tert-butyldimethylsilyl)oxy)tetrahydro-2H-pyran-2-carboxylic acid as a solid. LRMS (ESI) calc'd for C$_{12}$H$_{25}$O$_4$Si [M+H]$^+$: 261, found 261. $^1$H NMR (600 MHz, DMSO-d6): δ 12.56 (s, 1H), 3.78 (dd, J=11.1, 2.9 Hz, 1H), 3.73 (m, 1H), 3.58 (m, 1H), 3.03 (dd, J=10.8, 9.5 Hz, 1H), 1.90 (m, 2H), 1.48-1.40 (m, 2H), 0.81 (s, 9H), 0.05 (d, J=4.1 Hz, 6H).

Step 3: (2S,5R)-tert-butyl 5-((tert-butyldimethylsilyl)oxy)tetrahydro-2H-pyran-2-carboxylate

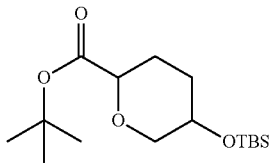 [SMILES: CC(C)(C)OC(=O)C1CCC(O[Si](C)(C)C(C)(C)C)CO1]

To a solution of (2S,5R)-5-((tert-butyldimethylsilyl)oxy)tetrahydro-2H-pyran-2-carboxylic acid (5.46 g, 19.8 mmol) in toluene (80 mL) at 950 was added 5 mL of a solution of N,N-dimethylformamide di-tert-butyl acetal (19.0 mL, 79 mmol) in toluene (10 mL) under nitrogen. The resulting solution was stirred at 95° C. for 1 hour, at which point the remaining acetal solution was added and the resulting solution was stirred for another 1 hour. The reaction was then concentrated in vacuo to afford a residue that was purified by silica chromatography, eluting with 10% EtOAc in hexanes. Concentration of the desired fractions afforded (2S,5R)-tert-butyl 5-((tert-butyldimethylsilyl)oxy)tetrahydro-2H-pyran-2-carboxylate as an oil. LRMS (ESI) calc'd for C$_{16}$H$_{33}$O$_4$Si [M+H]$^+$: 317, found 317. $^1$H NMR (600 MHz, DMSO-d6) δ 3.74 (m, 2H), 3.59 (tt, J=9.7, 4.6 Hz, 1H), 3.02 (dd, J=10.8, 9.5 Hz, 1H), 1.90-1.81 (m, 2H), 1.50-1.41 (m, 2H), 1.38 (s, 9H), 0.81 (s, 9H), 0.02 (d, J=4.7 Hz, 6H).

Step 4: tert-butyl 5-hydroxytetrahydro-2H-pyran-2-carboxylate

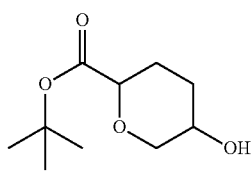

To tert-butyl 5-((tert-butyldimethylsilyl)oxy)tetrahydro-2H-pyran-2-carboxylate (4.58 g, 14.5 mmol) was added tetra-n-butylammonium fluoride (72.0 mL, 72.0 mmol, 1M in THF) and the reaction was stirred at room temperature for 2 hours, then concentrated in vacuo to afford a residue that was purified by silica chromatography, eluting with 44% EtOAc in hexanes. Concentration of the desired fraction afforded tert-butyl 5-hydroxytetrahydro-2H-pyran-2-carboxylate. LRMS (ESI) calc'd for C$_{10}$H$_{19}$O$_4$[M+H]$^+$: 203, found 203. $^1$H NMR (600 MHz, DMSO-d6): δ 4.79 (d, J=4.8 Hz, 1H), 3.77 (ddd, J=10.7, 4.7, 1.9 Hz, 1H), 3.71 (dd, J=10.9, 2.6 Hz, 1H), 3.40-3.34 (m, 1H), 2.96 (t, J=10.2 Hz, 1H), 1.83 (m, 2H), 1.36 (s, 9H), 1.48-1.13 (m, 2H).

Step 5: tert-butyl 5-oxotetrahydro-2H-pyran-2-carboxylate

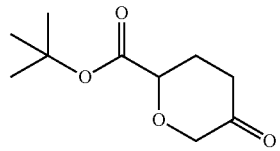

To a solution of tert-butyl 5-hydroxytetrahydro-2H-pyran-2-carboxylate (2.85 g, 14.1 mmol) in CH$_2$Cl$_2$ (45 mL) was added Dess-Martin periodinane (7.47 g, 17.6 mmol). The reaction was stirred at room temperature for 2 hours, then diluted with saturated sodium thiosulfate and saturated sodium bicarbonate solution. The aqueous layer was extracted with CH$_2$Cl$_2$ (×4), and the combined organic layers were washed with brine, dried over sodium sulfate, filtered, and concentrated in vacuo to afford a residue that was purified by silica chromatography, eluting with 25% EtOAc in hexanes. Concentration of the desired fractions afforded tert-butyl 5-oxotetrahydro-2H-pyran-2-carboxylate as an oil. $^1$H NMR (600 MHz, DMSO-d6): δ 4.31 (dd, J=9.5, 4.6 Hz, 1H), 4.05 (d, J=16.5 Hz, 2H), 2.75 (dt, J=16.8, 5.3 Hz, 1H), 2.37 (dt, J=16.8, 5.3 Hz, 1H), 2.24-2.08 (m, 1H), 1.98 (m, 1H), 1.38 (s, 9H).

Step 6: tert-butyl 5-(cyanomethylene)tetrahydro-2H-pyran-2-carboxylate

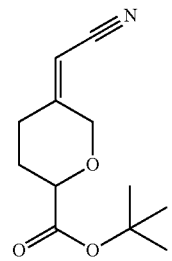 [SMILES: CC(C)(C)OC(=O)C1CC/C(=C/C#N)CO1]

A mixture of triethylamine (3.56 mL, 25.6 mmol), lithium bromide (2.05 g, 23.7 mmol) and diethyl (cyanomethyl) phosphonate (2.28 mL, 14.1 mmol) in THF (40 mL) was stirred for 30 minutes at room temperature before tert-butyl 5-oxotetrahydro-2H-pyran-2-carboxylate (2.56 g, 12.8 mmol) in THF (10 mL) was added. The reaction was stirred at room temperature overnight, quenched with water (20 mL), and extracted with ethyl acetate (×4). The combined organic layers was dried over sodium sulfate, filtered, and concentrated in vacuo to afford a residue that was purified by silica chromatography, eluting with 25% EtOAc in hexanes. Concentration of the desired fractions afforded tert-butyl 5-(cyanomethylene)tetrahydro-2H-pyran-2-carboxylate as a solid and as a 9:7 mixture of E and Z isomers. LRMS (ESI) calc'd for C$_{12}$H$_{18}$NO$_3$ [M+H]$^+$: 224, found 224. $^1$H NMR (400 MHz, DMSO-d6): δ 5.61 (d, J=14.9 Hz, 1H), 4.46 (d, J=14.1 Hz, 0.5H), 4.28 (d, J=13.5 Hz, 0.5H), 4.12 (m, 1.5H), 4.06 (d, J=13.4 Hz, 0.5H), 2.70-2.64 (m, 0.5H), 2.66-2.53 (m, 1.5H), 2.05-1.96 (m, 1H), 1.68-1.63 (m, 1H), 1.38 (s, 9H).

Step 7: tert-butyl 5-(3-amino-4-(benzyloxy)-1H-pyrazolo[4,3-c]pyridin-1-yl)-5-(cyanomethyl)tetrahydro-2H-pyran-2-carboxylate To a solution of 4-(benzyloxy)-1H-pyrazolo[4,3-c]pyridin-3-amine (10.8 g, 45.0 mmol) in acetonitrile (35 mL) was added tert-butyl 5-(cyanomethylene)tetrahydro-2H-pyran-2-carboxylate (2.00 g, 8.96 mmol) and DBU (1.35 mL, 8.96 mmol). The vial was sealed and stirred at 40° C. for 72 hours, then concentrated in vacuo to afford a residue that was purified by silica chromatography, eluting with 43% EtOAc in hexanes. Concentration of the desired fractions afforded tert-butyl 5-(3-amino-4-(benzyloxy)-1H-pyrazolo[4,3-c]pyridin-1-yl)-5-(cyanomethyl)tetrahydro-2H-pyran-2-carboxylate (Distereomer 1 and 2=3:1), both as solids. Diastereomer I-14-1: LRMS (ESI) calc'd for $C_{25}H_{30}N_5O_4$ [M+H]$^+$: 464, found 464. $^1$H NMR (600 MHz, DMSO-d6): δ 7.70 (d, J=6.5 Hz, 1H), 7.47 (d, J=7.6 Hz, 2H), 7.35 (t, J=7.6 Hz, 2H), 7.28 (t, J=7.5 Hz, 1H), 7.17 (d, J=6.5 Hz, 1H), 5.48 (s, 2H), 5.40 (bs, 2H), 4.21 (d, J=11.9 Hz, 1H), 4.11 (dd, J=9.1, 3.7 Hz, 1H), 4.02 (d, J=12.1 Hz, 1H), 3.23 (d, J=4.5 Hz, 2H), 2.45-2.38 (m, 2H), 1.86-1.75 (m, 2H), 1.38 (s, 9H). Diastereomer I-14-2: LRMS (ESI) calc'd for $C_{25}H_{30}N_5O_4$ [M+H]$^+$: 464, found 464. $^1$H NMR (600 MHz, DMSO-d6): δ 7.71 (d, J=6.4 Hz, 1H), 7.47 (d, J=7.6 Hz, 2H), 7.35 (t, J=7.5 Hz, 2H), 7.28 (t, J=7.4 Hz, 1H), 7.13 (d, J=6.4 Hz, 1H), 5.48 (s, 2H), 5.40 (br s, 2H), 4.68 (d, J=14.6 Hz, 1H), 4.15 (dd, J=10.6, 2.9 Hz, 1H), 3.75-3.68 (d, J=12.9 Hz, 1H), 3.00 (d, J=3.9 Hz, 2H), 2.80 (d, J=11.7 Hz, 1H), 2.05-1.95 (m, 1H), 1.85-1.80 (m, 1H), 1.55-1.48 (m, 1H), 1.32 (s, 9H). SFC separation of Diastereomer I-14-1 was performed by Chiralpak IA column 21×250 mm, eluting with 30% methanol in CO$_2$ to afford Enantiomer 1 (3.06 minutes—I-14-1A) and Enantiomer 2 (4.41 minutes—I-14-1B).

Intermediate 15

2-(8-(3-amino-4-(benzyloxy)-1H-pyrazolo[4,3-c]pyridin-1-yl)-1,4-dioxaspiro[4.5]decan-8-yl)acetonitrile

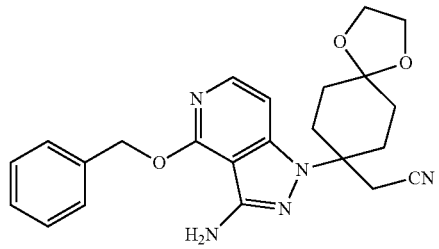

I-15

To a suspension of 4-(benzyloxy)-1H-pyrazolo[4,3-c]pyridin-3-amine (1.0 g, 4.2 mmol) in MeCN (10 mL) was added 2-(1,4-dioxaspiro[4.5]decan-8-ylidene)acetonitrile (7.5 g, 42 mmol) and DBU (1.3 g, 8.3 mmol). The resulting reaction mixture was stirred at 55° C. for 41 hours. The reaction mixture volume was reduced by half in vacuo, then purified by silica chromatography, eluting with 0-100 EtOAc in hexanes to give compound I-15. LRMS (ESI) calc'd for $C_{23}H_{26}N_5O_3$ [M+H]$^+$: 420, found 420. $^1$H NMR (600 MHz, DMSO-d6): δ 7.70 (d, J=6.4, 1H), 7.47 (d, J=7.5, 2H), 7.35 (t, J=7.5, 2H), 7.28 (t, J=7.3, 1H), 7.09 (d, J=6.4, 1H), 5.47 (s, 2H), 5.38 (s, 2H), 3.88-3.83 (m, 2H), 3.83-3.78 (m, 2H), 3.03 (s, 2H), 2.71 (d, J=13.9, 2H), 2.03-1.89 (m, 2H), 1.70-1.59 (m, 2H), 1.53-1.41 (m, 2H).

Intermediate 16

2-(1-(3-amino-4-(benzyloxy)-1H-pyrazolo[4,3-c]pyridin-1-yl)cyclohexyl)acetonitrile

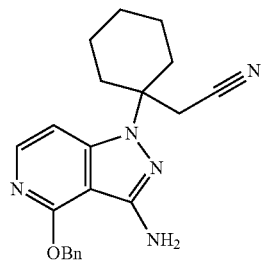

I-16

Step 1: 2-cyclohexylideneacetonitrile

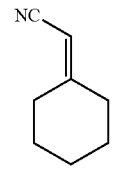

A solution of potassium hydroxide (2.86 g, 51.1 mmol) in acetonitrile (30 mL) was stirred at 80° C. for 5 minutes before a solution of cyclohexanone (5.00 g, 51.0 mmol) in acetonitrile (10 mL) was added dropwise. The resulting solution was stirred for 2 hours at 80° C. and then concentrated in vacuo. The residue was purified by silica chromatography, eluting with 0-1% EtOAc in hexanes to afford 2-cyclohexylideneacetonitrile as an oil. LR GCMS (EI) calc'd for $C_8H_{11}N$ [M]+$^+$: 121, found 121.

Step 2: 2-(1-(3-amino-4-(benzyloxy)-1H-pyrazolo[4,3-c]pyridin-1-yl)cyclohexyl)acetonitrile To 4-(benzyloxy)-1H-pyrazolo[4,3-c]pyridin-3-amine (0.050 g, 0.21 mmol) and 2-cyclohexylideneacetonitrile (0.050 g, 0.42 mmol) in ethanol (0.1 mL) was added DBU (0.031 g, 0.20 mmol). The resulting solution was stirred for 16 hours at 55° C., then concentrated in vacuo to afford crude compound I-16 as a solid. LRMS (ESI) calc'd for $C_{21}H_{24}N_5O$ [M+H]$^+$: 362, found 362.

Intermediate 17

2-(3-(3-amino-4-(benzyloxy)-1H-pyrazolo[4,3-c]pyridin-1-yl)tetrahydro-2H-pyran-3-yl)acetonitrile

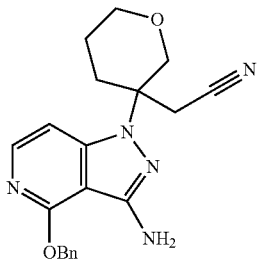

I-17

To 4-(benzyloxy)-1H-pyrazolo[4,3-c]pyridin-3-amine (500 mg, 2.08 mmol) in acetonitrile (6.9 mL) was added (E)-2-(dihydro-2H-pyran-3(4H)-ylidene)acetonitrile (436 mg, 3.54 mmol) and DBU (314 µL, 2.08 mmol). The flask was sealed and heated to 40° C. for 24 hours, then concentrated in vacuo and purified by silica chromatography, eluting with 10-100% EtOAc in hexanes. The product was collected and concentrated in vacuo to afford the desired product as a solid. $^1$H NMR (600 MHz, CDCl$_3$): δ 7.81 (d, J=6.4 Hz, 1H), 7.48 (d, J=7.3 Hz, 2H), 7.40 (apparent t, J=6.9 Hz, 2H), 7.35 (m, 1H), 7.00 (d, J=6.9 Hz, 1H), 5.53 (s, 2H), 4.49 (s, 2H), 4.21 (d, J=12.1 Hz, 1H), 4.08 (d, J=12.1 Hz, 1H), 3.82 (m, 1H), 3.69 (m, 1H), 3.09 (d, J=18.5 Hz, 1H), 3.01 (d, J=18.5 Hz, 1H), 2.65 (m, 1H), 2.46 (m, 1H), 1.75 (apparent quintet, J=5.8 Hz, 2H). SFC separation was performed by Chiral Technology OJ-H column, eluting with 25% methanol in CO$_2$ to afford Enantiomer 1 (3.6 minutes—I-17A) and Enantiomer 2 (4.7 minutes—I-17B).

Intermediate 18

2-(1-(3-amino-4-(benzyloxy)-1H-pyrazolo[4,3-c]pyridin-1-yl)cyclopentyl)acetonitrile

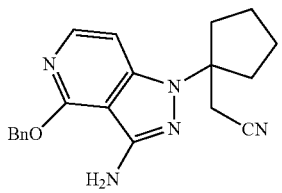

I-18

To a solution of 4-(benzyloxy)-1H-pyrazolo[4,3-c]pyridin-3-amine (1.7 g, 7.0 mmol) and EtOH (21.5 mL) was added 2-cyclopentylideneacetonitrile I-6-5 (3.8 g, 35 mmol), and DBU (2.1 mL, 14 mmol). The reation mixture was heated to 90° C. for 24 hours, concentrated in vacuo, and the residue was purified by silica chromatography, eluting with a hexanes/EtOAc gradient to afford 1-18. LRMS (ESI) Calc'd for C$_{20}$H$_{22}$N$_5$O [M+H]$^+$: 348, found 348. $^1$H NMR (CDCl$_3$, 500 MHz): δ 7.81 (d; J=6.4 Hz, 1H), 7.48 (d, J=7.5 Hz, 2H), 7.41-7.34 (m, 3H), 6.92 (d, J=6.3 Hz, 1H), 5.54 (s, 2H), 4.47 (bs, 2H), 2.88 (s, 2H), 2.67-2.63 (m, 2H), 2.31-2.27 (m, 2H), 1.90-1.82 (m, 4H).

Intermediate 19

2-((1R,2R)-1-(3-amino-4-(benzyloxy)-1H-pyrazolo[4,3-c]pyridin-1-yl)-2-fluorocyclohexyl)acetonitrile

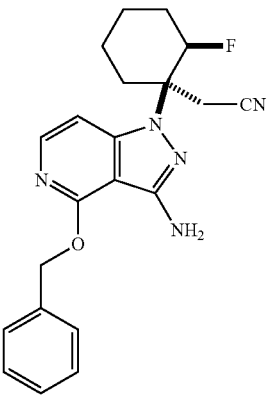

I-19

Step 1: 2-fluorocyclohexanone

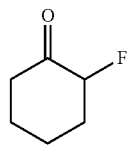

To a solution of cyclohexanone (275 g, 2.80 mol) in ACN (2.75 L), under nitrogen, was added 1-chloromethyl-4-fluoro-1,4-diazoniabicyclo[2.2.2]octane bis(tetrafluoroborate) (1.09 kg, 3.08 mol). The resulting solution was stirred for 24 hours at 80° C. The reaction was concentrated in vacuo, and the residue was dissolved in dichloromethane (2.00 L) and the insoluble materials were filtered off. The filtrate was washed with saturated aqueous NaHCO$_3$, dried over Na$_2$SO$_4$, and concentrated in vacuo to afford an oil that was used as is in the next step.

Step 2: 2-(2-fluorocyclohexylidene)acetonitrile

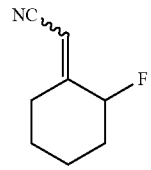

To a solution of diethyl (cyanomethyl)phosphonate (528 g, 2.98 mol) in THF (1.75 L) under nitrogen at 10° C., was added TEA (302 g, 2.98 mol) and LiBr (259 g, 2.98 mol). The resulting solution was stirred for 30 minutes and then a solution of 2-fluorocyclohexan-1-one (350 g, 2.71 mol, 90% pure) in THF (1.75 L) was added dropwise at 10° C. The reaction was stirred at room temperature for 2 hours, diluted with water (300 mL), and the resulting solution was extracted with ethyl acetate (×3). The organic layers were combined and washed with brine, dried over anhydrous sodium sulfate, filtered and concentrated in vacuo. The residue was purified by silica chromatography, eluting with 2-5% ethyl acetate/petroleum ether to afford an oil.

Step 3: 2-((1R,2R)-1-(3-amino-4-(benzyloxy)-1H-pyrazolo[4,3-c]pyridin-1-yl)-2-fluorocyclohexyl)acetonitrile To a solution of 4-(benzyloxy)-1H-pyrazolo[4,3-c]pyridin-3-amine (0.22 kg, 0.91 mol) in ACN (635 mL) under nitrogen, was added 2-(2-fluorocyclohexylidene)acetonitrile (0.13 kg, 0.91 mol). DBU (0.139 kg, 0.91 mol) was then added and the solution was stirred for 10 minutes before another batch of 4-(benzyloxy)-1H-pyrazolo[4,3-c]pyridin-3-amine (0.22 kg, 0.91 mmol) was added. The resulting solution was stirred for 48 hours at 50° C. in an oil bath, then diluted with water, and the resulting solution was extracted with ethyl acetate (×3). The combined organic layers were washed with brine (×3), dried over anhydrous sodium sulfate, filtered and concentrated in vacuo. The residue was diluted with diethyl ether, and the solids were collected by filtration and washed with additional ether. The filtrate was concentrated in vacuo and the residue was purified by silica chromatography, eluting with 20% ethyl acetate/petroleum ether. The desired fractions were combined and reduced in vacuo and the desired product was then recrystallized from disopropyl ether. The racemic cis (fluorine relative to the pyrazolo pyridine) was separated by preparative-SFC using a CHIRALPAK AD-H using 35% ethanol modifier in $CO_2$. Analytical SFC using a CHIRALPAK AD-H with 15% ethanol modifer in $CO_2$ gave Tr=3.5 minutes (desired R,R isomer, I-19A) and 4.0 minutes I-19B. LRMS (ESI) calc'd for $C_{21}H_{23}FN_5O$ [M+H]$^+$: 380, found: 380. $^1$H NMR (300 MHz, CDCl$_3$): δ 7.72 (d, J=6.3 Hz, 1H), 7.61-7.41 (m, 2H), 7.39-7.21 (m, 3H), 7.17 (d, J=7.5 Hz, 1H), 5.51 (s, 2H), 5.40 (s, 2H), 5.29-4.96 (m, 1H), 3.97-3.23 (m, 2H), 2.73-2.61 (m, 1H), 2.58-2.00 (m, 1H), 1.86 (m, 2H), 1.74-1.66 (m, 2H), 1.59-1.38 (m, 2H).

Intermediate 20

(2S,5S)-5-(3-((4-chlorophenyl)amino)-4-oxo-4,5-dihydro-1H-pyrazolo[4,3-c]pyridin-1-yl)-5-(cyanomethyl)tetrahydro-2H-pyran-2-carboxylic acid

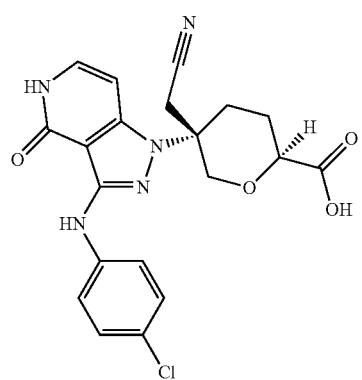 [SMILES: N#CC[C@@]1(n2nc(Nc3ccc(Cl)cc3)c3c(=O)[nH]ccc32)CC[C@@H](C(=O)O)OC1]

Step 1: (2S,5S)-tert-butyl 5-(4-(benzyloxy)-3-((4-chlorophenyl)amino)-1H-pyrazolo[4,3-c]pyridin-1-yl)-5-(cyanomethyl)tetrahydro-2H-pyran-2-carboxylate

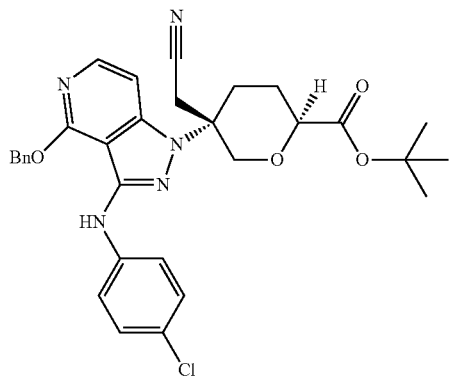 [SMILES: CC(C)(C)OC(=O)[C@@H]1CC[C@@](CC#N)(n2nc(Nc3ccc(Cl)cc3)c3c(OCc4ccccc4)nccc32)CO1]

(2S,5S)-tert-butyl 5-(3-amino-4-(benzyloxy)-1H-pyrazolo[4,3-c]pyridin-1-yl)-5-(cyanomethyl)tetrahydro-2H-pyran-2-carboxylate (500 mg, 1.08 mmol), 4-bromochlorobenzene (248 mg, 1.29 mmol), 2-di-tert-butylphosphino-2',4',6'-triisopropylbiphenyl (92 mg, 0.22 mmol), and potassium acetate (318 mg, 3.24 mmol) were combined in a microwave vial and dissolved in 2-propanol (5 mL). The reaction was degassed by bubbling argon through the solution for 10 minutes, and then Pd$_2$(dba)$_3$ (99 mg, 0.11 mmol) was added. The vial was then sealed and stirred at 85° C. overnight. The reaction was then diluted with ethyl acetate and filtered through Celite and concentrated in vacuo. The crude material was purified by silica chromatography, eluting with a 25-75% ethyl acetate in hexanes gradient to afford the title compound. LRMS (ESI) calc'd for $C_{31}H_{33}N_5O_4Cl$ [M+H]$^+$: 574, found 574.

Step 2: (2S,5S)-5-(3-((4-chlorophenyl)amino)-4-oxo-4,5-dihydro-1H-pyrazolo[4,3-c]pyridin-1-yl)-5-(cyanomethyl)tetrahydro-2H-pyran-2-carboxylic acid (I-20)

(2S,5S)-tert-butyl 5-(4-(benzyloxy)-3-((4-chlorophenyl)amino)-1H-pyrazolo[4,3-c]pyridin-1-yl)-5-(cyanomethyl)tetrahydro-2H-pyran-2-carboxylate (520 mg, 0.906 mmol) was dissolved in hydrochloric acid (5.00 mL, 20.0 mmol, 4M in dioxane) in a 250 mL round bottom flask. The reaction was stirred at room temperature for 1 hour and then concentrated in vacuo to obtain I-20. LRMS (ESI) calc'd for $C_{20}H_{19}ClN_5O_4$ [M+H]$^+$: 428, found: 428. $^1$H NMR (500 MHz, DMSO-d6): δ 12.94 (br s, 1H), 11.34 (d, J=5.6 Hz, 1H), 8.35 (s, 1H), 7.74 (d, J=9.2 Hz, 2H), 7.35 (d, J=9.2 Hz, 2H), 7.24 (dd, J=6.2, 7.6 Hz, 1H), 6.77 (d, J=7.6 Hz, 1H), 4.35 (d, J=11.8 Hz, 1H), 4.28 (dd, J=3.9, 8.6 Hz, 1H), 4.18 (d, J=12.1 Hz, 1H), 3.41 (s, 2H), 2.58 (m, 1H), 2.47 (m, 1H), 1.96 (m, 2H).

Intermediate 21-1

2-(3-(3-amino-4-(benzyloxy)-1H-pyrazolo[4,3-c]pyridin-1-yl)tetrahydrofuran-3-yl)acetonitrile

I-21-1

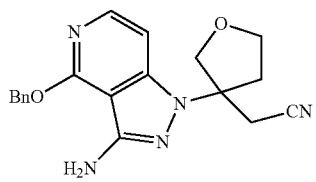

Step 1: 2-(dihydrofuran-3(2H)-ylidene)acetonitrile

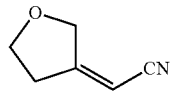

To a stirred solution of sodium hydride (1.34 g, 55.8 mmol, 60 wt. % dispersion in mineral oil) in THF (250 mL) was added diethyl (cyanomethyl)phosphonate (9.88 g, 55.8 mmol) by dropwise addition at 0° C. The mixture was stirred at 0° C. for 30 minutes then dihydrofuran-3(2H)-one (4.0 g, 47 mmol) was added by dropwise addition at 0° C. The resulting mixture was stirred for 2 hours at 0° C., then the mixture was diluted with dichloromethane (500 mL) and washed with water. The organic layer was washed with brine, dried over anhydrous sodium sulfate, filtered and concentrated in vacuo. The residue was purified by silica chromatography, eluting with 0-5% ethyl acetate in petroleum ether to afford the title compound as a mixture of E and Z isomers. $^1$H NMR (400 MHz, CDCl$_3$): δ 5.39 (s, 1H), 4.60 (s, 2H), 4.07-4.00 (m, 2H), 2.78 (m, 2H). $^1$H NMR (400 MHz, CDCl$_3$): δ 5.36 (s, 1H), 4.46 (s, 2H), 4.03 (m, 2H), 2.92 (m, 2H).

Step 2: 2-(3-(3-amino-4-(benzyloxy)-1H-pyrazolo[4,3-c]pyridin-1-yl)tetrahydrofuran-3-yl)acetonitrile A solution of 4-(benzyloxy)-1H-pyrazolo[4,3-c]pyridin-3-amine (Intermediate 1, 2.0 g, 8.3 mmol), 2-(dihydrofuran-3(2H)-ylidene)acetonitrile (1.82 g, 16.7 mmol) and DBU (3.80 g, 25.0 mmol) in acetonitrile (20 mL) was refluxed for 16 hours. The mixture was then concentrated in vacuo, and the residue was purified by silica chromatography, eluting with 10% methanol in dichloromethane to afford the title compound. $^1$H NMR (400 MHz, CD$_3$OD): δ 7.81 (d, J=6.4 Hz, 1H), 7.52 (d, J=7.2 Hz, 2H), 7.32-7.42 (m, 3H), 7.06 (d, J=6.4 Hz, 1H), 5.55 (s, 2H), 4.39 (d, J=9.6 Hz, 1H), 4.24 (d, J=9.6 Hz, 1H), 4.04-4.23 (m, 2H), 3.21 (s, 2H), 2.85-2.92 (m, 1H), 2.61-2.68 (m, 1H).

Following the analogous procedure outlined above, the following aryl bromides in Table 4 were prepared.

TABLE 4

| Intermediate # | Structure | Compound Name | LRMS |
|---|---|---|---|
| I-21-2 | | 2-(4-(3-amino-4-(benzyloxy)-1H-pyrazolo[4,3-c]pyridin-1-yl)tetrahydro-2H-pyran-4-yl)acetonitrile | LRMS (ESI) calc'd for $C_{20}H_{22}N_5O_2$ [M + H]$^+$: 364, found 364. |

Intermediate 22

2-((3R,4R or 3S,4S)-4-(3-amino-4-(benzyloxy)-1H-pyrazolo[4,3-c]pyridin-1-yl)-3-fluorotetrahydro-2H-pyran-4-yl)acetonitrile (I-22A) and 2-((3S,4S or 3R,4R)-4-(3-amino-4-(benzyloxy)-1H-pyrazolo[4,3-c]pyridine-1-yl)-3-fluorotetrahydro-2H-pyran-4-yl)acetonitrile (I-22B)

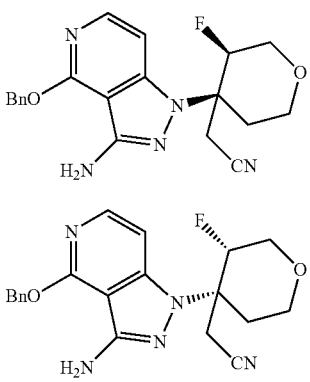

I-22A

I-22B

Step 1: 3-fluorodihydro-2H-pyran-4(3H)-one

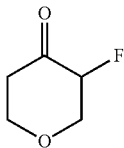

To a solution of dihydro-2H-pyran-4(3H)-one (20.0 g, 200 mmol) in acetonitrile/water (20/1, 210 mL) was added 1-(chloromethyl)-4-fluoro-1,4-diazabicyclo[2.2.2]octane-1,4-diium tetrafluoroborate (85.0 g, 240 mmol), and the resulting reaction was stirred at 80° C. for 12 hours. The reaction mixture was concentrated in vacuo and the residue was extracted with EtOAc (×3). The combined organic layers were dried over anhydrous Na$_2$SO$_4$, filtered, concentrated in vacuo, and the residue was purified by silica chromatography, eluting with a 0-100% EtOAc gradient in petroleum ether to afford the title compound as an oil: $^1$H NMR (300 MHz, CDCl$_3$): δ 4.94 (ddd, J=48, 9.6, 6.6 Hz, 1H), 4.42-4.35 (m, 1H), 4.23-4.13 (m, 1H), 3.77-3.61 (m, 2H), 2.76-2.61 (m, 2H).

Step 2: 2-(3-fluorodihydro-2H-pyran-4(3H)-ylidene)acetonitrile

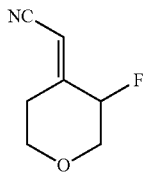

To a solution of diethyl (cyanomethyl)phosphonate (10.8 g, 61.0 mmol) in THF (300 mL) at −20° C., was added dropwise lithium bis(trimethylsilyl)amide (61.0 ml, 61.0 mmol, 1M in THF). The resulting solution was stirred at −20° C. for 30 minutes and 3-fluorodihydro-2H-pyran-4(3H)-one (6.00 g, 40.6 mmol) in THF (5 mL) was added dropwise. The reaction mixture was stirred at −20° C. for 1 hour, then quenched by addition of water (100 mL) and extracted with EtOAc (×3). The combined organic layers were dried over anhydrous Na$_2$SO$_4$, filtered, concentrated in vacuo, and the residue was purified by silica chromatography, eluting with 0-40% EtOAc/petroleum ether to afford the title compound as an oil: $^1$H NMR (300 MHz, CDCl$_3$): δ 5.51 (s, 1H), 5.00 (ddd, J=48.6, 7.9, 5.4 Hz, 1H), 4.15 (m, 1H), 3.99 (m, 1H), 3.59-3.41 (m, 2H), 3.02-2.94 (m, 1H), 2.54 (m, 1H).

Step 3: 2-((3R,4R or 3S,4S)-4-(3-amino-4-(benzyloxy)-1H-pyrazolo[4,3-c]pyridin-1-yl)-3-fluorotetrahydro-2H-pyran-4-yl)acetonitrile (I-22A) and 2-((3S,4S or 3R,4R)-4-(3-amino-4-(benzyloxy)-1H-pyrazolo[4,3-c]pyridine-1-yl)-3-fluorotetrahydro-2H-pyran-4-yl)acetonitrile (I-22B)

To a solution of 4-(benzyloxy)-1H-pyrazolo[4,3-c]pyridin-3-amine (4.00 g, 16.7 mmol) and 2-(3-fluorodihydro-2H-pyran-4(3H)-ylidene)acetonitrile (4.70 g, 33.3 mmol) in acetonitrile (80 mL), was added DBU (5.07 g, 33.3 mmol). The resulting solution was stirred at room temperature for 12 hours, then quenched by addition of water (100 mL), and extracted with EtOAc (×3). The combined organic layer was dried over anhydrous Na$_2$SO$_4$, filtered, and concentrated in vacuo. The residue was purified by silica chromatography, eluting with 0-40% EtOAc/petroleum ether to afford a racemic mixture of cis and trans product as an oil. The crude product was purified by reversed phase flash chromatography, eluting with 23-41% acetonitrile/water gradient with 0.05% NH$_4$HCO$_3$ modifer to afford 2-((3R,4R and 3S,4S)-4-(3-amino-4-(benzyloxy)-1H-pyrazolo[4,3-c]pyridin-1-yl)-3-fluorotetrahydro-2H-pyran-4-yl)acetonitrile at 35 minutes and the 2-((3R,4S and 3S,4R)-4-(3-amino-4-(benzyloxy)-1H-pyrazolo[4,3-c]pyridin-1-yl)-3-fluorotetrahydro-2H-pyran-4-yl)acetonitrile product at 60 minutes. Resolution of 2-((3R,4R and 3S,4S)-4-(3-amino-4-(benzyloxy)-1H-pyrazolo[4,3-c]pyridin-1-yl)-3-fluorotetrahydro-2H-pyran-4-yl)acetonitrile by chiral prep HPLC using a IC column and hexanes:EtOH=80:20 as mobile phase afforded both the enantiomers I-22A at 27 minutes and I-22B at 23 minutes: LRMS (ESI) calc'd for C$_{20}$H$_{21}$FN$_5$O$_2$ [M+H]$^+$: 382 found 382; $^1$H NMR (300 MHz, CDCl$_3$): δ 7.84 (d, J=6.6 Hz, 1H), 7.52-7.33 (m, 5H), 6.99 (d, J=6.6 Hz, 1H), 5.56 (s, 2H), 5.09 (d, J=46.2 Hz, 1H), 4.53 (br s, 2H), 4.22-4.15 (m, 1H), 4.07-3.98 (m, 1H), 3.83-3.68 (m, 2H), 3.37 (m, 1H), 3.13 (m, 1H), 3.05 (m, 1H), 2.47 (m, 1H).

Intermediate 23

5-bromo-2-(2,2,2-trifluoroethyl)-2,3-dihydro-1H-isoindol-1-one

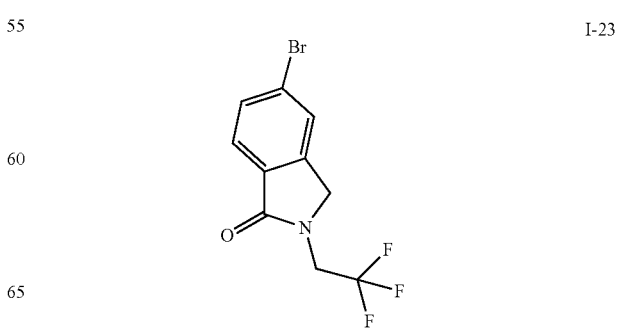

I-23

5-Bromo-2,3-dihydro-1H-isoindol-1-one (100 mg, 0.47 mmol) was dissolved in DMF (4.7 mL) and stirred at 0° C. NaH (38 mg, 0.94 mmol, 60 wt. % dispersion in oil) was carefully added in two portions, and the resulting mixture was allowed to stir at 0° C. for 15 minutes before 2,2,2-trifluoroethyl trifluoromethanesulfonate (110 mg, 0.47 mmol) was added. The mixture was allowed to stir at 0° C. for 30 minutes before saturated aqueous NaHCO₃ (10 mL) was carefully added, and the mixture was extracted with EtOAc. The organic layer was washed with water, brine, dried over anhydrous MgSO₄, filtered, and concentrated in vacuo. The residue was purified silica chromatography, eluting with 0-20% EtOAc in hexanes. Desired fractions were concentrated in vacuo to afford the title compound, 1-23. LRMS (ESI) calc'd for $C_{10}H_8BrF_3NO$ [M+H]⁺: 294, found: 294.

Intermediate 24

N-(4-bromobenzyl)-2,2,2-trifluoroethanamine

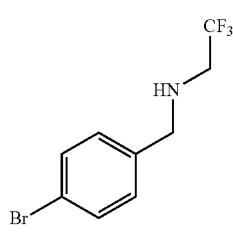

I-24

To a solution of 4-bromobenzylbromide (0.50 g, 2.0 mmol) in CH₃CN (8.0 mL) was added 2,2,2-trifluoroethanamine (0.60 g, 6.1 mmol) and Cs₂CO₃ (0.97 g, 3.0 mmol). The mixture was stirred at 40° C. for 8 hours, then partitioned between water and EtOAc. The organic phase was washed with brine, dried over Na₂SO₄, filtered and concentrated in vacuo. The residue was purified by silica chromatography, eluting with 9% EtOAc in hexanes to afford I-24. LRMS (ESI) calc'd for $C_9H_{10}NBrF_3$ [M+H]⁺: 268, found 268. ¹H NMR (400 MHz, CDCl₃): δ 7.43 (d, J=8.4 Hz, 2H), 7.19 (d, J=8.4 Hz, 2H), 3.83 (s, 2H), 3.18-3.10 (q, J=9.6 Hz, 2H).

Intermediate 25

(R and S)-1-(4-bromophenyl)-2,2,2-trifluoroethanol

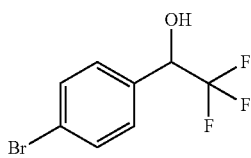

I-25

To a solution of 1-(4-bromophenyl)-2,2,2-trifluoroethanone (1.0 g, 3.95 mmol) in THF (10 mL) was added sodium borohydride (164 mg, 4.35 mmol). The mixture was stirred at room temperature for 2 hours, then quenched with water and concentrated in vacuo. The resulting residue was extracted with CH₂Cl₂ (×2), and the combined organic layers were washed with brine (×2), dried over sodium sulfate, filtered, and concentrated in vacuo to afford 1-(4-bromophenyl)-2,2,2-trifluoroethanol as a colorless liquid. ¹H NMR (600 MHz, DMSO-d6): δ 7.58 (d, J=8.4 Hz, 2H), 7.41 (d, J=8.2 Hz, 2H), 6.90 (d, J=5.6 Hz, 1H), 5.16 (m, 1H). Separation of the enantiomers was achieved by SFC using a Chiral Technologies OJ-H, eluting with 5% isopropanol modifier in CO₂. Retention times=4.1 (enantiomer A—Intermediate 25A) & 5.1 (enantiomer B—Intermediate 25B) minutes.

Intermediate 26-1

4-bromo-N-isopropylbenzenesulfonamide

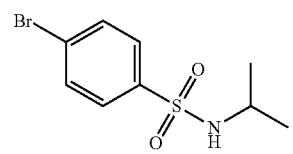

I-26-1

To a solution of propan-2-amine (0.16 g, 2.6 mmol) and DIPEA (0.78 g, 6.0 mmol) in CH₂Cl₂ (7 mL) was added a solution of compound 4-bromophenylsulfonyl chloride (0.51 g, 2.0 mmol) in CH₂Cl₂ (14 mL). The mixture was stirred at room temperature overnight, then poured into water and extracted with CH₂Cl₂ (×3). The organic layer was concentrated in vacuo and the residue was purified by silica chromatography, eluting with 5% EtOAc in hexanes. Concentration of the desired fractions afforded the title compound I-26-1. ¹H NMR (400 MHz, CDCl₃): δ 7.75-7.72 (m, 2H), 7.65-7.62 (m, 2H), 4.43 (d, J=7.5 Hz, 1H), 3.49-3.44 (m, 1H), 1.08 (d, J=6.4 Hz, 6H).

Following the analogous procedure outlined for I-26-1 above, the following aryl bromides in Table 5 were prepared. In certain instances the general procedure was modified by substituting TEA in place of DIPEA, or alternatively conducting the reaction in the absence of base.

TABLE 5

| Intermediate # | Structure | Compound Name | LRMS or NMR |
|---|---|---|---|
| 1-26-2 | 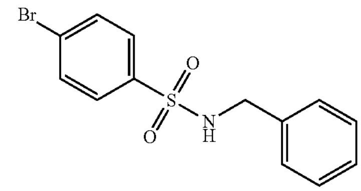 [SMILES: O=S(=O)(NCc1ccccc1)c1ccc(Br)cc1] | N-benzyl-4-bromobenzenesulfonamide | ¹H NMR (400 MHz, CDCl₃): δ 7.78 (d, J = 5.8 Hz, 2H), 7.70 (d, J = 5.8 Hz, 2H), 7.46-7.44 (m, 3H), 7.27-7.17 (m, 2H), 4.78-4.75 (m, 1H), 4.14 (d, J = 6 Hz, 2H). |
| 1-26-3 | 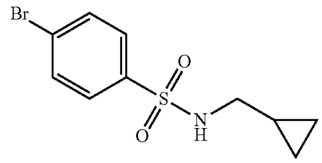 [SMILES: O=S(=O)(NCC1CC1)c1ccc(Br)cc1] | 4-bromo-N-(cyclopropylmethyl)benzenesulfonamide | ¹HNMR (400 MHz, CDCl₃): δ 7.65 (d, J = 5.6 Hz, 2H), 7.63 (d, J = 5.6 Hz, 2H), 4.48-4.45 (m, 1H), 2.77-2.73 (m, 2H), 0.81-0.76 (m, 1H) 0.47-0.38 (m, 2H), 0.27-0.25 (m, 2H). |
| 1-26-4 | 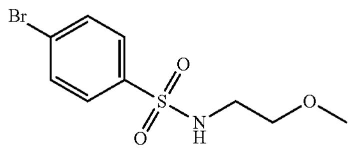 | 4-bromo-N-(2-methoxyethyl)benzenesulfonamide | ¹H NMR (400 MHz, CDCl₃): δ 7.72 (d, J = 5.8 Hz, 2H), 7.70 (d, J = 5.8 Hz, 2H), 4.48-4.45 (m, 1H), 3.49-3.84 (m, 2H), 3.30 (s, 3H), 3.13-3.09 (m, 2H). |
| 1-26-5 | 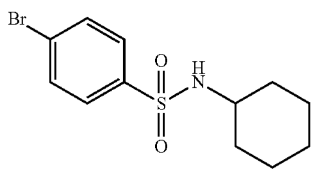 [SMILES: O=S(=O)(NC1CCCCC1)c1ccc(Br)cc1] | 4-bromo-N-cyclohexylbenzenesulfonamide | ¹H NMR (400 MHz, CDCl₃): δ 7.75-7.73 (m, 2H), 7.64-7.61 (m, 2H), 4.70 (d, J = 7.6 Hz, 1H), 3.17-3.09 (m, 1H), 1.75-1.72 (m, 2H), 1.64-1.59 (m, 2H), 1.52-1.48 (m, 1H), 1.24-1.14 (m, 2H). |
| 1-26-6 | 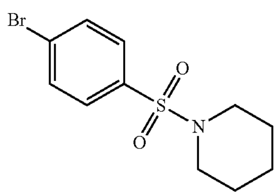 [SMILES: O=S(=O)(c1ccc(Br)cc1)N1CCCCC1] | 1-((4-bromophenyl)sulfonyl)piperidine | ¹H NMR (400 MHz, CDCl₃): δ 7.66-7.63 (m, 2H), 7.61-7.58 (m, 2H), 2.98-2.95 (m, 4H), 1.66-1.57 (m, 4H), 1.44-1.40 (m, 2H). |
| 1-26-7 | 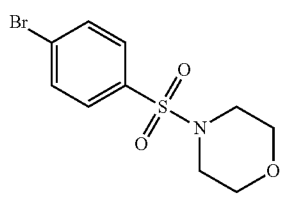 [SMILES: O=S(=O)(c1ccc(Br)cc1)N1CCOCC1] | 4-((4-bromophenyl)sulfonyl)morpholine | ¹H NMR (400 MHz, CDCl₃): δ 7.70-7.67 (m, 2H), 7.62-7.59 (m, 2H), 3.74-3.72 (m, 4H), 2.30-2.97 (m, 4H). |
| 1-26-8 | 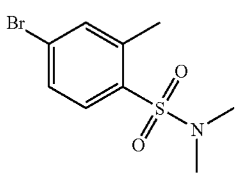 | 4-bromo-N,N,2-trimethylbenzenesulfonamide | ¹H NMR (600 MHz, CDCl₃): δ 7.75 (d, = 8.1 Hz, 1H), 7.50 (m, 1H), 7.47 (dm, J = 8.3 Hz, 1H), 2.80 (s, 6H), 2.61 (s, 3H). |
| 1-26-9A | 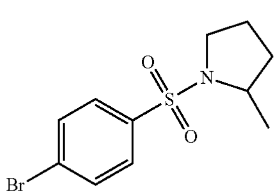 [SMILES: CC1CCCN1S(=O)(=O)c1ccc(Br)cc1] | (R or S)-1-((4-bromophenyl)sulfonyl)-2-methylpyrrolidine (Separated by SFC, Chiralpak AD-H, 15% MeOH in CO₂, Tr = 3.0 minutes.) | LRMS (ESI) calc'd for $C_{11}H_{15}BrNO_2S$ [M + H]⁺: 304, found 304 |

TABLE 5-continued

| Intermediate # | Structure | Compound Name | LRMS or NMR |
|---|---|---|---|
| 1-26-9B | 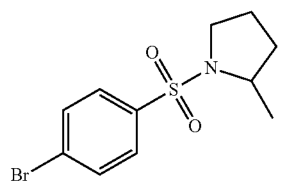 [SMILES: CC1CCCN1S(=O)(=O)c1ccc(Br)cc1] | (R or S)-1-((4-bromophenyl)sulfonyl)-2-methyl pyrrolidine (Separated by SFC, Chiralpak AD-H, 15% MeOH in $CO_2$, Tr = 4.4 minutes.) | LRMS (ESI) calc'd for $C_{11}H_{15}BrNO_2S$ $[M + H]^+$: 304, found 304 |
| 1-26-10 | 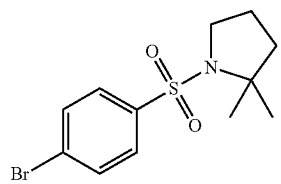 [SMILES: CC1(C)CCCN1S(=O)(=O)c1ccc(Br)cc1] | 1-((4-bromophenyl)sulfonyl)-2,2-dimethylpyrrolidine | LRMS (ESI) calc'd for $C_{12}H_{17}BrNO_2S$ $[M + H]^+$: 320, found 320. |
| 1-26-11 | 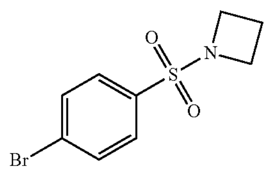 [SMILES: O=S(=O)(c1ccc(Br)cc1)N1CCC1] | 1-((4-bromophenyl)sulfonyl) azetidine | LRMS (ESI) calc'd for $C_9H_{11}BrNO_2S$ $[M + H]^+$: 278, found 278. |
| 1-26-12 | 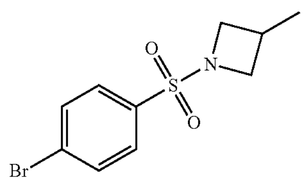 | 1-((4-bromophenyl)sulfonyl)-3-methylazetidine | LRMS (ESI) calc'd for $C_{10}H_{13}BrNO_2S$ $[M + H]^+$: 292, found 292. |
| 1-26-13 | 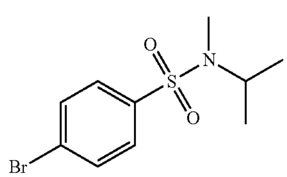 | 4-bromo-N-isopropyl-N-methylbenzenesulfonamide | LRMS (ESI) calc'd for $C_{10}H_{15}BrNO_2S$ $[M + H]^+$: 294, found 294. |
| 1-26-14 | 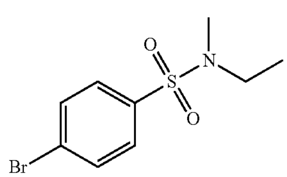 | 4-bromo-N-ethyl-N-methylbenzenesulfonamide | LRMS (ESI) calc'd for $C_9H_{13}BrNO_2S$ $[M + H]^+$: 280, found 280. |
| 1-26-15 | 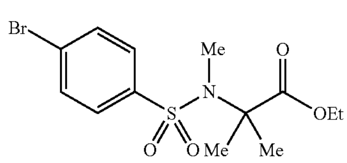 [SMILES: CCOC(=O)C(C)(C)N(C)S(=O)(=O)c1ccc(Br)cc1] | ethyl 2-(4-bromo-N-methylphenylsulfonamido)-2-methylpropanoate | $^1$H NMR (CDCl$_3$, 500 MHz): δ 7.86 (d, J = 8.2 Hz, 2H), 7.64 (d, J = 8.2 Hz, 2H), 4.25 (q, J = 7.1 Hz, 2H), 2.72 (s, 3H), 1.58 (s, 6H), 1.28 (m, 3H), |
| 1-26-16 | 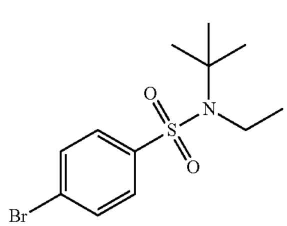 [SMILES: CCN(C(C)(C)C)S(=O)(=O)c1ccc(Br)cc1] | 4-bromo-N-(tert-butyl)-N-ethylbenzenesulfonamide | $^1$H NMR (600 MHz, CDCl$_3$): δ 7.69 (d, J = 8.6 Hz, 2H), 7.60 (d, J = 8.60 Hz, 2H), 3.48 (q, 2H, J = 7.0 Hz), 1.34 (t, 3H, J = 7.2 Hz), 1.33 (s, 9H). |

TABLE 5-continued

| Intermediate # | Structure | Compound Name | LRMS or NMR |
|---|---|---|---|
| 1-26-17A | 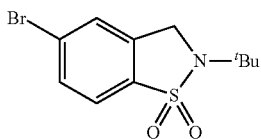 | (R or S)-1-((4-bromophenyl)sulfonyl)-2-methylazetidine (SFC separation using Chiralpak AD-H, 10% MeOH in CO₂ Tr = 3.9 minutes.) | LRMS (ESI) calc'd for $C_{11}H_{13}BrNO_2S$ $[M + H]^+$: 292, found 292. |
| 1-26-17B | 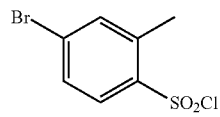 | (R or S)-1-((4-bromophenyl)sulfonyl)-2-methylazetidine (SFC separation using Chiralpak AD-H, 10% MeOH in CO₂ Tr = 4.5 minutes.) | LRMS (ESI) calc'd for $C_{11}H_{13}BrNO_2S$ $[M + H]^+$: 292, found 292. |

Intermediate 27-1

5-bromo-2-(tert-butyl)-2,3-dihydrobenzo[d]isothiazole-1,1-dioxide

I-27-1

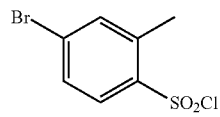

Step 1: 4-bromo-2-methylbenzene-1-sulfonyl chloride

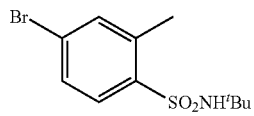

Chlorosulfonic acid (63 g, 0.54 mol) was added slowly to a cold solution (0° C.) of 1-bromo-3-methylbenzene (10.0 g, 58 mmol) in CHCl₃ (100 mL). The reaction was allowed to proceed with stirring for 2 hours at 0° C., then the reaction mixture was poured into ice water and extracted with EtOAc. The organic layer was then washed with brine, dried over NaSO₄, filtered and concentrated in vacuo to afford 4-bromo-2-methylbenzene-1-sulfonyl chloride as a solid. ¹H NMR (400 MHz, CDCl₃): δ 7.90 (d, J=8.4 Hz, 1H), 7.59-7.53 (m, 2H), 2.75 (s, 3H).

Step 2: 4-bromo-N-(tert-butyl)-2-methylbenzenesulfonamide

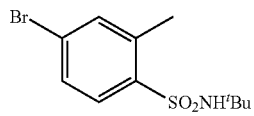

To a solution of 4-bromo-2-methylbenzene-1-sulfonyl chloride (2.0 g, 7.4 mmol) in CH₂Cl₂ (15 mL) was added a solution of 2-methylpropan-2-amine (0.65 g, 8.9 mmol) and triethylamine (0.90 g, 8.9 mmol) in CH₂Cl₂ (30 mL) at 0° C. The reaction mixture was stirred at 0° C. for 2 hours and then at room temperature for 16 hours. The mixture was washed with 0.1 M HCl, saturated aqueous NaHCO₃, dried over Na₂SO₄, filtered and concentrated in vacuo to afford 4-bromo-N-(tert-butyl)-2-methylbenzenesulfonamide as a solid. ¹H NMR (400 MHz, DMSO-d6): δ 7.78 (d, J=8.4 Hz, 1H), 7.63 (d, J=1.6 Hz, 1H), 7.59-7.56 (m, 2H), 2.57 (s, 3H), 1.09(s, 9H).

Step 3: 5-bromo-2-(tert-butyl)benzo[d]isothiazol-3(2H)-one-1,1-dioxide

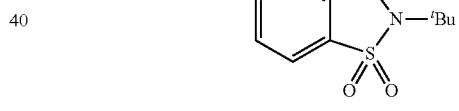

A mixture of H₅IO₆ (5.9 g, 26 mmol) in acetonitrile (50 mL) was stirred at room temperature for 1 hour, then CrO₃ (33 mg, 0.33 mmol) was added followed by acetic anhydride (2.67 g, 26 mmol). The resulting orange solution was cooled to 0° C., 4-bromo-N-(tert-butyl)-2-methyl benzenesulfonamide (1.0 g, 3.3 mmol) was added. After stirring at 0° C. for 15 minutes, the reaction was allowed to warm to room temperature and was stirred for 16 hours. The solvent was removed in vacuo and the residue was extracted with EtOAc (×3). The combined organic layers were washed with saturated aqueous NaHCO₃, brine, dried over Na₂SO₄, filtered and concentrated in vacuo. The residue was purified by silica chromatography, eluting with 5% EtOAc in hexanes and the desired fractions were concentrated in vacuo to afford 5-bromo-2-(tert-butyl)benzo[d]isothiazol-3(2H)-one 1,1-dioxide as a solid. ¹H NMR (400 MHz, DMSO-d6): δ 8.82-8.14 (m, 3H), 1.66 (s, 9H).

Step 4: 5-bromo-2-(tert-butyl)-2,3-dihydrobenzo[d]isothiazole-1,1-dioxide (I-27-1)

To a solution of 5-bromo-2-(tert-butyl)benzo[d]isothiazol-3(2H)-one 1,1-dioxide (0.20 g, 0.63 mmol) in THF (4 mL) was added BH$_3$.Me$_2$S (240 mg, 3.16 mmol). The reaction mixture was refluxed for 16 hours. After being cooled to room temperature, the reaction was quenched with 2 M HCl, and extracted with EtOAc (×2), the combined extracts were washed with brine, dried over Na$_2$SO$_4$, filtered, and the filtrate was concentrated in vacuo. The residue was purified by preparative TLC to afford compound I-27-1. $^1$H NMR (400 MHz, DMSO-d6) δ 7.83-7.56 (m, 3H), 4.55 (s, 2H), 1.46 (s, 9H).

Following an analogous method to that outlined for I-27-1 above, the following intermediates in Table 6 were prepared:

reaction mixture was warmed to room temperature and stirred overnight. The reaction mixture was then cooled to 0° C. and quenched with 1N HCl. The mixture was extracted with ethyl acetate (×4) and the combined organic layers were washed with brine, dried over Na$_2$SO$_4$, filtered and concentrated in vacuo. The crude oil was purified by silica chromatography, eluting with 20% EtOAc in hexanes to give I-28. $^1$H NMR (500 MHz, CDCl$_3$): δ 7.62-7.53 (m, 2H), 7.51 (s, 1H), 3.55-3.45 (m, 2H), 3.39-3.29 (m, 2H).

TABLE 6

| Intermediate # | Structure | Compound Name | NMR |
|---|---|---|---|
| I-27-2 | | 5-bromo-2-methyl-2,3-dihydrobenzo[d]isothiazole 1,1-dioxide | $^1$H NMR (400 MHz, CDCl$_3$): δ 7.63-7.60 (m, 2H), 7.5 (s, 1H), 4.25 (s, 2H), 2.89 (s, 3H). |
| I-27-3 | | 5-bromo-2-(2,2,2-trifluoroethyl)-2,3-dihydrobenzo[d]isothiazole 1,1-dioxide | $^1$H NMR (600 MHz, CDCl$_3$): δ 7.71 (s, 2H), 7.60 (s, 1H), 4.55 (s, 2H), 3.85 (q, J = 8.4 Hz, 2H). |
| I-27-4 | | 5-bromo-2,3-dihydrobenzo[d]isothiazole 1,1-dioxide | $^1$H NMR (600 MHz, DMSO-d6): δ 7.96 (br s, 1H), 7.88 (s, 1H), 7.83 (d, J = 8.0 Hz, 1H), 7.79 (d, J = 8.4 Hz, 1H), 4.44 (d, J = 4.8 Hz, 2H). |

Intermediate 28

5-bromo-2,3-dihydrobenzo[b]thiophene 1,1-dioxide

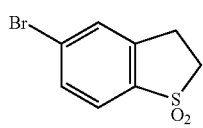

I-28

To a solution of 5-bromo-benzo[b]thiophene 1,1-dioxide (1.0 g, 4.1 mmol) in ethanol (13.6 mL) at 0° C., was added sodium borohydride (193 mg, 5.10 mmol). The resulting Intermediate 29

1-(4-bromophenyl)-2,2,2-trifluoroethanamine

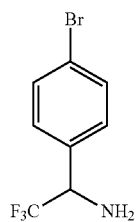

I-29

To a solution of 1-(4-bromophenyl)-2,2,2-trifluoroethanone (1.00 g, 3.95 mmol) in toluene (14 mL) at room temperature, was added (dropwise) a solution of lithium bis(trimethylsilyl)amide (4.35 mL, 4.35 mmol, 1M in THF). The reaction was stirred at room temperature for 15 minutes and then BH$_3$.THF (7.90 mL, 7.90 mmol, 1M in THF) was added. The reaction was stirred at room temperature for 20 minutes, then quenched at 0° C. by slow addition of 2M aqueous NaOH (5.93 mL, 11.9 mmol). The mixture was stirred at room temperature for 90 minutes, then the organic layer was separated and washed with 1N aqueous NaOH solution, dried over Na$_2$SO$_4$, filtered and concentrated in vacuo. SFC separation of the enantiomers on the crude reaction mixture was achieved using a ChiralPak AZ-H, with 7% methanol modifier in CO$_2$: retention times=2.37 (I-29A) & 2.89 (I-29B) minutes. LRMS (ESI) calc'd for $C_8H_8NBrF_3$ [M+H]$^+$: 254, found 254. $^1$H NMR (600 MHz, CDCl$_3$): δ 7.53 (d, J=8.5 Hz, 2H), 7.32 (d, J=8.5 Hz, 2H), 4.38 (q, J=7.5 Hz, 1H), 1.78 (br s, 2H).

Intermediate 30-1

1,1'-((5-bromo-1,3-phenylene)bis(methylene))bis(1H-pyrazole)

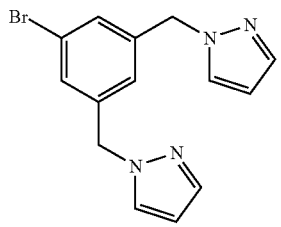

I-30-1

Step 1: 1-bromo-3,5-bis(bromomethyl)benzene

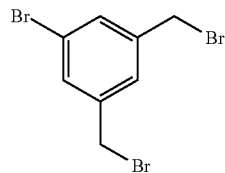 [SMILES: BrCc1cc(Br)cc(CBr)c1]

To 1-bromo-3,5-dimethylbenzene (5.00 g, 27.0 mmol), 1-bromopyrrolidine-2,5-dione (7.20 g, 40.5 mmol), (Z)-2,2'-(diazene-1,2-diyl)bis(2-methylpropanenitrile) (0.045 g, 0.27 mmol) under nitrogen, was added acetonitrile (80 mL). The resulting solution was stirred for 1 hour at 80° C. and then diluted with saturated aqueous ammonium chloride solution and extracted with dichloromethane (×3). The combined organic layers were concentrated in vacuo and the residue was purified by silica chromatography, eluting with hexanes to afford, after concentration of the desired fractions, 1-bromo-3,5-bis(bromomethyl)benzene as a solid.

Step 2: 1,1'-((5-bromo-1,3-phenylene)bis(methylene))bis(1H-pyrazole)

A solution of 1H-pyrazole (1.80 g, 26.4 mmol) in acetonitrile (120 mL) and potassium carbonate (3.60 g, 26.1 mmol) was stirred under nitrogen at 25° C. for hour, then 1-bromo-3,5-bis(bromomethyl)benzene (3.00 g, 8.75 mmol) was added to the mixture and the solution was stirred for 16 additional hours. The reaction was then quenched by addition of saturated aqueous ammonium chloride solution, extracted with ethyl acetate (×3), and the organic layers were combined, dried over sodium sulfate, filtered and concentrated in vacuo. The crude product was purified by silica chromatography, eluting with 50% EtOAc in hexanes. Concentration of the desired fractions affoded compound I-30-1 as a solid. LRMS (ESI) calc'd for $C_{14}H_{14}N_4Br$ [M+H]$^+$: 317, found 317.

Following the general procedure outlined above for I-30-1, the intermediates shown in Table 7 were prepared. In certain instances when the benzylic bromide was commercially available, only Step 2 was conducted. In certain instances the displacement reaction step could alternatively be modified by conducting it in the presence of catalytic KI, and/or in acetone at reflux.

TABLE 7

| Intermediate # | Structure | Compound Name | LRMS or NMR |
|---|---|---|---|
| I-30-2 | | 2,2'-((5-bromo-1,3-phenylene)bis(methylene))bis(2H-1,2,3-triazole) | LRMS (ESI) calc'd for $C_{12}H_{12}N_6Br$ [M + H]$^+$: 319, found 319. |
| I-30-3 | | 1,1'-((5-bromo-1,3-phenylene)bis(methylene))bis(1H-1,2,3-triazole) | LRMS (ESI) calc'd for $C_{12}H_{12}N_6Br$ [M + H]$^+$: 319, found 319. |
| I-30-4 | | 1-(3-((2H-1,2,3-triazol-2-yl)methyl)-5-bromobenzyl)-1H-1,2,3-triazole | LRMS (ESI) calc'd for $C_{12}H_{12}N_6Br$ [M + H]$^+$: 319, found 319. |

TABLE 7-continued

| Intermediate # | Structure | Compound Name | LRMS or NMR |
|---|---|---|---|
| 1-30-5 | 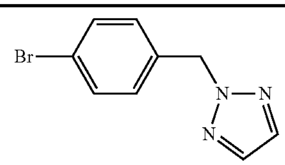 | 2-(4-bromobenzyl)-2H-1,2,3-triazole | $^1$H NMR (CDCl$_3$ 400 MHz): δ 7.62 (s, 2H), 7.46 (d, J = 8.4 Hz, 2H), 7.17 (d, J = 8 Hz, 2H), 5.55 (s, 2H). |
| 1-30-6 | 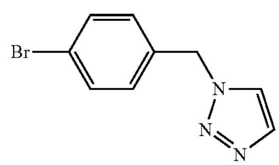 [SMILES: Brc1ccc(Cn2ccnn2)cc1] | 1-(4-bromobenzyl)-1H-1,2,3-triazole | $^1$H NMR (CDCl$_3$ 400 MHz): δ 7.66 (s, 1H), 7.41-7.45 (m, 3H), 7.07 (d, J = 6 Hz, 2H), 5.46 (s, 2H) |

Intermediate 31-1

4-bromo-N-(tert-butyl)-N-methylbenzenesulfonamide

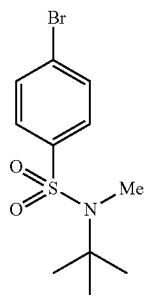

I-31-1

To a solution of 4-bromo-N-(tert-butyl)benzenesulfonamide (1.00 g, 3.42 mmol) and potassium carbonate (0.946 g, 6.84 mmol) in DMF (20.0 mL) was added methyl iodide (0.43 mL, 6.8 mmol) at room temperature. The reaction was stirred for 6 hours, then quenched by addition of water and extracted with EtOAc (×3). The organic layers were dried over sodium sulfate, filtered and concentrated in vacuo and purified by silica chromatrography, eluting with 0-10% EtOAc in hexanes to give I-31-1 as an oil. LRMS (ESI) calc'd for C$_{11}$H$_{17}$NBrO$_2$SNa [M+Na]$^+$: 328, found 328. $^1$H NMR (600 MHz, CDCl$_3$): δ 7.69 (d, J=8.7 Hz, 2H), 7.62 (d, J=8.7 Hz, 2H), 2.97 (s, 3H), 1.35 (s, 9H).

The following intermediate in Table 8 could made in analogy to I-31-1 above, using Cs$_2$CO$_3$ at 50° C. or NaH at 0-25° C.

TABLE 8

| Intermediate # | Structure | Name | 1H NMR |
|---|---|---|---|
| 1-31-2 | 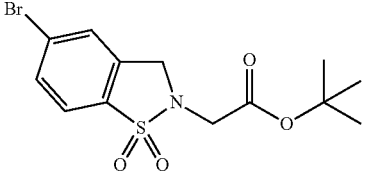 [SMILES: CC(C)(C)OC(=O)CN1Cc2cc(Br)ccc2S1(=O)=O] | tert-butyl 2-(5-bromo-1,1-dioxidobenzo[d]isothiazol-2(3H)-yl)acetate | $^1$H NMR (600 MHz, CDCl$_3$): δ 7.65 (s, 2H), 7.54 (s, 2H), 4.59 (s, 2H), 3.95 (s, 2H), 1.44 (s, 9H). |

Intermediates 32 and 33

(R or S) 2-(4-bromophenyl)-1,1,1-trifluoropropan-2-ol (I-32)

(R or S) 1-bromo-4-(1,1,1-trifluoro-2-methoxypropan-2-yl)benzene (I-33)

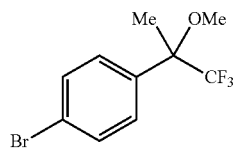
I-33A & I-33B

Step 1: (R or S) 2-(4-bromophenyl)-1,1,1-trifluoropropan-2-ol (I-32)

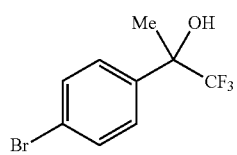
I-32A & I-32B

An oven dried round bottom flask with magnetic sir bar under an atmosphere of $N_2$ was charged with 1-(4-bromophenyl)-2,2,2-trifluoroethanone (2.0 g, 7.9 mmol) and THF (13 mL). The solution was cooled to 0° C., and methyl magnesium bromide (17 mL, 23.7 mmol, 1.4 M in diethyl ether) was added. The reaction mixture was warmed to room temperature over 1-2 hours, and was quenched by the addition of saturated aqueous $NH_4Cl$ (10 mL). The resulting mixture was extracted with $Et_2O$ (×3), and the combined organic layers were concentrated in vacuo to afford a residue that was purified by silica chromatography, eluting with hexanes/EtOAc gradient to yield racemic 2-(4-bromophenyl)-1,1,1-trifluoropropan-2-ol. LRMS (ESI) calc'd for $C_9H_9BrF_3O$ [M+H]$^+$: 269, found 269. $^1$H NMR (CDCl$_3$, 500 MHz): δ 7.54 (d, J=8.31 Hz, 2H), 7.47 (d, J=8.26 Hz, 2H), 2.44 (s, 1H), 1.78 (s, 3H). Resolution of enantiomers was achieved by SFC purification using a Chiral Technology AZ-H with 5% MeOH in $CO_2$. Tr=2.6 minutes (Intermediate I-32A) & 3.2 minutes (Intermediate I-32B).

Step 2: (R or S) 1-bromo-4-(1,1,1-trifluoro-2-methoxypropan-2-yl)benzene (I-33)

An oven dried round bottom flask with magnetic sir bar under an atmosphere of $N_2$ was charged with 2-(4-bromophenyl)-1,1,1-trifluoropropan-2-ol I-32A (300 mg, 1.10 mmol) and DMF (3.5 mL). The solution was cooled to 0° C., sodium hydride (67 mg, 1.7 mmol, 60% wt. in mineral oil) was added, and the reaction was stirred for 30 minutes. Iodomethane (0.21 mL, 3.3 mmol) was then added and the reaction mixture was warmed to room temperature over 1-2 hours, quenched by addition of saturated aqueous $NH_4Cl$ (10 mL), and extracted with $Et_2O$ (×3). The combined organic layers were concentrated in vacuo to afford a residue that was purified by silica chromatography, eluting with hexanes/EtOAc gradient, to yield I-33A. I-33B was prepared in an analogous manner to I-33A above, using I-32B. $^1$H NMR (CDCl$_3$, 500 MHz): δ 7.54 (d, J=8.19 Hz, 2H), 7.38 (d, J=8.14 Hz, 2H), 3.23 (s, 3H), 1.76 (s, 3H).

Intermediates 34-1

5-bromo-2-cyclopentyl-23-dihydro-1H-isoindol-1-one

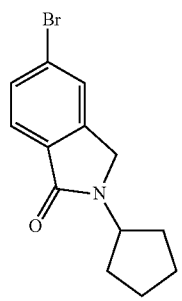
I-34-1

Step 1: methyl 4-bromo-2-(bromomethyl)benzoate

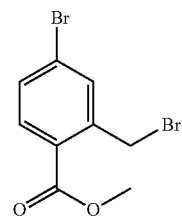

To a solution of NBS (38.8 g, 218 mmol) and methyl 4-bromo-2-methylbenzoate (50.0 g, 218 mmol) in $CCl_4$ (1.00 L) was added AIBN (3.58 g, 21.8 mmol) and the solution was stirred for 16 hours at reflux. The reaction was cooled to ambient temperature, quenched by addition of water (300 mL), and the organic layers were dried over sodium sulfate, filtered and concentrated in vacuo. The residue was purified by silica chromatography, eluting with hexanes:ethyl acetate (100:1) to afford the title compound as a solid. $^1$H NMR (300 MHz, CDCl$_3$) δ 7.81 (d, J=8.4 Hz, 1H), 7.63 (m, 1H), 7.51 (d, J=8.4 Hz, 1H), 4.90 (s, 2H), 3.94 (s, 3H).

Step 2: 5-bromo-2-cyclopentyl-2,3-dihydro-1H-isoindol-1-one (I-34-1)

To a solution of methyl 4-bromo-2-(bromomethyl)benzoate (6.00 g, 19.5 mmol), in toluene (100 mL), was added cyclopentylamine (1.83 g, 21.49 mmol) and toluene (100 mL). Triethylamine (3.96 g, 39.1 mmol) was added and the resulting solution was stirred for 16 hours at 110° C. The resulting mixture was cooled to room temperature and concentrated in vacuo and the residue was purified by silica chromatography, eluting with 0.5-1% methanol in dichloromethane to afford I-34-1 as a solid: LCMS (ESI) calc'd for $C_{13}H_{15}BrNO$ [M+H]$^+$: 280, 282, found 280, 282; $^1$H NMR (400 MHz, CD$_3$OD) δ 7.81 (s, 1H), 7.70-7.65 (m, 2H), 4.71-4.64 (m, 1H), 4.53 (s, 2H), 2.07-1.91 (m, 2H), 1.89-1.81 (m, 2H), 1.79-1.74 (m, 4H).

The following compounds in Table 9 were prepared in a similar manner as I-34-1 described above.

TABLE 9

| Intermediate # | Structure | Compound Name | LCMS or NMR |
| --- | --- | --- | --- |
| I-34-2 | | 5-bromo-2-tert-butylisoindolin-1-one | LCMS (ESI) calc'd for $C_{12}H_{15}BrN$ [M + H]$^+$: 268, 270, found 268, 270; $^1$H NMR (300 MHz, CDCl$_3$): δ 7.65 (s, 1H), 7.57 (m, 2H), 4.43 (s, 2H), 1.59 (s, 9H). |
| I-34-3 | | 5-bromo-2-cyclohexylisoindolin-1-one | LCMS (ESI) calc'd for $C_{14}H_{17}BrNO$ [M + H]$^+$: 294, 296, found 294, 296; $^1$H NMR (300 MHz, CDCl$_3$) δ 7.74 (d, J = 7.2 Hz, 1H), 7.60 (s, 1H), 7.62 (d, J = 7.2 Hz, 1H), 4.33 (s, 2H), 4.23 (m, 1H), 1.87 (m, 4H), 1.73 (m, 1H), 1.50-1.39 (m, 4H). |
| I-34-4 | | tert-butyl 2-(5-bromo-1-oxoisoindolin-2-yl)-2-methylpropanoate | $^1$H NMR (CDCl$_3$, 500 MHz): δ 7.68 (d, J = 8.0 Hz, 1H), 7.58 (m, 2H), 4.46 (s, 2H), 1.63 (s, 6H), 1.45 (s, 9H). |

Intermediate 35-1 ethyl 3-(4-bromophenyl)-4,4,4-trifluoro-3-hydroxy-2,2-dimethylbutanoate

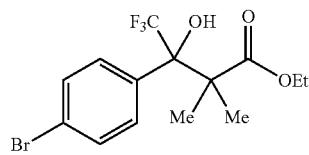

I-35-1

In an oven dried round bottom flask under an atmosphere of nitrogen was charged ethyl isobutyrate (0.69 g, 5.9 mmol) and THF (2.5 mL). The solution was cooled to −78° C., and lithium diisopropylamide (3.0 mL, 5.9 mmol, 2.0 M in THF) was added. The reaction mixture stirred for 30 minutes and then 1-(4-bromophenyl)-2,2,2-trifluoroethanone (0.50 g, 2.0 mmol) was added. The reaction mixture was warmed to room temperature over 1-2 hours, and quenched by the addition of saturated aqueous NH$_4$Cl. The resulting mixture was extracted with EtOAc (×3), and the combined organic layers were dried over sodium sulfate, filtered and concentrated in vacuo to afford a residue that was purified by silica chromatography, eluting with a hexanes/EtOAc gradient to yield I-35-1. LRMS (ESI) calc'd for $C_{14}H_{17}BrF_3O_3$ [M+H]$^+$: 369, found 369. $^1$H NMR (CDCl$_3$, 500 MHz): δ 7.60 (d, J=8.2 Hz, 2H), 7.53 (d, J=8.5 Hz, 2H), 4.31-4.27 (m, 2H), 1.38 (d, J=3.5 Hz, 3H), 1.30 (s, 6H).

The following compounds in Table 10 were prepared in a similar manner as I-35-1 described above.

TABLE 10

| Intermediate # | Structure | Compound Name | LCMS or NMR |
| --- | --- | --- | --- |
| I-35-2 | | isopropyl 3-(4-bromophenyl)-4,4,4-trifluoro-3-hydroxy-2,2-dimethylbutanoate | $^1$H NMR (CDCl$_3$, 500 MHz): δ 7.60 (d, J = 8.2 Hz, 2H), 7.53 (d, J = 8.5 Hz, 2H), 4.31 (m, 1H), 1.30 (s, 6H), 1.27 (d, J = 1.2 Hz, 3H), 1.16 (d, J = 1.3 Hz, 3H). |

Intermediate 36

5-bromo-2,2-dimethyl-1-(trifluoromethyl)-2,3-dihydro-1H-inden-1-ol

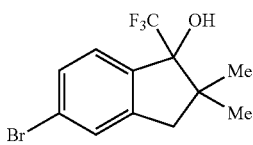

Step 1: 5-bromo-2,2-dimethyl-2,3-dihydro-1H-inden-1-one

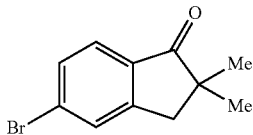 [SMILES: CC1(C)Cc2cc(Br)ccc2C1=O]

To a solution of 5-bromo-2,3-dihydro-1H-inden-1-one (0.50 g, 2.4 mmol) in DMF (7.5 mL) at 0° C., was added sodium hydride (237 mg, 5.9 mmol, 60 wt. % dispersion in mineral oil). The reaction mixture stirred for 30 minutes and then iodomethane (0.37 mL, 5.9 mmol) was added. The reaction mixture was warmed to room temperature over 1-2 hours, quenched by addition of saturated aqueous NH$_4$Cl, and the resulting mixture was extracted with Et$_2$O (×3). The combined organic layers were concentrated in vacuo to afford a residue that was purified by silica chromatography, eluting with a hexanes/EtOAc gradient to afford the title compound. LRMS (ESI) calc'd for C$_{11}$H$_{12}$BrO [M+H]$^+$: 240, found 240. $^1$H NMR (CDCl$_3$, 500 MHz): δ 7.64-7.61 (m, 2 H), 7.53 (d, J=8.2 Hz, 1H), 2.99 (s, 2 H), 1.26-1.24 (s, 6 H).

Step 2: 5-bromo-2,2-dimethyl-1-(trifluoromethyl)-2,3-dihydro-1H-inden-1-ol (I-36)

To a solution of 5-bromo-2,2-dimethyl-2,3-dihydro-1H-inden-1-one (2.2 g, 9.5 mmol) in THF (23 mL) at 0° C., was added (trifluoromethyl) trimethylsilane (7.00 mL, 47.4 mmol) followed by slow (exotherm) addition of tetrabutylammonium fluoride (11.9 mL, 11.9 mmol, 1M in THF). The reaction mixture was warmed to room temperature over 1-2 hours and stirred overnight before being quenched by addition of saturated aqueous NH$_4$Cl. The resulting mixture was extracted with EtOAc (×3) and the combined organic layers were concentrated in vacuo to afford a residue that was purified by silica chromatography, eluting with a hexanes/EtOAc gradient to yield I-36. $^1$H NMR (CDCl$_3$, 500 MHz): δ 7.43-7.41 (m, 2H), 7.33 (d, J=8.1 Hz, 1H), 2.89 (d, J=15.7 Hz, 1H), 2.82 (d, J=15.6 Hz, 1H), 1.27 (s, 3H), 1.16 (s, 3H).

Intermediate 37-1

2-(4-bromophenyl)-1,1,1-trifluoro-3,3-dimethylbutan-2-ol

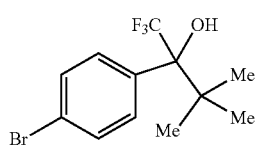

To a solution of 1-(4-bromophenyl)-2,2-dimethylpropan-1-one (0.20 g, 0.80 mmol) in THF (1 mL) at 0° C., was added (trifluoromethyl) trimethylsilane (0.60 mL, 4.2 mmol) followed by the slow (exotherm) addition of tetrabutylammonium fluoride (0.9 mL, 0.9 mmol, 1M in THF). The reaction mixture was warmed to room temperature over 1-2 hours, and stirred overnight. The reaction was quenched by the addition of saturated aqueous NH$_4$Cl (10 mL), and the resulting mixture was extracted with EtOAc (×3). The combined organic layers were concentrated in vacuo to afford a residue that was purified by silica chromatography, eluting with a hexanes/EtOAc gradient to yield I-37-1. $^1$H NMR (CDCl$_3$, 500 MHz): δ 7.55-7.47 (m, 4H), 1.04 (s, 9H).

The following compounds in Table 11 were prepared in a similar manner as I-37-1 described above.

TABLE 11

| Intermediate # | Structure | Compound Name | LRMS or NMR |
|---|---|---|---|
| I-37-2A | 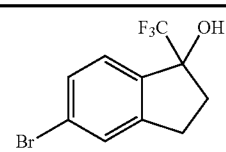 | (S or R) 5-bromo-1-(trifluoromethyl)-2,3-dihydro-1H-inden-1-ol (separated by SFC using a Chiral Technology AZ-H, 5% MeOH in CO2, Peak 1, Tr = 1.7 minutes) | $^1$H NMR (CDCl$_3$, 500 MHz): δ 7.43 (m, 2H), 7.35 (d, J = 8.2 Hz, 1H), 3.07 (m, 1H), 3.01-2.95 (m, 1H), 2.67 (m, 1H), 2.24 (m, 1H). LRMS (ESI) calc'd for C$_{10}$H$_9$BrF$_3$O [M + H]$^+$: 282, found 282. |
| I-37-2B | 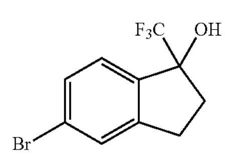 [SMILES: OC1(C(F)(F)F)CCc2cc(Br)ccc21] | (S or R) 5-bromo-1-(trifluoromethyl)-2,3-dihydro-1H-inden-1-ol (separated by SFC using a Chiral Technology AZ-H, 5% MeOH in CO$_2$, Peak 2, Tr = 2.1 minutes) | $^1$H NMR (CDCl$_3$, 500 MHz): δ 7.43 (m, 2H), 7.35 (d, J = 8.2 Hz, 1H), 3.07 (m, 1H), 3.01-2.95 (m, 1H), 2.67 (m, 1H), 2.24 (m, 1H). |

TABLE 11-continued

| Intermediate # | Structure | Compound Name | LRMS or NMR |
|---|---|---|---|
| | | | LRMS (ESI) calc'd for $C_{10}H_9BrF_3O$ [M + H]$^+$: 282, found 282. |

Intermediate 38 tert-butyl 2-(4-bromo-N-methylphenylsulfonamido)-2-methylpropanoate

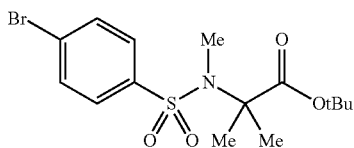

I-38

Step 1: tert-butyl 2-(4-bromophenylsulfonamido)-2-methylpropanoate

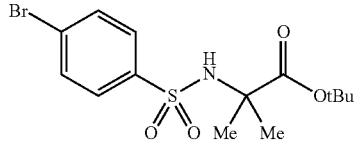 [SMILES: CC(C)(C)OC(=O)C(C)(C)NS(=O)(=O)c1ccc(Br)cc1]

To a solution of 4-bromobenzene-1-sulfonyl chloride (1 g, 4 mmol) in DCM (9 mL) at 0° C., was added triethylamine (1.3 mL, 9.4 mmol) and tert-butyl 2-amino-2-methylpropanoate (0.50 g, 3.1 mmol). The reaction mixture was warmed to room temperature overnight, quenched with saturated aqueous NH$_4$Cl and diluted with DCM. The organic layer was washed with brine, dried over Na$_2$SO$_4$, filtered through Celite, and concentrated in vacuo to afford the title compound that was used as is in the next step. $^1$H NMR (CDCl$_3$, 500 MHz): δ 7.74 (m, 2H), 7.61 (m, 2H), 5.40 (br s, 1H), 1.44 (s, 9H), 1.40 (s, 6H).

Step 2: tert-butyl 2-(4-bromo-N-methylphenylsulfonamido)-2-methylpropanoate (I-38)

To a solution of tert-butyl 2-(4-bromophenylsulfonamido)-2-methylpropanoate (815 mg, 2.2 mmol) in DMF (6.5 mL) at 0° C., was added sodium hydride (129 mg, 3.2 mmol, 60 wt. % dispersion in mineral oil). The reaction mixture was stirred for 30 minutes before methyl iodide (0.40 mL, 6.5 mmol) was added. The reaction was warmed to room temperature over 1-2 hours, then quenched with saturated aqueous NH$_4$Cl. The reaction was diluted with Et$_2$O and the organic layer was washed with brine, dried over Na$_2$SO$_4$, filtered through Celite, and concentrated in vacuo. The residue was purified by silica chromatography, eluting with a hexanes/EtOAc gradient to afford I-38. $^1$H NMR (CDCl$_3$, 500 MHz): δ $^1$H NMR (500 MHz, CDCl$_3$): δ 7.86 (m, 2H), 7.63 (m, 2H), 2.72 (s, 3H), 1.48 (s, 15H).

Intermediate 39-1

(4-bromo-2-methylphenyl)(4,4-difluoropiperidin-1-yl)methanone

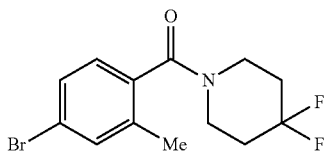

I-39-1

To a solution of 4-bromo-2-methylbenzoic acid (0.75 g, 3.5 mmol) in DMF (9 mL), was added HATU (2.6 g, 7.0 mmol), Hunig's base (2.4 mL, 14 mmol), and 4,4-difluoropiperidine (0.84 g, 7.0 mmol). The resulting reaction mixture was stirred for 16 hours, concentrated in vacuo, and the crude oil was purified by silica chromatography, eluting with a hexanes/EtOAc gradient to yield I-39-1. $^1$H NMR (500 MHz, CDCl$_3$): δ 7.42-7.37 (m, 2H), 7.05 (d, J=8.1 Hz, 1H), 4.02 (m, 1H), 3.82 (m, 1H), 3.36 (m, 2H), 2.30 (s, 3H), 2.11-2.07 (m, 2H), 1.88 (m, 2H).

Table 12 discloses Examples that were prepared in analogy to I-39-1.

TABLE 12

| Example | Structure | Compound Name | LRMS |
|---|---|---|---|
| I-39-2A | 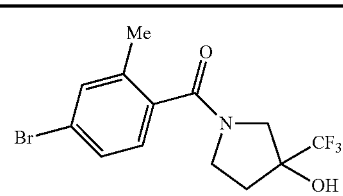 | (S or R)-(4-bromo-2-methylphenyl)(3-hydroxy-3-(trifluoromethyl)pyrrolidin-1-yl)methanone (Derived from Peak 1 via SFC: Chiralpak AS-H, 10% MeOH in CO$_2$, Tr = 2.57 minutes) | LRMS (ESI) Calc'd for $C_{13}H_{14}BrF_3NO_2$ [M + H]$^+$: 354, found 354. |

TABLE 12-continued

| Example | Structure | Compound Name | LRMS |
|---|---|---|---|
| I-39-2B | 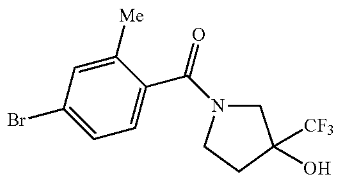 [SMILES: Cc1cc(Br)ccc1C(=O)N1CCC(O)(C(F)(F)F)C1] | (S or R)-(4-bromo-2-methylphenyl)(3-hydroxy-3-(trifluoromethyl)pyrrolidin-1-yl)methanone (Derived from Peak 2 via SFC: Chiralpak AS-H, 10% MeOH in $CO_2$, Tr = 3.10 minutes) | LRMS (ESI) Calc'd for $C_{13}H_{14}BrF_3NO_2$ $[M + H]^+$: 354, found 354. |
| I-39-3 | 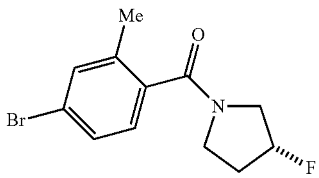 [SMILES: Cc1cc(Br)ccc1C(=O)N1CC[C@@H](F)C1] | (R)-(4-bromo-2-methylphenyl)(3-fluoropyrrolidin-1-yl)methanone | LRMS (ESI) Calc'd for $C_{12}H_{14}BrFNO$ $[M + H]^+$: 288, found 288. |
| I-39-4 | 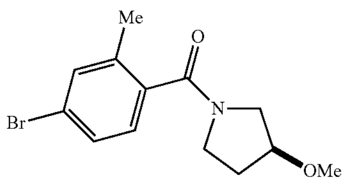 [SMILES: CO[C@H]1CCN(C(=O)c2ccc(Br)cc2C)C1] | (S)-(4-bromo-2-methylphenyl)(3-methoxypyrrolidin-1-yl)methanone | LRMS (ESI) Calc'd for $C_{13}H_{17}BrNO_2$ $[M + H]^+$: 300, found 300. |
| I-39-5 | 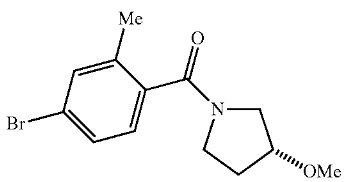 [SMILES: CO[C@@H]1CCN(C(=O)c2ccc(Br)cc2C)C1] | (R)-(4-bromo-2-methylphenyl)(3-methoxypyrrolidin-1-yl)methanone | LRMS (ESI) Calc'd for $C_{13}H_{17}BrNO_2$ $[M + H]^+$: 300, found 300. |
| I-39-6 | 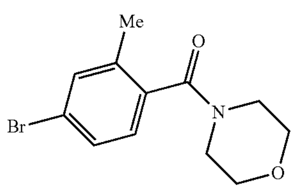 [SMILES: Cc1cc(Br)ccc1C(=O)N1CCOCC1] | (4-bromo-2-methylphenyl)(morpholino)methanone | LRMS (ESI) Calc'd for $C_{12}H_{15}BrNO_2$ $[M + H]^+$: 286, found 286. |
| I-39-7 | 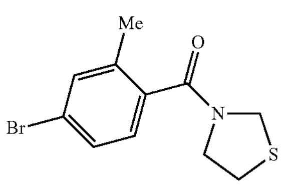 [SMILES: Cc1cc(Br)ccc1C(=O)N1CCSC1] | (4-bromo-2-methylphenyl)(thiazolidin-3-yl)methanone | LRMS (ESI) Calc'd for $C_{11}H_{13}BrNOS$ $[M + H]^+$: 288, found 288. |
| I-39-8 | 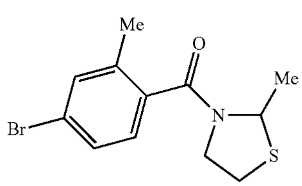 [SMILES: Cc1cc(Br)ccc1C(=O)N1CCSC1C] | (4-bromo-2-methylphenyl)(2-methylthiazolidin-3-yl)methanone | LRMS (ESI) Calc'd for $C_{12}H_{15}BrNOS$ $[M + H]^+$: 302, found 302. |
| I-39-9 | 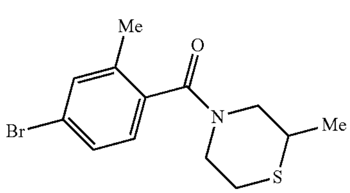 [SMILES: Cc1cc(Br)ccc1C(=O)N1CCSC(C)C1] | (4-bromo-2-methylphenyl)(2-methylthiomorpholino)methanone | LRMS (ESI) Calc'd for $C_{13}H_{17}BrNOS$ $[M + H]^+$: 316, found 316. |

TABLE 12-continued

| Example | Structure | Compound Name | LRMS |
|---|---|---|---|
| I-39-10 | 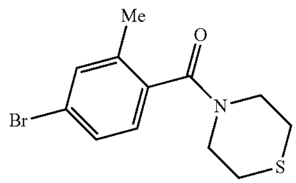 [SMILES: Cc1cc(Br)ccc1C(=O)N1CCSCC1] | (4-bromo-2-methylphenyl)(thiomorpholino)methanone | RH$_{15}$BrNOS [M + H]$^+$: 302, found 302. |
| I-39-11 | 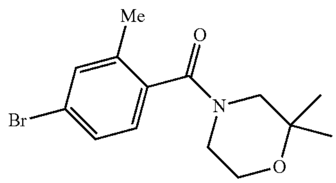 [SMILES: Cc1cc(Br)ccc1C(=O)N1CCOC(C)(C)C1] | (4-bromo-2-methylphenyl)(2,2-dimethylmorpholino)methanone | LRMS (ESI) Calc'd for C$_{14}$H$_{19}$BrNO$_2$ [M + H]$^+$: 312, 314 (1:1), found 312, 314 (1:1). |

Intermediate 40-1

8-oxa-3-azabicyclo[3.2.1]octan-3-yl(4-bromo-2-methylphenyl)methanone

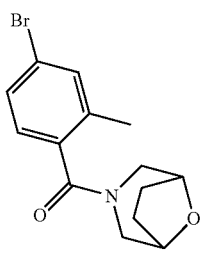

I-40-1

Step 1: 4-bromo-2-methylbenzoyl chloride

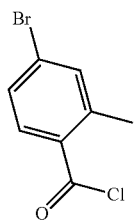

4-Bromo-2-methylbenzoic acid (1.40 g, 6.50 mmol) was dissolved in thionyl chloride (20 mL). The mixture was stirred at 80° C. for 2 hours and then concentrated in vacuo to afford 1.35 g (crude) of 4-bromo-2-methylbenzoyl chloride as a solid that was used as is in the next step.

Step 2: 8-oxa-3-azabicyclo[3.2.1]octan-3-yl(4-bromo-2-methylphenyl)methanone I-40-1

4-Bromo-2-methylbenzoyl chloride (1.24 g, 5.30 mmol) was added to a suspension of (1R,5S)-8-oxa-3-azabicyclo[3.2.1]octane (0.50 g, 4.42 mmol) and triethylamine (2.51 mL, 18.0 mmol) in DCM (10 mL) at ambient temperature. The reaction mixture was stirred at ambient temperature for 2 hours, then diluted with DCM (30 mL) and washed with brine (×2). The combined organic layers were dried over sodium sulfate, filtered and concentrated in vacuo to afford an oil that was purified by silica chromatography, eluting with petroleum ether/EtOAc (5/1) to afford the title compound as a solid: LRMS (ESI) calc'd for C$_{14}$H$_{17}$BrNO$_2$ [M+H]$^+$: 310 312 (1:1) found 310 312 (1:1); $^1$H NMR (300 MHz, CDCl$_3$): δ 7.41 (s, 1H), 7.36 (d, J=8.1 Hz, 1H), 7.08 (d, J=8.1 Hz, 1H), 4.76 (m, 1H), 3.85 (m, 1H), 3.72 (m, 1H), 3.60-3.50 (m, 3H), 2.34 (s, 3H), 2.15-1.86 (m, 4H).

Table 13 discloses Examples that were prepared in analogy to I-40-1.

TABLE 13

| Example | Structure | Compound Name | LRMS |
|---|---|---|---|
| I-40-2 | 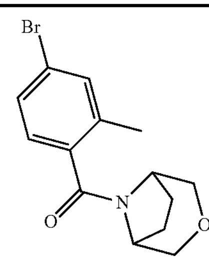 | 3-oxa-8-azabicyclo[3.2.1]octan-8-yl(4-bromo-2-methylphenyl)methanone | LRMS (ESI) calc'd for C$_{14}$H$_{17}$BrNO$_2$ [M + H]$^+$: 310, 312 (1:1) found 310, 312 (1:1). |

Intermediate 41

1-bromo-4-(tert-butylsulfonyl)benzene

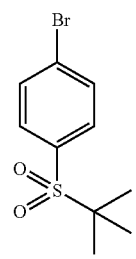

I-41

To a solution of (4-bromophenyl)(tert-butyl)sulfane (1.00 g, 4.08 mmol) in DCM (10.0 mL) was added m-CPBA (2.01 g, 8.97 mmol, 77 wt. %) at room temperature. The resulting solution was stirred at room temperature for one hour and then quenched with saturated aqueous $Na_2S_2O_3$ and saturated aqueous $Na_2CO_3$. The reaction was extracted with DCM (×3), dried over sodium sulfate, filtered and concentrated in vacuo to afford I-41 as a solid. $^1H$ NMR (600 MHz, DMSO-d6): δ 7.89 (d, J=8.7 Hz, 2H), 7.75 (d, J=8.7 Hz, 2H), 1.24 (s, 9H).

Intermediate 42-1

N-(1-(4-bromophenyl)-2,2,2-trifluoroethyl)-2-methylpropan-2-amine

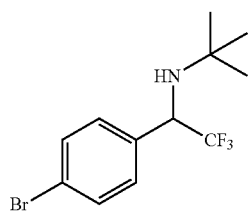

I-42-1

Step 1: 1-(4-bromophenyl)-2,2,2-trifluoroethanol

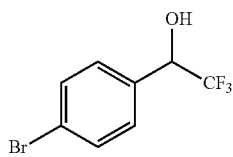 [SMILES: OC(c1ccc(Br)cc1)C(F)(F)F]

1-(4-Bromophenyl)-2,2,2-trifluoroethanone (1.73 g, 6.84 mmol) was dissolved in THF (3.4 mL) and treated with sodium borohydride (0.285 g, 7.52 mmol) at 0° C. The reaction was then warmed to room temperature and stirred overnight. The reaction mixture was diluted with DCM and washed with water and brine. The combined organic layers were dried over $Na_2SO_4$, filtered, and the filtrate was concentrated in vacuo. The residue was purified by silica chromatography, eluting with 5-30% EtOAc in hexanes and the desired fractions were concentrated in vacuo to afford the title compound as an oil. $^1H$ NMR (500 MHz, CDCl$_3$) δ 7.56 (d, J=8.5 Hz, 2H), 7.36 (d, J=8.5 Hz, 2H), 5.06-4.96 (m, 1H), 2.63 (d, J=4.5 Hz, 1H).

Step 2: 1-(4-bromophenyl)-2,2,2-trifluoroethyl trifluoromethanesulfonate

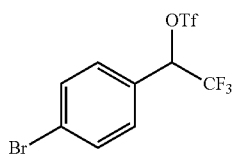 [SMILES: O=S(=O)(OC(c1ccc(Br)cc1)C(F)(F)F)C(F)(F)F]

A solution of 1-(4-bromophenyl)-2,2,2-trifluoroethanol (1.5 g, 5.9 mmol) and 2,6-lutidine (1.10 mL, 9.41 mmol) in DCE (12 mL) was cooled to −15° C. and triflic anhydride (8.82 mL, 8.82 mmol, 1.0 M in DCM) was added dropwise. The reaction stirred between −15° C. and room temperature for 1 hours, then diluted with DCM and washed with water, 1N aqueous HCl, and brine. The combined organic layers were dried over $Na_2SO_4$, filtered, and the filtrate was concentrated in vacuo to give the title compound as a liquid. $^1H$ NMR (500 MHz, CDCl$_3$) δ 7.64 (d, J=8.3 Hz, 2H), 7.37 (d, J=8.3 Hz, 2H), 5.85-5.74 (m, 1H).

Step 3: N-(1-(4-bromophenyl)-2,2,2-trifluoroethyl)-2-methylpropan-2-amine (I-42-1)

1-(4-Bromophenyl)-2,2,2-trifluoroethyl trifluoromethanesulfonate (7.59 g, 19.6 mmol) was dissolved in cyclohexane (70 mL) and 2-methylpropan-2-amine (6.23 mL, 58.8 mmol), DMAP (0.240 g, 1.96 mmol), and ground, dried potassium carbonate (5.42 g, 39.2 mmol) (dried over vacuum at 60° C. for one hour) was added. The reaction mixture was heated to 75° C. and stirred for 48 hours. The reaction mixture was diluted with DCM and washed with water. The combined organic layers were dried over $Na_2SO_4$, filtered, and the filtrate was concentrated in vacuo. The residue was purified by silica chromatography, eluting with 2-20% EtOAc in hexanes and the desired fractions were concentrated in vacuo to afford I-42-1 as a liquid. LRMS (ESI) calc'd for $C_{12}H_{16}BrF_3N$ [M+H]$^+$: 310, found 310.

Following analogous methodology to that outlined for Intermediate I-42-1 above, the following intermediates in Table 14 were synthesized. In select cases, the general procedure was modified by not using DMAP and/or the crude product was used as is, and/or to alternatively utilize 2.0-3.0 equivalents of amine and/or 1.5-3.0 equivalents of ground, dried potassium carbonate.

TABLE 14

| Intermediate | Structure | Name | LRMS |
|---|---|---|---|
| I-42-2 | 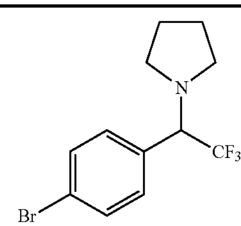 | 1-(1-(4-bromophenyl)-2,2,2-trifluoroethyl)pyrrolidine | LRMS (ESI) calc'd for $C_{12}H_{14}BrF_3N$ [M + H]$^+$: 308, found 308. |
| I-42-3 | 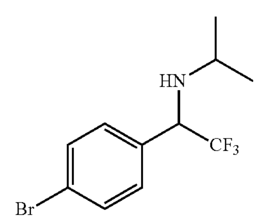 [SMILES: CC(C)NC(c1ccc(Br)cc1)C(F)(F)F] | N-(1-(4-bromophenyl)-2,2,2-trifluoroethyl)propan-2-amine | LRMS (ESI) calc'd for $C_{11}H_{14}BrF_3N$ [M + H]$^+$: 296, found 296. |
| I-42-5 | 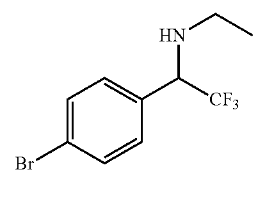 | 1-(4-bromophenyl)-N-ethyl-2,2,2-trifluoroethanamine | LRMS (ESI) calc'd for $C_{10}H_{12}BrF_3N$ [M + H]$^+$: 282, found 282. |

TABLE 14-continued

| Intermediate | Structure | Name | LRMS |
|---|---|---|---|
| I-42-6 | 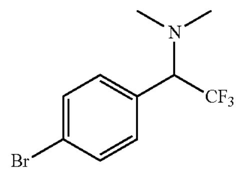 | 1-(4-bromo-phenyl)-2,2,2-trifluoro-N,N-dimethyl-ethanamine | LRMS (ESI) calc'd for $C_{10}H_{12}BrF_3N$ $[M + H]^+$: 282, found 282. |

Intermediate I-43

2-(4-bromophenyl)-N-isopropylpropan-2-amine

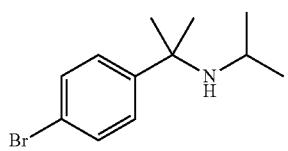

2-(4-Bromophenyl)propan-2-amine (0.5 g, 2.3 mmol) was dissolved in DCM (20 mL) and acetone (2.5 mL). Sodium triacetoxyborohydride (1.5 g, 7.0 mmol) was then added portionwise and the cloudy reaction mixture was stirred at room temperature for 48 hours. The reaction mixture was then diluted with ethyl acetate and washed with saturated sodium bicarbonate and brine. The combined organic layers were dried over $Na_2SO_4$, filtered, and the filtrate was concentrated in vacuo. The residue was purified by silica chromatography, eluting with 5-40% EtOAc in hexanes and the desired fractions were concentrated in vacuo to afford I-43 as a liquid. LRMS (ESI) calc'd for $C_{12}H_{19}BrN$ $[M+H]^+$: 256, found 256.

Intermediate I-44 tert-butyl 3-((4-bromophenyl)sulfonyl)-3-methylbutanoate

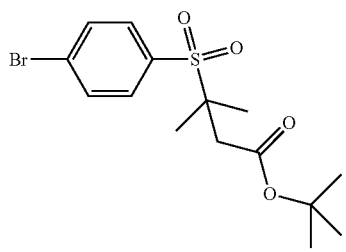

1-Bromo-4-(propane-2-sulfonyl)benzene (0.25 g, 0.90 mmol) was dissolved in THF (4.75 mL) and cooled to 0° C. LDA (0.57 mL, 1.1 mmol, 2.0 M in THF) was then added dropwise. The reaction mixture was stirred at 0° C. for 1 hour and then tert-butyl bromoacetate (0.42 mL, 2.85 mmol) was added and the reaction was warmed to room temperature overnight. The reaction mixture was diluted with ethyl acetate and washed with saturated aqueous ammonium chloride and brine. The combined organic layers were dried over $Na_2SO_4$, filtered, and the filtrate was concentrated in vacuo. The residue was purified by silica chromatography, eluting with 2-30% EtOAc in hexanes and the desired fractions were concentrated in vacuo to afford I-44 as an oil. LRMS (ESI) calc'd for $C_{15}H_{22}BrO_4S$ $[M+H]^+$: 377, found 377.

Intermediate I-45

1-(1-(4-bromophenyl)ethyl)pyrrolidine

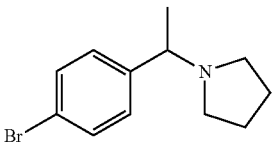

1-(4-Bromophenyl)ethanone (0.50 g, 2.5 mmol) and pyrroldine (1.04 mL, 12.6 mmol) were dissolved in methanol (8.5 mL) and sodium cyanoborohydride (0.17 g, 2.8 mmol) was added. The reaction was stirred at room temperature over 48 hours. The reaction mixture was diluted with ethyl acetate, washed with saturated sodium bicarbonate, brine and the combined organic layers were dried over $Na_2SO_4$, filtered, and concentrated in vacuo. The residue was purified by silica chromatography, eluting with 5-40% EtOAc in hexanes and the desired fractions were concentrated in vacuo to afford I-45. LRMS (ESI) calc'd for $C_{12}H_{17}BrN$ $[M+H]^+$: 254, found 254.

Intermediate I-46

1-bromo-4-((2,2-dimethylcyclopentyl)sulfonyl)benzene

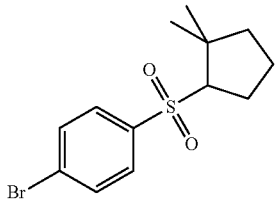

Step 1: 2,2-dimethylcyclopentanol

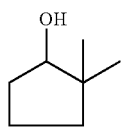

2,2-Dimethylcyclopentanone (0.56 mL, 4.5 mmol) was dissolved in THF (2.0 mL) and methanol (0.5 mL) and cooled to 0° C. Sodium borohydride (0.25 g, 6.7 mmol) was added and the reaction mixture was warmed to room temperature, and stirred for 2 hours. Methanol (1.0 mL) and aqueous NaOH (2.0 mL, 1.0 N) was then added and the reaction was stirred overnight. The reaction mixture was diluted with dichloromethane and washed with water and brine. The combined organic layers were dried over Na$_2$SO$_4$, filtered, and concentrated in vacuo. The residue was purified by silica chromatography, eluting with 5-40% EtOAc in hexanes and the desired fractions were concentrated in vacuo to afford the title compound as a liquid. $^1$H NMR (500 MHz, CDCl$_3$) δ 3.73-3.64 (m, 1H), 2.10-1.98 (m, 1H), 1.80-1.67 (m, 1H), 1.65-1.50 (m, 3H), 1.42-1.35 (m, 1H), 1.32 (d, J=4.2 Hz, 1H), 0.97 (s, 3H), 0.95 (s, 3H).

Step 2: 2,2-dimethylcyclopentyl methanesulfonate

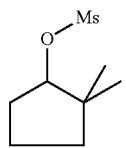

2,2-Dimethylcyclopentanol (257 mg, 2.20 mmol) was dissolved in DCM (4.0 mL) and triethylamine (0.94 mL, 6.8 mmol) was added. The reaction mixture was cooled to 0° C. and methanesulfonyl chloride (0.26 mL, 3.4 mmol) was added. The reaction was warmed to room temperature and stirred for two hours. Additional triethylamine (0.94 mL, 6.8 mmol) and methanesulfonyl chloride (0.26 mL, 3.4 mmol) were added and the reaction stirred at 40° C. for one hour. Methanesulfonic anhydride (0.59 g, 3.4 mmol) was then added and the reaction was stirred at room temperature for one hour. The reaction mixture was diluted with dichloromethane and washed with aqueous HCl (1.0 N) and brine. The combined organic layers were dried over Na$_2$SO$_4$, filtered, and concentrated in vacuo. The residue was purified by silica chromatography, eluting with 5-40% EtOAc in hexanes and the desired fractions were concentrated in vacuo to afford the title compound as a liquid. $^1$H NMR (500 MHz, CDCl$_3$) δ 4.61-4.55 (m, 1H), 3.00 (s, 3H), 2.22-2.15 (m, 1H), 1.98-1.92 (m, 1H), 1.89-1.79 (m, 1H), 1.74-1.65 (m, 1H), 1.65-1.59 (m, 1H), 1.50-1.43 (m, 1H), 1.06 (s, 3H), 1.02 (s, 3H).

Step 3: (4-bromophenyl)(2,2-dimethylcyclopentyl)sulfane

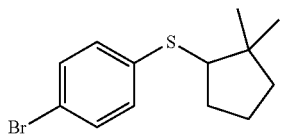

4-Bromobenzenethiol (170 mg, 0.900 mmol), 2,2-dimethylcyclopentyl methanesulfonate (190 mg, 0.989 mmol), and potassium carbonate (250 mg, 1.80 mmol) were dissolved in DMF (4.5 mL) and the reaction was stirred at 60° C. for 3.5 hours then heated to 100° C. by microwave irradiation for 30 minutes. The reaction mixture was diluted with ethyl acetate and washed with water and brine. The combined organic layers were dried over Na$_2$SO$_4$, filtered, and the filtrate was concentrated in vacuo to afford the title compound that was sufficiently pure to use in the next step without further purification. $^1$H NMR (500 MHz, CDCl$_3$) δ 7.44 (d, J=8.5 Hz, 2H), 7.35 (d, J=8.5 Hz, 2H), 3.10 (t, J=8.6 Hz, 1H), 2.26-2.18 (m, 2H), 1.79-1.73 (m, 2H), 1.62 (m, 1H), 1.52-1.46 (m, 1H), 1.08 (s, 3H), 0.99 (s, 3H).

Step 4: 1-bromo-4-((2,2-dimethylcyclopentyl)sulfonyl)benzene (I-46)

(4-Bromophenyl)(2,2-dimethylcyclopentyl)sulfane (0.2 g, 0.7 mmol) was dissolved in DCM (2.0 mL) and mCPBA (0.27 g, 1.5 mmol, 77 wt. % max) was added. The reaction was stirred at room temperature for one hour. The reaction mixture was diluted with dichloromethane and washed with aqueous NaOH (1.0 N) and brine. The combined organic layers were dried over Na$_2$SO$_4$, filtered, and concentrated in vacuo. The residue was purified by silica chromatography, eluting with 5-30% EtOAc in hexanes and the desired fractions were concentrated in vacuo to afford I-46 as a solid. LRMS (ESI) calc'd for C$_{13}$H$_{18}$BrO$_2$S [M+H]$^+$: 317, found 317.

Intermediate 47-1

1-bromo-4-((2,3-dimethylbutan-2-yl)sulfonyl)benzene

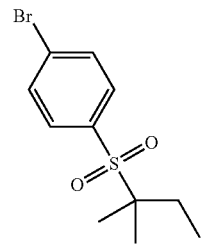

I-47-1

To a solution of 1-bromo-4-(isopropylsulfonyl)benzene (100 mg, 0.38 mmol) in dry THF (2 mL) was slowly added LDA (0.19 mL, 0.38 mmol, 2.9 M in THF/heptane/ethylbenzene) at −78° C. After 1.5 hours, iodoethane (91 μL, 1.1 mmol) was added and the mixture was allowed to warm up to room temperature overnight. The mixture was diluted with saturated aqueous ammonium chloride, extracted with ethyl acetate (×3), and the combined organic layers were dried over Na$_2$SO$_4$, filtered and concentrated in vacuo. The residue was purified by silica chromatography, eluting with 0-40% ethyl acetate/hexanes to afford intermediate I-47-1 as a solid. $^1$H NMR (600 MHz, CDCl$_3$): δ 7.71 (d, J=8.8 Hz, 2H), 7.67 (d, J=8.2 Hz, 2H), 1.71 (q, J=7.6 Hz, 2H), 1.25 (s, 6H), 0.93 (t, J=7.6 Hz, 3H).

The following intermediates in Table 15 were prepared by analogy using the procedure outlined above for I-47-1.

TABLE 15

| Intermediate | Structure | Compound Name | NMR |
|---|---|---|---|
| I-47-2 | 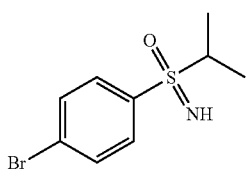 | 1-bromo-4-((2,3-dimethylbutan-2-yl)sulfonyl)benzene | $^1$H NMR (600 MHz, CDCl$_3$): δ 7.73 (d, J = 8.4 Hz, 2H), 7.69 (d, J = 8.5 Hz, 2H), 2.19 (septet, J = 6.4 Hz, 1H), 1.23 (s, 6H), 1.08 (d, J = 6.6 Hz, 6H) |

Intermediate 48

1-bromo-4-((S and R)-propan-2-ylsulfonimidoyl)benzene

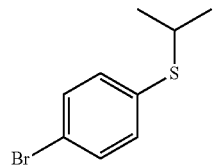

I-48

Step 1: (4-bromophenyl)(isopropyl)sulfane

To 4-bromothiophenol (1.00 g, 5.29 mmol) was added THF (17.6 mL) and then NaH (233 mg, 5.82 mmol, 60 wt %. in mineral oil) and the reaction was stirred at 0° C. for 1 hour before 2-bromopropane (1.24 g, 10.1 mmol) was added. The reaction was stirred overnight, filtered through Celite, and concentrated in vacuo. The residue was then purified on silica, eluting with 2-30% EtOAc/hexanes to afford the desired product as an oil. $^1$H NMR (600 MHz, CDCl$_3$) δ 7.41 (d, J=8.4 Hz, 2H), 7.25 (d, J=8.4 Hz, 2H), 3.34 (septet, J=6.6 Hz, 1H), 1.29 (d, J=6.6 Hz, 6H).

Step 2: 1-bromo-4-(isopropylsulfinyl)benzene

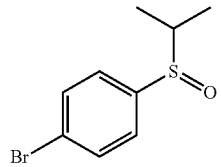

To (4-bromophenyl)(isopropyl)sulfane (1.25 g, 5.40 mmol) was added CH$_2$Cl$_2$ (18.0 mL) and then m-CPBA (1.21 g, 5.40 mmol, 77 wt. % max) at 0° C. The reaction was stirred overnight, then quenched by addition of saturated NaHCO$_3$ and sodium sulfite solutions. The solution was then stirred for 15 minutes, extracted with DCM (×3), and the organic layers were dried over sodium sulfate, filtered and concentrated in vacuo. The crude product was purified on silica, eluting with 2-40% EA/hexanes to afford an oil. $^1$H NMR (600 MHz, CDCl$_3$) δ 7.65 (d, J=8.4 Hz, 2H), 7.46 (d, J=8.4 Hz, 2H), 2.81 (septet, J=6.6 Hz, 1H), 1.23 (d, J=6.6 Hz, 3H), 1.12 (d, J=6.6 Hz, 3H).

Step 3: 4-methyl-N-[(R and S)-isopropyloxido-(4-bromophenyl)-λ$^4$-sulfanylidene]-benzenesulfonamide

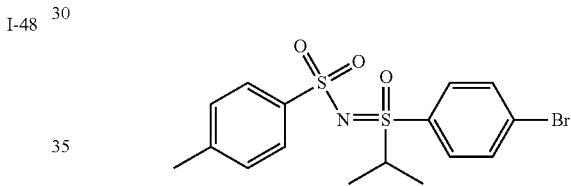

Degassed copper(II) trifluoromethanesulfonate (21 mg, 0.057 mmol) and acetonitrile (17.2 mL) along with 1-bromo-4-(isopropylsulfinyl)benzene (175 mg, 0.708 mmol) were stirred under argon for 10 minutes before [N-(p-toluenesulfonyl)imino]phenyliodinane (378 mg, 1.01 mmol) was added and the reaction was stirred at 25° C. overnight, and then at 50° C. for 7 hours. The reaction was concentrated in vacuo, and loaded directly onto silica and eluted with 0-40% EtOAc/hexanes. Concentration of the desired fractions afford the title compound as a foam. LRMS (ESI) calc'd for C$_{16}$H$_{19}$NO$_3$S$_2$Br [M+H]$^+$: 416, found 416. $^1$H NMR (600 MHz, CDCl$_3$) δ 7.80 (m, 4H), 7.73 (d, J=7.5 Hz, 2H), 7.24 (m, 2H), 3.60 (septet, J=6.6 Hz, 1H), 2.37 (s, 3H), 1.35 (d, J=6.6 Hz, 3H), 1.25 (d, J=6.6 Hz, 3H).

Step 4: 1-bromo-4-((S and R)-propan-2-ylsulfonimidoyl)benzene (I-48)

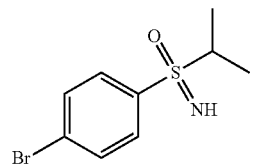

To 4-methyl-N-[(R and S)-isopropyloxido-(4-bromophenyl)-λ$^4$-sulfanylidene]-benzenesulfonamide (1.39 g, 3.34 mmol) was added concentrated sulfuric acid (20 mL) at 0° C. and the reaction was stirred at this temperature for 45 minutes, before being allowed to warm to room temperature over 15 minutes. The reaction was then diluted with CH$_2$Cl$_2$ and quenched by slow addition of saturated sodium bicarbonate solution. The neutralized solution was then extracted with CH$_2$Cl$_2$ (×3), then EtOAc (×2), and the combined organic layers were dried over Na$_2$SO$_4$, filtered and concentrated in vacuo. Purification on silica, eluting with 5-80% EtOAc in hexanes afforded an oil. $^1$H NMR (600 MHz, CDCl$_3$): δ 7.80 (m, 4H), 7.81 (d, J=8.4 Hz, 2H), 7.69 (d, J=8.4 Hz, 2H), 3.27 (septet, J=6.6 Hz, 1H), 1.33 (d, J=7.2 Hz, 3H), 1.28 (d, J=6.6 Hz, 3H).

Intermediate 49

1-(4-bromophenyl)-3,5-dimethyl-1H-pyrazole

I-49

Step 1: (4-bromophenyl)hydrazine

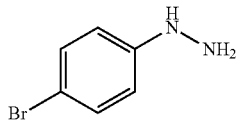

A suspension of 4-bromoaniline (100 g, 0.581 mol) in water (500 mL) and concentrated HCl (1.0 L) was charged with a solution of NaNO$_2$ (40 g, 0.58 mol) in water (250 mL) dropwise at 0° C. over 30 minutes and the resulting reaction mixture was stirred at 0° C. for 30 minutes. The reaction mixture was then charged to a solution of SnCl$_2$ (523 g, 2.32 mol) in concentrated HCl (1.0 L) at 0° C. over 30 minutes. The reaction mixture was stirred at room temperature for 3 hours, then cooled to 5° C. and the precipitated solids were filtered and dried at 40° C. to afford the title compound as a solid. $^1$H NMR (300 MHz, DMSO-d$_6$): δ 10.40 (br s, 3H), 7.45 (d, J=8.7 Hz, 2H), 6.96 (d, J=8.7 Hz, 2H).

Step 2: 1-(4-bromophenyl)-3,5-dimethyl-1H-pyrazole (I-49)

A solution of (4-bromophenyl)hydrazine (95 g, 0.42 mol) in EtOH (950 mL) was charged with KOAc (42 g, 0.42 mol) and pentane-2,4-dione (51 g, 0.51 mol) at room temperature and the mixture was heated to reflux for 3 hours. The reaction mixture was then concentrated under reduced pressure and diluted with water (500 mL) and extracted with MTBE (×2). The combined organic layers were washed with brine, dried over anhydrous Na$_2$SO$_4$, and concentrated in vacuo. The residue was suspended in hexanes (500 mL) and filtered and the filtrate was concentrated in vacuo to afford I-49 as a liquid. $^1$H NMR (400 MHz, CDCl$_3$): δ 7.58-7.55 (m, 2H), 7.34-7.30 (m, 2H), 6.01 (s, 1H), 2.30 (d, J=5.2 Hz, 6H).

Intermediate 50

1-(4-bromo-2-methylphenyl)-1H-pyrazole

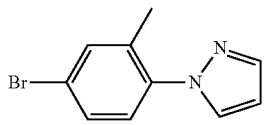

I-50

5-Bromo-2-iodotoluene (0.144 mL, 1.01 mmol), pyrazole (68.8 mg, 1.01 mmol), copper(I) oxide (7.2 mg, 0.051 mmol), (1S,2S)-bis(pyridin-2-ylmethylene)cyclohexane-1,2-diamine (59.1 mg, 0.202 mmol), and cesium carbonate (658 mg, 2.02 mmol) were combined in a sealed microwave vial, and dissolved in acetonitrile (1.4 mL). The reaction was stirred at 82° C. overnight and then cooled to room temperature and filtered through Celite, rinsing the Celite pad with dichloromethane. The solution was concentrated in vacuo and the crude material was purified by silica chromatography, eluting with a gradient of 0-25% ethyl acetate in hexanes. LRMS (ESI) calc'd for C$_{10}$H$_{10}$N$_2$Br [M+H]$^+$: 237, 239 (1:1), found 237, 239 (1:1). $^1$H NMR (500 MHz, CDCl$_3$): δ 7.72 (s, 1H), 7.57 (s, 1H), 7.47 (s, 1H), 7.40 (d, J=8.0 Hz, 1H), 7.19 (d, J=8.5 Hz, 1H), 6.44 (s, 1H), 2.22 (s, 3H).

Intermediate 51-1

6-bromo-N,N-dimethylquinolin-2-amine

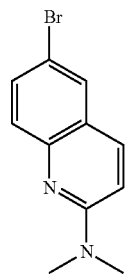

I-51-1

6-Bromo-2-chloroquinoline (200 mg, 0.825 mmol) and dimethylamine (2.0 mL, 4.0 mmol, 2M in THF) were combined in a microwave vial and heated at 60° C. overnight. The reaction was diluted with ethyl acetate and washed with water and brine. The organic layer was dried with MgSO$_4$, filtered, and concentrated in vacuo to the title compound. LRMS (ESI) calc'd for C$_{11}$H$_{12}$BrN$_2$ [M+H]$^+$: 251, 253 (1:1), found: 251, 253 (1:1). $^1$H NMR (500 MHz, Acetone-d6): δ 7.96 (d, J=9.4 Hz, 1H), 7.84 (s, 1H), 7.61 (dd, J=8.9, 2.2 Hz, 1H), 7.56 (d, J=8.9 Hz, 1H), 7.11 (d, J=9.4 Hz, 1H), 3.21 (s, 6H).

The following compounds in Table 16 were prepared using the same procedure as for Intermediate 51-1 above.

TABLE 16

| Intermediate | Structure | Compound Name | LRMS |
|---|---|---|---|
| I-51-2 | ![structure] | 4-(6-bromoquinolin-2-yl)morpholine | LRMS (ESI) calc'd for $C_{13}H_{14}BrN_2O$ $[M + H]^+$: 293, 295 (1:1), found 293, 295 (1:1). |
| I-51-3 | ![structure] | (S)-4-(6-bromo-quinolin-2-yl)-2-methylmorpholine | LRMS (ESI) calc'd for $C_{14}H_{16}BrN_2O$ $[M + H]^+$: 307, 309 (1:1), found 307, 309 (1:1). |
| I-51-4 | ![structure] | 3-(6-bromoquinolin-2-yl)-8-oxa-3-azabicyclo[3.2.1]octane | LRMS (ESI) calc'd for $C_{15}H_{16}BrN_2O$ $[M + H]^+$: 319, 321 (1:1), found 319, 321 (1:1). |

Intermediate 52

6-bromo-N,N-dimethylquinoline-2-carboxamide

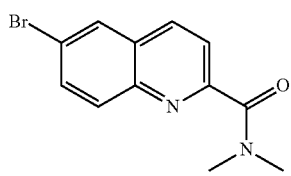

I-52

Step 1: 6-bromoquinoline-2-carboxylic acid

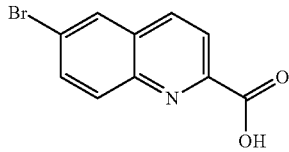 [SMILES: O=C(O)c1ccc2cc(Br)ccc2n1]

6-Bromo-quinoline-2-carbonitrile (250 mg, 1.07 mmol) was dissolved in MeOH (4.5 mL) in a microwave vial and 5N aqueous sodium hydroxide (1.5 mL, 2.25 mmol) was added. The reaction was heated at 100° C. for 20 minutes, then cooled to room temperature and concentrated in vacuo. The residue was acidified to pH 5 using 1M aqueous HCl and the reaction was extracted using ethyl acetate (×1). The organic layer was then dried using $MgSO_4$, filtered, and concentrated in vacuo to giv the title compound. $^1H$ NMR (500 MHz, DMSO-d6): δ 13.58 (br s, 1H), 8.57 (d, J=8.5 Hz, 1H), 8.46 (d, J=2.2 Hz, 1H), 8.19 (d, J=8.5 Hz, 1H), 8.13 (d, J=9.3 Hz, 1H), 8.02 (dd, J=9.3, 2.2 Hz, 1H).

Step 2: 6-bromo-N,N-dimethylquinoline-2-carboxamide

6-Bromoquinoline-2-carboxylic acid (40 mg, 0.16 mmol) and HATU (121 mg, 0.317 mmol) were dissolved in DMF (0.50 mL) and stirred at room temperature for 5 minutes. A separate solution of DMF (0.50 mL), dimethylamine (0.159 mL, 0.317 mmol, 2M in THF)) and DIPEA (0.083 mL, 0.48 mmol) was then added and the reaction was stirred at room temperature for 1 hour before being diluted with EtOAc, and washed with water. The organic layer was then dried using $MgSO_4$, filtered, and concentrated in vacuo to give the title compound. $^1H$ NMR (500 MHz, $CDCl_3$): δ 8.17 (d, J=8.2 Hz, 1H), 8.02 (s, 1H), 7.98 (d, J=8.2 Hz, 1H), 7.82 (d, J=8.2 Hz, 1H), 7.74 (d, J=8.2 Hz, 1H), 3.20 (s, 3H), 3.16 (s, 3H).

Intermediate 53

6-bromoquinoline-2-carboxamide

I-53

Potassium carbonate (59.3 mg, 0.429 mmol) and hydrogen peroxide (0.31 mL, 3.0 mmol) were dissolved in acetonitrile (2.0 mL). 6-Bromo-quinoline-2-carbonitrile (100 mg, 0.429 mmol) was then added. The reaction was stirred at room temperature overnight and then additional hydrogen peroxide (0.22 mL, 2.2 mmol) was added to the reaction mixture which was then heated at 50° C. overnight. The reaction was cooled to room temperature, diluted with ethyl acetate, washed with water, brine, dried over $MgSO_4$, filtered, and concentrated in vacuo to give the title compound. $^1H$ NMR (500 MHz, $CDCl_3$): δ 8.33 (d, J=8.5 Hz, 1H), 8.25 (d, J=8.5 Hz, 1H), 8.07 (d, J=2.1 Hz, 1H), 8.03 (br s, 1H), 8.00 (d, J=8.8 Hz, 1H), 7.85 (dd, J=8.8, 2.5 Hz, 1H), 5.74 (br s, 1H).

Intermediates I-54A and I-54B (R or S)-2-(4-bromophenyl)-2-(trifluoromethyl)piperidine

I-54A

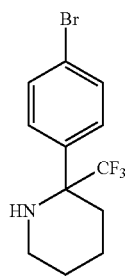

I-54B

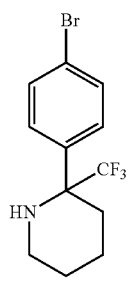

Step 1: 4-bromobenzoyl chloride

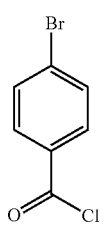

A solution of 4-bromobenzoic acid (10.0 g, 49.7 mmol) in sulfurous dichloride (59.2 g, 0.50 mol) was heated at 80° C. for 16 hours. The mixture was then concentrated in vacuo to afford the title compound which was carried onto the next step without further purification.

Step 2: tert-butyl 3-(4-bromobenzoyl)-2-oxopiperidine-1-carboxylate

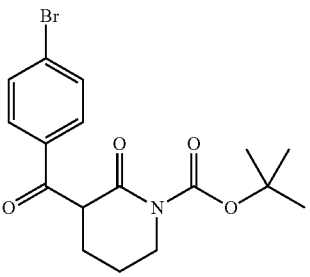 [SMILES: CC(C)(C)OC(=O)N1CCCC(C(=O)c2ccc(Br)cc2)C1=O]

Lithium bis(trimethylsilyl)amide (2.11 mL, 2.11 mmol, 1.0 M in THF) was added to a solution of tert-butyl 2-oxopiperidine-1-carboxylate (0.20 g, 1.0 mmol) in THF (2 mL) at −78° C. The resulting mixture was stirred for 10 minutes, then 4-bromobenzoyl chloride (0.22 g, 1.0 mmol) was added. The reaction was warmed to ambient temperature and stirred for 1 hour, then saturated aqueous ammonium chloride (20 mL) was added. The quenched reaction was extracted with EtOAc (×3) and the combined organic layers were dried over anhydrous $Na_2SO_4$, filtered and concentrated in vacuo. The residue was purified on silica, eluting with 0-1% EtOAc in hexanes to afford the title compound. LRMS (ESI) calc'd for: $C_{17}H_{21}BrNO_4$ [M+H]$^+$: 382, 384 (1:1), found 382, 384 (1:1).

Step 3: 6-(4-bromophenyl)-2,3,4,5-tetrahydropyridine

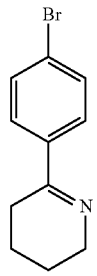 [SMILES: Brc1ccc(C2=NCCCC2)cc1]

tert-Butyl 3-(4-bromobenzoyl)-2-oxopiperidine-1-carboxylate (2.00 g, 5.23 mmol) was combined with HCl (8.0 M, 43.6 mL, 0.52 mol) at ambient temperature. The resulting solution was heated at 80° C. for 16 hours. The reaction was then poured into saturated aqueous $Na_2CO_3$ (50 mL) and extracted with EtOAc (×3). The combined organic layers were dried over $Na_2SO_4$, filtered and concentrated in vacuo. The residue was purified on silica, eluting with 0-1% EtOAc in hexanes to afford the title compound. LRMS (ESI) calc'd for: $C_{11}H_{13}BrN$ [M+H]$^+$: 238, 240 (1:1), found 238, 240 (1:1); $^1$H NMR (300 MHz, CDCl$_3$) δ 7.66-7.63 (m, 2H), 7.52-7.47 (m, 2H), 3.90 (m, 2H), 2.59 (m, 2H), 1.88-1.79 (m, 2H), 1.78-1.66 (m, 2H).

Step 4: (R or S)-2-(4-bromophenyl)-2-(trifluoromethyl)piperidine and (R or S)-2-(4-bromophenyl)-2-(trifluoromethyl)piperidine (I-54A and I-54B)

To a solution of 6-(4-bromophenyl)-2,3,4,5-tetrahydropyridine (1.0 g, 4.2 mmol) in acetonitrile (10 mL), was successively added trifluoromethanesulfonic acid (3.30 g, 22.0 mmol), potassium hydrogen fluoride (3.94 g, 50.4 mmol) and trimethyl(trifluoromethyl)silane (5.97 g, 42.0 mmol) at 0-4° C. The resulted mixture was stirred at ambient temperature for 48 hours. The reaction was then quenched with saturated aqueous $NaHCO_3$ (50 mL) followed by extraction with EtOAc (×3). The combined organic layers were dried over anhydrous $Na_2SO_4$, filtered and concentrated in vacuo. The residue was purified on silica, eluting with 0-1% DCM in petroleum ether to afford the racemic title compound. The title compounds were then separated by SFC using a Chiralpak IA column, eluting with 15% i-PrOH in $CO_2$ to afford Peak A (I-54A) (Tr=4.7 minutes) and Peak B (I-54B) (Tr=5.5 minutes). LRMS (ESI) calc'd for $C_{12}H_{14}BrF_3N$ [M+H]$^+$: 308, 310 (1:1), found 308, 310 (1:1); $^1$H NMR (300 MHz, CDCl$_3$): δ 7.66 (m, 2H), 7.59 (m, 2H), 3.16-3.03 (m, 1H), 2.73-2.63 (m, 1H), 2.50-2.42 (m, 1H), 2.25-1.93 (m, 1H), 1.75 (m, 1H), 1.67-1.53 (m, 3H), 1.33 (m, 1H).

Intermediates I-55A and I-55B (R) and (S)-2-(4-bromophenyl)-2-(trifluoromethyl)pyrrolidine

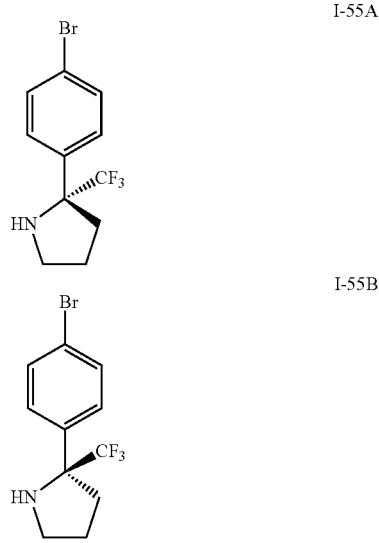

I-55A

I-55B

Step 1: 3-(4-bromobenzoyl)-1-vinylpyrrolidin-2-one

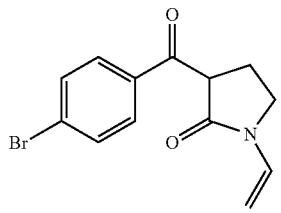 [SMILES: C=CN1CCC(C(=O)c2ccc(Br)cc2)C1=O]

Potassium tert-butoxide (6.26 g, 55.80 mmol) was added to a solution of 1-vinylpyrrolidin-2-one (6.20 g, 55.8 mmol) and methyl 4-bromobenzoate (10.00 g, 46.50 mmol) in THF (150 mL). The mixture was stirred at ambient temperature for an hour at which time water (200 mL) was added and the pH was adjusted to 7 with aqueous hydrochloric acid (1 M). The resulting mixture was extracted with EtOAc (×3). The combined organic layers were dried over anhydrous $Na_2SO_4$, filtered and concentrated in vacuo. The resulting residue was purified by silica chromatography, eluting with 0-20% EtOAc in petroleum ether to afford the title compound as a solid. LRMS (ESI) calc'd for $C_{13}H_{13}BrNO_2$ [M+H]$^+$: 294, 296 (1:1), found 294, 296 (1:1); $^1$H NMR (300 MHz, CDCl$_3$): δ 7.90 (d, J=6.6 Hz, 2H), 7.65 (d, J=6.6 Hz, 2H), 7.06-6.97 (m, 1H), 4.53 (m, 3H), 3.77-3.68 (m, 1H), 3.59 (m, 1H), 2.80-2.71 (m, 1H), 2.37-2.28 (m, 1H).

Step 2: 5-(4-bromophenyl)-3,4-dihydro-2H-pyrrole

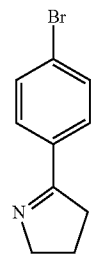

A suspension of 3-(4-bromobenzoyl)-1-vinylpyrrolidin-2-one (5.00 g, 17.0 mmol) in aqueous HCl (20 mL, 8 M) was heated at reflux for 16 hours. The mixture was cooled to ambient temperature and extracted with EtOAc (×3). The aqueous layer was basified to pH=13 with NaOH (15% aqueous solution) and then extracted with DCM (×5). The combined organic layers were dried over anhydrous $Na_2SO_4$, filtered and concentrated in vacuo. The resulting residue was purified by silica chromatography, eluting with 0-20% EtOAc in petroleum ether the title compound as a solid. LRMS (ESI) calc'd for $C_{10}H_{11}BrN$ [M+H]$^+$: 224, 226 (1:1), found 224, 226 (1:1); $^1$H NMR (300 MHz, CDCl$_3$): δ 7.74-7.69 (m, 2H), 7.54 (m, 2H), 4.06 (m, 2H), 2.96-2.88 (m, 2H), 2.10-2.00 (m, 2H).

Step 3: (S) and (R)-2-(4-bromophenyl)-2-(trifluoromethyl)pyrrolidine

To an ice-cooled solution of 5-(4-bromophenyl)-3,4-dihydro-2H-pyrrole (0.80 g, 3.6 mmol) in dry acetonitrile (3 mL) was successively added trifluoromethanesulfonic acid (0.67 g, 4.5 mmol), potassium hydrogen fluoride (0.840 g, 10.7 mmol) and trimethyl(trifluoromethyl) silane (5.08 g, 35.7 mmol). The reaction solution was warmed to ambient temperature and stirred for 48 hours before being quenched with saturated aqueous $NaHCO_3$ until pH>7. The solution was extracted with EtOAc (×3) and the combined organic layers were dried over anhydrous $Na_2SO_4$, filtered and concentrated in vacuo. The residue was purified by silica chromatography, eluting with 0-20% DCM in petroleum ether to afford the title compound as an oil. LRMS (ESI) calc'd for $C_{11}H_{12}BrF_3N$ [M+H]$^+$: 294, 296 (1:1), found 294, 296 (1:1); $^1$H NMR (300 MHz, CDCl$_3$): δ 7.49 (d, J=5.4 Hz, 2H), 7.42 (d, J=5.4 Hz, 2H), 3.29-3.21 (m, 1H), 3.16-3.08 (m, 1H), 2.60-2.51 (m, 1H), 2.25-2.16 (m, 1H), 2.08-1.94 (m, 1H), 1.89-1.75 (m, 1H). This racemic mixture was resolved by chiral HPLC using a Chiralpak AD-H column and methanol (with 0.2% DEA modifier) to Peak 1 (I-55A, retention time=4.4 minutes) and Peak 2 (I-55B, retention time=5.2 minues).

Intermediate 56 tert-butyl 4-(5-bromo-1,1-dioxidobenzo[d]isothiazol-2(3H)-yl)piperidine-1-carboxylate

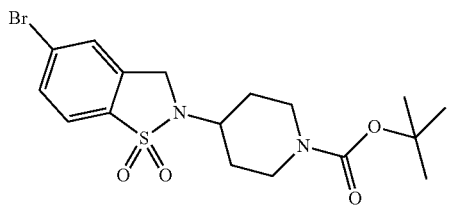

I-56

Step 1: 4-bromo-2-(bromomethyl)benzene-1-sulfonyl chloride

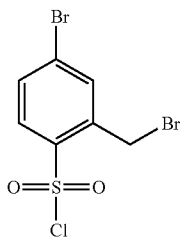

To a solution of N-bromosuccinimide (26.4 g, 148 mmol) and 4-bromo-2-methylbenzene-1-sulfonyl chloride (20.0 g, 74.2 mmol) in carbon tetrachloride (1.00 L) was added 2,2'-azobis(2-methylpropionitrile) (2.43 g, 14.8 mmol) at ambient temperature. The reaction mixture was stirred at 80° C. for 16 hours under argon, then cooled and the solids filtered. To the filtrate was then charged another portion of N-bromosuccinimide (26.4 g, 148 mmol) and 2,2'-azobis(2-methylpropionitrile) (2.43 g, 14.8 mmol) and the reaction was stirred at 80° C. for an additional 16 hours under argon. The solids were again filtered, and the filtrate was concentrated in vacuo. The residue was used next step without further purification.

Step 2: tert-butyl 4-(4-bromo-2-(bromomethyl)phenylsulfonamido)piperidine-1-carboxylate

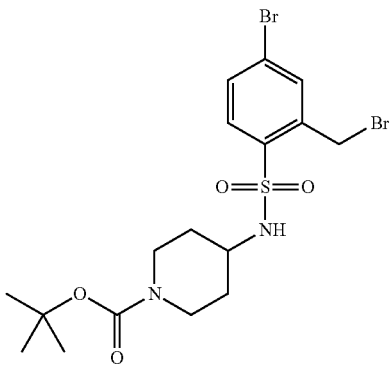 [SMILES: CC(C)(C)OC(=O)N1CCC(NS(=O)(=O)c2ccc(Br)cc2CBr)CC1]

To a solution of 4-bromo-2-(bromomethyl)benzene-1-sulfonyl chloride (60.0 g, 172 mmol) in DCM (1.00 L) was added a solution of tert-butyl 4-aminopiperidine-1-carboxylate (20.7 g, 103 mmol) and triethylamine (34.8 g, 344 mmol) in DCM (100 mL) at ambient temperature. The mixture was stirred at ambient temperature for 3 hours, then quenched with water (500 mL), extracted with DCM (×3), and the combined organic layers were washed with brine, dried over anhydrous $Na_2SO_4$ and filtered. The filtrate was concentrated in vacuo and the residue was purified by silica chromatography, eluting with 25% EtOAc in petroleum ether to afford the title compound as a solid. LRMS (ESI) calc'd for $C_{13}H_{17}Br_2N_2O_4S$ $[M-t-Bu+H]^+$: 455, 457, 459 (1:2:1) found 455, 457, 459 (1:2:1).

Step 3: tert-butyl 4-(5-bromo-1,1-dioxidobenzo[d]isothiazol-2(3)-yl)piperidine-1-carboxylate (I-56)

To a room temperature solution of tert-butyl 4-(4-bromo-2-(bromomethyl)phenylsulfonamido)piperidine-1-carboxylate (50.0 g, 98.0 mmol) in acetonitrile/water (3/1, 400 mL), was added sodium bicarbonate (24.6 g, 293 mmol). The mixture was stirred at 80° C. for 16 hours and then concentrated in vacuo. The residue was diluted with water (200 mL), extracted with EtOAc (×3), and the combined organic layers were dried over anhydrous $Na_2SO_4$ and filtered. The filtrate was concentrated in vacuo and the residue was purified by silica chromatography, eluting with 20% ethyl acetate in petroleum ether to afford the title compound as a solid. LRMS (ESI) calc'd for $C_{13}H_{16}BrN_2O_4S$ $[M-t-Bu+H]^+$: 375, 377 (1:1) found 375, 377 (1:1); 1H NMR (400 MHz, $CD_3OD$): δ 7.76 (s, 1H), 7.74 (d, J=8.4 Hz, 1H), 7.65 (d, J=8.4 Hz, 1H), 4.44 (s, 2H), 4.08 (d, J=13.5 Hz, 2H), 3.78-3.71 (m, 1H), 2.98-2.83 (m, 2H), 2.00-1.94 (m, 2H), 1.85-1.73 (m, 2H), 1.43 (s, 9H).

Intermediate 57

5-bromo-2-(N-trifluoroethylpiperidine-4-yl)cyclohexyl-2,3-dihydrobenzo[d]isothiazole 1,1-dioxide

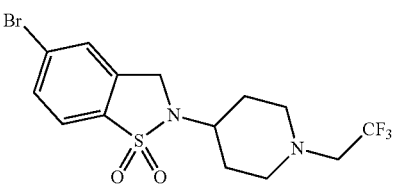

I-57

Step 1: 5-bromo-2-(piperidine-4-yl)cyclohexyl-2,3-dihydrobenzo[d]isothiazole 1,1-dioxide

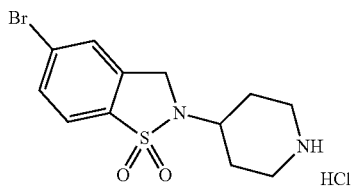 [SMILES: O=S1(=O)c2ccc(Br)cc2CN1C1CCNCC1 ; Cl]

To 5-bromo-2-(N-tert-butyl carbomatepiperidine-4-yl)cyclohexyl-2,3-dihydrobenzo[d]isothiazole 1,1-dioxide (Intermediate 56) (0.10 g, 0.23 mmol), was added a solution of hydrogen chloride gas in EtOAc (5 mL) at ambient temperature. The reaction was maintained at the same temperature for an additional hour at which time the precipitate was collected by filtration and washed with EtOAc to give the title compound as an HCl salt as solid. It was then used in the next step without further purification. LRMS (ESI) calc'd for $C_{12}H_{16}BrN_2O_2S$ [M+H]$^+$: 331, 333 (1:1), found 331, 333 (1:1).

Step 2: 5-bromo-2-(N-trifluoroethylpiperidine-4-yl) cyclohexyl-2,3-dihydrobenzo[d]isothiazole 1,1-dioxide (I-57)

5-Bromo-2-(piperidine-4-yl)cyclohexyl-2,3-dihydrobenzo[d]isothiazole 1,1-dioxide (50 mg, 0.15 mmol), diisopropylethylamine (60 mg, 0.47 mmol), and 2,2,2-trifluoroethyl trifluoromethanesulfonate (0.10 g, 0.43 mmol) were combined with acetonitrile (15 mL) at ambient temperature. The resulting solution was maintained at the same temperature for 16 hours and then concentrated in vacuo. The residue was dissolved in water (30 mL) and extracted with EtOAc (×3). The organic layers were combined, dried over Na$_2$SO$_4$, filtered, concentrated in vacuo and the residue purified by silica chromatography, eluting with EtOAc/ petroleum ether (2/5) to give the title compound as a solid. LRMS (ESI) calc'd for $C_{14}H_{17}BrF_3N_2O_2S$ [M+H]$^+$: 413, 415 (1:1), found 413, 415 (1:1); $^1$H NMR (400 MHz, CDCl$_3$): δ 7.67 (m, 2H), 7.58 (s, 1H), 4.38 (s, 2H), 3.76-3.68 (m, 1H), 3.13-3.02 (m, 4H), 2.68-2.56 (m, 2H), 2.05 (m, 4H).

Intermediate 58

(R and S)-1-benzyl-3-(4-bromophenyl)-3-(trifluoromethyl)pyrrolidine

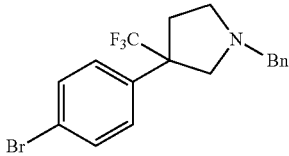

I-58

Step 1:
1-bromo-4-(3,3,3-trifluoroprop-1-en-2-yl)benzene

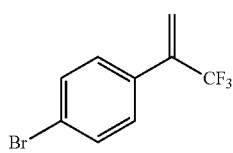

To a solution of methyltripenylposphonium bromide (6.35 g, 17.8 mmol) in THF (13.2 mL) under nitrogen at 0° C., was added lithium bis(trimethylsilyamide (17.8 mL, 17.8 mmol, 1M in THF). The reaction mixture was stirred for 30 minutes, then cooled to −78° C. 1-(4-bromophenyl)-2,2,2-trifluoroethanone (3 g, 11.86 mmol) was then added and the reaction mixture was allowed to warm to room temperature over 1 hour. Then reaction was poured into 1:1 ice water/ NH$_4$Cl, and the aqeuous layer was extracted with EtOAc (×3). The combined organic layers were washed with brine, dried over Na$_2$SO$_4$, filtered and concentrated in vacuo to afford the title compound. $^1$H NMR (600 MHz, CDCl$_3$): δ 7.50 (d, J=8.3 Hz, 2H), 7.30 (d, J=8.2 Hz, 2H), 5.96 (s, 1H), 5.75 (s, 1H).

Step 2: (R and S) 1-benzyl-3-(4-bromophenyl)-3-(trifluoromethyl)pyrrolidine (I-58)

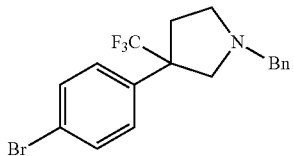 [SMILES: FC(F)(F)C1(c2ccc(Br)cc2)CCN(Cc2ccccc2)C1]

To a solution of 1-bromo-4-(3,3,3-trifluoroprop-1-en-2-yl)benzene (0.25 g, 1.0 mmol) and N-benzyl-1-methoxy-N-((trimethylsilyl)methyl)methanamine (0.51 mL, 2.0 mmol) in DCM (5 mL) at 0° C., was added trifluoroacetic acid (7.7 µL, 0.1 mmol). The reaction mixture was stirred and warmed to room temperature over 3 hours. Then reaction was quenched with saturated aqueous NaHCO$_3$ (20 mL), and the aqeuous layer was extracted with EtOAc (×3). The combined organic layers were washed with brine, dried over Na$_2$SO$_4$, filtered and concentrated in vacuo to afford the title compound. $^1$H NMR (600 MHz, CDCl$_3$): δ 7.45 (d, J=8.2 Hz, 2H), 7.29-7.35, (m, 4H), 7.19-7.23 (m, 3H), 3.65-3.67 (m, 2H), 3.18 (m, 1H), 2.77 (m, 1H), 2.58 (m, 1H), 2.37 (m, 1H), 1.25 (m, 1H), 0.85 (m, 1H).

Example 1-1 tert-butyl 3-(cyanomethyl)-3-(4-oxo-3-(phenylamino)-4,5-dihydro-1H-pyrazolo[4,3-c]pyridin-1-yl)azetidine-1-carboxylate

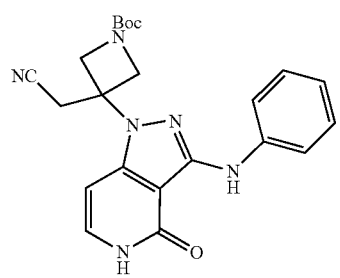

1-1

3-(Phenylamino)-1H-pyrazolo[4,3-c]pyridin-4(5H)-one (11.3 mg, 0.0499 mmol) and tert-butyl 3-(cyanomethylene) azetidine-1-carboxylate (17.0 mg, 0.088 mmol) were dissolved in DMF (1.0 mL). DBU (14 µL, 0.093 mmol) was added and the reaction mixture was stirred overnight at room temperature. After 18 hours the reaction mixture was diluted in EtOAc and washed with saturated aqueous sodium hydrogen carbonate and brine. The combined aqueous layers were back extracted with 3:1 chloroform/isopropanol (×1) and the combined organic layers were dried over Na$_2$SO$_4$, filtered, and concentrated in vacuo. The residue was purified by silica chromatography, eluting with a 10-100% EtOAc/isohexane, followed by a 0-5% MeOH/EtOAc gradient to afford compound 1-1. LRMS (ESI) calc'd for $C_{22}H_{25}N_6O_3$ [M+H]$^+$: 421, found 421. $^1$H NMR (600 MHz, DMSO-d6): δ 11.28 (s, 1H), 8.06 (s, 1H), 7.62-7.56 (m, 2H), 7.28-7.19 (m, 3H), 6.86 (dd, J=7.2, 6.6 Hz, 1H), 6.36 (dd, J=7.2, 1.8 Hz, 1H), 4.46 (d, J=8.4 Hz, 2H), 4.25 (d, J=6.6 Hz, 2H), 3.41 (s, 2 H), 1.36 (s, 9H).

The following examples outlined in Table 17 were prepared by analogy using the general procedure outlined above for Example 1-1, using 1.2 equivalents DBU, 1.5 equivalents Michael acceptor in DMF (0.15 M) at 50° C.

TABLE 17

| Example | Structure | Compound Name | LRMS |
|---------|-----------|---------------|------|
| 1-2 | 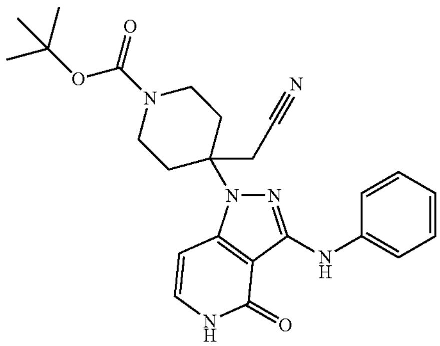 [SMILES: CC(C)(C)OC(=O)N1CCC(CC#N)(n2nc(Nc3ccccc3)c3c(=O)[nH]ccc32)CC1] | tert-butyl 4-(cyanomethyl)-4-(4-oxo-3-(phenylamino)-4,5-dihydro-1H-pyrazolo[4,3-c]pyridin-1-yl)piperidine-1-carboxylate | LRMS (ESI) calc'd for $C_{24}H_{29}N_6O_3$ [M + H]$^+$: 449, found 449. |

Example 2-1 tert-butyl 4-(cyanomethyl)-4-[3-(ethylamino)-4-oxo-4,5-dihydro-1H-pyrazolo[4,3-c]pyridin-1-yl]piperidine-1-carboxylate

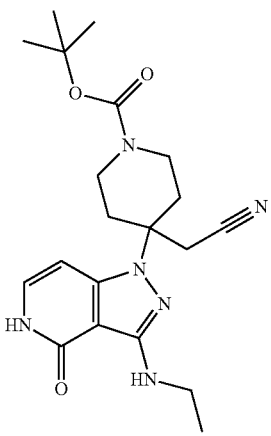

2-1

Step 1: tert-butyl 4-(4-(benzyloxy)-3-(ethylamino)-1H-pyrazolo[4,3-c]pyridin-1-yl)-4-(cyanomethyl) piperidine-1-carboxylate

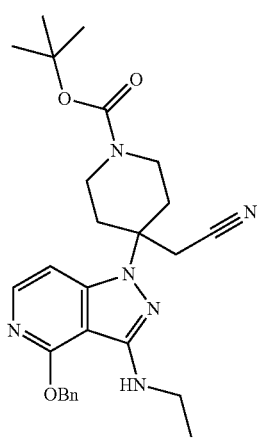

2-1a

To a solution of tert-butyl 4-[3-amino-4-(benzyloxy)-1H-pyrazolo[4,3-c]pyridin-1-yl]-4-(cyanomethyl)piperidine-1-carboxylate (20 mg, 0.043 mmol) in dichloroethane (0.30 mL) was added a solution of acetaldehyde (3.0 μL, 0.054 mmol) and acetic acid (2.5 μL, 0.043 mmol) in dichloroethane (0.24 mL). This mixture was stirred at room temperature for 10 minutes before sodium triacetoxyborohydride (16 mg, 0.076 mmol) was added. The reaction was stirred at room temperature for 5.5 hours, then diluted with EtOAc and washed with 1N NaOH and brine. The organic layer was dried over $Na_2SO_4$, filtered, and concentrated in vacuo.

The residue was purified by silica chromatography, eluting with 0-100% EtOAc/hexanes to afford Example 2-1a. LRMS (ESI) calc'd for $C_{27}H_{35}N_6O_3$ [M+H]$^+$: 491, found 491.

Step 2: tert-butyl 4-(cyanomethyl)-4-[3-(ethylamino)-4-oxo-4,5-dihydro-1H-pyrazolo-[4,3-c]pyridin-1-yl]piperidine-1-carboxylate tert-Butyl 4-(4-(benzyloxy)-3-(ethylamino)-1H-pyrazolo[4,3-c]pyridin-1-yl)-4-(cyanomethyl)piperidine-1-carboxylate (2-1a) (9.0 mg, 0.018 mmol) was dissolved in EtOAc (2.0 mL) and EtOH (0.20 mL). Pd/C (10 mg, 0.094 mmol) was added and the reaction was stirred under 1 atmosphere of hydrogen for 2 hours. The reaction was then filtered through Celite and washed with DCM and the filtrate was concentrated in vacuo. The crude reaction mixture was purified by silica chromatrography, eluting with 100% EtOAc. Concentration of the desired fractions afforded compound 2-1. LRMS (ESI) calc'd for $C_{20}H_{29}N_6O_3$ [M+H]$^+$: 401. found 401. $^1$H NMR (600 MHz, DMSO-d6): δ 10.93 (d, J=5.0 Hz, 1H), 7.01 (t, J=6.6 Hz, 1H), 6.49 (d, J=7.5 Hz, 1H), 5.42 (t, J=5.8 Hz, 1H), 3.68 (d, J=13.8 Hz, 2H), 3.18 (dt, J=13.4 Hz, 6.8, 2H), 3.10 (s, 2H), 2.98 (br s, 2H), 2.57 (d, J=13.9 Hz, 2H), 1.85 (t, J=10.2 Hz, 2H), 1.35 (s, 9H), 1.12 (t, J=7.1 Hz, 3H).

The following Examples shown in Table 18 were prepared in analogy to Example 2-1 above:

TABLE 18

| Example | Structure | Compound Name | LRMS |
|---|---|---|---|
| 2-2 | 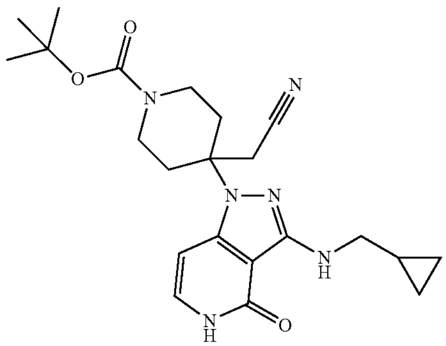 [SMILES: CC(C)(C)OC(=O)N1CCC(CC#N)(n2nc(NCC3CC3)c3c(=O)[nH]ccc32)CC1] | tert-butyl 4-(cyanomethyl)-4-{3-[(cyclopropylmethyl)amino]-4-oxo-4,5-dihydro-1H-pyrazolo[4,3-c]pyridin-1-yl}piperidine-1-carboxylate | LRMS (ESI) calc'd for $C_{22}H_{31}N_6O_3$ [M + H]$^+$: 427, found 427 |
| 2-3 | 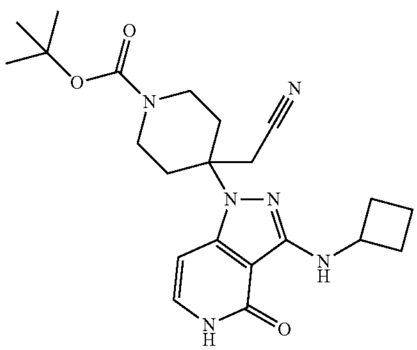 [SMILES: CC(C)(C)OC(=O)N1CCC(CC#N)(n2nc(NC3CCC3)c3c(=O)[nH]ccc32)CC1] | tert-butyl 4-(cyanomethyl)-4-[3-(cyclobutylamino)-4-oxo-4,5-dihydro-1H-pyrazolo[4,3-c]pyridin-1-yl]piperidine-1-carboxylate | LRMS (ESI) calc'd for $C_{22}H_{31}N_6O_3$ [M + H]$^+$: 427, found 427 |
| 2-4 | 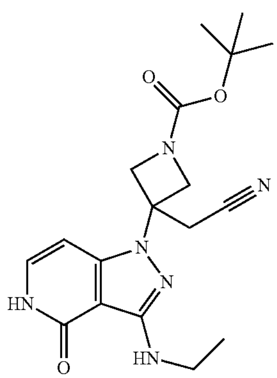 [SMILES: CCNc1nn(C2(CC#N)CN(C(=O)OC(C)(C)C)C2)c2cc[nH]c(=O)c12] | tert-butyl 3-(cyanomethyl)-3-[3-(ethylamino)-4-oxo-4,5-dihydro-1H-pyrazolo[4,3-c]pyridin-1-yl]azetidine-1-carboxylate | LRMS (ESI) calc'd for $C_{18}H_{25}N_6O_3$ [M + H]$^+$: 373, found 373 |
| 2-5 | 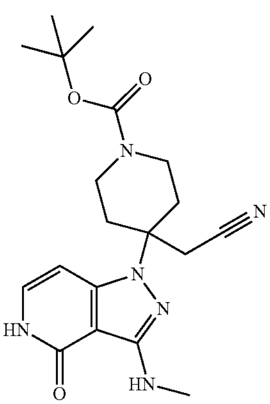 [SMILES: CNc1nn(C2(CC#N)CCN(C(=O)OC(C)(C)C)CC2)c2cc[nH]c(=O)c12] | tert-butyl 4-(cyanomethyl)-4-[3-(methylamino)-4-oxo-4,5-dihydro-1H-pyrazolo[4,3-c]pyridin-1-yl]piperidine-1-carboxylate | LRMS (ESI) calc'd for $C_{19}H_{27}N_6O_3$ [M + H]$^+$: 387, found 387 |

Example 3 tert-butyl 3-(cyanomethyl)-3-[3-(cyclopropylamino)-4-oxo-4,5-dihydro-1H-pyrazolo[4,3-c]pyridin-1-yl]azetidine-1-carboxylate

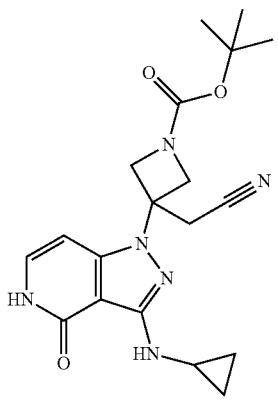

Step 1: tert-butyl 3-[4-(benzyloxy)-3-iodo-1H-pyrazolo[4,3-c]pyridin-1-yl]-3-(cyanomethyl)azetidine-1-carboxylate

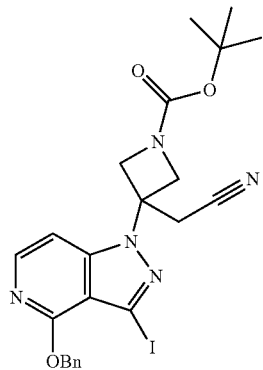

To a solution of tert-butyl 3-[3-amino-4-(benzyloxy)-1H-pyrazolo[4,3-c]pyridin-1-yl]-3-(cyanomethyl)azetidine-1-carboxylate (250 mg, 0.575 mmol) in dichloroethane (10 mL) was added $I_2$ (365 mg, 1.44 mmol). The mixture was stirred for 10 minutes under nitrogen and was then cooled to 0° C. and tert-butyl nitrite (0.137 mL, 1.15 mmol) was added dropwise. The reaction was stirred at 0° C. for 10 minutes, then warmed to room temperature and stirred for 2 additional hours. The reaction was diluted with EtOAc (100 mL) and washed with aqueous $NaHSO_3$, brine, saturated aqueous $NaHCO_3$ and brine. The organic layer was dried over $Na_2SO_4$, filtered, and concentrated in vacuo. The residue was purified by silica chromatography, eluting with 0-75% EtOAc in hexanes to afford compound 3a. LRMS (ESI) calc'd for $C_{23}H_{25}IN_5O_3$ [M+H]$^+$: 546, found 546. $^1$H NMR (600 MHz, CDCl$_3$): δ 7.96 (d, J=6.0 Hz, 1H), 7.58 (d, J=7.8 Hz, 2H), 7.38 (t, J=7.8 Hz, 2H), 7.31 (t, J=7.2 Hz, 1H), 6.87 (d, J=6.6 Hz, 1H), 5.59 (s, 2H), 4.66 (d, J=9.6 Hz, 2H), 4.33 (d, J=9.0 Hz, 2H), 3.16 (s, 2H), 1.44 (s, 9H).

Step 2: tert-butyl 3-[4-(benzyloxy)-3-(cyclopropylamino)-1H-pyrazolo[4,3-c]pyridin-1-yl]-3-(cyanomethyl)azetidine-1-carboxylate

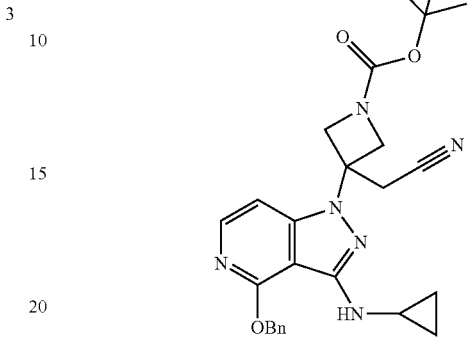

A vial equipped with a stir bar was charged with CuI (4.4 mg, 0.023 mmol), potassium phosphate tribasic (24.3 mg, 0.115 mmol), L-proline (5.3 mg, 0.046 mmol), tert-butyl 3-[4-(benzyloxy)-3-iodo-1H-pyrazolo[4,3-c]pyridin-1-yl]-3-(cyanomethyl)azetidine-1-carboxylate (25 mg, 0.046 mmol) and DMSO (460 μL). The mixture was sparged with nitrogen for 2 minutes and then cyclopropylamine (22 μL, 0.32 mmol) was added. The mixture was sparged with nitrogen for an additional 2 minutes and then the vial was sealed and heated to 80° C. for 2 hours. The reaction was cooled to room temperature, diluted with EtOAc, and the organic layers were washed with water, brine, and dried over $Na_2SO_4$, filtered, and concentrated in vacuo. Purification of the residue by silica chromatography, eluting with 0-100% EtOAc in hexanes followed by further purification by preparatory thin layer chromatography (PTLC) with 2% MeOH/CH$_2$Cl$_2$ (3 elutions) afforded compound 3b. LRMS (ESI) calc'd for $C_{26}H_{31}N_6O_3$ [M+H]$^+$: 475, found 475. $^1$H NMR (600 MHz, CDCl$_3$): δ 7.82 (d, J=6.0 Hz, 1H), 7.42 (d, J=7.2 Hz, 2H), 7.38 (t, J=7.2 Hz, 2H), 7.33 (t, J=7.2 Hz, 1H), 6.64 (d, J=6.0 Hz, 1H), 5.51 (s, 2H), 5.06 (s, 1H), 4.65 (d, J=9.6 Hz, 2H), 4.26 (d, J=9.0 Hz, 2H), 3.08 (s, 2H), 2.63 (m, 1H), 1.45 (s, 9H), 0.71 (m, 2H), 0.51 (m, 2H).

Step 3: tert-butyl 3-(cyanomethyl)-3-[3-(cyclopropylamino)-4-oxo-4,5-dihydro-1H-pyrazolo-[4,3-c]pyridin-1-yl]azetidine-1-carboxylate To a solution of tert-butyl 3-[4-(benzyloxy)-3-(cyclopropylamino)-1H-pyrazolo[4,3-c]pyridin-1-yl]-3-(cyanomethyl)azetidine-1-carboxylate (3.0 mg, 0.0063 mmol) in EtOAc (1 mL) was added 10% Pd/C (5 mg). The reaction was stirred under 1 atmosphere of hydrogen at room temperature for 2 hours. The balloon of hydrogen was removed and the reaction was filtered through Celite (washing with DCM) and the filtrate concentrated in vacuo. The residue was purified by preparatory thin layer chromatography (PTLC) with 4% MeOH/CH$_2$Cl$_2$ to afford compound 3. LRMS (ESI) calc'd for $C_{19}H_{25}N_6O_3$ [M+H]$^+$: 385, found 385. $^1$H NMR (600 MHz, DMSO-d6): δ 10.98 (d, J=6.0 Hz, 1H), 7.09 (dd, J=7.2, 6.0 Hz, 1H), 6.20 (d, J=7.2 Hz, 1H), 5.67 (d, J=2.4 Hz, 1H), 4.41 (m, 2H), 4.19 (m, 2H), 3.29 (s, 2H), 2.54 (m, 1H), 1.36 (s, 9H), 0.59 (m, 2H), 0.48 (m, 2H).

Example 4-1 tert-butyl 3-(cyanomethyl)-3-(4-oxo-3-((2-(trifluoromethyl)pyridin-4-yl)amino)-4,5-dihydro-1H-pyrazolo[43-c]pyridin-1-yl)azetidine-1-carboxylate

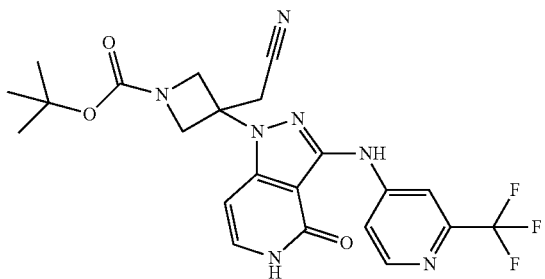

4-1

To a vial was charged with tert-butyl 3-(3-amino-4-oxo-4,5-dihydro-1H-pyrazolo[4,3-c]pyridin-1-yl)-3-(cyanomethyl)azetidine-1-carboxylate (35 mg, 0.10 mmol), 4-bromo-2-trifluoromethyl pyridine (34.5 mg, 0.152 mmol), $Pd_2(dba)_3$ (4.65 mg, 5.08 gmol), 4,5-bis(diphenylphosphino)-9,9-dimethylxanthene (12 mg, 0.020 mmol), and $Cs_2CO_3$ (66.2 mg, 0.203 mmol). Dioxane (0.68 mL) was added and the mixture was purged with argon for 5 minutes. The vial was then sealed and heated at 90° C. for 3 hours. The mixture was cooled and filtered through Celite with 3:1 $CHCl_3$:IPA and the resulting solution was concentrated in vacuo. The residue was taken up in DMSO and purified by mass triggered reverse phase HPLC, eluting with acetonitrile/water containing 0.1% TFA modifier. Fractions containing desired product were diluted with EtOAc, washed with saturated aqueous $NaHCO_3$, dried over $Na_2SO_4$, filtered, and concentrated in vacuo to afford compound 4-1. LRMS (ESI) calc'd for $C_{22}H_{23}F_3N_7O_3$ [M+H]$^+$: 490, found 490. $^1$H NMR (600 MHz, DMSO-d6): δ 11.36 (s, 1H), 9.20 (s, 1H), 8.42 (d, J=4.8 Hz, 1H), 8.17 (s, 1H), 7.87 (m, 1H), 7.25 (m, 1H), 6.40 (d, J=7.2 Hz, 1H), 4.47 (m, 2H), 4.27 (d, J=8.4 Hz, 2H), 3.45 (s, 2H), 1.36 (s, 9H).

The following Examples in Table 19 were prepared in analogy to Example 4-1:

TABLE 19

| Example | Structure | Compound Name | LRMS |
|---|---|---|---|
| 4-2 | 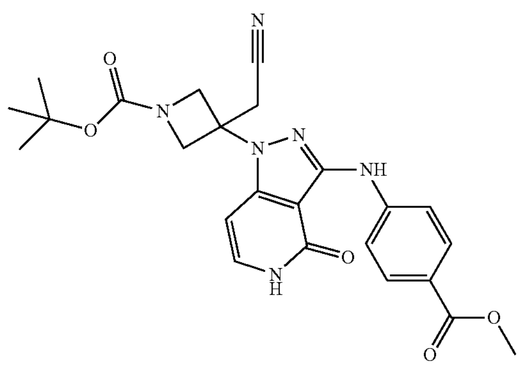 [SMILES: COC(=O)c1ccc(Nc2nn(C3(CC#N)CN(C(=O)OC(C)(C)C)C3)c3cc[nH]c(=O)c23)cc1] | tert-butyl 3-(cyanomethyl)-3-(3((4(methoxycarbonyl)phenyl)amino)-4-oxo-4,5-dihydro-1H-pyrazolo[4,3-c]pyridin-1-yl)azetidine-1-carboxylate | LRMS (ESI) calc'd for $C_{24}H_{27}N_6O_5$ [M + H]$^+$: 479, found 479. |
| 4-3 | 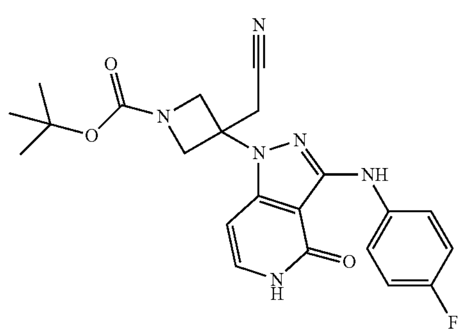 [SMILES: CC(C)(C)OC(=O)N1CC(CC#N)(n2nc(Nc3ccc(F)cc3)c3c(=O)[nH]ccc32)C1] | tert-butyl 3-(cyanomethyl)-3-(3-((4-fluorophenyl)amino)-4-oxo-4,5-dihydro-1H-pyrazolo[4,3-c]pyridin-1-yl)azetidine-1-carboxylate | LRMS (ESI) calc'd for $C_{22}H_{24}FN_6O_3$ [M + H]$^+$: 439, found 439. |

Example 5-1 tert-butyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate

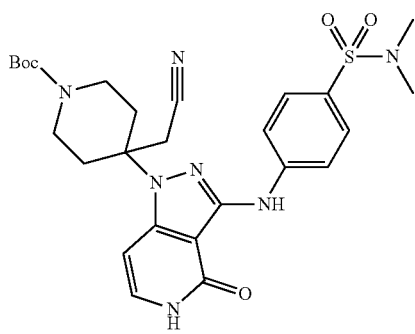

5-1

Step 1: tert-butyl 4-(4-(benzyloxy)-3-((4-(N,N-dimethylsulfamoyl)phenyl)amino)-1H-pyrazolo[4,3-c]pyridin-1-yl)-4-(cyanomethyl)piperidine-1-carboxylate

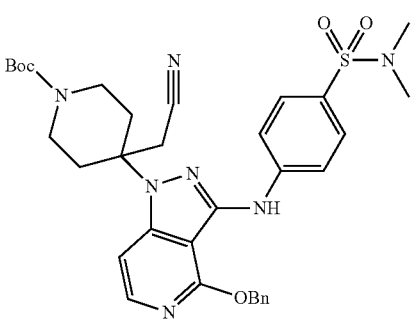

5-1a

To tert-butyl 4-(3-amino-4-(benzyloxy)-1H-pyrazolo[4,3-c]pyridin-1-yl)-4-(cyanomethyl)piperidine-1-carboxylate (3.00 g, 6.49 mmol), 4-bromo-N,N-dimethylbenzenesulfonamide (3.43 g, 13.0 mmol), Pd$_2$dba$_3$ (0.594 g, 0.649 mmol), 2-di-tert-butylphosphino-3,4,5,6-tetramethyl-2',4',6'-triisopropyl-1,1'-biphenyl (0.935 g, 1.95 mmol) and potassium phosphate tribasic (2.75 g, 13.0 mmol) in a degassed sealed microwave vial, was added t-amyl alcohol (86 mL) and the reaction was degassed again by evacuation/argon backfill (×3) and heated to 75° C. overnight. The reaction was concentrated and purified by silica chromatography, eluting with 10-80% EtOAc in hexanes. The desired product, 5-1a, was collected and concentrated in vacuo to afford the desired product as a solid. LRMS (ESI) calc'd for C$_{33}$H$_{40}$N$_7$O$_5$S [M+H]: 646, found 646. $^1$H NMR (600 MHz, DMSO-d6): δ 8.53 (s, 1H), 7.85 (d, J=6.0 Hz, 1H), 7.68 (d, J=9.0 Hz, 2H), 7.60 (d, J=9.0 Hz, 2H), 7.46 (d, J=7.8 Hz, 2H), 7.35 (m, 3H), 7.28 (m, 1H), 5.57 (s, 2H), 3.75 (d, J=14.4 Hz, 2H), 3.28 (s, 2H), 3.03 (br s, 2H), 2.74 (d, J=14.4 Hz, 2H), 2.47 (s, 6H), 2.03 (t, J=10.8 Hz, 2H), 1.37 (s, 9H).

Step 2: tert-butyl 4-(cyanomethyl)-4-(3-((4-(N,N-dimethylsulfamol)phenyl)amino)-4-oxo-4,5-dihydro-1H-pyrazolo[4,3-c]pyridin-1-yl)piperidine-1-carboxylate To tert-butyl 4-(4-(benzyloxy)-3-((4-(N,N-dimethylsulfamoyl)phenyl)amino)-1H-pyrazolo[4,3-c]pyridin-1-yl)-4-(cyanomethyl)piperidine-1-carboxylate (3.37 g, 5.22 mmol) was added Pd/C (10 wt % Pd loading, 0.27 g) and ethyl acetate (26 mL). The suspension was then evacuated and backfilled with hydrogen and the reaction was stirred under hydrogen at 1 atmosphere overnight at room temperature. The reaction was filtered through Celite and the filter pad was washed with DCM and the organic solvents were concentrated in vacuo. The solid was purified by silica chromatography, eluting with 0-6% methanol in DCM to afford 5-1, as a green solid that was triturated from DCM to afford analytically pure solid. LRMS (ESI) calc'd for C$_{21}$H$_{26}$N$_7$O$_3$S [M-Boc+H]$^+$: 456, found 456. $^1$H NMR (600 MHz, DMSO-d6): δ 11.33 (s, 1H), 8.68 (s, 1H), 7.82 (d, J=9.0 Hz, 2H), 7.60 (d, J=9.0 Hz, 2H), 7.17 (d, J=7.8 Hz, 1H), 6.67 (d, J=7.8 Hz, 1H), 3.70 (d, J=13.8 Hz, 2H), 3.24 (s, 6H), 3.05 (br s, 2H), 2.64 (d, J=13.8 Hz, 2H), 2.45 (s, 6H), 1.99 (apparent t, J=12.0 Hz, 2H), 1.35 (s, 9H).

The following examples outlined in Table 20 were prepared by analogy using the general procedure outlined above for Example 5-1. In select cases, the general procedure could be modified to alternatively utilize KOAc base, 2-di-tert-butylphosphino-2',4',6'-triisopropyl-1,1'-biphenyl ligand instead, [(2-di-tert-butylphosphino-2',4',6'-triisopropyl-1,1'-biphenyl)-2-(2'-amino-1,1'-biphenyl)]palladium(II) methanesulfonate (t-BuXPhos Pd G3) precatalyst in place of the individual phosphine and palladium source, and/or 2-propanol in place of t-amyl alcohol. Additionally, in certain instances the cross coupling could be run between 70-90° C. thermally, or at 105° C. in a microwave. In certain instances, the general procedure for the hydrogenolysis could be modified to employ a suitable alternate solvent (such as MeOH, EtOH etc.) or cosolvent thereof with EtOAc to ensure dissolution of the substrate. In certain other instances, such as for Examples 5-224 to 5-226, removal of the Bn protecting group could alternatively be achieved via hydrolysis in 1,4-dioxane (0.04 M) using concentrated aqueous HCl (~2:1 ratio by volume of 1,4-dioxane:conc. HCl) or via saturated HCl in ethyl acetate at room temperature (as done for Examples 5-271, 5-272, 5-277 and 5-278 for instance).

TABLE 20

| Example | Structure | Compound Name | LRMS |
|---|---|---|---|
| 5-2 | 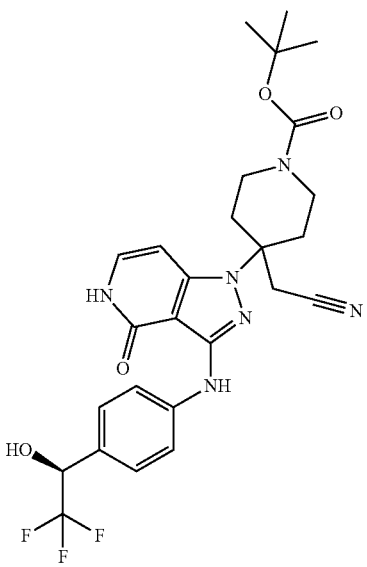 [SMILES: CC(C)(C)OC(=O)N1CCC(CC#N)(n2nc(Nc3ccc([C@H](O)C(F)(F)F)cc3)c3c(=O)[nH]ccc32)CC1] | tert-butyl 4-(cyanomethyl)-4-[4-oxo-3-({4-[(1S or 1R)-2,2,2-trifluoro-1-hydroxyethyl]phenyl}amino)-4,5-dihydro-1H-pyrazolo[4,3-c]pyridin-1-yl]piperidine-1-carboxylate<br>Chiral separation on free pyridone using SFC, Chiralpak IA, 29% MeOH in $CO_2$ Tr = 4.4 minutes. | LRMS (ESI) calc'd for $C_{26}H_{30}N_6O_4F_3$ $[M + H]^+$: 547, found 547. |
| 5-3 | 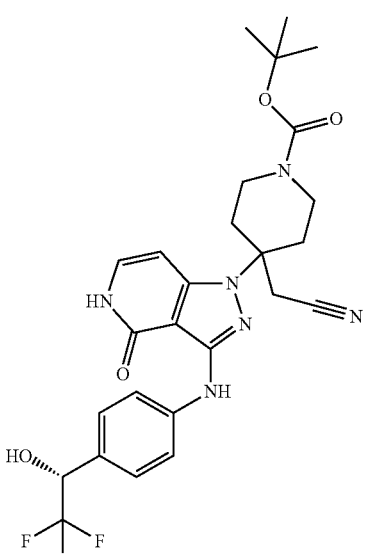 | tert-butyl 4-(cyanomethyl)-4-[4-oxo-3-({4-[(1R or 1S)-2,2,2-trifluoro-1-hydroxyethyl]phenyl}amino)-4,5-dihydro-1H-pyrazolo[4,3-c]pyridin-1-yl]piperidine-1-carboxylate<br>Chiral separation on free pyridone using SFC, Chiralpak IA, 29% MeOH in $CO_2$ Tr = 3.7 minutes. | LRMS (ESI) calc'd for $C_{26}H_{30}N_6O_4F_3$ $[M + H]^+$: 547, found 547. |

TABLE 20-continued

| Example | Structure | Compound Name | LRMS |
|---|---|---|---|
| 5-4 | 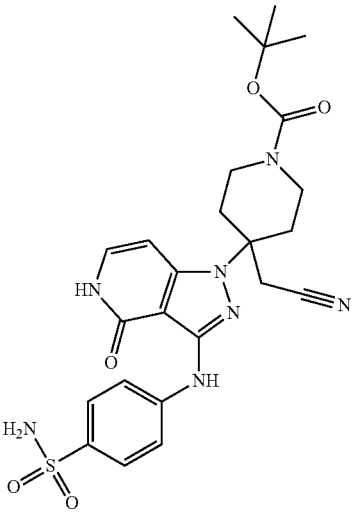 [SMILES: CC(C)(C)OC(=O)N1CCC(CC#N)(n2nc(Nc3ccc(S(N)(=O)=O)cc3)c3c(=O)[nH]ccc32)CC1] | tert-butyl 4-(cyanomethyl)-4-{4-oxo-3-[(4-sulfamoylphenyl)amino]-4,5-dihydro-1H-pyrazolo[4,3-c]pyridin-1-yl}piperidine-1-carboxylate | LRMS (ESI) calc'd for $C_{24}H_{30}N_7O_5S$ $[M + H]^+$: 528, found 528. |
| 5-5 | 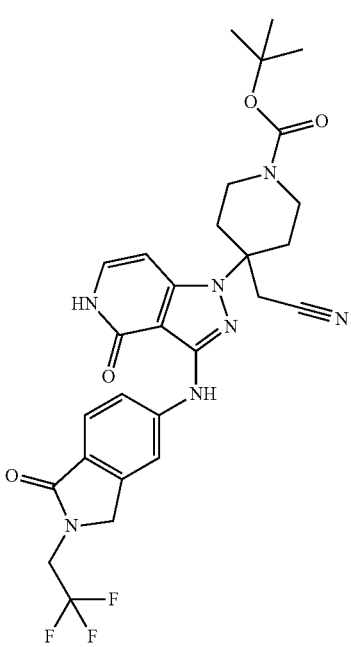 [SMILES: CC(C)(C)OC(=O)N1CCC(CC#N)(n2nc(Nc3ccc4c(c3)CN(CC(F)(F)F)C4=O)c3c(=O)[nH]ccc32)CC1] | tert-butyl 4-(cyanomethyl)-4-(4-oxo-3-{[1-oxo-2-(2,2,2-trifluoroethyl)-2,3-dihydro-1H-isoindol-5-yl]amino}-4,5-dihydro-1H-pyrazolo[4,3-c]pyridin-1-yl)piperidine-1-carboxylate | LRMS (ESI) calc'd for $C_{28}H_{31}N_7O_4F_3$ $[M + H]^+$: 586, found 586. |

TABLE 20-continued

| Example | Structure | Compound Name | LRMS |
|---|---|---|---|
| 5-6 | 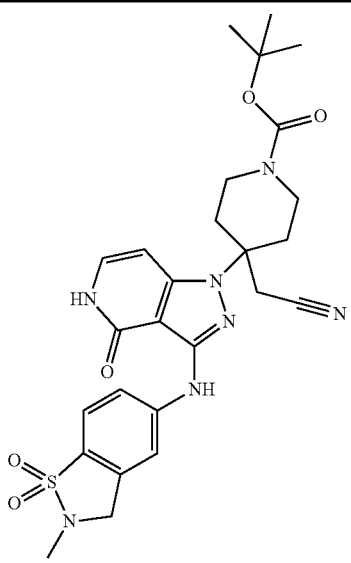 | tert-butyl 4-(cyanomethyl)-4-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}piperidine-1-carboxylate | LRMS (ESI) calc'd for $C_{21}H_{24}N_7O_3S$ $[M - Boc + H]^+$: 454, found 454. |
| 5-7 | 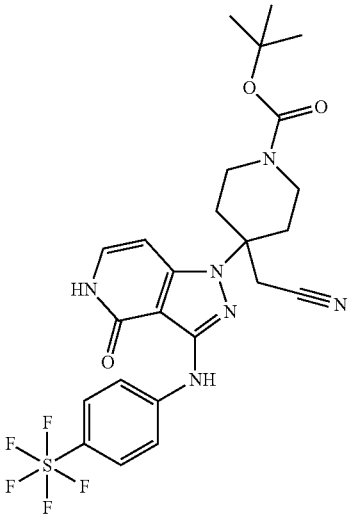 [SMILES: CC(C)(C)OC(=O)N1CCC(CC#N)(n2nc(Nc3ccc(S(F)(F)(F)(F)F)cc3)c3c(=O)[nH]ccc32)CC1] | tert-butyl 4-(cyanomethyl)-4-(4-oxo-3-{[4-(pentafluorosulfanyl)phenyl]amino}-4,5-dihydro-1H-pyrazolo[4,3-c]pyridin-1-yl)piperidine-1-carboxylate | LRMS (ESI) calc'd for $C_{19}H_{20}N_6OSF_5$ $[M - Boc + H]^+$: 475, found 475. |
| 5-8 | 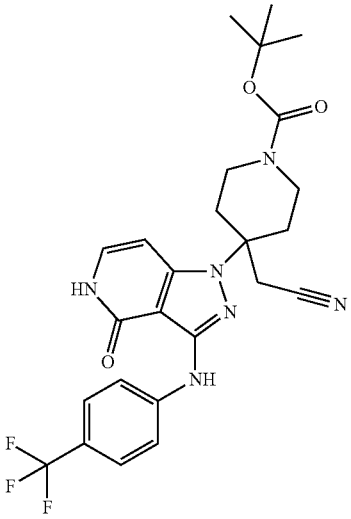 [SMILES: CC(C)(C)OC(=O)N1CCC(CC#N)(n2nc(Nc3ccc(C(F)(F)F)cc3)c3c(=O)[nH]ccc32)CC1] | tert-butyl 4-(cyanomethyl)-4-(4-oxo-3-{[4-(trifluoromethyl)phenyl]amino}-4,5-dihydro-1H-pyrazolo[4,3-c]pyridin-1-yl)piperidine-1-carboxylate | LRMS (ESI) calc'd for $C_{25}H_{28}N_6O_3F_3$ $[M + H]^+$: 517, found 517. |

TABLE 20-continued

| Example | Structure | Compound Name | LRMS |
|---|---|---|---|
| 5-9 | 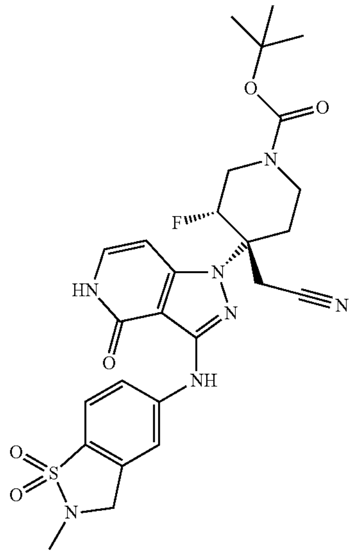 | tert-butyl (3R,4R)-4-(cyanomethyl)-3-fluoro-4-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}piperidine-1-carboxylate (from I-6-2B) | LRMS (ESI) calc'd for $C_{21}H_{23}N_7O_3FS$ [M − Boc + H]$^+$: 472, found 472. |
| 5-10 | 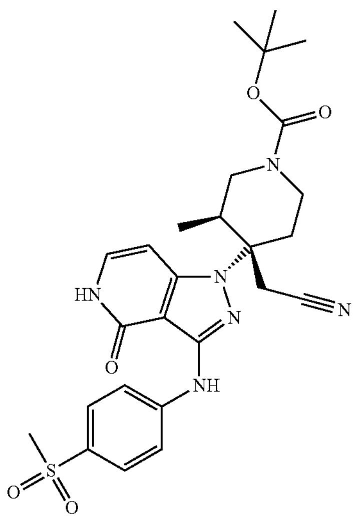 | tert-butyl (3R,4S and 3S,4R)-4-(cyanomethyl)-3-methyl-4-(3-{[4-(methylsulfonyl)phenyl]amino}-4-oxo-4,5-dihydro-1H-pyrazolo[4,3-c]pyridin-1-yl)piperidine-1-carboxylate | LRMS (ESI) calc'd for $C_{26}H_{33}N_6O_5S$ [M + H]$^+$: 541, found 541. |
| 5-11 | 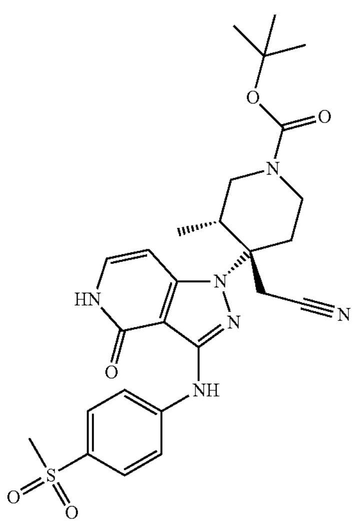 | tert-butyl (3S,4S and 3R,4R)-4-(cyanomethyl)-3-methyl-4-(3-{[4-(methylsulfonyl)phenyl]amino}-4-oxo-4,5-dihydro-1H-pyrazolo[4,3-c]pyridin-1-yl)piperidine-1-carboxylate | LRMS (ESI) calc'd for $C_{26}H_{33}N_6O_5S$ [M + H]$^+$: 541, found 541. |

TABLE 20-continued

| Example | Structure | Compound Name | LRMS |
|---|---|---|---|
| 5-12 | 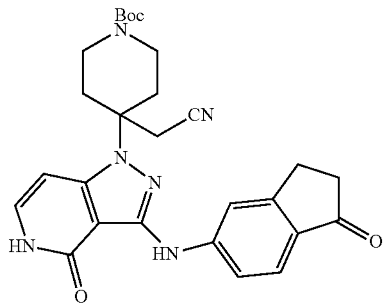 [SMILES: CC(C)(C)OC(=O)N1CCC(CC#N)(n2nc(Nc3ccc4c(c3)CCC4=O)c3c(=O)[nH]ccc32)CC1] | tert-butyl 4-(cyanomethyl)-4-(4-oxo-3-((1-oxo-2,3-dihydro-1H-inden-5-yl)amino)-4,5-dihydro-1H-pyrazolo[4,3-c]pyridin-1-yl)piperidine-1-carboxylate | LRMS (ESI) calc'd for $C_{27}H_{31}N_6O_4$ [M + H]$^+$: 503, found 503. |
| 5-13 | 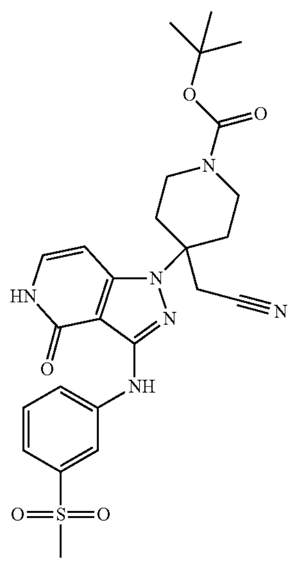 [SMILES: CC(C)(C)OC(=O)N1CCC(CC#N)(n2nc(Nc3cccc(S(C)(=O)=O)c3)c3c(=O)[nH]ccc32)CC1] | tert-butyl 4-(cyanomethyl)-4-(3-{[3-(methylsulfonyl)phenyl]amino}-4-oxo-4,5-dihydro-1H-pyrazolo[4,3-c]pyridin-1-yl)piperidine-1-carboxylate | LRMS (ESI) calc'd for $C_{25}H_{31}N_6O_5S$ [M + H]$^+$: 527, found 527. |
| 5-14 | 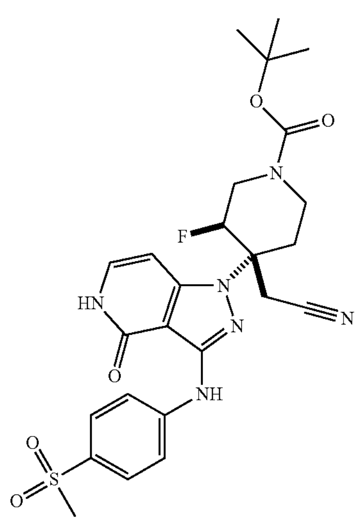 | tert-butyl (3S,4R or 3R,4S)-4-(cyanomethyl)-3-fluoro-4-(3-{[4-(methylsulfonyl)phenyl]amino}-4-oxo-4,5-dihydro-1H-pyrazolo[4,3-c]pyridin-1-yl)piperidine-1-carboxylate (from I-7-1A) | LRMS (ESI) calc'd for $C_{25}H_{30}FN_6O_5S$ [M + H]$^+$: 545, found 545. |

TABLE 20-continued

| Example | Structure | Compound Name | LRMS |
|---|---|---|---|
| 5-15 | 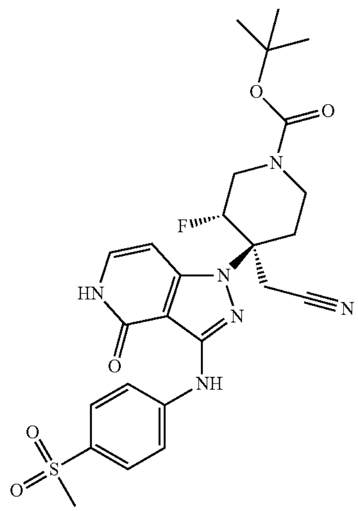 [SMILES: CC(C)(C)OC(=O)N1CC[C@@](CC#N)(n2nc(Nc3ccc(S(C)(=O)=O)cc3)c3c(=O)[nH]ccc32)[C@H](F)C1] | tert-butyl (3R,4S or 3S,4R)-4-(cyanomethyl)-3-fluoro-4-(3-{[4-(methylsulfonyl)phenyl]amino}-4-oxo-4,5-dihydro-1H-pyrazolo[4,3-c]pyridin-1-yl)piperidine-1-carboxylate (from I-7-1B) | LRMS (ESI) calc'd for $C_{25}H_{30}FN_6O_5S$ [M + H]$^+$: 545, found 545. |
| 5-16 | 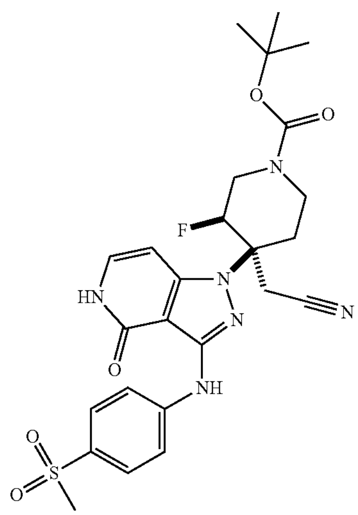 | tert-butyl (3S,4S)-4-(cyanomethyl)-3-fluoro-4-(3-{[4-(methylsulfonyl)phenyl]amino}-4-oxo-4,5-dihydro-1H-pyrazolo[4,3-c]pyridin-1-yl)piperidine-1-carboxylate (from I-7-2A) | LRMS (ESI) calc'd for $C_{25}H_{30}FN_6O_5S$ [M + H]$^+$: 545, found 545. |
| 5-17 | 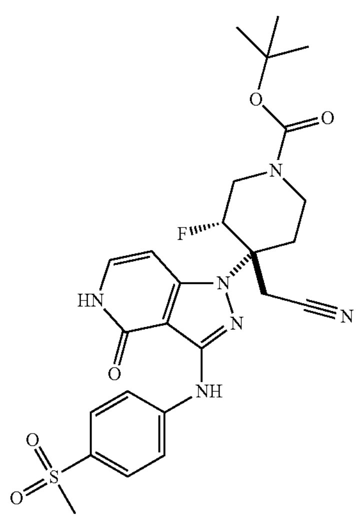 | tert-butyl (3R,4R)-4-(cyanomethyl)-3-fluoro-4-(3-{[4-(methylsulfonyl)phenyl]amino}-4-oxo-4,5-dihydro-1H-pyrazolo[4,3-c]pyridin-1-yl)piperidine-1-carboxylate (from I-7-2B) | LRMS (ESI) calc'd for $C_{25}H_{30}FN_6O_5S$ [M + H]$^+$: 545, found 545. |

TABLE 20-continued

| Example | Structure | Compound Name | LRMS |
|---|---|---|---|
| 5-18 | 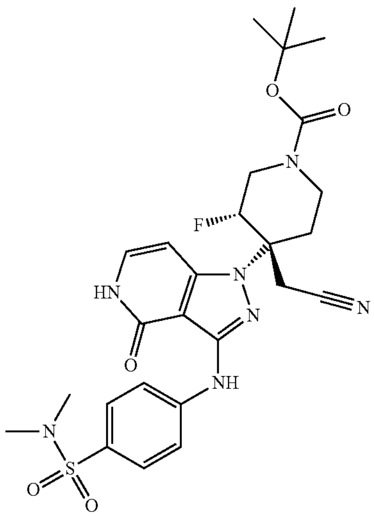 | tert-butyl (3R,4R)-4-(cyanomethyl)-4-(3-{[4-(dimethylsulfamoyl)phenyl]amino}-4-oxo-4,5-dihydro-1H-pyrazolo[4,3-c]pyridin-1-yl)-3-fluoropiperidine-1-carboxylate (from I-7-2B) | LRMS (ESI) calc'd for $C_{26}H_{33}FN_7O_5S$ [M + H]$^+$: 574, found 574. |
| 5-19 | 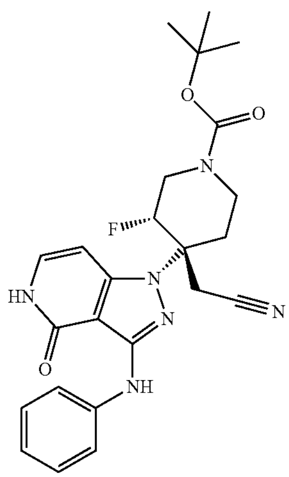 | tert-butyl (3R,4R)-4-(cyanomethyl)-3-fluoro-4-[4-oxo-3-(phenylamino)-4,5-dihydro-1H-pyrazolo[4,3-c]pyridin-1-yl]piperidine-1-carboxylate (from I-7-2B) | LRMS (ESI) calc'd for $C_{24}H_{28}FN_6O_3$ [M + H]$^+$: 467, found 467. |
| 5-20 | 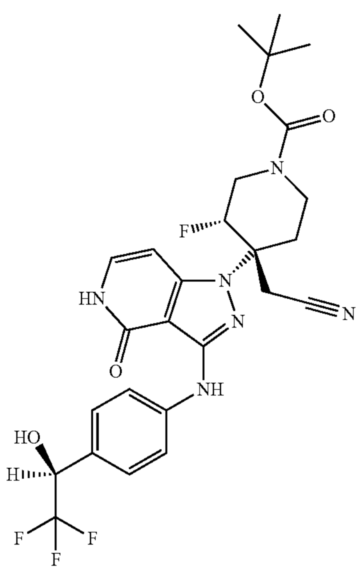 | tert-butyl (3R,4R)-4-(cyanomethyl)-3-fluoro-4-[4-oxo-3-({4-[(1S or 1R)-2,2,2-trifluoro-1-hydroxyethyl]phenyl}amino)-4,5-dihydro-1H-pyrazolo[4,3-c]pyridin-1-yl]piperidine-1-carboxylate (from I-7-2B & I-25B) | LRMS (ESI) calc'd for $C_{26}H_{29}F_4N_6O_4$ [M + H]$^+$: 565, found 565. |

TABLE 20-continued

| Example | Structure | Compound Name | LRMS |
|---|---|---|---|
| 5-21 | 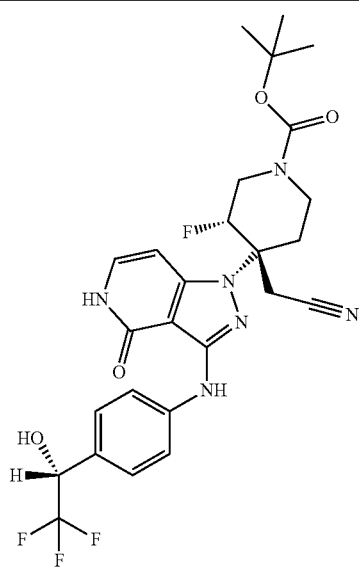 | tert-butyl (3R,4R)-4-(cyanomethyl)-3-fluoro-4-[4-oxo-3-({4-[(1R or 1S)-2,2,2-trifluoro-1-hydroxyethyl]phenyl}amino)-4,5-dihydro-1H-pyrazolo[4,3-c]pyridin-1-yl]piperidine-1-carboxylate (from I-7-2B & I-25A) | LRMS (ESI) calc'd for $C_{26}H_{29}F_4N_6O_4$ [M + H]$^+$: 565, found 565. |
| 5-22 | 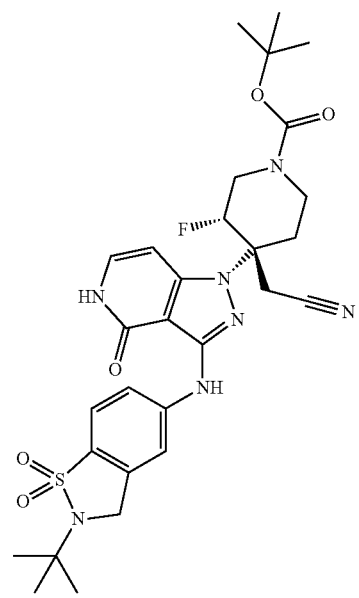 | tert-butyl (3R,4R)-4-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}-4-(cyanomethyl)-3-fluoropiperidine-1-carboxylate (from I-7-2B) | LRMS (ESI) calc'd for $C_{29}H_{37}FN_7O_5S$ [M + H]$^+$: 614, found 614. |

TABLE 20-continued

| Example | Structure | Compound Name | LRMS |
| --- | --- | --- | --- |
| 5-23 | 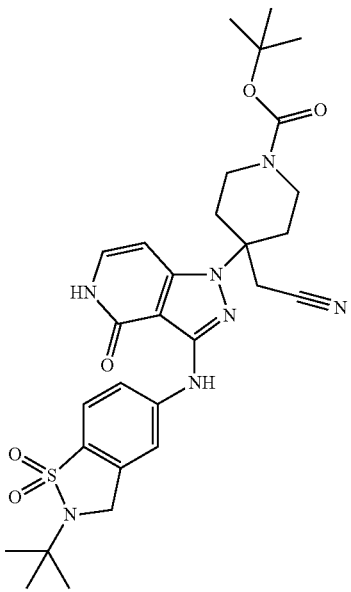 [SMILES: CC(C)(C)OC(=O)N1CCC(CC#N)(n2nc(Nc3ccc4c(c3)CN(C(C)(C)C)S4(=O)=O)c3c(=O)[nH]ccc32)CC1] | tert-butyl 4-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}-4-(cyanomethyl)piperidine-1-carboxylate | LRMS (ESI) calc'd for $C_{29}H_{38}N_7O_5S$ $[M + H]^+$: 596, found 596. |
| 5-24 | 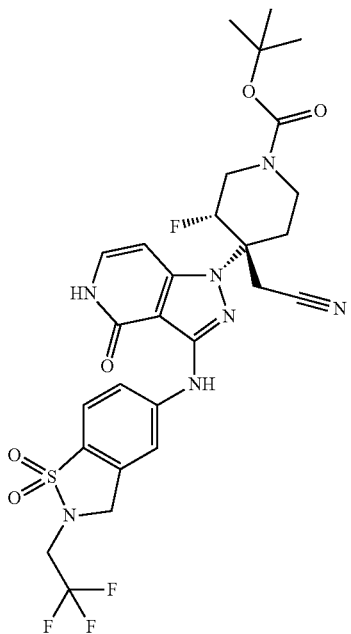 | tert-butyl (3R,4R)-4-(cyanomethyl)-4-(3-{[1,1-dioxido-2-(2,2,2-trifluoroethyl)-2,3-dihydro-1,2-benzisothiazol-5-yl]amino}-4-oxo-4,5-dihydro-1H-pyrazolo[4,3-c]pyridin-1-yl)-3-fluoropiperidine-1-carboxylate (from I-7-2B) | LRMS (ESI) calc'd for $C_{27}H_{30}F_4N_7O_5S$ $[M + H]^+$: 640, found 640. |

TABLE 20-continued

| Example | Compound Name | LRMS |
|---|---|---|
| 5-25 | tert-butyl 4-(cyanomethyl)-4-(3-((1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)piperidine-1-carboxylate | LRMS (ESI) calc'd for $C_{27}H_{31}F_3N_7O_5S$ [M + H]$^+$: 622, found 622. |
| 5-26 | 2-(4-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-1-(2,2-difluoropropanoyl)piperidin-4-yl)acetonitrile | LRMS (ESI) calc'd for $C_{27}H_{32}F_2N_7O_4S$ [M + H]$^+$: 588, found 588. |
| 5-27 | (S)-2-(3-(4-oxo-3-(phenylamino)-4,5-dihydro-1H-pyrazolo[4,3-c]pyridin-1-yl)tetrahydro-2H-pyran-3-yl)acetonitrile (from I-17B) | LRMS (ESI) calc'd for $C_{19}H_{20}N_5O_2$ [M + H]$^+$: 350, found 350. |

TABLE 20-continued

| Example | Structure | Compound Name | LRMS |
|---|---|---|---|
| 5-28 | 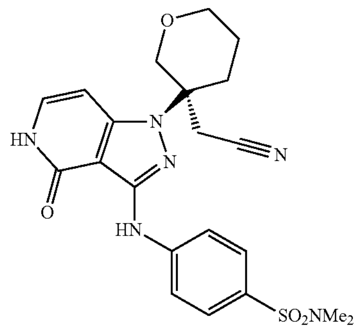 | (S)-4-((1-(3-(cyanomethyl) tetrahydro-2H-pyran-3-yl)-4-oxo-4,5-dihydro-1H-pyrazolo[4,3-c]pyridin-3-yl)amino)-N,N-dimethyl benzenesulfonamide (from I-17B) | LRMS (ESI) calc'd for $C_{21}H_{25}N_6O_4S$ $[M + H]^+$: 457, found 457. |
| 5-29 | 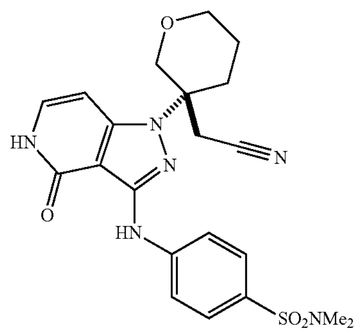 | (R)-4-((1-(3-(cyanomethyl) tetrahydro-2H-pyran-3-yl)-4-oxo-4,5-dihydro-1H-pyrazolo[4,3-c]pyridin-3-yl)amino)-N,N-dimethyl benzenesulfonamide (from I-17A) | LRMS (ESI) calc'd for $C_{21}H_{25}N_6O_4S$ $[M + H]^+$: 457, found 457. |
| 5-30 | 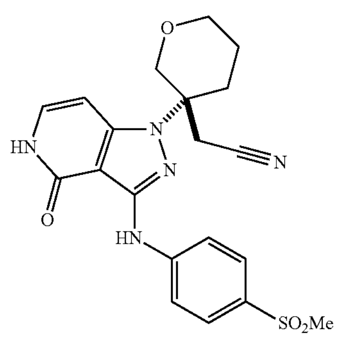 | (R)-2-(3-(3-((4-(methylsulfonyl)phenyl) amino)-4-oxo-4,5-dihydro-1H-pyrazolo[4,3-c]pyridin-1-yl)tetrahydro-2H-pyran-3-yl)acetonitrile (from I-17A) | LRMS (ESI) calc'd for $C_{20}H_{22}N_5O_4S$ $[M + H]^+$: 428, found 428. |
| 5-31 | 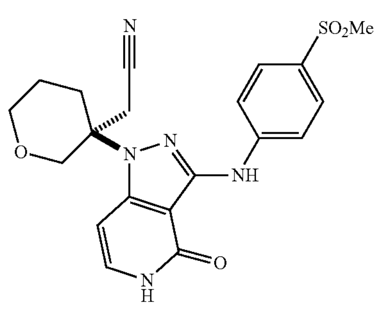 | (S)-2-(3-(3-((4-(methylsulfonyl)phenyl) amino)-4-oxo-4,5-dihydro-1H-pyrazolo[4,3-c]pyridin-1-yl) tetrahydro-2H-pyran-3-yl)acetonitrile (from I-17B) | LRMS (ESI) calc'd for $C_{20}H_{22}N_5O_4S$ $[M + H]^+$: 428, found 428. |

TABLE 20-continued

| Example | Structure | Compound Name | LRMS |
|---|---|---|---|
| 5-32 | 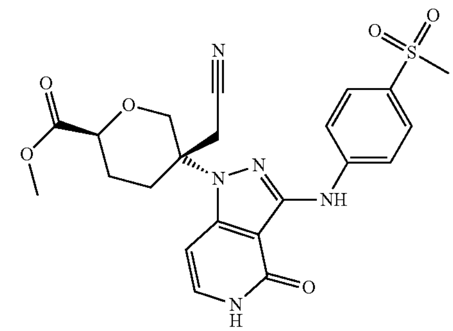 | (2S,5S and 2R,5R)-methyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate (racemic mixture) | LRMS (ESI) calc'd for $C_{22}H_{24}N_5O_6S$ $[M + H]^+$: 486, found 486. |
| 5-33 | 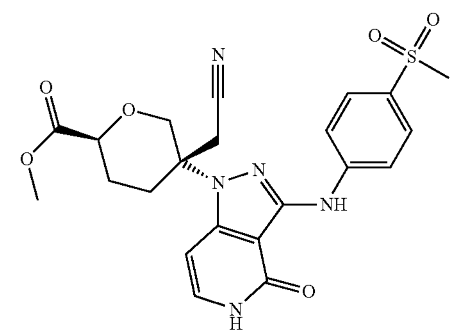 | (2S,5S or 2R,5R)-methyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate Chiral separation on free pyridone using SFC, AD-H column, 35% MeOH in $CO_2$ Tr = 5.9 minutes. | LRMS (ESI) calc'd for $C_{22}H_{24}N_5O_6S$ $[M + H]^+$: 486, found 486. |
| 5-34 | 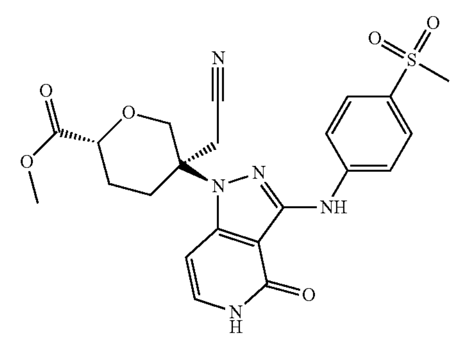 | (2S,5S or 2R,5R)-methyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate Chiral separation on free pyridone using SFC, AD-H column, 35% MeOH in $CO_2$ TR = 7.5 minutes. | LRMS (ESI) calc'd for $C_{22}H_{24}N_5O_6S$ $[M + H]^+$: 486, found 486. |
| 5-35 | 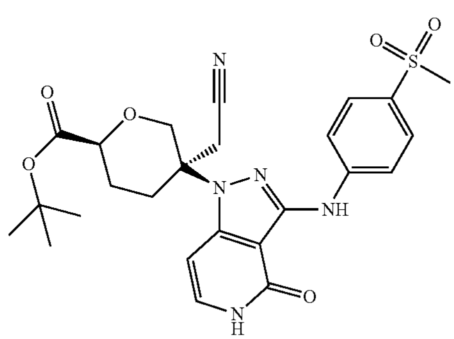 | (2R,5S and 2S,5R)-tert-butyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate (from racemic I-14-2) | LRMS (ESI) calc'd for $C_{25}H_{30}N_5O_6S$ $[M + H]^+$: 528, found 528. |

TABLE 20-continued

| Example | Structure | Compound Name | LRMS |
|---|---|---|---|
| 5-36 | 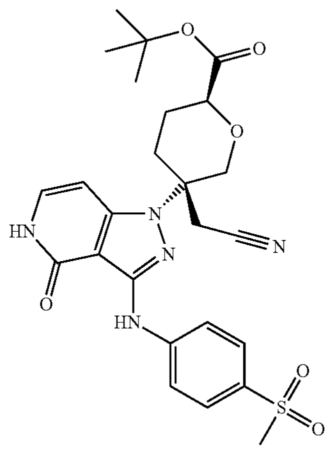 | (2S,5S and 2R,5R)-tert-butyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate (from racemic I-14-1) | LRMS (ESI) calc'd for $C_{25}H_{30}N_5O_6S$ [M + H]$^+$: 528, found 528. |
| 5-37 | 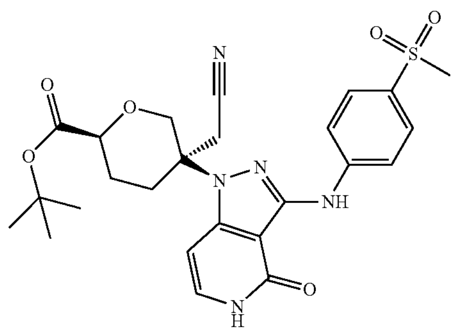 | (2R,5S or 2S,5R)-tert-butyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate (from Example 5-35)<br>Chiral separation of free pyridone using SFC, AD-H column, 25% MeOH in CO$_2$ Tr = 3.8 minutes. | LRMS (ESI) calc'd for $C_{25}H_{30}N_5O_6S$ [M + H]$^+$: 528, found 528. |
| 5-38 | 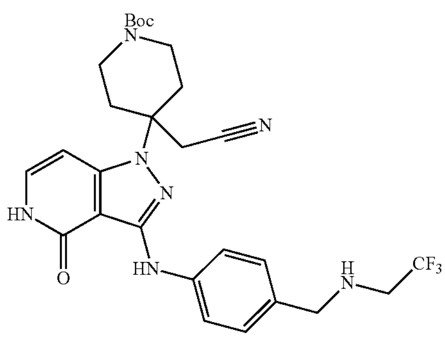 [SMILES: CC(C)(C)OC(=O)N1CCC(CC#N)(n2nc(Nc3ccc(CNCC(F)(F)F)cc3)c3c(=O)[nH]ccc32)CC1] | tert-butyl 4-(cyanomethyl)-4-(4-oxo-3-((4-(((2,2,2-trifluoroethyl)amino)methyl)phenyl)amino)-4,5-dihydro-1H-pyrazolo[4,3-c]pyridin-1-yl)piperidine-1-carboxylate | LRMS (ESI) calc'd for $C_{25}H_{29}N_6O_3$ [M − NHCH$_2$CF$_3$]$^+$: 461, found 461. |
| 5-39 | 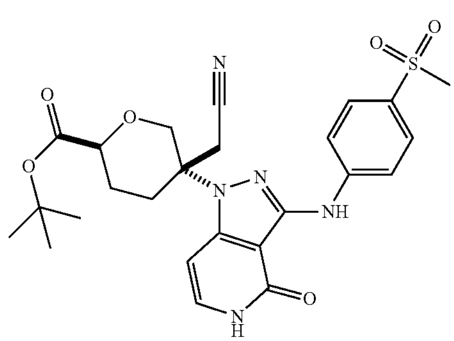 | (2S,5S)-tert-butyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate (from Example 5-36)<br>Chiral separation of free pyridone using LC column, IB column, 40% MeOH/EtOH = 3:2, 60% heptanes, Tr = 8.1 minutes. | LRMS (ESI) calc'd for $C_{25}H_{30}N_5O_6S$ [M + H]$^+$: 528, found 528. |

TABLE 20-continued

| Example | Structure | Compound Name | LRMS |
|---|---|---|---|
| 5-40 | 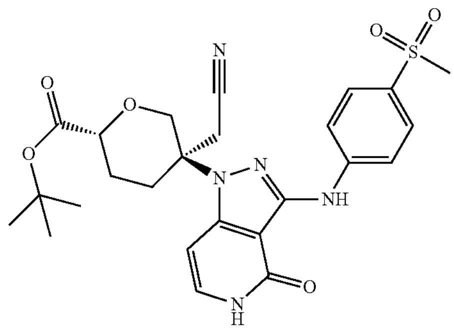 [SMILES: CC(C)(C)OC(=O)[C@H]1CC[C@](CC#N)(n2nc(Nc3ccc(S(C)(=O)=O)cc3)c3c(=O)[nH]ccc32)CO1] | (2R,5R)-tert-butyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate (from Example 5-36) Chiral separation of free pyridone using LC column, IB column, 40% MeOH/EtOH = 3:2, 60% heptanes, Tr = 9.6 minutes. | LRMS (ESI) calc'd for $C_{25}H_{30}N_5O_6S$ [M + H]$^+$: 528, found 528. |
| 5-41 | 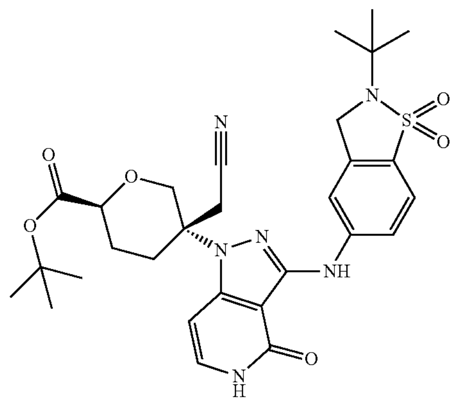 [SMILES: CC(C)(C)OC(=O)[C@@H]1CC[C@@](CC#N)(n2nc(Nc3ccc4c(c3)CN(C(C)(C)C)S4(=O)=O)c3c(=O)[nH]ccc32)CO1] | (2S,5S)-tert-butyl 5-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-5-(cyanomethyl)tetrahydro-2H-pyran-2-carboxylate (from I-14-1A) | LRMS (ESI) calc'd for $C_{29}H_{37}N_6O_6S$ [M + H]$^+$: 597, found 597. |
| 5-42 | 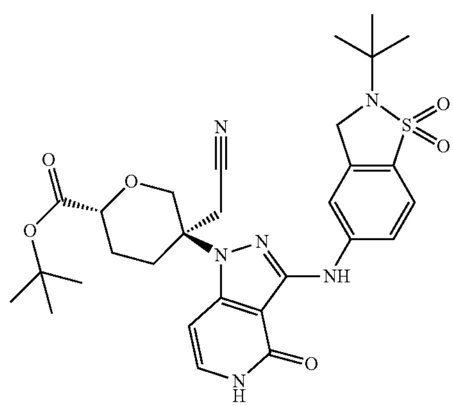 [SMILES: CC(C)(C)OC(=O)[C@H]1CC[C@](CC#N)(n2nc(Nc3ccc4c(c3)CN(C(C)(C)C)S4(=O)=O)c3c(=O)[nH]ccc32)CO1] | (2R,5R)-tert-butyl 5-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-5-(cyanomethyl)tetrahydro-2H-pyran-2-carboxylate (from I-14-1B) | LRMS (ESI) calc'd for $C_{29}H_{37}N_6O_6S$ [M + H]$^+$: 597, found 597. |
| 5-43 | 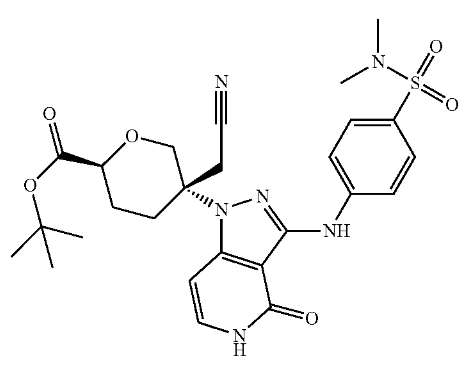 [SMILES: CN(C)S(=O)(=O)c1ccc(Nc2nn([C@]3(CC#N)CC[C@@H](C(=O)OC(C)(C)C)OC3)c3cc[nH]c(=O)c23)cc1] | (2S,5S)-tert-butyl 5-(cyanomethyl)-5-(3-((4-(N,N-dimethylsulfamoyl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{26}H_{33}N_6O_6S$ [M + H]$^+$: 557, found 557. |

| Example | Structure | Compound Name | LRMS |
|---|---|---|---|
| 5-44 | 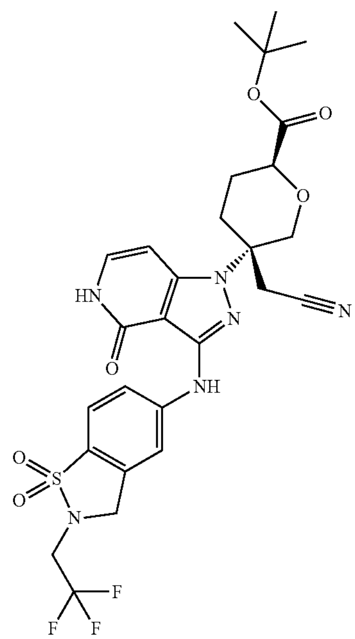 [SMILES: CC(C)(C)OC(=O)[C@@H]1CC[C@@](CC#N)(n2nc(Nc3ccc4c(c3)CN(CC(F)(F)F)S4(=O)=O)c3c(=O)[nH]ccc32)CO1] | (2S,5S)-tert-butyl 5-(cyanomethyl)-5-(3-((1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{27}H_{30}F_3N_6O_6S$ $[M + H]^+$: 623, found 623. |
| 5-45 | 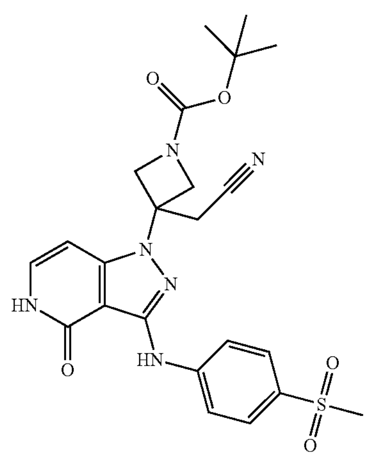 [SMILES: CC(C)(C)OC(=O)N1CC(CC#N)(n2nc(Nc3ccc(S(C)(=O)=O)cc3)c3c(=O)[nH]ccc32)C1] | tert-butyl 3-(cyanomethyl)-3-(3-{[4-(methylsulfonyl)phenyl]amino}-4-oxo-4,5-dihydro-1H-pyrazolo[4,3-c]pyridin-1-yl)azetidine-1-carboxylate | LRMS (ESI) calc'd for $C_{18}H_{19}N_6O_3S$ $[M - Boc + H]^+$: 399, found 399. |
| 5-46 | 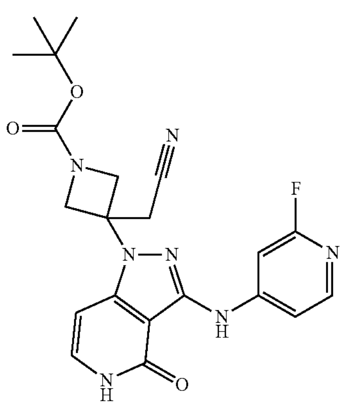 [SMILES: CC(C)(C)OC(=O)N1CC(CC#N)(n2nc(Nc3ccnc(F)c3)c3c(=O)[nH]ccc32)C1] | tert-butyl 3-(cyanomethyl)-3-{3-[(2-fluoropyridin-4-yl)amino]-4-oxo-4,5-dihydro-1H-pyrazolo[4,3-c]pyridin-1-yl}azetidine-1-carboxylate | LRMS (ESI) calc'd for $C_{21}H_{23}FN_7O_3$ $[M + H]^+$: 440, found 440. |

| Example | Structure | Compound Name | LRMS |
|---|---|---|---|
| 5-47 | 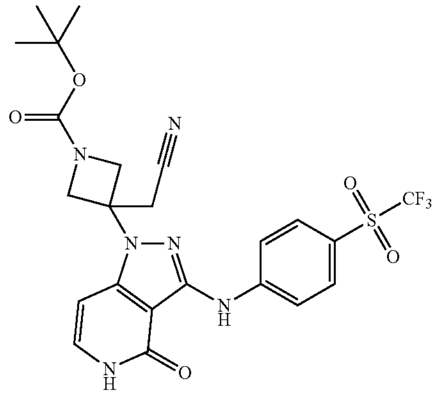 [SMILES: CC(C)(C)OC(=O)N1CC(CC#N)(n2nc(Nc3ccc(S(=O)(=O)C(F)(F)F)cc3)c3c(=O)[nH]ccc32)C1] | tert-butyl 3-(cyanomethyl)-3-[4-oxo-3-({4-[(trifluoromethyl)sulfonyl]phenyl}amino)-4,5-dihydro-1H-pyrazolo[4,3-c]pyridin-1-yl]azetidine-1-carboxylate | LRMS (ESI) calc'd for $C_{23}H_{24}F_3N_6O_5S$ [M + H]$^+$: 553, found 553. |
| 5-48 | 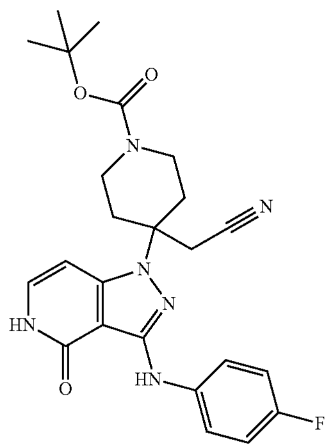 [SMILES: CC(C)(C)OC(=O)N1CCC(CC#N)(n2nc(Nc3ccc(F)cc3)c3c(=O)[nH]ccc32)CC1] | tert-butyl 4-(cyanomethyl)-4-{3-[(4-fluorophenyl)amino]-4-oxo-4,5-dihydro-1H-pyrazolo[4,3-c]pyridin-1-yl}piperidine-1-carboxylate | LRMS (ESI) calc'd for $C_{24}H_{28}FN_6O_3$ [M + H]$^+$: 467, found 467. |
| 5-49 | 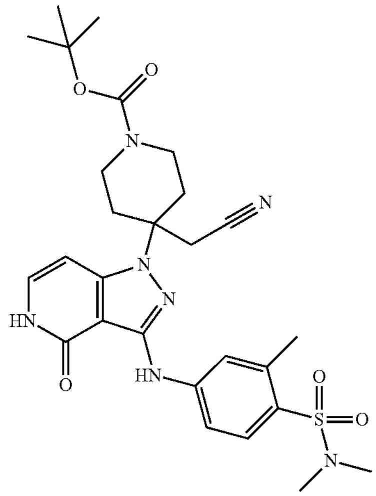 [SMILES: Cc1cc(Nc2nn(C3(CC#N)CCN(C(=O)OC(C)(C)C)CC3)c3cc[nH]c(=O)c23)ccc1S(=O)(=O)N(C)C] | tert-butyl 4-(cyanomethyl)-4-(3-((4-(N,N-dimethylsulfamoyl)-3-methylphenyl)amino)-4-oxo-4,5-dihydro-1H-pyrazolo[4,3-c]pyridin-1-yl)piperidine-1-carboxylate | LRMS (ESI) calc'd for $C_{27}H_{35}N_7O_4S$ [M − Boc + H]$^+$: 470, found 470. |

TABLE 20-continued

| Example | Structure | Compound Name | LRMS |
|---|---|---|---|
| 5-50 | 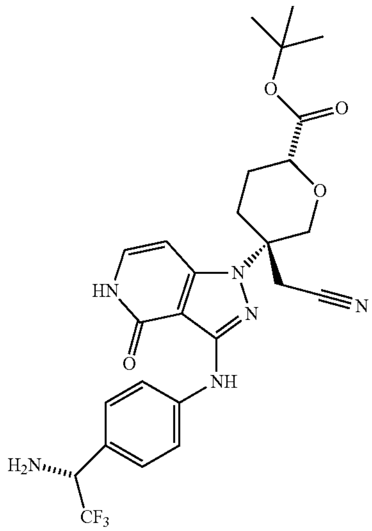 [SMILES: CC(C)(C)OC(=O)[C@H]1CC[C@@](CC#N)(n2nc(Nc3ccc([C@@H](N)C(F)(F)F)cc3)c3c(=O)[nH]ccc32)CO1] | (2R,5S)-tert-butyl 5-(3-((4-((R or S)-1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate (from epimerized I-14-1A & I-29A) | LRMS (ESI) calc'd for $C_{26}H_{30}F_3N_6O_4$ $[M + H]^+$: 547, found 547. |
| 5-51 | 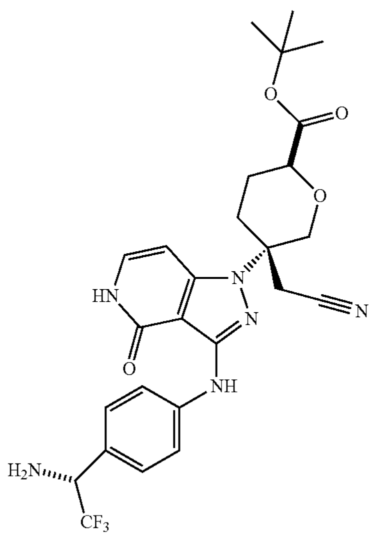 [SMILES: CC(C)(C)OC(=O)[C@@H]1CC[C@@](CC#N)(n2nc(Nc3ccc([C@@H](N)C(F)(F)F)cc3)c3c(=O)[nH]ccc32)CO1] | (2S,5S)-tert-butyl 5-(3-((4-((R or S)-1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate (from I-14-1A & I-29A) | LRMS (ESI) calc'd for $C_{26}H_{30}F_3N_6O_4$ $[M + H]^+$: 547, found 547. |
| 5-52 | 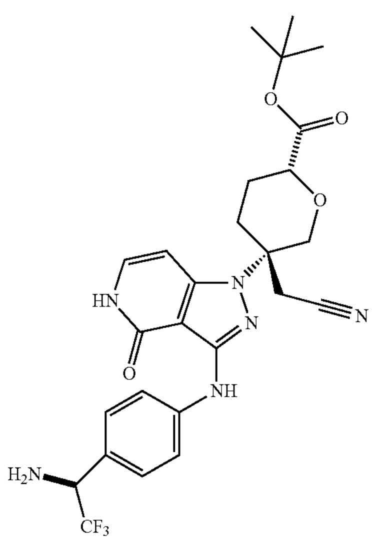 [SMILES: CC(C)(C)OC(=O)[C@H]1CC[C@@](CC#N)(n2nc(Nc3ccc([C@H](N)C(F)(F)F)cc3)c3c(=O)[nH]ccc32)CO1] | (2R,5S)-tert-butyl 5-(3-((4-((S or R)-1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate (from epimerized I-14-1A & I-29B) | LRMS (ESI) calc'd for $C_{26}H_{30}F_3N_6O_4$ $[M + H]^+$: 547, found 547. |

TABLE 20-continued

| Example | Structure | Compound Name | LRMS |
|---|---|---|---|
| 5-53 | 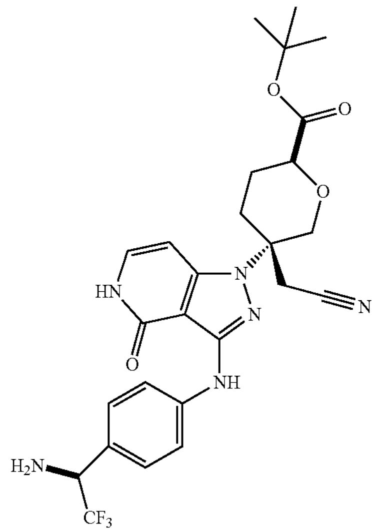 [SMILES: CC(C)(C)OC(=O)[C@@H]1CC[C@@](CC#N)(n2nc(Nc3ccc([C@H](N)C(F)(F)F)cc3)c3c(=O)[nH]ccc32)CO1] | (2S,5S)-tert-butyl 5-(3-((4-((S or R)-1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate (from I-14-1A & I-29B) | LRMS (ESI) calc'd for $C_{26}H_{30}F_3N_6O_4$ $[M + H]^+$: 547, found 547. |
| 5-54 | 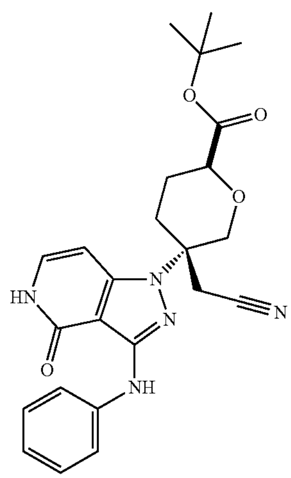 [SMILES: CC(C)(C)OC(=O)[C@@H]1CC[C@@](CC#N)(n2nc(Nc3ccccc3)c3c(=O)[nH]ccc32)CO1] | (2S,5S)-tert-butyl 5-(cyanomethyl)-5-(4-oxo-3-(phenylamino)-4,5-dihydro-1H-pyrazolo[4,3-c]pyridin-1-yl)tetrahydro-2H-pyran-2-carboxylate (from I-14-1A) | LRMS (ESI) calc'd for $C_{24}H_{28}N_5O_4$ $[M + H]^+$: 450, found 450. |
| 5-55 | 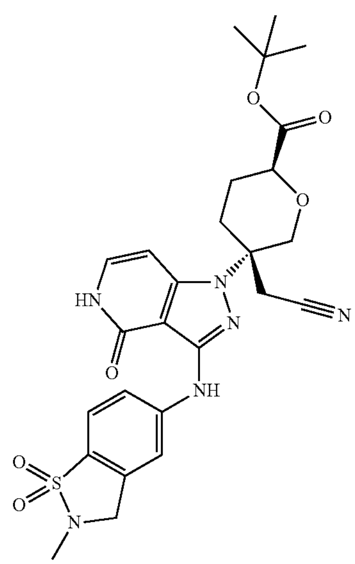 [SMILES: CN1Cc2cc(Nc3nn([C@]4(CC#N)CC[C@@H](C(=O)OC(C)(C)C)OC4)c4cc[nH]c(=O)c34)ccc2S1(=O)=O] | (2S,5S)-tert-butyl 5-(cyanomethyl)-5-(3-((2-methyl-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{26}H_{31}N_6O_6S$ $[M + H]^+$: 555, found 555. |

TABLE 20-continued

| Example | Structure | Compound Name | LRMS |
|---|---|---|---|
| 5-56 | 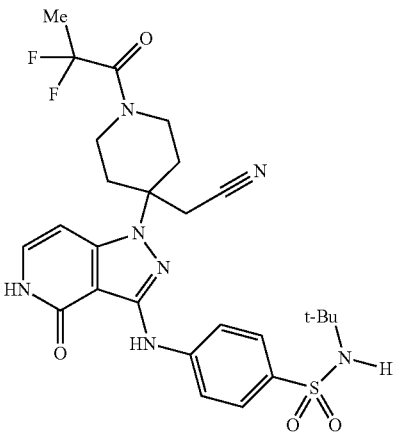 [SMILES: CC(C)(C)NS(=O)(=O)c1ccc(Nc2nn(C3(CC#N)CCN(C(=O)C(C)(F)F)CC3)c3cc[nH]c(=O)c23)cc1] | N-(tert-butyl)-4-((1-(4-(cyanomethyl)-1-(2,2-difluoropropanoyl)piperidin-4-yl)-4-oxo-4,5-dihydro-1H-pyrazolo[4,3-c]pyridin-3-yl)amino)benzene-sulfonamide | LRMS (ESI) calc'd for $C_{26}H_{32}F_2N_7O_4S$ $[M + H]^+$: 576, found 576. |
| 5-57 | 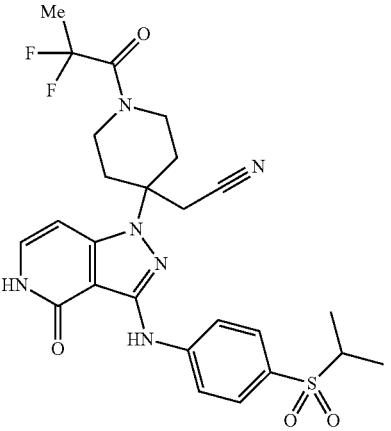 [SMILES: CC(C)S(=O)(=O)c1ccc(Nc2nn(C3(CC#N)CCN(C(=O)C(C)(F)F)CC3)c3cc[nH]c(=O)c23)cc1] | 2-(1-(2,2-difluoropropanoyl)-4-(3-((4-(isopropylsulfonyl)phenyl)amino)-4-oxo-4,5-dihydro-1H-pyrazolo[4,3-c]pyridin-1-yl)piperidin-4-yl)acetonitrile | LRMS (ESI) calc'd for $C_{25}H_{29}F_2N_6O_4S$ $[M + H]^+$: 547, found 547. |
| 5-58 | 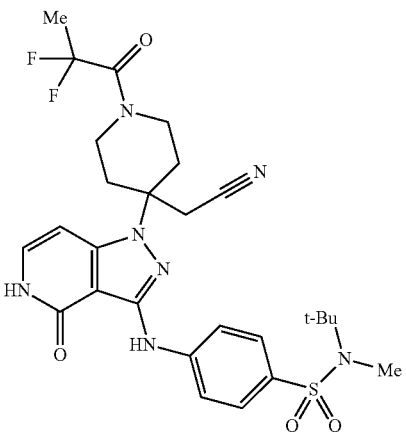 [SMILES: CN(C(C)(C)C)S(=O)(=O)c1ccc(Nc2nn(C3(CC#N)CCN(C(=O)C(C)(F)F)CC3)c3cc[nH]c(=O)c23)cc1] | N-(tert-butyl)-4-((1-(4-(cyanomethyl)-1-(2,2-difluoropropanoyl)piperidin-4-yl)-4-oxo-4,5-dihydro-1H-pyrazolo[4,3-c]pyridin-3-yl)amino)-N-methylbenzenesulfonamide | LRMS (ESI) calc'd for $C_{27}H_{33}F_2N_7O_4SNa$ $[M + Na]^+$: 612, found 612. |

TABLE 20-continued

| Example | Structure | Compound Name | LRMS |
|---|---|---|---|
| 5-59 | 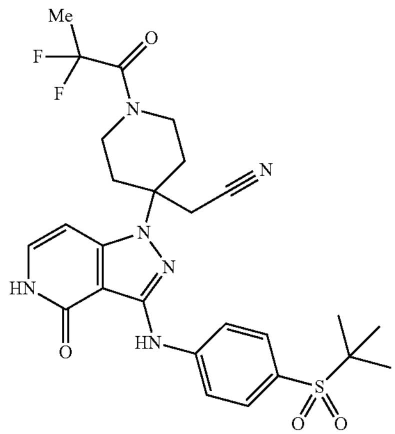 [SMILES: CC(F)(F)C(=O)N1CCC(CC#N)(n2nc(Nc3ccc(S(=O)(=O)C(C)(C)C)cc3)c3c(=O)[nH]ccc32)CC1] | 2-(4-(3-((4-(tert-butylsulfonyl)phenyl)amino)-4-oxo-4,5-dihydro-1H-pyrazolo[4,3-c]pyridin-1-yl)-1-(2,2-difluoro-propanoyl)piperidin-4-yl)acetonitrile | LRMS (ESI) calc'd for $C_{26}H_{30}F_2N_6O_4S$ [M + H]$^+$: 561, found 561. |
| 5-60 | 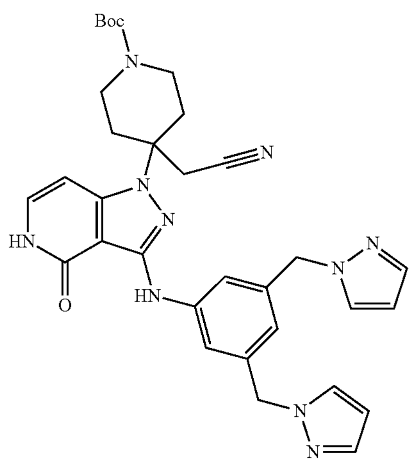 [SMILES: CC(C)(C)OC(=O)N1CCC(CC#N)(n2nc(Nc3cc(Cn4cccn4)cc(Cn4cccn4)c3)c3c(=O)[nH]ccc32)CC1] | tert-butyl 4-(3-(3,5-bis((1H-pyrazol-1-yl)methyl)phenyl amino)-4-oxo-4,5-dihydro pyrazolo[4,3-c]pyridin-1-yl)-4-(cyanomethyl)piperidine-1-carboxylate | LRMS (ESI) calc'd for $C_{32}H_{37}N_{10}O_3$ [M + H]$^+$: 609, found 609. |
| 5-61 | 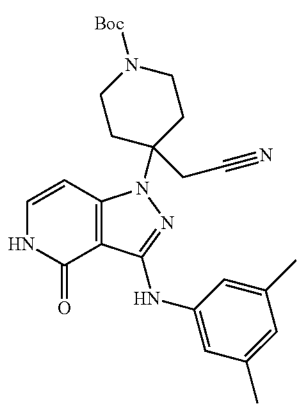 [SMILES: Cc1cc(C)cc(Nc2nn(C3(CC#N)CCN(C(=O)OC(C)(C)C)CC3)c3cc[nH]c(=O)c23)c1] | tert-butyl 4-(cyanomethyl)-4-(3-(3,5-dimethylphenylamino)-4-oxo-4,5-dihydropyrazolo[4,3-c]pyridin-1-yl)piperidine-1-carboxylate | LRMS (ESI) calc'd for $C_{26}H_{33}N_6O_3$ [M + H]$^+$: 477, found 477. |

TABLE 20-continued

| Example | Structure | Compound Name | LRMS |
|---|---|---|---|
| 5-62 | 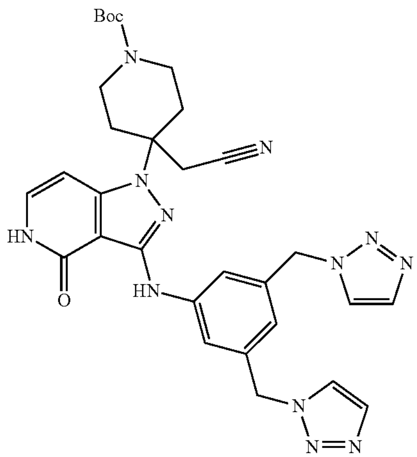 [SMILES: CC(C)(C)OC(=O)N1CCC(CC#N)(n2nc(Nc3cc(Cn4ccnn4)cc(Cn4ccnn4)c3)c3c(=O)[nH]ccc32)CC1] | tert-butyl 4-(3-(3,5-bis((1H-1,2,3-triazol-1-yl)methyl)phenylamino)-4-oxo-4,5-dihydropyrazolo[4,3-c]pyridin-1-yl)-4-(cyanomethyl)piperidine-1-carboxylate | LRMS (ESI) calc'd for $C_{30}H_{35}N_{12}O_3$ [M + H]$^+$: 611, found 611. |
| 5-63 | 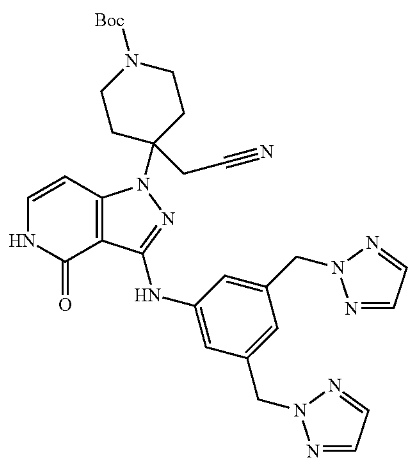 [SMILES: CC(C)(C)OC(=O)N1CCC(CC#N)(n2nc(Nc3cc(Cn4nccn4)cc(Cn4nccn4)c3)c3c(=O)[nH]ccc32)CC1] | tert-butyl 4-(3-(3,5-bis((2H-1,2,3-triazol-2-yl)methyl)phenylamino)-4-oxo-4,5-dihydropyrazolo[4,3-c]pyridin-1-yl)-4-(cyanomethyl)piperidine-1-carboxylate | LRMS (ESI) calc'd for $C_{30}H_{35}N_{12}O_3$ [M + H]$^+$: 611, found 611 |
| 5-64 | 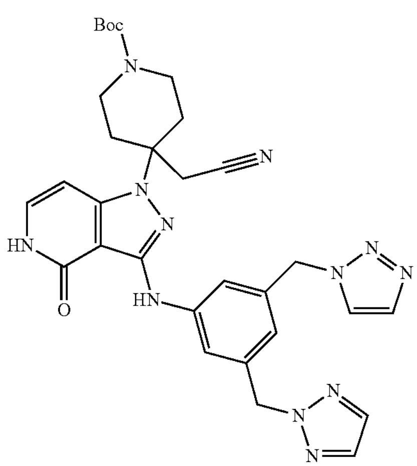 [SMILES: CC(C)(C)OC(=O)N1CCC(CC#N)(n2nc(Nc3cc(Cn4ccnn4)cc(Cn4nccn4)c3)c3c(=O)[nH]ccc32)CC1] | tert-butyl 4-(3-(3-((1H-1,2,3-triazol-1-yl)methyl)-5-((2H-1,2,3-triazol-2-yl)methyl)phenylamino)-4-oxo-4,5-dihydropyrazolo[4,3-c]pyridin-1-yl)-4-(cyanomethyl)piperidine-1-carboxylate | LRMS (ESI) calc'd for $C_{30}H_{35}N_{12}O_3$ [M + H]$^+$: 611, found 611. |

TABLE 20-continued

| Example | Structure | Compound Name | LRMS |
|---|---|---|---|
| 5-65 | 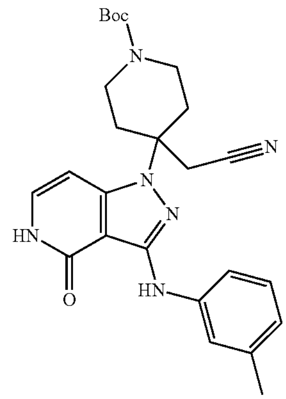 [SMILES: Cc1cccc(Nc2nn(C3(CC#N)CCN(C(=O)OC(C)(C)C)CC3)c3cc[nH]c(=O)c23)c1] | tert-butyl 4-(3-(m-toluidino)-4-oxo-4,5-dihydropyrazolo[4,3-c]pyridin-1-yl)-4-(cyanomethyl)piperidine-1-carboxylate | LRMS (ESI) calc'd for $C_{25}H_{31}N_6O_3$ [M + H]$^+$: 463, found 463. |
| 5-66 | 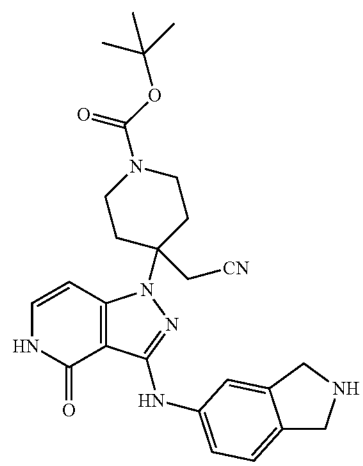 [SMILES: CC(C)(C)OC(=O)N1CCC(CC#N)(n2nc(Nc3ccc4c(c3)CNC4)c3c(=O)[nH]ccc32)CC1] | tert-butyl 4-(cyanomethyl)-4-(3-(isoindolin-5-ylamino)-4-oxo-4,5-dihydropyrazolo[4,3-c]pyridin-1-yl)piperidine-1-carboxylate | LRMS (ESI) calc'd for $C_{26}H_{32}N_7O_3$ [M + H]$^+$: 490, found 490. |
| 5-67 | 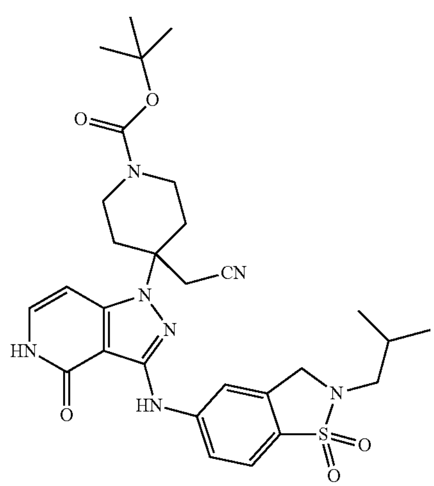 [SMILES: CC(C)CN1Cc2cc(Nc3nn(C4(CC#N)CCN(C(=O)OC(C)(C)C)CC4)c4cc[nH]c(=O)c34)ccc2S1(=O)=O] | 1,1-dioxo-2,3-dihydro-1,2-benzothiazol-5-yl]amino}-4-oxo-1H,4H,5H-pyrazolo[4,3-c]pyridin-1-yl)piperidine-1-carboxylate | LRMS (ESI) calc'd for $C_{29}H_{38}N_7O_5S$ [M + H]$^+$: 596, found 596. |

TABLE 20-continued

| Example | Structure | Compound Name | LRMS |
|---|---|---|---|
| 5-68 | 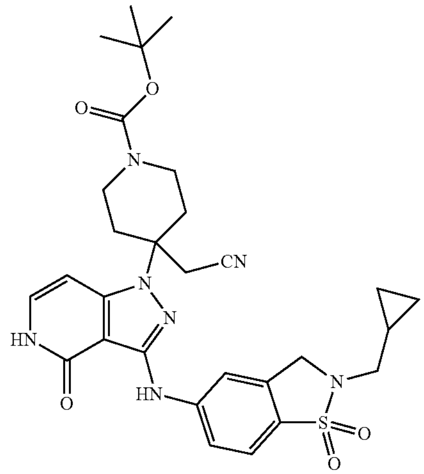 [SMILES: CC(C)(C)OC(=O)N1CCC(CC#N)(n2nc(Nc3ccc4c(c3)CN(CC3CC3)S4(=O)=O)c3c(=O)[nH]ccc32)CC1] | tert-butyl 4-(cyanomethyl)-4-(3-{[2-(cyclopropylmethyl)-1,1-dioxo-2,3-dihydro-1,2-benzothiazol-5-yl]amino}-4-oxo-1H,4H,5H-pyrazolo[4,3-c]pyridin-1-yl)piperidine-1-carboxylate | MS (ESI) calc'd for $C_{29}H_{36}N_7O_5S$ [M + H]$^+$: 594, found 594. |
| 5-69 | 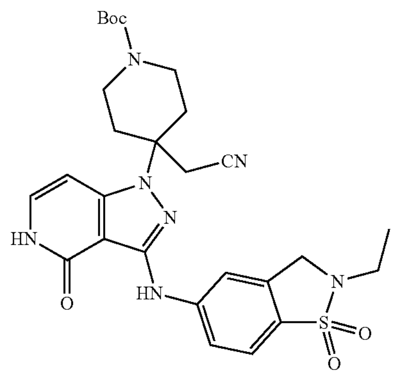 [SMILES: CCN1Cc2cc(Nc3nn(C4(CC#N)CCN(C(=O)OC(C)(C)C)CC4)c4cc[nH]c(=O)c34)ccc2S1(=O)=O] | tert-butyl 4-(cyanomethyl)-4-{3-[(2-ethyl-1,1-dioxo-2,3-dihydro-1,2-benzothiazol-5-yl)amino]-4-oxo-1H,4H,5H-pyrazolo[4,3-c]pyridin-1-yl}piperidine-1-carboxylate | LRMS (ESI) calc'd for $C_{22}H_{26}N_7O_3S$ [M − Boc + H]$^+$: 468, found 468. |
| 5-70 | 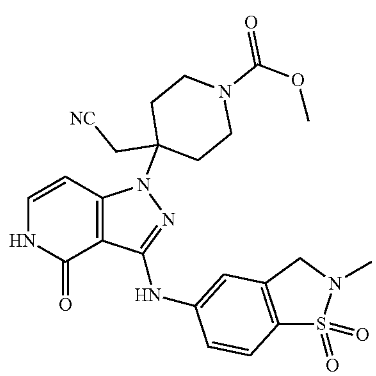 [SMILES: COC(=O)N1CCC(CC#N)(n2nc(Nc3ccc4c(c3)CN(C)S4(=O)=O)c3c(=O)[nH]ccc32)CC1] | methyl 4-(cyanomethyl)-4-[3-[(2-methyl-1,1-dioxo-2,3-dihydro-1,2-benzothiazol-5-yl)amino]-4-oxo-1H,4H,5H-pyrazolo[4,3-c]pyridin-1-yl]piperidine-1-carboxylate | LRMS (ESI) calc'd for $C_{23}H_{26}N_7O_5S$ [M + H]$^+$: 512, found 512. |
| 5-71 | 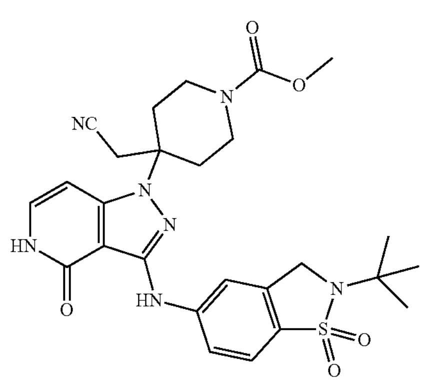 [SMILES: COC(=O)N1CCC(CC#N)(n2nc(Nc3ccc4c(c3)CN(C(C)(C)C)S4(=O)=O)c3c(=O)[nH]ccc32)CC1] | methyl 4-{3-[(2-tert-butyl-1,1-dioxo-2,3-dihydro-1,2-benzothiazol-5-yl)amino]-4-oxo-1H,4H,5H-pyrazolo[4,3-c]pyridin-1-yl}-4-(cyanomethyl)piperidine-1-carboxylate | LRMS (ESI) calc'd for $C_{26}H_{32}N_7O_5S$ [M + H]$^+$: 554, found 554. |

TABLE 20-continued

| Example | Structure | Compound Name | LRMS |
|---------|-----------|---------------|------|
| 5-72 | 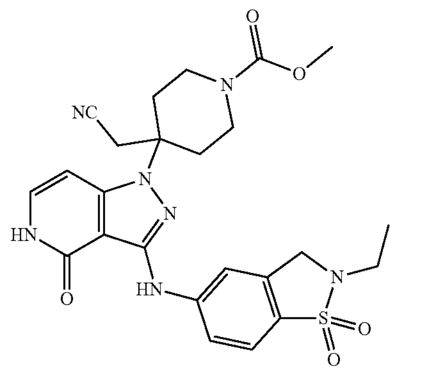 [SMILES: CCN1Cc2cc(Nc3nn(C4(CC#N)CCN(C(=O)OC)CC4)c4cc[nH]c(=O)c34)ccc2S1(=O)=O] | methyl 4-{3-[(2-ethyl-1,1-dioxo-2,3-dihydro-1,2-benzothiazol-5-yl)amino]-4-oxo-1H,4H,5H-pyrazolo[4,3-c]pyridin-1-yl}-4-(cyanomethyl)piperidine-1-carboxylate | LRMS (ESI) calc'd for $C_{24}H_{28}N_7O_5S$ [M + H]$^+$: 526, found 526. |
| 5-73 | 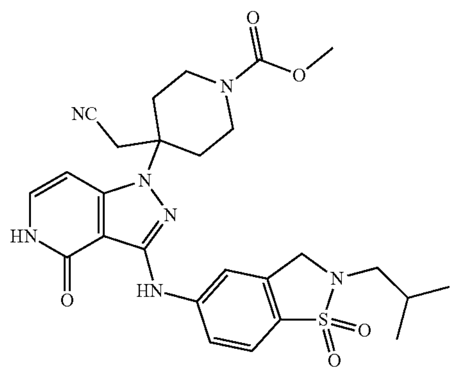 [SMILES: COC(=O)N1CCC(CC#N)(n2nc(Nc3ccc4c(c3)CN(CC(C)C)S4(=O)=O)c3c(=O)[nH]ccc32)CC1] | methyl 4-(cyanomethyl)-4-(3-{[2-(2-methylpropyl)-1,1-dioxo-2,3-dihydro-1,2-benzothiazol-5-yl]amino}-4-oxo-1H,4H,5H-pyrazolo[4,3-c]pyridin-1-yl)piperidine-1-carboxylate | LRMS (ESI) calc'd for $C_{26}H_{32}N_7O_5S$ [M + H]$^+$: 554, found 554. |
| 5-74 | 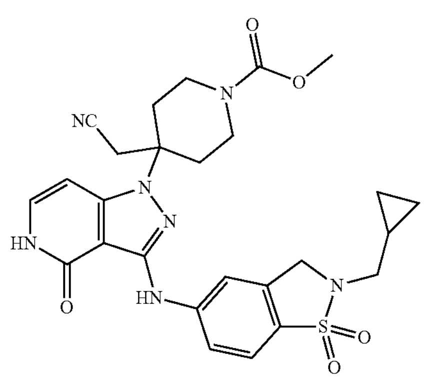 [SMILES: COC(=O)N1CCC(CC#N)(n2nc(Nc3ccc4c(c3)CN(CC3CC3)S4(=O)=O)c3c(=O)[nH]ccc32)CC1] | methyl 4-(cyanomethyl)-4-(3-{[2-(cyclopropylmethyl)-1,1-dioxo-2,3-dihydro-1,2-benzothiazol-5-yl]amino}-4-oxo-1H,4H,5H-pyrazolo[4,3-c]pyridin-1-yl)piperidine-1-carboxylate | LRMS (ESI) calc'd for $C_{26}H_{30}N_7O_5S$ [M + H]$^+$: 552, found 552. |
| 5-75 | 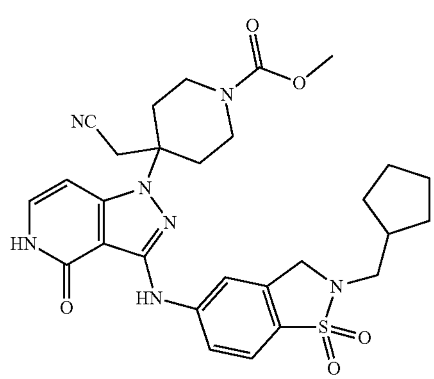 [SMILES: COC(=O)N1CCC(CC#N)(n2nc(Nc3ccc4c(c3)CN(CC3CCCC3)S4(=O)=O)c3c(=O)[nH]ccc32)CC1] | methyl 4-(cyanomethyl)-4-(3-{[2-(cyclopentylmethyl)-1,1-dioxo-2,3-dihydro-1,2-benzothiazol-5-yl]amino}-4-oxo-1H,4H,5H-pyrazolo[4,3-c]pyridin-1-yl)piperidine-1-carboxylate | LRMS (ESI) calc'd for $C_{28}H_{34}N_7O_5S$ [M + H]$^+$: 580, found 580. |

TABLE 20-continued

| Example | Structure | Compound Name | LRMS |
|---|---|---|---|
| 5-76 | 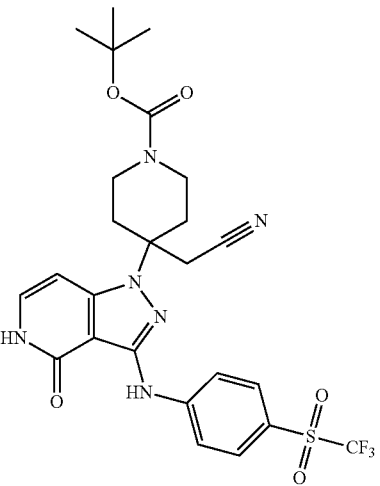 [SMILES: CC(C)(C)OC(=O)N1CCC(CC#N)(n2nc(Nc3ccc(S(=O)(=O)C(F)(F)F)cc3)c3c(=O)[nH]ccc32)CC1] | tert-butyl 4-(cyanomethyl)-4-[4-oxo-3-({4-[(trifluoromethyl)sulfonyl]phenyl}amino)-4,5-dihydro-1H-pyrazolo[4,3-c]pyridin-1-yl]piperidine-1-carboxylate | LRMS (ESI) calc'd for $C_{25}H_{28}F_3N_6O_5S$ $[M + H]^+$: 581, found 525. |
| 5-77 | 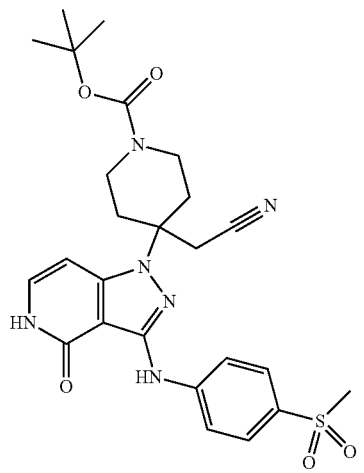 [SMILES: CC(C)(C)OC(=O)N1CCC(CC#N)(n2nc(Nc3ccc(S(C)(=O)=O)cc3)c3c(=O)[nH]ccc32)CC1] | tert-butyl 4-(cyanomethyl)-4-(3-{[4-(methylsulfonyl)phenyl]amino}-4-oxo-4,5-dihydro-1H-pyrazolo[4,3-c]pyridin-1-yl)piperidine-1-carboxylate | LRMS (ESI) calc'd for $C_{20}H_{23}N_6O_3S$ $[M - Boc + H]^+$: 427, found 427. |
| 5-78 | 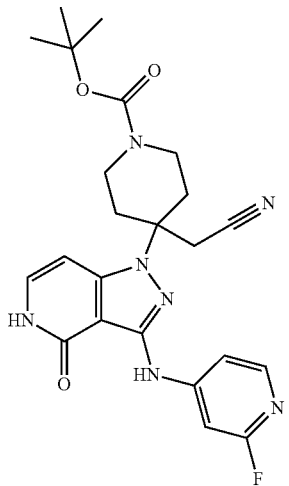 [SMILES: CC(C)(C)OC(=O)N1CCC(CC#N)(n2nc(Nc3ccnc(F)c3)c3c(=O)[nH]ccc32)CC1] | tert-butyl 4-(cyanomethyl)-4-{3-[(2-fluoropyridin-4-yl)amino]-4-oxo-4,5-dihydro-1H-pyrazolo[4,3-c]pyridin-1-yl}piperidine-1-carboxylate | LRMS (ESI) calc'd for $C_{23}H_{27}FN_7O_3$ $[M + H]^+$: 468, found 468. |

TABLE 20-continued

| Example | Structure | Compound Name | LRMS |
|---|---|---|---|
| 5-79 | 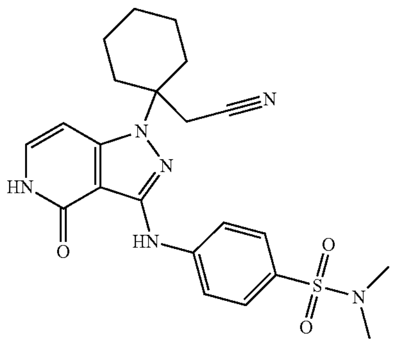 [SMILES: CN(C)S(=O)(=O)c1ccc(Nc2nn(C3(CC#N)CCCCC3)c3cc[nH]c(=O)c23)cc1] | 4-(1-(1-(cyanomethyl)cyclohexyl)-4-oxo-4,5-dihydro-1H-pyrazolo[4,3-c]pyridin-3-ylamino)-N,N-dimethylbenzenesulfonamide | LRMS (ESI) calc'd for $C_{22}H_{27}N_6O_3S$ [M + H]$^+$: 455, found 455. |
| 5-80 | 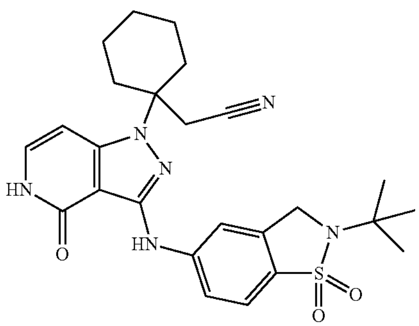 [SMILES: CC(C)(C)N1Cc2cc(Nc3nn(C4(CC#N)CCCCC4)c4cc[nH]c(=O)c34)ccc2S1(=O)=O] | 2-(1-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)cyclohexyl)acetonitrile | LRMS (ESI) calc'd for $C_{25}H_{31}N_6O_3S$ [M + H]$^+$: 495, found 495. |
| 5-81 | 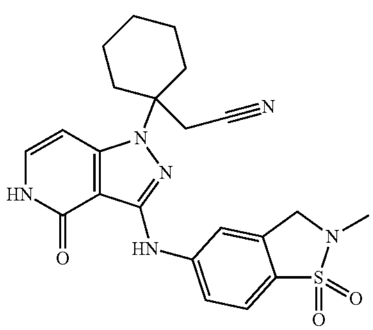 [SMILES: CN1Cc2cc(Nc3nn(C4(CC#N)CCCCC4)c4cc[nH]c(=O)c34)ccc2S1(=O)=O] | 2-(1-(3-((2-methyl-1,1-dioxido-2,3-dihydrobenzo[d]isothiazol-5-yl)amino)-4-oxo-4,5-dihydro-1H-pyrazolo[4,3-c]pyridin-1-yl)cyclohexyl)acetonitrile | LRMS (ESI) calc'd for $C_{22}H_{25}N_6O_3S$ [M + H]$^+$: 453, found 453. |
| 5-82 | 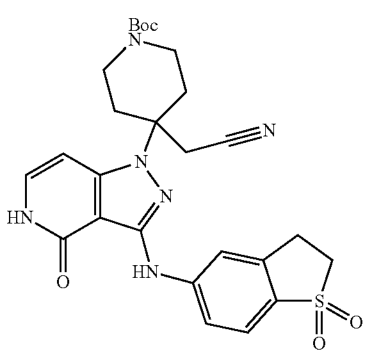 [SMILES: CC(C)(C)OC(=O)N1CCC(CC#N)(n2nc(Nc3ccc4c(c3)CCS4(=O)=O)c3c(=O)[nH]ccc32)CC1] | tert-butyl 4-(cyanomethyl)-4-(3-(((1,1-dioxido-2,3-dihydrobenzo[d]thiophen-5-yl)amino)-4-oxo-4,5-dihydro-1H-pyrazolo[4,3-c]pyridin-1-yl)piperidine-1-carboxylate | LRMS (ESI) calc'd for $C_{26}H_{31}N_6O_5S$ [M + H]$^+$: 539, found 539. |

TABLE 20-continued

| Example | Structure | Compound Name | LRMS |
|---|---|---|---|
| 5-83 | 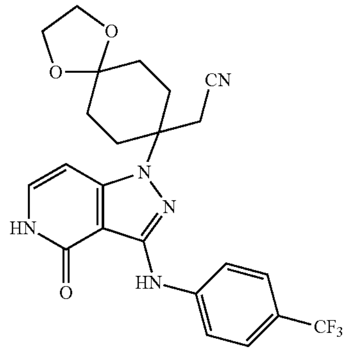 | 2-(8-(4-oxo-3-((4-(trifluoromethyl)phenyl)amino)-4,5-dihydro-1H-pyrazolo[4,3-c]pyridin-1-yl)-1,4-dioxaspiro[4.5]decan-8-yl)acetonitrile | LRMS (ESI) calc'd for $C_{30}H_{28}F_3N_5O_3$ [M + H]$^+$: 474, found 474. |
| 5-84 | 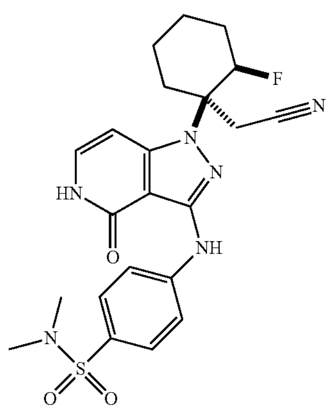 | 4-({1-[(1R,2R))-1-(cyanomethyl)-2-fluorocyclohexyl]-4-oxo-4,5-dihydro-1H-pyrazolo[4,3-c]pyridin-3-yl}amino)-N,N-dimethylbenzenesulfonamide (from I-19A) | LRMS (ESI) calc'd for $C_{22}H_{26}N_6O_3FS$ [M + H]$^+$: 473, found 473. |
| 5-85 | 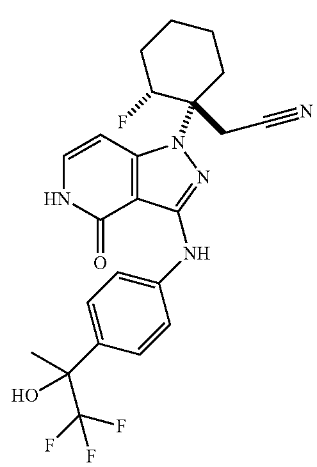 | {(1R,2R)-2-fluoro-1-[4-oxo-3-({4-[(1S or 1R)-2,2,2-trifluoro-1-hydroxy-1-methylethyl]phenyl}amino)-4,5-dihydro-1H-pyrazolo[4,3-c]pyridin-1-yl]cyclohexyl}acetonitrile (derived from aryl bromide I-32A and I-19A) | LRMS (ESI) calc'd for $C_{23}H_{24}F_4N_5O_2$ [M + H]$^+$: 478, found 478. |

| Example | Structure | Compound Name | LRMS |
|---|---|---|---|
| 5-86 | 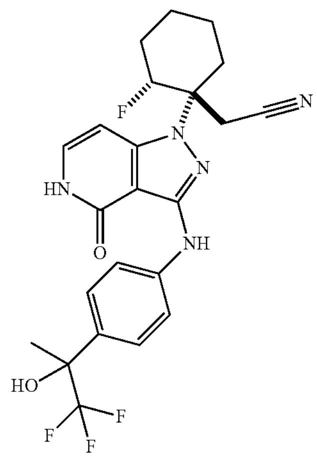 | {(1R,2R)-2-fluoro-1-[4-oxo-3-({4-[(1R or 1S)-2,2,2-trifluoro-1-hydroxy-1-methylethyl]phenyl}amino)-4,5-dihydro-1H-pyrazolo[4,3-c]pyridin-1-yl]cyclohexyl}acetonitrile (derived from aryl bromide I-32B and I-19A) | LRMS (ESI) calc'd for $C_{23}H_{24}F_4N_5O_2$ [M + H]$^+$: 478, found 478. |
| 5-87 | 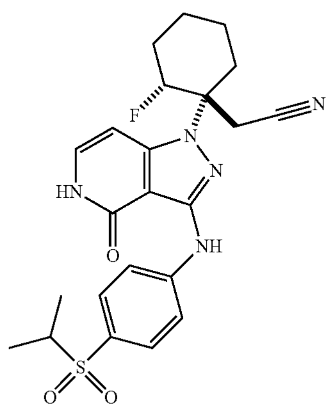 | {(1R,2R)-2-fluoro-1-[3-({4-[(1-methylethyl)sulfonyl]phenyl}amino)-4-oxo-4,5-dihydro-1H-pyrazolo[4,3-c]pyridin-1-yl]cyclohexyl}acetonitrile (from I-19A) | LRMS (ESI) calc'd for $C_{23}H_{27}N_5O_3F$ [M + H]$^+$: 472, found 472. |
| 5-88 | 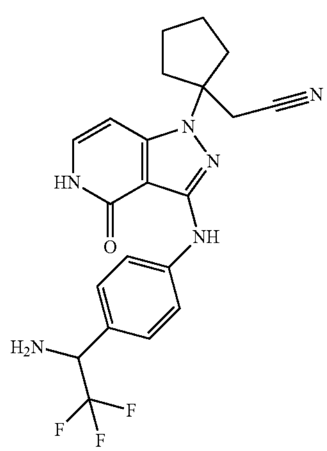 [SMILES: N#CCC1(n2nc(Nc3ccc(C(N)C(F)(F)F)cc3)c3c(=O)[nH]ccc32)CCCC1] | (R or S)-2-(1-(3-((4-(1-amino-2,2,2-trifluoroethyl)phenyl)amino)-4-oxo-4,5-dihydro-1H-pyrazolo[4,3-c]pyridin-1-yl)cyclopentyl)acetonitrile (derived from aryl bromide I-29A) | LRMS (ESI) calc'd for $C_{21}H_{22}N_6OF_3$ [M + H]$^+$: 431, found 431. |

TABLE 20-continued

| Example | Structure | Compound Name | LRMS |
|---|---|---|---|
| 5-89 | 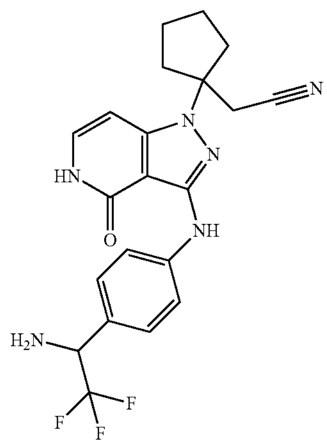 [SMILES: N#CCC1(n2nc(Nc3ccc(C(N)C(F)(F)F)cc3)c3c(=O)[nH]ccc32)CCCC1] | (R or S)-2-(1-(3-((4-(1-amino-2,2,2-trifluoroethyl)phenyl)amino)-4-oxo-4,5-dihydro-1H-pyrazolo[4,3-c]pyridin-1-yl)cyclopentyl)acetonitrile (derived from aryl bromide I-29B) | LRMS (ESI) calc'd for $C_{21}H_{22}N_6OF_3$ $[M + H]^+$: 431, found 431. |
| 5-90 | 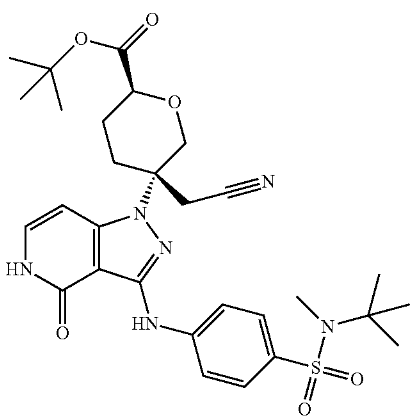 [SMILES: CN(C(C)(C)C)S(=O)(=O)c1ccc(Nc2nn([C@]3(CC#N)CC[C@@H](C(=O)OC(C)(C)C)OC3)c3cc[nH]c(=O)c23)cc1] | (2S,5S)-tert-butyl 5-(3-((4-(N-(tert-butyl)-N-methylsulfamoyl)phenyl)amino)-4-oxo-4,5-dihydro-1H-pyrazolo[4,3-c]pyridin-1-yl)-5-(cyanomethyl)tetrahydro-2H-pyran-2-carboxylate (from I-14-1A) | LRMS (ESI) calc'd for $C_{29}H_{39}N_6O_6S$ $[M + H]^+$: 599, found 599. |
| 5-91 | 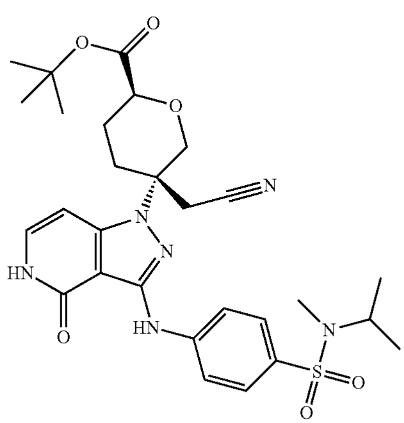 [SMILES: CC(C)N(C)S(=O)(=O)c1ccc(Nc2nn([C@]3(CC#N)CC[C@@H](C(=O)OC(C)(C)C)OC3)c3cc[nH]c(=O)c23)cc1] | (2S,5S)-tert-butyl 5-(cyanomethyl)-5-(3-((4-(N-isopropyl-N-methylsulfamoyl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{28}H_{37}N_6O_6S$ $[M + H]^+$: 585, found 585. |

TABLE 20-continued

| Example | Structure | Compound Name | LRMS |
|---|---|---|---|
| 5-92 | 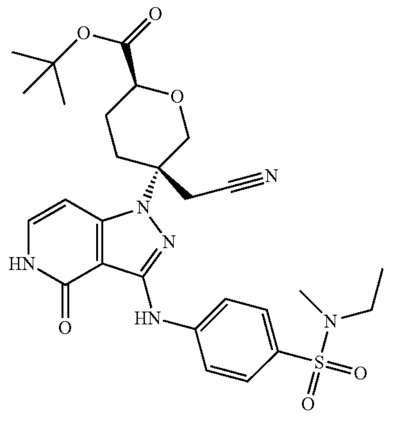 [SMILES: CCN(C)S(=O)(=O)c1ccc(Nc2nn([C@]3(CC#N)CC[C@@H](C(=O)OC(C)(C)C)OC3)c3cc[nH]c(=O)c23)cc1] | (2S,5S)-tert-butyl 5-(cyanomethyl)-5-(3-((4-(N-ethyl-N-methylsulfamoyl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{27}H_{35}N_6O_6S$ [M + H]$^+$: 571, found 571. |
| 5-93 | 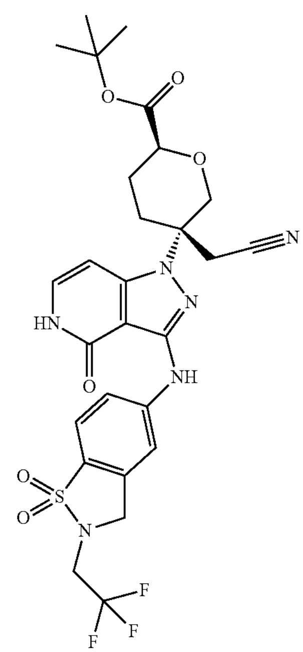 [SMILES: CC(C)(C)OC(=O)[C@@H]1CC[C@@](CC#N)(n2nc(Nc3ccc4c(c3)CN(CC(F)(F)F)S4(=O)=O)c3c(=O)[nH]ccc32)CO1] | (2S,5S)-tert-butyl 5-(cyanomethyl)-5-(3-((1,1-dioxido-2-(2,2,2-trifluoroethyl)-2,3-dihydrobenzo[d]isothiazol-yl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{27}H_{30}N_6O_6F_3S$ [M + H]$^+$: 623, found 623. |
| 5-94 | 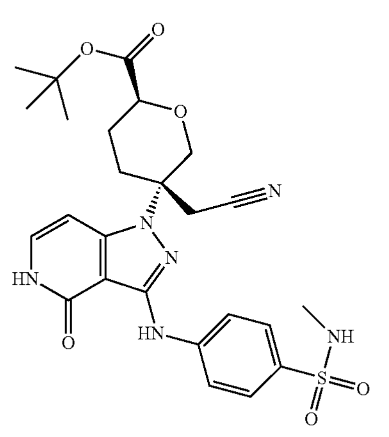 [SMILES: CNS(=O)(=O)c1ccc(Nc2nn([C@]3(CC#N)CC[C@@H](C(=O)OC(C)(C)C)OC3)c3cc[nH]c(=O)c23)cc1] | (2S,5S)-tert-butyl 5-(cyanomethyl)-5-(3-((4-(N-methylsulfamoyl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{26}H_{31}N_6O_6S$ [M + H]$^+$: 543, found 543. |

TABLE 20-continued

| Example | Structure | Compound Name | LRMS |
|---------|-----------|---------------|------|
| 5-95 | 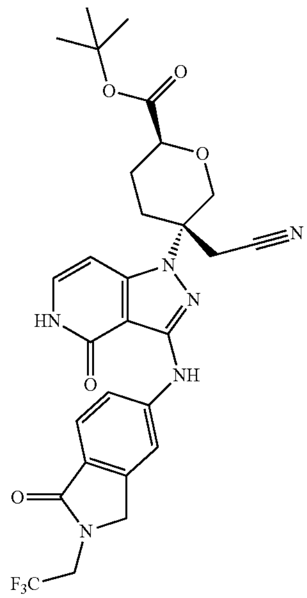 [SMILES: CC(C)(C)OC(=O)[C@@H]1CC[C@@](CC#N)(n2nc(Nc3ccc4c(c3)CN(CC(F)(F)F)C4=O)c3c(=O)[nH]ccc32)CO1] | (2S,5S)-tert-butyl 5-(cyanomethyl)-5-(4-oxo-3-((1-oxo-2-(2,2,2-trifluoroethyl)isoindolin-5-yl)amino)-4,5-dihydro-1H-pyrazolo[4,3-c]pyridin-1-yl)tetrahydro-2H-pyran-2-carboxylate (from I-14-1A) | LRMS (ESI) calc'd for $C_{28}H_{30}N_6O_5F_3$ [M + H]$^+$: 587, found 587. |
| 5-96 | 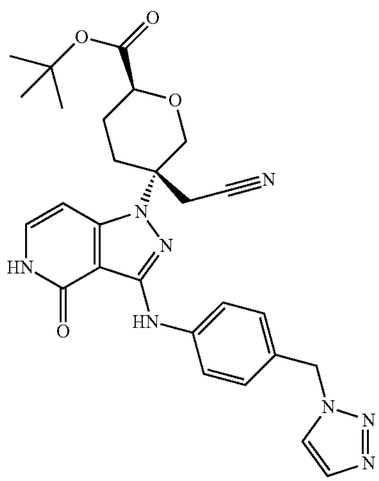 [SMILES: CC(C)(C)OC(=O)[C@@H]1CC[C@@](CC#N)(n2nc(Nc3ccc(Cn4ccnn4)cc3)c3c(=O)[nH]ccc32)CO1] | (2S,5S)-tert-butyl 5-(3-((4-((1H-1,2,3-triazol-1-yl)methyl)phenyl)amino)-4-oxo-4,5-dihydro-1H-pyrazolo[4,3-c]pyridin-1-yl)-5-(cyanomethyl)tetrahydro-2H-pyran-2-carboxylate (from I-14-1A) | LRMS (ESI) calc'd for $C_{27}H_{31}N_8O_4$ [M + H]$^+$: 531, found 531. |
| 5-97 | 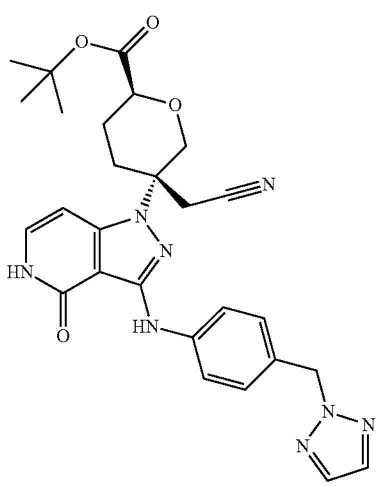 [SMILES: CC(C)(C)OC(=O)[C@@H]1CC[C@@](CC#N)(n2nc(Nc3ccc(Cn4nccn4)cc3)c3c(=O)[nH]ccc32)CO1] | (2S,5S)-tert-butyl 5-(3-((4-((2H-1,2,3-triazol-2-yl)methyl)phenyl)amino)-4-oxo-4,5-dihydro-1H-pyrazolo[4,3-c]pyridin-1-yl)-5-(cyanomethyl)tetrahydro-2H-pyran-2-carboxylate (from I-14-1A) | LRMS (ESI) calc'd for $C_{27}H_{31}N_8O_4$ [M + H]$^+$: 531, found 531. |

TABLE 20-continued

| Example | Structure | Compound Name | LRMS |
|---|---|---|---|
| 5-98 | 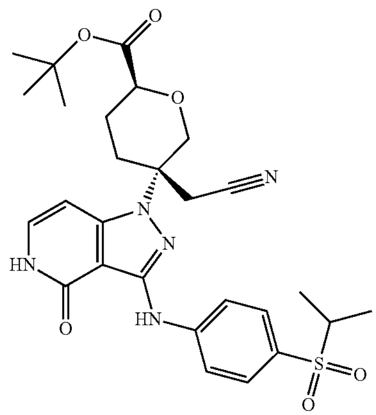 [SMILES: CC(C)S(=O)(=O)c1ccc(Nc2nn([C@]3(CC#N)CC[C@@H](C(=O)OC(C)(C)C)OC3)c3cc[nH]c(=O)c23)cc1] | (2S,5S)-tert-butyl 5-(cyanomethyl)-5-(3-((4-(isopropylsulfonyl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{27}H_{34}N_5O_6S$ [M + H]$^+$: 556, found 556. |
| 5-99 | 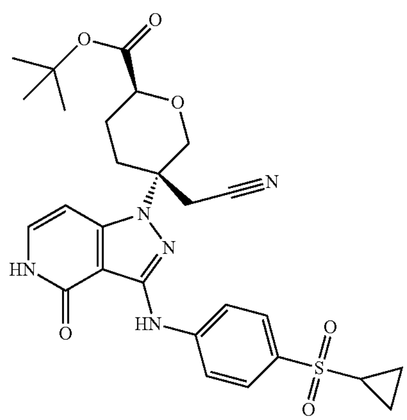 [SMILES: CC(C)(C)OC(=O)[C@@H]1CC[C@@](CC#N)(n2nc(Nc3ccc(S(=O)(=O)C4CC4)cc3)c3c(=O)[nH]ccc32)CO1] | (2S,5S)-tert-butyl 5-(cyanomethyl)-5-(3-((4-(cyclopropylsulfonyl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{27}H_{32}N_5O_6S$ [M + H]$^+$: 554, found 554. |
| 5-100 | 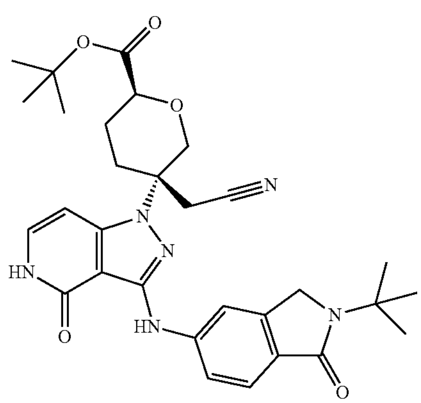 [SMILES: CC(C)(C)OC(=O)[C@@H]1CC[C@@](CC#N)(n2nc(Nc3ccc4c(c3)CN(C(C)(C)C)C4=O)c3c(=O)[nH]ccc32)CO1] | (2S,5S)-tert-butyl 5-(3-((2-(tert-butyl)-1-oxoisoindolin-5-yl)amino)-4-oxo-4,5-dihydro-1H-pyrazolo[4,3-c]pyridin-1-yl)-5-(cyanomethyl)tetrahydro-2H-pyran-2-carboxylate (from I-14-1A) | LRMS (ESI) calc'd for $C_{30}H_{37}N_6O_5$ [M + H]$^+$: 561, found 561. |
| 5-101 | 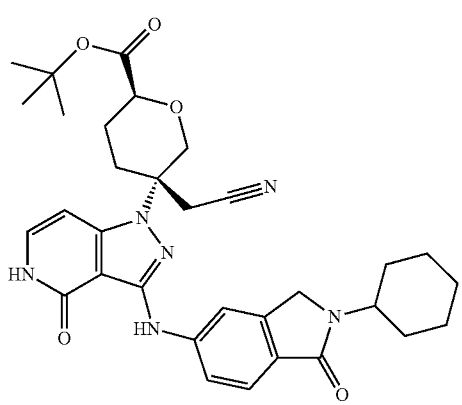 [SMILES: CC(C)(C)OC(=O)[C@@H]1CC[C@@](CC#N)(n2nc(Nc3ccc4c(c3)CN(C3CCCCC3)C4=O)c3c(=O)[nH]ccc32)CO1] | (2S,5S)-tert-butyl 5-(cyanomethyl)-5-(3-((2-cyclohexyl-1-oxoisoindolin-5-yl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{32}H_{39}N_6O_5$ [M + H]$^+$: 587, found 587. |

TABLE 20-continued

| Example | Structure | Compound Name | LRMS |
|---|---|---|---|
| 5-102 | 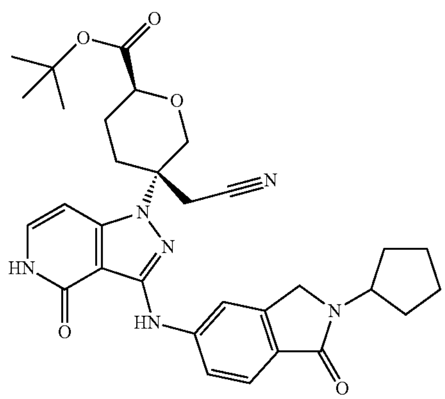 [SMILES: CC(C)(C)OC(=O)[C@@H]1CC[C@@](CC#N)(n2nc(Nc3ccc4c(c3)CN(C3CCCC3)C4=O)c3c(=O)[nH]ccc32)CO1] | (2S,5S)-tert-butyl 5-(cyanomethyl)-5-(3-((2-cyclopentyl-1-oxoisoindolin-5-yl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{31}H_{37}N_6O_5$ [M + H]$^+$: 573, found 573. |
| 5-103 | 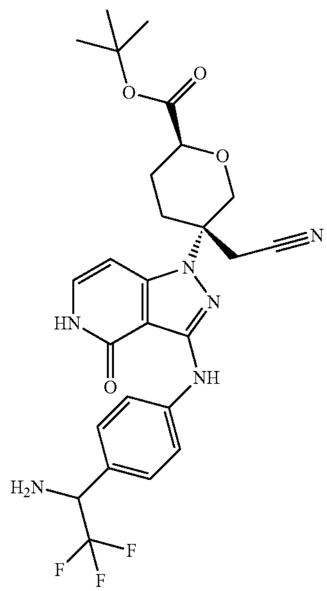 [SMILES: CC(C)(C)OC(=O)[C@@H]1CC[C@@](CC#N)(n2nc(Nc3ccc(C(N)C(F)(F)F)cc3)c3c(=O)[nH]ccc32)CO1] | (2S,5S)-tert-butyl 5-(3-((4-(1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate (derived from aryl bromide I-29A and I-14-1A) | LRMS (ESI) calc'd for $C_{26}H_{30}N_6O_4F_3$ [M + H]$^+$: 547, found 547. |
| 5-104 | 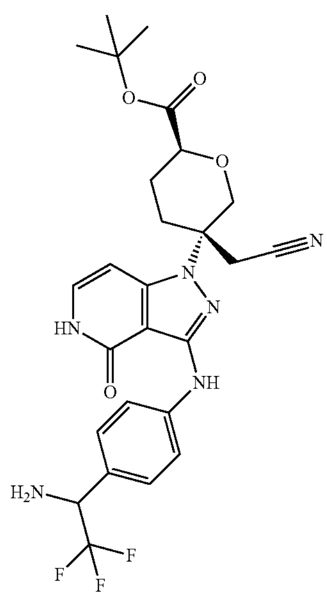 [SMILES: CC(C)(C)OC(=O)[C@@H]1CC[C@@](CC#N)(n2nc(Nc3ccc(C(N)C(F)(F)F)cc3)c3c(=O)[nH]ccc32)CO1] | (2S,5S)-tert-butyl 5-(3-((4-(1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate (derived from aryl bromide I-29B and I-14-1A) | LRMS (ESI) calc'd for $C_{26}H_{30}N_6O_4F_3$ [M + H]$^+$: 547, found 547. |

TABLE 20-continued

| Example | Structure | Compound Name | LRMS |
|---|---|---|---|
| 5-105 | 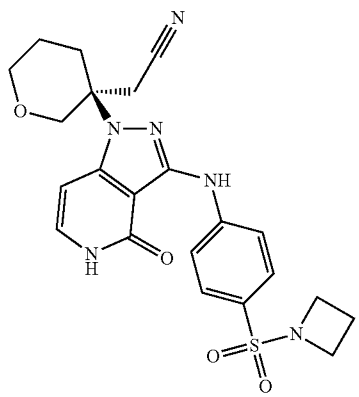 [SMILES: N#CC[C@@]1(n2nc(Nc3ccc(S(=O)(=O)N4CCC4)cc3)c3c(=O)[nH]ccc32)CCCOC1] | [(3S)-3-(3-{[4-(azetidin-1-ylsulfonyl)phenyl]amino}-4-oxo-4,5-dihydro-1H-pyrazolo[4,3-c]pyridin-1-yl)tetrahydro-2H-pyran-3-yl]acetonitrile (from I-17B) | LRMS (ESI) calc'd for $C_{22}H_{25}N_6O_4S$ $[M + H]^+$: 469, found 469. |
| 5-106 | 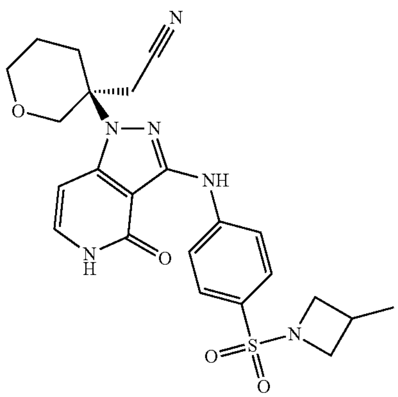 [SMILES: CC1CN(S(=O)(=O)c2ccc(Nc3nn([C@]4(CC#N)CCCOC4)c4cc[nH]c(=O)c34)cc2)C1] | {(3S)-3-[3-({4-[(3-methylazetidin-1-yl)sulfonyl]phenyl}amino)-4-oxo-4,5-dihydro-1H-pyrazolo[4,3-c]pyridin-1-yl]tetrahydro-2H-pyran-3-yl}acetonitrile (from I-17B) | LRMS (ESI) calc'd for $C_{23}H_{27}N_6O_4S$ $[M + H]^+$: 483, found 483. |
| 5-107 | 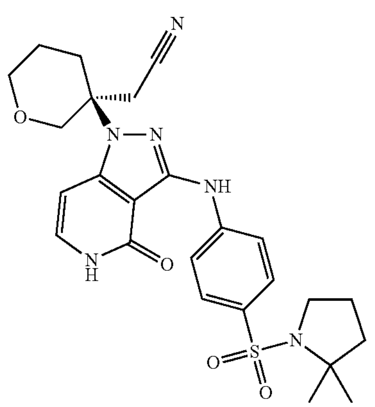 [SMILES: CC1(C)CCCN1S(=O)(=O)c1ccc(Nc2nn([C@]3(CC#N)CCCOC3)c3cc[nH]c(=O)c23)cc1] | {(3S)-3-[3-({4-[(2,2-dimethylpyrrolidin-1-yl)sulfonyl]phenyl}amino)-4-oxo-4,5-dihydro-1H-pyrazolo[4,3-c]pyridin-1-yl]tetrahydro-2H-pyran-3-yl}acetonitrile (from I-17B) | LRMS (ESI) calc'd for $C_{25}H_{31}N_6O_4S$ $[M + H]^+$: 511, found 511. |
| 5-108 | 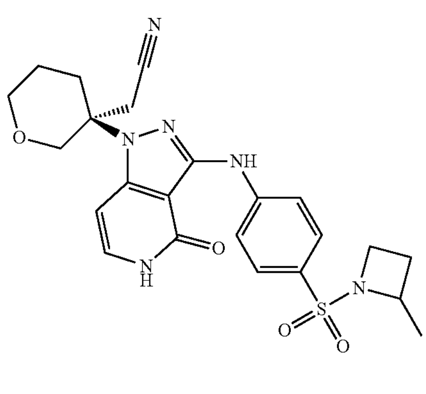 [SMILES: CC1CCN1S(=O)(=O)c1ccc(Nc2nn([C@]3(CC#N)CCCOC3)c3cc[nH]c(=O)c23)cc1] | [(3S)-3-{3-[(4-{[(2R or 2S)-2-methylazetidin-1-yl]sulfonyl}phenyl)amino]-4-oxo-4,5-dihydro-1H-pyrazolo[4,3-c]pyridin-1-yl}tetrahydro-2H-pyran-3-yl]acetonitrile (derived from aryl bromide I-20-17A and I-17B) | LRMS (ESI) calc'd for $C_{23}H_{27}N_6O_4S$ $[M + H]^+$: 483, found 483. |

TABLE 20-continued

| Example | Structure | Compound Name | LRMS |
|---|---|---|---|
| 5-109 | 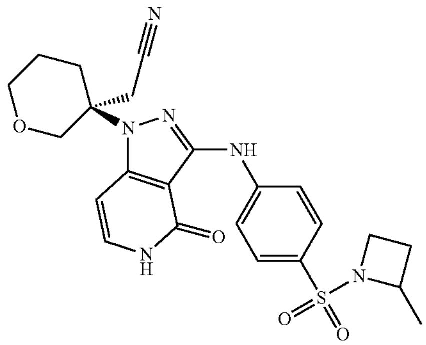 [SMILES: CC1CCN1S(=O)(=O)c1ccc(Nc2nn([C@]3(CC#N)CCCOC3)c3cc[nH]c(=O)c23)cc1] | [(3S)-3-{3-[(4-{[(2S or 2R)-2-methylazetidin-1-yl]sulfonyl}phenyl)amino]-4-oxo-4,5-dihydro-1H-pyrazolo[4,3-c]pyridin-1-yl}tetrahydro-2H-pyran-3-yl]acetonitrile (derived from aryl bromide I-20-17B and I-17B) | LRMS (ESI) calc'd for $C_{23}H_{27}N_6O_4S$ [M + H]$^+$: 483, found 483. |
| 5-110 | 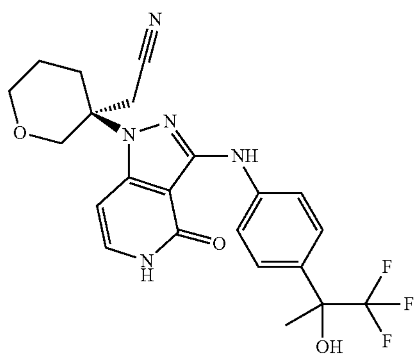 [SMILES: CC(O)(c1ccc(Nc2nn([C@]3(CC#N)CCCOC3)c3cc[nH]c(=O)c23)cc1)C(F)(F)F] | {(3S)-3-[4-oxo-3-({4-[(1S or 1R)-2,2,2-trifluoro-1-hydroxy-1-methylethyl]phenyl}amino)-4,5-dihydro-1H-pyrazolo[4,3-c]pyridin-1-yl]tetrahydro-2H-pyran-3-yl}acetonitrile (derived from aryl bromide I-32A and I-17B) | LRMS (ESI) calc'd for $C_{22}H_{23}N_5O_3F_3$ [M + H]$^+$: 462, found 462. |
| 5-111 | 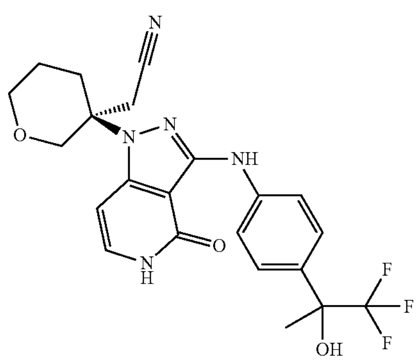 [SMILES: CC(O)(c1ccc(Nc2nn([C@]3(CC#N)CCCOC3)c3cc[nH]c(=O)c23)cc1)C(F)(F)F] | {(3S)-3-[4-oxo-3-({4-[(1R or 1S)-2,2,2-trifluoro-1-hydroxy-1-methylethyl]phenyl}amino)-4,5-dihydro-1H-pyrazolo[4,3-c]pyridin-1-yl]tetrahydro-2H-pyran-3-yl}acetonitrile (derived from aryl bromide I-32B and I-17B) | LRMS (ESI) calc'd for $C_{22}H_{23}N_5O_3F_3$ [M + H]$^+$: 462, found 462. |
| 5-112 | 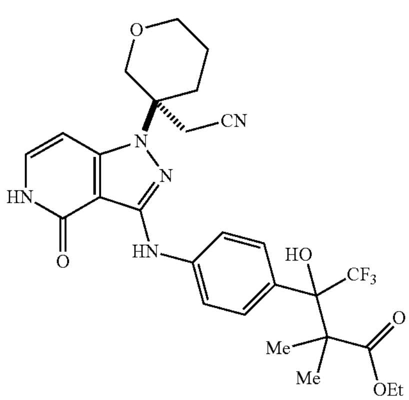 | (S or R)-ethyl 3-(4-((1-((3S)-3-(cyanomethyl)tetrahydro-2H-pyran-3-yl)-4-oxo-4,5-dihydro-1H-pyrazolo[4,3-c]pyridin-3-yl)amino)phenyl)-4,4,4-trifluoro-3-hydroxy-2,2-dimethylbutanoate (from I-17B, derived from Peak I via SFC on free pyridone: Chiralpak IC, 25% MeOH in $CO_2$, Tr = 6.2 minutes) | LCMS (ESI) Calc'd for $C_{27}H_{31}F_3N_5O_5$ [M + H]$^+$: 562, found 562. |

TABLE 20-continued

| Example | Structure | Compound Name | LRMS |
|---|---|---|---|
| 5-113 | 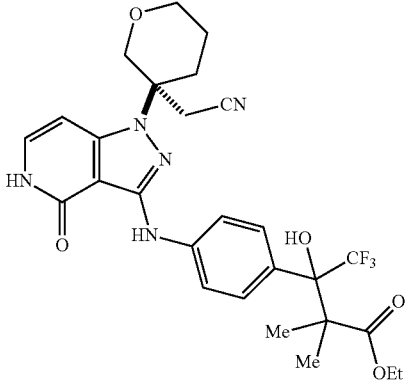 | (S or R)-ethyl 3-(4-((1-((3S)-3-(cyanomethyl)tetrahydro-2H-pyran-3-yl)-4-oxo-4,5-dihydro-1H-pyrazolo[4,3-c]pyridin-3-yl)amino)phenyl)-4,4,4-trifluoro-3-hydroxy-2,2-dimethylbutanoate (from I-17B, derived from Peak 2 via SFC on free pyridone: Chiralpak IC, 25% MeOH in $CO_2$, Tr = 7.9 minutes) | LCMS (ESI) Calc'd for $C_{27}H_{31}F_3N_5O_5$ $[M + H]^+$: 562, found 562. |
| 5-114 | 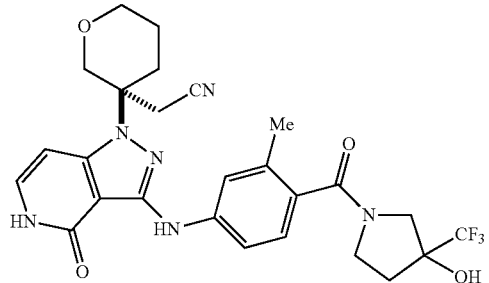 | 2-((S)-3-(3-((4-((S or R)-3-hydroxy-3-(trifluoromethyl)pyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile (from I-17B and I-39-2A.) | LCMS (ESI) Calc'd for $C_{26}H_{28}F_3N_6O_4$ $[M + H]^+$: 545, found 545. |
| 5-115 | 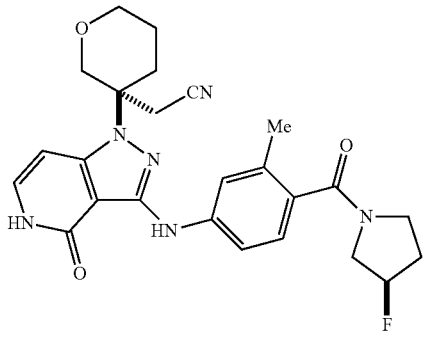 | 2-((S)-3-(3-((4-((R)-3-fluoropyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile (from I-17B and I-39-3) | LCMS (ESI) Calc'd for $C_{25}H_{28}FN_6O_3$ $[M + H]^+$: 479, found 479. |
| 5-116 | 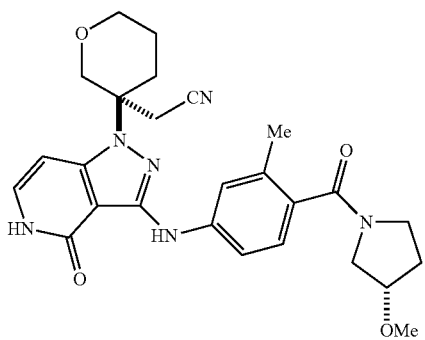 | 2-((S)-3-(3-((4-((S)-3-methoxypyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile (from I-17B and I-39-4.) | LCMS (ESI) Calc'd for $C_{26}H_{31}N_6O_4$ $[M + H]^+$: 491, found 491. |

TABLE 20-continued

| Example | Structure | Compound Name | LRMS |
|---|---|---|---|
| 5-117 | 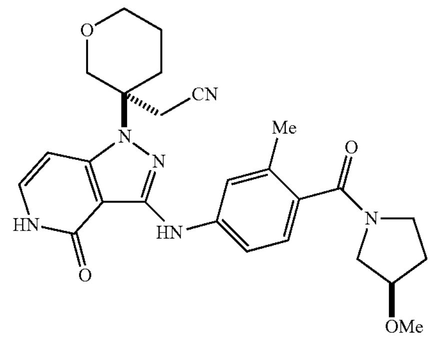 | 2-((S)-3-(3-((4-((R)-3-methoxypyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile (from I-17B and I-39-5) | LCMS (ESI) Calc'd for $C_{26}H_{31}N_6O_4$ [M + H]$^+$: 491, found 491. |
| 5-118 | 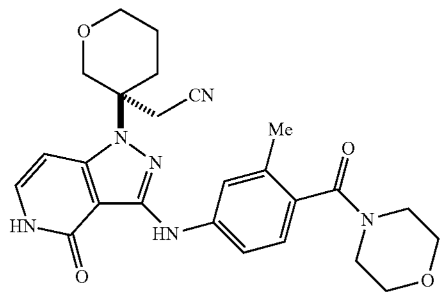 | (S)-2-(3-(3-((3-methyl-4-(morpholine-4-carbonyl)phenyl)amino)-4-oxo-4,5-dihydro-1H-pyrazolo[4,3-c]pyridin-1-yl)tetrahydro-2H-pyran-3-yl)acetonitrile (from I-17B) | LCMS (ESI) Calc'd for $C_{25}H_{29}N_6O_4$ [M + H]$^+$: 477, found 477. |
| 5-119 | 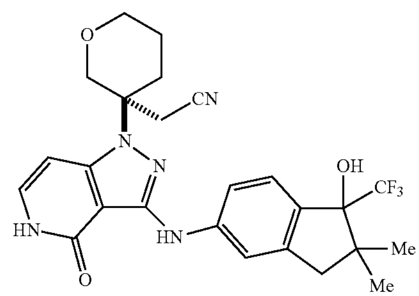 | 2-((S)-3-(3-(((S or R)-1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)tetrahydro-2H-pyran-3-yl)acetonitrile (from I-17B and I-36. Derived from Peak 1 on free pyridone via SFC: Chiralpak OJ-H, 20% MeOH in CO$_2$, Tr = 4.8 minutes) | LCMS (ESI) Calc'd for $C_{25}H_{27}F_3N_5O_3$ [M + H]$^+$: 502, found 502. |
| 5-120 | 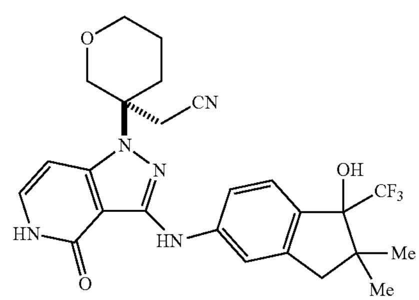 | 2-((S)-3-(3-((S or R)-1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)tetrahydro-2H-pyran-3-yl)acetonitrile (from I-17B and I-36. Derived from Peak 2 on free pyridone via SFC: Chiralpak OJ-H, 20% MeOH in CO$_2$, Tr = 5.8 minutes) | LRMS (ESI) Calc'd for $C_{25}H_{27}F_3N_5O_3$ [M + H]$^+$: 502, found 502. |
| 5-121 | 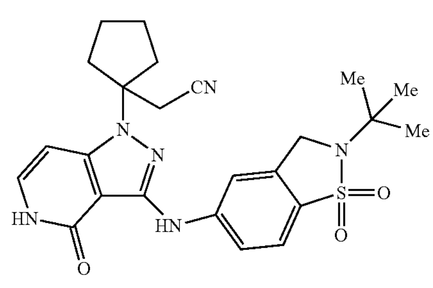 [SMILES: CC(C)(C)N1Cc2cc(Nc3nn(C4(CC#N)CCCC4)c4cc[nH]c(=O)c34)ccc2S1(=O)=O] | 2-(1-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)cyclopentyl)acetonitrile | LRMS (ESI) Calc'd for $C_{24}H_{29}N_6O_3S$ [M + H]$^+$: 481, found 481. |

TABLE 20-continued

| Example | Structure | Compound Name | LRMS |
|---|---|---|---|
| 5-122 | 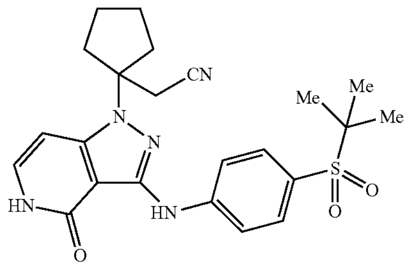 [SMILES: CC(C)(C)S(=O)(=O)c1ccc(Nc2nn(C3(CC#N)CCCC3)c3cc[nH]c(=O)c23)cc1] | 2-(1-(3-((4-(tert-butylsulfonyl)phenyl)amino)-4-oxo-4,5-dihydro-1H-pyrazolo[4,3-c]pyridin-1-yl)cyclopentyl)acetonitrile | LRMS (ESI) Calc'd for $C_{23}H_{28}N_5O_3S$ [M + H]$^+$: 454, found 454. |
| 5-123 | 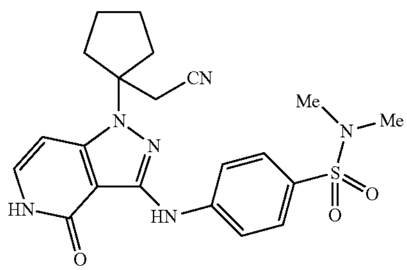 [SMILES: CN(C)S(=O)(=O)c1ccc(Nc2nn(C3(CC#N)CCCC3)c3cc[nH]c(=O)c23)cc1] | 4-((1-(1-(cyanomethyl)cyclopentyl)-4-oxo-4,5-dihydro-1H-pyrazolo[4,3-c]pyridin-3-yl)amino-N,N-dimethylbenzenesulfonamide | LRMS (ESI) Calc'd for $C_{21}H_{25}N_6O_3S$ [M + H]$^+$: 441, found 441. |
| 5-124 | 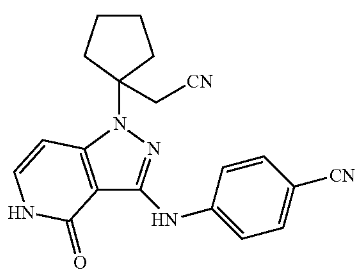 [SMILES: N#CCC1(n2nc(Nc3ccc(C#N)cc3)c3c(=O)[nH]ccc32)CCCC1] | 4-((1-(1-(cyanomethyl)cyclopentyl)-4-oxo-4,5-dihydro-1H-pyrazolo[4,3-c]pyridin-3-yl)amino)benzonitrile | LRMS (ESI) Calc'd for $C_{20}H_{19}N_6O$ [M + H]$^+$: 359, found 359. |
| 5-125 | 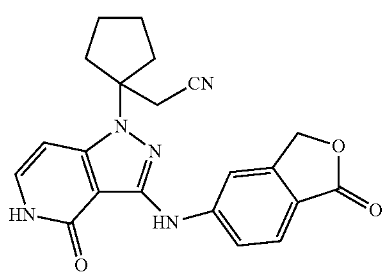 [SMILES: N#CCC1(n2nc(Nc3ccc4c(c3)COC4=O)c3c(=O)[nH]ccc32)CCCC1] | 2-(1-(4-oxo-3-((1-oxo-1,3-dihydroisobenzofuran-5-yl)amino)-4,5-dihydro-1H-pyrazolo[4,3-c]pyridin-1-yl)cyclopentyl)acetonitrile | LRMS (ESI) Calc'd for $C_{21}H_{20}N_5O_3$ [M + H]$^+$: 390, found 390. |
| 5-126 | 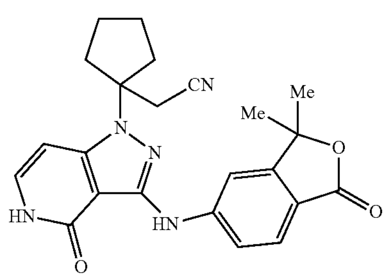 [SMILES: CC1(C)OC(=O)c2ccc(Nc3nn(C4(CC#N)CCCC4)c4cc[nH]c(=O)c34)cc21] | (1-{3-[(3,3-dimethyl-1-oxo-1,3-dihydro-2-benzofuran-5-yl)amino]-4-oxo-4,5-dihydro-1H-pyrazolo[4,3-c]pyridin-1-yl}cyclopentyl)acetonitrile | LRMS (ESI) Calc'd for $C_{23}H_{24}N_5O_3$ [M + H]$^+$: 418, found 418. |

TABLE 20-continued

| Example | Structure | Compound Name | LRMS |
|---|---|---|---|
| 5-127 | 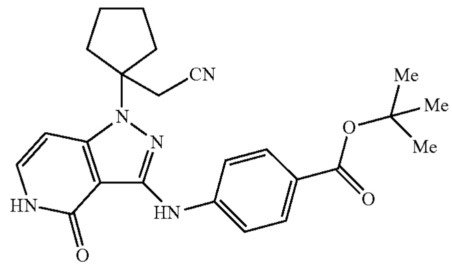 [SMILES: CC(C)(C)OC(=O)c1ccc(Nc2nn(C3(CC#N)CCCC3)c3cc[nH]c(=O)c23)cc1] | tert-butyl 4-((1-(1-(cyanomethyl)cyclopentyl)-4-oxo-4,5-dihydro-1H-pyrazolo[4,3-c]pyidin-3-yl)amino)benzoate | LRMS (ESI) Calc'd for $C_{24}H_{28}N_5O_3$ [M + H]$^+$: 434, found 434. |
| 5-128 | 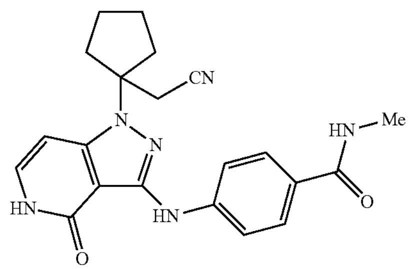 [SMILES: CNC(=O)c1ccc(Nc2nn(C3(CC#N)CCCC3)c3cc[nH]c(=O)c23)cc1] | 4-((1-(1-(cyanomethyl)cyclopentyl)-4-oxo-4,5-dihydro-1H-pyrazolo[4,3-c]pyridin-3-yl)amino)-N-methylbenzamide. | LRMS (ESI) Calc'd for $C_{21}H_{23}N_6O_2$ [M + H]$^+$: 391, found 391. |
| 5-129 | 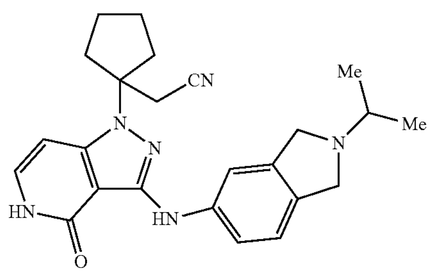 [SMILES: CC(C)N1Cc2ccc(Nc3nn(C4(CC#N)CCCC4)c4cc[nH]c(=O)c34)cc2C1] | 2-(1-(3-((2-isopropyl-1-oxoisoindolin-5-yl)amino)-4-oxo-4,5-dihydro-1H-pyrazolo[4,3-c]pyridin-1-yl)cyclopentyl)acetonitrile | LRMS (ESI) Calc'd for $C_{24}H_{27}N_6O_2$ [M + H]$^+$: 431, found 431. |
| 5-130 | 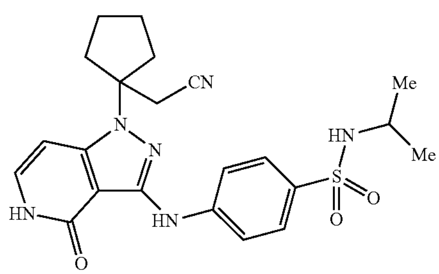 [SMILES: CC(C)NS(=O)(=O)c1ccc(Nc2nn(C3(CC#N)CCCC3)c3cc[nH]c(=O)c23)cc1] | 4-((1-(1-(cyanomethyl)cyclopentyl)-4-oxo-4,5-dihydro-1H-pyrazolo[4,3-c]pyridin-3-yl)amino)-N-isopropylbenzene-sulfonamide | LRMS (ESI) Calc'd for $C_{22}H_{27}N_6O_3S$ [M + H]$^+$: 455, found 455. |
| 5-131 | 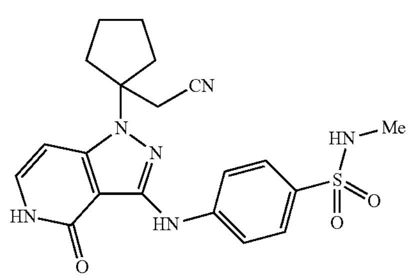 [SMILES: CNS(=O)(=O)c1ccc(Nc2nn(C3(CC#N)CCCC3)c3cc[nH]c(=O)c23)cc1] | 4-((1-(1-(cyanomethyl)cyclopentyl)-4-oxo-4,5-dihydro-1H-pyrazolo[4,3-c]pyridin-3-yl)amino)-N-methylbenzenesulfonamide | LRMS (ESI) Calc'd for $C_{20}H_{23}N_6O_3S$ [M + H]$^+$: 427, found 427. |

TABLE 20-continued

| Example | Structure | Compound Name | LRMS |
|---|---|---|---|
| 5-132 | 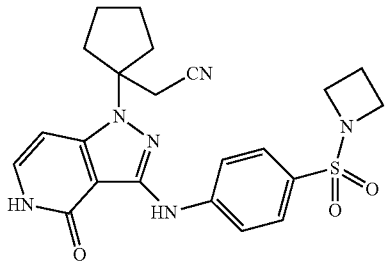 [SMILES: N#CCC1(n2nc(Nc3ccc(S(=O)(=O)N4CCC4)cc3)c3c(=O)[nH]ccc32)CCCC1] | 2-(1-(3-((4-(azetidin-1-ylsulfonyl)phenyl)amino)-4-oxo-4,5-dihydro-1H-pyrazolo[4,3-c]pyridin-1-yl)cyclopentyl)acetonitrile | LRMS (ESI) Calc'd for $C_{22}H_{25}N_6O_3S$ $[M + H]^+$: 453, found 453. |
| 5-133 | 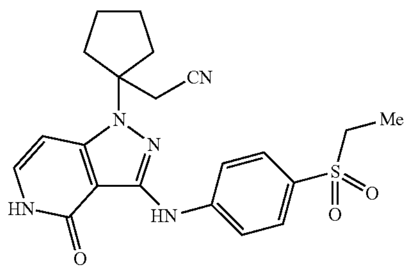 [SMILES: CCS(=O)(=O)c1ccc(Nc2nn(C3(CC#N)CCCC3)c3cc[nH]c(=O)c23)cc1] | 2-(1-(3-((4-(ethylsulfonyl)phenyl)amino)-4-oxo-4,5-dihydro-1H-pyrazolo[4,3-c]pyridin-1-yl)cyclopentyl)acetonitrile | LRMS (ESI) Calc'd for $C_{21}H_{24}N_5O_3S$ $[M + H]^+$: 426, found 426. |
| 5-134 | 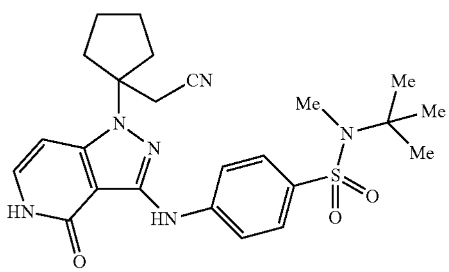 [SMILES: CN(C(C)(C)C)S(=O)(=O)c1ccc(Nc2nn(C3(CC#N)CCCC3)c3cc[nH]c(=O)c23)cc1] | N-(tert-butyl)-4-((1-(1-(cyanomethyl)cyclopentyl)-4-oxo-4,5-dihydro-1H-pyrazolo[4,3-c]pyridin-3-yl)amino)-N-methylbenzenesulfonamide | LRMS (ESI) Calc'd for $C_{24}H_{31}N_6O_3S$ $[M + H]^+$: 483, found 483. |
| 5-135 | 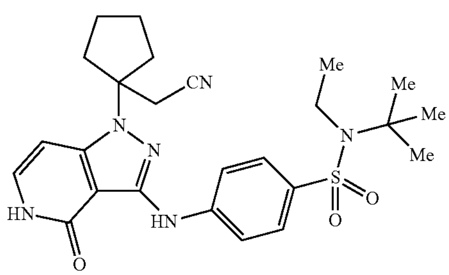 [SMILES: CCN(C(C)(C)C)S(=O)(=O)c1ccc(Nc2nn(C3(CC#N)CCCC3)c3cc[nH]c(=O)c23)cc1] | N-(tert-butyl)-4-((1-(1-(cyanomethyl)cyclopentyl)-4-oxo-4,5-dihydro-1H-pyrazolo[4,3-c]pyridin-3-yl)amino)-N-ethylbenzenesulfonamide | LRMS (ESI) Calc'd for $C_{25}H_{33}N_6O_3S$ $[M + H]^+$: 497, found 497. |
| 5-136 | 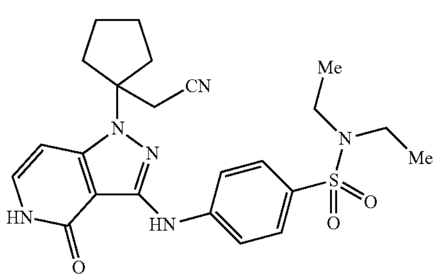 [SMILES: CCN(CC)S(=O)(=O)c1ccc(Nc2nn(C3(CC#N)CCCC3)c3cc[nH]c(=O)c23)cc1] | 4-((1-(1-(cyanomethyl)cyclopentyl)-4-oxo-4,5-dihydro-1H-pyrazolo[4,3-c]pyridin-3-yl)amino)-N,N-diethylbenzenesulfonamide | LRMS (ESI) Calc'd for $C_{23}H_{29}N_6O_3S$ $[M + H]^+$: 469, found 469. |

TABLE 20-continued

| Example | Structure | Compound Name | LRMS |
|---|---|---|---|
| 5-137 | 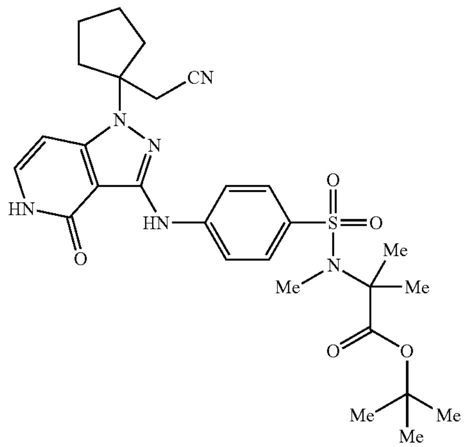 [SMILES: CN(C(C)(C)C(=O)OC(C)(C)C)S(=O)(=O)c1ccc(Nc2nn(C3(CC#N)CCCC3)c3cc[nH]c(=O)c23)cc1] | tert-butyl 2-(4-((1-(1-(cyanomethyl)cyclopentyl)-4-oxo-4,5-dihydro-1H-pyrazolo[4,3-c]pyridin-3-yl)amino)-N-methylphenylsulfonamido)-2-methylpropanoate | LRMS (ESI) Calc'd for $C_{28}H_{37}N_6O_5S$ $[M + H]^+$: 569, found 569. |
| 5-138 | 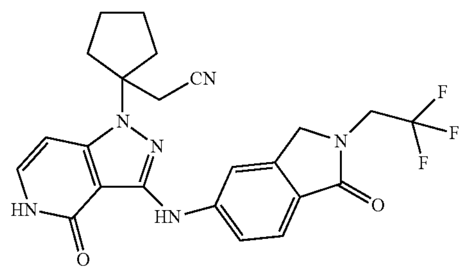 [SMILES: N#CCC1(n2nc(Nc3ccc4c(c3)CN(CC(F)(F)F)C4=O)c3c(=O)[nH]ccc32)CCCC1] | 2-(1-(4-oxo-3-((1-oxo-2-(2,2,2-trifluoroethyl)isoindolin-5-yl)amino)-4,5-dihydro-1H-pyrazolo[4,3-c]pyridin-1-yl)cyclopentyl)acetonitrile | LRMS (ESI) Calc'd for $C_{23}H_{22}F_3N_6O_2$ $[M + H]^+$: 471, found 471. |
| 5-139 | 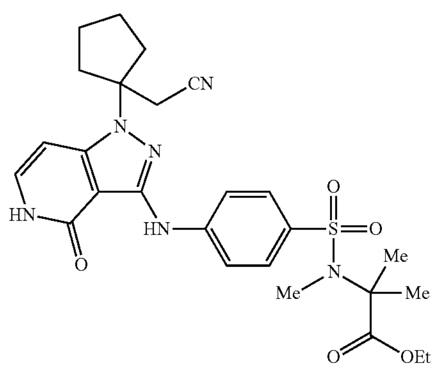 [SMILES: CCOC(=O)C(C)(C)N(C)S(=O)(=O)c1ccc(Nc2nn(C3(CC#N)CCCC3)c3cc[nH]c(=O)c23)cc1] | ethyl 2-(4-((1-(1-(cyanomethyl)cyclopentyl)-4-oxo-4,5-dihydro-1H-pyrazolo[4,3-c]pyridin-3-yl)amino)-N-methylphenylsulfonamido)-2-methylpropanoate | LRMS (ESI) Calc'd for $C_{26}H_{33}N_6O_5S$ $[M + H]^+$: 541, found 541. |
| 5-140 | 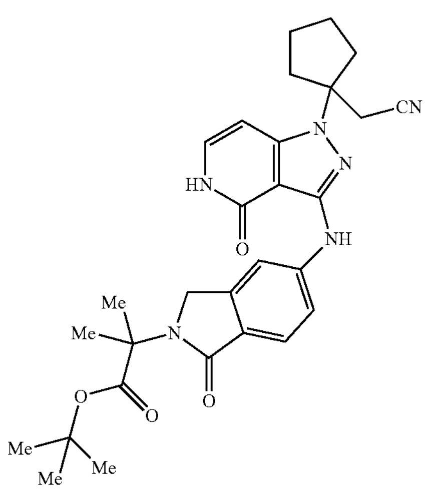 [SMILES: CC(C)(C)OC(=O)C(C)(C)N1Cc2cc(Nc3nn(C4(CC#N)CCCC4)c4cc[nH]c(=O)c34)ccc2C1=O] | tert-butyl 2-(5-((1-(1-(cyanomethyl)cyclopentyl)-4-oxo-4,5-dihydro-1H-pyrazolo[4,3-c]pyridin-3-yl)amino)-1-oxoisoindolin-2-yl)-2-methylpropanoate | LRMS (ESI) Calc'd for $C_{29}H_{35}N_6O_4$ $[M + H]^+$: 531, found 531. |

TABLE 20-continued

| Example | Structure | Compound Name | LRMS |
|---|---|---|---|
| 5-141 | 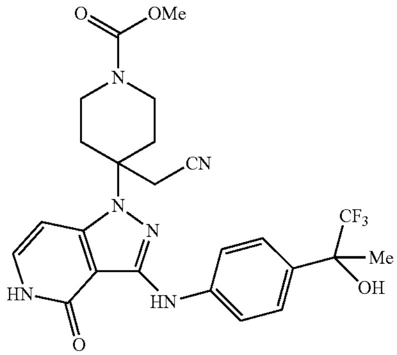 [SMILES: COC(=O)N1CCC(CC#N)(n2nc(Nc3ccc(C(C)(O)C(F)(F)F)cc3)c3c(=O)[nH]ccc32)CC1] | (R or S)-methyl 4-(cyanomethyl)-4-(4-oxo-3-((4-(1,1,1-trifluoro-2-hydroxypropan-2-yl)phenyl)amino)-4,5-dihydro-1H-pyrazolo[4,3-c]pyridin-1-yl)piperidine-1-carboxylate (from I-32A) | LRMS (ESI) Calc'd for $C_{24}H_{26}F_3N_6O_4$ $[M + H]^+$: 519, found 519. |
| 5-142 | 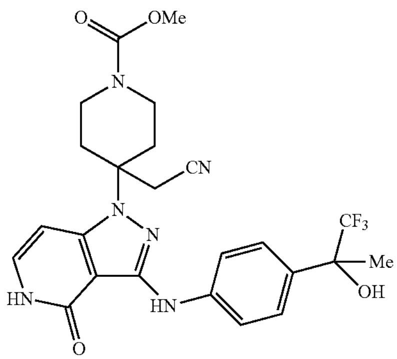 [SMILES: COC(=O)N1CCC(CC#N)(n2nc(Nc3ccc(C(C)(O)C(F)(F)F)cc3)c3c(=O)[nH]ccc32)CC1] | (R or S)-methyl 4-(cyanomethyl)-4-(4-oxo-3-((4-(1,1,1-trifluoro-2-hydroxypropan-2-yl)phenyl)amino)-4,5-dihydro-1H-pyrazolo[4,3-c]pyridin-1-yl)piperidine-1-carboxylate (from I-32B) | LRMS (ESI) Calc'd for $C_{24}H_{26}F_3N_6O_4$ $[M + H]^+$: 519, found 519. |
| 5-143 | 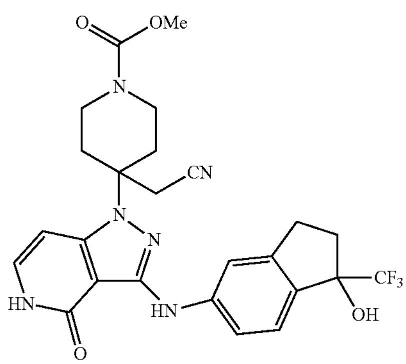 [SMILES: COC(=O)N1CCC(CC#N)(n2nc(Nc3ccc4c(c3)CCC4(O)C(F)(F)F)c3c(=O)[nH]ccc32)CC1] | (R or S)-methyl 4-(cyanomethyl)-4-(3-((1-hydroxy-1-(trifluoromethyl)-2,3-dihydro-1H-inden-5-yl)amino)-4-oxo-4,5-dihydro-1H-pyrazolo[4,3-c]pyridin-1-yl)piperidin-1-carboxylate (from I-37A) | LRMS (ESI) Calc'd for $C_{25}H_{26}F_3N_6O_4$ $[M + H]^+$: 531, found 531. |
| 5-144 | 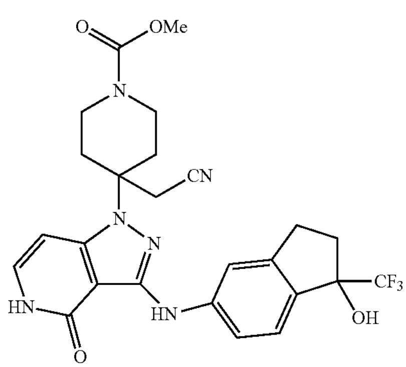 [SMILES: COC(=O)N1CCC(CC#N)(n2nc(Nc3ccc4c(c3)CCC4(O)C(F)(F)F)c3c(=O)[nH]ccc32)CC1] | (R or S)-methyl 4-(cyanomethyl)-4-(3-((1-hydroxy-1-(trifluoromethyl)-2,3-dihydro-1H-inden-5-yl)amino)-4-oxo-4,5-dihydro-1H-pyrazolo[4,3-c]pyridin-1-yl)piperidine-1-carboxylate (from I-37B) | LRMS (ESI) Calc'd for $C_{25}H_{26}F_3N_6O_4$ $[M + H]^+$: 531, found 531. |

TABLE 20-continued

| Example | Structure | Compound Name | LRMS |
|---|---|---|---|
| 5-145 | 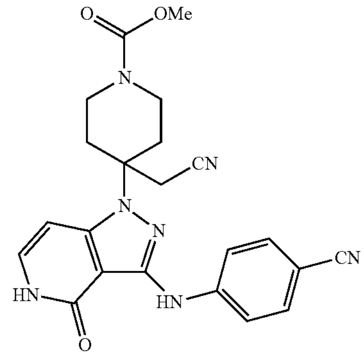 [SMILES: COC(=O)N1CCC(CC#N)(n2nc(Nc3ccc(C#N)cc3)c3c(=O)[nH]ccc32)CC1] | methyl 4-(cyanomethyl)-4-(3-((4-cyanophenyl)amino)-4-oxo-4,5-dihydro-1H-pyrazolo[4,3-c]pyridin-1-yl)piperidine-1-carboxylate | LRMS (ESI) Calc'd for $C_{22}H_{22}N_7O_3$ [M + H]$^+$: 432, found 432. |
| 5-146 | 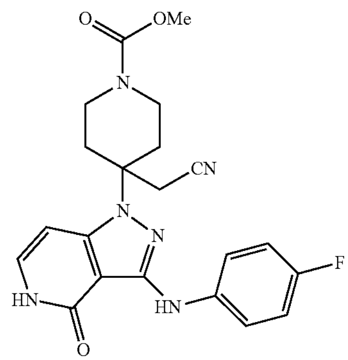 [SMILES: COC(=O)N1CCC(CC#N)(n2nc(Nc3ccc(F)cc3)c3c(=O)[nH]ccc32)CC1] | methyl 4-(cyanomethyl)-4-(3-((4-fluorophenyl)amino)-4-oxo-4,5-dihydro-1H-pyrazolo[4,3-c]pyridin-1-yl)piperidine-1-carboxylate | LRMS (ESI) Calc'd for $C_{21}H_{22}FN_6O_3$ [M + H]$^+$: 425, found 425. |
| 5-147 | 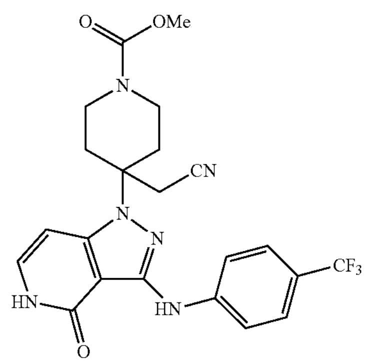 [SMILES: COC(=O)N1CCC(CC#N)(n2nc(Nc3ccc(C(F)(F)F)cc3)c3c(=O)[nH]ccc32)CC1] | methyl 4-(cyanomethyl)-4-(4-oxo-3-((4-(trifluoromethyl)phenyl)amino)-4,5-dihydro-1H-pyrazolo[4,3-c]pyridin-1-yl)piperidine-1-carboxylate | LRMS (ESI) Calc'd for $C_{22}H_{22}F_3N_6O_3$ [M + H]$^+$: 475, found 475. |
| 5-148 | 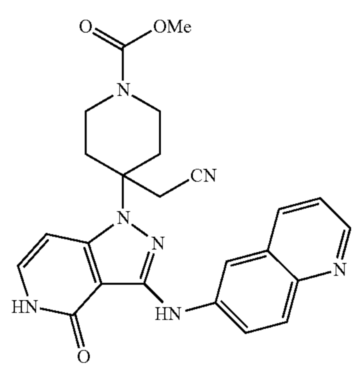 [SMILES: COC(=O)N1CCC(CC#N)(n2nc(Nc3ccc4ncccc4c3)c3c(=O)[nH]ccc32)CC1] | methyl 4-(cyanomethyl)-4-(4-oxo-3-(quinolin-6-ylamino)-4,5-dihydro-1H-pyrazolo[4,3-c]pyridin-1-yl)piperidine-1-carboxylate | LRMS (ESI) Calc'd for $C_{24}H_{24}N_7O_3$ [M + H]$^+$: 458, found 458. |

TABLE 20-continued

| Example | Structure | Compound Name | LRMS |
|---|---|---|---|
| 5-149 | 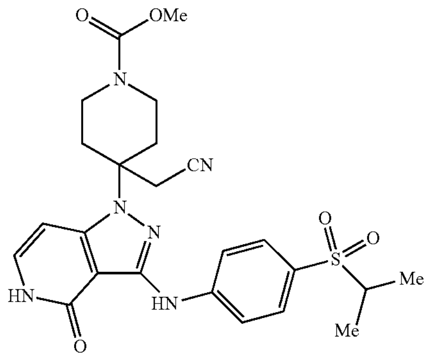 [SMILES: COC(=O)N1CCC(CC#N)(n2nc(Nc3ccc(S(=O)(=O)C(C)C)cc3)c3c(=O)[nH]ccc32)CC1] | methyl 4-(cyanomethyl)-4-(3-((4-(isopropylsulfonyl)phenyl)amino)-4-oxo-4,5-dihydro-1H-pyrazolo[4,3-c]pyridin-1-yl)piperidine-1-carboxylate | LRMS (ESI) Calc'd for $C_{24}H_{29}N_6O_5S$ [M + H]$^+$: 513, found 513. |
| 5-150 | 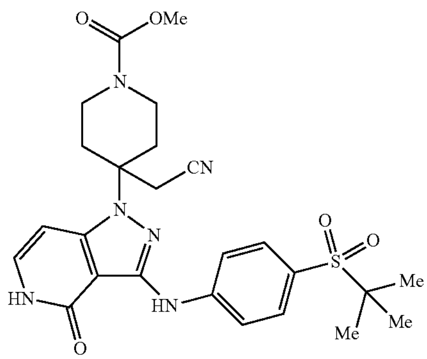 [SMILES: COC(=O)N1CCC(CC#N)(n2nc(Nc3ccc(S(=O)(=O)C(C)(C)C)cc3)c3c(=O)[nH]ccc32)CC1] | methyl 4-(3-((4-(tert-butylsulfonyl)phenyl)amino)-4-oxo-4,5-dihydro-1H-pyrazolo[4,3-c]pyridin-1-yl)-4-(cyanomethyl)piperidine-1-carboxylate | LRMS (ESI) Calc'd for $C_{25}H_{31}N_6O_5S$ [M + H]$^+$: 527, found 527. |
| 5-151 | 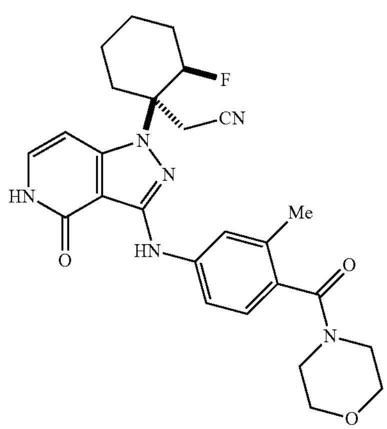 | 2-((1R,2R)-2-fluoro-1-(3-((3-methyl-4-(morpholine-4-carbonyl)phenyl)amino)-4-oxo-4,5-dihydro-1H-pyrazolo[4,3-c]pyridin-1-yl)cyclohexyl)acetonitrile (from I-19A) | LRMS (ESI) Calc'd for $C_{26}H_{30}FN_7O_3$ [M + H]$^+$: 493, found 493. |
| 5-152 | 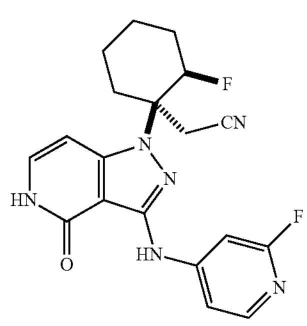 | 2-((1R,2R)-2-fluoro-1-(3-((2-fluoropyridin-4-yl)amino)-4-oxo-4,5-dihydro-1H-pyrazolo[4,3-c]pyridin-1-yl)cyclohexyl)acetonitrile (from I-19A) | LRMS (ESI) Calc'd for $C_{19}H_{19}F_2N_6O$ [M + H]$^+$: 385, found 385. |

TABLE 20-continued

| Example | Compound Name | LRMS |
|---|---|---|
| 5-153 | 2-((1R,2R)-1-(3-((4-(4,4-difluoropiperidine-1-carbonyl)-3-methylphenyl)amino)-4-oxo-4,5-dihydro-1H-pyrazolo[4,3-c]pyridin-1-yl)-2-fluorocyclohexyl)acetonitrile (from I-19A) | LRMS (ESI) Calc'd for $C_{27}H_{30}F_3N_6O_2$ $[M + H]^+$: 527, found 527. |
| 5-154 | 2-((1R,2R)-2-fluoro-1-(3-((3-methyl-4-(thiomorpholine-4-carbonyl)phenyl)amino)-4-oxo-4,5-dihydro-1H-pyrazolo[4,3-c]pyridin-1-yl)cyclohexyl)acetonitrile (from I-19A) | LRMS (ESI) Calc'd for $C_{26}H_{30}FN_6O_2S$ $[M + H]^+$: 509, found 509. |
| 5-155 | (2S,5S)-tert-butyl 5-(cyanomethyl)-5-(3-((3-methyl-4-(thiazolidine-3-carbonyl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) Calc'd for $C_{29}H_{35}N_6O_5S$ $[M + H]^+$: 579, found 579. |
| 5-156 | (2S,5S)-tert-butyl 5-(cyanomethyl)-5-(3-((3-methyl-4-((S or R)-2-methylthiazolidine-3-carbonyl)phenyl)amino)-4-oxo-4,5-dihydro-1H-pyrazolo[4,3-c]pyridin-1-yl)tetrahydro-2H-pyran-2-carboxylate (from I-14-1A. Derived from Peak 1 via SFC on pyridone: Chiralpak AD-H, 20% iPrOH in $CO_2$, Tr = 17.8 minutes) | LRMS (ESI) Calc'd for $C_{30}H_{37}N_6O_5S$ $[M + H]^+$: 593, found 593. |

TABLE 20-continued

| Example | Structure | Compound Name | LRMS |
|---|---|---|---|
| 5-157 | 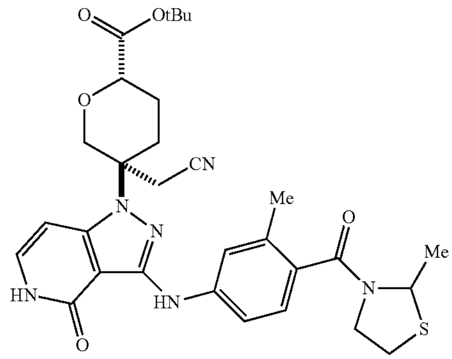 [SMILES: Cc1cc(Nc2nn([C@]3(CC#N)CC[C@@H](C(=O)OC(C)(C)C)OC3)c3cc[nH]c(=O)c23)ccc1C(=O)N1CCSC1C] | (2S,5S)-tert-butyl 5-(cyanomethyl)-5-(3-((3-methyl-4-((S or R)-2-methylthiazolidine-3-carbonyl)phenyl)amino)-4-oxo-4,5-dihydro-1H-pyrazolo[4,3-c]pyridin-1-yl)tetrahydro-2H-pyran-2-carboxylate (from I-14-1A. Derived from Peak 2 via SFC on pyridone: Chiralpak AD-H, 20% iPrOH in $CO_2$, Tr = 19.9 minutes) | LRMS (ESI) Calc'd for $C_{30}H_{37}N_6O_5S$ $[M + H]^+$: 593, found 593. |
| 5-158 | 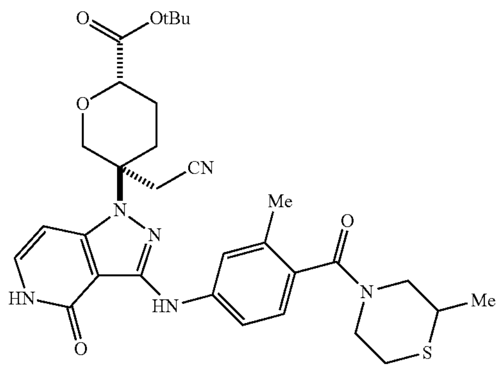 [SMILES: Cc1cc(Nc2nn([C@]3(CC#N)CC[C@@H](C(=O)OC(C)(C)C)OC3)c3cc[nH]c(=O)c23)ccc1C(=O)N1CCSC(C)C1] | (2S,5S)-tert-butyl 5-(cyanomethyl)-5-(3-((3-methyl-4-((S or R)-2-methylthiomorpholine-4-carbonyl)phenyl)amino)-4-oxo-4,5-dihydro-1H-pyrazolo[4,3-c]pyridin-1-yl)tetrahydro-2H-pyran-2-carboxylate (from I-14-1A. Derived from Peak 1 via SFC on pyridone: Chiralpak AD-H, 25% iPrOH in $CO_2$, Tr = 7.1 minutes) | LRMS (ESI) Calc'd for $C_{31}H_{39}N_6O_5S$ $[M + H]^+$: 607, found 607. |
| 5-159 | 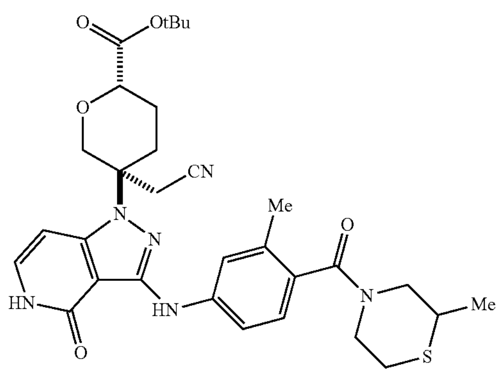 [SMILES: Cc1cc(Nc2nn([C@]3(CC#N)CC[C@@H](C(=O)OC(C)(C)C)OC3)c3cc[nH]c(=O)c23)ccc1C(=O)N1CCSC(C)C1] | (2S,5S)-tert-butyl 5-(cyanomethyl)-5-(3-((3-methyl-4-((S or R)-2-methylthiomorpholine-4-carbonyl)phenyl)amino)-4-oxo-4,5-dihydro-1H-pyrazolo[4,3-c]pyridin-1-yl)tetrahydro-2H-pyran-2-carboxylate (from I-14-1A. Derived from Peak 2 via SFC on pyridone: Chiralpak AD-H, 25% iPrOH in $CO_2$, Tr = 8.4 minutes) | LRMS (ESI) Calc'd for $C_{31}H_{39}N_6O_3S$ $[M + H]^+$: 607, found 607. |
| 5-160 | 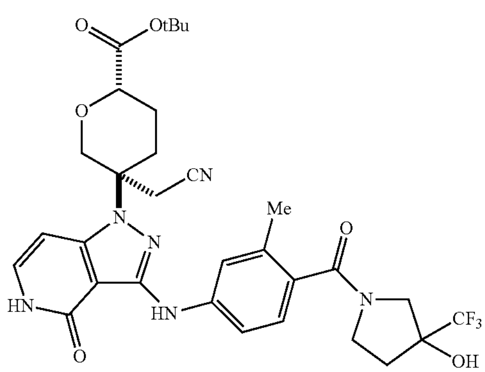 [SMILES: Cc1cc(Nc2nn([C@]3(CC#N)CC[C@@H](C(=O)OC(C)(C)C)OC3)c3cc[nH]c(=O)c23)ccc1C(=O)N1CCC(O)(C(F)(F)F)C1] | (2S,5S)-tert-butyl 5-(cyanomethyl)-5-(3-((4-((S or R)-3-hydroxy-3-(trifluoromethyl)pyrrolidine-1-carbonyl)-3-methylphenyl)amino)-4-oxo-4,5-dihydro-1H-pyrazolo[4,3-c]pyridin-1-yl)tetrahydro-2H-pyran-2-carboxylate (from I-14-1A and I-39-2A) | LRMS (ESI) Calc'd for $C_{31}H_{36}F_3N_6O_6$ $[M + H]^+$: 645, found 645. |

TABLE 20-continued

| Example | Structure | Compound Name | LRMS |
|---|---|---|---|
| 5-161 | 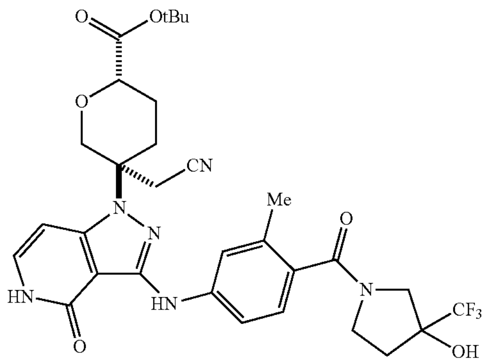 [SMILES: Cc1cc(Nc2nn([C@]3(CC#N)CC[C@@H](C(=O)OC(C)(C)C)OC3)c3cc[nH]c(=O)c23)ccc1C(=O)N1CCC(O)(C(F)(F)F)C1] | (2S,5S)-tert-butyl 5-(cyanomethyl)-5-(3-((4-((S or R)-3-hydroxy-3-(trifluoromethyl)pyrrolidine-1-carbonyl)-3-methylphenyl)amino)-4-oxo-4,5-dihydro-1H-pyrazolo[4,3-c]pyridin-1-yl)tetrahydro-2H-pyran-2-carboxylate (from I-14-1A and I-39-2B) | LRMS (ESI) Calc'd for $C_{31}H_{36}F_3N_6O_6$ [M + H]$^+$: 645, found 645. |
| 5-162 | 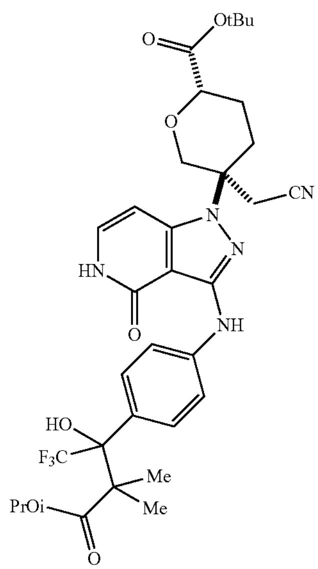 | (2S,5S)-tert-butyl 5-(cyanomethyl)-5-(4-oxo-3-((4-((S or R)-1,1,1-trifluoro-2-hydroxy-4-isopropoxy-3,3-dimethyl-4-oxobutan-2-yl)phenyl)amino)-4,5-dihydro-1H-pyrazolo[4,3-c]pyridin-1-yl)tetrahydro-2H-pyran-2-carboxylate (from I-14-1A and I-35-2. Derived from Peak 1 via SFC on pyridone: Chiralpak IC, 30% MeOH in $CO_2$, Tr = 4.2 minutes) | LRMS (ESI) Calc'd for $C_{33}H_{41}F_3N_5O_7$ [M + H]$^+$: 676, found 676. |
| 5-163 | 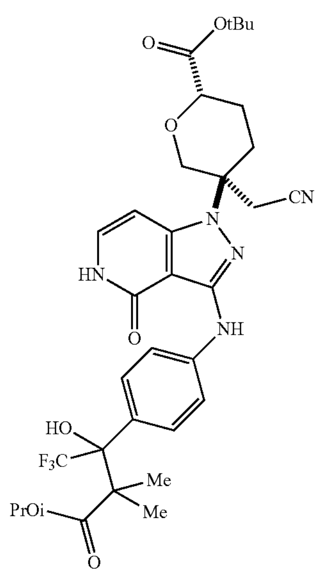 | (2S,5S)-tert-butyl 5-(cyanomethyl)-5-(4-oxo-3-((4-((S or R)-1,1,1-trifluoro-2-hydroxy-4-isopropoxy-3,3-dimethyl-4-oxobutan-2-yl)phenyl)amino)-4,5-dihydro-1H-pyrazolo[4,3-c]pyridin-1-yl)tetrahydro-2H-pyran-2-carboxylate (from I-14-1A and I-35-2. Derived from Peak 2 via SFC on pyridone: Chiralpak IC, 30% MeOH in $CO_2$, Tr = 5.9 minutes) | LRMS (ESI) Calc'd for $C_{33}H_{41}F_3N_5O_7$ [M + H]$^+$: 676, found 676. |

TABLE 20-continued

| Example | Structure | Compound Name | LRMS |
|---|---|---|---|
| 5-164 | 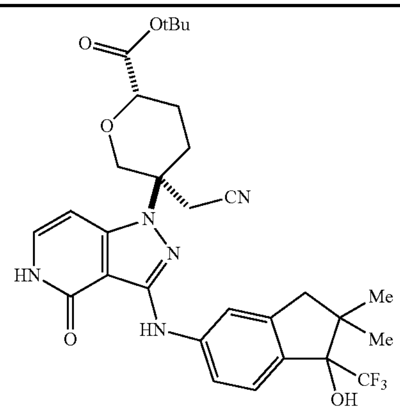 | (2S,5S)-tert-butyl 5-(cyanomethyl)-5-(3-(((S or R)-1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)tetrahydro-2H-pyran-2-carboxylate (from I-14-1A and I-36. Derived from Peak 1 via SFC on pyridone: Phenomenex Lux-4, 35% MeOH in $CO_2$, Tr = 3.1 minutes) | LRMS (ESI) Calc'd for $C_{30}H_{35}F_3N_5O_3$ [M + H]$^+$: 602, found 602. |
| 5-165 | 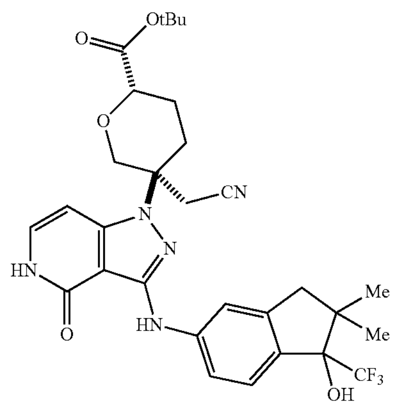 | (2S,5S)-tert-butyl 5-(cyanomethyl)-5-(3-(((S or R)-1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)tetrahydro-2H-pyran-2-carboxylate (from I-14-1A and I-36. Derived from Peak 2 via SFC on pyridone: Phenomenex Lux-4, 35% MeOH in $CO_2$, Tr = 3.9 minutes) | LRMS (ESI) Calc'd for $C_{30}H_{35}F_3N_5O_5$ [M + H]$^+$: 602, found 602. |
| 5-166 | 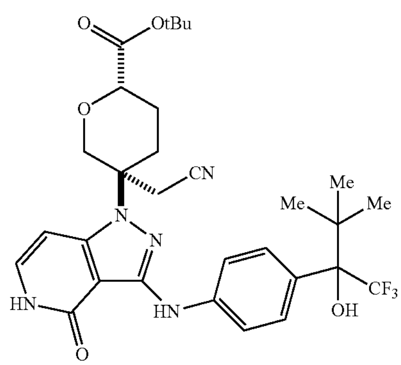 [SMILES: CC(C)(C)OC(=O)[C@@H]1CC[C@@](CC#N)(n2nc(Nc3ccc(C(O)(C(C)(C)C)C(F)(F)F)cc3)c3c(=O)[nH]ccc32)CO1] | (2S,5S)-tert-butyl 5-(cyanomethyl)-5-(4-oxo-3-((4-((S or R)-1,1,1-trifluoro-2-hydroxy-3,3-dimethylbutan-2-yl)phenyl)amino)-4,5-dihydro-1H-pyrazolo[4,3-c]pyridin-1-yl)tetrahydro-2H-pyran-2-carboxylate (from I-14-1A and I-37. Derived from Peak 1 via SFC on pyridone: Chiralpak AS-H, 15% MeOH in $CO_2$, Tr = 6.1 minutes) | LRMS (ESI) Calc'd for $C_{30}H_{37}F_3N_5O_5$ [M + H]$^+$: 604, found 604. |
| 5-167 | 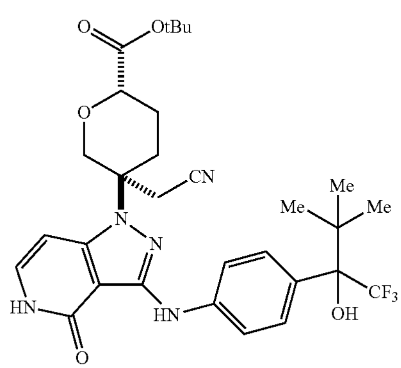 [SMILES: CC(C)(C)OC(=O)[C@@H]1CC[C@@](CC#N)(n2nc(Nc3ccc(C(O)(C(C)(C)C)C(F)(F)F)cc3)c3c(=O)[nH]ccc32)CO1] | (2S,5S)-tert-butyl 5-(cyanomethyl)-5-(4-oxo-3-((4-((S or R)-1,1,1-trifluoro-2-hydroxy-3,3-dimethylbutan-2-yl)phenyl)amino)-4,5-dihydro-1H-pyrazolo[4,3-c]pyridin-1-yl)tetrahydro-2H-pyran-2-carboxylate (from I-14-IA and I-37. Derived from Peak 2 via SFC on pyridone: Chiralpak AS-H, 15% MEOH in $CO_2$, Tr = 7.6 minutes) | LRMS (ESI) Calc'd for $C_{30}H_{37}F_3N_5O_5$ [M + H]$^+$: 604, found 604. |

TABLE 20-continued

| Example | Structure | Compound Name | LRMS |
|---|---|---|---|
| 5-168 | 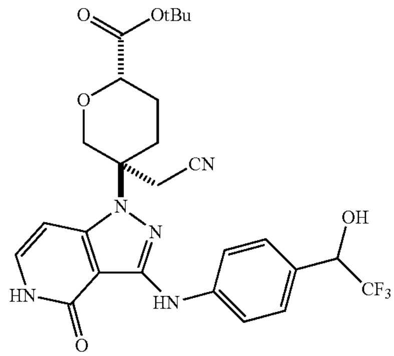 [SMILES: CC(C)(C)OC(=O)[C@@H]1CC[C@@](CC#N)(n2nc(Nc3ccc(C(O)C(F)(F)F)cc3)c3c(=O)[nH]ccc32)CO1] | (2S,5S)-tert-butyl 5-(cyanomethyl)-5-(4-oxo-3-((4-((S or R)-2,2,2-trifluoro-1-hydroxyethyl)phenyl)amino)-4,5-dihydro-1H-pyrazolo[4,3-c]pyridin-1-yl)tetrahydro-2H-pyran-2-carboxylate (from I-14-1A and I-25. Derived from Peak 1 via SFC on free pyridone: Chiralpak AD-H, 25% MeOH in CO$_2$, Tr = 3.8 minutes) | LRMS (ESI) Calc'd for C$_{26}$H$_{29}$F$_3$N$_5$O$_5$ [M + H]$^+$: 548, found 548. |
| 5-169 | 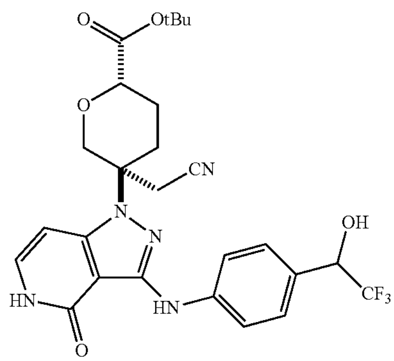 [SMILES: CC(C)(C)OC(=O)[C@@H]1CC[C@@](CC#N)(n2nc(Nc3ccc(C(O)C(F)(F)F)cc3)c3c(=O)[nH]ccc32)CO1] | (2S,5S)-tert-butyl 5-(cyanomethyl)-5-(4-oxo-3-((4-((S or R)-2,2,2-trifluoro-1-hydroxyethyl)phenyl)amino)-4,5-dihydro-1H-pyrazolo[4,3-c]pyridin-1-yl)tetrahydro-2H-pyran-2-carboxylate (from I-14-1A and I-25. Derived from Peak 2 via SFC on free pyridone: Chiralpak AD-H, 25% MeOH in CO$_2$, Tr = 6.4 mins) | LRMS (ESI) Calc'd for C$_{26}$H$_{29}$F$_3$N$_5$O$_5$ [M + H]$^+$: 548, found 548. |
| 5-170 | 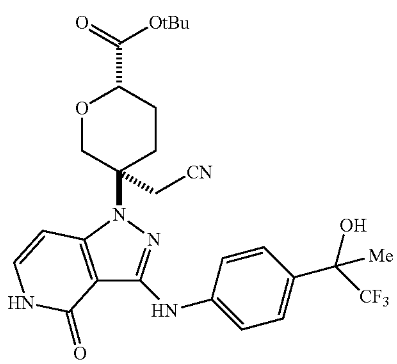 [SMILES: CC(C)(C)OC(=O)[C@@H]1CC[C@@](CC#N)(n2nc(Nc3ccc(C(C)(O)C(F)(F)F)cc3)c3c(=O)[nH]ccc32)CO1] | (2S,5S)-tert-butyl 5-(cyanomethyl)-5-(4-oxo-3-((4-((S or R)-1,1,1-trifluoro-2-hydroxypropan-2-yl)phenyl)amino)-4,5-dihydro-1H-pyrazolo[4,3-c]pyridin-1-yl)tetrahydro-2H-pyran-2-carboxylate (from I-14-1A and I-32A) | LRMS (ESI) Calc'd for C$_{27}$H$_{31}$F$_3$N$_5$O$_5$ [M + H]$^+$: 562, found 562. |
| 5-171 | 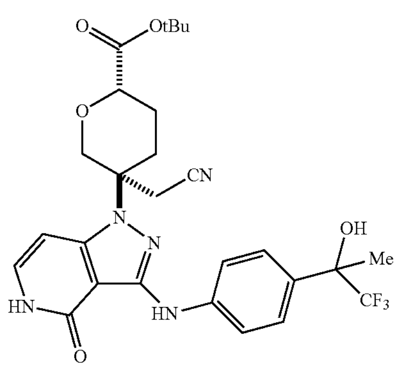 [SMILES: CC(C)(C)OC(=O)[C@@H]1CC[C@@](CC#N)(n2nc(Nc3ccc(C(C)(O)C(F)(F)F)cc3)c3c(=O)[nH]ccc32)CO1] | (2S,5S)-tert-butyl 5-(cyanomethyl)-5-(4-oxo-3-((4-((S or R)-1,1,1-trifluoro-2-hydroxypropan-2-yl)phenyl)amino)-4,5-dihydro-1H-pyrazolo[4,3-c]pyridin-1-yl)tetrahydro-2H-pyran-2-carboxylate (from I-14-1A and I-32B) | LRMS (ESI) Calc'd for C$_{27}$H$_{31}$F$_3$N$_5$O$_5$ [M + H]$^+$: 562, found 562. |

TABLE 20-continued

| Example | Structure | Compound Name | LRMS |
|---|---|---|---|
| 5-172 | 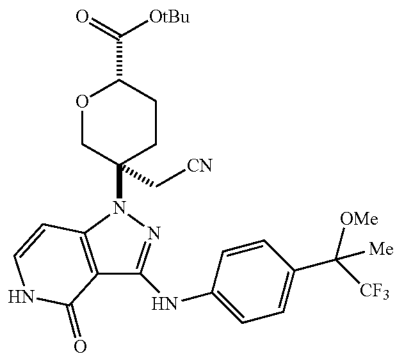 [SMILES: COC(C)(c1ccc(Nc2nn([C@]3(CC#N)CC[C@@H](C(=O)OC(C)(C)C)OC3)c3cc[nH]c(=O)c23)cc1)C(F)(F)F] | (2S,5S)-tert-butyl 5-(cyanomethyl)-5-(4-oxo-3-((4-((S or R)-1,1,1-trifluoro-2-methoxypropan-2-yl)phenyl)amino)-4,5-dihydro-1H-pyrazolo[4,3-c]pyridin-1-yl)tetrahydro-2H-pyran-2-carboxylate (from I-14-1A and I-33A) | LRMS (ESI) Calc'd for $C_{28}H_{33}F_3N_5O_5$ [M + H]$^+$: 576, found 576. |
| 5-173 | 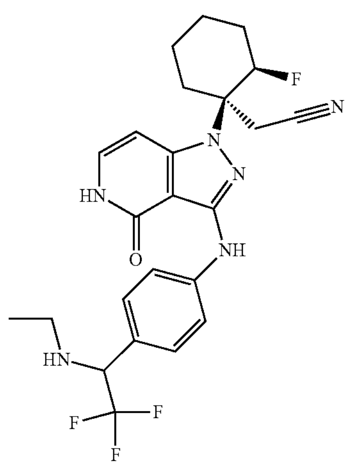 [SMILES: CCNC(c1ccc(Nc2nn([C@@]3(CC#N)CCCC[C@H]3F)c3cc[nH]c(=O)c23)cc1)C(F)(F)F] | {(1R,2R)-1-[3-({4-[(1R or 1S)-1-(ethylamino)-2,2,2-trifluoroethyl]phenyl}amino)-4-oxo-4,5-dihydro-1H-pyrazolo[4,3-c]pyridin-1-yl]-2-fluorocyclohexyl}acetonitrile (from I-19A. Derived from Peak A via SFC on pyridone: AS-H, 20% MEOH + 0.25% DMEA in $CO_2$, Tr = 4.4 minutes) | LRMS (ESI) calc'd for $C_{24}H_{27}F_4N_6O$ [M + H]$^+$: 491, found 491. |
| 5-174 | 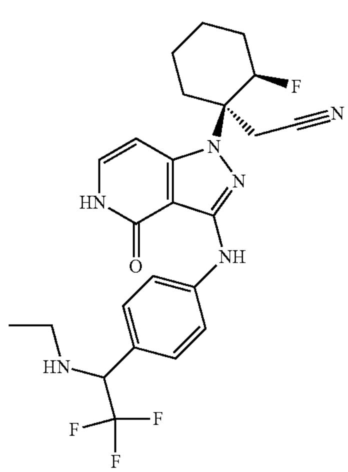 [SMILES: CCNC(c1ccc(Nc2nn([C@@]3(CC#N)CCCC[C@H]3F)c3cc[nH]c(=O)c23)cc1)C(F)(F)F] | {(1R,2R)-1-[3-({4-[(1R or 1S)-1-(ethylamino)-2,2,2-trifluoroethyl]phenyl}amino)-4-oxo-4,5-dihydro-1H-pyrazolo[4,3-c]pyridin-1-yl]-2-fluorocyclohexyl}acetonitrile (from from I-19A. Derived from Peak B via SFC on pyridone, AS-H, 20% MeOH + 0.25% DMEA in $CO_2$, Tr = 5.9 minutes) | LRMS (ESI) calc'd for $C_{24}H_{27}F_4N_6O$ [M + H]$^+$: 491, found 491. |

TABLE 20-continued

| Example | Structure | Compound Name | LRMS |
|---|---|---|---|
| 5-175 | 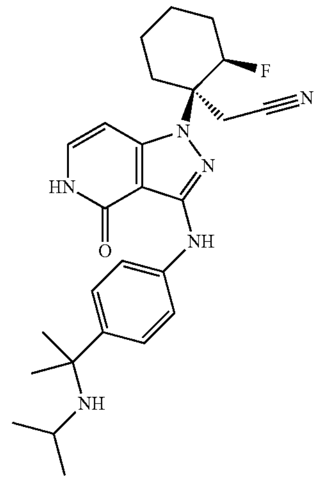 [SMILES: CC(C)NC(C)(C)c1ccc(Nc2nn([C@@]3(CC#N)CCCC[C@H]3F)c3cc[nH]c(=O)c23)cc1] | [(1R,2R)-2-fluoro-1-{3-[(4-{1-methyl-1-[(1-methylethyl)amino]ethyl}phenyl)amino]-4-oxo-4,5-dihydro-1H-pyrazolo[4,3-c]pyridin-1-yl}cyclohexyl]acetonitrile (from I-19A) | LRMS (ESI) calc'd for $C_{26}H_{34}FN_6O$ $[M + H]^+$: 465, found 465. |
| 5-176 | 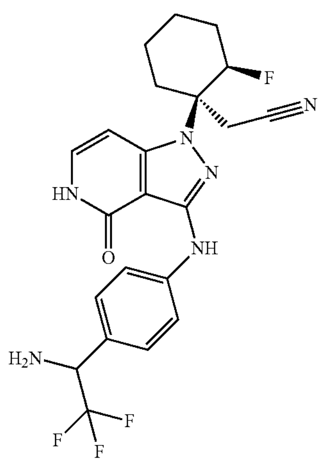 [SMILES: N#CC[C@]1(n2nc(Nc3ccc(C(N)C(F)(F)F)cc3)c3c(=O)[nH]ccc32)CCCC[C@H]1F] | {(1R,2R)-1-[3-({4-[(1R or 1S)-1-amino-2,2,2-trifluoroethyl]phenyl}amino)-4-oxo-4,5-dihydro-1H-pyrazolo[4,3-c]pyridin-1-yl]-2-fluorocyclohexyl}acetonitrile (from I-19A and I-29A) | LRMS (ESI) calc'd for $C_{22}H_{23}F_4N_6O$ $[M + H]^+$: 463, found 463. |
| 5-177 | 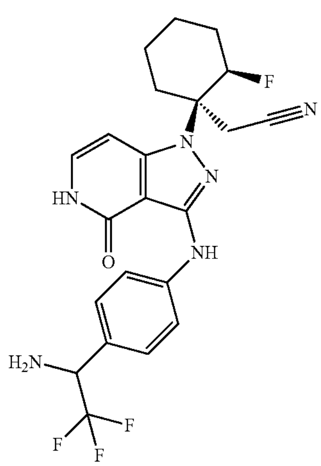 [SMILES: N#CC[C@]1(n2nc(Nc3ccc(C(N)C(F)(F)F)cc3)c3c(=O)[nH]ccc32)CCCC[C@H]1F] | {(1R,2R)-1-[3-({4-[(1S or 1R)-1-amino-2,2,2-trifluoroethyl]phenyl}amino)-4-oxo-4,5-dihydro-1H-pyrazolo[4,3-c]pyridin-1-yl]-2-fluorocyclohexyl}acetonitrile (from I-19A and I-29B) | LRMS (ESI) calc'd for $C_{22}H_{23}F_4N_6O$ $[M + H]^+$: 463, found 463. |

TABLE 20-continued

| Example | Structure | Compound Name | LRMS |
|---|---|---|---|
| 5-178 | 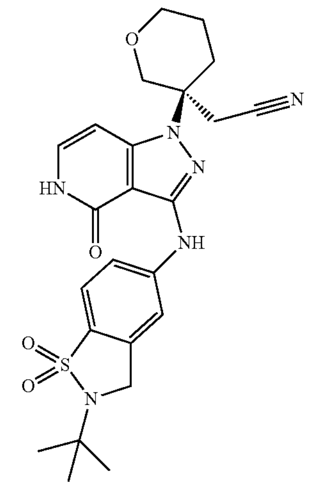 [SMILES: CC(C)(C)N1Cc2cc(Nc3nn([C@]4(CC#N)CCCOC4)c4cc[nH]c(=O)c34)ccc2S1(=O)=O] | [(3S)-3-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}tetrahydro-2H-pyran-3-yl]acetonitrile (from I-17B) | LRMS (ESI) calc'd for $C_{24}H_{29}N_6O_4S$ $[M + H]^+$: 497, found 497. |
| 5-179 | 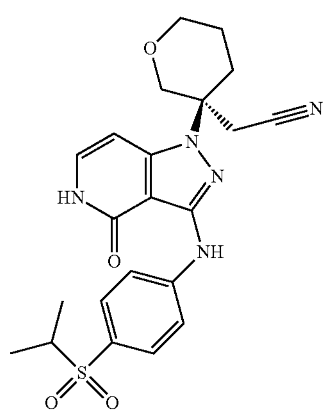 [SMILES: CC(C)S(=O)(=O)c1ccc(Nc2nn([C@]3(CC#N)CCCOC3)c3cc[nH]c(=O)c23)cc1] | {(3S)-3-[3-({4-[(1-methylethyl)sulfonyl]phenyl}amino)-4-oxo-4,5-dihydro-1H-pyrazolo[4,3-c]pyridin-1-yl]tetrahydro-2H-pyran-3-yl}acetonitrile (from I-17B) | LRMS (ESI) calc'd for $C_{22}H_{26}N_5O_4S$ $[M + H]^+$: 456, found 456. |
| 5-180 | 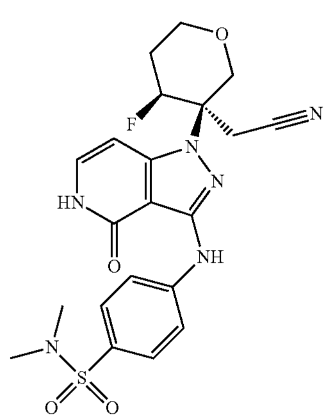 [SMILES: CN(C)S(=O)(=O)c1ccc(Nc2nn([C@]3(CC#N)COCC[C@@H]3F)c3cc[nH]c(=O)c23)cc1] | 4-({1-[(3R,4S or 3S,4R)-3-(cyanomethyl)-4-fluorotetrahydro-2H-pyran-3-yl]-4-oxo-4,5-dihydro-1H-pyrazolo[4,3-c]pyridin-3-yl}amino)-N,N-dimethylbenzenesulfonamide (from I-7-3A) | LRMS (ESI) calc'd for $C_{21}H_{24}FN_6O_4S$ $[M + H]^+$: 475, found 475. |

TABLE 20-continued

| Example | Structure | Compound Name | LRMS |
|---|---|---|---|
| 5-181 | 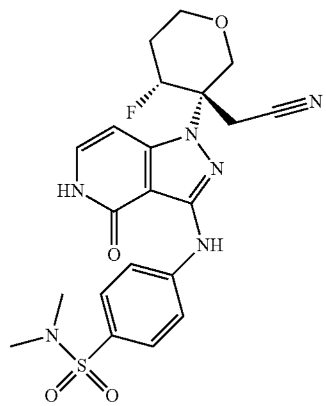 [SMILES: CN(C)S(=O)(=O)c1ccc(Nc2nn([C@@]3(CC#N)COCC[C@H]3F)c3cc[nH]c(=O)c23)cc1] | 4-({1-[(3S,4R or 3S,4R)-3-(cyanomethyl)-4-fluorotetrahydro-2H-pyran-3-yl]-4-oxo-4,5-dihydro-1H-pyrazolo[4,3-c]pyridin-3-yl}amino)-N,N-dimethylbenzenesulfonamide (from I-7-3B) | LRMS (ESI) calc'd for $C_{21}H_{24}FN_6O_4S$ $[M + H]^+$: 475, found 475. |
| 5-182 | 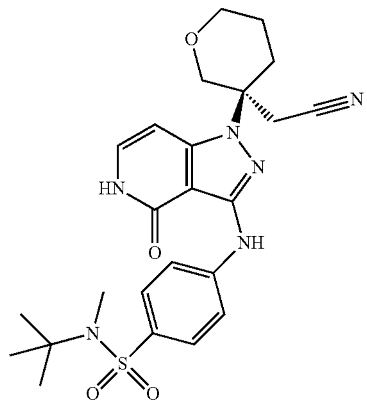 [SMILES: CN(C(C)(C)C)S(=O)(=O)c1ccc(Nc2nn([C@]3(CC#N)CCCOC3)c3cc[nH]c(=O)c23)cc1] | N-tert-butyl-4-({1-[(3S)-3-(cyanomethyl)tetrahydro-2H-pyran-3-yl]-4-oxo-4,5-dihydro-1H-pyrazolo[4,3-c]pyridin-3-yl}amino)-N-methylbenzenesulfonamide (from I-17B) | LRMS (ESI) calc'd for $C_{24}H_{31}N_6O_4S$ $[M + H]^+$: 499, found 499. |
| 5-183 | 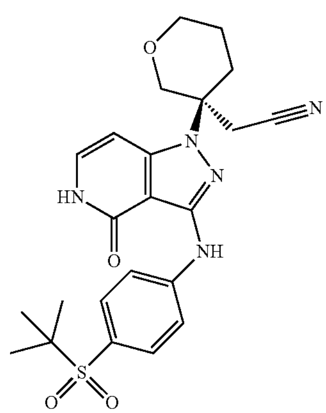 [SMILES: CC(C)(C)S(=O)(=O)c1ccc(Nc2nn([C@]3(CC#N)CCCOC3)c3cc[nH]c(=O)c23)cc1] | [(3S)-3-(3-{[4-(tert-butylsulfonyl)phenyl]amino}-4-oxo-4,5-dihydro-1H-pyrazolo[4,3-c]pyridin-1-yl)tetrahydro-2H-pyran-3-yl]acetonitrile (from I-17B) | LRMS (ESI) calc'd for $C_{23}H_{28}N_5O_4S$ $[M + H]^+$: 470, found 470. |
| 5-184 | 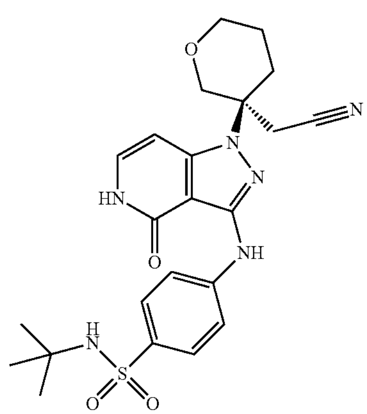 [SMILES: CC(C)(C)NS(=O)(=O)c1ccc(Nc2nn([C@]3(CC#N)CCCOC3)c3cc[nH]c(=O)c23)cc1] | N-tert-butyl-4-({1-[(3S)-3-(cyanomethyl)tetrahydro-2H-pyran-3-yl]-4-oxo-4,5-dihydro-1H-pyrazolo[4,3-c]pyridin-3-yl}amino)benzenesulfonamide (from I-17B) | LRMS (ESI) calc'd for $C_{23}H_{29}N_6O_4S$ $[M + H]^+$: 485, found 485. |

TABLE 20-continued

| Example | Structure | Compound Name | LRMS |
|---|---|---|---|
| 5-185 | 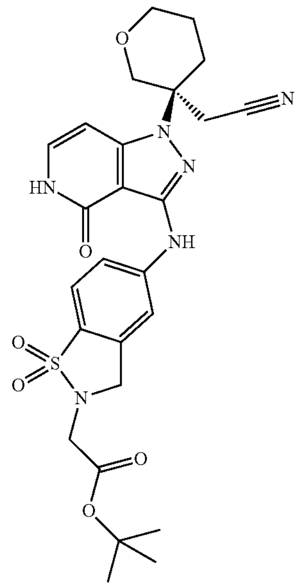 [SMILES: CC(C)(C)OC(=O)CN1Cc2cc(Nc3nn([C@]4(CC#N)CCCOC4)c4cc[nH]c(=O)c34)ccc2S1(=O)=O] | tert-butyl [5-({1-[(3S)-3-(cyanomethyl)tetrahydro-2H-pyran-3-yl]-4-oxo-4,5-dihydro-1H-pyrazolo[4,3-c]pyridin-3-yl}amino)-1,1-dioxido-1,2-benzisothiazol-2(3H)-yl]acetate (from I-17B) | LRMS (ESI) calc'd for $C_{26}H_{31}N_6O_6S$ [M + H]$^+$: 555, found 555. |
| 5-186 | 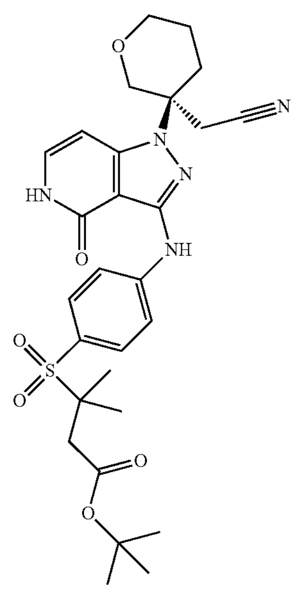 [SMILES: CC(C)(C)OC(=O)CC(C)(C)S(=O)(=O)c1ccc(Nc2nn([C@]3(CC#N)CCCOC3)c3cc[nH]c(=O)c23)cc1] | tert-butyl 3-{[4-({1-[(3S)-3-(cyanomethyl)tetrahydro-2H-pyran-3-yl]-4-oxo-4,5-dihydro-1H-pyrazolo[4,3-c]pyridin-3-yl}amino)phenyl]sulfonyl}-3-methylbutanoate (from I-17B) | LRMS (ESI) calc'd for $C_{24}H_{26}N_5O_6S$ [M − $C_4H_{10}$ + H]$^+$: 514, found 514. |

TABLE 20-continued

| Example | Structure | Compound Name | LRMS |
|---|---|---|---|
| 5-187 | 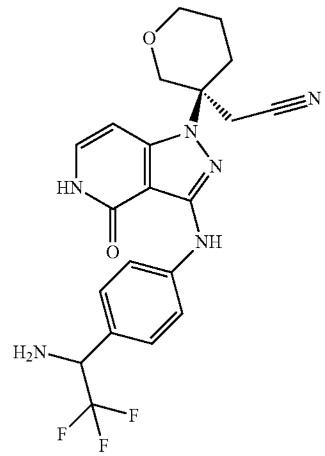 [SMILES: N#CC[C@@]1(n2nc(Nc3ccc(C(N)C(F)(F)F)cc3)c3c(=O)[nH]ccc32)CCCOC1] | {(3S)-3-[3-({4-[(1R or 1S)-1-amino-2,2,2-trifluoroethyl]phenyl}amino)-4-oxo-4,5-dihydro-1H-pyrazolo[4,3-c]pyridin-1-yl]tetrahydro-2H-pyran-3-yl}acetonitrile (from I-17B and I-29A) | LRMS (ESI) calc'd for $C_{21}H_{22}F_3N_6O_2$ $[M + H]^+$: 447, found 447. |
| 5-188 | 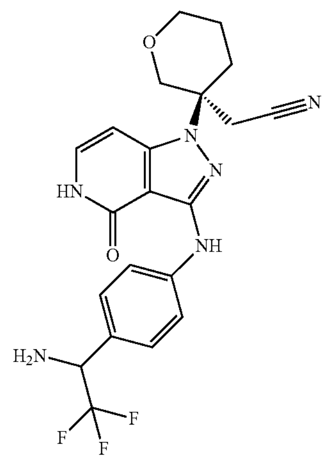 [SMILES: N#CC[C@@]1(n2nc(Nc3ccc(C(N)C(F)(F)F)cc3)c3c(=O)[nH]ccc32)CCCOC1] | {(3S)-3-[3-({4-[(1S or 1R)-1-amino-2,2,2-trifluoroethyl]phenyl}amino)-4-oxo-4,5-dihydro-1H-pyrazolo[4,3-c]pyridin-1-yl]tetrahydro-2H-pyran-3-yl}acetonitrile (from I-17B and I-29B) | LRMS (ESI) calc'd for $C_{21}H_{22}F_3N_6O_2$ $[M + H]^+$: 447, found 447. |
| 5-189 | 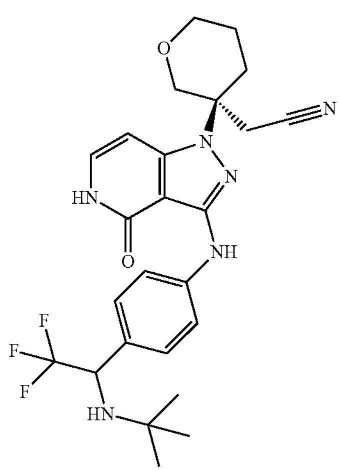 [SMILES: CC(C)(C)NC(c1ccc(Nc2nn([C@]3(CC#N)CCCOC3)c3cc[nH]c(=O)c23)cc1)C(F)(F)F] | {(3S)-3-[3-({4-[(1R or 1S)-1-(tert-butylamino)-2,2,2-trifluoroethyl]phenyl}amino)-4-oxo-4,5-dihydro-1H-pyrazolo[4,3-c]pyridin-1-yl]tetrahydro-2H-pyran-3-yl}acetonitrile (from I-17B. Derived from Peak A via SFC: IA column, 35% MeOH in $CO_2$, Tr = 2.8 minutes on OBn intermediate) | LRMS (ESI) calc'd for $C_{25}H_{29}F_3N_6O_2Na$ $[M + Na]^+$: 525, found 525. |

TABLE 20-continued

| Example | Structure | Compound Name | LRMS |
| --- | --- | --- | --- |
| 5-190 | 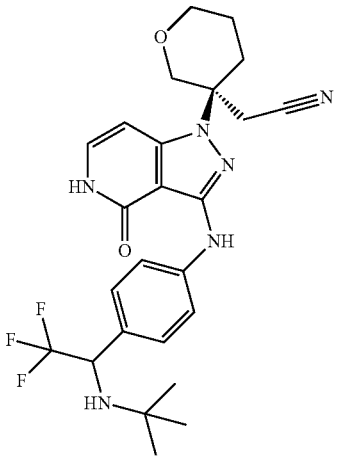 [SMILES: CC(C)(C)NC(c1ccc(Nc2nn([C@]3(CC#N)CCCOC3)c3cc[nH]c(=O)c23)cc1)C(F)(F)F] | {(3S)-3-[3-({4-[(1S or 1R)-1-(tert-butylamino)-2,2,2-trifluoroethyl]phenyl}amino)-4-oxo-4,5-dihydro-1H-pyrazolo[4,3-c]pyridin-1-yl]tetrahydro-2H-pyran-3-yl}acetonitrile (from I-17B. Derived from Peak B via SFC: IA column, 35% MeOH in $CO_2$, Tr = 3.9 minutes on OBn intermediate) | LRMS (ESI) calc'd for $C_{25}H_{30}F_3N_6O_2$ $[M + H]^+$: 503, found 503. |
| 5-191 | 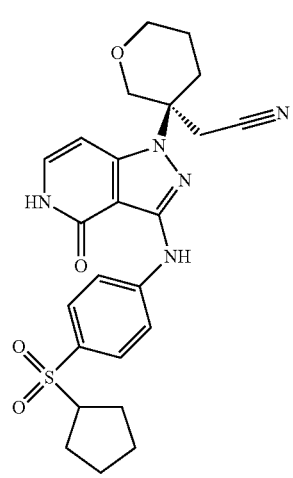 [SMILES: N#CC[C@@]1(n2nc(Nc3ccc(S(=O)(=O)C4CCCC4)cc3)c3c(=O)[nH]ccc32)CCCOC1] | [(3S)-3-(3-{[4-(cyclopentylsulfonyl)phenyl]amino}-4-oxo-4,5-dihydro-1H-pyrazolo[4,3-c]pyridin-1-yl)tetrahydro-2H-pyran-3-yl]acetonitrile (from I-17B) | LRMS (ESI) calc'd for $C_{24}H_{28}N_5O_4S$ $[M + H]^+$: 482, found 482. |
| 5-192 | 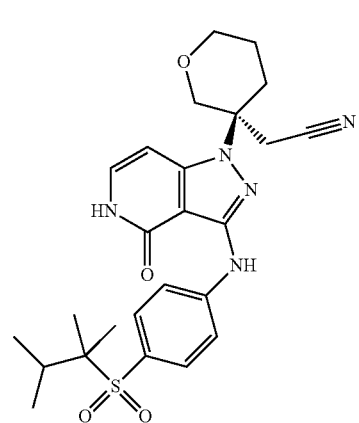 [SMILES: CC(C)C(C)(C)S(=O)(=O)c1ccc(Nc2nn([C@]3(CC#N)CCCOC3)c3cc[nH]c(=O)c23)cc1] | {(3S)-3-[4-oxo-3-({4-[(1,1,2-trimethylpropyl)sulfonyl]phenyl}amino)-4,5-dihydro-1H-pyrazolo[4,3-c]pyridin-1-yl]tetrahydro-2H-pyran-3-yl}acetonitrile (from I-17B) | LRMS (ESI) calc'd for $C_{25}H_{32}N_5O_4S$ $[M + H]^+$: 498, found 498. |

TABLE 20-continued

| Example | Structure | Compound Name | LRMS |
|---|---|---|---|
| 5-193 | 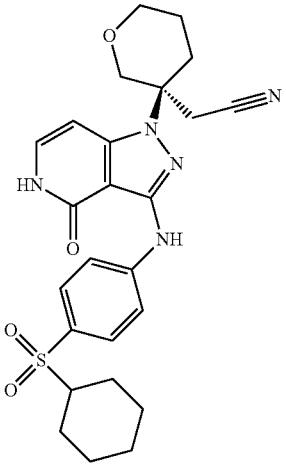 [SMILES: N#CC[C@@]1(n2nc(Nc3ccc(S(=O)(=O)C4CCCCC4)cc3)c3c(=O)[nH]ccc32)CCCOC1] | [(3S)-3-(3-{[4-(cyclohexylsulfonyl)phenyl]amino}-4-oxo-4,5-dihydro-1H-pyrazolo[4,3-c]pyridin-1-yl)tetrahydro-2H-pyran-3-yl]acetonitrile (from I-17B) | LRMS (ESI) calc'd for $C_{25}H_{30}N_5O_4S$ [M + H]$^+$: 496, found 496. |
| 5-194 | 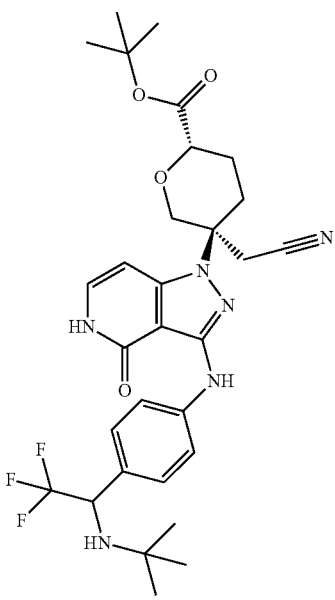 [SMILES: CC(C)(C)NC(c1ccc(Nc2nn([C@]3(CC#N)CC[C@@H](C(=O)OC(C)(C)C)OC3)c3cc[nH]c(=O)c23)cc1)C(F)(F)F] | (2S,5S)-tert-butyl 5-(3-((4-((R or S)-1-(tert-butylamino)-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate (from I-14-1A. Derived from Peak A via SFC: AD-H, 15% 2-propanol + 0.25% DMEA in $CO_2$, Tr = 4.9 minutes on OBn intermediate) | LRMS (ESI) calc'd for $C_{30}H_{37}F_3N_6O_4Na$ [M + Na]$^+$: 625, found 625. |

TABLE 20-continued

| Example | Structure | Compound Name | LRMS |
|---|---|---|---|
| 5-195 | 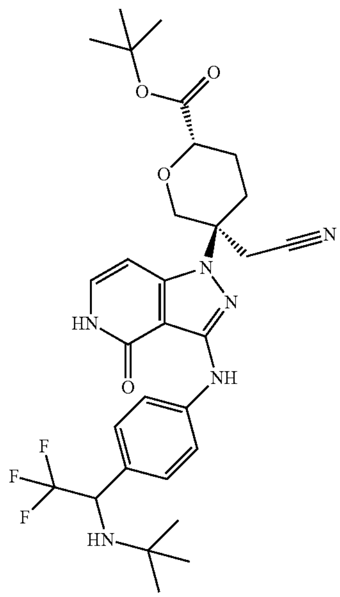 [SMILES: CC(C)(C)NC(c1ccc(Nc2nn([C@]3(CC#N)CC[C@@H](C(=O)OC(C)(C)C)OC3)c3cc[nH]c(=O)c23)cc1)C(F)(F)F] | (2S,5S)-tert-butyl 5-(3-((4-((R or S)-1-(tert-butylamino)-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate (from I-14-1A. Derived from Peak B via SFC: AD-H, 15% 2-propanol + 0.25% DMEA in $CO_2$, Tr = 5.5 minutes on OBn intermediate) | LRMS (ESI) calc'd for $C_{30}H_{38}F_3N_6O_4$ [M + H]$^+$: 603, found 603. |
| 5-196 | 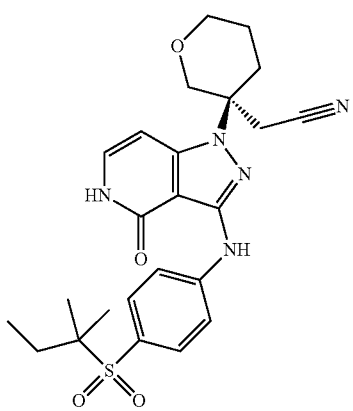 [SMILES: CCC(C)(C)S(=O)(=O)c1ccc(Nc2nn([C@]3(CC#N)CCCOC3)c3cc[nH]c(=O)c23)cc1] | {(3S)-3-[3-({4-[(1,1-dimethylpropyl)sulfonyl]phenyl}amino)-4-oxo-4,5-dihydro-1H-pyrazolo[4,3-c]pyridin-1-yl]tetrahydro-2H-pyran-3-yl}acetonitrile (from I-17B) | LRMS (ESI) calc'd for $C_{24}H_{30}N_5O_4S$ [M + H]$^+$: 484, found 484. |
| 5-197 | 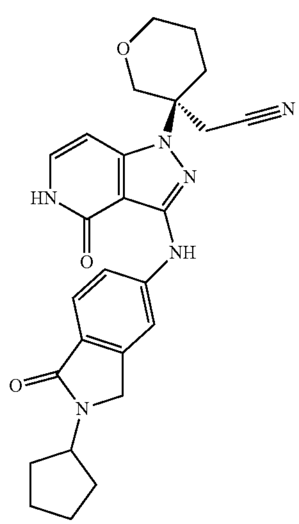 [SMILES: N#CC[C@@]1(n2nc(Nc3ccc4c(c3)CN(C3CCCC3)C4=O)c3c(=O)[nH]ccc32)CCCOC1] | [(3S)-3-{3-[(2-cyclopentyl-1-oxo-2,3-dihydro-1H-isoindol-5-yl)amino]-4-oxo-4,5-dihydro-1H-pyrazolo[4,3-c]pyridin-1-yl}tetrahydro-2H-pyran-3-yl]acetonitrile (from I-17B) | LRMS (ESI) calc'd for $C_{26}H_{29}N_6O_3$ [M + H]$^+$: 473, found 473. |

| Example | Structure | Compound Name | LRMS |
|---|---|---|---|
| 5-198 | 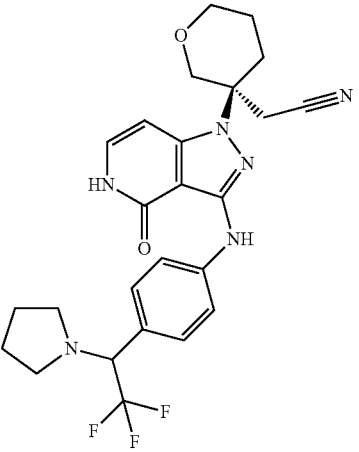 [SMILES: N#CC[C@@]1(n2nc(Nc3ccc(C(N4CCCC4)C(F)(F)F)cc3)c3c(=O)[nH]ccc32)CCCOC1] | {(3S)-3-[4-oxo-3-({4-[(1R or 1S)-2,2,2-trifluoro-1-pyrrolidin-1-ylethyl]phenyl}amino)-4,5-dihydro-1H-pyrazolo[4,3-c]pyridin-1-yl]tetrahydro-2H-pyran-3-yl}acetonitrile (from I-17B. Derived from Peak A via SFC: IB, 20% MeOH + 0.25% DMEA in $CO_2$, Tr = 7.4 minutes on OBn intermediate) | LRMS (ESI) calc'd for $C_{25}H_{28}F_3N_6O_2$ $[M + H]^+$: 501, found 501. |
| 5-199 | 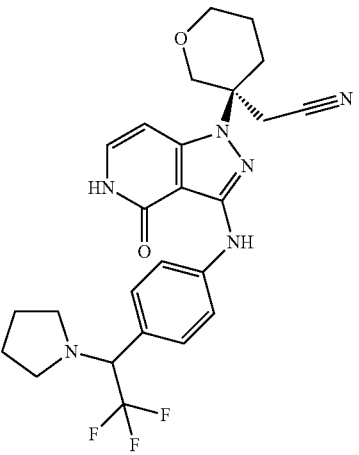 [SMILES: N#CC[C@@]1(n2nc(Nc3ccc(C(N4CCCC4)C(F)(F)F)cc3)c3c(=O)[nH]ccc32)CCCOC1] | {(3S)-3-[4-oxo-3-({4-[(1S or 1R)-2,2,2-trifluoro-1-pyrrolidin-1-ylethyl]phenyl}amino)-4,5-dihydro-1H-pyrazolo[4,3-c]pyridin-1-yl]tetrahydro-2H-pyran-3-yl}acetonitrile (from I-17B. Derived from Peak B via SFC: IB, 20% MeOH + 0.25% DMEA in $CO_2$, Tr = 7.9 minutes on OBn intermediate) | LRMS (ESI) calc'd for $C_{25}H_{28}F_3N_6O_2$ $[M + H]^+$: 501, found 501. |
| 5-200 | 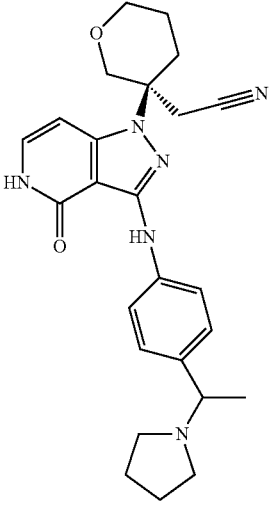 [SMILES: CC(c1ccc(Nc2nn([C@]3(CC#N)CCCOC3)c3cc[nH]c(=O)c23)cc1)N1CCCC1] | {(3S)-3-[4-oxo-3-({4-[(1S or 1R)-1-pyrrolidin-1-ylethyl]phenyl}amino)-4,5-dihydro-1H-pyrazolo[4,3-c]pyridin-1-yl]tetrahydro-2H-pyran-3-yl}acetonitrile (from I-17B. Derived from Peak A via SFC: AS-H, 15% MeOH + 0.25% DMEA in $CO_2$, Tr = 10.3 minutes on OBn intermediate) | LRMS (ESI) calc'd for $C_{25}H_{31}N_6O_2$ $[M + H]^+$: 447, found 447. |

TABLE 20-continued

| Example | Structure | Compound Name | LRMS |
|---|---|---|---|
| 5-201 | 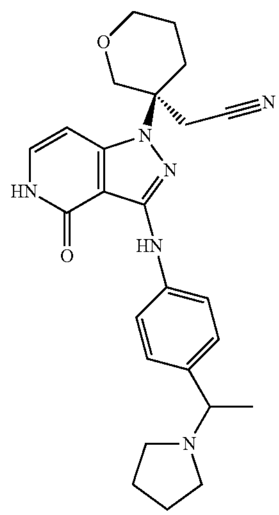 [SMILES: CC(c1ccc(Nc2nn([C@]3(CC#N)CCCOC3)c3cc[nH]c(=O)c23)cc1)N1CCCC1] | {(3S)-3-[4-oxo-3-({4-[(1R or 1S)-1-pyrrolidin-1-ylethyl]phenyl}amino)-4,5-dihydro-1H-pyrazolo[4,3-c]pyridin-1-yl]tetrahydro-2H-pyran-3-yl}acetonitrile (from I-17B. Derived from Peak B via SFC, AS-H, 15% MeOH + 0.25% DMEA in $CO_2$, Tr = 12.0 minutes on OBn intermediate) | LRMS (ESI) calc'd for $C_{25}H_{31}N_6O_2$ $[M + H]^+$: 447, found 447. |
| 5-202 | 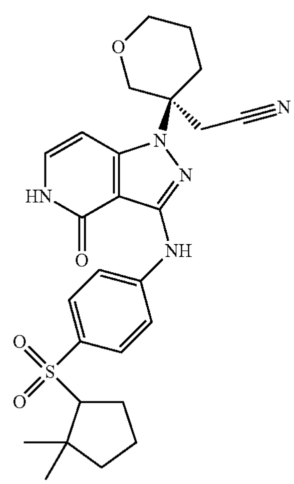 [SMILES: CC1(C)CCCC1S(=O)(=O)c1ccc(Nc2nn([C@]3(CC#N)CCCOC3)c3cc[nH]c(=O)c23)cc1] | {(3S)-3-[3-({4-[(2,2-dimethylcyclopentyl)sulfonyl]phenyl}amino)-4-oxo-4,5-dihydro-1H-pyrazolo[4,3-c]pyridin-1-yl]tetrahydro-2H-pyran-3-yl}acetonitrile (from I-17B) | LRMS (ESI) calc'd for $C_{26}H_{32}N_5O_4S$ $[M + H]^+$: 510, found 510. |
| 5-203 | 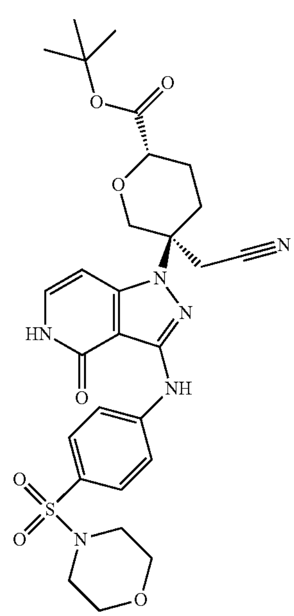 [SMILES: CC(C)(C)OC(=O)[C@@H]1CC[C@@](CC#N)(n2nc(Nc3ccc(S(=O)(=O)N4CCOCC4)cc3)c3c(=O)[nH]ccc32)CO1] | (2S,5S)-tert-butyl 5-(cyanomethyl)-5-(3-((4-(morpholinosulfonyl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{28}H_{35}N_6O_7S$ $[M + H]^+$: 599, found 599. |

TABLE 20-continued

| Example | Structure | Compound Name | LRMS |
|---|---|---|---|
| 5-204 | 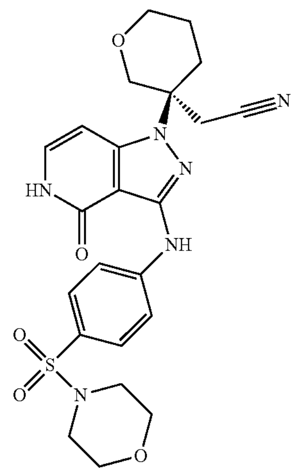 [SMILES: N#CC[C@@]1(n2nc(Nc3ccc(S(=O)(=O)N4CCOCC4)cc3)c3c(=O)[nH]ccc32)CCCOC1] | [(3S)-3-(3-{[4-(morpholin-4-ylsulfonyl)phenyl]amino}-4-oxo-4,5-dihydro-1H-pyrazolo[4,3-c]pyridin-1-yl)tetrahydro-2H-pyran-3-yl]acetonitrile (from I-17B) | LRMS (ESI) calc'd for $C_{23}H_{27}N_6O_5S$ $[M + H]^+$: 499, found 499. |
| 5-205 | 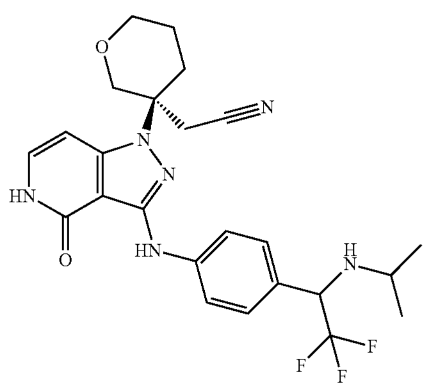 [SMILES: CC(C)NC(c1ccc(Nc2nn([C@]3(CC#N)CCCOC3)c3cc[nH]c(=O)c23)cc1)C(F)(F)F] | [(3S)-3-{4-oxo-3-[(4-{(1R or 1S)-2,2,2-trifluoro-1-[(1-methylethyl)amino]ethyl}phenyl)amino]-4,5-dihydro-1H-pyrazolo[4,3-c]pyridin-1-yl}tetrahydro-2H-pyran-3-yl]acetonitrile (from I-17B. Derived from Peak A via SFC: OJ-H, 15% MeOH + 0.25% DMEA in CO₂, Tr = 4.1 minutes on pyridone final compound) | LRMS (ESI) calc'd for $C_{24}H_{28}F_3N_6O_2$ $[M + H]^+$: 489, found 489. |
| 5-206 | 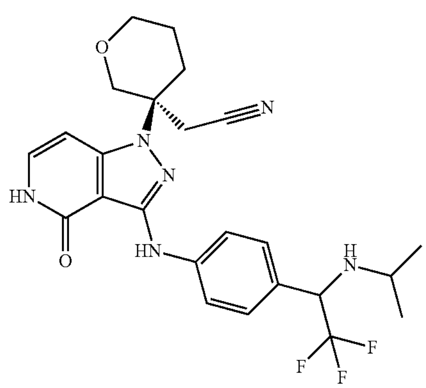 [SMILES: CC(C)NC(c1ccc(Nc2nn([C@]3(CC#N)CCCOC3)c3cc[nH]c(=O)c23)cc1)C(F)(F)F] | [(3S)-3-{4-oxo-3-[(4-{(1S or 1R)-2,2,2-trifluoro-1-[(1-methylethyl)amino]ethyl}phenyl)amino]-4,5-dihydro-1H-pyrazolo[4,3-c]pyridin-1-yl}tetrahydro-2H-pyran-3-yl]acetonitrile (from I-17B. Derived from Peak B via SFC: OJ-H, 15% MeOH + 0.25% DMEA in CO₂, Tr = 4.9 minutes on pyridone final compound) | LRMS (ESI) calc'd for $C_{24}H_{28}F_3N_6O_2$ $[M + H]^+$: 489, found 489. |

TABLE 20-continued

| Example | Structure | Compound Name | LRMS |
|---|---|---|---|
| 5-207 | 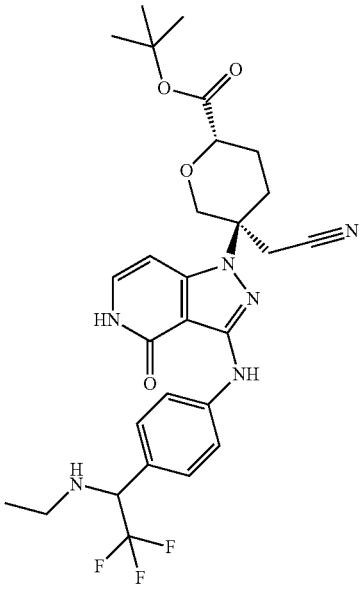 [SMILES: CCNC(c1ccc(Nc2nn([C@]3(CC#N)CC[C@@H](C(=O)OC(C)(C)C)OC3)c3cc[nH]c(=O)c23)cc1)C(F)(F)F] | (2S,5S)-tert-butyl 5-(cyanomethyl)-5-(3-((4-((R or S)-1-(ethylamino)-2,2,2-trifluoroethyl)phenyl)amino)-4-oxo-4,5-dihydro-1H-pyrazolo[4,3-c]pyridin-1-yl)tetrahydro-2H-pyran-2-carboxylate (from I-14-1A. Derived from Peak A via SFC: AS-H, 15% MeOH + 0.25% DMEA in $CO_2$, Tr = 3.8 minutes on pyridone final compound) | LRMS (ESI) calc'd for $C_{28}H_{34}F_3N_6O_4$ $[M + H]^+$: 575, found 575. |
| 5-208 | 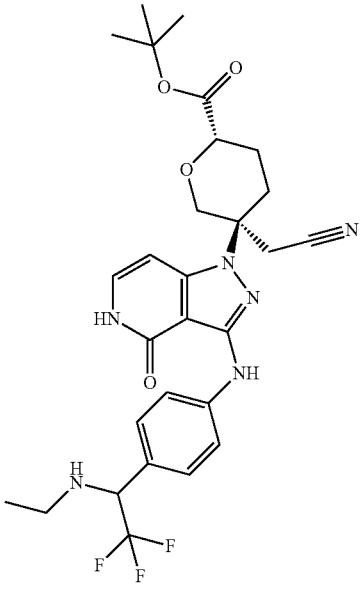 [SMILES: CCNC(c1ccc(Nc2nn([C@]3(CC#N)CC[C@@H](C(=O)OC(C)(C)C)OC3)c3cc[nH]c(=O)c23)cc1)C(F)(F)F] | (2S,5S)-tert-butyl 5-(cyanomethyl)-5-(3-((4-((R or S)-1-(ethylamino)-2,2,2-trifluoroethyl)phenyl)amino)-4-oxo-4,5-dihydro-1H-pyrazolo[4,3-c]pyridin-1-yl)tetrahydro-2H-pyran-2-carboxylate (from I-14-1A. Derived from Peak B via SFC: AS-H, 15% MeOH + 0.25% DMEA in $CO_2$, Tr = 5.8 minutes on pyridone final compound) | LRMS (ESI) calc'd for $C_{28}H_{34}F_3N_6O_4$ $[M + H]^+$: 575, found 575. |

TABLE 20-continued

| Example | Structure | Compound Name | LRMS |
|---|---|---|---|
| 5-209 | 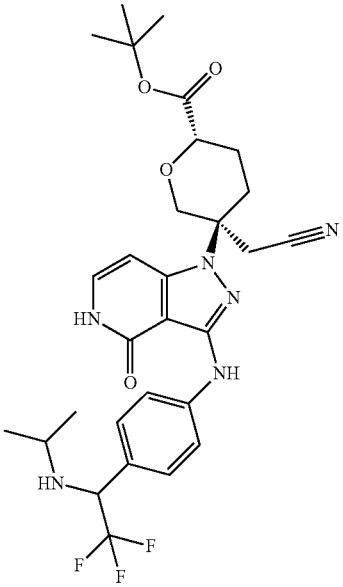 [SMILES: CC(C)NC(c1ccc(Nc2nn([C@]3(CC#N)CC[C@@H](C(=O)OC(C)(C)C)OC3)c3cc[nH]c(=O)c23)cc1)C(F)(F)F] | (2S,5S)-tert-butyl 5-(cyanomethyl)-5-(4-oxo-3-((4-((R or S)-2,2,2-trifluoro-1-(isopropylamino)ethyl)phenyl)amino)-4,5-dihydro-1H-pyrazolo[4,3-c]pyridin-1-yl)tetrahydro-2H-pyran-2-carboxylate (from I-14-1A. Derived from Peak A via SFC: AD-H, 20% 2-propanol + 0.25% DMEA in $CO_2$, Tr = 3.9 minutes on pyridone final compound) | LRMS (ESI) calc'd for $C_{29}H_{36}F_3N_6O_4$ $[M + H]^+$: 589, found 589. |
| 5-210 | 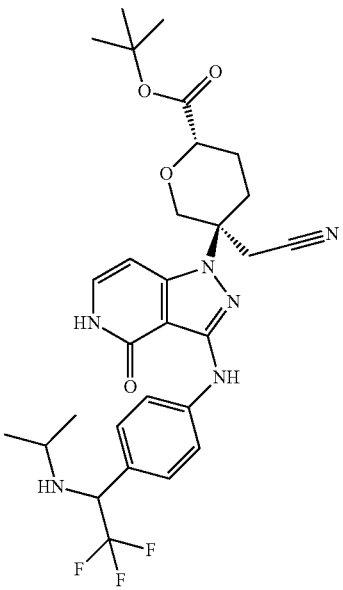 [SMILES: CC(C)NC(c1ccc(Nc2nn([C@]3(CC#N)CC[C@@H](C(=O)OC(C)(C)C)OC3)c3cc[nH]c(=O)c23)cc1)C(F)(F)F] | (2S,5S)-tert-butyl 5-(cyanomethyl)-5-(4-oxo-3-((4-((R or S)-2,2,2-trifluoro-1-(isopropylamino)ethyl)phenyl)amino)-4,5-dihydro-1H-pyrazolo[4,3-c]pyridin-1-yl)tetrahydro-2H-pyran-2-carboxylate (from I-14-1A. Derived from Peak B via SFC, AD-H, 20% 2-propanol + 0.25% DMEA in $CO_2$, Tr = 5.1 minutes on pyridone final compound) | LRMS (ESI) calc'd for $C_{29}H_{36}F_3N_6O_4$ $[M + H]^+$: 589, found 589. |

TABLE 20-continued

| Example | Structure | Compound Name | LRMS |
|---|---|---|---|
| 5-211 | 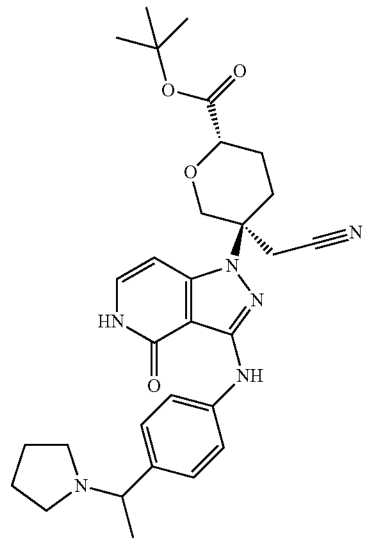 [SMILES: CC(c1ccc(Nc2nn([C@]3(CC#N)CC[C@@H](C(=O)OC(C)(C)C)OC3)c3cc[nH]c(=O)c23)cc1)N1CCCC1] | (2S,5S)-tert-butyl 5-(cyanomethyl)-5-(4-oxo-3-((4-((S or R)-1-(pyrrolidin-1-yl)ethyl)phenyl)amino)-4,5-dihydro-1H-pyrazolo[4,3-c]pyridin-1-yl)tetrahydro-2H-pyran-2-carboxylate (from I-14-1A. Derived from Peak A via SFC: Lux-2, 40% MeOH + 0.25% DMEA in $CO_2$, Tr = 10.4 minutes on pyridone final compound) | LRMS (ESI) calc'd for $C_{30}H_{39}N_6O_4$ $[M + H]^+$: 547, found 547. |
| 5-212 | 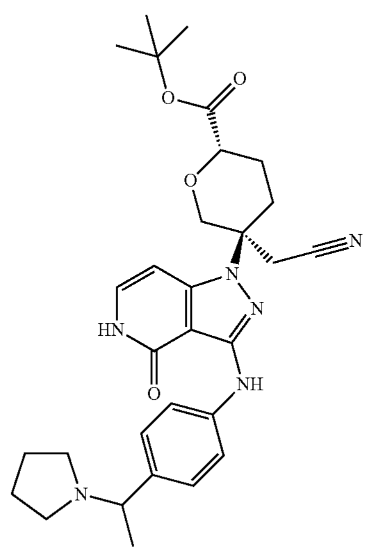 [SMILES: CC(c1ccc(Nc2nn([C@]3(CC#N)CC[C@@H](C(=O)OC(C)(C)C)OC3)c3cc[nH]c(=O)c23)cc1)N1CCCC1] | (2S,5S)-tert-butyl 5-(cyanomethyl)-5-(4-oxo-3-((4-((S or R)-1-(pyrrolidin-1-yl)ethyl)phenyl)amino)-4,5-dihydro-1H-pyrazolo[4,3-c]pyridin-1-yl)tetrahydro-2H-pyran-2-carboxylate (from I-14-1A. Derived from Peak B via SFC: Lux-2, 40% MeOH + 0.25% DMEA in $CO_2$, Tr = 11.8 mins on pyridone final compound) | LRMS (ESI) calc'd for $C_{30}H_{39}N_6O_4$ $[M + H]^+$: 547, found 547. |

TABLE 20-continued

| Example | Structure | Compound Name | LRMS |
|---|---|---|---|
| 5-213 | 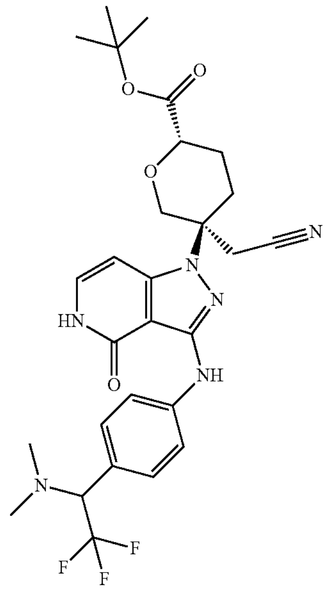 [SMILES: CN(C)C(c1ccc(Nc2nn([C@]3(CC#N)CC[C@@H](C(=O)OC(C)(C)C)OC3)c3cc[nH]c(=O)c23)cc1)C(F)(F)F] | (2S,5S)-tert-butyl 5-(cyanomethyl)-5-(3-((4-((R or S)-1-(dimethylamino)-2,2,2-trifluoroethyl) phenyl)amino)-4-oxo-4,5-dihydro-1H-pyrazolo[4,3-c]pyridin-1-yl)tetrahydro-2H-pyran-2-carboxylate (from I-14-1A. Derived from Peak A via SFC: ID, 25% 2-propanol + 0.25% DMEA in $CO_2$, Tr = 5.3 minutes on pyridone final compound) | LRMS (ESI) calc'd for $C_{28}H_{34}F_3N_6O_4$ [M + H]$^+$: 575, found 575. |
| 5-214 | 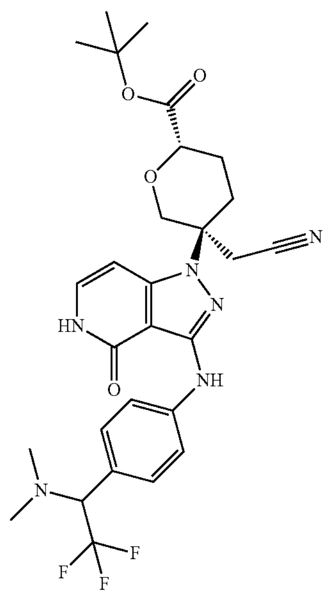 [SMILES: CN(C)C(c1ccc(Nc2nn([C@]3(CC#N)CC[C@@H](C(=O)OC(C)(C)C)OC3)c3cc[nH]c(=O)c23)cc1)C(F)(F)F] | (2S,5S)-tert-butyl 5-(cyanomethyl)-5-(3-((4-((R or S)-1-(dimethylamino)-2,2,2-trifluoroethyl) phenyl)amino)-4-oxo-4,5-dihydro-1H-pyrazolo[4,3-c]pyridin-1-yl)tetrahydro-2H-pyran-2-carboxylate (from I-14-1A. Derived from Peak B via SFC: ID, 25% 2-propanol + 0.25% DMEA in $CO_2$, Tr = 6.9 minutes on pyridone final compound) | LRMS (ESI) calc'd for $C_{28}H_{34}F_3N_6O_4$ [M + H]$^+$: 575, found 575. |
| 5-215 | 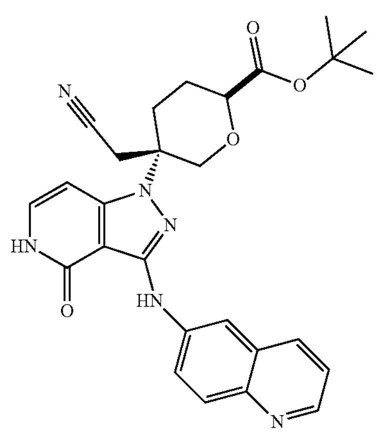 [SMILES: CC(C)(C)OC(=O)[C@@H]1CC[C@@](CC#N)(n2nc(Nc3ccc4ncccc4c3)c3c(=O)[nH]ccc32)CO1] | (2S,5S)-tert-butyl 5-(cyanomethyl)-5-(4-oxo-3-(quinolin-6-ylamino)-4,5-dihydro-1H-pyrazolo[4,3-c]pyridin-1-yl)tetrahydro-2H-pyran-2-carboxylate (from I-14-1A) | LRMS (ESI) calc'd for $C_{27}H_{29}N_6O_4$ [M + H]$^+$: 501, found 501. |

TABLE 20-continued

| Example | Structure | Compound Name | LRMS |
|---|---|---|---|
| 5-216 | 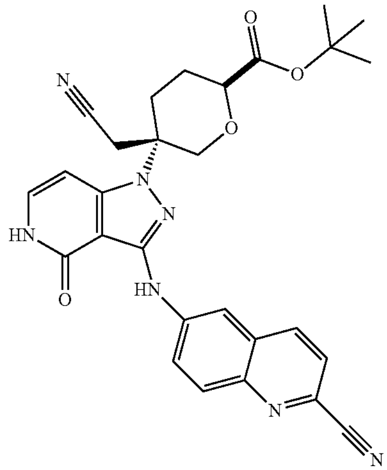 [SMILES: CC(C)(C)OC(=O)[C@@H]1CC[C@@](CC#N)(n2nc(Nc3ccc4nc(C#N)ccc4c3)c3c(=O)[nH]ccc32)CO1] | (2S,5S)-tert-butyl 5-(cyanomethyl)-5-(3-((2-cyanoquinolin-6-yl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{28}H_{28}N_7O_4$ [M + H]$^+$: 526, found 526. |
| 5-217 | 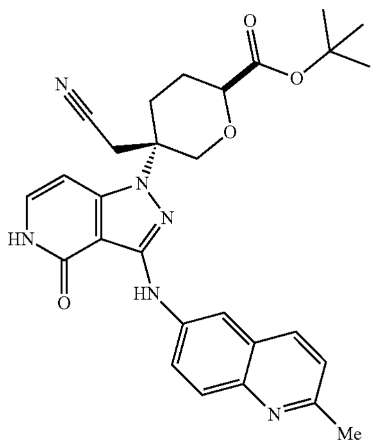 [SMILES: Cc1ccc2cc(Nc3nn([C@]4(CC#N)CC[C@@H](C(=O)OC(C)(C)C)OC4)c4cc[nH]c(=O)c34)ccc2n1] | (2S,5S)-tert-butyl 5-(cyanomethyl)-5-(3-((2-methylquinolin-6-yl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{28}H_{31}N_6O_4$ [M + H]$^+$: 515, found 515. |
| 5-218 | 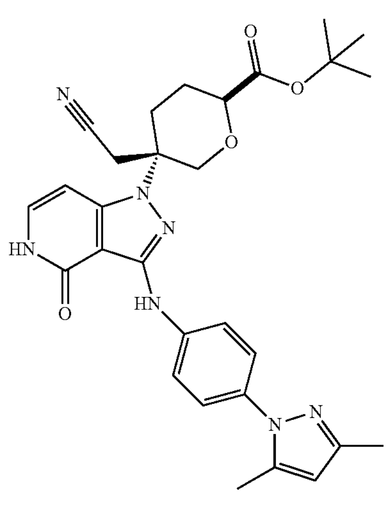 [SMILES: Cc1cc(C)n(-c2ccc(Nc3nn([C@]4(CC#N)CC[C@@H](C(=O)OC(C)(C)C)OC4)c4cc[nH]c(=O)c34)cc2)n1] | (2S,5S)-tert-butyl 5-(cyanomethyl)-5-(3-((4-(3,5-dimethyl-1H-pyrazol-1-yl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{29}H_{34}N_7O_4$ [M + H]$^+$: 544, found 544. |

TABLE 20-continued

| Example | Structure | Compound Name | LRMS |
|---|---|---|---|
| 5-219 | 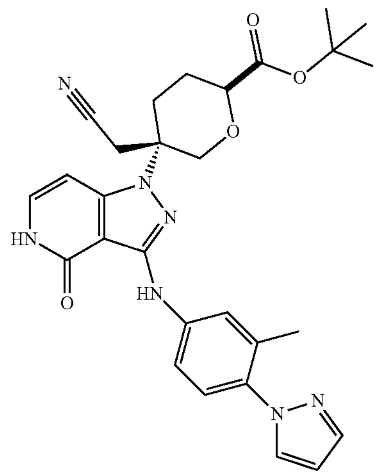 [SMILES: Cc1cc(Nc2nn([C@]3(CC#N)CC[C@@H](C(=O)OC(C)(C)C)OC3)c3cc[nH]c(=O)c23)ccc1-n1cccn1] | (2S,5S)-tert-butyl 5-(cyanomethyl)-5-(3-((3-methyl-4-(1H-pyrazol-1-yl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{28}H_{32}N_7O_4$ [M + H]$^+$: 530, found 530. |
| 5-220 | 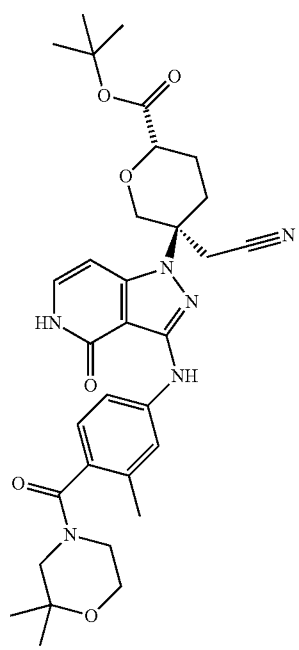 [SMILES: Cc1cc(Nc2nn([C@]3(CC#N)CC[C@@H](C(=O)OC(C)(C)C)OC3)c3cc[nH]c(=O)c23)ccc1C(=O)N1CCOC(C)(C)C1] | (2S,5S)-tert-butyl 5-(cyanomethyl)-5-(3-((4-(2,2-dimethylmorpholine-4-carbonyl)-3-methylphenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{32}H_{41}N_6O_6$ [M + H]$^+$: 605, found 605. |
| 5-221 | 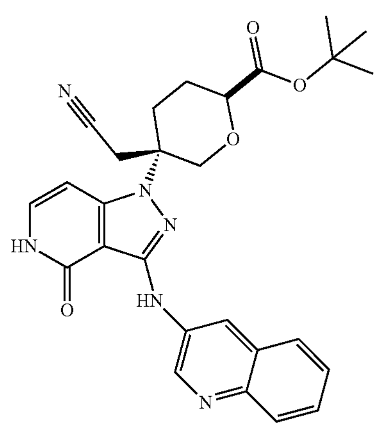 [SMILES: CC(C)(C)OC(=O)[C@@H]1CC[C@@](CC#N)(n2nc(Nc3cnc4ccccc4c3)c3c(=O)[nH]ccc32)CO1] | (2S,5S)-tert-butyl 5-(cyanomethyl)-5-(4-oxo-3-(quinolin-3-ylamino)-4,5-dihydro-1H-pyrazolo[4,3-c]pyridin-1-yl)tetrahydro-2H-pyran-2-carboxylate (from I-14-1A) | LRMS (ESI) calc'd for $C_{27}H_{29}N_6O_4$ [M + H]$^+$: 501, found 501. |

| Example | Structure | Compound Name | LRMS |
|---|---|---|---|
| 5-222 | 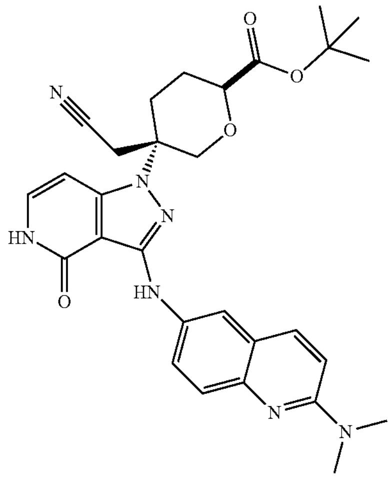 [SMILES: CN(C)c1ccc2cc(Nc3nn([C@]4(CC#N)CC[C@@H](C(=O)OC(C)(C)C)OC4)c4cc[nH]c(=O)c34)ccc2n1] | (2S,5S)-tert-butyl 5-(cyanomethyl)-5-(3-((2-(dimethylamino)quinolin-6-yl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{29}H_{34}N_7O_4$ $[M + H]^+$: 544, found 544. |
| 5-223 | 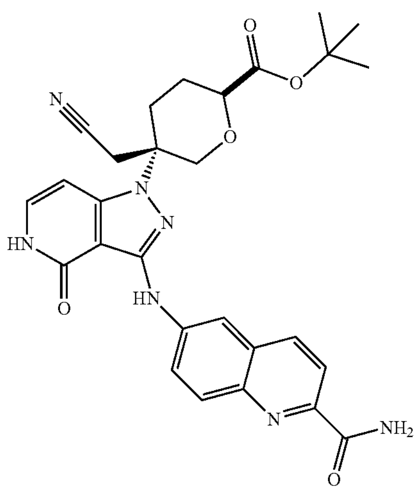 [SMILES: CC(C)(C)OC(=O)[C@@H]1CC[C@@](CC#N)(n2nc(Nc3ccc4nc(C(N)=O)ccc4c3)c3c(=O)[nH]ccc32)CO1] | (2S,5S)-tert-butyl 5-(3-((2-carbamoylquinolin-6-yl)amino)-4-oxo-4,5-dihydro-1H-pyrazolo[4,3-c]pyridin-1-yl)-5-(cyanomethyl)tetrahydro-2H-pyran-2-carboxylate (from I-14-1A) | LRMS (ESI) calc'd for $C_{27}H_{30}N_7O_5$ $[M + H]^+$: 544, found 544. |
| 5-224 | 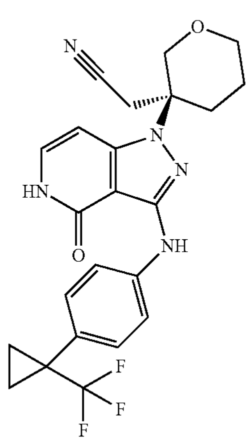 [SMILES: N#CC[C@@]1(n2nc(Nc3ccc(C4(C(F)(F)F)CC4)cc3)c3c(=O)[nH]ccc32)CCCOC1] | (S)-2-(3-(4-oxo-3-((4-(1-(trifluoromethyl)cyclopropyl)phenyl)amino)-4,5-dihydro-1H-pyrazolo[4,3-c]pyridin-1-yl)tetrahydro-2H-pyran-3-yl)acetonitrile (from I-17B) | LRMS (ESI) calc'd for $C_{23}H_{23}F_3N_5O_2$ $[M + H]^+$: 458, found 458. |

TABLE 20-continued

| Example | Structure | Compound Name | LRMS |
|---|---|---|---|
| 5-225 | 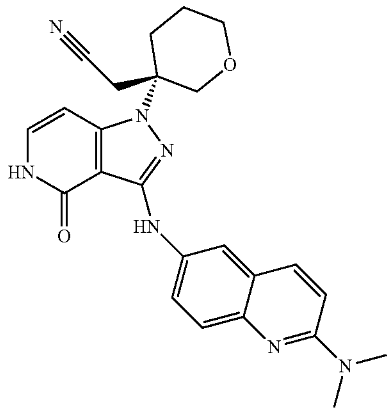 [SMILES: CN(C)c1ccc2cc(Nc3nn([C@]4(CC#N)CCCOC4)c4cc[nH]c(=O)c34)ccc2n1] | (S)-2-(3-(3-((2-(dimethylamino)quinolin-6-yl)amino)-4-oxo-4,5-dihydro-1H-pyrazolo[4,3-c]pyridin-1-yl)tetrahydro-2H-pyran-3-yl)acetonitrile (from I-17B) | LRMS (ESI) calc'd for $C_{24}H_{26}N_7O_2$ [M + H]$^+$: 444, found 444. |
| 5-226 | 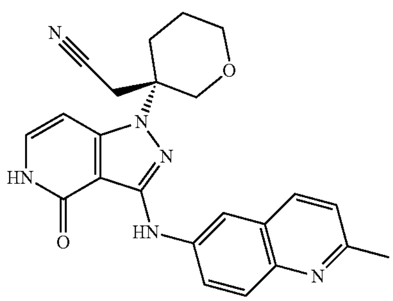 [SMILES: Cc1ccc2cc(Nc3nn([C@]4(CC#N)CCCOC4)c4cc[nH]c(=O)c34)ccc2n1] | (S)-2-(3-(3-((2-methylquinolin-6-yl)amino)-4-oxo-4,5-dihydro-1H-pyrazolo[4,3-c]pyridin-1-yl)tetrahydro-2H-pyran-3-yl)acetonitrile (from I-17B) | LRMS (ESI) calc'd for $C_{23}H_{23}N_6O_2$ [M + H]$^+$: 415, found 415. |
| 5-227 | 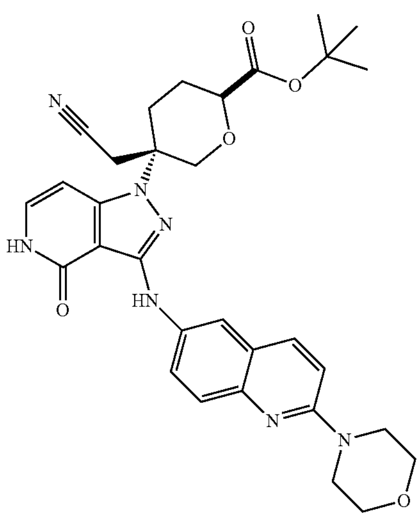 [SMILES: CC(C)(C)OC(=O)[C@@H]1CC[C@@](CC#N)(n2nc(Nc3ccc4nc(N5CCOCC5)ccc4c3)c3c(=O)[nH]ccc32)CO1] | (2S,5S)-tert-butyl 5-(cyanomethyl)-5-(3-((2-morpholinoquinolin-6-yl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{31}H_{36}N_7O_5$ [M + H]$^+$: 586, found 586. |

TABLE 20-continued

| Example | Structure | Compound Name | LRMS |
|---|---|---|---|
| 5-228 | 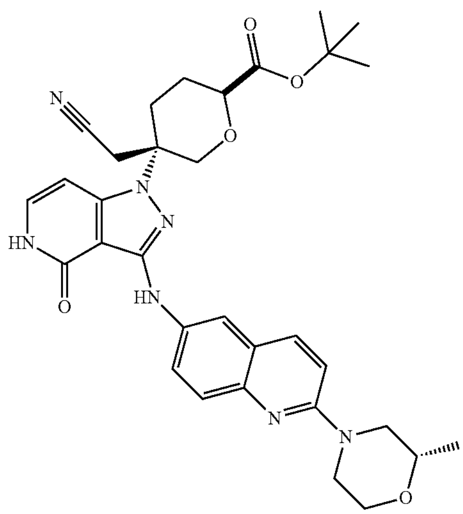 [SMILES: C[C@H]1CN(c2ccc3cc(Nc4nn([C@]5(CC#N)CC[C@@H](C(=O)OC(C)(C)C)OC5)c5cc[nH]c(=O)c45)ccc3n2)CCO1] | (2S,5S)-tert-butyl 5-(cyanomethyl)-5-(3-((2-((S)-2-methylmorpholino)quinolin-6-yl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{32}H_{38}N_7O_5$ $[M + H]^+$: 600, found 600. |
| 5-229 | 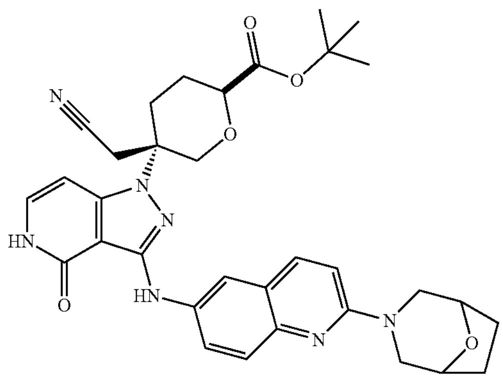 [SMILES: CC(C)(C)OC(=O)[C@@H]1CC[C@@](CC#N)(n2nc(Nc3ccc4nc(N5CC6CCC(C5)O6)ccc4c3)c3c(=O)[nH]ccc32)CO1] | (2S,5S)-tert-butyl 5-(3-((2-(8-oxa-3-azabicyclo[3.2.1]octan-3-yl)quinolin-6-yl)amino)-4-oxo-4,5-dihydro-1H-pyrazolo[4,3-c]pyridin-1-yl)-5-(cyanomethyl)tetrahydro-2H-pyran-2-carboxylate (from I-14-1A) | LRMS (ESI) calc'd for $C_{27}H_{35}N_6O_5S$ $[M + H]^+$: 612, found 612. |
| 5-230 | 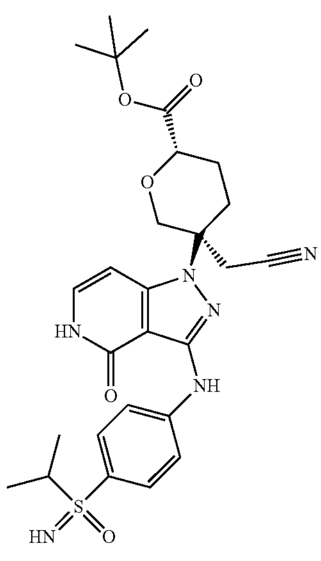 | (2S,5S)-tert-butyl 5-(cyanomethyl)-5-(4-oxo-3-((4-(propan-2-yl-(S or R)-sulfonimidoyl)phenyl)amino)-4,5-dihydro-1H-pyrazolo[4,3-c]pyridin-1-yl)tetrahydro-2H-pyran-2-carboxylate (from I-14-1A) (derived from Peak 2, SFC on OBn intermediate using Chiralcel OJ-H, 45% MeOH in $CO_2$, Tr = 7.6 minutes) | LRMS (ESI) calc'd for $C_{27}H_{35}N_6O_5S$ $[M + H]^+$: 555, found 555. |

TABLE 20-continued

| Example | Structure | Compound Name | LRMS |
|---|---|---|---|
| 5-231 | 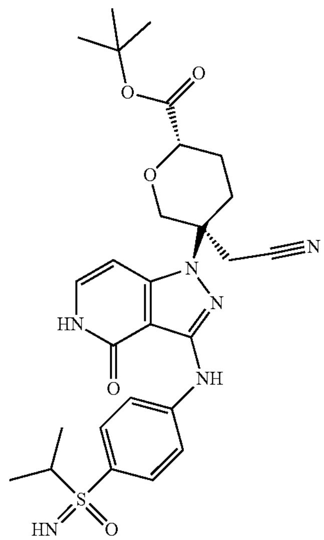 | (2S,5S)-tert-butyl 5-(cyanomethyl)-5-(4-oxo-3-((4-(propan-2-yl-(S or R)-sulfonimidoyl)phenyl)amino)-4,5-dihydro-1H-pyrazolo[4,3-c]pyridin-1-yl)tetrahydro-2H-pyran-2-carboxylate (from I-14-1A) (derived from Peak 1, SFC on OBn intermediate using Chiralcel OJ-H, 45% MeOH in $CO_2$, Tr = 4.1 minutes) | LRMS (ESI) calc'd for $C_{27}H_{35}N_6O_5S$ $[M + H]^+$: 555, found 555. |
| 5-232 | 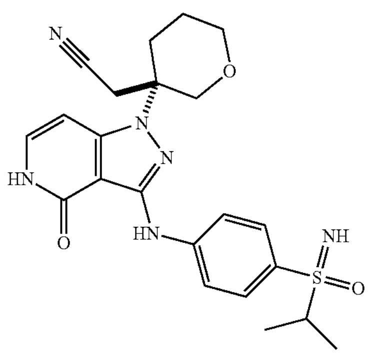 | 2-((3S)-3-(4-oxo-3-((4-(propan-2-yl-(S or R)-sulfonimidoyl)phenyl)amino)-4,5-dihydro-1H-pyrazolo[4,3-c]pyridin-1-yl)tetrahydro-2H-pyran-3-yl)acetonitrile (from I-17B) (derived from Peak 2, SFC on OBn intermediate using Chiralcel OJ-H, 20% MeOH in $CO_2$, Tr = 10.3 minutes) | LRMS (ESI) calc'd for $C_{22}H_{27}N_6O_3S$ $[M + H]^+$: 455, found 455. |
| 5-233 | 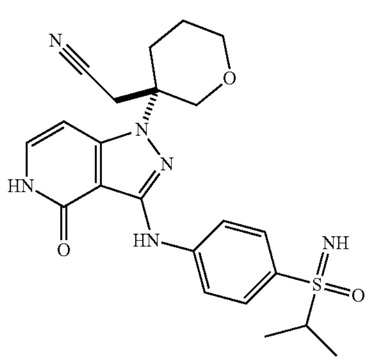 | 2-((3S)-3-(4-oxo-3-((4-(propan-2-yl-(S or R)-sulfonimidoyl)phenyl)amino)-4,5-dihydro-1H-pyrazolo[4,3-c]pyridin-1-yl)tetrahydro-2H-pyran-3-yl)acetonitrile (from I-17B) (derived from Peak 1, SFC on OBn intermediate using Chiralcel OJ-H, 20% MeOH in $CO_2$, Tr = 8.7 minutes) | LRMS (ESI) calc'd for $C_{22}H_{27}N_6O_3S$ $[M + H]^+$: 455, found 455. |

| Example | Structure | Compound Name | LRMS |
|---------|-----------|---------------|------|
| 5-234 | 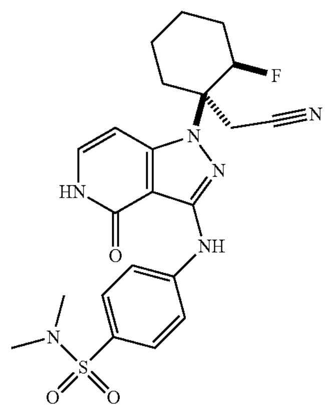 | 4-({1-[(1R,2R)-1-(cyanomethyl)-2-fluorocyclohexyl]-4-oxo-4,5-dihydro-1H-pyrazolo[4,3-c]pyridin-3-yl}amino)-N,N-dimethyl-benzenesulfonamide (from I-19A) | LRMS (ESI) calc'd for $C_{22}H_{26}N_6O_3SF$ [M + H]$^+$: 473, found 473. |
| 5-235 | 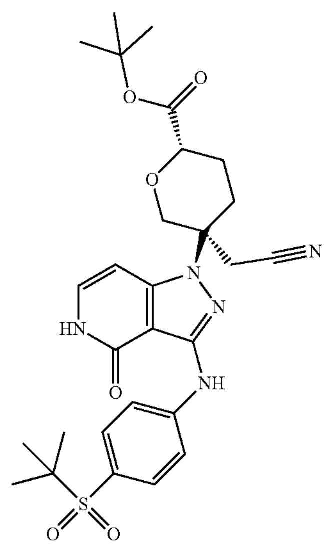 | (2S,5S)-tert-butyl 5-(3-((4-(tert-butylsulfonyl)phenyl)amino)-4-oxo-4,5-dihydro-1H-pyrazolo[4,3-c]pyridin-1-yl)-5-(cyanomethyl)tetrahydro-2H-pyran-2-carboxylate (from I-14-1A) | LRMS (ESI) calc'd for $C_{28}H_{36}N_5O_6S$ [M + H]$^+$: 570, found 570. |
| 5-236 | 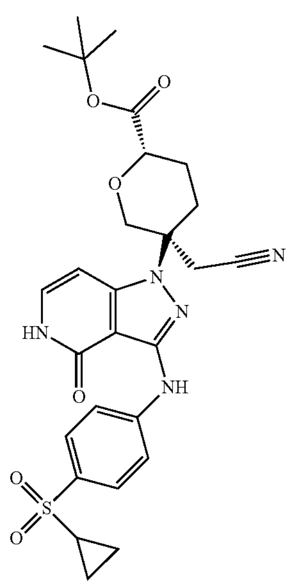 | (2S,5S)-tert-butyl 5-(cyanomethyl)-5-(3-((4-(cyclopropylsulfonyl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{27}H_{32}N_5O_6S$ [M + H]$^+$: 554, found 554. |

TABLE 20-continued

| Example | Structure | Compound Name | LRMS |
|---|---|---|---|
| 5-237 | 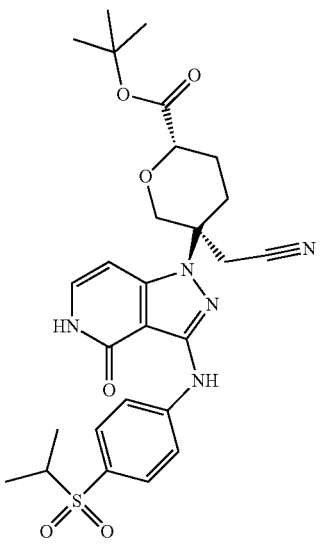 | (2S,5S)-tert-butyl 5-(cyanomethyl)-5-(3-((4-(isopropylsulfonyl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{27}H_{34}N_5O_6S$ $[M + H]^+$: 556, found 556. |
| 5-238 | 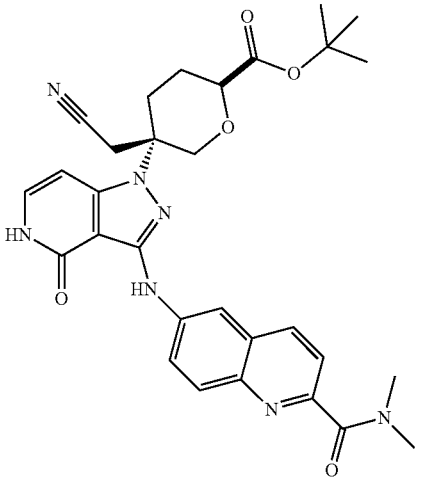 [SMILES: CN(C)C(=O)c1ccc2cc(Nc3nn([C@]4(CC#N)CC[C@@H](C(=O)OC(C)(C)C)OC4)c4cc[nH]c(=O)c34)ccc2n1] | (2S,5S)-tert-butyl 5-(cyanomethyl)-5-(3-((2-(dimethylcarbamoyl)quinolin-6-yl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{30}H_{34}N_7O_5$ $[M + H]^+$: 572, found 572. |
| 5-239 | 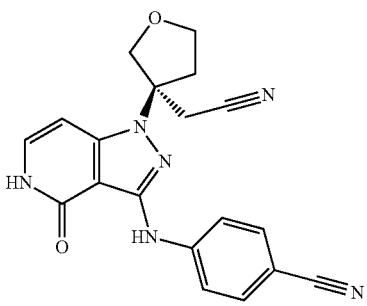 [SMILES: N#CC[C@@]1(n2nc(Nc3ccc(C#N)cc3)c3c(=O)[nH]ccc32)CCOC1] | 4-({1-[(3R or 3S)-3-(cyanomethyl)tetrahydrofuran-3-yl]-4-oxo-4,5-dihydro-1H-pyrazolo[4,3-c]pyridin-3-yl}amino)benzonitrile (Chiral HPLC on free pyridone using Chiralpak IA, 0.1% TEA, 1:1 Hex:EtOH, Tr = 3.1 minutes) | LRMS (ESI) calc'd for $C_{19}H_{17}N_5O_2Cl$ $[M + H]^+$: 361, found 361. |

TABLE 20-continued

| Example | Structure | Compound Name | LRMS |
|---|---|---|---|
| 5-240 | 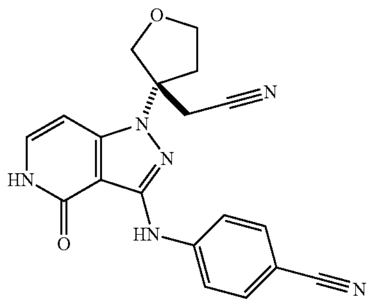 | 4-({1-[(3S or 3R)-3-(cyanomethyl)tetrahydrofuran-3-yl]-4-oxo-4,5-dihydro-1H-pyrazolo[4,3-c]pyridin-3-yl}amino)benzonitrile (Chiral HPLC on free pyridone using Chiralpak IA, 0.1% TEA, 1:1 Hex:EtOH, Tr = 7.5 minutes) | LRMS (ESI) calc'd for $C_{19}H_{17}N_5O_2Cl$ $[M + H]^+$: 361, found 361. |
| 5-241 | 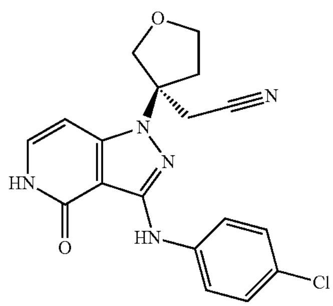 [SMILES: N#CC[C@@]1(n2nc(Nc3ccc(Cl)cc3)c3c(=O)[nH]ccc32)CCOC1] | [(3R or 3S)-3-{3-[(4-chlorophenyl)amino]-4-oxo-4,5-dihydro-1H-pyrazolo[4,3-c]pyridin-1-yl}tetrahydrofuran-3-yl]acetonitrile (Chiral HPLC on free pyridone using Chiralpak IA, 30:70 DCM/MeOH, Tr = 3.3 minutes) | LRMS (ESI) calc'd for $C_{18}H_{17}ClN_5O_2$ $[M + H]^+$: 370, found 370. |
| 5-242 | 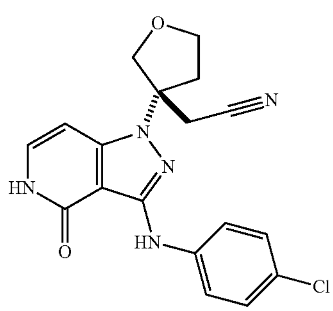 | [(3S or 3R)-3-{3-[(4-chlorophenyl)amino]-4-oxo-4,5-dihydro-1H-pyrazolo[4,3-c]pyridin-1-yl}tetrahydrofuran-3-yl]acetonitrile (Chiral HPLC on free pyridone using Chiralpak IA, 30:70 DCM/MeOH, Tr = 7.1 minutes) | LRMS (ESI) calc'd for $C_{18}H_{17}ClN_5O_2$ $[M + H]^+$: 370, found 370. |
| 5-243 | 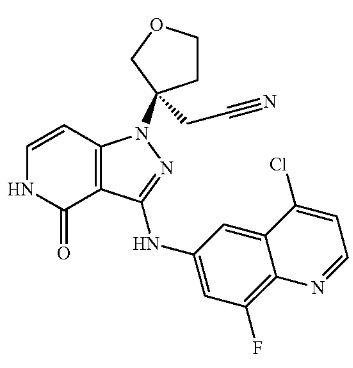 [SMILES: N#CC[C@@]1(n2nc(Nc3cc(F)c4nccc(Cl)c4c3)c3c(=O)[nH]ccc32)CCOC1] | [(3R or 3S)-3-{3-[(4-chloro-8-fluoroquinolin-6-yl)amino]-4-oxo-4,5-dihydro-1H-pyrazolo[4,3-c]pyridin-1-yl}tetrahydrofuran-3-yl]acetonitrile (Chiral HPLC on free pyridone using Chiralpak IA, Hex (0.1% TEA):IPA = 75:25, Tr = 5.2 minutes) | LRMS (ESI) calc'd for $C_{21}H_{17}ClFN_6O_2$ $[M + H]^+$: 439, found 439. |

TABLE 20-continued

| Example | Structure | Compound Name | LRMS |
|---|---|---|---|
| 5-244 | 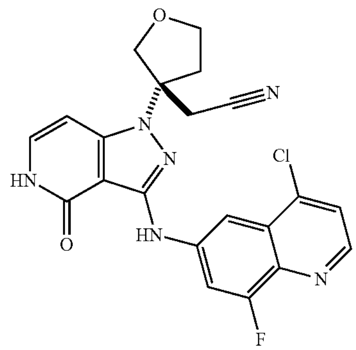 | [(3S or 3R)-3-{3-[(4-chloro-8-fluoroquinolin-6-yl)amino]-4-oxo-4,5-dihydro-1H-pyrazolo[4,3-c]pyridin-1-yl}tetrahydrofuran-3-yl]acetonitrile (Chiral HPLC on free pyridone using Chiralpak IA, Hex (0.1% TEA):IPA = 75:25, Tr = 6.6 minutes) | LRMS (ESI) calc'd for $C_{21}H_{17}ClFN_6O_2$ [M + H]$^+$: 439, found 439. |
| 5-245 | 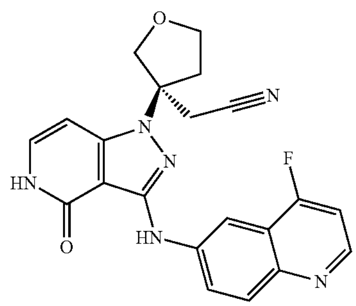 [SMILES: N#CC[C@@]1(n2nc(Nc3ccc4nccc(F)c4c3)c3c(=O)[nH]ccc32)CCOC1] | [(3R or 3S)-3-{3-[(4-fluoroquinolin-6-yl)amino]-4-oxo-4,5-dihydro-1H-pyrazolo[4,3-c]pyridin-1-yl}tetrahydrofuran-3-yl]acetonitrile (Chiral HPLC on free pyridone using Chiralpak IA, Hex (0.1% TEA):EtOH = 50:50, Tr = 3.2 minutes) | LRMS (ESI) calc'd for $C_{21}H_{18}FN_6O_2$ [M + H]$^+$: 405, found 405. |
| 5-246 | 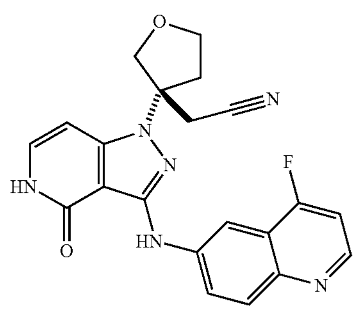 | [(3S or 3R)-3-{3-[(4-fluoroquinolin-6-yl)amino]-4-oxo-4,5-dihydro-1H-pyrazolo[4,3-c]pyridin-1-yl}tetrahydrofuran-3-yl]acetonitrile (Chiral HPLC on free pyridone Chiralpak IA, Hex (0.1% TEA):EtOH = 50:50, Tr = 5.0 minutes) | LRMS (ESI) calc'd for $C_{21}H_{18}FN_6O_2$ [M + H]$^+$: 405, found 405. |
| 5-247 | 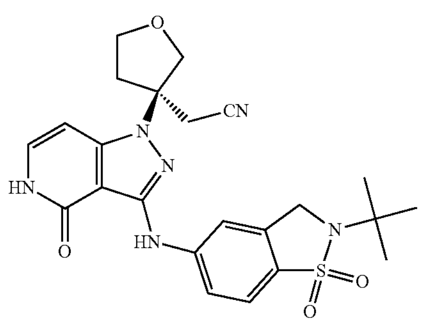 [SMILES: CC(C)(C)N1Cc2cc(Nc3nn([C@@]4(CC#N)CCOC4)c4cc[nH]c(=O)c34)ccc2S1(=O)=O] | (S or R)-2-(3-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)tetrahydrofuran-3-yl)acetonitrile (Chiral HPLC on free pyridone Chiralpak IA, MeOH (0.1% TEA) Tr = 15.5 minutes) | LRMS (ESI) calc'd for $C_{23}H_{27}N_6O_4S$ [M + H]$^+$: 483, found 483. |
| 5-248 | 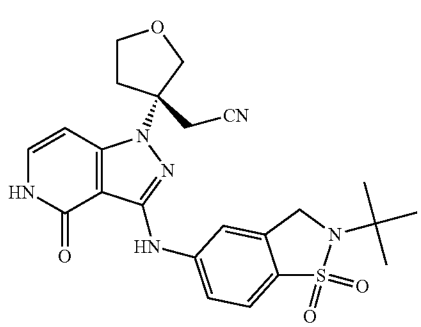 [SMILES: CC(C)(C)N1Cc2cc(Nc3nn([C@]4(CC#N)CCOC4)c4cc[nH]c(=O)c34)ccc2S1(=O)=O] | (R or S)-2-(3-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)tetrahydrofuran-3-yl)acetonitrile (Chiral HPLC on free pyridone using Chiralpak IA, MeOH (0.1% TEA), Tr = 23.5 minutes) | LRMS (ESI) calc'd for $C_{23}H_{27}N_6O_4S$ [M + H]$^+$: 483, found 483. |

| Example | Structure | Compound Name | LRMS |
|---|---|---|---|
| 5-249 | 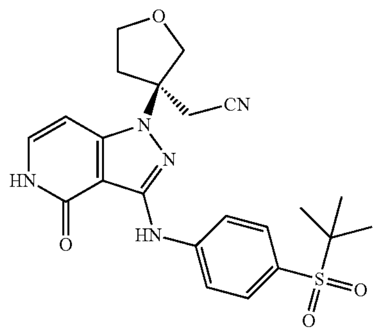 [SMILES: CC(C)(C)S(=O)(=O)c1ccc(Nc2nn([C@@]3(CC#N)CCOC3)c3cc[nH]c(=O)c23)cc1] | (S or R)-2-(3-(3-((4-(tert-butylsulfonyl)phenyl)amino)-4-oxo-4,5-dihydro-1H-pyrazolo[4,3-c]pyridin-1-yl)tetrahydrofuran-3-yl)acetonitrile (Chiral HPLC on free pyridone using Chiralpak IA, 1:1 hexanes (0.1% DEA): iPrOH (0.1% DEA), Tr = 15.3 minutes) | LRMS (ESI) calc'd for $C_{22}H_{26}N_5O_4S$ $[M + H]^+$: 456, found 456. |
| 5-250 | 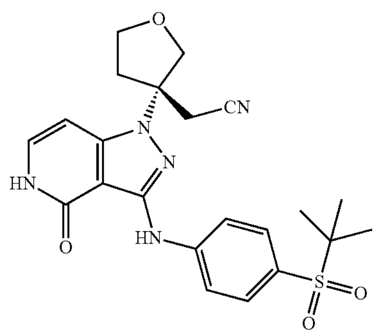 [SMILES: CC(C)(C)S(=O)(=O)c1ccc(Nc2nn([C@]3(CC#N)CCOC3)c3cc[nH]c(=O)c23)cc1] | (R or S)-2-(3-(3-((4-(tert-butylsulfonyl)phenyl)amino)-4-oxo-4,5-dihydro-1H-pyrazolo[4,3-c]pyridin-1-yl)tetrahydrofuran-3-yl)acetonitrile (Chiral HPLC on free pyridone using Chiralpak IA, 1:1 hexanes (0.1% DEA): iPrOH (0.1% DEA), Tr = 37.6 minutes) | LRMS (ESI) calc'd for $C_{23}H_{27}N_6O_4S$ $[M + H]^+$: 456, found 456. |
| 5-251 | 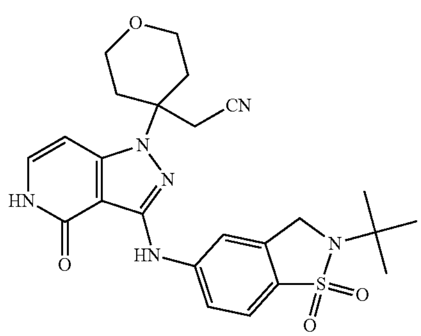 [SMILES: CC(C)(C)N1Cc2cc(Nc3nn(C4(CC#N)CCOCC4)c4cc[nH]c(=O)c34)ccc2S1(=O)=O] | 2-(4-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-4-yl)acetonitrile | LRMS (ESI) calc'd for $C_{24}H_{29}N_6O_4S$ $[M + H]^+$: 497, found 497. |
| 5-252 | 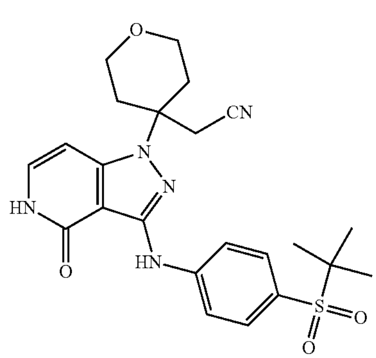 [SMILES: CC(C)(C)S(=O)(=O)c1ccc(Nc2nn(C3(CC#N)CCOCC3)c3cc[nH]c(=O)c23)cc1] | 2-(4-(3-((4-(tert-butylsulfonyl)phenyl)amino)-4-oxo-4,5-dihydro-1H-pyrazolo[4,3-c]pyridin-1-yl)tetrahydro-2H-pyran-4-yl)acetonitrile | LRMS (ESI) calc'd for $C_{23}H_{28}N_5O_4S$ $[M + H]^+$: 470, found 470. |

TABLE 20-continued

| Example | Structure | Compound Name | LRMS |
|---|---|---|---|
| 5-253 | 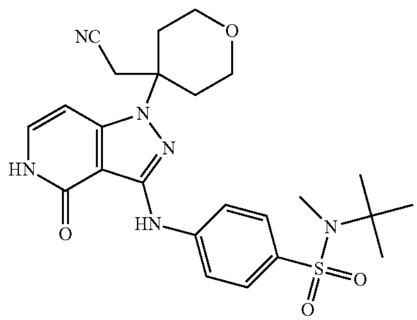 [SMILES: CN(C(C)(C)C)S(=O)(=O)c1ccc(Nc2nn(C3(CC#N)CCOCC3)c3cc[nH]c(=O)c23)cc1] | N-(tert-butyl)-4-((1-(4-(cyanomethyl)tetrahydro-2H-pyran-4-yl)-4-oxo-4,5-dihydro-1H-pyrazolo[4,3-c]pyridin-3-yl)amino)-N-methylbenzenesulfonamide | LRMS (ESI) calc'd for $C_{24}H_{31}N_6O_4S$ $[M + H]^+$: 499, found 499. |
| 5-254 | 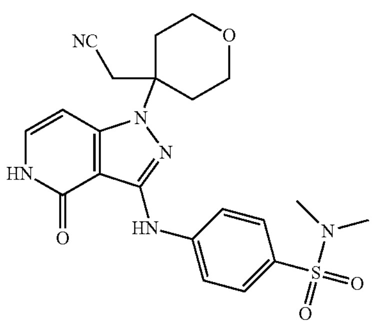 [SMILES: CN(C)S(=O)(=O)c1ccc(Nc2nn(C3(CC#N)CCOCC3)c3cc[nH]c(=O)c23)cc1] | 4-((1-(4-(cyanomethyl)tetrahydro-2H-pyran-4-yl)-4-oxo-4,5-dihydro-1H-pyrazolo[4,3-c]pyridin-3-yl)amino)-N,N-dimethylbenzenesulfonamide | LRMS (ESI) calc'd for $C_{21}H_{25}N_6O_4S$ $[M + H]^+$: 457, found 457. |
| 5-255 | 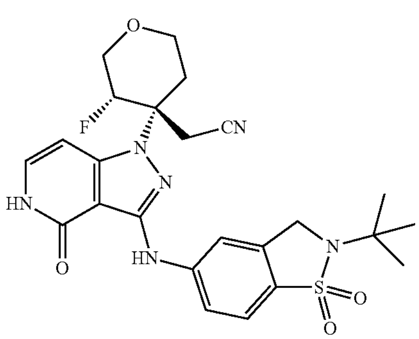 [SMILES: CC(C)(C)N1Cc2cc(Nc3nn([C@@]4(CC#N)CCOC[C@H]4F)c4cc[nH]c(=O)c34)ccc2S1(=O)=O] | 2-((3S,4S or 3R,4R)-4-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-3-fluorotetrahydro-2H-pyran-4-yl)acetonitrile (from racemic cis I-22) (Chiral HPLC on free pyridone using AD-H; Hexanes (0.1% DEA):EtOH (0.1% DEA) = 50:50, Tr = 21 minutes) | LRMS (ESI) calc'd for $C_{24}H_{28}FN_6O_4S$ $[M + H]^+$: 515 found 515. |
| 5-256 | 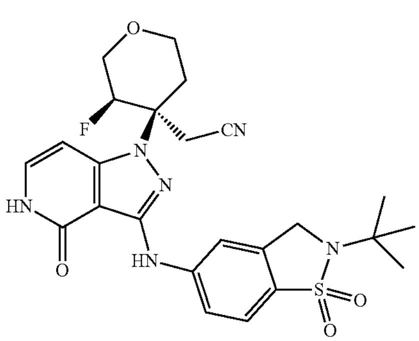 [SMILES: CC(C)(C)N1Cc2cc(Nc3nn([C@]4(CC#N)CCOC[C@@H]4F)c4cc[nH]c(=O)c34)ccc2S1(=O)=O] | 2-((3R,4R or 3S,4S)-4-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-3-fluorotetrahydro-2H-pyran-4-yl)acetonitrile (from racemic cis I-22) (Chiral HPLC on freee pyridone using AD-H; Hexanes (0.1% DEA):EtOH (0.1% DEA) = 50:50, Tr = 26 minutes) | LRMS (ESI) calc'd for $C_{24}H_{28}FN_6O_4S$ $[M + H]^+$: 515 found 515. |

TABLE 20-continued

| Example | Structure | Compound Name | LRMS |
|---|---|---|---|
| 5-257 | 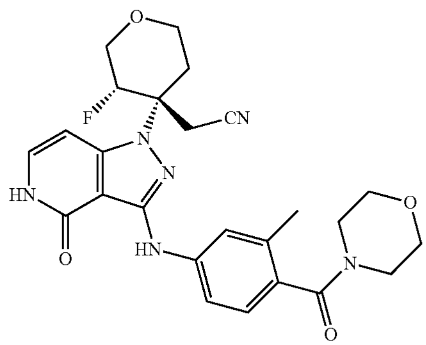 | 2-((3S,4S or 3R,4R)-3-fluoro-4-(3-(3-methyl-4-(morpholine-4-carbonyl)phenylamino)-4-oxo-4,5-dihydropyrazolo[4,3-c]pyridin-1-yl)-tetrahydro-2H-pyran-4-yl)acetonitrile (derived from I-22B) | LRMS (ESI) calc'd for $C_{25}H_{28}FN_6O_4$ [M + H]$^+$: 495, found 495. |
| 5-258 | 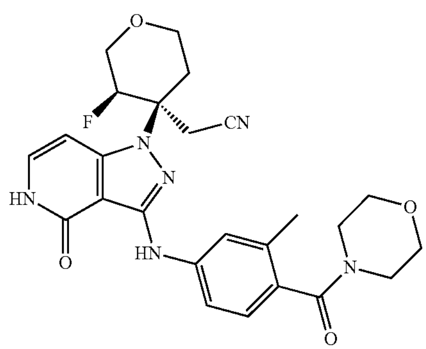 [SMILES: Cc1cc(Nc2nn([C@]3(CC#N)CCOC[C@@H]3F)c3cc[nH]c(=O)c23)ccc1C(=O)N1CCOCC1] | 2-((3R,4R or 3S,4S)-3-fluoro-4-(3-((3-methyl-4-(morpholine-4-carbonyl)phenyl)amino)-4-oxo-4,5-dihydro-1H-pyrazolo[4,3-c]pyridin-1-yl)tetrahydro-2H-pyran-4-yl)acetonitrile (derived from I-22A) | LRMS (ESI) calc'd for $C_{25}H_{28}FN_6O_4$ [M + H]$^+$: 495, found 495. |
| 5-259 | 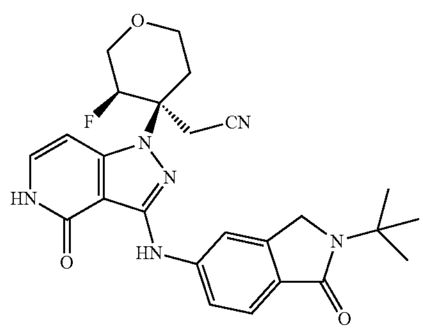 [SMILES: CC(C)(C)N1Cc2cc(Nc3nn([C@]4(CC#N)CCOC[C@@H]4F)c4cc[nH]c(=O)c34)ccc2C1=O] | 2-((3R,4R or 3S,4S)-4-(3-((2-(tert-butyl)-1-oxoisoindolin-5-yl)amino)-4-oxo-4,5-dihydro-1H-pyrazolo[4,3-c]pyridin-1-yl)-3-fluorotetrahydro-2H-pyran-4-yl)acetonitrile (derived from I-22A) | LRMS (ESI) calc'd for $C_{25}H_{28}FN_6O_3$ [M + H]$^+$: 479, found 479. |
| 5-260 | 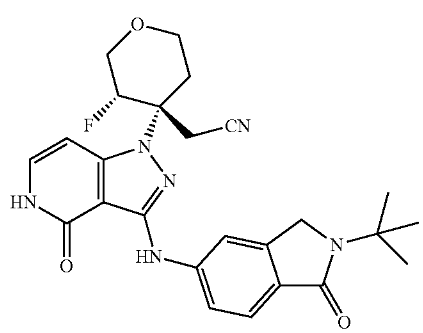 [SMILES: CC(C)(C)N1Cc2cc(Nc3nn([C@@]4(CC#N)CCOC[C@H]4F)c4cc[nH]c(=O)c34)ccc2C1=O] | 2-((3S,4S or 3R,4R)-4-(3-(2-tert-butyl-1-oxoisoindolin-5-ylamino)-4-oxo-4,5-dihydropyrazolo[4,3-c]pyridin-1-yl)-3-fluoro-tetrahydro-2H-pyran-4-yl)acetonitrile (derived from I-22B) | LRMS (ESI) calc'd for $C_{25}H_{28}FN_6O_3$ [M + H]$^+$: 479, found 479. |

TABLE 20-continued

| Example | Structure | Compound Name | LRMS |
|---|---|---|---|
| 5-261 | 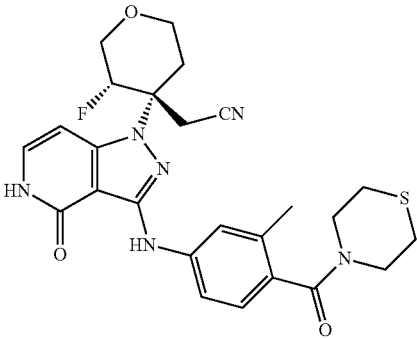 | 2-((3S,4S or 3R,4R)-3-fluoro-4-(3-(3-methyl-4-(thiomorpholine-4-carbonyl)phenylamino)-4-oxo-4,5-dihydropyrazolo[4,3-c]pyridin-1-yl)-tetrahydro-2H-pyran-4-yl)acetonitrile (derived from I-22B) | LRMS (ESI) calc'd for $C_{25}H_{28}FN_6O_3S$ $[M + H]^+$: 511, found 511. |
| 5-262 | 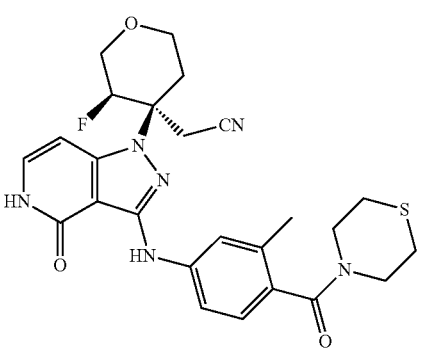 [SMILES: Cc1cc(Nc2nn([C@]3(CC#N)CCOC[C@@H]3F)c3cc[nH]c(=O)c23)ccc1C(=O)N1CCSCC1] | 2-((3R,4R or 3S,4S)-3-fluoro-4-(3-((3-methyl-4-(thiomorpholine-4-carbonyl)phenyl)amino)-4-oxo-4,5-dihydro-1H-pyrazolo[4,3-c]pyridin-1-yl)tetrahydro-2H-pyran-4-yl)acetonitrile (derived from I-22A) | LCMS (ESI) calc'd for $C_{25}H_{28}FN_6O_3S$ $[M + H]^+$: 511, found 511. |
| 5-263 | 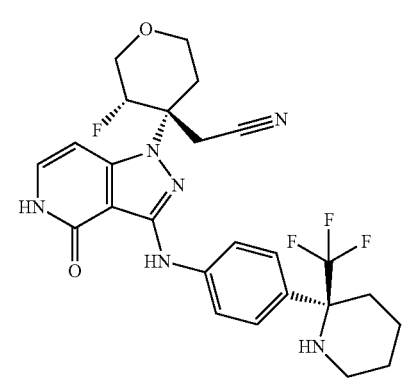 [SMILES: N#CC[C@]1(n2nc(Nc3ccc([C@]4(C(F)(F)F)CCCCN4)cc3)c3c(=O)[nH]ccc32)CCOC[C@H]1F] | 2-((3S,4S or 3R,4R)-3-fluoro-4-(4-oxo-3-((4-((S or R)-2-(trifluoromethyl)piperidin-2-yl)phenyl)amino)-4,5-dihydro-1H-pyrazolo[4,3-c]pyridin-1-yl)tetrahydro-2H-pyran-4-yl)acetonitrile (derived from I-22B and I-54B) | LRMS (ESI) calc'd for $C_{25}H_{27}F_4N_6O_2$ $[M + H]^+$: 519, found 519. |
| 5-264 | 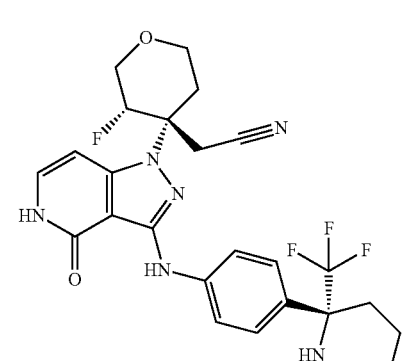 | 2-((3S,4S or 3R,4R)-3-fluoro-4-(4-oxo-3-((4-((R or S)-2-(trifluoromethyl)piperidin-2-yl)phenyl)amino)-4,5-dihydro-1H-pyrazolo[4,3-c]pyridin-1-yl)tetrahydro-2H-pyran-4-yl)acetonitrile (derived from I-22B and I-54A) | LRMS (ESI) calc'd for $C_{25}H_{27}F_4N_6O_2$ $[M + H]^+$: 519, found 519. |

TABLE 20-continued

| Example | Structure | Compound Name | LRMS |
|---|---|---|---|
| 5-265 | 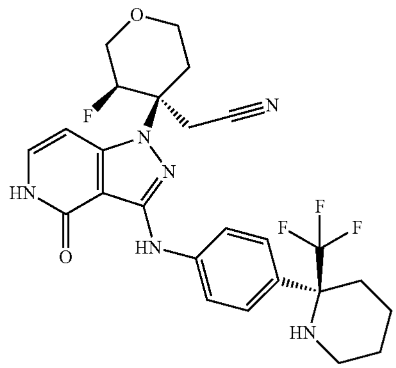 [SMILES: N#CC[C@@]1(n2nc(Nc3ccc([C@]4(C(F)(F)F)CCCCN4)cc3)c3c(=O)[nH]ccc32)CCOC[C@@H]1F] | 2-((3R,4R or 3S,4S)-3-fluoro-4-(4-oxo-3-((4-((S or R)-2-(trifluoromethyl)piperidin-2-yl)phenyl)amino)-4,5-dihydro-1H-pyrazolo[4,3-c]pyridin-1-yl)tetrahydro-2H-pyran-4-yl)acetonitrile (derived from I-22A and I-54B) | LRMS (ESI) calc'd for $C_{25}H_{27}F_4N_6O_2$ [M + H]$^+$: 519, found 519. |
| 5-266 | 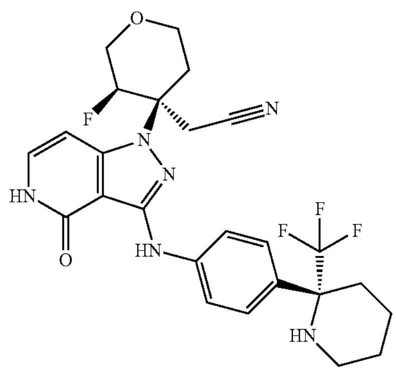 [SMILES: N#CC[C@@]1(n2nc(Nc3ccc([C@@]4(C(F)(F)F)CCCCN4)cc3)c3c(=O)[nH]ccc32)CCOC[C@@H]1F] | 2-((3R,4R or 3S,4S)-3-fluoro-4-(4-oxo-3-((4-((R or S)-2-(trifluoromethyl)piperidin-2-yl)phenyl)amino)-4,5-dihydro-1H-pyrazolo[4,3-c]pyridin-1-yl)tetrahydro-2H-pyran-4-yl)acetonitrile (derived from I-22A and I-54A) | LRMS (ESI) calc'd for $C_{25}H_{27}F_4N_6O_2$ [M + H]$^+$: 519, found 519. |
| 5-267 | 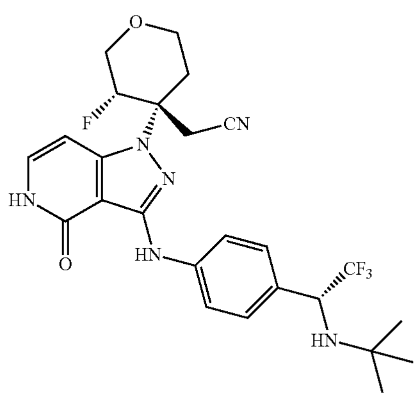 [SMILES: CC(C)(C)N[C@H](c1ccc(Nc2nn([C@@]3(CC#N)CCOC[C@H]3F)c3cc[nH]c(=O)c23)cc1)C(F)(F)F] | 2-((3S,4S or 3R,4R)-4-(3-((4-((R or S)-1-(tert-butylamino)-2,2,2-trifluoroethyl)phenyl)amino)-4-oxo-4,5-dihydro-1H-pyrazolo[4,3-c]pyridin-1-yl)-3-fluorotetrahydro-2H-pyran-4-yl)acetonitrile (from I-22B. The mixture was purified by Chiral HPLC with a Venusil Chiral ODH column, with hexanes:EtOH = 80:20, Tr = 27.5 minutes) | LRMS (ESI) calc'd for $C_{25}H_{29}F_4N_6O_2$ [M + H]$^+$: 521 found 521. |
| 5-268 | 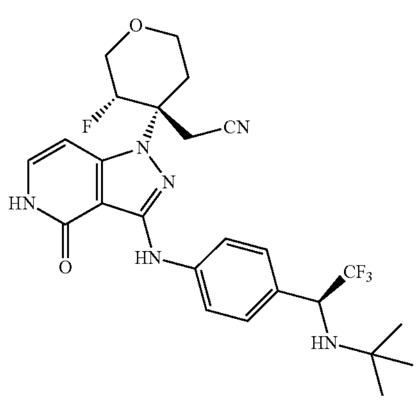 [SMILES: CC(C)(C)N[C@@H](c1ccc(Nc2nn([C@@]3(CC#N)CCOC[C@H]3F)c3cc[nH]c(=O)c23)cc1)C(F)(F)F] | 2-((3S,4S or 3R,4R)-4-(3-((4-((S or R)-1-(tert-butylamino)-2,2,2-trifluoroethyl)phenyl)amino)-4-oxo-4,5-dihydro-1H-pyrazolo[4,3-c]pyridin-1-yl)-3-fluorotetrahydro-2H-pyran-4-yl)acetonitrile (from I-22B. The mixture was purified by Chiral HPLC with a Venusil Chiral ODH column, with hexanes:EtOH = 80:20, Tr = 35.0 minutes) | LRMS (ESI) calc'd for $C_{25}H_{29}F_4N_6O_2$ [M + H]$^+$: 521 found 521. |

TABLE 20-continued

| Example | Structure | Compound Name | LRMS |
|---|---|---|---|
| 5-269 | 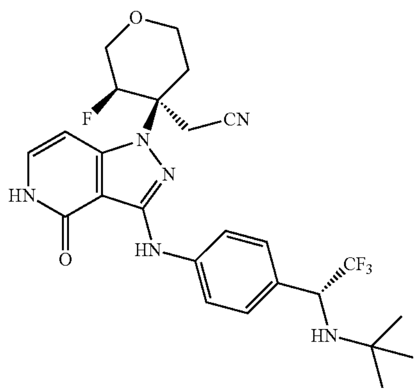 [SMILES: CC(C)(C)N[C@H](c1ccc(Nc2nn([C@]3(CC#N)CCOC[C@@H]3F)c3cc[nH]c(=O)c23)cc1)C(F)(F)F] | 2-((3R,4R or 3S,4S)-4-(3-((4-((R or S)-1-(tert-butylamino)-2,2,2-trifluoroethyl)phenyl)amino)-4-oxo-4,5-dihydro-1H-pyrazolo[4,3-c]pyridin-1-yl)-3-fluorotetrahydro-2H-pyran-4-yl)acetonitrile (from I-22A. The mixture was purified by Chiral HPLC with a Venusil Chiral ODH column using hexanes:EtOH (80:20), Tr = 38.0 minutes) | LRMS (ESI) calc'd for $C_{25}H_{29}F_4N_6O_2$ [M + H]$^+$: 521 found 521. |
| 5-270 | 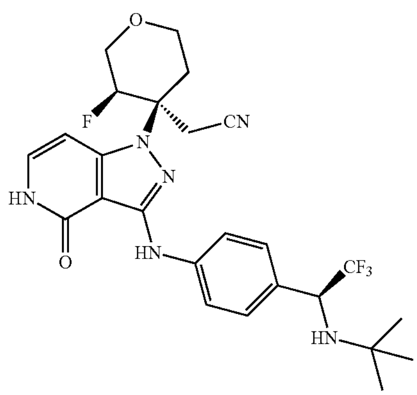 [SMILES: CC(C)(C)N[C@@H](c1ccc(Nc2nn([C@]3(CC#N)CCOC[C@@H]3F)c3cc[nH]c(=O)c23)cc1)C(F)(F)F] | 2-((3R,4R or 3S,4S)-4-(3-((4-((S or R)-1-(tert-butylamino)-2,2,2-trifluoroethyl)phenyl)amino)-4-oxo-4,5-dihydro-1H-pyrazolo[4,3-c]pyridin-1-yl)-3-fluorotetrahydro-2H-pyran-4-yl)acetonitrile (from I-22A. The mixture was purified by Chiral HPLC with a Venusil Chiral ODH column using hexanes:EtOH (80:20), Tr = 45.0 minutes) | LRMS (ESI) calc'd for $C_{25}H_{29}F_4N_6O_2$ [M + H]$^+$: 521 found 521. |
| 5-271 | 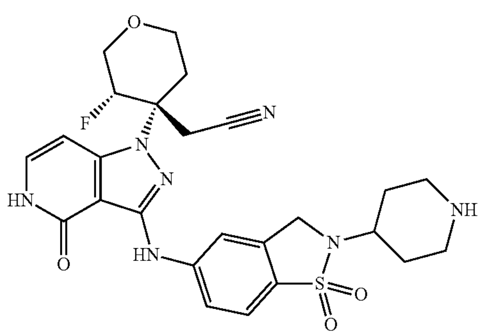 [SMILES: N#CC[C@]1(n2nc(Nc3ccc4c(c3)CN(C3CCNCC3)S4(=O)=O)c3c(=O)[nH]ccc32)CCOC[C@H]1F] | 2-[(3S,4S or 3R,4R)-4-(3-{[1,1-dioxo-2-(piperidin-4-yl)-3H-1,2-benzothiazol-5-yl]amino}-4-oxo-5H-pyrazolo[4,3-c]pyridin-1-yl)-3-fluorooxan-4-yl]acetonitrile (from I-22B) | LRMS (ESI) calc'd for $C_{25}H_{29}FN_7O_4S$ [M + H]$^+$: 542, found 542. |
| 5-272 | 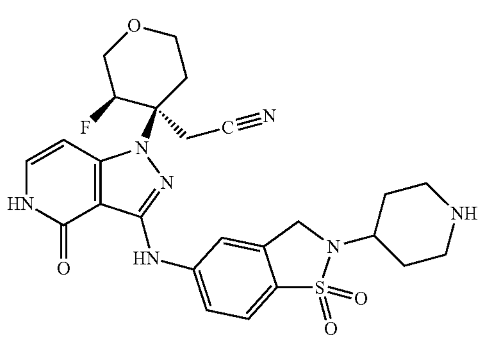 [SMILES: N#CC[C@@]1(n2nc(Nc3ccc4c(c3)CN(C3CCNCC3)S4(=O)=O)c3c(=O)[nH]ccc32)CCOC[C@@H]1F] | 2-((3R,4R or 3S,4S)-4-(3-((1,1-dioxido-2-(piperidin-4-yl)-2,3-dihydrobenzo[d]isothiazol-5-yl)amino)-4-oxo-4,5-dihydro-1H-pyrazolo[4,3-c]pyridin-1-yl)-3-fluorotetrahydro-2H-pyran-4-yl)acetonitrile (from I-22A) | LRMS (ESI) calc'd for $C_{25}H_{29}FN_7O_4S$ [M + H]$^+$: 542, found 542. |

TABLE 20-continued

| Example | Structure | Compound Name | LRMS |
|---|---|---|---|
| 5-273 | 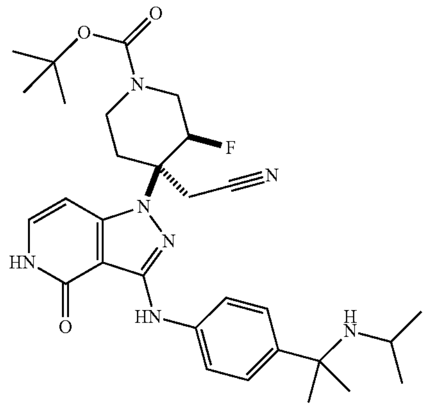 | tert-butyl (3R,4R)-4-(cyanomethyl)-3-fluoro-4-{3-[(4-{1-methyl-1-[(1-methylethyl)amino]ethyl}phenyl)amino]-4-oxo-4,5-dihydro-1H-pyrazolo[4,3-c]pyridin-1-yl}piperidine-1-carboxylate (from I-7-2B) | LRMS (ESI) calc'd for $C_{30}H_{41}FN_7O_3$ [M + H]$^+$: Calc'd 566, found 566. |
| 5-274 | 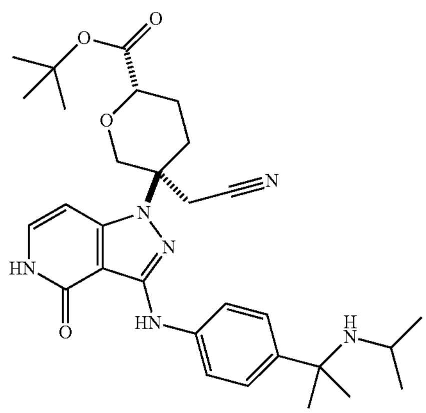 | (2S,5S)-tert-butyl 5-(cyanomethyl)-5-(3-((4-(2-(isopropylamino)propan-2-yl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{30}H_{41}N_6O_4$ [M + H]$^+$: Calc'd 549, found 549. |
| 5-275 | 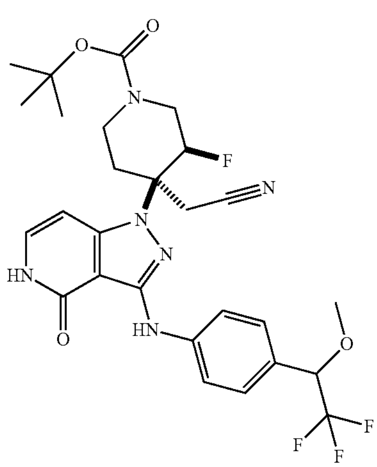 | tert-butyl (3R,4R)-4-(cyanomethyl)-3-fluoro-4-(3-{[4-(1-methoxyethyl)phenyl]amino}-4-oxo-4,5-dihydro-1H-pyrazolo[4,3-c]pyridin-1-yl)piperidine-1-carboxylate (from I-7-2B, as a mixture of ether diastereomers) | LRMS (ESI) calc'd for $C_{27}H_{31}F_4N_6O_4$ [M + H]$^+$: Calc'd 579, found 579. |

TABLE 20-continued

| Example | Structure | Compound Name | LRMS |
|---|---|---|---|
| 5-276 | 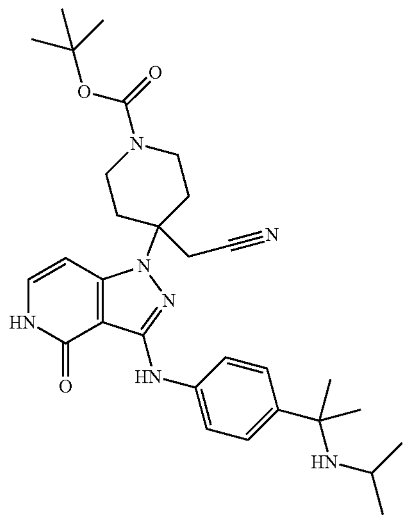 [SMILES: CC(C)NC(C)(C)c1ccc(Nc2nn(C3(CC#N)CCN(C(=O)OC(C)(C)C)CC3)c3cc[nH]c(=O)c23)cc1] | tert-butyl 4-(cyanomethyl)-4-{3-[(4-{1-methyl-1-[(1-methylethyl)amino]ethyl}phenyl)amino]-4-oxo-4,5-dihydro-1H-pyrazolo[4,3-c]pyridin-1-yl}piperidine-1-carboxylate | LRMS (ESI) calc'd for $C_{30}H_{42}N_7O_3$ [M + H]$^+$: Calc'd 548, found 548. |
| 5-277 | 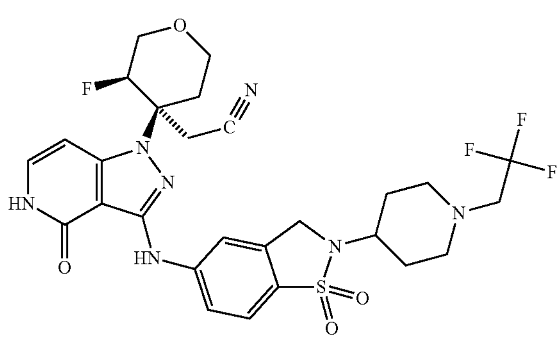 [SMILES: N#CC[C@@]1(n2nc(Nc3ccc4c(c3)CN(C3CCN(CC(F)(F)F)CC3)S4(=O)=O)c3c(=O)[nH]ccc32)CCOC[C@@H]1F] | 2-((3R,4R or 3S,4S)-4-(3-((1,1-dioxido-2-(1-(2,2,2-trifluoroethyl)piperidin-4-yl)-2,3-dihydrobenzo[d]isothiazol-5-yl)amino)-4-oxo-4,5-dihydro-1H-pyrazolo[4,3-c]pyridin-1-yl)-3-fluorotetrahydro-2H-pyran-4-yl)acetonitrile (from I-22A) | LRMS (ESI) calc'd for $C_{27}H_{30}F_4N_7O_4S$ [M + H]$^+$: 624, found 624. |
| 5-278 | 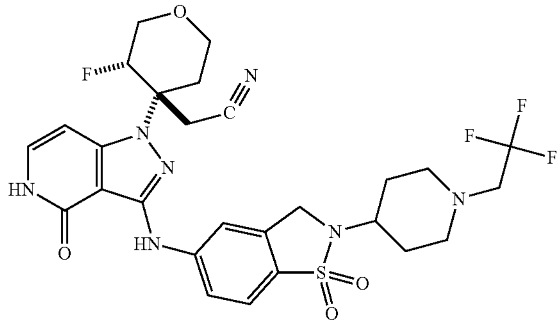 | 2-((3S,4S or 3R,4R)-4-(3-((1,1-dioxido-2-(1-(2,2,2-trifluoroethyl)piperidin-4-yl)-2,3-dihydrobenzo[d]isothiazol-5-yl)amino)-4-oxo-4,5-dihydro-1H-pyrazolo[4,3-c]pyridin-1-yl)-3-fluorotetrahydro-2H-pyran-4-yl)acetonitrile (from I-22B) | LRMS (ESI) calc'd for $C_{27}H_{30}F_4N_7O_4S$ [M + H]$^+$: 624, found 624. |

TABLE 20-continued

| Example | Structure | Compound Name | LRMS |
|---|---|---|---|
| 5-279 | 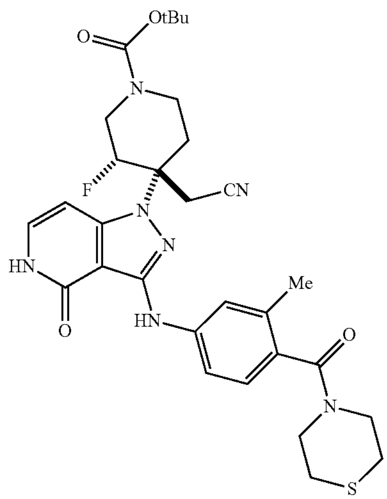 | (3R,4R)-tert-butyl 4-(cyanomethyl)-3-fluoro-4-(3-((3-methyl-4-(thiomorpholine-4-carbonyl)phenyl)amino)-4-oxo-4,5-dihydro-1H-pyrazolo[4,3-c]pyridin-1-yl)piperidine-1-carboxylate (from I-7-2B) | LRMS (ESI) Calc'd for $C_{30}H_{37}FN_7O_4S$ $[M + H]^+$: 610, found 610. |
| 5-280 | 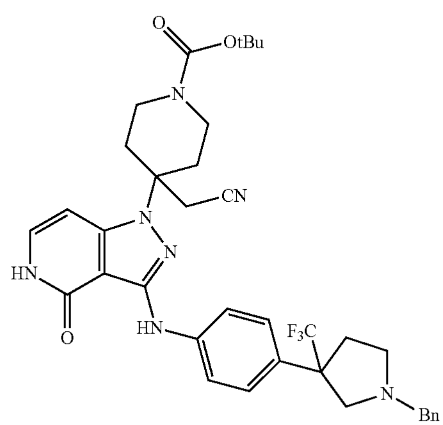 [SMILES: CC(C)(C)OC(=O)N1CCC(CC#N)(n2nc(Nc3ccc(C4(C(F)(F)F)CCN(Cc5ccccc5)C4)cc3)c3c(=O)[nH]ccc32)CC1] | (S or R) tert-butyl 4-(3-((4-(1-benzyl-3-(trifluoromethyl)pyrrolidin-3-yl)phenyl)amino)-4-oxo-4,5-dihydro-1H-pyrazolo[4,3-c]pyridin-1-yl)-4-(cyanomethyl)piperidine-1-carboxylate (Derived from free pyridone Peak 2 via SFC: AD-H, 30% MeOH + 0.25% DMEA in $CO_2$, Tr = 7.8 minutes) | LRMS (ESI) Calc'd for $C_{36}H_{41}F_3N_7O_3$ $[M + H]^+$: 676, found 676. |
| 5-281 | 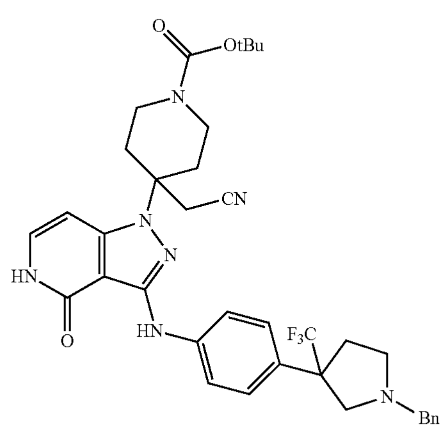 [SMILES: CC(C)(C)OC(=O)N1CCC(CC#N)(n2nc(Nc3ccc(C4(C(F)(F)F)CCN(Cc5ccccc5)C4)cc3)c3c(=O)[nH]ccc32)CC1] | (S or R) tert-butyl 4-(3-((4-(1-benzyl-3-(trifluoromethyl)pyrrolidin-3-yl)phenyl)amino)-4-oxo-4,5-dihydro-1H-pyrazolo[4,3-c]pyridin-1-yl)-4-(cyanomethyl)piperidine-1-carboxylate (Derived from free pyridone Peak 1 via SFC: AD-H, 30% MeOH + 0.25% DMEA in $CO_2$, Tr = 4.7 minutes) | LRMS (ESI) Calc'd for $C_{36}H_{41}F_3N_7O_3$ $[M + H]^+$: 676, found 676. |

TABLE 20-continued

| Example | Structure | Compound Name | LRMS |
|---|---|---|---|
| 5-282 | 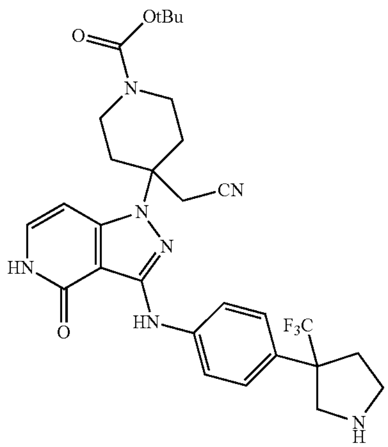 [SMILES: CC(C)(C)OC(=O)N1CCC(CC#N)(n2nc(Nc3ccc(C4(C(F)(F)F)CCNC4)cc3)c3c(=O)[nH]ccc32)CC1] | (S or R) tert-butyl 4-(cyanomethyl)-4-(4-oxo-3-((4-(3-(trifluoromethyl)pyrrolidin-3-yl)phenyl)amino)-4,5-dihydro-1H-pyrazolo[4,3-c]pyridin-1-yl)piperidine-1-carboxylate (Derived from free pyridone Peak 1 via SFC: ID, 35% MeOH + 0.25% DMEA in $CO_2$, Tr = 3.5 minutes) | LRMS (ESI) Calc'd for $C_{29}H_{35}F_3N_7O_3$ $[M + H]^+$: 586, found 586. |
| 5-283 | 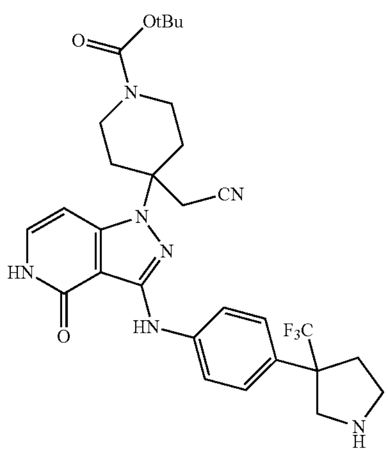 [SMILES: CC(C)(C)OC(=O)N1CCC(CC#N)(n2nc(Nc3ccc(C4(C(F)(F)F)CCNC4)cc3)c3c(=O)[nH]ccc32)CC1] | (S or R) tert-butyl 4-(cyanomethyl)-4-(4-oxo-3-((4-(3-(trifluoromethyl)pyrrolidin-3-yl)phenyl)amino)-4,5-dihydro-1H-pyrazolo[4,3-c]pyridin-1-yl)piperidine-1-carboxylate (Derived from free pyridone Peak 2 via SFC: ID, 35% MeOH + 0.25% DMEA in $CO_2$, Tr = 5.2 minutes) | LRMS (ESI) Calc'd for $C_{29}H_{35}F_3N_7O_3$ $[M + H]^+$: 586, found 586. |
| 5-284 | 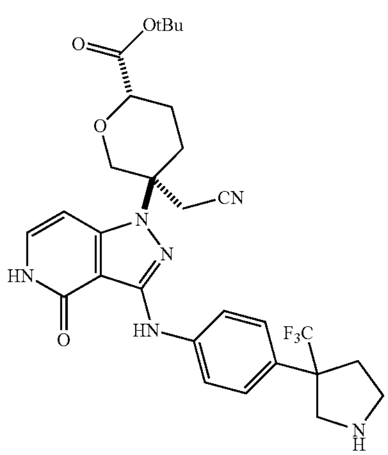 | (2S,5S)-tert-butyl 5-(cyanomethyl)-5-(4-oxo-3-((4-((R or S)-3-(trifluoromethyl)pyrrolidin-3-yl)phenyl)amino)-4,5-dihydro-1H-pyrazolo[4,3-c]pyridin-1-yl)tetrahydro-2H-pyran-2-carboxylate (from I-14-1A. Derived from free pyridone Peak 1 via SFC: ID, 35% MeOH + 0.25% DMEA in $CO_2$, Tr = 3.9 minutes) | LRMS (ESI) Calc'd for $C_{29}H_{34}F_3N_6O_4$ $[M + H]^+$: 587, found 587. |

TABLE 20-continued

| Example | Structure | Compound Name | LRMS |
|---|---|---|---|
| 5-285 | 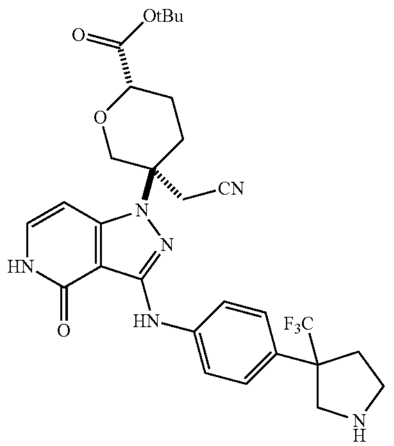 | (2S,5S)-tert-butyl 5-(cyanomethyl)-5-(4-oxo-3-((4-((R or S)-3-(trifluoromethyl)pyrrolidin-3-yl)phenyl)amino)-4,5-dihydro-1H-pyrazolo[4,3-c]pyridin-1-yl)tetrahydro-2H-pyran-2-carboxylate (from I-14-1A. Derived from free pyridone Peak 2 via SFC: ID, 35% MeOH + 0.25% DMEA in $CO_2$, Tr = 5.7 minutes) | LRMS (ESI) Calc'd for $C_{29}H_{34}F_3N_6O_4$ $[M + H]^+$: 587, found 587. |
| 5-286 | 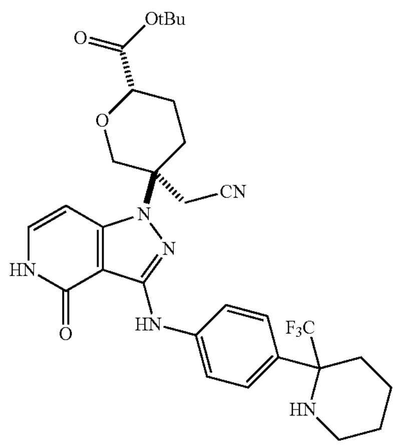 | (2S,5S)-tert-butyl 5-(cyanomethyl)-5-(4-oxo-3-((4-((S or R)-2-(trifluoromethyl)piperidin-2-yl)phenyl)amino)-4,5-dihydro-1H-pyrazolo[4,3-c]pyridin-1-yl)tetrahydro-2H-pyran-2-carboxylate (from I-14-1A. Derived from free pyridone Peak 1 via SFC: ID, 30% iPrOH + 0.25% DMEA in $CO_2$, Tr = 6.7 minutes) | LRMS (ESI) Calc'd for $C_{30}H_{36}F_3N_6O_4$ $[M + H]^+$: 601, found 601. |
| 5-287 | 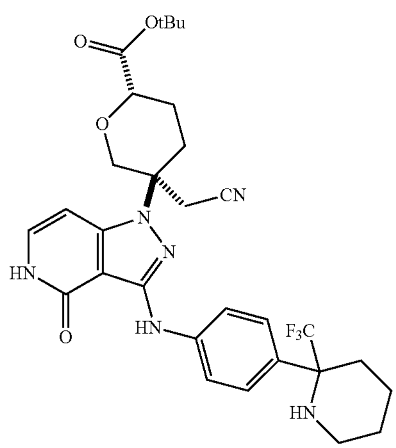 | (2S,5S)-tert-butyl 5-(cyanomethyl)-5-(4-oxo-3-((4-((S or R)-2-(trifluoromethyl)piperidin-2-yl)phenyl)amino)-4,5-dihydro-1H-pyrazolo[4,3-c]pyridin-1-yl)tetrahydro-2H-pyran-2-carboxylate (from I-14-1A. Derived from free pyridone Peak 2 via SFC: ID, 30% iPrOH + 0.25% DMEA in $CO_2$, Tr = 8.3 minutes) | LRMS (ESI) Calc'd for $C_{30}H_{36}F_3N_6O_4$ $[M + H]^+$: 601, found 601. |
| 5-288 | 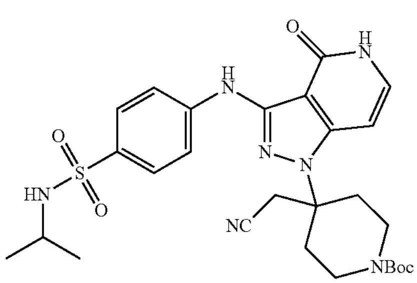 [SMILES: CC(C)NS(=O)(=O)c1ccc(Nc2nn(C3(CC#N)CCN(C(=O)OC(C)(C)C)CC3)c3cc[nH]c(=O)c23)cc1] | tert-butyl 4-(cyanomethyl)-4-(3-((4-(N-isopropylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{27}H_{36}N_7O_5S$ $[M + H]^+$: 570, found 570. |

TABLE 20-continued

| Example | Structure | Compound Name | LRMS |
|---|---|---|---|
| 5-289 | 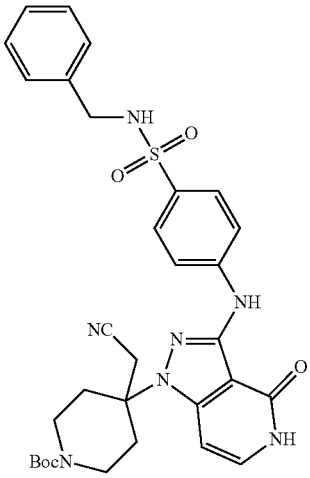 [SMILES: CC(C)(C)OC(=O)N1CCC(CC#N)(n2nc(Nc3ccc(S(=O)(=O)NCc4ccccc4)cc3)c3c(=O)[nH]ccc32)CC1] | tert-butyl 4-(3-((4-(N-benzylsulfamoyl)phenyl)amino)-4-oxo-4,5-dihydro-1H-pyrazolo[4,3-c]pyridin-1-yl)-4-(cyanomethyl)piperidine-1-carboxylate | LRMS (ESI) calc'd for $C_{26}H_{28}N_7O_3S$ [M − Boc + H]$^+$: 518, found 518. |
| 5-290 | 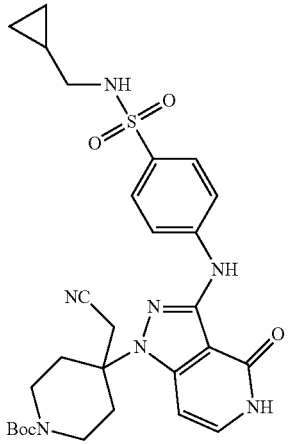 [SMILES: CC(C)(C)OC(=O)N1CCC(CC#N)(n2nc(Nc3ccc(S(=O)(=O)NCC4CC4)cc3)c3c(=O)[nH]ccc32)CC1] | tert-butyl 4-(cyanomethyl)-4-(3-((4-(N-(cyclopropylmethyl)sulfamoyl)phenyl)amino)-4-oxo-4,5-dihydro-1H-pyrazolo[4,3-c]pyridin-1-yl)piperidine-1-carboxylate | LRMS (ESI) calc'd for $C_{23}H_{28}N_7O_3S$ [M − Boc + H]$^+$: 482, found 482. |
| 5-291 | 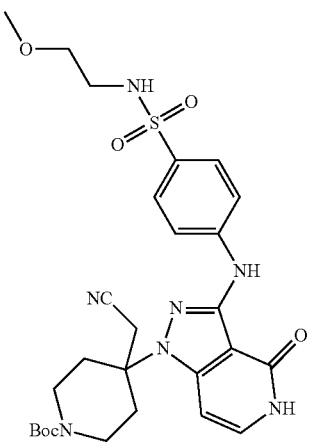 [SMILES: COCCNS(=O)(=O)c1ccc(Nc2nn(C3(CC#N)CCN(C(=O)OC(C)(C)C)CC3)c3cc[nH]c(=O)c23)cc1] | tert-butyl 4-(cyanomethyl)-4-(3-((4-(N-(2-methoxyethyl)sulfamoyl)phenyl)amino)-4-oxo-4,5-dihydro-1H-pyrazolo[4,3-c]pyridin-1-yl)piperidine-1-carboxylate | LRMS (ESI) calc'd for $C_{22}H_{28}N_7O_4S$ [M − Boc + H]$^+$: 486, found 486. |

TABLE 20-continued

| Example | Structure | Compound Name | LRMS |
|---|---|---|---|
| 5-292 | 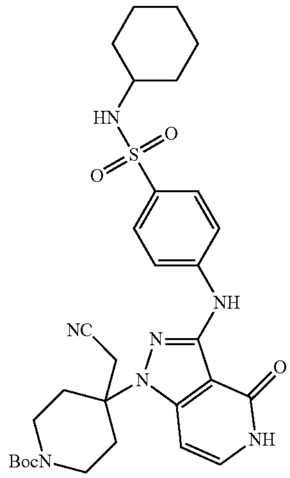 [SMILES: CC(C)(C)OC(=O)N1CCC(CC#N)(n2nc(Nc3ccc(S(=O)(=O)NC4CCCCC4)cc3)c3c(=O)[nH]ccc32)CC1] | tert-butyl 4-(cyanomethyl)-4-(3-((4-(N-cyclohexylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{30}H_{40}N_7O_5S$ $[M + H]^+$: 610, found 610. |
| 5-293 | 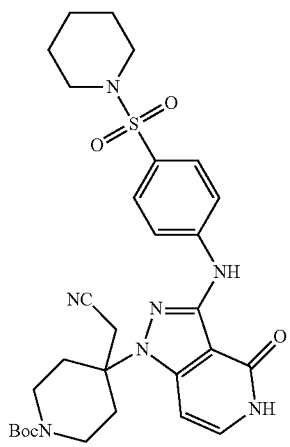 [SMILES: CC(C)(C)OC(=O)N1CCC(CC#N)(n2nc(Nc3ccc(S(=O)(=O)N4CCCCC4)cc3)c3c(=O)[nH]ccc32)CC1] | tert-butyl 4-(cyanomethyl)-4-(4-oxo-3-((4-(piperidin-1-ylsulfonyl)phenyl)amino)-4,5-dihydro-1H-pyrazolo[4,3-c]pyridin-1-yl)piperidine-1-carboxylate | LRMS (ESI) calc'd for $C_{29}H_{38}N_7O_5S$ $[M + H]^+$: 596, found 596. |
| 5-294 | 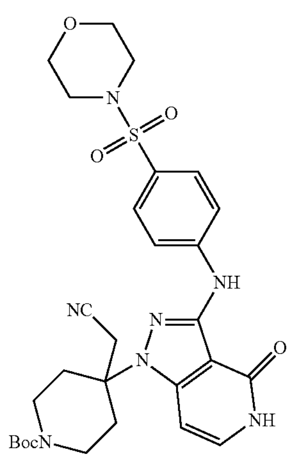 [SMILES: CC(C)(C)OC(=O)N1CCC(CC#N)(n2nc(Nc3ccc(S(=O)(=O)N4CCOCC4)cc3)c3c(=O)[nH]ccc32)CC1] | tert-butyl 4-(cyanomethyl)-4-(3-((4-(morpholinosulfonyl)phenyl)amino)-4-oxo-4,5-dihydro-1H-pyrazolo[4,3-c]pyridin-1-yl)piperidine-1-carboxylate | LRMS (ESI) calc'd for $C_{28}H_{36}N_7O_6S$ $[M + H]^+$: 598, found 598. |

TABLE 20-continued

| Example | Structure | Compound Name | LRMS |
|---|---|---|---|
| 5-295 | 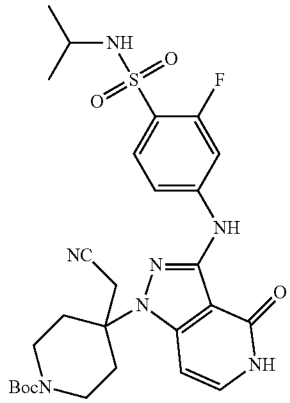 [SMILES: CC(C)NS(=O)(=O)c1ccc(Nc2nn(C3(CC#N)CCN(C(=O)OC(C)(C)C)CC3)c3cc[nH]c(=O)c23)cc1F] | tert-butyl 4-(cyanomethyl)-4-(3-((3-fluoro-4-(N-isopropylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{27}H_{34}FN_7O_5SNa$ [M + Na]$^+$: 610, found 610. |
| 5-296 | 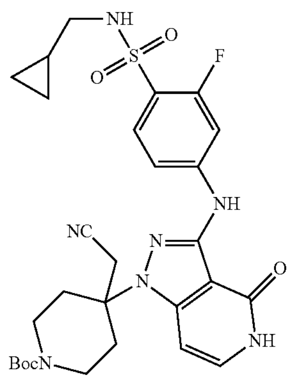 [SMILES: CC(C)(C)OC(=O)N1CCC(CC#N)(n2nc(Nc3ccc(S(=O)(=O)NCC4CC4)c(F)c3)c3c(=O)[nH]ccc32)CC1] | tert-butyl 4-(cyanomethyl)-4-(3-((4-(N-(cyclopropylmethyl)sulfamoyl)-3-fluorophenyl)amino)-4-oxo-4,5-dihydro-1H-pyrazolo[4,3-c]pyridin-1-yl)piperidine-1-carboxylate | LRMS (ESI) calc'd for $C_{28}H_{34}FN_7O_5SNa$ [M + Na]$^+$: 622, found 622. |

Example 6

(4-{3-[(4-fluorophenyl)amino]-4-oxo-4,5-dihydro-1H-pyrazolo[4,3-c]pyridin-1-yl}piperidin-4-yl)acetonitrile

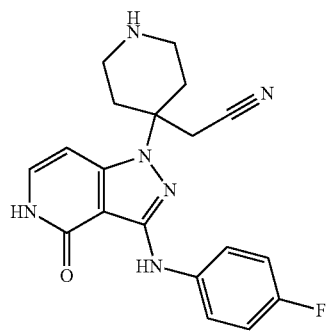

Step 1: (4-{4-(benzyloxy)-3-[(4-fluorophenyl)amino]-1H-pyrazolo[4,3-c]pyridin-1-yl}piperidin-4-yl)acetonitrile

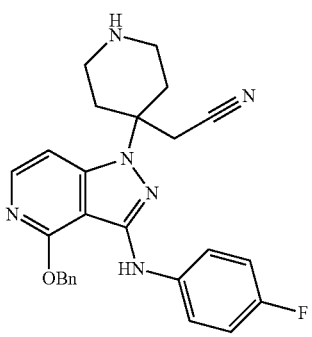 [SMILES: N#CCC1(n2nc(Nc3ccc(F)cc3)c3c(OCc4ccccc4)nccc32)CCNCC1]

To a solution of tert-butyl 4-{4-(benzyloxy)-3-[(4-fluorophenyl)amino]-1H-pyrazolo[4,3-c]pyridin-1-yl}-4-(cyanomethyl)piperidine-1-carboxylate (Example 5-48, step 1) (32 mg, 0.057 mmol) in $CH_2Cl_2$ (1 mL) was added TFA (0.10 mL, 1.3 mmol). The reaction was stirred at room temperature for 30 minutes, diluted with EtOAc, and then washed with 1N NaOH and brine. The organic layer was dried over $Na_2SO_4$, filtered, and concentrated in vacuo. The crude title compound was used as is in the next step. LRMS (ESI) calc'd for $C_{26}H_{26}FN_6O$ [M+H]$^+$: 457, found 457.

Step 2: (4-{3-[(4-fluorophenyl)amino]-4-oxo-4,5-dihydro-1H-pyrazolo[4,3-c]pyridin-1-yl}piperidin-4-yl)acetonitrile (6)

To a solution of crude (4-{4-(benzyloxy)-3-[(4-fluorophenyl)amino]-1H-pyrazolo[4,3-c]pyridin-1-yl}piperidin-4-yl)acetonitrile (28 mg, 0.061 mmol) in EtOAc (0.5 mL) and EtOH (0.5 mL) was added 10% wt. Pd/C (5 mg). The reaction was placed under 1 atmosphere of hydrogen and stirred vigorously at room temperature for 2 hours. The hydrogen atmosphere was removed and then the catalyst was removed by filtration through Celite. The filtrate was concentrated in vacuo and the residue was purified by mass triggered reverse phase HPLC, eluting with acetonitrile/water containing 0.1% TFA modifier. Fractions containing desired product were lyophilized to afford compound 7 as the TFA salt. LRMS (ESI) calc'd for $C_{19}H_{20}FN_6O$ [M+H]$^+$: 367, found 367. $^1$H NMR (600 MHz, DMSO-d6): δ 11.35 (d, J=6.0 Hz, 1H), 8.40-8.55 (m, 2H), 8.20 (s, 1H), 7.63 (m, 2H), 7.21 (t, J=6.6 Hz, 1H), 7.07 (t, J=8.4 Hz, 2H), 6.66 (d, J=7.2 Hz, 1H), 3.26-3.34 (m, 4H), 2.97 (m, 2H), 2.82 (m, 2H), 2.19 (m, 2H).

Example 7

[1-(cyclopropylcarbonyl)-4-{3-[(4-fluorophenyl)amino]-4-oxo-4,5-dihydro-1H-pyrazolo[4,3-c]pyridin-1-yl}piperidin-4-yl]acetonitrile

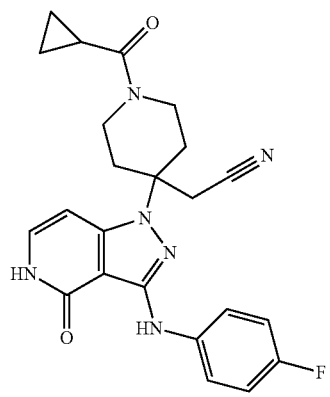

7

Step 1: [4-{4-(benzyloxy)-3-[(4-fluorophenyl)amino]-1H-pyrazolo[4,3-c]pyridin-1-yl}-1-(cyclopropylcarbonyl)piperidin-4-yl]acetonitrile

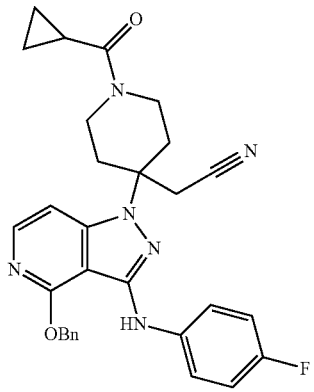 [SMILES: N#CCC1(n2nc(Nc3ccc(F)cc3)c3c(OCc4ccccc4)nccc32)CCN(C(=O)C2CC2)CC1]

To a solution of crude (4-{4-(benzyloxy)-3-[(4-fluorophenyl)amino]-1H-pyrazolo[4,3-c]pyridin-1-yl}piperidin-4-yl)acetonitrile (Example 6, Step 1) (21 mg, 0.046 mmol) in $CH_2Cl_2$ (1.0 mL) was added DIPEA (24.0 µL, 0.138 mmol) followed by cyclopropanecarbonyl chloride (6.3 µL, 0.069 mmol). The reaction was stirred at room temperature for 30 minutes and then diluted with EtOAc and washed with saturated aqueous NaHCO$_3$ and brine. The organic layer was dried over Na$_2$SO$_4$, filtered, and concentrated in vacuo. Purification of the residue using silica chromatography, eluting with 0-100% EtOAc in hexanes afforded the title compound. LRMS (ESI) calc'd for $C_{30}H_{30}FN_6O_2$ [M+H]$^+$: 525, found 525.

Step 2: [1-(cyclopropylcarbonyl)-4-{3-[(4-fluorophenyl)amino]-4-oxo-4,5-dihydro-1H-pyrazolo[4,3-c]pyridin-1-yl}piperidin-4-yl]acetonitrile (7)

To a solution of [4-{4-(benzyloxy)-3-[(4-fluorophenyl)amino]-1H-pyrazolo[4,3-c]pyridin-1-yl}-1-(cyclopropylcarbonyl)piperidin-4-yl]acetonitrile (12 mg, 0.024 mmol) in EtOAc (1.5 mL) and EtOH (0.5 mL) was added Pd/C (5.0 mg, 10% wt.). The reaction was placed under 1 atmosphere of hydrogen and stirred vigorously at room temperature for 2 hours. The hydrogen atmosphere was removed and the reaction was filtered through Celite and the filtrate was concentrated in vacuo. The residue was purified by silica chromatography, eluting with 0-5% MeOH in EtOAc to afford compound 7. LRMS (ESI) calc'd for $C_{23}H_{24}FN_6O_2$ [M+H]$^+$: 435, found 435. $^1$H NMR (600 MHz, CD$_3$OD): δ 8.06 (s, 1H), 7.60 (m, 2H), 7.19 (d, J=7.2 Hz, 1H), 7.01 (t, J=8.4 Hz, 2H), 6.73 (d, J=7.8 Hz, 1H), 5.47 (s, 1H), 4.25 (m, 2H), 3.51 (m, 1H), 3.14 (s, 2H), 2.86-3.15 (m, 3H), 1.95-2.18 (m, 3H), 0.74-0.90 (m, 4H).

Example 8-1

4-({1-[1-benzyl-4-(cyanomethyl)piperidin-4-yl]-4-oxo-4,5-dihydro-1H-pyrazolo[4,3-c]pyridin-3-yl}amino)-N,N-dimethylbenzenesulfonamide 8-1

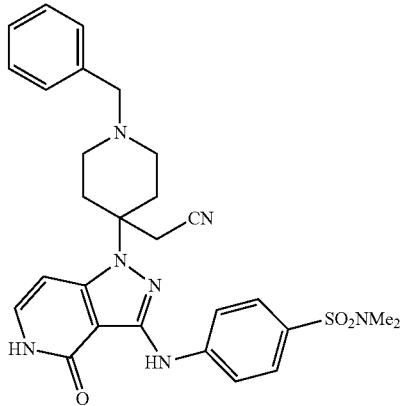

Step 1: 3-((4-(benzyloxy)-1-(4-(cyanomethyl)piperidin-4-yl)-1H-pyrazolo[4,3-c]pyridin-3-yl)amino)-N,N-dimethylbenzenesulfonamide

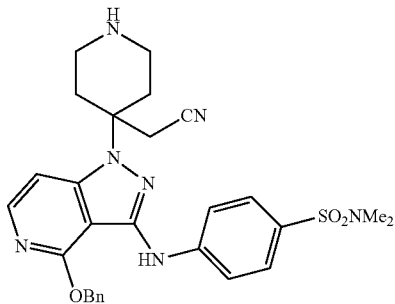

To a solution of tert-butyl 4-(4-(benzyloxy)-3-((3-(N,N-dimethylsulfamoyl)phenyl)amino)-1H-pyrazolo[4,3-c]pyridin-1-yl)-4-(cyanomethyl)piperidine-1-carboxylate (5-1a) (3.50 g, 5.42 mmol) in $CH_2Cl_2$ (46 mL) at 0° C., was added tetrafluoroboric acid-diethyl ether complex (1.55 mL, 11.4 mmol). The reaction mixture was stirred and warmed to room temperature over 4 hours. The reaction was quenched with saturated aqueous $NaHCO_3$, and diluted with $CH_2Cl_2$. The layers were separated, and the aqueous layer was extracted with $CH_2Cl_2$ (×3). The combined organics were washed with brine, dried over $Na_2SO_4$, filtered and concentrated in vacuo to afford the title compound as a solid. $^1H$ NMR (500 MHz, $CDCl_3$): δ 7.93 (d, J=6.5 Hz, 1H), 7.73-7.70 (m, 3H), 7.56-7.44 (m, 6 H), 6.98 (d, J=6.5 Hz, 1H), 5.60 (s, 2H), 3.21-3.10 (m, 2H), 3.02-2.96 (m, 6H), 2.69 (s, 6H), 2.28-2.24 (m, 2H).

Step 2: 4-({1-[1-benzyl-4-(cyanomethyl)piperidin-4-yl]-4,5-dihydro-1H-pyrazolo[4,3-c]pyridin-3-yl}amino)-N,N-dimethylbenzenesulfonamide (8-1)

An oven dried reaction vessel was charged with 3-((4-(benzyloxy)-1-(4-(cyanomethyl)piperidin-4-yl)-1H-pyrazolo[4,3-c]pyridin-3-yl)amino)-N,N-dimethylbenzenesulfonamide (20 mg, 0.037 mmol), DMF (0.19 mL, 0.2 M), benzaldehyde (3.8 mg, 0.037 mmol), TFA (18.8 mg, 0.165 mmol), and triacetoxyborohydride (39 mg, 0.183 mmol). The reaction vessel was sealed and heated to 50° C. overnight. Upon cooling to room temperature, HCl in dioxane (0.10 mL, 2M) was added, and the reaction mixture was stirred for an additional 4 hours. The crude reaction mixture was filtered and purified using mass directed reverse phase column chromatography to afford Example 8-1. LRMS (ESI) calc'd for $C_{28}H_{32}N_7O_3S$ [M+H]+: 546, found 546. $^1H$ NMR (600 MHz, DMSO-d6): δ 11.31 (s, 1H) 8.68 (s, 1H), 7.83 (d, J=8.5 Hz, 2H), 7.59 (d, J=8.5 Hz, 2H), 7.26 (m, 3H), 7.18 (m, 1H), 7.16 (m, 1H), 6.67 (m, 1H), 6.51 (m, 1H), 3.71 (br s, 1H), 2.65 (d, 2H), 2.54 (s, 6H), 2.08 (m, 1H), 1.36 (s, 2H).

The following compounds in Table 21 were prepared in analogy to Example 8-1 above.

TABLE 21

| Example | Structure | Compound Name | LRMS |
|---|---|---|---|
| 8-2 | 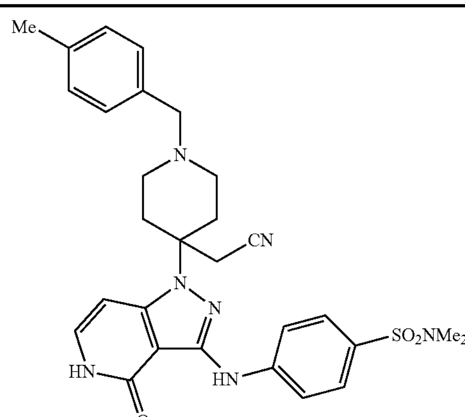 | 4-({1-[4-(cyanomethyl)-1-(4-methylbenzyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{29}H_{34}N_7O_3S$ [M + H]+: 560, found 560. |

TABLE 21-continued

| Example | Structure | Compound Name | LRMS |
|---|---|---|---|
| 8-3 | 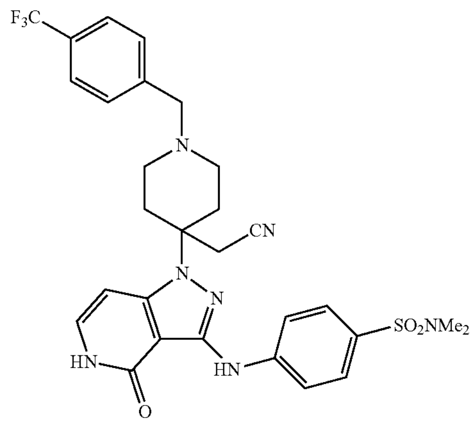 | 4-[(1-{4-(cyanomethyl)-1-[4-(trifluoromethyl)benzyl]piperidin-4-yl}-4-oxo-4,5-dihydro-1H-pyrazolo[4,3-c]pyridin-3-yl)amino]-N,N-dimethyl benzenesulfonamide | LRMS (ESI) calc'd for $C_{29}H_{31}F_3N_7O_3S$ $[M + H]^+$: 614, found 614. |
| 8-4 | 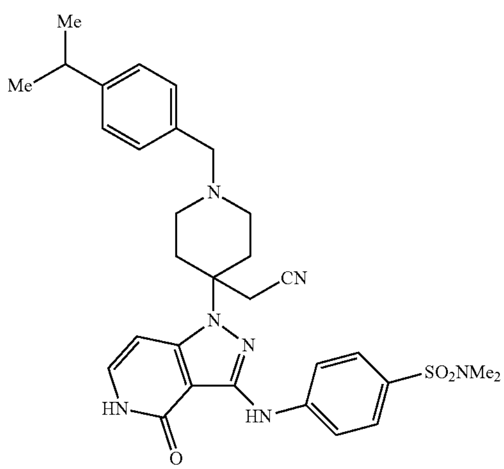 | 4-[(1-{4-(cyanomethyl)-1[4-(1-methylethyl)benzyl]piperidin-4-yl}-4-oxo-4,5-dihydro-1H-pyrazolo[4,3-c]pyridin-3-yl)amino]-N,N-dimethylbenzene sulfonamide | LRMS (ESI) calc'd for $C_{31}H_{38}N_7O_3S$ $[M + H]^+$: 588, found 588. |
| 8-5 | 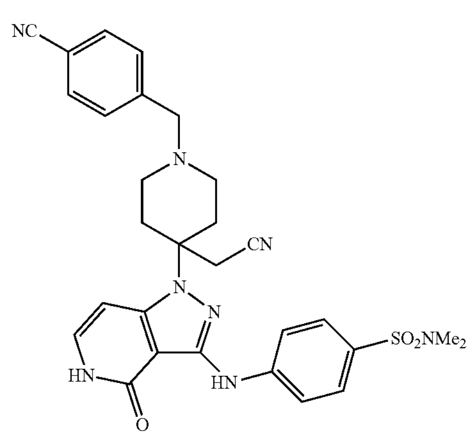 | 4-[(1-{4-(cyanomethyl)-1-[4-(1-methylethyl)benzyl]piperidin-4-yl}-4-oxo-4,5-dihydro-1H-pyrazolo[4,3-c]pyridin-3-yl)amino]-N,N-dimethylbenzene sulfonamide | LRMS (ESI) calc'd for $C_{29}H_{31}N_8O_3S$ $[M + H]^+$: 571, found 571. |

TABLE 21-continued

| Example | Structure | Compound Name | LRMS |
|---|---|---|---|
| 8-6 | 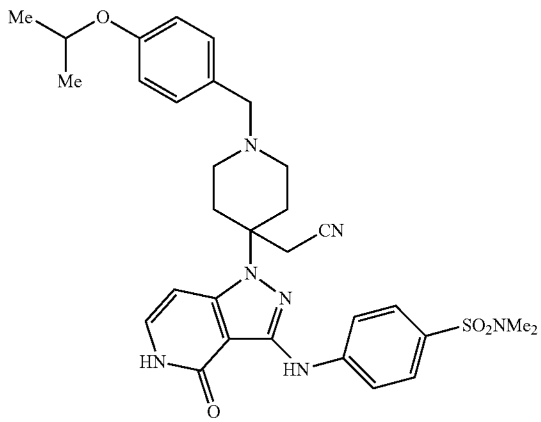 | 4-[(1-{4-(cyanomethyl)-1-[4-(1methylethoxy)benzyl]piperidin-4-yl}-4-oxo-4,5-dihydro-1H-pyrazolo[4,3-c]pyridin-3-yl)amino]-N,N-dimethylbenzene sulfonamide | LRMS (ESI) calc'd for $C_{31}H_{38}N_7O_4S$ $[M + H]^+$: 604, found 604. |
| 8-7 | 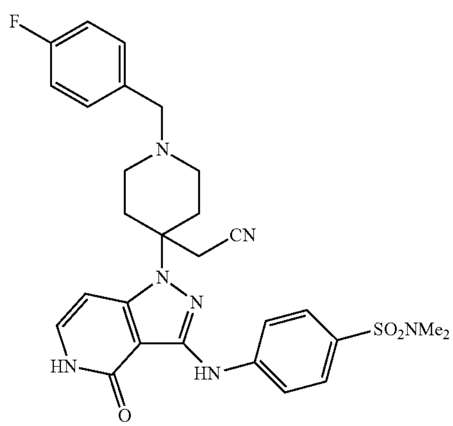 | 4-({1-[4-(cyanomethyl)-1-(4-fluorobenzyl)piperidin-4-yl]-4-oxo-4,5-dihydro-1H-pyrazolo[4,3-c]pyridin-3-yl}amino)-N,N-dimethylbenzene sulfonamide | LRMS (ESI) calc'd for $C_{28}H_{31}FN_7O_3S$ $[M + H]^+$: 564, found 564. |
| 8-8 | 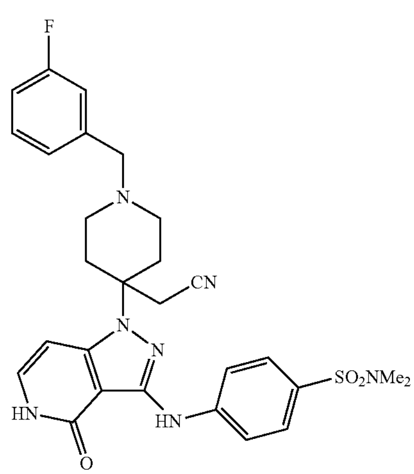 | 4-({1-[4-(cyanomethyl)-1-(3-fluorobenzyl)piperidin-4-yl]-4-oxo-4,5-dihydro-1H-pyrazolo[4,3-c]pyridin-3-yl}amino)-N,N-dimethylbenzene sulfonamide | LRMS (ESI) calc'd for $C_{28}H_{31}FN_7O_3S$ $[M + H]^+$: 564, found 564. |

TABLE 21-continued

| Example | Structure | Compound Name | LRMS |
|---------|-----------|---------------|------|
| 8-9 | 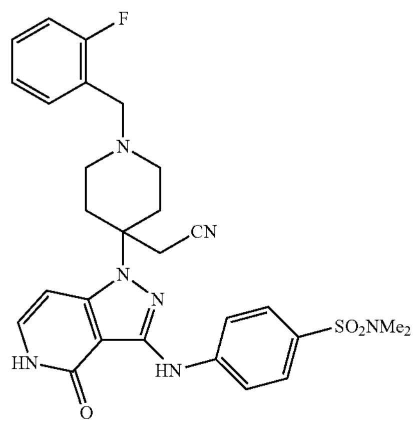 | 4-({1-[4-(cyanomethyl)-1-(2-fluorobenzyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{28}H_{31}FN_7O_3S$ [M + H]$^+$: 564, found 564. |
| 8-10 | 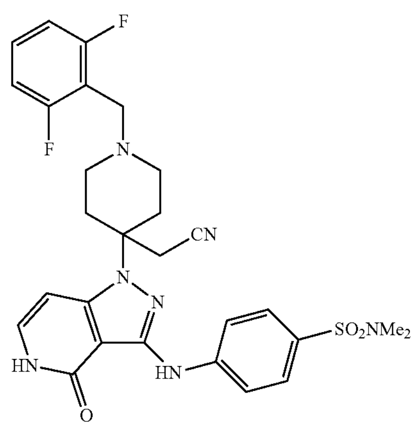 | 4-({1-[4-(cyanomethyl)-1-(2,6-difluorobenzyl) piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{28}H_{30}F_2N_7O_3S$ [M + H]$^+$: 582, found 582. |
| 8-11 | 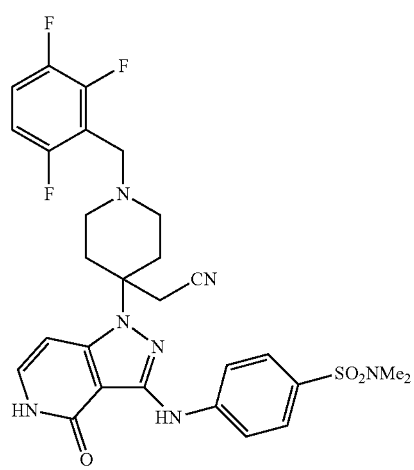 | 4-({1-[4-(cyanomethyl)-1-(2,3,6-trifluorobenzyl) piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{28}H_{29}F_3N_7O_3S$ [M + H]$^+$: 600, found 600. |

TABLE 21-continued

| Example | Structure | Compound Name | LRMS |
|---------|-----------|---------------|------|
| 8-12 | 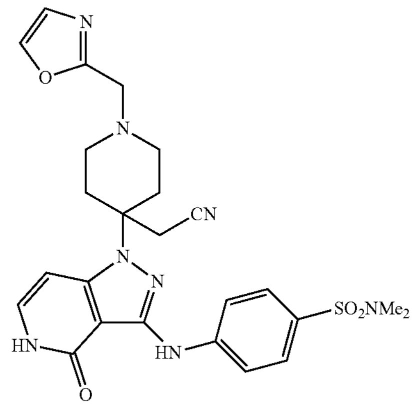 | 4-({1-[4-(cyanomethyl)-1-(1,3-oxazol-2-ylmethyl) piperidin-4-yl]-4-oxo-4,5-dihydro-1H-pyrazolo[4,3-c]pyridin-3-yl}amino)-N,N-dimethylbenzene sulfonamide | LRMS (ESI) calc'd for $C_{25}H_{29}N_8O_4S$ $[M + H]^+$: 537, found 537. |
| 8-13 | 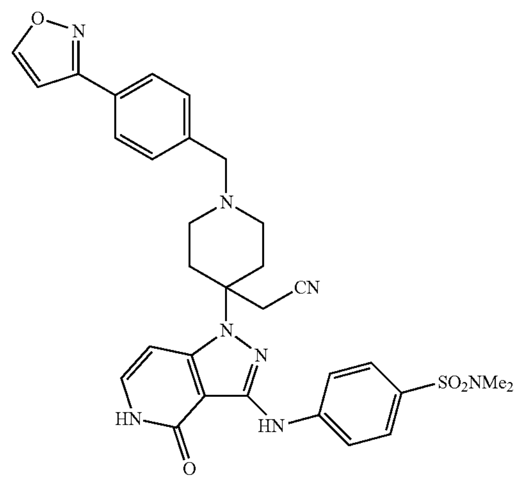 | 4-({1-[4-(cyanomethyl)-1-(4-isoxazol-3-ylbenzyl) piperidin-4-yl]-4-oxo-4,5-dihydro-1H-pyrazolo[4,3-c]pyridin-3-yl}amino)-N,N-dimethylbenzene sulfonamide | LRMS (ESI) calc'd for $C_{31}H_{33}N_8O_4S$ $[M + H]^+$: 613, found 613. |
| 8-14 | 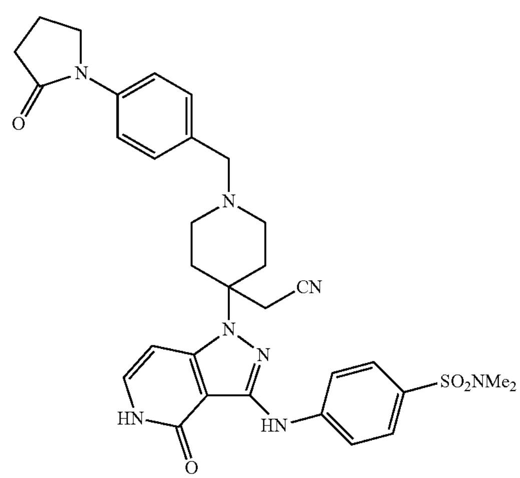 | 4-[(1-{4-(cyanomethyl)-1-[4-(2-oxopyrrolidin-1-yl)benzyl] piperidin-4-yl}-4-oxo-4,5-dihydro-1H-pyrazolo[4,3-c]pyridin-3-yl)amino]-N,N-dimethylbenzene sulfonamide | LRMS (ESI) calc'd for $C_{32}H_{37}N_8O_4S$ $[M + H]^+$: 629, found 629. |

TABLE 21-continued

| Example | Structure | Compound Name | LRMS |
|---|---|---|---|
| 8-15 | 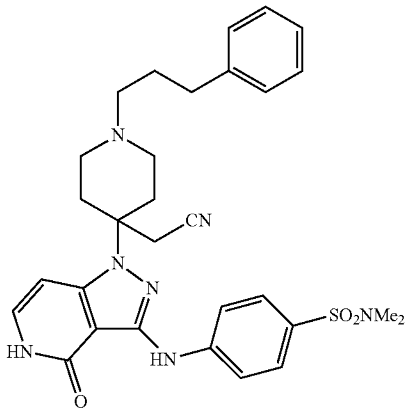 | 4-({1-[4-(cyanomethyl)-1-(3-phenylpropyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{30}H_{36}N_7O_3S$ $[M + H]^+$: 574, found 574. |
| 8-16 | 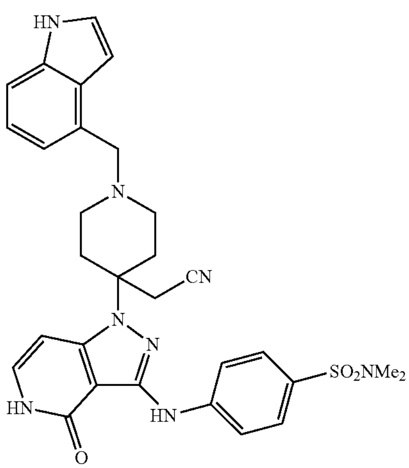 | 4-({1-[4-(cyanomethyl)-1-(1H-indol-4-ylmethyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{30}H_{33}N_8O_3S$ $[M + H]^+$: 585, found 585. |
| 8-17 | 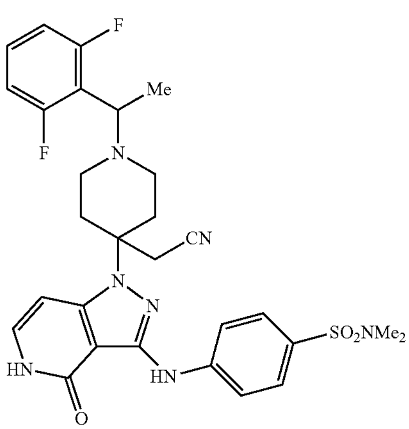 | 4-((1-(4-(cyanomethyl)-1-(1-(2,6-difluorophenyl)ethyl)piperidin-4-yl)-4-oxo-4,5-dihydro-1H-pyrazolo[4,3-c]pyridin-3-yl)amino)-N,N-dimethylbenzenesulfonamide | LRMS (ESI) calc'd for $C_{29}H_{32}F_2N_7O_3S$ $[M + H]^+$: 596, found 596. |

TABLE 21-continued

| Example | Structure | Compound Name | LRMS |
|---|---|---|---|
| 8-18 | 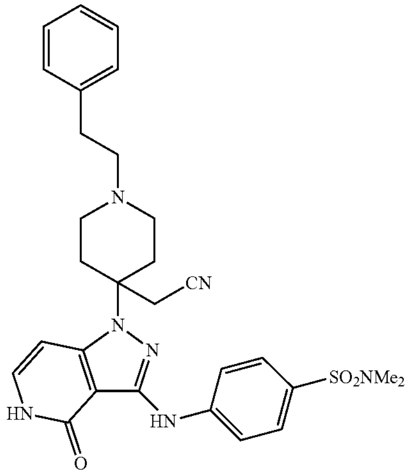 | 4-((1-(4-(cyanomethyl)-1-phenethylpiperidin-4-yl)-4-oxo-4,5-dihydro-1H-pyrazolo[4,3-c]pyridin-3-yl)amino)-N,N-dimethylbenzenesulfonamide | LRMS (ESI) calc'd for $C_{29}H_{34}N_7O_3S$ $[M + H]^+$: 560, found 560. |
| 8-19 | 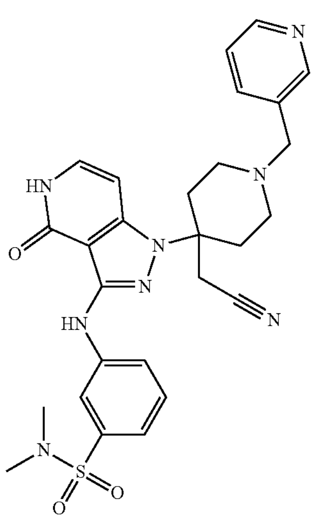 [SMILES: CN(C)S(=O)(=O)c1cccc(Nc2nn(C3(CC#N)CCN(Cc4cccnc4)CC3)c3cc[nH]c(=O)c23)c1] | 3-({1-[4-(cyanomethyl)-1-(pyridin-3-ylmethyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{27}H_{31}N_8O_3S$ $[M + H]^+$: 547, found 547. |

Example 9-1

4-({1-[4-(cyanomethyl)-1-propanoylpiperidin-4-yl]-4-oxo-4,5-dihydro-1H-pyrazolo[4,3-c]pyridin-3-yl}amino)-N,N-dimethylbenzenesulfonamide

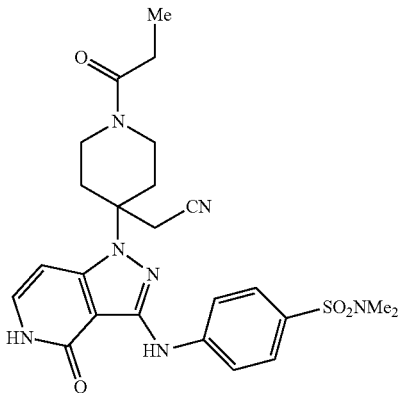

9-1

An oven dried reaction vessel was charged with PS-CDI (97 mg, 0.137 mmol) and DMF (0.55 mL, 0.1 M), and was shaken for 5 minutes. To this suspension, HOBt (11 mg, 0.082 mmol), 3-((4-(benzyloxy)-1-(4-(cyanomethyl)piperidin-4-yl)-1H-pyrazolo[4,3-c]pyridin-3-yl)amino)-N,N-dimethylbenzenesulfonamide (Example 8-1, Step 1) (30 mg, 0.055 mmol), and propionic acid (4.1 mg, 0.055 mmol) were added followed by DIPEA (14 mg, 0.11 mmol). The reaction mixture was stirred at room temperature overnight, then HCl in dioxane (0.20 mL, 2M) was added, and the reaction mixture was stirred at room temperature for an additional 2 hours. To this reaction mixture, Si-Carbonate (250 mg, 0.11 mmol) and additional DMF (1.0 mL) were added. The reaction was stirred overnight at room temperature. The reaction mixture was filtered, and the crude material containing compound 9-1 was purified using mass directed reverse phase column chromatography. LRMS (ESI) calc'd for $C_{24}H_{30}N_7O_4S$ [M+H]$^+$: 512, found 512. $^1$H NMR (600 MHz, DMSO-d6): δ 11.33 (d, J=5.9 Hz, 1H), 8.68 (s, 1H), 7.83 (d, J=8.6 Hz, 2H), 7.61 (d, J=8.6 Hz, 2H), 7.19 (t, J=6.7 Hz, 1H), 6.70 (d, J=7.6 Hz, 1H), 4.00 (m, 1H), 3.73 (m, 1H), 3.29-3.23 (m, 3H), 3.05-3.01 (m, 1H), 2.69-2.65 (m, 2H), 2.54 (s, 6H), 2.34-2.30 (m, 2H), 2.05 (m, 1H), 1.96 (m, 1H), 0.94 (t, J=7.4 Hz, 3H).

The following compounds in Table 22 were prepared in analogy to Example 9-1.

TABLE 22

| Example | Structure | Compound Name | LRMS |
| --- | --- | --- | --- |
| 9-2 | 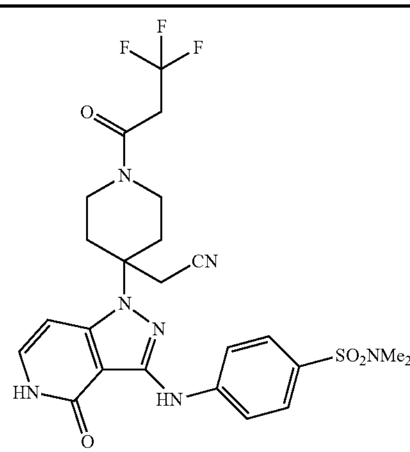 | 4-({1-[4-(cyanomethyl)-1-(3,3,3-trifluoropropanoyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{24}H_{27}F_3N_7O_4S$ [M + H]$^+$: 566, found 566. |
| 9-3 | 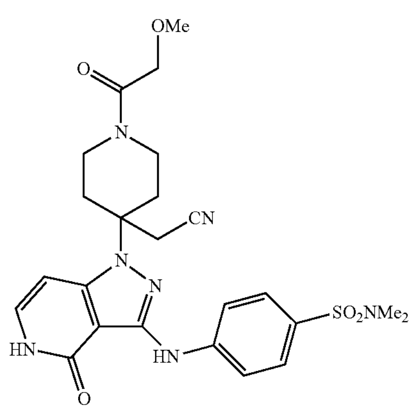 | 4-({1-[4-(cyanomethyl)-1-(methoxyacetyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{24}H_{30}N_7O_5S$ [M + H]$^+$: 528, found 528. |

TABLE 22-continued

| Example | Structure | Compound Name | LRMS |
|---|---|---|---|
| 9-4 | 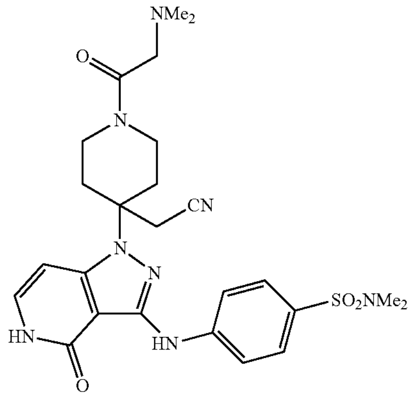 | 4-({1-[4-(cyanomethyl)-1-(N,N-dimethylglycyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{25}H_{33}N_8O_4S$ $[M + H]^+$: 541, found 541. |
| 9-5 | 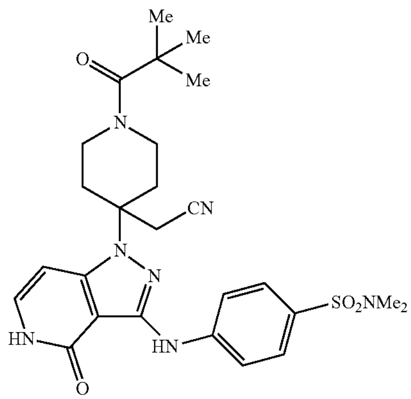 | 4-({1-[4-(cyanomethyl)-1-(2,2-dimethylpropanoyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{26}H_{34}N_7O_4S$ $[M + H]^+$: 540, found 540. |
| 9-6 | 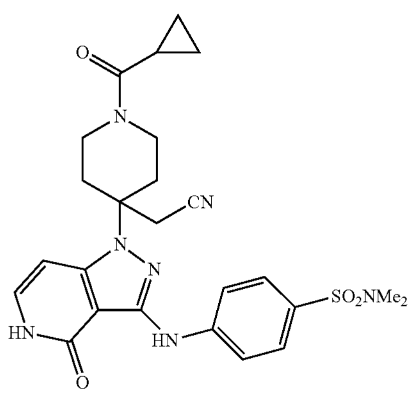 | 4-({1-[4-(cyanomethyl)-1-(cyclopropylcarbonyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{26}H_{30}N_7O_4S$ $[M + H]^+$: 524, found 524. |
| 9-7 | 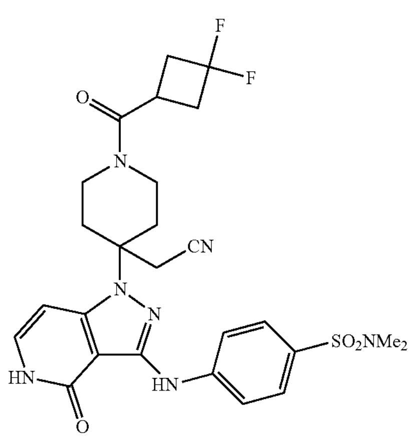 | 4-[(1-{4-(cyanomethyl)-1-[(3,3-difluorocyclobutyl)carbonyl]piperidin-4-yl}-4-oxo-4,5-dihydro-1H-pyrazolo[4,3-c]pyridin-3-yl)amino]-N,N-dimethylbenzenesulfonamide | LRMS (ESI) calc'd for $C_{26}H_{30}F_2N_7O_4S$ $[M + H]^+$: 574, found 574. |

TABLE 22-continued

| Example | Structure | Compound Name | LRMS |
|---|---|---|---|
| 9-8 | 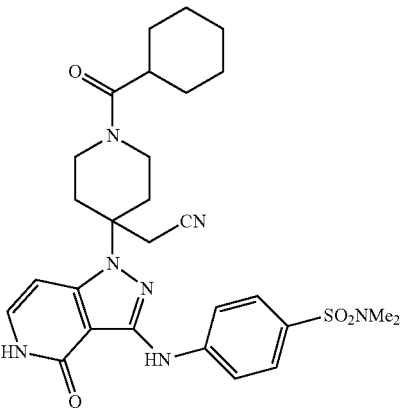 | 4-({1-[4-(cyanomethyl)-1-(cyclohexylcarbonyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{28}H_{36}N_7O_4S$ $[M + H]^+$: 566, found 566. |
| 9-9 | 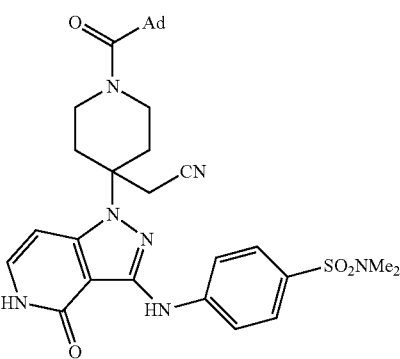 | 4-[(1-{4-(cyanomethyl)-1-[(3S,5S,7S)-tricyclo[3.3.1.1$^{3,7}$]dec-1-ylcarbonyl]piperidin-4-yl}-4-oxo-4,5-dihydro-1H-pyrazolo[4,3-c]pyridin-3-yl)amino]-N,N-dimethylbenzenesulfonamide | LRMS (ESI) calc'd for $C_{32}H_{40}N_7O_4S$ $[M + H]^+$: 618, found 618. |
| 9-10 | 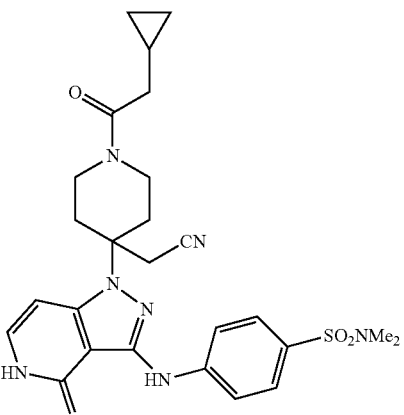 | 4-({1-[4-(cyanomethyl)-1-(cyclopropylacetyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{26}H_{32}N_7O_4S$ $[M + H]^+$: 538, found 538. |

TABLE 22-continued

| Example | Structure | Compound Name | LRMS |
|---|---|---|---|
| 9-11 | 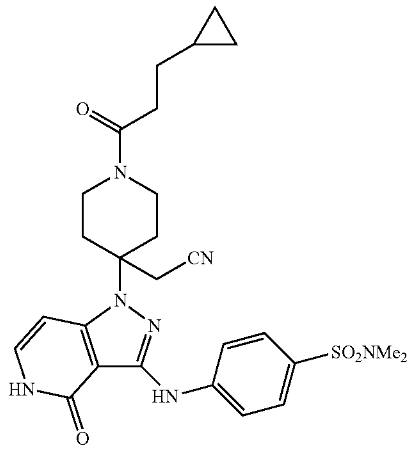 | 4-({1-[4-(cyanomethyl)-1-(3-cyclopropylpropanoyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{27}H_{34}N_7O_4S$ $[M + H]^+$: 552, found 552. |
| 9-12 | 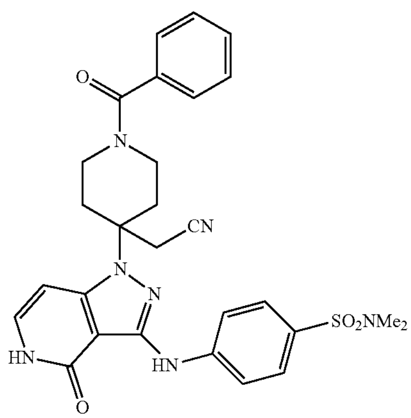 | 4-({1-[4-(cyanomethyl)-1-(phenylcarbonyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{28}H_{30}N_7O_4S$ $[M + H]^+$: 560, found 560. |
| 9-13 | 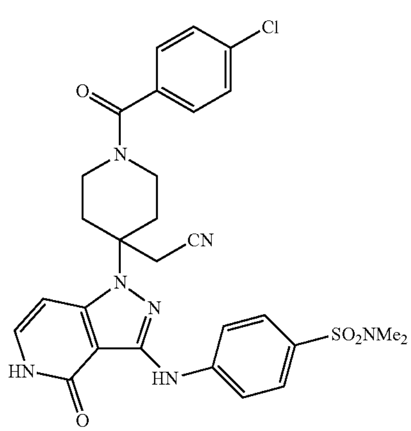 | 4-[(1-{1-[(4-chlorophenyl)carbonyl]-4-(cyanomethyl)piperidin-4-yl}-4-oxo-4,5-dihydro-1H-pyrazolo[4,3-c]pyridin-3-yl)amino]-N,N-dimethylbenzenesulfonamide | LRMS (ESI) calc'd for $C_{28}H_{29}ClN_7O_4S$ $[M + H]^+$: 594, found 594. |

TABLE 22-continued

| Example | Structure | Compound Name | LRMS |
|---------|-----------|---------------|------|
| 9-14 | 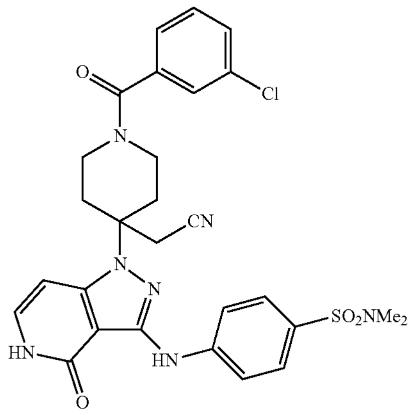 | 4-[(1-{1-[(3-chlorophenyl)carbonyl]-4-(cyanomethyl)piperidin-4-yl}-4-oxo-4,5-dihydro-1H-pyrazolo[4,3-c]pyridin-3-yl)amino]-N,N-dimethylbenzenesulfonamide | LRMS (ESI) calc'd for $C_{28}H_{29}ClN_7O_4S$ $[M + H]^+$: 594, found 594. |
| 9-15 | 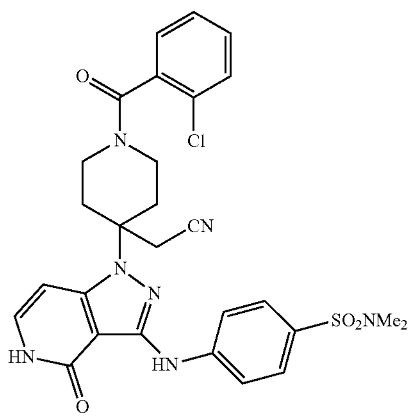 | 4-[(1-{1-[(2-chlorophenyl)carbonyl]-4-(cyanomethyl)piperidin-4-yl}-4-oxo-4,5-dihydro-1H-pyrazolo[4,3-c]pyridin-3-yl)amino]-N,N-dimethylbenzenesulfonamide | LRMS (ESI) calc'd for $C_{28}H_{29}ClN_7O_4S$ $[M + H]^+$: 594, found 594. |
| 9-16 | 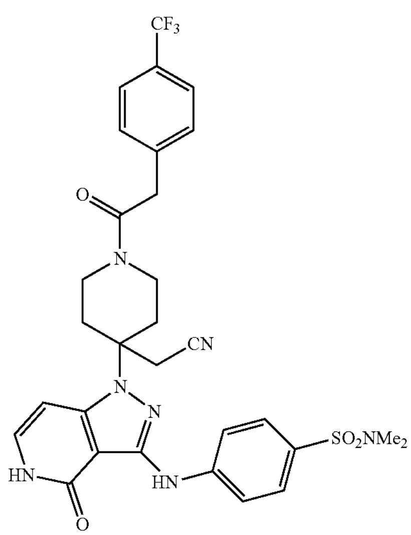 | 4-({1-[4-(cyanomethyl)-1-{[4-(trifluoromethyl)phenyl]acetyl}piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{30}H_{31}F_3N_7O_4S$ $[M + H]^+$: 642, found 642. |

TABLE 22-continued

| Example | Structure | Compound Name | LRMS |
|---------|-----------|---------------|------|
| 9-17 | 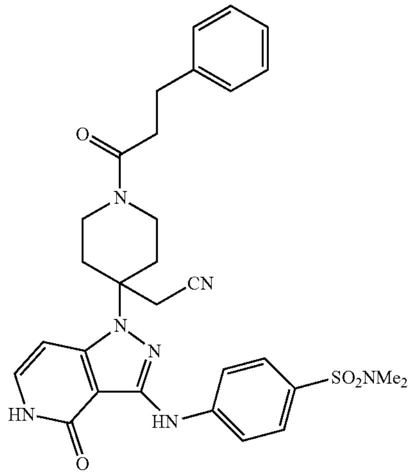 | 4-({1-[4-(cyanomethyl)-1-(3-phenylpropanoyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{30}H_{34}N_7O_4S$ $[M + H]^+$: 588, found 588. |
| 9-18 | 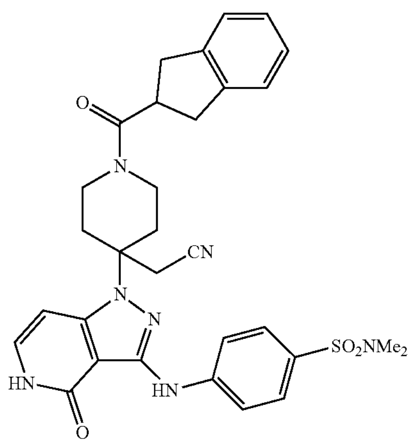 | 4-({1-[4-(cyanomethyl)-1-(2,3-dihydro-1H-inden-2-ylcarbonyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{31}H_{34}N_7O_4S$ $[M + H]^+$: 600, found 600. |
| 9-19 | 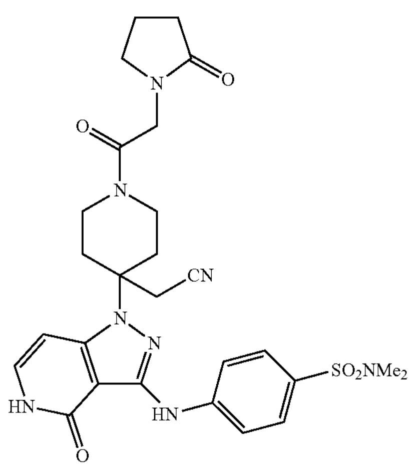 | 4-[(1-{4-(cyanomethyl)-1-[(2-oxopyrrolidin-1-yl)acetyl]piperidin-4-yl}-4-oxo-4,5-dihydro-1H-pyrazolo[4,3-c]pyridin-3-yl)amino]-N,N-dimethylbenzenesulfonamide | LRMS (ESI) calc'd for $C_{27}H_{33}N_8O_5S$ $[M + H]^+$: 581, found 581. |

TABLE 22-continued

| Example | Structure | Compound Name | LRMS |
|---|---|---|---|
| 9-20 | 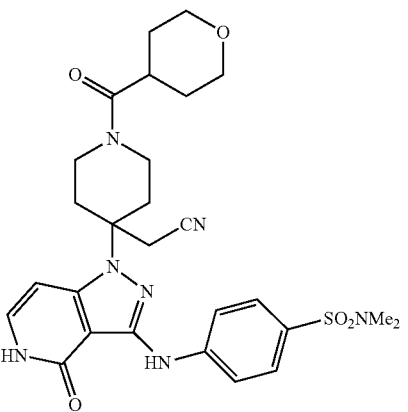 | 4-({1-[4-(cyanomethyl)-1-(tetrahydro-2H-pyran-4-ylcarbonyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{27}H_{34}N_7O_5S$ $[M + H]^+$: 568, found 568. |
| 9-21 | 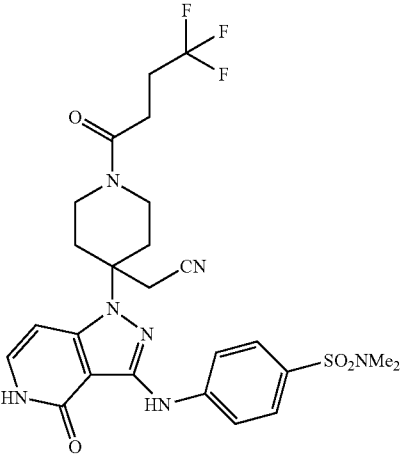 | 4-({1-[4-(cyanomethyl)-1-(4,4,4-trifluorobutanoyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{25}H_{29}F_3N_7O_4S$ $[M + H]^+$: 580, found 580. |
| 9-22 | 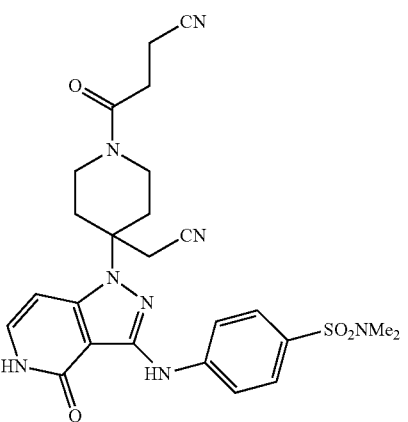 | 4-({1-[4-(cyanomethyl)-1-(3-cyanopropanoyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{25}H_{29}N_8O_4S$ $[M + H]^+$: 537, found 537. |

TABLE 22-continued

| Example | Structure | Compound Name | LRMS |
|---|---|---|---|
| 9-23 | 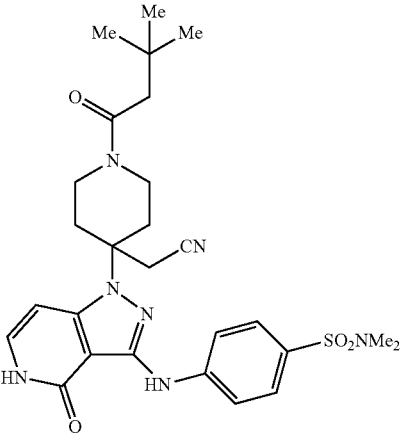 | 4-({1-[4-(cyanomethyl)-1-(3,3-dimethylbutanoyl)piperidin-4-yl]-4-oxo-4,5-dihydro-1H-pyrazolo[4,3-c]pyridin-3-yl}amino)-N,N-dimethylbenzenesulfonamide | LRMS (ESI) calc'd for $C_{27}H_{36}N_7O_4S$ $[M + H]^+$: 554, found 554. |
| 9-24 | 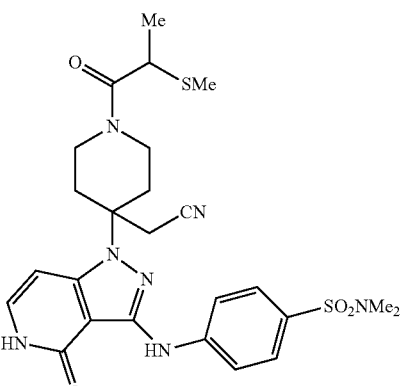 | 4-((1-(4-(cyanomethyl)-1-(2-(methylthio)propanoyl)piperidin-4-yl)-4-oxo-4,5-dihydro-1H-pyrazolo[4,3-c]pyridin-3-yl)amino)-N,N-dimethylbenzenesulfonamide | LRMS (ESI) calc'd for $C_{25}H_{32}N_7O_4S_2$ $[M + H]^+$: 558, found 558. |

TABLE 22-continued

| Example | Structure | Compound Name | LRMS |
|---|---|---|---|
| 9-25 | 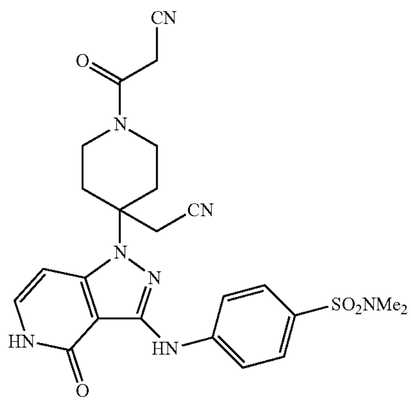 | 4-((1-(1-(2-cyanoacetyl)-4-(cyanomethyl)piperidin-4-yl)-4-oxo-4,5-dihydro-1H-pyrazolo[4,3-c]pyridin-3-yl)amino)-N,N-dimethylbenzenesulfonamide | LRMS (ESI) calc'd for $C_{24}H_{27}N_8O_4S$ $[M + H]^+$: 523, found 523. |

Example 10-1 methyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate

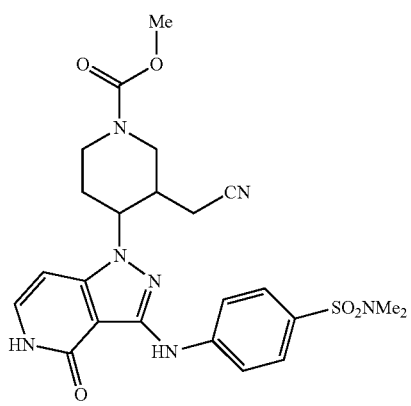

10-1

To a solution of 3-((4-(benzyloxy)-1-(4-(cyanomethyl)piperidin-4-yl)-1H-pyrazolo[4,3-c]pyridin-3-yl)amino)-N,N-dimethylbenzenesulfonamide (Example 8-1, Step 1) (25 mg, 0.046 mmol), in $CH_2Cl_2$ (0.2 M), was added 2,6-lutidine (12.3 mg, 0.115 mmol). The reaction mixture was cooled to 0° C. and methyl chloroformate (4.76 mg, 0.050 mmol) was added. The reaction was stirred to room temperature until the reaction was judged complete by LCMS, at which point it was cooled to 0° C. and 0.2 mL of TFA was added. The reaction mixture was filtered and purified using mass directed reverse phase chromatography. LRMS (ESI) calc'd for $C_{23}H_{28}N_7O_5S$ $[M+H]^+$: 514, found 514. $^1$H NMR (600 MHz, DMSO-d6): δ 11.33 (d, J=5.9 Hz, 1H), 8.71 (s, 1H), 7.85 (d, J=8.6 Hz, 2H), 7.63 (d, J=8.6 Hz, 2H), 7.19 (m, 1H), 6.70 (m, 1H), 3.82-3.78 (m, 2H), 3.58 (s, 3H), 3.31 (m, 1H), 3.29 (m, 1H), 3.21-3.13 (m, 1H), 2.72-2.64 (m, 1H), 2.57 (s, 6H), 2.48-2.44 (m, 2H), 2.10-2.02 (m, 2H).

The following compounds in Table 23 were prepared in analogy to that of Example 10-1.

TABLE 23

| Example | Structure | Compound Name | LRMS |
|---|---|---|---|
| 10-2 | 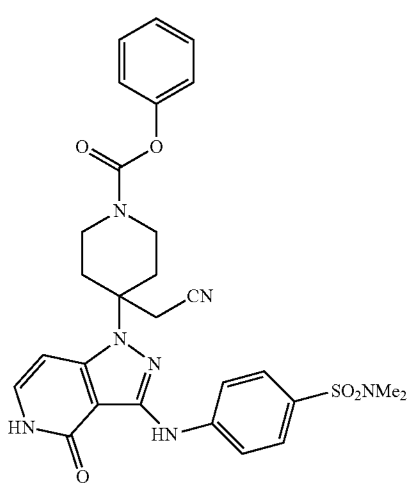 | phenyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{28}H_{30}N_7O_5S$ $[M + H]^+$: 576, found 576. |

TABLE 23-continued

| Example | Structure | Compound Name | LRMS |
|---|---|---|---|
| 10-3 | 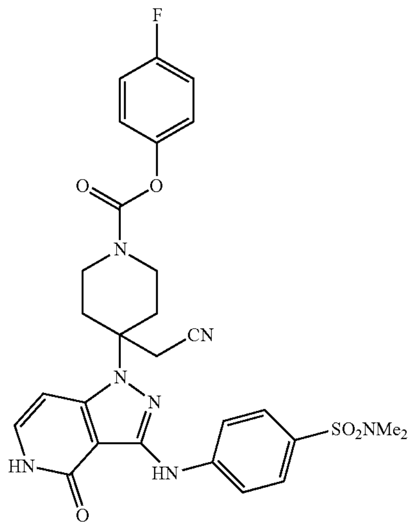 | 4-fluorophenyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{28}H_{29}FN_7O_5S$ $[M + H]^+$: 594, found 594. |
| 10-4 | 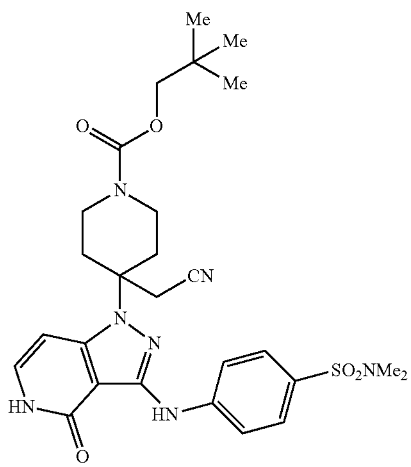 | neopentyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{27}H_{36}N_7O_5S$ $[M + H]^+$: 570, found 570. |
| 10-5 | 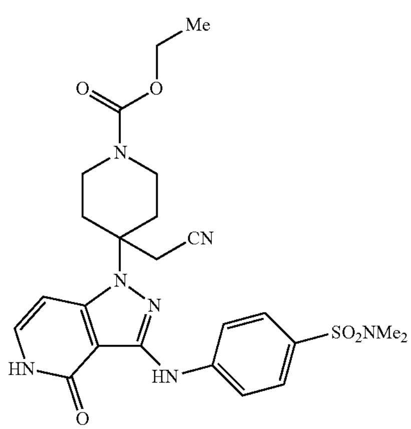 | ethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{24}H_{30}N_7O_5S$ $[M + H]^+$: 528, found 528. |

TABLE 23-continued

| Example | Structure | Compound Name | LRMS |
|---|---|---|---|
| 10-6 | 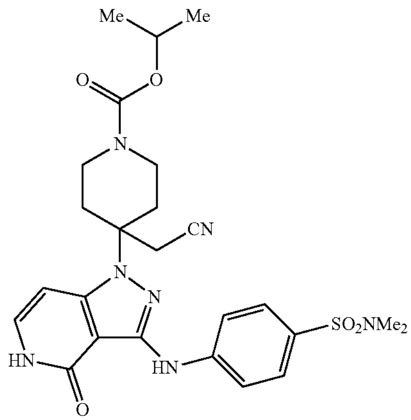 | isopropyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{25}H_{32}N_7O_5S$ $[M + H]^+$: 542, found 542. |

Example 11-1 methyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate

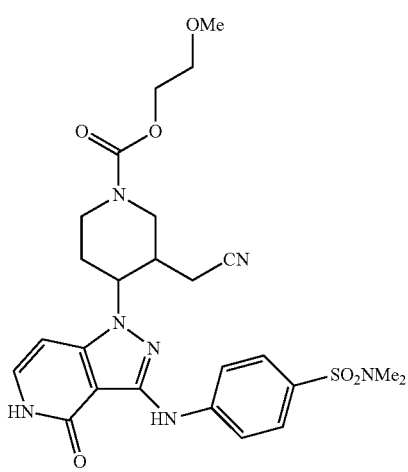

11-1

To a DMSO solution (0.5 M) of triethylamine (46 mg, 0.45 mmol) and 2-methoxy ethanol (11 mg, 0.15 mmol) was added N,N'-disuccinimidyl carbonate (38 mg, 0.15 mmol). The reaction mixture was stirred at room temperature for 4 hours then a DMSO (0.5 M) solution of 3-((4-(benzyloxy)-1-(4-(cyanomethyl)piperidin-4-yl)-1H-pyrazolo[4,3-c]pyridin-3-yl)amino)-N,N-dimethylbenzenesulfonamide (Example 8-1, Step 1) (41 mg, 0.075 mmol) was added. The reaction mixture was stirred at room temperature overnight, then quenched by addition of TFA (0.10 mL) and then neutralized after benzyl ether cleavage by addition of PS-Carbonate (300 mg). The reaction was filtered and purified using mass directed reverse phase chromatography to afford compound 11-1. LRMS (ESI) calc'd for $C_{25}H_{32}N_7O_6S$ $[M+H]^+$: 558, found 558. $^1$H NMR (600 MHz, DMSO-d6): δ 11.31 (d, J=5.9 Hz, 1H), 8.71 (s, 1H), 7.85 (d, J=8.6 Hz, 2H), 7.63 (d, J=8.6 Hz, 2H), 7.19 (m, 1H), 6.70 (m, 1H), 3.85-3.65 (m, 4H), 3.47-3.37 (m, 4H), 3.32 (s, 3H), 2.72-2.64 (m, 2H), 2.57 (s, 6H), 2.10-2.02 (m, 2H), 1.85-1.75 (m, 2H).

The following compounds in Table 24 were prepared in an analogous manner to that of Example 11-1.

TABLE 24

| Example | Structure | Compound Name | LRMS |
|---|---|---|---|
| 11-2 | 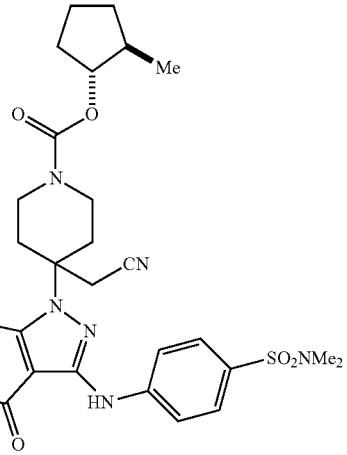 | (trans racemic)-2-methylcyclopentyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{28}H_{36}N_7O_5S$ $[M + H]^+$: 582, found 582. |
| 11-3 | 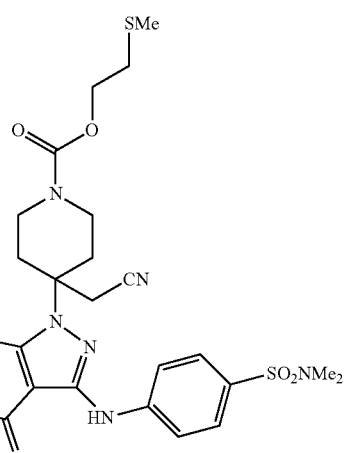 | 2-(methylthio)ethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{25}H_{32}N_7O_5S_2$ $[M + H]^+$: 574, found 574. |
| 11-4 | 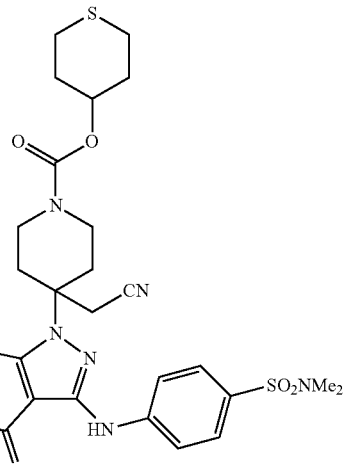 | tetrahydro-2H-thiopyran-4-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{27}H_{34}N_7O_5S_2$ $[M + H]^+$: 600, found 600. |

TABLE 24-continued

| Example | Structure | Compound Name | LRMS |
|---|---|---|---|
| 11-5 | 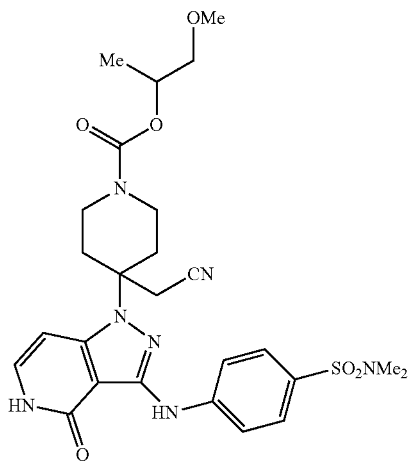 | 1-methoxypropan-2-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{26}H_{34}N_7O_6S$ [M + H]$^+$: 572, found 572. |
| 11-6 | 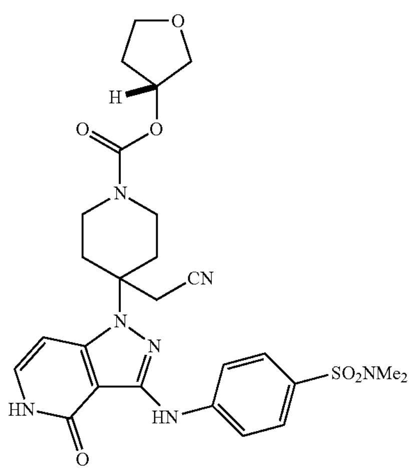 | (R)-tetrahydrofuran-3-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{26}H_{32}N_7O_6S$ [M + H]$^+$: 570, found 570. |
| 11-7 | 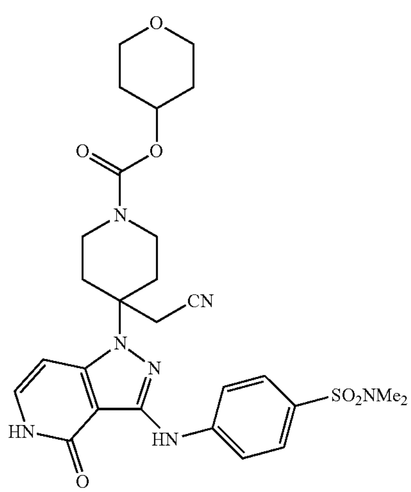 | tetrahydro-2H-pyran-4-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{27}H_{34}N_7O_6S$ [M + H]$^+$: 584, found 584. |

TABLE 24-continued

| Example | Structure | Compound Name | LRMS |
|---|---|---|---|
| 11-8 | 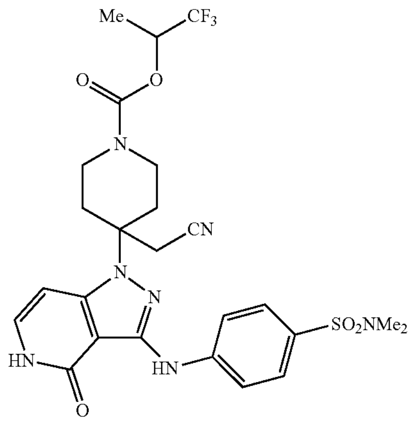 | 1,1,1-trifluoropropan-2-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{25}H_{29}F_3N_7O_5S$ $[M + H]^+$: 596, found 596. |
| 11-9 | 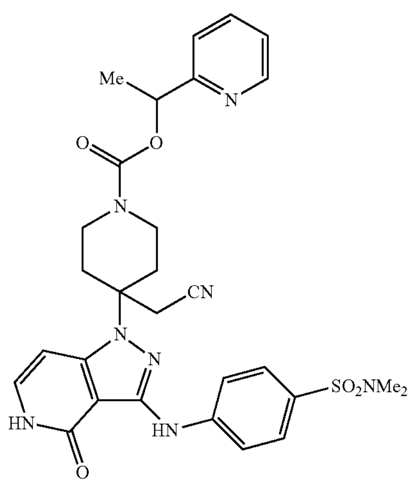 | 1-(pyridin-2-yl)ethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{29}H_{33}N_8O_5S$ $[M + H]^+$: 605, found 605. |
| 11-10 | 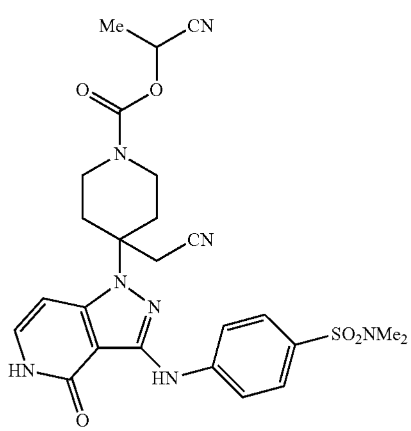 | 1-cyanoethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{25}H_{29}N_8O_5S$ $[M + H]^+$: 553, found 553. |

TABLE 24-continued

| Example | Structure | Compound Name | LRMS |
|---|---|---|---|
| 11-11 | 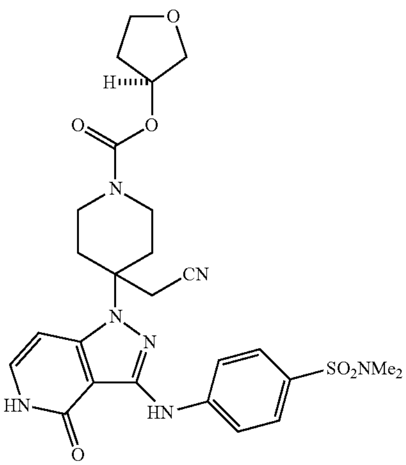 | (S)-tetrahydrofuran-3-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate | LRMS (ESI) calc'd for $C_{26}H_{32}N_7O_6S$ [M + H]+: 570, found 570. |

Example 12

2,2,2-trifluoroethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate

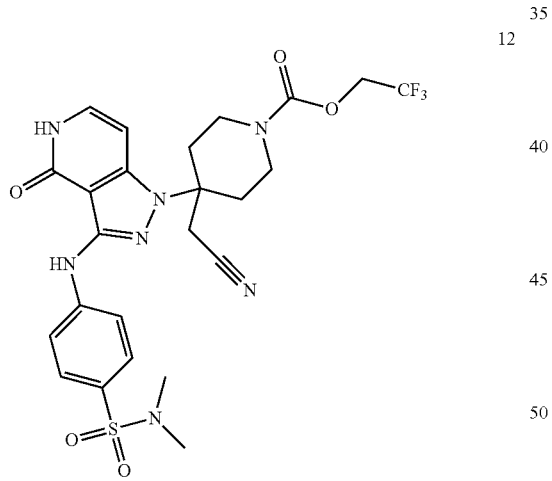

12

To a solution of 4-((1-(4-(cyanomethyl)piperidin-4-yl)-4-oxo-4,5-dihydro-1H-pyrazolo[4,3-c]pyridin-3-yl)amino)-N,N-dimethylbenzenesulfonamide (Example 8-1, Step 1) (82 mg, 0.25 mmol) in DMF (1.0 mL) was added 2,2,2-trifluoroethanol (50 mg, 0.50 mmol) and Et₃N (50 mg, 0.50 mmol). The solution was cooled to −20° C., then triphosgene (4.0 mg, 1.3 mmol) was added and the resulting solution was stirred at −20° C. for 4 hours. The mixture was filtered, and the filtrate was concentrated in vacuo and purified by reverse phase HPLC using water/acetonitrile with 0.225% formic acid modifier to give compound 12 as a solid. LRMS (ESI) calc'd for $C_{24}H_{27}F_3N_7O_5S$ [M+H]+: 582, found 582. ¹H NMR (400 MHz, DMSO-d6): δ 11.37 (s, 1H), 8.72 (s, 1H), 7.85 (d, J=8.8 Hz, 2H), 7.66-7.64 (m, 2H), 7.24-7.21 (m, 1H), 6.74 (d, J=7.6 Hz, 1H), 4.71-4.69 (m, 2H), 3.86-3.82 (m, 2H), 3.28 (s, 2H), 2.73-2.73 (m, 2H), 2.59 (s, 6H), 2.13-1.97 (m, 4H).

Example 13-1 isopropyl-4-(cyanomethyl)-4-(3-(2-fluoropyridin-4-ylamino)-4-oxo-4,5-dihydropyrazolo[4,3-c]pyridin-1-yl)piperidine-1-carboxylate

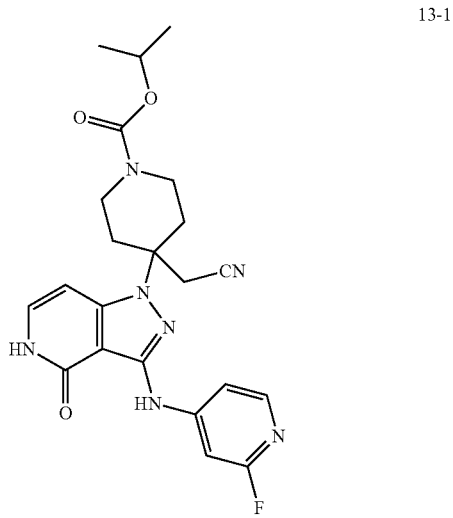 [SMILES: CC(C)OC(=O)N1CCC(CC#N)(n2nc(Nc3ccnc(F)c3)c3c(=O)[nH]ccc32)CC1]

13-1

Step 1: tert-butyl 4-(4-(benzyloxy)-3-((2-fluoropyridin-4-yl)amino)-1H-pyrazolo[4,3-c]pyridin-1-yl)-4-(cyanomethyl)piperidine-1-carboxylate

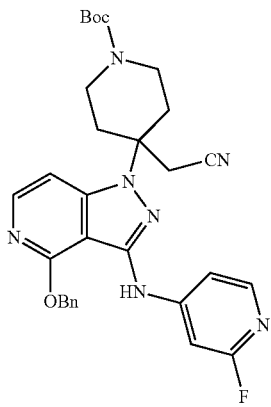 [SMILES: CC(C)(C)OC(=O)N1CCC(CC#N)(n2nc(Nc3ccnc(F)c3)c3c(OCc4ccccc4)nccc32)CC1]

To tert-butyl 4-(3-amino-4-(benzyloxy)-1H-pyrazolo[4,3-c]pyridin-1-yl)-4-(cyanomethyl)piperidine-1-carboxylate (0.20 g, 0.44 mmol), 4-bromo-2-fluoropyridine (93 mg, 0.54 mmol), di-tert-butyl (2',4',6'-triisopropylbiphenyl-2-yl)phosphine (37 mg, 0.090 mmol), tris(dibenzylideneacetone)dipalladium(0) chloroform adduct (46 mg, 0.050 mmol) and potassium acetate (88 mg, 0.90 mmol), was added isopropanol (30 mL). The mixture was degassed by purging with nitrogen and then heated to 80° C. for 6 hours. The solution was cooled and water (10 mL) was added. The mixture was extracted with ethyl acetate (×3) and the combined organic layers were washed with brine (×2), dried over anhydrous sodium sulfate, filtered and the filtrate was concentrated in vacuo. The residue was purified by silica chromatography, eluting with ethyl acetate/petroleum ether (1/3) to afford the title compound as a solid. LRMS (ESI) calc'd for $C_{30}H_{33}FN_7O_3$ [M+H]$^+$: 558, found 558.

Step 2: 2-(4-(3-((2-fluoropyridin-4-yl)amino)-4-oxo-4,5-dihydro-1H-pyrazolo[4,3-c]pyridin-1-yl)piperidin-4-yl)acetonitrile

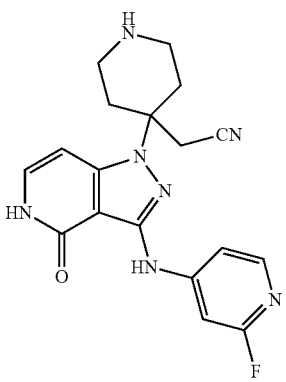 [SMILES: N#CCC1(n2nc(Nc3ccnc(F)c3)c3c(=O)[nH]ccc32)CCNCC1]

To a solution of tert-butyl 4-(4-(benzyloxy)-3-(2-fluoropyridin-4-ylamino)-1H-pyrazolo[4,3-c]pyridin-1-yl)-4-(cyanomethyl)piperidine-1-carboxylate (0.21 g, 0.37 mmol) in dichloromethane (20 mL), was added TFA (0.42 g, 3.70 mmol). The reaction mixture was stirred for 2 hours at ambient temperature, then concentrated in vacuo to afford a solid that was used as is in the next step. LRMS (ESI) calc'd for $C_{18}H_{19}FN_7O$ [M+H]$^+$: 368, found 368.

Step 3: isopropyl-4-(cyanomethyl)-4-(3-(2-fluoropyridin-4-ylamino)-4-oxo-4,5-dihydropyrazolo[4,3-c]pyridin-1-yl)piperidine-1-carboxylate (13-1)

To a solution of 2-(4-(3-(2-fluoropyridin-4-ylamino)-4-oxo-4,5-dihydropyrazolo[4,3-c]pyridin-1-yl)piperidin-4-yl)acetonitrile (30 mg, 0.06 mmol) in methanol (5 mL) was added isopropyl chloroformate (9 mg, 0.07 mmol) and sodium carbonate (20 mg, 0.18 mmol). The mixture was stirred for 2 hours at ambient temperature, then cooled and quenched by addition of water (10 mL). The mixture was extracted with ethyl acetate (×2) and the combined organic layers were washed with brine (×2), dried over anhydrous sodium sulfate, filtered and the filtrate was concentrated in vacuo. The crude product was purified by reverse phase chromatography, using water (with 0.05% ammonium bicarbonate modifier) and acetonitrile. Desired fractions were concentrated in vacuo to afford a solid. LCMS (ESI) calc'd for $C_{22}H_{25}FN_7O_3$ [M+H]$^+$: 454, found 454; $^1$H NMR (400 MHz, DMSO-d$_6$): δ 11.40 (br s, 1H), 9.02 (s, 1H), 7.97 (d, J=6.0 Hz, 1H), 7.52 (d, J=6.0 Hz, 1H), 7.39 (d, J=1.5 Hz, 1H), 7.25-7.21 (m, 1H), 6.73 (d, J=7.5 Hz, 1H), 4.77 (m, 1H) 3.78 (m, 2H), 3.18 (m, 2H), 2.67 (m, 2H), 2.50 (m, 2H), 2.11-2.05 (m, 2H), 1.18 (d, J=8.0 Hz, 6H).

The following examples in Table 25 were prepared in an analogous manner as outlined above, using an appropriate chloroformate reagent.

TABLE 25

| Example | Structure | Compound Name | LRMS |
|---|---|---|---|
| 13-2 | 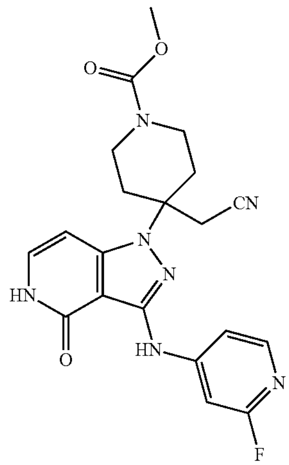 [SMILES: COC(=O)N1CCC(CC#N)(n2nc(Nc3ccnc(F)c3)c3c(=O)[nH]ccc32)CC1] | methyl 4-(cyanomethyl)-4-(3-(2-fluoropyridin-4-ylamino)-4-oxo-4,5-dihydropyrazolo[4,3-c]pyridin-1-yl)piperidine-1-carboxylate | LRMS (ESI) calc'd for $C_{20}H_{21}FN_7O_3$ [M + H]$^+$: 426, found 426. |

Example 14-1

4-((1-(4-(cyanomethyl)-1-((2,2,2-trifluoroethyl)sulfonyl)piperidin-4-yl)-4-oxo-4,5-dihydro-1H-pyrazolo[4,3-c]pyridin-3-yl)amino)-N,N-dimethylbenzenesulfonamide

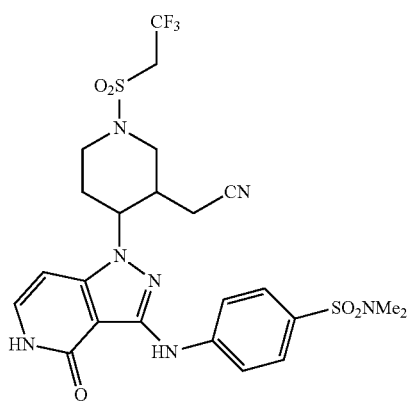

14-1

To a CH$_2$Cl$_2$ solution (0.51 mL, 0.1 M) of 2,6-lutidine (28 mg, 0.257 mmol) and 3-((4-(benzyloxy)-1-(4-(cyanomethyl)piperidin-4-yl)-1H-pyrazolo[4,3-c]pyridin-3-yl)amino)-N,N-dimethylbenzenesulfonamide (Example 8-1, Step 1) (28 mg, 0.051 mmol), 2,2,2-trifluoroethanesulfonyl chloride (12 mg, 0.063 mmol) was added. The reaction mixture was stirred at room temperature for 24 hours followed by the addition of TFA (0.2 mL). The reaction mixture was stirred at room temperature for an additional 4 hours. The reaction was quenched with PS-Carbonate (250 mg), filtered, and purified using mass directed reverse phase column chromatography to afford compound 14-1. LRMS (ESI) calc'd for $C_{23}H_{27}F_3N_7O_5S_2$ [M+H]+$^+$: 602, found 602. $^1$H NMR (500 MHz, DMSO-d6): δ 11.31 (d, J=5.9 Hz, 1H), 8.71 (s, 1H), 7.85 (d, J=8.6 Hz, 2H), 7.63 (d, J=8.6 Hz, 2H), 7.19 (m, 1H), 6.70 (m, 1H), 4.49-4.41 (m, 2H), 3.75-3.65 (m, 2H), 3.47-3.37 (m, 2H), 3.30-3.23 (m, 2H), 2.89-2.82 (m, 2H), 2.57 (s, 6H), 2.24-2.12 (m, 2H).

The following compound in Table 27 was prepared in an analogous manner to that of Example 14-1:

TABLE 27

| Example | Structure | Compound Name | LRMS |
|---|---|---|---|
| 14-2 | 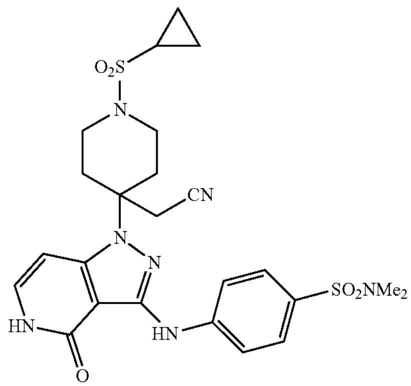 | 4-((1-(4-(cyanomethyl)-1-(cyclopropylsulfonyl)piperidin-4-yl)-4-oxo-4,5-dihydro-1H-pyrazolo[4,3-c]pyridin-3-yl)amino)-N,N-dimethylbenzenesulfonamide | LRMS (ESI) calc'd for $C_{24}H_{30}N_7O_5S_2$ [M + H]$^+$: 560, found 560. |

Example 15-1

2-(4-(3-((4-(methylsulfonyl)phenyl)amino)-4-oxo-4,5-dihydro-1H-pyrazolo[4,3-c]pyridin-1-yl)-1-(4-(trifluoromethyl)pyridin-2-yl)piperidin-4-yl)acetonitrile

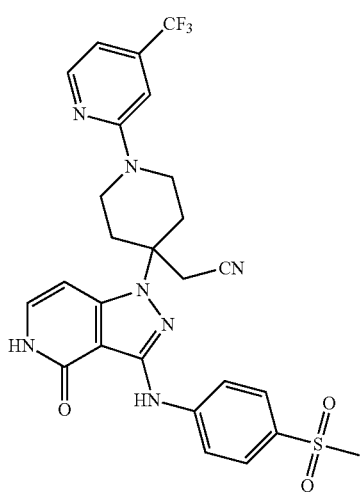

Step 1: tert-butyl 4-(4-(benzyloxy)-3-((4-(methylsulfonyl)phenyl)amino)-1H-pyrazolo[4,3-c]pyridin-1-yl)-4-(cyanomethyl)piperidine-1-carboxylate

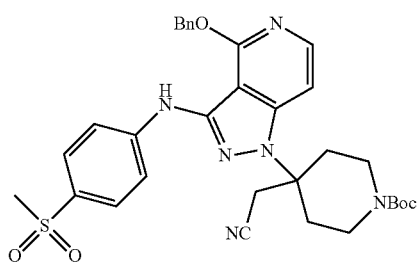 [SMILES: CC(C)(C)OC(=O)N1CCC(CC#N)(n2nc(Nc3ccc(S(C)(=O)=O)cc3)c3c(OCc4ccccc4)nccc32)CC1]

To a suspension of tert-butyl 4-(3-amino-4-(benzyloxy)-1H-pyrazolo[4,3-c]pyridin-1-yl)-4-(cyanomethyl)piperidine-1-carboxylate (0.69 g, 1.5 mmol) and KOAc (200 mg, 2.04 mmol) in i-PrOH (4.0 mL) was added 4-bromophenyl methyl sulfone (0.47 g, 2.0 mmol) followed by Pd$_2$(dba)$_3$ (140 mg, 0.153 mmol) and 2-di-tert-butylphosphino-2',4',6'-triisopropylbiphenyl (60 mg, 0.15 mmol) under nitrogen. The resulting suspension was heated to 105° C. by microwave for 1 hour. The mixture was then cooled to room temperature and filtered. The filtrate was purified by preparative TLC, eluting with 50% EtOAc in hexanes, to give the title compound as a solid. LRMS (ESI) calc'd for $C_{32}H_{37}N_6O_5S$ [M+H]$^+$: 617, found 617. $^1$H NMR (400 MHz, CDCl$_3$): δ 7.95 (d, J=6.4 Hz, 1H), 7.86 (d, J=7.2 Hz, 2H), 7.76 (br s, 1 H), 7.56-7.42 (m, 7H), 6.99 (d, J=6.4 Hz, 1H), 5.61 (s, 2H), 4.10-3.92 (m, 2H), 3.21-3.10 (m, 2H), 3.04 (s, 3H), 2.99-2.95 (m, 2H), 2.92 (s, 2H), 2.14-2.08 (m, 2H), 1.49 (s, 9H).

Step 2: 2-(4-(3-((4-(methylsulfonyl)phenyl)amino)-4-oxo-4,5-dihydro-1H-pyrazolo[4,3-c]pyridin-1-yl)piperidin-4-yl)acetonitrile (HCl salt)

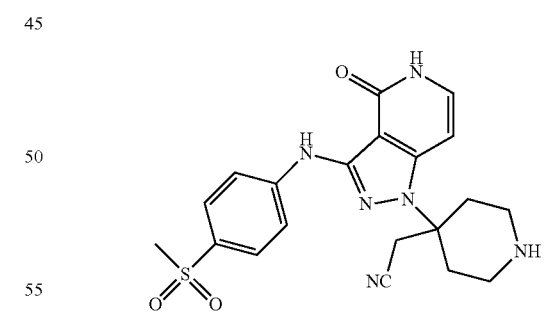

To a suspension of tert-butyl 4-(4-(benzyloxy)-3-((4-(methylsulfonyl)phenyl)amino)-1H-pyrazolo[4,3-c]pyridin-1-yl)-4-(cyanomethyl)piperidine-1-carboxylate (160 mg, 0.260 mmol) in EtOAc (2 mL) was added HCl (2 mL, 4M in EtOAc, 8 mmol). The resulting suspension was stirred for 4 hours at room temperature. The mixture was then filtered, and the solid was washed with EtOAc and dried to afford the title compound as the HCl salt. LRMS (ESI) calc'd for $C_{20}H_{23}N_6O_3S$ [M+H]$^+$: 427, found 427. $^1$H NMR (400 MHz, DMSO-d6): δ 11.46 (d, J=5.6 Hz, 1H), 8.90 (br s, 2H), 8.77 (s, 1H), 7.87 (d, J=8.8 Hz, 4H), 7.80 (d, J=9.2 Hz, 2H), 7.30-7.26 (m, 1H), 6.79 (d, J=7.6 Hz, 2H), 3.34-3.29 (m, 2H), 3.27 (s, 2H), 3.12 (s, 3H), 3.04-2.98 (m, 2H), 2.91-2.88 (m, 2H), 2.30-2.25 (m, 2H).

Step 3: 6-(4-(cyanomethyl)-4-(3-((4-((difluoromethyl)sulfonyl)phenyl)amino)-4-oxo-4,5-dihydro-1H-pyrazolo[4,3-c]pyridin-1-yl)piperidin-1-yl)nicotinonitrile To a solution of 2-(4-(3-((4-(methylsulfonyl)phenyl)amino)-4-oxo-4,5-dihydro-1H-pyrazolo[4,3-c]pyridin-1-yl)piperidin-4-yl)acetonitrile (0.10 g, 0.24 mmol) in DMF (1.0 mL) was added 2-chloro-4-(trifluoromethyl)pyridine (56 mg, 0.31 mmol) and DIPEA (61 mg, 0.48 mmol). The reaction was sealed and heated to 120° C. for 16 hours, then cooled and filtered and the filtrate was purified by reverse phase HPLC. LRMS (ESI) calc'd for $C_{26}H_{25}N_7O_3SF_3$ [M+H]$^+$: 572, found 572. $^1$H NMR (400 MHz, DMSO-d6): δ 11.41 (br s, 1H), 8.75 (s, H), 8.34 (d, J=4.8 Hz, 1H), 7.89 (d, J=8.8 Hz, 2H), 7.81 (d, J=8.8 Hz, 2H), 7.28-7.23 (m, 1H), 7.15 (s, 1H), 6.86 (d, J=4.8 Hz), 6.75 (d, J=7.6 Hz, 1H), 4.18-4.09 (m, 2 H), 3.44-3.28 (m, 4H), 3.16 (s, 3H), 2.81-2.72 (m, 2H), 2.18-2.04 (m, 2H).

Following analogous procedures to that outlined for Example 15-1 above, the following compounds in Table 28 were prepared. In certain instances the Boc deprotection (Step 2) could be achieved on the free pyridone compound of the type depicted in Example 5 shown in Table 20 using TFA in DCM at room temperature prior to the S$_N$Ar reaction. In certain instances the S$_N$Ar reaction could be conducted using alternate suitable bases, such as TEA for example, typically at temperatures >80° C.

TABLE 28

| Example | Structure | Compound Name | LRMS |
|---------|-----------|---------------|------|
| 15-2 | 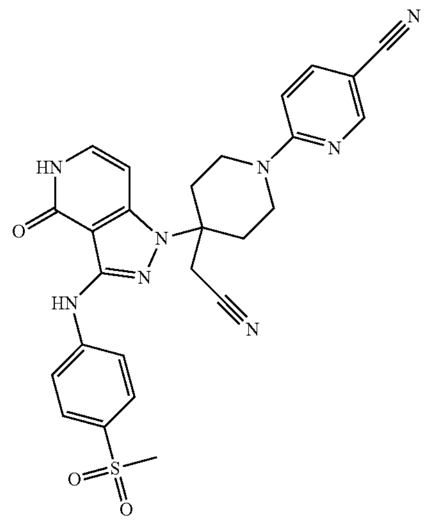 [SMILES: CS(=O)(=O)c1ccc(Nc2nn(C3(CC#N)CCN(c4ccc(C#N)cn4)CC3)c3cc[nH]c(=O)c23)cc1] | 6-(4-(cyanomethyl)-4-(3-((4(methylsulfonyl)phenyl)amino)-4-oxo-4,5-dihydro-1H-pyrazolo[4,3-c]pyridin-1-yl)piperidin-1-yl)nicotinonitrile | LRMS (ESI) calc'd for $C_{26}H_{25}N_8O_3S$ [M + H]$^+$: 529, found 529. |
| 15-3 | 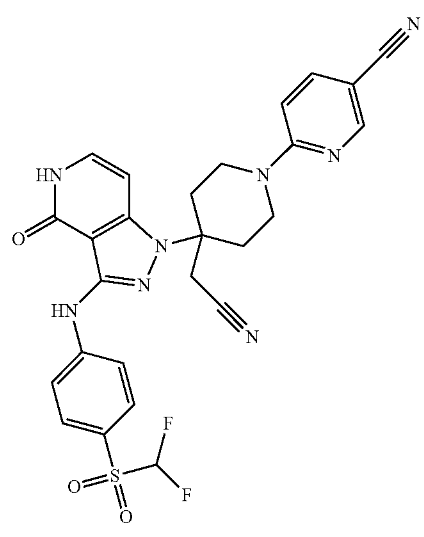 [SMILES: N#CCC1(n2nc(Nc3ccc(S(=O)(=O)C(F)F)cc3)c3c(=O)[nH]ccc32)CCN(c2ccc(C#N)cn2)CC1] | 6-(4-(cyanomethyl)-4-(3-((4((difluoromethyl)sulfonyl)phenyl)amino)-4-oxo-4,5-dihydro-1H-pyrazolo[4,3-c]pyridin-1-yl)piperidin-1-yl)nicotinonitrile | LRMS (ESI) calc'd for $C_{26}H_{23}N_8O_3SF_2$ [M + H]$^+$: 565, found 565. |

… TABLE 28-continued

| Example | Structure | Compound Name | LRMS |
|---|---|---|---|
| 15-4 | 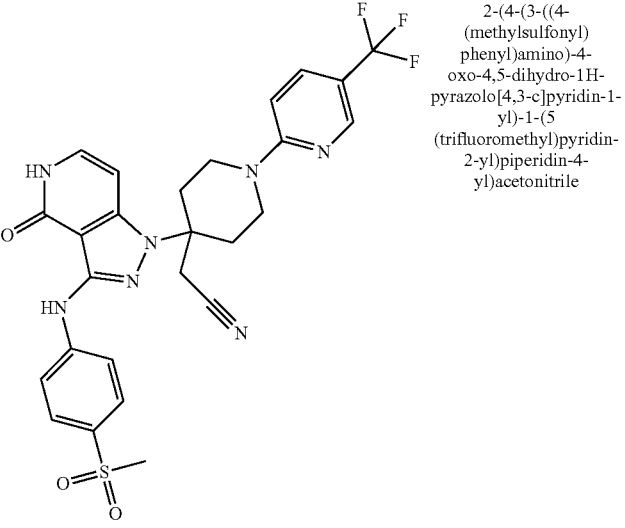 | 2-(4-(3-((4-(methylsulfonyl)phenyl)amino)-4-oxo-4,5-dihydro-1H-pyrazolo[4,3-c]pyridin-1-yl)-1-(5(trifluoromethyl)pyridin-2-yl)piperidin-4-yl)acetonitrile | LRMS (ESI) calc'd for $C_{26}H_{25}N_7O_3SF_3$ $[M + H]^+$: 572, found 572. |
| 15-5 | 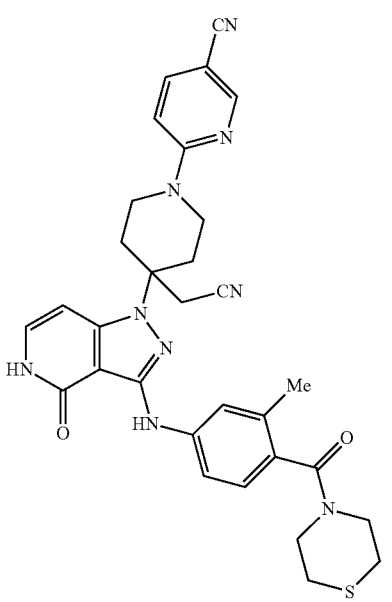 [SMILES: Cc1cc(Nc2nn(C3(CC#N)CCN(c4ccc(C#N)cn4)CC3)c3cc[nH]c(=O)c23)ccc1C(=O)N1CCSCC1] | 6-(4-(cyanomethyl)-4-(3-((3-methyl-4-(thiomorpholine-4-carbonyl)phenyl)amino)-4-oxo-4,5-dihydro-1H-pyrazolo[4,3-c]pyridin-1-yl)piperidin-1-yl)nicotinonitrile | LRMS (ESI) Calc'd for $C_{31}H_{32}N_9O_2S$ $[M + H]^+$: 594, found 594. |

TABLE 28-continued

| Example | Structure | Compound Name | LRMS |
|---|---|---|---|
| 15-6 | 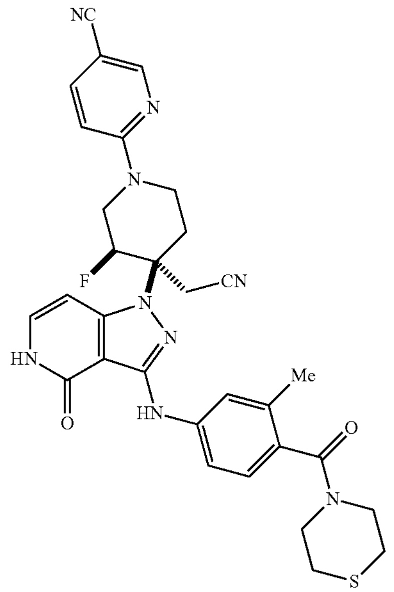 | 6-((3R,4R)-4-(cyanomethyl)-3-fluoro-4-(3-((3-methyl-4-(thiomorpholine-4-carbonyl)phenyl)amino)-4-oxo-4,5-dihydro-1H-pyrazolo[4,3-c]pyridin-1-yl)piperidin-1-yl)nicotinonitrile (from I-7-2B) | LRMS (ESI) Calc'd for $C_{31}H_{31}FN_9O_2S$ [M + H]$^+$: 612, found 612. |
| 15-7 | 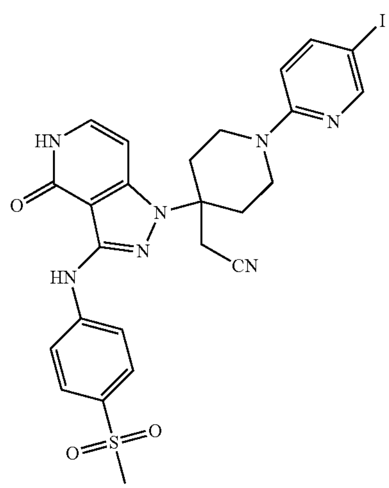 [SMILES: CS(=O)(=O)c1ccc(Nc2nn(C3(CC#N)CCN(c4ccc(I)cn4)CC3)c3cc[nH]c(=O)c23)cc1] | 2-(1-(5-iodopyridin-2-yl)-4-(3-((4-(methylsulfonyl)phenyl)amino)-4-oxo-4,5-dihydro-1H-pyrazolo[4,3-c]pyridin-1-yl)piperidin-4-yl)acetonitrile | LRMS (ESI) calc'd for $C_{25}H_{25}IN_7O_3S$ [M + H]$^+$: 630, found 630. |
| 15-8 | 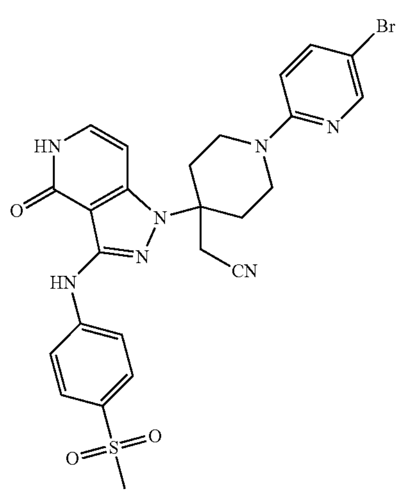 [SMILES: CS(=O)(=O)c1ccc(Nc2nn(C3(CC#N)CCN(c4ccc(Br)cn4)CC3)c3cc[nH]c(=O)c23)cc1] | 2-(1-(5-bromopyridin-2-yl)-4-(3-((4-(methylsulfonyl)phenyl)amino)-4-oxo-4,5-dihydro-1H-pyrazolo[4,3-c]pyridin-1-yl)piperidin-4-yl)acetonitrile | LRMS (ESI) calc'd for $C_{25}H_{25}BrN_7O_3S$ [M + H]$^+$: 582, 584 (1:1), found 582, 584 (1:1). |

Example 16-1

2-(4-(3-(3-methyl-4-(thiomorpholine-4-carbonyl)phenylamino)-4-oxo-4,5-dihydropyrazolo[4,3-c]pyridin-1-yl)-1-(4-(trifluoromethyl)pyridin-2-yl)piperidin-4-yl)acetonitrile

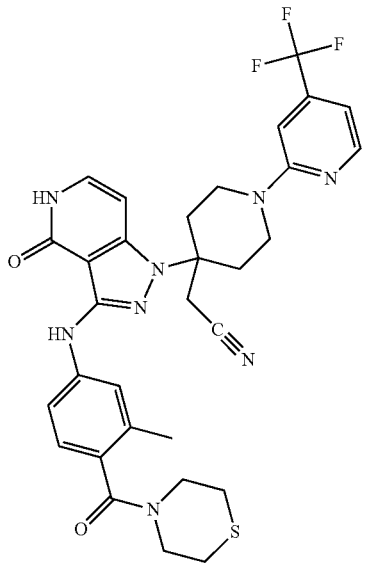

16-1

Step 1: 2-(4-(3-amino-4-oxo-4,5-dihydro-1H-pyrazolo[4,3-c]pyridin-1-yl)piperidin-4-yl)acetonitrile hydrochloride

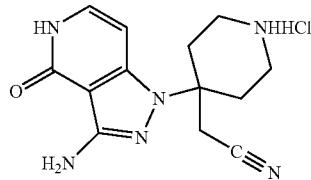

To tert-butyl 4-(3-amino-4-(benzyloxy)-1H-pyrazolo[4,3-c]pyridin-1-yl)-4-(cyanomethyl)piperidine-1-carboxylate (0.50 g, 1.1 mmol) was added a solution of hydrogen chloride (80 mL, 160 mmol, 2M in EtOAc). The mixture was stirred for 6 hours at ambient temperature, then concentrated in vacuo to obtain the crude title compound that was used directly in the next step. LRMS (ESI) calc'd for $C_{13}H_{17}N_6O$ [M+H]$^+$: 273, found 273.

Step 2: 2-(4-(3-amino-4-oxo-4,5-dihydro-1H-pyrazolo[4,3-c]pyridin-1-yl)-1-(4-(trifluoromethyl)pyridin-2-yl)piperidin-4-yl)acetonitrile

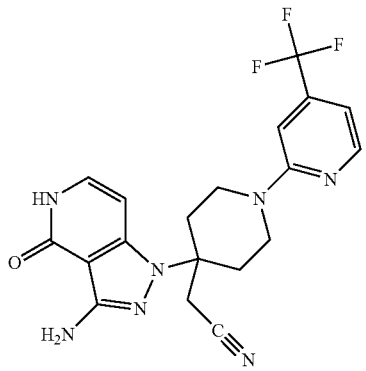 [SMILES: N#CCC1(n2nc(N)c3c(=O)[nH]ccc32)CCN(c2cc(C(F)(F)F)ccn2)CC1]

To a solution of 2-(4-(3-amino-4-oxo-4,5-dihydro-1H-pyrazolo[4,3-c]pyridin-1-yl)piperidin-4-yl)acetonitrile hydrochloride (0.37 g, 1.2 mmol) in DMF (4 mL), was added 2-fluoro-4-(trifluoromethyl)pyridine (0.24 g, 1.4 mmol) and triethylamine (0.24 g, 2.4 mmol). The mixture was stirred for 4 hours at 110° C., then cooled and diluted with water and extracted with EtOAc (×2). The combined organic layers were washed with water (×2), brine (×2), dried over anhydrous $Na_2SO_4$, filtered and concentrated in vacuo. The residue was purified by silica chromatography, eluting with 25% EtOAc in petroleum ether to afford the title compound as a solid. LRMS (ESI) calc'd for $C_{19}H_{19}F_3N_7O$ [M+H]$^+$: 418, found 418. $^1$H NMR (400 MHz, DMSO-d$_6$): δ 10.95 (s, 1H), 8.33 (s, 1H), 7.19-7.13 (m, 1H), 7.09-7.01 (m, 1H), 6.88 (m, 1H), 6.56 (d, J=7.2 Hz, 1H), 5.46 (br s, 2H), 4.11 (m, 2H), 3.27-3.18 (m, 4H), 2.68 (m, 2H), 2.09-2.01 (m, 2H).

Step 3: 2-(4-(3-((3-methyl-4-(thiomorpholine-4-carbonyl)phenyl)amino)-4-oxo-4,5-dihydro-1H-pyrazolo[4,3-c]pyridin-1-yl)-1-(4-(trifluoromethyl)pyridin-2-yl)piperidin-4-yl)acetonitrile To a stirred solution of 2-(4-(3-amino-4-oxo-4,5-dihydro-1H-pyrazolo[4,3-c]pyridin-1-yl)-1-(4-(trifluoromethyl)pyridin-2-yl)piperidin-4-yl)acetonitrile (30 mg, 0.070 mmol) in 2-propanol (10 mL) at ambient temperature under nitrogen, was added potassium acetate (14 mg, 0.14 mmol), tris(dibenzylideneacetonyl)bis-palladium(0) chloroform adduct (10 mg, 0.010 mmol), di-tert-butyl(2',4',6'-triisopropyl-[1,1'-biphenyl]-2-yl)phosphine (8 mg, 0.02 mmol) and (4-bromo-2-methylphenyl)(thiomorpholino)methanone (24 mg, 0.080 mmol). The reaction mixture was stirred at 80° C. for 4 hours, then cooled and quenched with water and extracted with EtOAc (×2). The combined organic layers were washed with brine (×2), dried over anhydrous $Na_2SO_4$, filtered and the filtrate was concentrated in vacuo. The product was purified by reverse phase HPLC using water (with 0.05% $NH_4HCO_3$ modifier) and acetonitrile. The desired fractions were combined and concentrated in vacuo to the title compound as a solid. LCMS (ESI) calc'd for $C_{31}H_{32}F_3N_8O_2S$ [M+H]$^+$: 637, found 637. $^1$H NMR (400 MHz, DMSO-d$_6$): δ 11.34 (br s, 1H), 8.35 (m, 1H), 8.27 (s, 1H), 7.58-7.50 (m, 2H), 7.24-7.13 (m, 3H), 6.88 (d, J=6.8 Hz, 1H), 6.72 (d, J=10.0 Hz, 1H), 4.17-4.29 (m, 2H), 3.88 (m, 2H), 3.46-3.37 (m, 2H), 3.30 (m, 4H), 2.79-2.67 (m, 6H), 2.27 (s, 3H), 2.21-2.01 (m, 2H).

Following analogous procedures to that outlined for Example 16-1 above, the following compounds in Table 29 were prepared.

TABLE 29

| Example | Structure | Compound Name | LRMS |
|---|---|---|---|
| 16-2 | 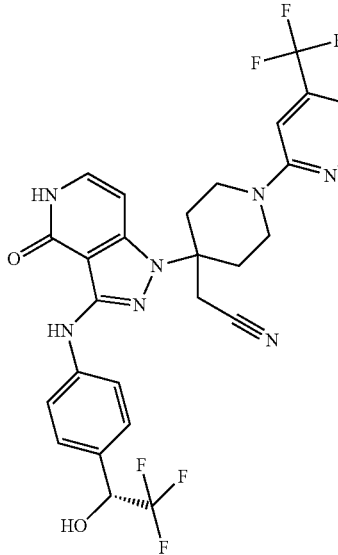 | (R or S)-2-(4-(4-oxo-3-(4-(2,2,2-trifluoro-1-hydroxyethyl)phenylamino)-4,5-dihydropyrazolo[4,3-c]pyridin-1-yl)-1-(4-(trifluoromethyl)pyridin-2-yl)piperidin-4-yl)acetonitrile (Separated as free pyridone using chiral HPLC Chiralpak IA, hexane:EtOH = 40:60, Tr = 4.4 minutes) | LRMS (ESI) calc'd for $C_{27}H_{24}F_6N_7O_2$ [M + H]$^+$: 592, found 592. |
| 16-3 | 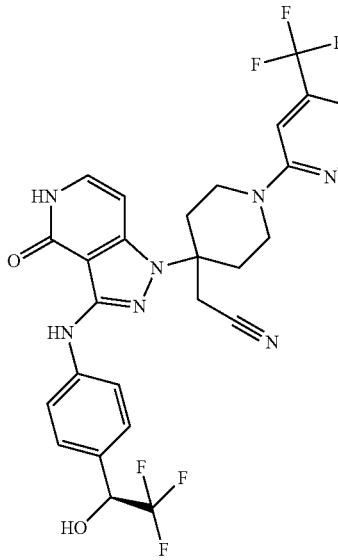 | (R or S)-2-(4-(4-Oxo-3-(4-(2,2,2-trifluoro-1-hydroxyethyl)phenylamino)-4,5-dihydropyrazolo[4,3-c]pyridin-1-yl)-1-(4-(trifluoromethyl)pyridin-2-yl)piperidin-4-yl)acetonitrile (Separated as free pyridone using chiral HPLC Chiralpak IA, hexane:EtOH = 40:60, Tr = 15.2 minutes) | LRMS (ESI) calc'd for $C_{27}H_{24}F_6N_7O_2$ [M + H]$^+$: 592, found 592. |

TABLE 29-continued

| Example | Structure | Compound Name | LRMS |
|---|---|---|---|
| 16-4 | 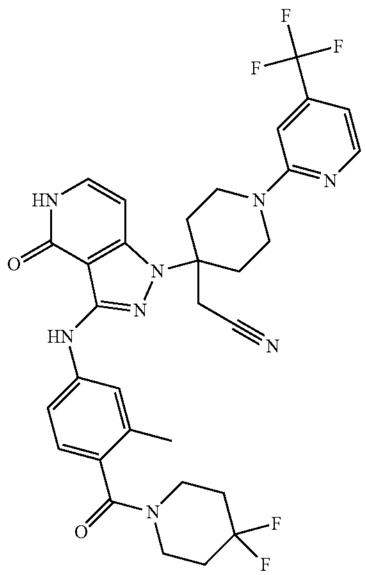 [SMILES: Cc1cc(Nc2nn(C3(CC#N)CCN(c4cc(C(F)(F)F)ccn4)CC3)c3cc[nH]c(=O)c23)ccc1C(=O)N1CCC(F)(F)CC1] | 2-(4-(3-(4-(4,4-difluoropiperidine-1-carbonyl)-3-methylphenylamino)-4-oxo-4,5-dihydropyrazolo[4,3-c]pyridin-1-yl)-1-(4-(trifluoromethyl)pyridin-2-yl)piperidin-4-yl)acetonitrile | LRMS (ESI) calc'd for $C_{32}H_{32}F_5N_8O_2$ [M + H]$^+$: 655, found 655. |

Example 17

2-(1-(2,2-difluoropropanoyl)-4-(3-((4-(methylsulfonyl)phenyl)amino)-4-oxo-4,5-dihydro-1H-pyrazolo[4,3-c]pyridin-1-yl)piperidin-4-yl)acetonitrile

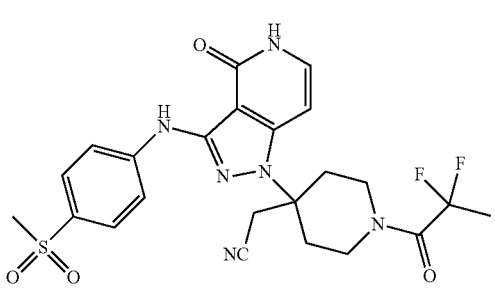

17

To a suspension of 2-(4-(3-((4-(methylsulfonyl)phenyl)amino)-4-oxo-4,5-dihydro-1H-pyrazolo[4,3-c]pyridin-1-yl)piperidin-4-yl)acetonitrile (Example 15-1, Step 2) (0.10 g, 0.22 mmol) in DMF (2.0 mL) was added HATU (20 mg) and 2,2-difluoropropanoic acid (24 mg, 0.023 mmol). The resulting suspension was stirred for 4 hours at room temperature, then partitioned between water and DCM, and the organic phase was washed with brine and concentrated in vacuo. The residue was purified by reverse phase HPLC, eluting with water/acetonitrile with 0.225% formic acid modifier to obtain compound 17. LRMS (ESI) calc'd for $C_{23}H_{24}F_2N_6O_4S$ [M+H]$^+$: 519, found 519. $^1$H NMR (400 MHz, DMSO-d6): δ 11.40 (d, J=4.4 Hz, 1H), 8.75 (s, 1H), 7.88 (d, J=8.8 Hz, 1H), 7.81 (d, J=8.8 Hz, 2H), 7.26-7.22 (m, 1H), 6.75 (d, J=7.6 Hz, 1H), 4.13-4.02 (m, 2H), 3.45-3.40 (m, 2H), 3.31 (s, 2H), 3.15 (s, 3H), 2.88-2.77 (m, 2H), 2.16-2.12 (m, 2H), 1.86 (t, J=20 Hz, 3H).

Examples 18-1 and 18-2

(cis and trans) 2-(4-(3-fluoroazetidin-1-yl)-1-(4-oxo-3-((4-(trifluoromethyl)phenyl)amino)-4,5-dihydro-1H-pyrazolo[4,3-c]pyridin-1-yl)cyclohexyl)acetonitrile

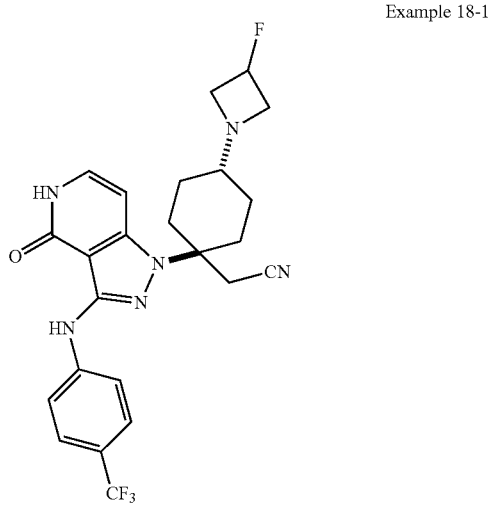

Example 18-1

Diastereomer 1 "trans"

-continued

Example 18-2

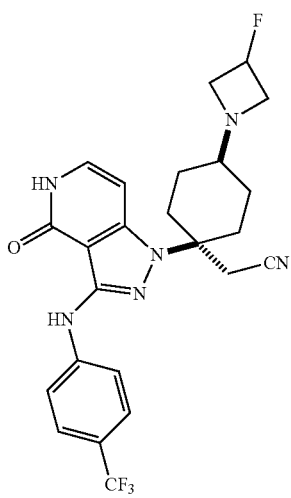

Diastereomer 2 "cis"

Step 1: 2-(4-oxo-1-(4-oxo-3-((4-(trifluoromethyl)phenyl)amino)-4,5-dihydro-1H-pyrazolo[4,3-c]pyridin-1-yl)cyclohexyl)acetonitrile

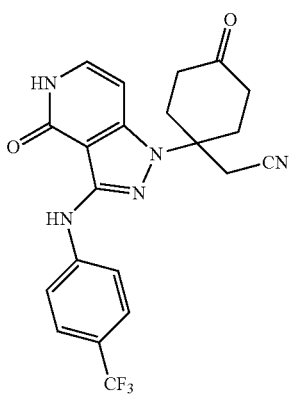 [SMILES: N#CCC1(n2nc(Nc3ccc(C(F)(F)F)cc3)c3c(=O)[nH]ccc32)CCC(=O)CC1]

To a suspension of 2-(8-(4-oxo-3-((4-(trifluoromethyl)phenyl)amino)-4,5-dihydro-1H-pyrazolo[4,3-c]pyridin-1-yl)-1,4-dioxaspiro[4.5]decan-8-yl)acetonitrile (Example 5-83) (0.30 g, 0.63 mmol) in THF (3.2 mL) was added 2.0 M aqueous HCl (0.64 mL, 1.3 mmol). The reaction mixture was stirred at 75° C. for 2 hours, then the reaction was neutralized with aqueous 2M sodium carbonate. The reaction was then purified by silica chromatography, eluting with 0-6% MeOH in DCM to give the title compound. LRMS (ESI) calc'd for $C_{21}H_{19}F_3N_5O_2$ [M+H]$^+$: 430, found 430. $^1$H NMR (600 MHz, DMSO-d6): δ 11.34 (d, J=5.6 Hz, 1H), 8.59 (s, 1H), 7.81 (d, J=8.6 Hz, 2H), 7.57 (d, J=8.6 Hz, 2H), 7.20 (dd, J=7.4, 5.9 Hz, 1H), 6.73 (d, J=7.5 Hz, 1H), 3.30 (s, 2H), 3.00-2.94 (m, 2H), 2.40-2.28 (m, 6H).

Step 2: (cis and trans) 2-(4-(3-fluoroazetidin-1-yl)-1-(4-oxo-3-((4-(trifluoromethyl)phenyl)amino)-4,5-dihydro-1H-pyrazolo[4,3-c]pyridin-1-yl)cyclohexyl)acetonitrile To a suspension of 2-(4-oxo-1-(4-oxo-3-((4-(trifluoromethyl)phenyl)amino)-4,5-dihydro-1H-pyrazolo[4,3-c]pyridin-1-yl)cyclohexyl)acetonitrile (0.12 g, 0.27 mmol) in a mixture of THF (1.1 mL) and MeOH (1.1 mL) was added 3-fluoroazetidine hydrochloride (0.75 g, 0.67 mmol) and acetic acid (0.12 mL, 2.1 mmol). The reaction mixture was stirred at room temperature for 15 minutes then sodium cyanoborohydride (0.42 g, 0.67 mmol) was added and the reaction mixture was allowed to stir for an additional 30 minutes at room temperature. The reaction mixture was concentrated in vacuo to afford a residue that was purified by silica chromatography, eluting with 0.5-5% MeOH in DCM to give pure trans compound 18-1 (diastereomer 1). LRMS (ESI) calc'd for $C_{24}H_{25}F_4N_6O$ [M+H]$^+$: 489, found 489. $^1$H NMR (600 MHz, DMSO-d6): δ 11.27 (d, J=5.6 Hz, 1H), 8.55 (s, 1H), 7.80 (d, J=8.5 Hz, 2H), 7.56 (d, J=8.7 Hz, 2H), 7.16-7.13 (m, 1H), 6.64 (d, J=7.6 Hz, 1H), 5.20-5.04 (m, 1H), 3.57-3.48 (m, 2H), 3.16 (s, 2H), 3.05-3.01 (m, 1H), 3.01-2.96 (m, 1H), 2.40-2.33 (m, 2H), 2.25-2.21 (m, 1H), 2.13 (t, J=10.0 Hz, 2H), 1.53-1.38 (m, 4H). Cis compound 18-2, (diastereomer 2) was subjected to subsequent purification by reverse phase chromatography using AcCN in water with 0.1% TFA modifier. The desired fractions were diluted with EtOAc and neutralized with saturated aqueous NaHCO$_3$ and the organic layer was dried over sodium sulfate, filtered and concentrated in vacuo. LRMS (ESI) calc'd for $C_{24}H_{25}F_4N_6O$ [M+H]$^+$: 489, found 489. $^1$H NMR (600 MHz, DMSO-d6): δ 11.27 (d, J=5.7 Hz, 1H), 8.56 (s, 1H), 7.80 (d, J=8.6 Hz, 2H), 7.56 (d, J=8.7 Hz, 2H), 7.16 (dd, J=7.4, 5.9 Hz, 1H), 6.63 (d, J=7.5 Hz, 1H), 5.10-4.94 (m, 1H), 3.48-3.39 (m, 2H), 3.13 (s, 2H), 3.01-2.91 (m, 2H), 2.73 (d, J=13.7 Hz, 2H), 2.19-2.12 (m, 1H), 1.84-1.72 (m, 2H), 1.68 (dd, J=9.9, 3.9 Hz, 2H), 1.08-0.97 (m, 2H).

The following examples in Table 30 were prepared in an analogous fashion to that of Examples 18-1 and 18-2 above and relative stereochemistry was assigned by either NMR proof or by analogy based on biochemical activity. In the following examples, cis and trans stereochemistry refers to the relative orientation of the pyrrolopyrimidinone and amine substituents. In some cases, Step 1 of the sequence could be carried out using by substituting t-BuXphos ligand, i-PrOH and KOAc while using microwave irradiation.

TABLE 30

| Example | Structure | Compound Name | LRMS |
|---|---|---|---|
| 18-3 | 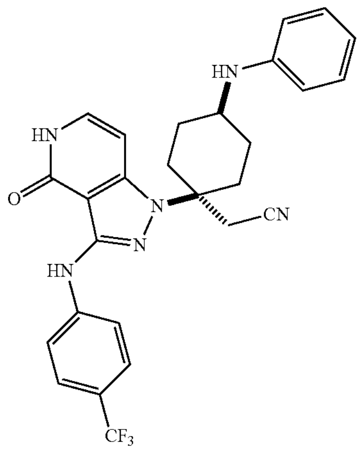 | Cis 2-(1-(4-oxo-3-((4-(trifluoromethyl)phenyl)amino)-4,5-dihydro-1H-pyrazolo[4,3-c]pyridin-1-yl)-4-(phenylamino)cyclohexyl)acetonitrile | LRMS (ESI) calc'd for $C_{27}H_{26}F_3N_6O$ $[M + H]^+$: 507, found 507. |
| 18-4 | 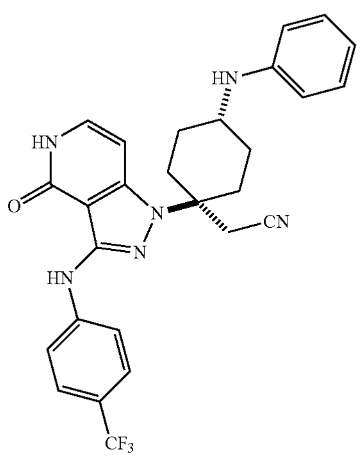 | Trans 2-(1-(4-oxo-3-((4-(trifluoromethyl)phenyl)amino)-4,5-dihydro-1H-pyrazolo[4,3-c]pyridin-1-yl)-4-(phenylamino)cyclohexyl)acetonitrile | LRMS (ESI) calc'd for $C_{27}H_{26}F_3N_6O$ $[M + H]^+$: 507, found 507. |
| 18-5 | 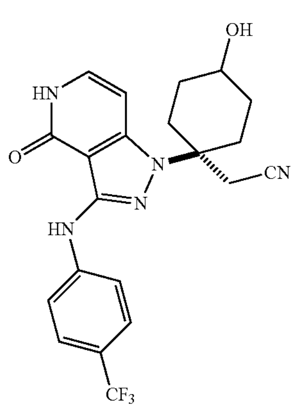 | (cis and trans) 2-(4-hydroxy-1-(4-oxo-3-((4-(trifluoromethyl)phenyl)amino)-4,5-dihydro-1H-pyrazolo[4,3-c]pyridin-1-yl)cyclohexyl)acetonitrile | LRMS (ESI) calc'd for $C_{21}H_{21}F_3N_5O_2$ $[M + H]^+$: 432, found 432. |

TABLE 30-continued

| Example | Structure | Compound Name | LRMS |
|---|---|---|---|
| 18-6 | 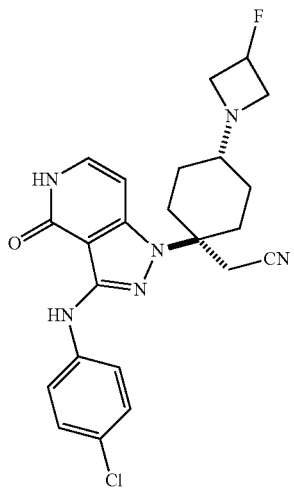 | Trans 2-(1-(3-((4-chlorophenyl)amino)-4-oxo-4,5-dihydro-1H-pyrazolo[4,3-c]pyridin-1-yl)-4-(3-fluoroazetidin-1-yl)cyclohexyl)acetonitrile | LRMS (ESI) calc'd for $C_{23}H_{25}ClFN_6O$ $[M + H]^+$: 455, found 455. |
| 18-7 | 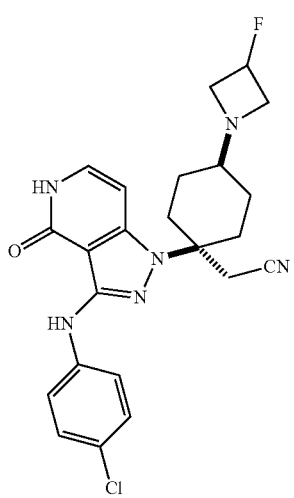 | Cis 2-(1-(3-((4-chlorophenyl)amino)-4-oxo-4,5-dihydro-1H-pyrazolo[4,3-c]pyridin-1-yl)-4-(3-fluoroazetidin-1-yl)cyclohexyl)acetonitrile | LRMS (ESI) calc'd for $C_{23}H_{25}ClFN_6O$ $[M + H]^+$: 455, found 455. |
| 18-8 | 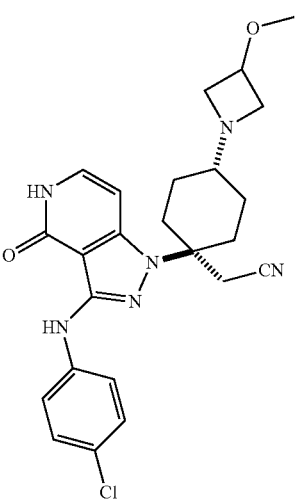 | Trans 2-(1-(3-((4-chlorophenyl)amino)-4-oxo-4,5-dihydro-1H-pyrazolo[4,3-c]pyridin-1-yl)-4-(3-methoxyazetidin-1-yl)cyclohexyl)acetonitrile | LRMS (ESI) calc'd for $C_{24}H_{28}ClN_6O_2$ $[M + H]^+$: 467, found 467. |

TABLE 30-continued

| Example | Structure | Compound Name | LRMS |
|---|---|---|---|
| 18-9 | 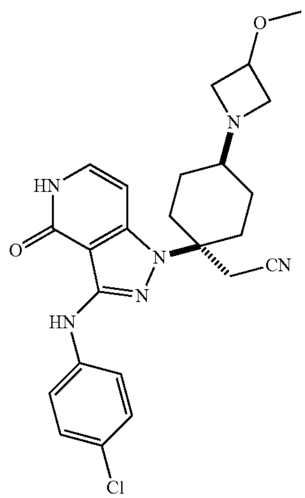 | Cis 2-(1-(3-((4-chlorophenyl)amino)-4-oxo-4,5-dihydro-1H-pyrazolo[4,3-c]pyridin-1-yl)-4-(3-methoxyazetidin-1-yl)cyclohexyl)acetonitrile | LRMS (ESI) calc'd for $C_{24}H_{28}ClN_6O_2$ $[M + H]^+$: 467, found 467. |
| 18-10 | 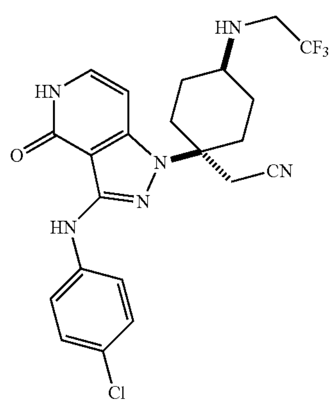 | Cis 2-(1-(3-((4-chlorophenyl)amino)-4-oxo-4,5-dihydro-1H-pyrazolo[4,3-c]pyridin-1-yl)-4-((2,2,2-trifluoroethyl)amino)cyclohexyl)acetonitrile | LRMS (ESI) calc'd for $C_{22}H_{23}ClF_3N_6O$ $[M + H]^+$: 479, found 479. |
| 18-11 | 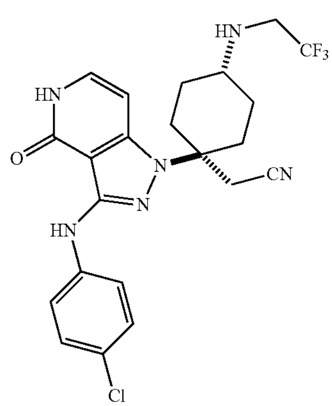 | Trans 2-(1-(3-((4-chlorophenyl)amino)-4-oxo-4,5-dihydro-1H-pyrazolo[4,3-c]pyridin-1-yl)-4-((2,2,2-trifluoroethyl)amino)cyclohexyl)acetonitrile | LRMS (ESI) calc'd for $C_{22}H_{23}ClF_3N_6O$ $[M + H]^+$: 479, found 479. |

TABLE 30-continued

| Example | Structure | Compound Name | LRMS |
|---------|-----------|---------------|------|
| 18-12 | 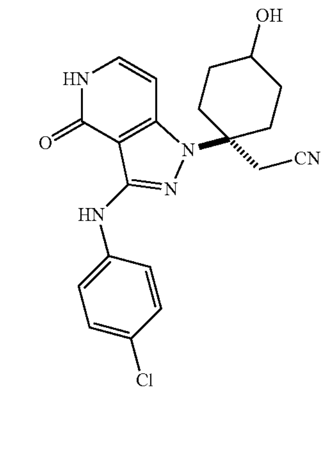 | Cis and trans 2-(1-(3-((4-chlorophenyl)amino)-4-oxo-4,5-dihydro-1H-pyrazolo[4,3-c]pyridin-1-yl)-4-hydroxycyclohexyl)acetonitrile | LRMS (ESI) calc'd for $C_{20}H_{21}ClN_5O_2$ [M + H]$^+$: 398, found 398. |
| 18-13 | 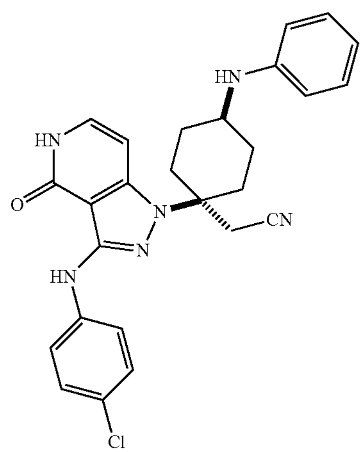 | Cis 2-(1-(3-((4-chlorophenyl)amino)-4-oxo-4,5-dihydro-1H-pyrazolo[4,3-c]pyridin-1-yl)-4-(phenylamino)cyclohexyl)acetonitrile | LRMS (ESI) calc'd for $C_{26}H_{26}ClN_6O$ [M + H]$^+$: 473, found 473. |
| 18-14 | 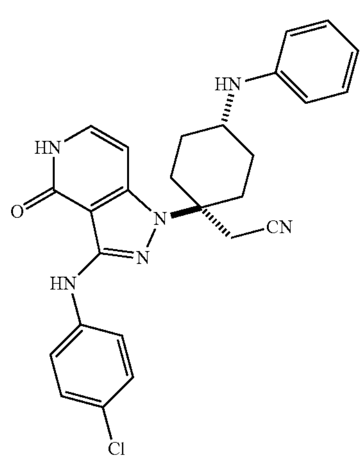 | Trans 2-(1-(3-((4-chlorophenyl)amino)-4-oxo-4,5-dihydro-1H-pyrazolo[4,3-c]pyridin-1-yl)-4-(phenylamino)cyclohexyl)acetonitrile | LRMS (ESI) calc'd for $C_{26}H_{26}ClN_6O$ [M + H]$^+$: 473, found 473. |

TABLE 30-continued

| Example | Structure | Compound Name | LRMS |
|---|---|---|---|
| 18-15 | 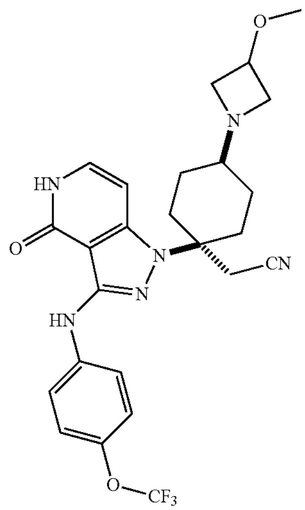 | Cis 2-(4-(3-methoxyazetidin-1-yl)-1-(4-oxo-3-((4-(trifluoromethoxy)phenyl)amino)-4,5-dihydro-1H-pyrazolo[4,3-c]pyridin-1-yl)cyclohexyl)acetonitrile | LRMS (ESI) calc'd for $C_{25}H_{28}F_3N_6O_3$ [M + H]⁺: 517, found 517. |
| 18-16 | 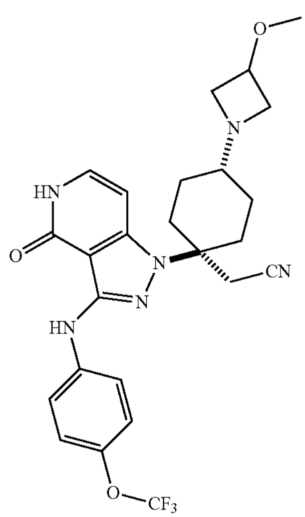 | Trans 2-(4-(3-methoxyazetidin-1-yl)-1-(4-oxo-3-((4-(trifluoromethoxy)phenyl)amino)-4,5-dihydro-1H-pyrazolo[4,3-c]pyridin-1-yl)cyclohexyl)acetonitrile | LRMS (ESI) calc'd for $C_{25}H_{28}F_3N_6O_3$ [M + H]⁺: 517, found 517. |
| 18-17 | 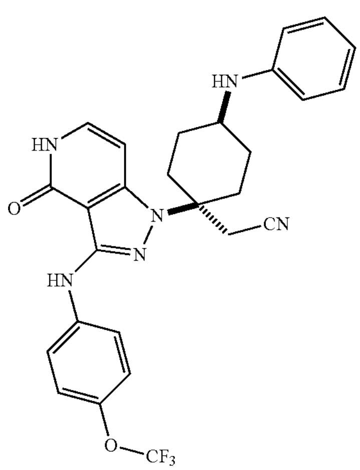 | Cis 2-(1-(4-oxo-3-((4-(trifluoromethoxy)phenyl)amino)-4,5-dihydro-1H-pyrazolo[4,3-c]pyridin-1-yl)-4-(phenylamino)cyclohexyl)acetonitrile | LRMS (ESI) calc'd for $C_{27}H_{26}F_3N_6O_2$ [M + H]⁺: 523, found 523. |

TABLE 30-continued

| Example | Structure | Compound Name | LRMS |
|---|---|---|---|
| 18-18 | 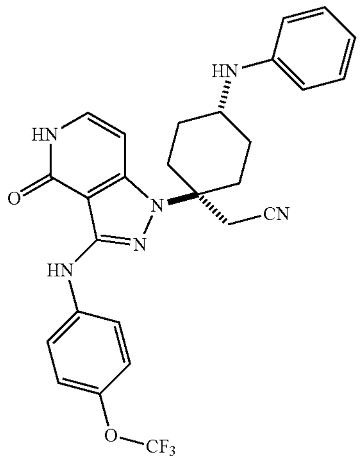 | Trans 2-(1-(4-oxo-3-((4-(trifluoromethoxy)phenyl)amino)-4,5-dihydro-1H-pyrazolo[4,3-c]pyridin-1-yl)-4-(phenylamino)cyclohexyl)acetonitrile | LRMS (ESI) calc'd for $C_{27}H_{26}F_3N_6O_2$ [M + H]⁺: 523, found 523. |
| 18-19 | 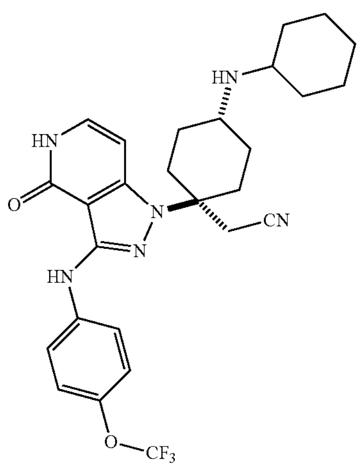 | Trans 2-(4-(cyclohexylamino)-1-(4-oxo-3-((4-(trifluoromethoxy)phenyl)amino)-4,5-dihydro-1H-pyrazolo[4,3-c]pyridin-1-yl)cyclohexyl)acetonitrile | LRMS (ESI) calc'd for $C_{27}H_{32}F_3N_6O_2$ [M + H]⁺: 529, found 529. |
| 18-20 | 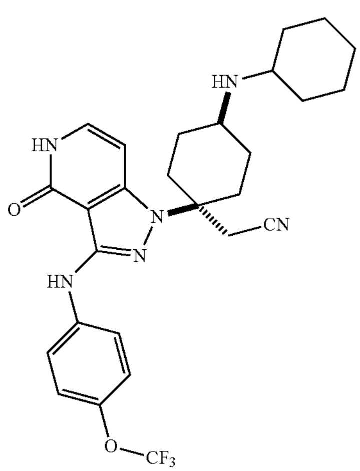 | Cis 2-(4-(cyclohexylamino)-1-(4-oxo-3-((4-(trifluoromethoxy)phenyl)amino)-4,5-dihydro-1H-pyrazolo[4,3-c]pyridin-1-yl)cyclohexyl)acetonitrile | LRMS (ESI) calc'd for $C_{27}H_{32}F_3N_6O_2$ [M + H]⁺: 529, found 529. |

TABLE 30-continued

| Example | Structure | Compound Name | LRMS |
|---|---|---|---|
| 18-21 | 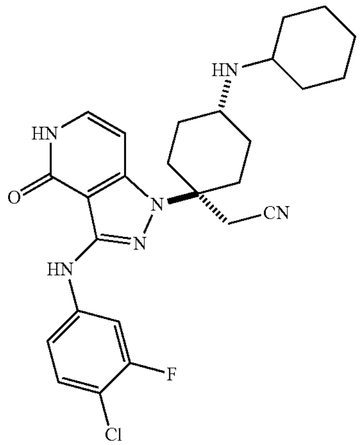 | Trans 2-(1-(3-((4-chloro-3-fluorophenyl)amino)-4-oxo-4,5-dihydro-1H-pyrazolo[4,3-c]pyridin-1-yl)-4-(cyclohexylamino)cyclohexyl)acetonitrile | LRMS (ESI) calc'd for $C_{26}H_{31}ClFN_6O$ $[M + H]^+$: 497, found 497. |
| 18-22 | 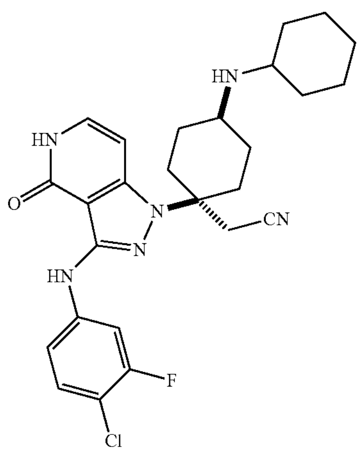 | Cis 2-(1-(3-((4-chloro-3-fluorophenyl)amino)-4-oxo-4,5-dihydro-1H-pyrazolo[4,3-c]pyridin-1-yl)-4-(cyclohexylamino)cyclohexyl)acetonitrile | LRMS (ESI) calc'd for $C_{26}H_{31}ClFN_6O$ $[M + H]^+$: 497, found 497. |
| 18-23 | 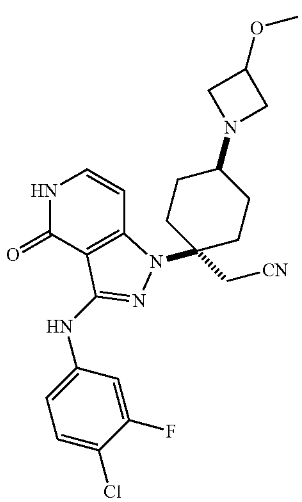 | Cis 2-(1-(3-((4-chloro-3-fluorophenyl)amino)-4-oxo-4,5-dihydro-1H-pyrazolo[4,3-c]pyridin-1-yl)-4-(3-methoxyazetidin-1-yl)cyclohexyl)acetonitrile | LRMS (ESI) calc'd for $C_{24}H_{27}ClFN_6O_2$ $[M + H]^+$: 485, found 485. |

TABLE 30-continued

| Example | Structure | Compound Name | LRMS |
|---|---|---|---|
| 18-24 | 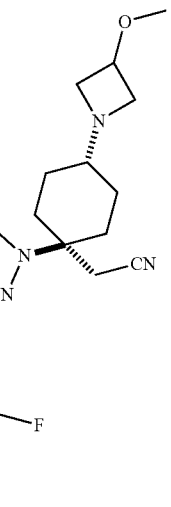 | Trans 2-(1-(3-((4-chloro-3-fluorophenyl)amino)-4-oxo-4,5-dihydro-1H-pyrazolo[4,3-c]pyridin-1-yl)-4-(3-methoxyazetidin-1-yl)cyclohexyl)acetonitrile | LRMS (ESI) calc'd for $C_{24}H_{27}ClFN_6O_2$ [M + H]$^+$: 485, found 485. |
| 18-25 | 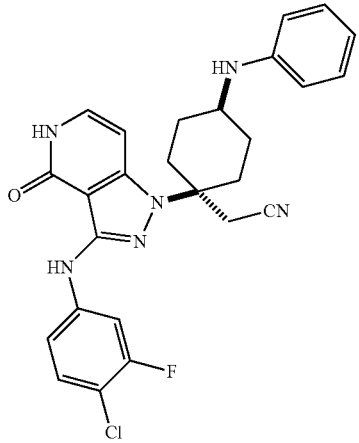 | Cis 2-(1-(3-((4-chloro-3-fluorophenyl)amino)-4-oxo-4,5-dihydro-1H-pyrazolo[4,3-c]pyridin-1-yl)-4-(phenylamino)cyclohexyl)acetonitrile | LRMS (ESI) calc'd for $C_{26}H_{25}ClFN_6O$ [M + H]$^+$: 491, found 491. |
| 18-26 | 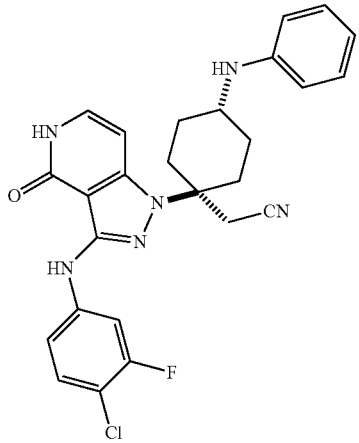 | Trans 2-(1-(3-((4-chloro-3-fluorophenyl)amino)-4-oxo-4,5-dihydro-1H-pyrazolo[4,3-c]pyridin-1-yl)-4-(phenylamino)cyclohexyl)acetonitrile | LRMS (ESI) calc'd for $C_{26}H_{25}ClFN_6O$ [M + H]$^+$: 491, found 491. |

TABLE 30-continued

| Example | Structure | Compound Name | LRMS |
|---|---|---|---|
| 18-27 | 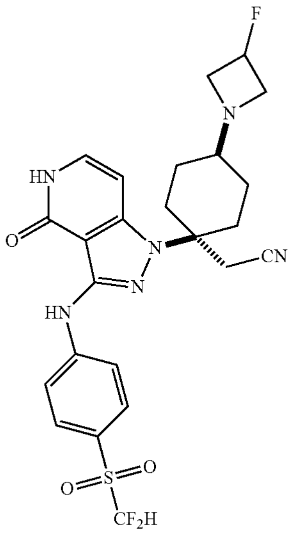 | Cis 2-(1-(3-((4-((difluoromethyl)sulfonyl)phenyl)amino)-4-oxo-4,5-dihydro-1H-pyrazolo[4,3-c]pyridin-1-yl)-4-(3-fluoroazetidin-1-yl)cyclohexyl)acetonitrile | LRMS (ESI) calc'd for $C_{24}H_{26}F_3N_6O_3S$ $[M + H]^+$: 535, found 535. |
| 18-28 | 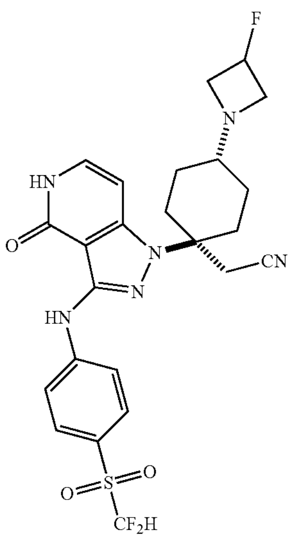 | Trans 2-(1-(3-((4-((difluoromethyl)sulfonyl)phenyl)amino)-4-oxo-4,5-dihydro-1H-pyrazolo[4,3-c]pyridin-1-yl)-4-(3-fluoroazetidin-1-yl)cyclohexyl)acetonitrile | LRMS (ESI) calc'd for $C_{24}H_{26}F_3N_6O_3S$ $[M + H]^+$: 535, found 535. |
| 18-29 | 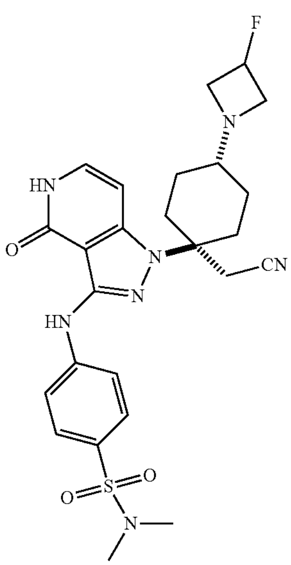 | Trans 4-((1-(1-(cyanomethyl)-4-(3-fluoroazetidin-1-yl)cyclohexyl)-4-oxo-4,5-dihydro-1H-pyrazolo[4,3-c]pyridin-3-yl)amino)-N,N-dimethylbenzenesulfonamide | LRMS (ESI) calc'd for $C_{25}H_{31}N_7O_3FS$ $[M + H]^+$: 528, found 528. |

TABLE 30-continued

| Example | Structure | Compound Name | LRMS |
|---|---|---|---|
| 18-30 | 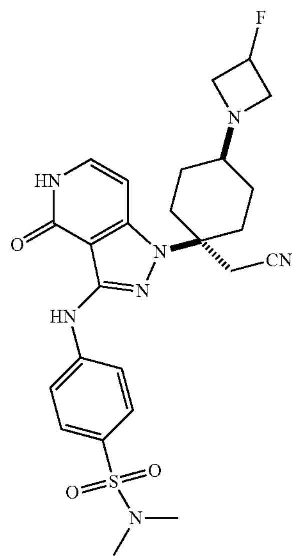 | Cis 4-((1-(1-(cyanomethyl)-4-(3-fluoroazetidin-1-yl)cyclohexyl)-4-oxo-4,5-dihydro-1H-pyrazolo[4,3-c]pyridin-3-yl)amino)-N,N-dimethylbenzenesulfonamide | LRMS (ESI) calc'd for $C_{25}H_{31}N_7O_3FS$ [M + H]$^+$: 528, found 528. |
| 18-31 | 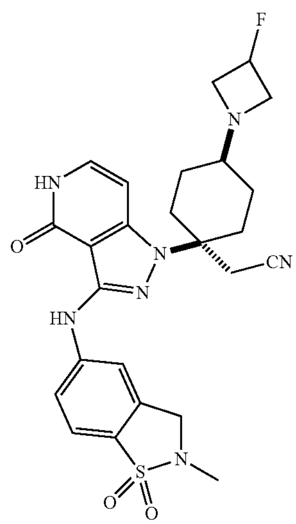 | Cis 2-(4-(3-Fluoroazetidin-1-yl)-1-(3-((2-methyl-1,1-dioxido-2,3-dihydro-benzo[d]isothiazol-6-yl)amino)-4-oxo-4,5-dihydro-1H-pyrazolo[4,3-c]pyridin-1-yl)cyclohexyl)acetonitrile | LRMS (ESI) calc'd for $C_{25}H_{29}N_7O_3SF$ [M + H]$^+$: 526, found 526. |
| 18-32 | 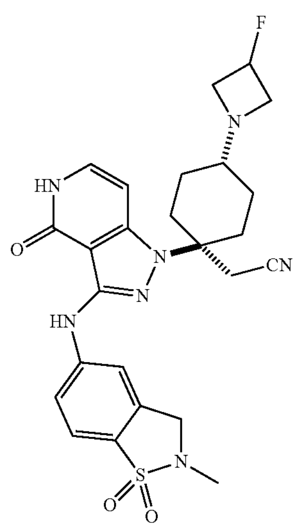 | Trans 2-(4-(3-Fluoroazetidin-1-yl)-1-(3-((2-methyl-1,1-dioxido-2,3-dihydro-benzo[d]isothiazol-6-yl)amino)-4-oxo-4,5-dihydro-1H-pyrazolo[4,3-c]pyridin-1-yl)cyclohexyl)acetonitrile | LRMS (ESI) calc'd for $C_{25}H_{29}N_7O_3SF$ [M + H]$^+$: 526, found 526. |

TABLE 30-continued

| Example | Structure | Compound Name | LRMS |
|---|---|---|---|
| 18-33 | 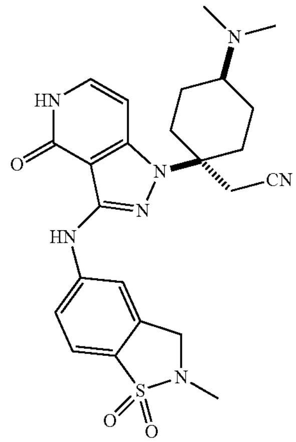 | Cis 2-(4-(Dimethylamino)-1-(3-((2-methyl-1,1-dioxido-2,3-dihydrobenzo-[d]isothiazol-6-yl)amino)-4-oxo-4,5-dihydro-1H-pyrazolo[4,3-c]pyridin-1-yl)cyclohexyl)acetonitrile | LRMS (ESI) calc'd for $C_{24}H_{30}N_7O_3S$ $[M + H]^+$: 496, found 496. |
| 18-34 | 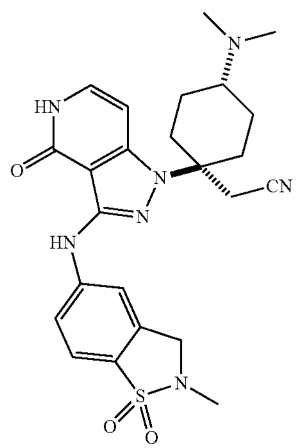 | Trans 2-(4-(Dimethylamino)-1-(3-((2-methyl-1,1-dioxido-2,3-dihydrobenzo-[d]isothiazol-6-yl)amino)-4-oxo-4,5-dihydro-1H-pyrazolo[4,3-c]pyridin-1-yl)cyclohexyl)acetonitrile | LRMS (ESI) calc'd for $C_{24}H_{30}N_7O_3S$ $[M + H]^+$: 496, found 496. |
| 18-35 | 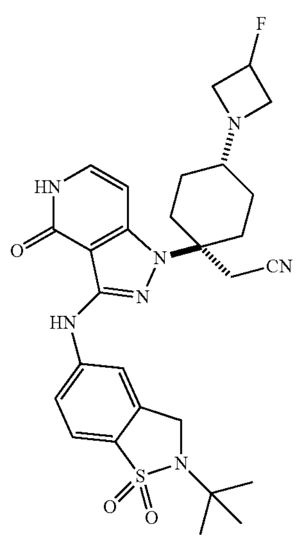 | Trans 2-(4-(3-Fluoroazetidin-1-yl)-1-(3-((2-methyl-1,1-dioxido-2,3-dihydro-benzo[d]isothiazol-6-yl)amino)-4-oxo-4,5-dihydro-1H-pyrazolo[4,3-c]pyridin-1-yl)cyclohexyl)acetonitrile | LRMS (ESI) calc'd for $C_{28}H_{35}N_7O_3SF$ $[M + H]^+$: 568, found 568. |

TABLE 30-continued

| Example | Structure | Compound Name | LRMS |
|---|---|---|---|
| 18-36 | 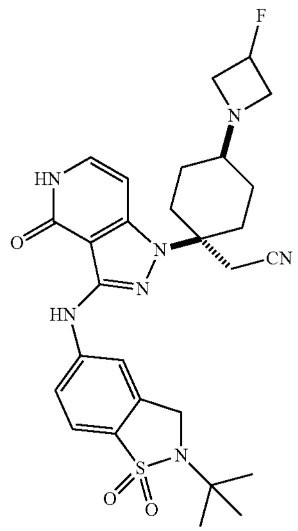 | Cis 2-(4-(3-fluoroazetidin-1-yl)-1-(3-((2-methyl-1,1-dioxido-2,3-dihydro-benzo[d]isothiazol-6-yl)amino)-4-oxo-4,5-dihydro-1H-pyrazolo[4,3-c]pyridin-1-yl)cyclohexyl)acetonitrile | LRMS (ESI) calc'd for $C_{28}H_{35}N_7O_3SF$ $[M + H]^+$: 568, found 568. |
| 18-37 | 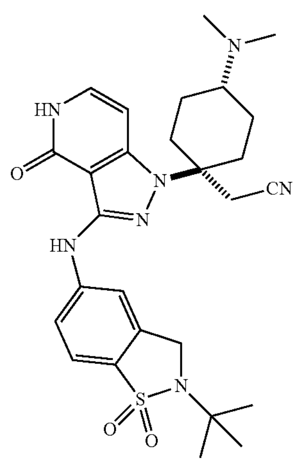 | Trans 2-(1-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-4-(dimethylamino)cyclohexyl)acetonitrile | LRMS (ESI) calc'd for $C_{27}H_{36}N_7O_3S$ $[M + H]^+$: 538, found 538. |
| 18-38 | 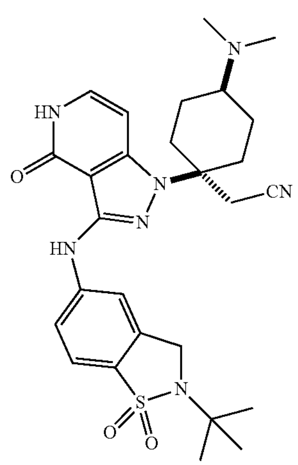 | Cis 2-(1-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-4-(dimethylamino)cyclohexyl)acetonitrile | LRMS (ESI) calc'd for $C_{27}H_{36}N_7O_3S$ $[M+H]^+$: 538, found 538. |

TABLE 30-continued

| Example | Structure | Compound Name | LRMS |
|---|---|---|---|
| 18-39 | 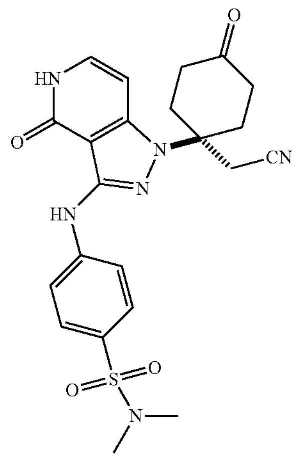 | 4-((1-(1-(cyanomethyl)-4-oxocyclohexyl)-4-oxo-4,5-dihydro-1H-pyrazolo[4,3-c]pyridin-3-yl)amino)-N,N-dimethylbenzenesulfonamide | LRMS (ESI) calc'd for $C_{22}H_{25}N_6O_4S$ [M + H]$^+$: 469, found 469. |

Example 19-1

(2S,5S)-N-(tert-butyl)-5-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-5-(cyanomethyl)tetrahydro-2H-pyran-2-carboxamide 19-1

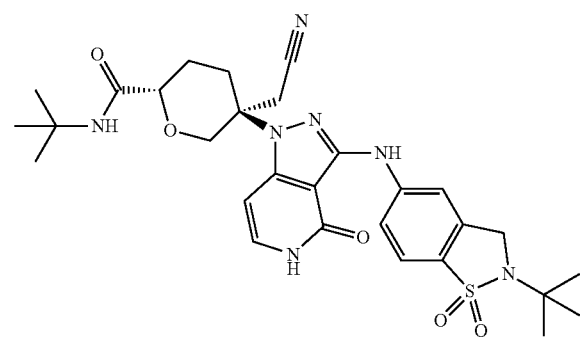

Step 1: (2S,5S)-5-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-5-(cyanomethyl)tetrahydro-2H-pyran-2-carboxylic acid

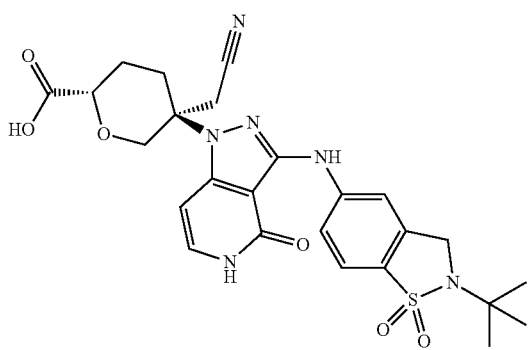 [SMILES: CC(C)(C)N1Cc2cc(Nc3nn([C@]4(CC#N)CC[C@@H](C(=O)O)OC4)c4cc[nH]c(=O)c34)ccc2S1(=O)=O]

To a solution of (2S,5S)-tert-butyl 5-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-5-(cyanomethyl)tetrahydro-2H-pyran-2-carboxylate (Example 5-41) (390 mg, 0.654 mmol) in DCM (6.5 mL) was added TFA (0.50 mL, 6.5 mmol) portionwise at 25° C. The reaction solution was stirred overnight, diluted in DCM and quenched by the addition of saturated ammonium chloride solution. The reaction mixture was extracted with iPA/CHCl$_3$ (×3). The combined organic layers were dried over sodium sulfate, filtered and concentrated in vacuo to afford the title compound as a solid.

Step 2: (2S,5S)-N-(tert-butyl)-5-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-5-(cyanomethyl)tetrahydro-2H-pyran-2-carboxamide (19-1)

To (2S,5S)-5-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-5-(cyanomethyl)tetrahydro-2H-pyran-2-carboxylic acid (30 mg, 0.046 mmol) in DMF (0.4 mL), was added tert-butylamine (24 μL, 0.23 mmol), DIPEA (40 μL, 0.229 mmol) and HATU (52.4 mg, 0.138 mmol). The reaction was stirred at room temperature for 4 hours, then concentrated and purified by mass triggered reverse phase HPLC using acetonitrile in water with 0.1% TFA modifier to afford 19-1. LRMS (ESI) calc'd for $C_{29}H_{38}N_7O_5S$ [M+H]$^+$: 596, found 596. $^1$H NMR (600 MHz, DMSO-d6): δ 11.32 (d, J=5.8 Hz, 1H), 8.66 (s, 1H), 7.64-7.62 (d, J=7.1 Hz, 1H), 7.56-7.54 (d, J=8.2 Hz, 1H), 7.19 (t, J=5.8 Hz, 1H), 6.90 (s, 1H), 6.73-6.72 (d, J=7.6 Hz, 1H), 4.46 (s, 1H), 4.42-4.40 (d, J=11.7 Hz, 1H), 3.88 (d, J=11.2 Hz, 2H), 3.85-3.84 (d, J=11.2 Hz, 1H), 3.48 (d, J=11.7 Hz, 2H), 2.63-2.62 (d, J=12.9 Hz, 2H), 2.97-2.94 (d, J=15.8 Hz, 2H), 1.69 (m, 2H), 1.42 (s, 9H), 1.27 (s, 9H).

The following examples outlined in Table 31 were prepared by analogy using the general procedure outlined above.

TABLE 31

| Example | Structure | Compound Name | LRMS |
|---|---|---|---|
| 19-2 | 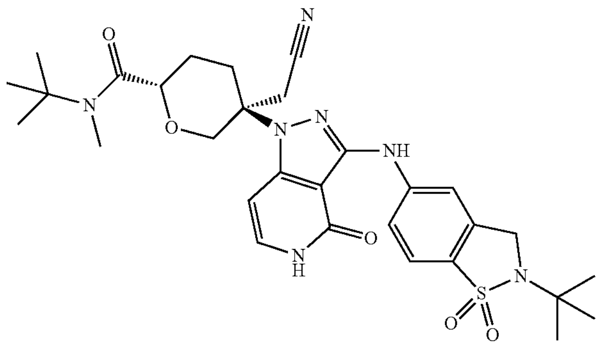 [SMILES: CN(C(=O)[C@@H]1CC[C@@](CC#N)(n2nc(Nc3ccc4c(c3)CN(C(C)(C)C)S4(=O)=O)c3c(=O)[nH]ccc32)CO1)C(C)(C)C] | (2S,5S)-N-tert-butyl-5-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}-5-(cyanomethyl)-N-methyltetrahydro-2H-pyran-2-carboxamide | LRMS (ESI) calc'd for $C_{30}H_{40}N_7O_5S$ $[M + H]^+$: 610, found 610. |
| 19-3 | 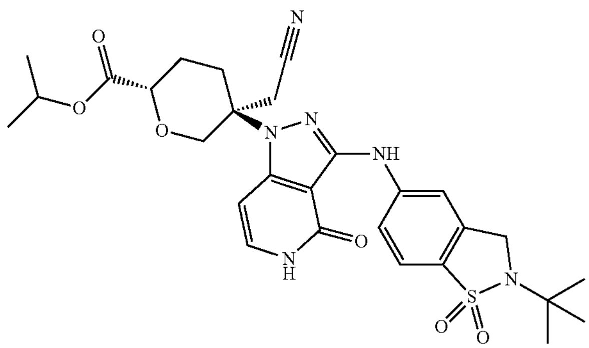 [SMILES: CC(C)OC(=O)[C@@H]1CC[C@@](CC#N)(n2nc(Nc3ccc4c(c3)CN(C(C)(C)C)S4(=O)=O)c3c(=O)[nH]ccc32)CO1] | (2S,5S)-isopropyl 5-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-5-(cyanomethyl)tetrahydro-2H-pyran-2-carboxylate | LRMS (ESI) calc'd for $C_{28}H_{35}N_6O_6S$ $[M + H]^+$: 583, found 583. |

Example 20-1

(S)-2-(3-(3-((4-(4,4-difluoropiperidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile

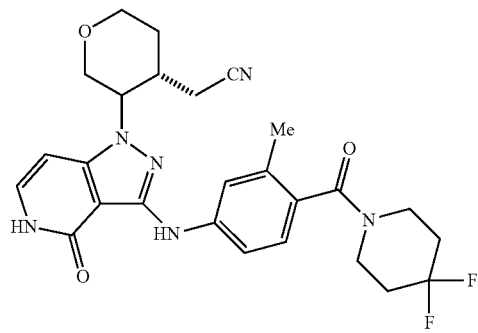

20-1

Step 1: (S)-4-((4-(benzyloxy)-1-(3-(cyanomethyl)tetrahydro-2H-pyran-3-yl)-1H-pyrazolo[4,3-c]pyridin-3-yl)amino)-2-methylbenzoic acid

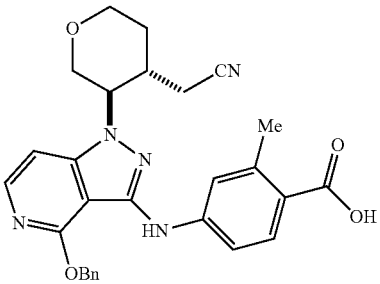

To an oven dried pressure tube equipped with magnetic sir bar under an atmosphere of nitrogen was charged with (S)-2-(3-(3-amino-4-(benzyloxy)-1H-pyrazolo[4,3-c]pyridin-1-yl)tetrahydro-2H-pyran-3-yl)acetonitrile (I-17B) (1.5 g, 4.1 mmol), 4-bromo-2-methylbenzoic acid (1.6 g, 7.4 mmol), potassium acetate (1.10 g, 11.4 mmol), and t-Bu XPhos 3rd Generation precatalyst (0.36 g, 0.50 mmol). The flasks was degassed by successive evacuation/nitrogen backfill (x3) and t-amyl alcohol (41.3 mL) was added. The reaction mixture was heated to 90° C. for 16 hours, then concentrated in vacuo and purified by silica chromatography, eluting with a hexanes/EtOAc gradient to yield the title compound. LRMS (ESI) calc'd for $C_{28}H_{28}N_5O_4$ [M+H]$^+$:

498, found 498. ¹H NMR (CDCl₃, 500 MHz): δ 8.08 (d, J=8.64 Hz, 1H), 7.93 (d, J=6.5 Hz, 1H), 7.63 (s, 1H), 7.60-7.57 (m, 2H), 7.55-7.46 (m, 3H), 7.36 (d, J=8.8 Hz, 1H), 7.19-7.14 (m, 2H), 5.67 (s, 2H), 4.37 (d, J=12.0 Hz, 1H), 4.19 (d, J=12.2 Hz, 1H), 3.88 (m, 1H), 3.77 (m, 1H), 3.24 (d, J=17.1 Hz, 1H), 3.10 (d, J=17.1 Hz, 1H), 2.78 (m, 1H), 2.66 (s, 3H), 2.53 (m, 1H), 1.88-1.74 (m, 2H).

Step 2: (S)-4-((1-(3-(cyanomethyl)tetrahydro-2H-pyran-3-yl)-4-oxo-4,5-dihydro-1H-pyrazolo[4,3-c]pyridin-3-yl)amino)-2-methylbenzoic acid

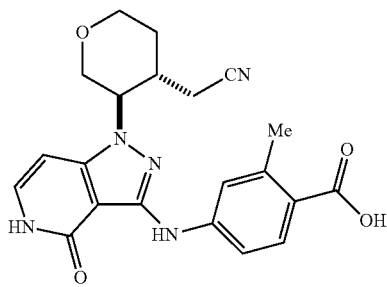

To a solution of (S)-4-((4-(benzyloxy)-1-(3-(cyanomethyl)tetrahydro-2H-pyran-3-yl)-1H-pyrazolo[4,3-c]pyridin-3-yl)amino)-2-methylbenzoic acid (440 mg, 0.9 mmol) in EtOAc (9 mL), was added Pd/C (188 mg, 0.2 mmol, 10 wt. %). The reaction mixture was stirred under an atmosphere of H₂ for 4 hours, diluted with EtOAc, and filtered through a pad of Celite. Concentration in vacuo afforded a residue that was purified by silica chromatography, eluting with a hexanes/EtOAc gradient to yield the title compound. LRMS (ESI) calc'd for $C_{21}H_{22}N_5O_4$ [M+H]⁺: 408, found 408.

Step 3: (S)-2-(3-(3-((4-(4,4-difluoropiperidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile (20-1)

A reaction vial with magnetic sir bar was charged with (S)-4-((1-(3-(cyanomethyl)tetrahydro-2H-pyran-3-yl)-4-oxo-4,5-dihydro-1H-pyrazolo[4,3-c]pyridin-3-yl)amino)-2-methylbenzoic acid (15 mg, 0.040 mmol), HATU (28 mg, 0.070 mmol), Hunig's base (26 μL, 0.15 mmol), DMF (0.13 mL), and 4,4-difluoropiperidine (9 mg, 0.07 mmol). The reaction mixture was stirred at room temperature for 16 hours, and then purified by reverse phase chromatography using acetonitrile in water with 0.1% TFA modifier to yield 20-1. LRMS (ESI) calc'd for $C_{26}H_{29}F_2N_6O_3$ [M+H]⁺: 511, found 511. ¹H NMR (DMSO, 500 MHz): δ 11.29 (s, 1H), 8.28 (s, 1H), 7.54 (d, J=11.4 Hz, 2H), 7.19-7.15 (m, 2H), 6.68 (d, J=7.5 Hz, 1H), 4.32 (d, J=12.1 Hz, 1H), 3.96-3.92 (m, 4H), 3.69-3.65 (m, 2H), 3.37-3.20 (m, 4H), 2.64 (m, 1H), 2.21 (s, 3H), 2.05-2.01 (m, 4H), 1.70 (m, 1H), 1.60 (m, 1H).

Table 32 discloses Examples that were prepared in analogy to 20-1, using the appropriate starting material. In certain instances another amide coupling reagent such as HOBt and EDC could be employed in the last step.

TABLE 32

| Example | Structure | Compound Name | LRMS |
|---------|-----------|---------------|------|
| 20-2 | 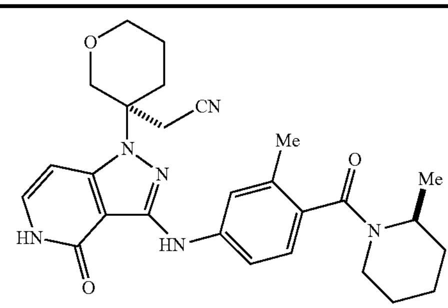 | 2-((S)-3-(3-((3-methyl-4-((S)-2-methylpiperidine-1-carbonyl)phenyl)amino)-4-oxo-4,5-dihydro-1H-pyrazolo[4,3-c]pyridin-1-yl)tetrahydro-2H-pyran-3-yl)acetonitrile (from I-17B) | LRMS (ESI) Calc'd for $C_{27}H_{33}N_6O_3$ [M + H]⁺: 489, found 489. |
| 20-3 | 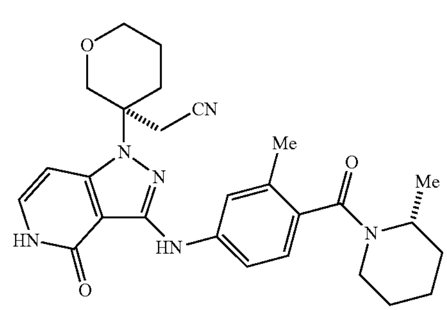 [SMILES: Cc1cc(Nc2nn([C@]3(CC#N)CCCOC3)c3cc[nH]c(=O)c23)ccc1C(=O)N1CCCC[C@H]1C] | 2-((S)-3-(3-((3-methyl-4-((R)-2-methylpiperidine-1-carbonyl)phenyl)amino)-4-oxo-4,5-dihydro-1H-pyrazolo[4,3-c]pyridin-1-yl)tetrahydro-2H-pyran-3-yl)acetonitrile (from I-17B) | LRMS (ESI) Calc'd for $C_{27}H_{33}N_6O_3$ [M + H]⁺: 489, found 489. |

TABLE 32-continued

| Example | Structure | Compound Name | LRMS |
|---------|-----------|---------------|------|
| 20-4 | 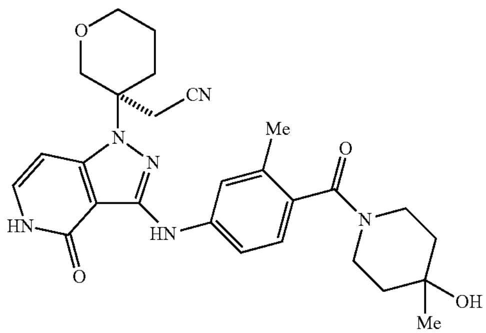 [SMILES: Cc1cc(Nc2nn([C@]3(CC#N)CCCOC3)c3cc[nH]c(=O)c23)ccc1C(=O)N1CCC(C)(O)CC1] | (S)-2-(3-(3-((4-(4-hydroxy-4-methylpiperidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile (from I-17B) | LRMS (ESI) Calc'd for $C_{27}H_{33}N_6O_4$ [M + H]$^+$: 505, found 505. |
| 20-5 | 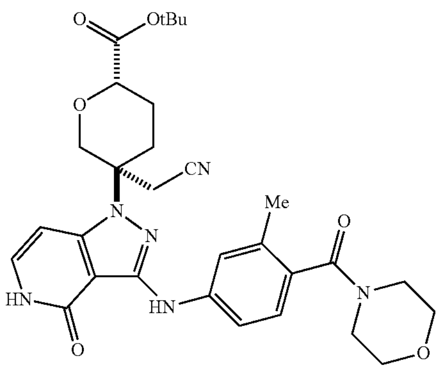 [SMILES: Cc1cc(Nc2nn([C@]3(CC#N)CC[C@@H](C(=O)OC(C)(C)C)OC3)c3cc[nH]c(=O)c23)ccc1C(=O)N1CCOCC1] | (2S,5S)-tert-butyl 5-(cyanomethyl)-5-(3-((3-methyl-4-(morpholine-4-carbonyl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) Calc'd for $C_{30}H_{37}N_6O_6$ [M + H]$^+$: 577, found 577. |
| 20-6 | 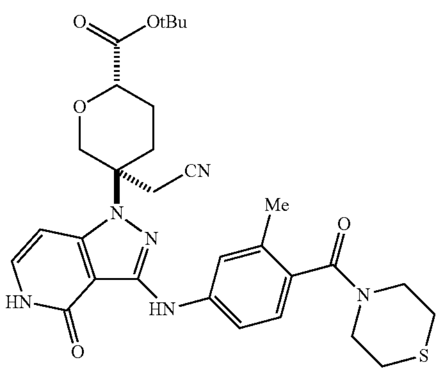 [SMILES: Cc1cc(Nc2nn([C@]3(CC#N)CC[C@@H](C(=O)OC(C)(C)C)OC3)c3cc[nH]c(=O)c23)ccc1C(=O)N1CCSCC1] | (2S,5S)-tert-butyl 5-(cyanomethyl)-5-(3-((3-methyl-4-(thiomorpholine-4-carbonyl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) Calc'd for $C_{30}H_{37}N_6O_5S$ [M + H]$^+$: 593, found 593. |
| 20-7 | 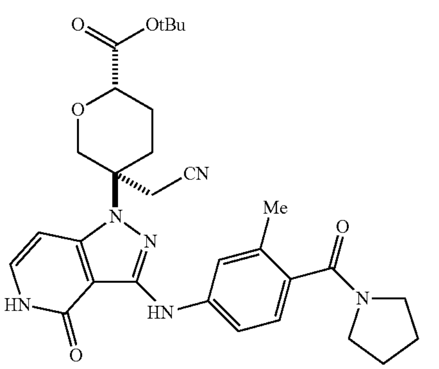 | (2S,5S)-tert-butyl 5-(cyanomethyl)-5-(3-((3-methyl-4-(pyrrolidine-1-carbonyl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) Calc'd for $C_{30}H_{37}N_6O_5$ [M + H]$^+$: 561, found 561. |

TABLE 32-continued

| Example | Structure | Compound Name | LRMS |
|---|---|---|---|
| 20-8 | 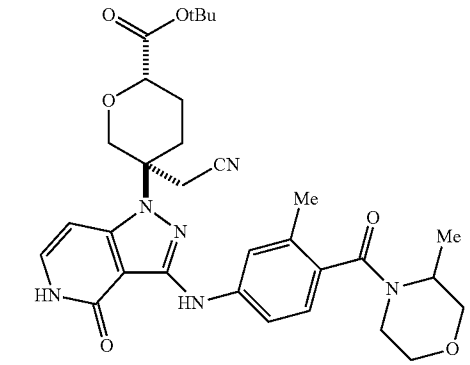 [SMILES: Cc1cc(Nc2nn([C@]3(CC#N)CC[C@@H](C(=O)OC(C)(C)C)OC3)c3cc[nH]c(=O)c23)ccc1C(=O)N1CCOCC1C] | (2S,5S)-tert-butyl 5-(cyanomethyl)-5-(3-((3-methyl-4-((S or R)-3-methylmorpholine-4-carbonyl)phenyl)amino)-4-oxo-4,5-dihydro-1H-pyrazolo[4,3-c]pyridin-1-yl)tetrahydro-2H-pyran-2-carboxylate (from I-14-1A. Derived from Peak 1 via SFC: Chiralcel OJ-H, 20% MeOH in CO$_2$, Tr = 7.1 minutes) | LRMS (ESI) Calc'd for C$_{31}$H$_{39}$N$_6$O$_6$ [M + H]$^+$: 591, found 591. |
| 20-9 | 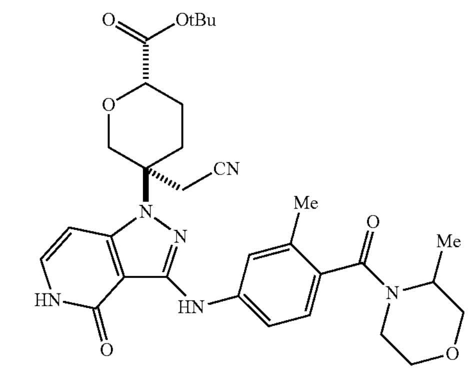 [SMILES: Cc1cc(Nc2nn([C@]3(CC#N)CC[C@@H](C(=O)OC(C)(C)C)OC3)c3cc[nH]c(=O)c23)ccc1C(=O)N1CCOCC1C] | (2S,5S)-tert-butyl 5-(cyanomethyl)-5-(3-((3-methyl-4-((S or R)-3-methylmorpholine-4-carbonyl)phenyl)amino)-4-oxo-4,5-dihydro-1H-pyrazolo[4,3-c]pyridin-1-yl)tetrahydro-2H-pyran-2-carboxylate (from I-14-1A. Derived from Peak 2 via SFC: Chiralcel OJ-H, 20% MeOH in CO$_2$, Tr = 9.3 minutes) | LRMS (ESI) Calc'd for C$_{33}$H$_{39}$N$_6$O$_6$ [M + H]$^+$: 591, found 591. |
| 20-10 | 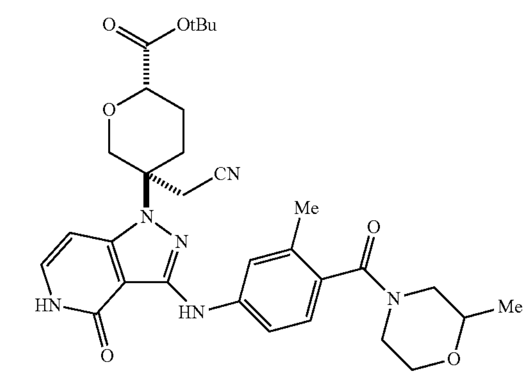 | (2S,5S)-tert-butyl 5-(cyanomethyl)-5-(3-((3-methyl-4-((S or R)-2-methylmorpholine-4-carbonyl)phenyl)amino)-4-oxo-4,5-dihydro-1H-pyrazolo[4,3-c]pyridin-1-yl)tetrahydro-2H-pyran-2-carboxylate (from I-14-1A. Derived from Peak 1 via SFC: Chiralpak AD-H, 20% iPrOH in CO$_2$, Tr = 10.3 minutes) | LRMS (ESI) Calc'd for C$_{31}$H$_{39}$N$_6$O$_6$ [M + H]$^+$: 591, found 591. |
| 20-11 | 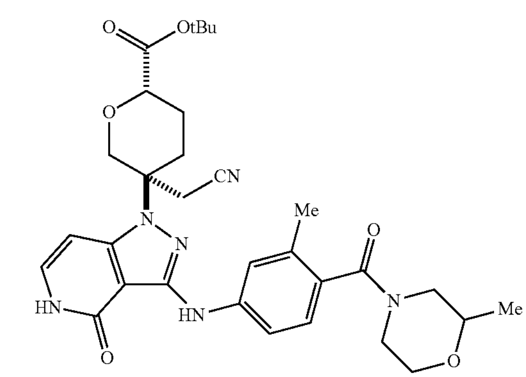 | (2S,5S)-tert-butyl 5-(cyanomethyl)-5-(3-((3-methyl-4-((S or R)-2-methylmorpholine-4-carbonyl)phenyl)amino)-4-oxo-4,5-dihydro-1H-pyrazolo[4,3-c]pyridin-1-yl)tetrahydro-2H-pyran-2-carboxylate (from I-14-1A. Derived from Peak 2 via SFC: Chiralpak AD-H, 20% iPrOH in CO$_2$, Tr = 11.7 minutes) | LRMS (ESI) Calc'd for C$_{31}$H$_{39}$N$_6$O$_6$ [M + H]$^+$: 591, found 591. |

TABLE 32-continued

| Example | Structure | Compound Name | LRMS |
|---|---|---|---|
| 20-12 | 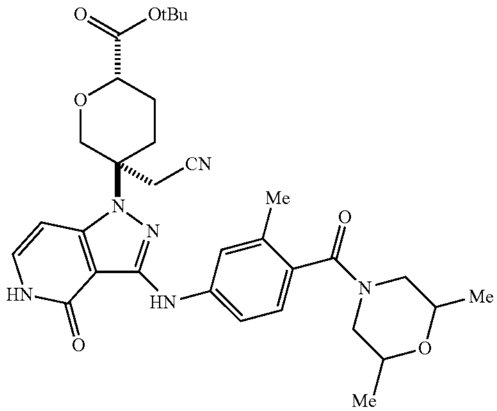 [SMILES: Cc1cc(Nc2nn([C@]3(CC#N)CC[C@@H](C(=O)OC(C)(C)C)OC3)c3cc[nH]c(=O)c23)ccc1C(=O)N1CC(C)OC(C)C1] | (2S,5S)-tert-butyl 5-(cyanomethyl)-5-(3-((4-((2S,6S or 2R,6R)-2,6-dimethylmorpholine-4-carbonyl)-3-methylphenyl)amino)-4-oxo-4,5-dihydro-1H-pyrazolo[4,3-c]pyridin-1-yl)tetrahydro-2H-pyran-2-carboxylate (from I-14-1A. Derived from Peak 1 via SFC: Chiralpak AD-H, 20% i-PrOH in CO$_2$, Tr = 9.4 minutes) | LRMS (ESI) Calc'd for C$_{32}$H$_{41}$N$_6$O$_6$ [M + H]$^+$: 605, found 605. |
| 20-13 | 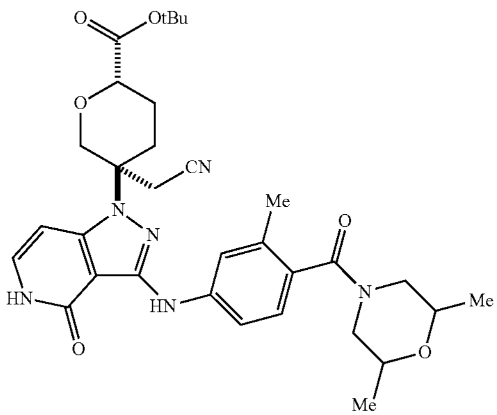 [SMILES: Cc1cc(Nc2nn([C@]3(CC#N)CC[C@@H](C(=O)OC(C)(C)C)OC3)c3cc[nH]c(=O)c23)ccc1C(=O)N1CC(C)OC(C)C1] | (2S,5S)-tert-butyl 5-(cyanomethyl)-5-(3-((4-((2S,6S or 2R,6R)-2,6-dimethylmorpholine-4-carbonyl)-3-methylphenyl)amino)-4-oxo-4,5-dihydro-1H-pyrazolo[4,3-c]pyridin-1-yl)tetrahydro-2H-pyran-2-carboxylate (from I-14-1A) (Derived from Peak 2 via SFC: Chiralpak AD-H, 20% i-PtOH in CO$_2$, Tr = 11.0 mins) | LRMS (ESI) Calc'd for C$_{32}$H$_{41}$N$_6$O$_6$ [M + H]$^+$: 605, found 605. |
| 20-14 | 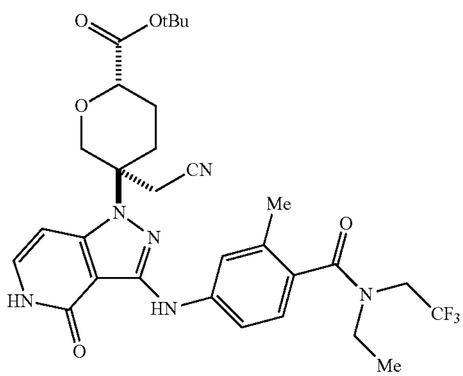 [SMILES: CCN(CC(F)(F)F)C(=O)c1ccc(Nc2nn([C@]3(CC#N)CC[C@@H](C(=O)OC(C)(C)C)OC3)c3cc[nH]c(=O)c23)cc1C] | (2S,5S)-tert-butyl 5-(cyanomethyl)-5-(3-((4-(ethyl(2,2,2-trifluoroethyl)carbamoyl)-3-methylphenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for C$_{30}$H$_{36}$F$_3$N$_6$O$_5$ [M + H]$^+$: 617, found 617. |
| 20-15 | 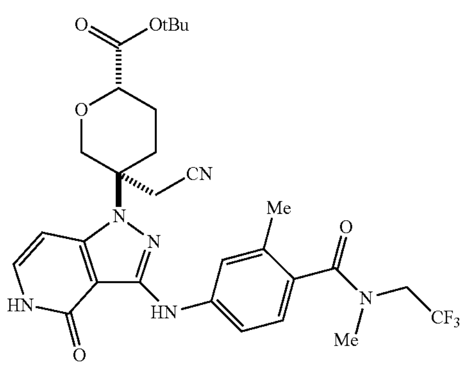 [SMILES: Cc1cc(Nc2nn([C@]3(CC#N)CC[C@@H](C(=O)OC(C)(C)C)OC3)c3cc[nH]c(=O)c23)ccc1C(=O)N(C)CC(F)(F)F] | (2S,5S)-tert-butyl 5-(cyanomethyl)-5-(3-((3-methyl-4-(methyl(2,2,2-trifluoroethyl)carbamoyl)phenyl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for C$_{29}$H$_{34}$F$_3$N$_6$O$_5$ [M + H]$^+$: 603, found 603. |

TABLE 32-continued

| Example | Structure | Compound Name | LRMS |
|---------|-----------|---------------|------|
| 20-16 | 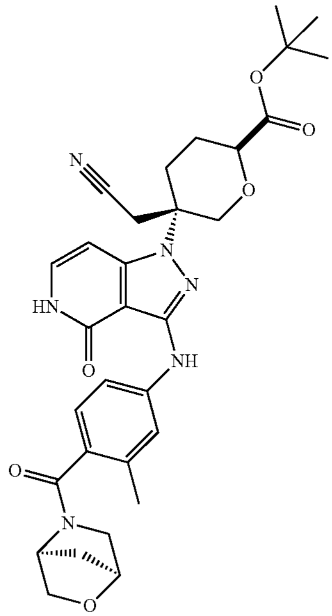 [SMILES: Cc1cc(Nc2nn([C@]3(CC#N)CC[C@@H](C(=O)OC(C)(C)C)OC3)c3cc[nH]c(=O)c23)ccc1C(=O)N1C[C@@H]2C[C@H]1CO2] | (2S,5S)-tert-butyl 5-(3-((4-((1S,4S)-2-oxa-5-azabicyclo[2.2.1]heptane-5-carbonyl)-3-methylphenyl)amino)-4-oxo-4,5-dihydro-1H-pyrazolo[4,3-c]pyridin-1-yl)-5-(cyanomethyl)tetrahydro-2H-pyran-2-carboxylate (from I-14-1A) | LRMS (ESI) calc'd for $C_{31}H_{36}N_6O_6$ [M + H]$^+$: 589, found 589. |

Example 21-1

(2S,5S)-tert-butyl 5-(cyanomethyl)-5-(3-((2-methylbenzo[d]thiazol-6-yl)amino)-4-oxo-4,5-dihydro-1H-pyrazolo[4,3-c]pyridin-1-yl)tetrahydro-2H-pyran-2-carboxylate 21-1

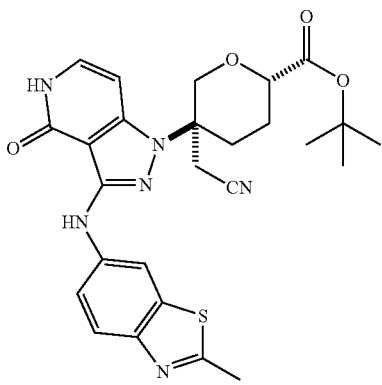

Step 1: (2S,5S)-tert-butyl 5-(3-amino-4-oxo-4,5-dihydro-1H-pyrazolo[4,3-c]pyridin-1-yl)-5-(cyanomethyl)tetrahydro-2H-pyran-2-carboxylate

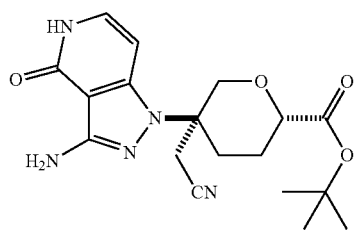

To a solution of (2S,5S)-tert-butyl 5-(3-amino-4-(benzyloxy)-1H-pyrazolo[4,3-c]pyridin-1-yl)-5-(cyanomethyl)tetrahydro-2H-pyran-2-carboxylate (4.64 g, 10.0 mmol) in a mixture of EtOAc (66.7 mL) and MeOH (33.3 mL) at room temperature, was added palladium on carbon (1.06 g, 10 wt. %). The flask was sealed, and evacuated and backfilled with hydrogen (×3). The reaction was then stirred at room temperature for 18 hours under 1 atmosphere of hydrogen. The reaction was then diluted with MeOH, filtered through Celite, and the filter cake was washed with additional MeOH. The filtrate was concentrated in vacuo to give the title compound as a solid. LRMS (ESI) Calc'd for $C_{26}H_{29}N_6O_4S$ [M+H]$^+$: 521, found 521.

Step 2: (2S,5S)-tert-butyl 5-(cyanomethyl)-5-(3-((2-methylbenzo[d]thiazol-6-yl)amino)-4-oxo-4,5-dihydro-1H-pyrazolo[4,3-c]pyridin-1-yl)tetrahydro-2H-pyran-2-carboxylate (21-1)

(2S,5S)-tert-Butyl 5-(3-amino-4-oxo-4,5-dihydro-1H-pyrazolo[4,3-c]pyridin-1-yl)-5-(cyanomethyl)tetrahydro-2H-pyran-2-carboxylate (93 mg, 0.25 mmol), 6-bromo-2-methylbenzo[d]thiazole (62.7 mg, 0.275 mmol), Pd$_2$(dba)$_3$ (27.5 mg, 0.030 mmol), t-Bu-X-Phos (26 mg, 0.060 mmol) and potassium acetate (49.1 mg, 0.500 mmol) were added to a 5 mL Biotage microwave vial followed by 2-propanol (2.50 mL). The vial was sealed and degassed by evacuation/argon backfill (×3) and heated to 85° C. for 18 hours. The reaction was cooled to room temperature and concentrated in vacuo. The residue was taken into DMSO (2.50 mL), filtered, and the resulting solution was purified directly by mass directed reverse-phase HPLC (5-50% acetonitrile in water with 0.1% TFA modifier). Fractions containing pure product were frozen and lyophilized to afford the title compound as the TFA salt and as a solid. LRMS (ESI) Calc'd for $C_{18}H_{24}N_5O_4$ [M+H]$^+$: 374, found 374. $^1$H NMR (DMSO-d$_6$, 500 MHz): δ 8.44 (d, J=2.3 Hz, 1H), 8.38 (s, 1H), 7.77 (d, J=8.5 Hz, 1H), 7.59 (dd, J=8.5, 2.5 Hz, 1H), 7.20 (dd, J=7.5, 6.0 Hz, 1H), 6.74 (d, J=7.5 Hz, 1H), 4.35 (d, J=11.7 Hz, 1H), 4.22 (dd, J=9.4, 4.2 Hz, 1H), 4.12 (d, J=12.2 Hz, 1H), 3.43 (AB, J=17.4 Hz, 1H), 3.38 (AB, J=17.4 Hz, 1H), 2.74 (s, 3H), 2.56 (m, 1H), 2.44 (m, 1H), 1.92 (m, 2H), 1.46 (s, 9H).

The following examples outlined in Table 32 were prepared by analogy using the general procedure outlined above for Example 21-1. In select cases, the general procedure could alternatively be modified to utilize $K_3PO_4$ base, [(2-di-tert-butylphosphino-2',4',6'-triisopropyl-1,1'-biphenyl)-2-(2'-amino-1,1'-biphenyl)]palladium(II) methanesulfonate (t-BuXPhos Pd G3) precatalyst in place of the individual phosphine and palladium source, and/or t-amyl alcohol. Additionally, in certain instances the cross coupling could be run between 70-90° C.

TABLE 32

| Example | Structure | Compound Name | LRMS |
|---------|-----------|---------------|------|
| 21-2 | 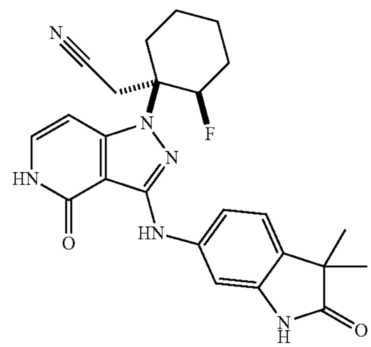 [SMILES: CC1(C)C(=O)Nc2cc(Nc3nn([C@@]4(CC#N)CCCC[C@H]4F)c4cc[nH]c(=O)c34)ccc21] | [(1R,2R)-1-{3-[(3,3-dimethyl-2-oxo-2,3-dihydro-1H-indol-6-yl)amino]-4-oxo-4,5-dihydro-1H-pyrazolo[4,3-c]pyridin-1-yl}-2-fluorocyclohexyl]acetonitrile (from I-19A) | LRMS (ESI) calc'd for $C_{24}H_{26}N_6O_2F$ [M + H]$^+$: 449, found 449. |
| 21-3 | 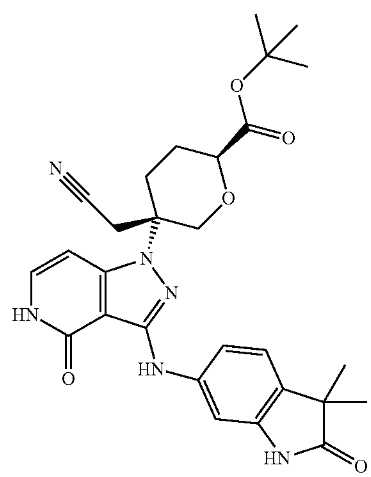 | (2S,5S)-tert-butyl 5-(cyanomethyl)-5-(3-((3,3-dimethyl-2-oxoindolin-6-yl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{28}H_{33}N_6O_5$ [M + H]$^+$: 533, found 533. |
| 21-4 | 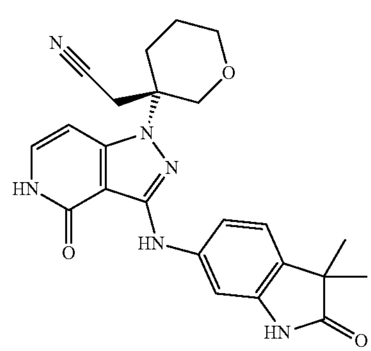 | [(3S)-3-{3-[(3,3-dimethyl-2-oxo-2,3-dihydro-1H-indol-6-yl)amino]-4-oxo-4,5-dihydro-1H-pyrazolo[4,3-c]pyridin-1-yl}tetrahydro-2H-pyran-3-yl]acetonitrile (from I-17B) | LRMS (ESI) calc'd for $C_{23}H_{25}N_6O_3$ [M + H]$^+$: 433, found 433. |

TABLE 32-continued

| Example | Structure | Compound Name | LRMS |
|---|---|---|---|
| 21-5 | 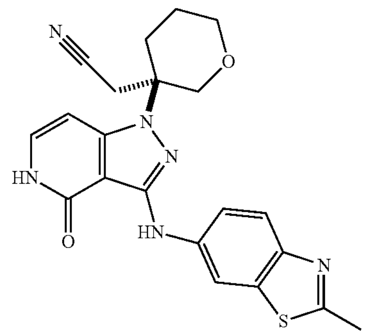 [SMILES: Cc1nc2ccc(Nc3nn([C@@]4(CC#N)CCCOC4)c4cc[nH]c(=O)c34)cc2s1] | [(3S)-3-{3-[(2-methyl-1,3-benzothiazol-6-yl)amino]-4-oxo-4,5-dihydro-1H-pyrazolo[4,3-c]pyridin-1-yl}tetrahydro-2H-pyran-3-yl]acetonitrile (from I-17B) | LRMS (ESI) calc'd for $C_{21}H_{21}N_6O_2S$ [M + H]$^+$: 421, found 421. |
| 21-6 | 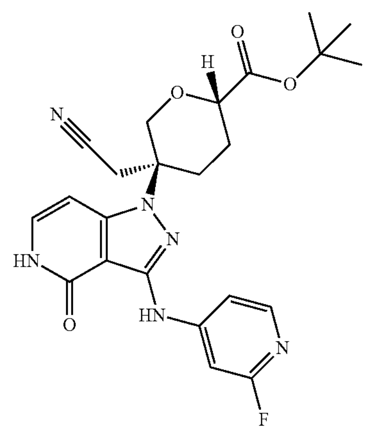 [SMILES: CC(C)(C)OC(=O)[C@@H]1CC[C@@](CC#N)(n2nc(Nc3ccnc(F)c3)c3c(=O)[nH]ccc32)CO1] | (2S,5S)-tert-butyl 5-(cyanomethyl)-5-(3-((2-fluoropyridin-4-yl)amino)-4-oxo-4,5-dihydro-1H-pyrazolo[4,3-c]pyridin-1-yl)tetrahydro-2H-pyran-2-carboxylate (from I-14-1A) | LRMS (ESI) calc'd for $C_{23}H_{26}FN_6O_4$ [M + H]$^+$: Calc'd 469, found 469. |
| 21-7 | 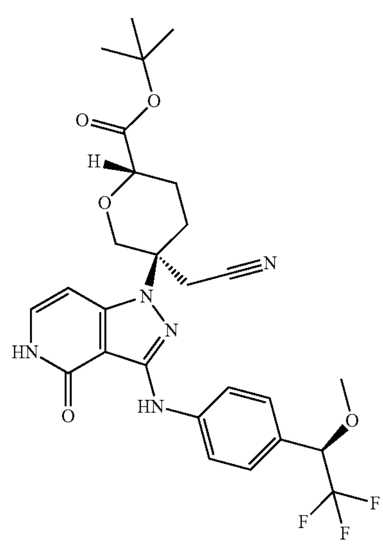 [SMILES: CO[C@H](c1ccc(Nc2nn([C@]3(CC#N)CC[C@@H](C(=O)OC(C)(C)C)OC3)c3cc[nH]c(=O)c23)cc1)C(F)(F)F] | (2S,5S)-tert-butyl 5-(cyanomethyl)-5-(4-oxo-3-((4-((R or S)-2,2,2-trifluoro-1-methoxyethyl)phenyl)amino)-4,5-dihydro-1H-pyrazolo[4,3-c]pyridin-1-yl)tetrahydro-2H-pyran-2-carboxylate (from I-14-1A. The mixture of diastereomers was purified as the free pyridone by chiral SFC using AD-H column and 15% MeOH with 0.25% DMEA, Tr = 5.6 minutes) | LRMS (ESI) calc'd for $C_{27}H_{31}F_3N_5O_5$ [M + H]$^+$: Calc'd 562, found 562. |

TABLE 32-continued

| Example | Structure | Compound Name | LRMS |
|---------|-----------|---------------|------|
| 21-8 | 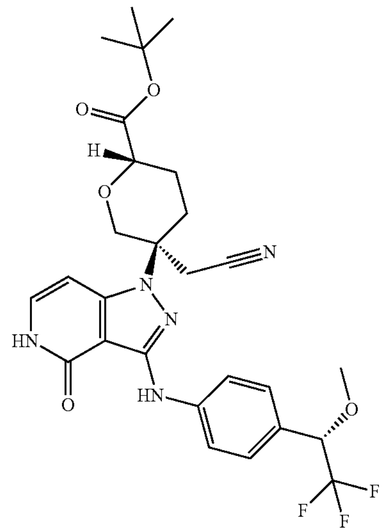 [SMILES: CO[C@@H](c1ccc(Nc2nn([C@]3(CC#N)CC[C@@H](C(=O)OC(C)(C)C)OC3)c3cc[nH]c(=O)c23)cc1)C(F)(F)F] | (2S,5S)-tert-butyl 5-(cyanomethyl)-5-(4-oxo-3-((4-((S or R)-2,2,2-trifluoro-1-methoxyethyl)phenyl)amino)-4,5-dihydro-1H-pyrazolo[4,3-c]pyridin-1-yl)tetrahydro-2H-pyran-2-carboxylate (from I-14-1A. The mixture of diastereomers was purified as the free pyridone by chiral SFC using AD-H column and 15% MeOH with 0.25% DMEA, Tr = 7.5 minutes) | LRMS (ESI) calc'd for $C_{27}H_{31}F_3N_5O_5$ [M + H]$^+$: Calc'd 562, found 562. |
| 21-9 | 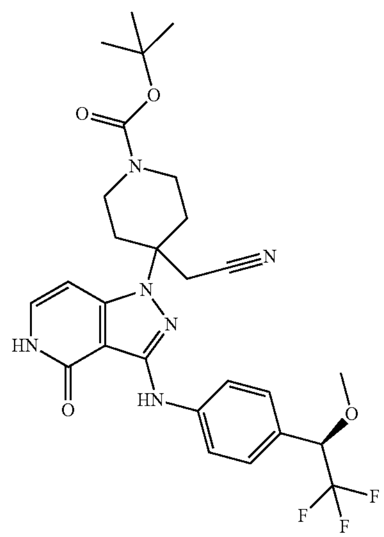 [SMILES: CO[C@H](c1ccc(Nc2nn(C3(CC#N)CCN(C(=O)OC(C)(C)C)CC3)c3cc[nH]c(=O)c23)cc1)C(F)(F)F] | tert-butyl 4-(cyanomethyl)-4-[4-oxo-3-({4-[(1R or 1S)-2,2,2-trifluoro-1-methoxyethyl]phenyl}amino)-4,5-dihydro-1H-pyrazolo[4,3-c]pyridin-1-yl]piperidine-1-carboxylate The mixture of diastereomers was purified as the free pyridone by chiral SFC using AD-H column and 20% MeOH with 0.25% DMEA, Tr = 3.7 minutes. | LRMS (ESI) calc'd for $C_{27}H_{32}F_3N_6O_4$ [M + H]$^+$: Calc'd 561, found 561. |
| 21-10 | 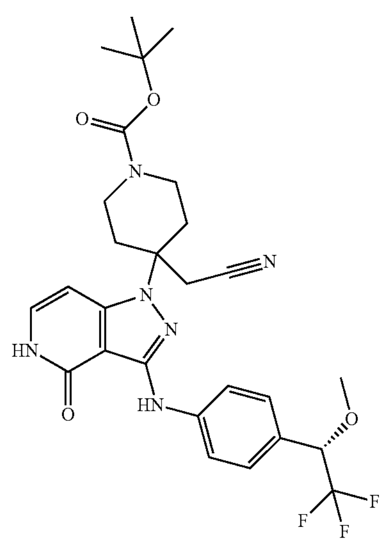 [SMILES: CO[C@@H](c1ccc(Nc2nn(C3(CC#N)CCN(C(=O)OC(C)(C)C)CC3)c3cc[nH]c(=O)c23)cc1)C(F)(F)F] | tert-butyl 4-(cyanomethyl)-4-[4-oxo-3-({4-[(1S or 1R)-2,2,2-trifluoro-1-methoxyethyl]phenyl}amino)-4,5-dihydro-1H-pyrazolo[4,3-c]pyridin-1-yl]piperidine-1-carboxylate The mixture of diastereomers was purified as the free pyridone by chiral SFC using AD-H column and 20% MeOH with 0.25% DMEA, Tr = 5.3 minutes. | LRMS (ESI) calc'd for $C_{27}H_{32}F_3N_6O_4$ [M + H]$^+$: Calc'd 561, found 561. |

TABLE 32-continued

| Example | Structure | Compound Name | LRMS |
|---|---|---|---|
| 21-11 | 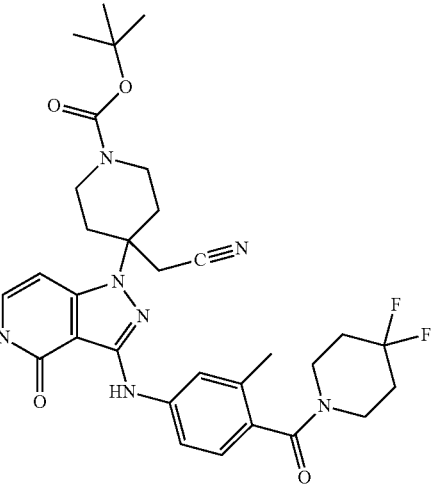 | tert-butyl 4-(cyanomethyl)-4-(3-((4-(4,4-difluoropiperidine-1-carbonyl)-3-methylphenyl)amino)-4-oxo-4,5-dihydro-1H-pyrazolo[4,3-c]pyridin-1-yl)piperidine-1-carboxylate | LRMS (ESI) calc'd for $C_{31}H_{38}F_2N_7O_4$ $[M + H]^+$: 610, found 610. |
| 21-12 | 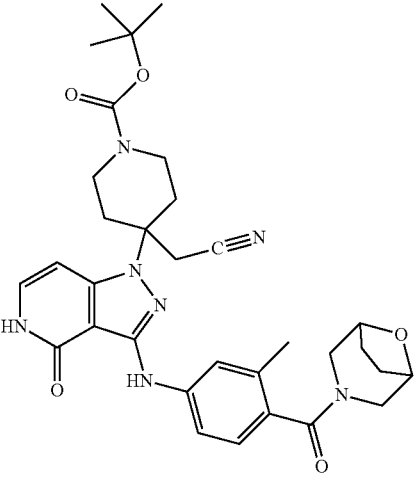 [SMILES: Cc1cc(Nc2nn(C3(CC#N)CCN(C(=O)OC(C)(C)C)CC3)c3cc[nH]c(=O)c23)ccc1C(=O)N1CC2CCC(C1)O2] | tert-butyl 4-(3-((4-(8-oxa-3-azabicyclo[3.2.1]octane-3-carbonyl)-3-methylphenyl)amino)-4-oxo-4,5-dihydro-1H-pyrazolo[4,3-c]pyridin-1-yl)-4-(cyanomethyl)piperidine-1-carboxylate | LRMS (ESI) calc'd for $C_{32}H_{40}N_7O_5$ $[M + H]^+$: 602, found 602. |
| 21-13 | 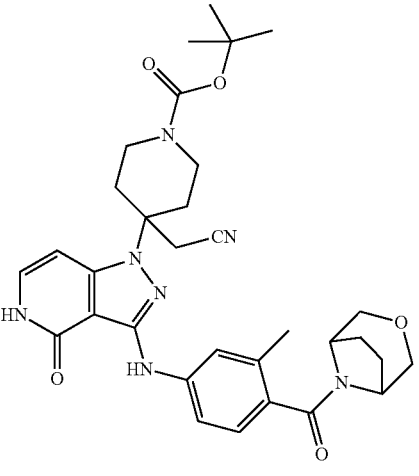 [SMILES: Cc1cc(Nc2nn(C3(CC#N)CCN(C(=O)OC(C)(C)C)CC3)c3cc[nH]c(=O)c23)ccc1C(=O)N1C2CCC1COC2] | tert-butyl 4-(cyanomethyl)-4-{3-[(5-methyl-4-{3-oxa-8-azabicyclo[3.2.1]octan-8-ylcarbonyl}cyclohexa-1,3,5-trien-1-yl)amino]-4-oxo-5H-pyrazolo[4,3-c]pyridin-1-yl}piperidine-1-carboxylate | LRMS (ESI) calc'd for $C_{32}H_{40}N_7O_5$ $[M + H]^+$: 602, found 602. |

TABLE 32-continued

| Example | Structure | Compound Name | LRMS |
|---|---|---|---|
| 21-14 | 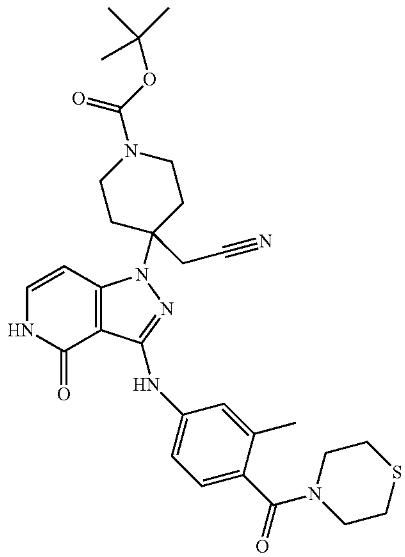 [SMILES: Cc1cc(Nc2nn(C3(CC#N)CCN(C(=O)OC(C)(C)C)CC3)c3cc[nH]c(=O)c23)ccc1C(=O)N1CCSCC1] | tert-butyl-4-(cyanomethyl)-4-(3-(3-methyl-4-(thiomorpholine-4-carbonyl)phenylamino)-4-oxo-4,5-dihydropyrazolo[4,3-c]pyridin-1-yl)piperidine-1-carboxylate | LRMS (ESI) calc'd for $C_{30}H_{38}N_7O_4S$ [M + H]$^+$: 592, found 592. |
| 21-15 | 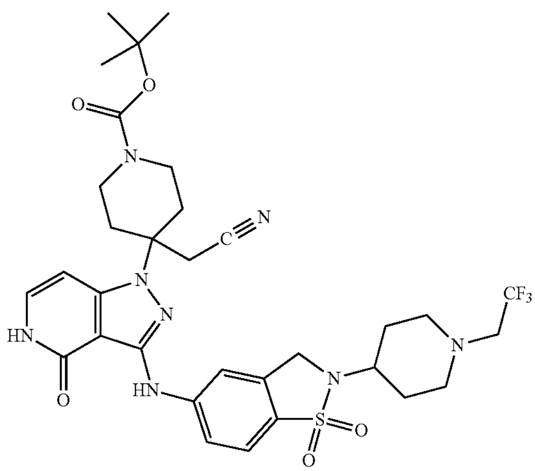 [SMILES: CC(C)(C)OC(=O)N1CCC(CC#N)(n2nc(Nc3ccc4c(c3)CN(C3CCN(CC(F)(F)F)CC3)S4(=O)=O)c3c(=O)[nH]ccc32)CC1] | tert-butyl-4-(cyanomethyl)-4-(3-((1,1-dioxido-2-(1-(2,2,2-trifluoroethyl)piperidin-4-yl)-2,3-dihydrobenzo[d]isothiazol-5-yl)amino)-4-oxo-4,5-dihydro-1H-pyrazolo[4,3-c]pyridin-1-yl)piperidine-1-carboxylate | LRMS (ESI) calc'd for $C_{32}H_{40}F_3N_8O_5S$ [M + H]$^+$: 705, found 705. |
| 21-16 | 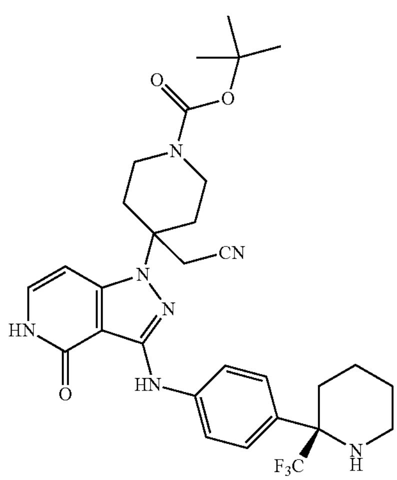 [SMILES: CC(C)(C)OC(=O)N1CCC(CC#N)(n2nc(Nc3ccc([C@]4(C(F)(F)F)CCCCN4)cc3)c3c(=O)[nH]ccc32)CC1] | (S or R)-tert-butyl 4-(cyanomethyl)-4-(4-oxo-3-(4-(2-(trifluoromethyl)piperidin-2-yl)phenylamino)-4,5-dihydropyrazolo[4,3-c]pyridin-1-yl)piperidine-1-carboxylate (from I-54B) | LRMS (ESI) calc'd for $C_{30}H_{37}F_3N_7O_3$ [M + H]$^+$: 600, found 600. |

TABLE 32-continued

| Example | Structure | Compound Name | LRMS |
|---|---|---|---|
| 21-17 | 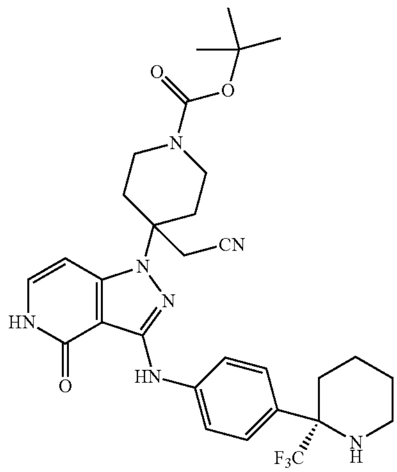 [SMILES: CC(C)(C)OC(=O)N1CCC(CC#N)(n2nc(Nc3ccc([C@@]4(C(F)(F)F)CCCCN4)cc3)c3c(=O)[nH]ccc32)CC1] | (R or S)-tert-butyl 4-(cyanomethyl)-4-(4-oxo-3-(4-(2-(trifluoromethyl)piperidin-2-yl)phenylamino)-4,5-dihydropyrazolo[4,3-c]pyridin-1-yl)piperidine-1-carboxylate (from I-54A) | LRMS (ESI) calc'd for $C_{30}H_{37}F_3N_7O_3$ [M + H]$^+$: 600, found 600. |
| 21-18 | 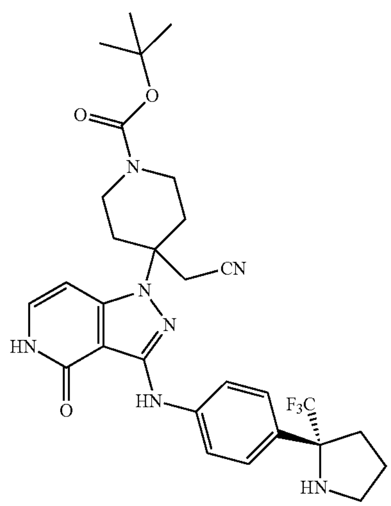 [SMILES: CC(C)(C)OC(=O)N1CCC(CC#N)(n2nc(Nc3ccc([C@@]4(C(F)(F)F)CCCN4)cc3)c3c(=O)[nH]ccc32)CC1] | (R or S)-tert-butyl 4-(cyanomethyl)-4-(4-oxo-3-(4-(2-(trifluoromethyl)pyrrolidin-2-yl)phenylamino)-4,5-dihydropyrazolo[4,3-c]pyridin-1-yl)piperidine-1-carboxylate (from I-55A) | LRMS (ESI) calc'd for $C_{29}H_{35}F_3N_7O_3$ [M + H]$^+$: 586, found 586. |
| 21-19 | 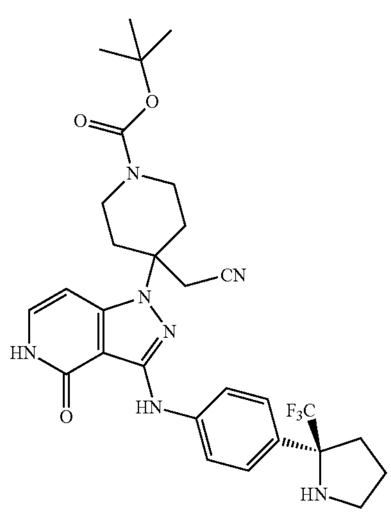 [SMILES: CC(C)(C)OC(=O)N1CCC(CC#N)(n2nc(Nc3ccc([C@]4(C(F)(F)F)CCCN4)cc3)c3c(=O)[nH]ccc32)CC1] | (S or R)-tert-butyl 4-(cyanomethyl)-4-(4-oxo-3-(4-(2-(trifluoromethyl)pyrrolidin-2-yl)phenylamino)-4,5-dihydropyrazolo[4,3-c]pyridin-1-yl)piperidine-1-carboxylate (from I-55B) | LRMS (ESI) calc'd for $C_{29}H_{35}F_3N_7O_3$ [M + H]$^+$: 586, found 586. |

| Example | Structure | Compound Name | LRMS |
|---|---|---|---|
| 21-20 | 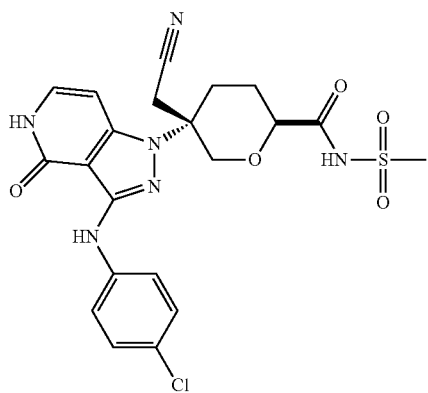 | tert-butyl 4-(cyanomethyl)-4-(3-(3-methyl-4-(morpholine-4-carbonyl)phenylamino)-4-oxo-4,5-dihydropyrazolo[4,3-c]pyridin-1-yl)piperidine-1-carboxylate | LRMS (ESI) calc'd for $C_{30}H_{38}N_7O_5$ $[M + H]^+$: 576, found 576. |

Example 22

(2S,5S)-5-(3-((4-chlorophenyl)amino)-4-oxo-4,5-dihydro-1H-pyrazolo[4,3-c]pyridin-1-yl)-5-(cyanomethyl)-N-(methylsulfonyl)tetrahydro-2H-pyran-2-carboxamide To a solution of 1,1'-carbonyldiimidazole (76 mg, 0.467 mmol) in THF (0.80 mL), was added a solution of (2S,5S)-5-(3-((4-chlorophenyl)amino)-4-oxo-4,5-dihydro-1H-pyrazolo[4,3-c]pyridin-1-yl)-5-(cyanomethyl)tetrahydro-2H-pyran-2-carboxylic acid (Intermediate 20) (100 mg, 0.234 mmol) in THF (0.80 mL). The reaction was stirred at reflux for 30 minutes, cooled, and then methanesulfonamide (44.5 mg, 0.467 mmol) was added followed by a solution of DBU (0.070 mL, 0.467 mmol) in THF (0.80 mL). The reaction was stirred at room temperature for two hours and then concentrated in vacuo. The crude material was dissolved in DMSO (3.0 mL), filtered, and submitted for mass-triggered HPLC purification. Lyophilization of the desired fractions gave the desired title compound as the TFA salt. LRMS (ESI) calc'd for $C_{21}H_{22}ClN_6O_5S$ $[M+H]^+$: 505, found: 505. $^1$H NMR (500 MHz, DMSO-d6): δ 11.76 (s, 1H), 11.37 (d, J=6.2 Hz, 1H), 8.34 (s, 1H), 7.74 (d, J=9.0 Hz, 2H), 7.34 (d, J=9.0 Hz, 2H), 7.25 (dd, J=7.4, 6.0 Hz, 1H), 6.77 (d, J=7.4 Hz, 1H), 4.42 (d, J=12.5 Hz, 1H), 4.25 (dd, J=13.8, 3.3 Hz, 1H), 4.12 (d, J=11.3 Hz, 1H), 3.60 (AB, J=11.3 Hz, 1H), 3.55 (AB, J=11.3 Hz, 1H), 3.34 (s, 3H), 2.65 (m, 1H), 2.43 (m, 2H), 2.00 (m, 1H), 1.89 (m, 1H).

Example 23

(2S,5S)-5-(3-((4-chlorophenyl)amino)-4-oxo-4,5-dihydro-1H-pyrazolo[4,3-c]pyridin-1-yl)-5-(cyanomethyl)-N,N-dimethyltetrahydro-2H-pyran-2-carboxamide

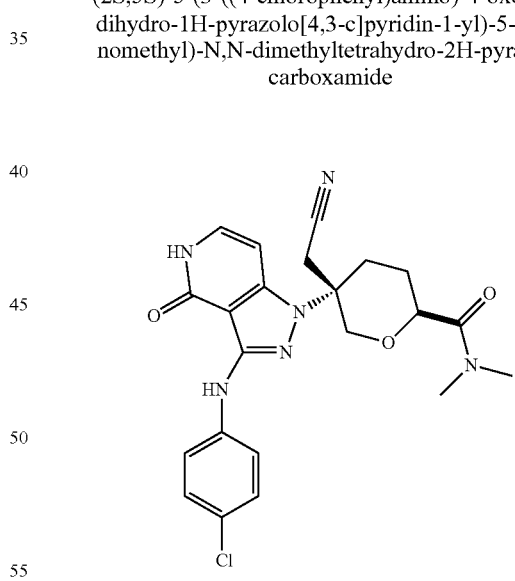

(2S,5S)-5-(3-((4-Chlorophenyl)amino)-4-oxo-4,5-dihydro-1H-pyrazolo[4,3-c]pyridin-1-yl)-5-(cyanomethyl)tetrahydro-2H-pyran-2-carboxylic acid (Intermediate 20) (30 mg, 0.070 mmol) and HATU (53.3 mg, 0.140 mmol) were dissolved in DMF (0.5 mL) and stirred at room temperature for 5 minutes. Dimethylamine (0.070 mL, 0.140 mmol, 2M in THF) and DIPEA (0.037 mL, 0.21 mmol) were then added and the reaction was stirred at room temperature for 1 hour. The solution was diluted with DMSO (0.5 mL) and submitted for mass-triggered reverse phase purification. The desired fractions were reduced in vacuo to give the title compound. LRMS (ESI) calc'd for $C_{22}H_{24}ClN_6O_3$ [M+H]$^+$: 455, found: 455. $^1$H NMR (500 MHz, DMSO-d6): δ 11.36 (d, J=6.0 Hz, 1H), 8.34 (s, 1H), 7.73 (d, J=8.8 Hz, 2H), 7.35 (d, J=8.8 Hz, 2H), 7.25 (dd, J=5.9, 7.6 Hz, 1H), 6.80 (d, J=7.6 Hz, 1H), 4.51 (dd, J=10.4, 3.6 Hz, 1H), 4.35 (d, J=11.6 Hz, 1H), 4.17 (d, J=11.6 Hz, 1H), 3.41 (s, 2H), 3.08 (s, 3H), 2.89 (s, 3H), 2.66 (m, 1H), 2.49 (m, 1H), 1.97 (m, 1H), 1.82 (m, 1H).

Example 24

2-((3S,6S)-3-(3-((4-chlorophenyl)amino)-4-oxo-4,5-dihydro-1H-pyrazolo[4,3-c]pyridin-1-yl)-6-(2-hydroxypropan-2-yl)tetrahydro-2H-pyran-3-yl)acetonitrile

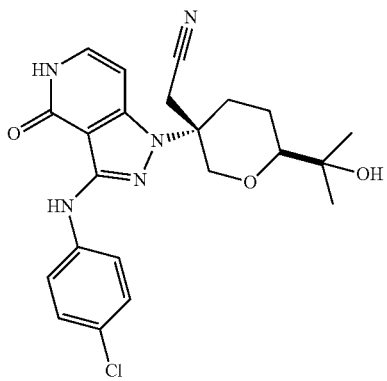 [SMILES: CC(C)(O)[C@@H]1CC[C@@](CC#N)(n2nc(Nc3ccc(Cl)cc3)c3c(=O)[nH]ccc32)CO1]

Step 1: (2S,5S)-5-(3-((4-chlorophenyl)amino)-4-oxo-4,5-dihydro-1H-pyrazolo[4,3-c]pyridin-1-yl)-5-(cyanomethyl)-N-methoxy-N-methyltetrahydro-2H-pyran-2-carboxamide

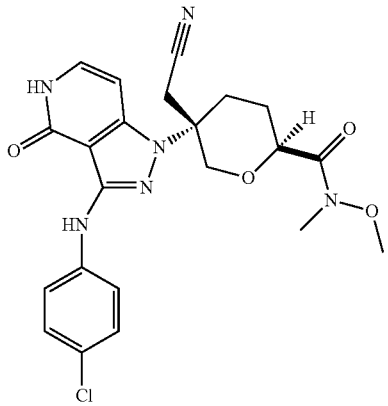 [SMILES: CON(C)C(=O)[C@@H]1CC[C@@](CC#N)(n2nc(Nc3ccc(Cl)cc3)c3c(=O)[nH]ccc32)CO1]

(2S,5S)-5-(3-((4-chlorophenyl)amino)-4-oxo-4,5-dihydro-1H-pyrazolo[4,3-c]pyridin-1-yl)-5-(cyanomethyl)tetrahydro-2H-pyran-2-carboxylic acid (Intermediate 20) (840 mg, 1.96 mmol) and HATU (1.49 g, 3.93 mmol) were dissolved in DMF (4.0 mL) and stirred at room temperature for 5 minutes before a solution of N, O-dimethylhydroxylamine hydrochloride (383 mg, 3.93 mmol) and DIPEA (1.03 mL, 5.89 mmol) in DMF (2.0 mL) was added. The reaction was stirred at room temperature for 1 hour, then diluted with ethyl acetate and washed with water, brine, and dried over MgSO$_4$. The solvent was filtered, and concentrated in vacuo and then purified by silica chromatography, eluting with a 0-5% methanol in dichloromethane gradient to afford the title compound. LRMS (ESI) calc'd for $C_{22}H_{24}ClN_6O_4$ [M+H]$^+$: 471, found: 471.

Step 2: 2-((3S,6S)-6-acetyl-3-(3-((4-chlorophenyl)amino)-4-oxo-4,5-dihydro-1H-pyrazolo[4,3-c]pyridin-1-yl)tetrahydro-2H-pyran-3-yl)acetonitrile

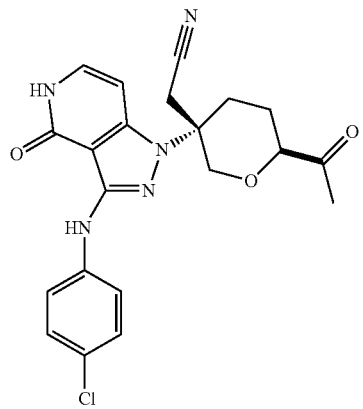 [SMILES: CC(=O)[C@@H]1CC[C@@](CC#N)(n2nc(Nc3ccc(Cl)cc3)c3c(=O)[nH]ccc32)CO1]

(2S,5S)-5-(3-((4-Chlorophenyl)amino)-4-oxo-4,5-dihydro-1H-pyrazolo[4,3-c]pyridin-1-yl)-5-(cyanomethyl)-N-methoxy-N-methyltetrahydro-2H-pyran-2-carboxamide (100 mg, 0.212 mmol) was dissolved in THF (2.0 mL) and the flask was then sealed, flushed with argon, and cooled to −78° C. Methylmagnesium bromide (0.283 mL, 0.849 mmol, 3M in diethyl ether) was then added. The reaction was stirred for 2 hours to 0° C., and then stirred for an additional hour before being quenched with water. The reaction was then extracted with ethyl acetate (×3) and the combined organic layers was dried using MgSO$_4$, filtered, concentrated in vacuo. The crude material was purified by silica chromatography, eluting with a 0-10% methanol in dichloromethane gradient to afford the title compound. LRMS (ESI) calc'd for $C_{21}H_{21}ClN_5O_3$ [M+H]$^+$: 426, found: 426.

Step 3: 2-((3S,6S)-3-(3-((4-chlorophenyl)amino)-4-oxo-4,5-dihydro-1H-pyrazolo[4,3-c]pyridin-1-yl)-6-(2-hydroxypropan-2-yl)tetrahydro-2H-pyran-3-yl)acetonitrile (Example 24)

A solution of 2-((3S,6S)-6-acetyl-3-(3-((4-chlorophenyl)amino)-4-oxo-4,5-dihydro-1H-pyrazolo[4,3-c]pyridin-1-yl)tetrahydro-2H-pyran-3-yl)acetonitrile (26 mg, 0.061 mmol) in THF (2.0 mL) was sealed, flushed with argon, and cooled to −78° C. Methylmagnesium bromide (0.081 mL, 0.244 mmol, 3M in diethyl ether) was then added and the reaction was stirred for 2 hours before being quenched with saturated aqueous NH$_4$Cl. The reaction was then extracted using ethyl acetate (×3), and the combined organic layers were washed with brine, dried with MgSO$_4$, filtered and concentrated in vacuo. The crude material was purified using mass-triggered reverse phase HPLC. The fractions were pooled and concentrated in vacuo to give Example 24. LRMS (ESI) calc'd for $C_{22}H_{25}ClN_5O_3$ [M+H]$^+$: 442, found: 442 $^1$H NMR (500 MHz, Acetone-d6): δ 10.27 (d, J=4.2 Hz, 1H), 8.29 (s, 1H), 7.78 (d, J=8.9 Hz, 2H), 7.36 (d, J=8.9 Hz, 2H), 7.32 (d, J=7.1 Hz, 1H), 6.81 (d, J=7.1 Hz, 1H), 4.61 (d, J=11.0, 2.8 Hz, 1H), 3.99 (d, J=11.0 Hz, 1H), 3.49 (s, 2H), 3.41 (d, J=11.1 Hz, 1H), 2.93 (m, 1H), 2.51 (m, 1H), 2.03 (m, 1H), 1.86 (m, 1H), 1.26 (3H), 1.24 (s, 3H).

BIOLOGICAL ASSAYS

Jak Biochemical HTRF Assay Protocol

The ability of compounds to inhibit the activity of JAK1, JAK2, JAK3, and Tyk2 was measured using a recombinant purified GST-tagged catalytic domain for each enzyme (Invitrogen JAK1 #M4290, JAK2 #M4290, JAK3 #M4290, Tyk2 #M4290) in an HTRF format biochemical assay. The reactions employed a common peptide substrate, LCB-EQEDEPEGDYFEWLW-NH2 (in-house). The basic assay protocol is as follows: First, 250 nL of diluted compounds in DMSO were dispensed into the wells of a dry 384-well Black plate (Greiner #781076) using a Labcyte Echo 555 acoustic dispenser. Subsequent reagent additions employed an Agilent Bravo. Next, 18 μL of 1.11× enzyme and 1.11× substrate in 1× assay buffer (Invitrogen kinase buffer #PV3189, 2 mM DTT, 0.05% BSA) were added to the wells and shaken and then preincubated for 30 minutes at room temperature to allow compound binding to equilibrate. After equilibration, 2 μL of 10×ATP in 1× assay buffer was added to initiate the kinase reaction and the plates were shaken and then incubated at room temperature for 120 minutes. At the end of the incubation, 20 μL of 2× stop buffer (streptavidin-Dylight 650 (Thermo #84547B/100 mL), Eu-tagged pY20 antibody (Perkin Elmer #AD0067), EDTA, HEPES, and Triton) was added to quench the reaction. Plates were shaken and centrifuged and then incubated 60 minutes at room temperature and then read on a Perkin Elmer Envision ($\lambda_{ex}$=337 nm, $\lambda_{em}$=665 and 615 nm, TRF delay time=20 μs). HTRF signal=10,000*665 nm reading/615 nm reading. After normalization to untreated controls, the percent inhibition of the HTRF signal at each compound concentration was calculated. The plot of percent inhibition versus the log of compound concentration was fit with a 4-parameter dose response equation to calculate $IC_{50}$ values.

Final reaction conditions were:

| Enzyme | [E] (nM) | [S] (μM) | [ATP] (μM) | [Eu-pY20] (nM) | [SA-Dylight] (nM) |
|---|---|---|---|---|---|
| JAK1 | 1.405 | 0.75 | 31.8 | 9 | 312.5 |
| JAK2 | 0.052 | 0.75 | 8.5 | 9 | 312.5 |
| JAK3 | 0.031 | 0.75 | 2.9 | 9 | 312.5 |
| Tyk2 | 2.612 | 0.75 | 6.9 | 9 | 312.5 |

Compound concentrations tested were 1496, 499, 175, 49.9, 18.7, 6.2, 2.1, 0.75, 0.24, 0.075, and 0.0125 nM, with 1.25% residual DMSO.

BIOLOGICAL DATA

Examples of the instant invention were evaluated in JAK1 and JAK2 in vitro binding assays as described above. The following table tabulates the JAK1 $IC_{50}$ values and JAK2 $IC_{50}$ values disclosed for the instant invention.

| Example | JAK1 $IC_{50}$ (nM) | JAK2 $IC_{50}$ (nM) |
|---|---|---|
| 1-1 | 2.23 | 24.97 |
| 1-2 | 0.45 | 11.86 |
| 2-1 | 48.2 | 60.3 |
| 2-2 | 49.91 | 39.82 |
| 2-3 | 67.56 | >1496 |
| 2-4 | 207.9 | >1481 |
| 2-5 | 20.26 | 490 |
| 3 | 40.76 | 2.51 |
| 4-1 | 32.90 | 217.90 |
| 4-2 | 2.47 | 37.72 |
| 4-3 | 2.64 | 35.95 |
| 5-1 | 0.22 | 0.28 |
| 5-2 | 0.21 | 0.44 |
| 5-3 | 0.43 | 1.11 |
| 5-4 | 0.12 | 0.23 |
| 5-5 | 0.28 | 0.31 |
| 5-6 | 0.11 | 0.19 |
| 5-7 | 8.23 | 46.98 |
| 5-8 | 1.96 | 20.03 |
| 5-9 | 0.10 | 0.07 |
| 5-10 | 0.23 | 1.09 |
| 5-11 | 0.20 | 0.17 |
| 5-12 | 0.12 | 0.61 |
| 5-13 | 0.50 | 4.86 |
| 5-14 | 1.07 | 17.68 |
| 5-15 | 0.27 | 3.45 |
| 5-16 | 0.12 | 0.35 |
| 5-17 | 0.09 | 0.08 |
| 5-18 | 0.10 | 0.12 |
| 5-19 | 0.08 | 0.08 |
| 5-20 | 0.15 | 0.12 |
| 5-21 | 0.15 | 0.14 |
| 5-22 | 0.15 | 0.19 |
| 5-23 | 0.24 | 0.34 |
| 5-24 | 0.20 | 0.25 |
| 5-25 | 0.19 | 0.30 |
| 5-26 | 0.09 | 0.10 |
| 5-27 | 0.22 | 2.81 |
| 5-28 | 0.13 | 0.29 |
| 5-29 | 13.46 | 27.69 |
| 5-30 | 12.63 | 58.01 |
| 5-31 | 0.26 | 1.64 |
| 5-32 | 0.13 | 0.87 |
| 5-33 | 0.03 | 0.23 |
| 5-34 | 4.74 | 22.56 |
| 5-35 | 3.43 | 29.31 |
| 5-36 | 0.09 | 0.34 |
| 5-37 | 1.93 | 17.08 |
| 5-38 | 0.23 | 0.49 |
| 5-39 | 0.06 | 0.43 |
| 5-40 | 2.06 | 14.58 |
| 5-41 | 0.09 | 0.11 |
| 5-42 | 1.60 | 7.21 |
| 5-43 | 0.07 | 0.14 |
| 5-44 | 0.14 | 0.37 |
| 5-45 | 0.82 | 8.55 |
| 5-46 | 3.53 | 43.53 |
| 5-47 | 7.27 | 108.00 |
| 5-48 | 0.22 | 2.26 |
| 5-49 | 0.20 | 0.34 |
| 5-50 | 11.83 | 34.51 |
| 5-51 | 0.18 | 0.49 |
| 5-52 | 11.74 | 30.31 |
| 5-53 | 0.19 | 0.57 |
| 5-54 | 0.12 | 1.62 |
| 5-55 | 0.05 | 0.12 |
| 5-56 | 0.12 | 0.19 |
| 5-57 | 0.08 | 0.13 |
| 5-58 | 0.14 | 0.18 |
| 5-59 | 0.10 | 0.15 |
| 5-60 | 1.07 | 0.46 |
| 5-61 | 0.64 | 12.68 |
| 5-62 | 0.31 | 0.32 |
| 5-63 | 2.10 | 0.70 |
| 5-64 | 0.57 | 0.46 |
| 5-65 | 0.21 | 3.22 |
| 5-66 | 0.26 | 0.43 |
| 5-67 | 0.47 | 0.52 |
| 5-68 | 0.25 | 0.33 |

| Example | JAK1 IC$_{50}$ (nM) | JAK2 IC$_{50}$ (nM) | Example | JAK1 IC$_{50}$ (nM) | JAK2 IC$_{50}$ (nM) |
|---|---|---|---|---|---|
| 5-69 | 0.12 | 0.17 | 5-146 | 0.30 | 2.00 |
| 5-70 | 0.07 | 0.58 | 5-147 | 0.32 | 2.95 |
| 5-71 | 0.08 | 0.15 | 5-148 | 0.08 | 0.84 |
| 5-72 | 0.06 | 0.26 | 5-149 | 0.12 | 0.23 |
| 5-73 | 0.12 | 0.35 | 5-150 | 0.10 | 0.14 |
| 5-74 | 0.06 | 0.27 | 5-151 | 0.09 | 0.10 |
| 5-75 | 0.12 | 0.37 | 5-152 | 0.09 | 0.68 |
| 5-76 | 0.90 | 7.89 | 5-153 | 0.09 | 0.08 |
| 5-77 | 0.16 | 0.34 | 5-154 | 0.09 | 0.08 |
| 5-78 | 0.18 | 2.12 | 5-155 | 0.18 | 0.39 |
| 5-79 | 0.78 | 1.27 | 5-156 | 0.17 | 0.30 |
| 5-80 | 0.08 | 1.21 | 5-157 | 0.19 | 0.27 |
| 5-81 | 0.24 | 3.73 | 5-158 | 0.28 | 0.38 |
| 5-82 | 0.10 | 0.31 | 5-159 | 0.24 | 0.30 |
| 5-83 | 1.97 | 21.6 | 5-160 | 0.22 | 0.58 |
| 5-84 | <0.02 | 0.05 | 5-161 | 0.29 | 0.51 |
| 5-85 | 0.07 | 0.17 | 5-162 | 2.76 | 12.88 |
| 5-86 | 0.07 | 0.11 | 5-163 | 1.96 | 2.21 |
| 5-87 | 0.04 | 0.05 | 5-164 | 0.59 | 0.68 |
| 5-88 | 0.46 | 1.56 | 5-165 | 0.46 | 1.00 |
| 5-89 | 0.50 | 1.74 | 5-166 | 1.28 | 1.95 |
| 5-90 | 0.33 | 0.41 | 5-167 | 0.83 | 4.32 |
| 5-91 | 0.14 | 0.23 | 5-168 | 0.12 | 0.51 |
| 5-92 | 0.09 | 0.13 | 5-169 | 0.10 | 0.41 |
| 5-93 | 0.14 | 0.37 | 5-170 | 0.14 | 0.48 |
| 5-94 | 0.04 | 0.18 | 5-171 | 0.07 | 0.18 |
| 5-95 | 0.07 | 0.20 | 5-172 | 0.75 | 1.14 |
| 5-96 | 0.07 | 0.34 | 5-173 | 0.07 | 0.07 |
| 5-97 | 0.09 | 0.14 | 5-174 | 0.06 | 0.06 |
| 5-98 | 0.07 | 0.18 | 5-175 | 0.09 | 0.06 |
| 5-99 | 0.05 | 0.14 | 5-176 | 0.05 | 0.09 |
| 5-100 | 0.14 | 0.26 | 5-177 | 0.09 | 0.16 |
| 5-101 | 0.18 | 0.40 | 5-178 | 0.04 | 0.17 |
| 5-102 | 0.10 | 0.20 | 5-179 | 0.08 | 0.26 |
| 5-103 | 0.07 | 0.23 | 5-180 | 0.84 | 1.84 |
| 5-104 | 0.07 | 0.27 | 5-181 | 0.29 | 0.95 |
| 5-105 | 0.23 | 0.55 | 5-182 | 0.25 | 0.57 |
| 5-106 | 0.39 | 0.99 | 5-183 | 0.17 | 0.47 |
| 5-107 | 0.20 | 0.33 | 5-184 | 0.20 | 0.60 |
| 5-108 | 0.12 | 0.23 | 5-185 | 0.08 | 1.50 |
| 5-109 | 0.25 | 0.29 | 5-186 | 0.36 | 1.34 |
| 5-110 | 0.16 | 0.59 | 5-187 | 0.19 | 0.58 |
| 5-111 | 0.09 | 0.35 | 5-188 | 0.11 | 0.34 |
| 5-112 | 1.07 | 2.53 | 5-189 | 0.14 | 0.17 |
| 5-113 | 0.28 | 0.34 | 5-190 | 0.21 | 0.38 |
| 5-114 | 0.33 | 1.31 | 5-191 | 0.16 | 0.52 |
| 5-115 | 0.33 | 0.99 | 5-192 | 0.17 | 0.30 |
| 5-116 | 0.61 | 1.22 | 5-193 | 0.42 | 0.66 |
| 5-117 | 0.45 | 1.36 | 5-194 | 0.52 | 0.82 |
| 5-118 | 0.34 | 0.76 | 5-195 | 0.56 | 0.68 |
| 5-119 | 0.15 | 0.63 | 5-196 | 0.15 | 0.33 |
| 5-120 | 0.07 | 0.12 | 5-197 | 0.13 | 1.13 |
| 5-121 | 0.04 | 0.51 | 5-198 | 0.16 | 0.39 |
| 5-122 | 0.22 | 0.48 | 5-199 | 0.15 | 0.33 |
| 5-123 | 0.23 | 0.46 | 5-200 | 1.15 | 0.53 |
| 5-124 | 0.58 | 3.69 | 5-201 | 0.49 | 0.27 |
| 5-125 | 0.27 | 2.71 | 5-202 | 0.39 | 1.20 |
| 5-126 | 4.53 | 37.3 | 5-203 | 0.15 | 0.27 |
| 5-127 | 4.76 | 30.5 | 5-204 | 0.29 | 0.48 |
| 5-128 | 0.22 | 2.24 | 5-205 | 0.17 | 0.20 |
| 5-129 | 2.07 | 3.54 | 5-206 | 0.13 | 0.16 |
| 5-130 | 0.50 | 1.07 | 5-207 | 0.19 | 0.26 |
| 5-131 | 0.25 | 0.98 | 5-208 | 0.24 | 0.31 |
| 5-132 | 0.39 | 0.68 | 5-209 | 0.32 | 0.35 |
| 5-133 | 0.44 | 1.38 | 5-210 | 0.41 | 0.51 |
| 5-134 | 0.70 | 1.07 | 5-211 | 0.19 | 0.12 |
| 5-135 | 0.98 | 1.53 | 5-212 | 0.22 | 0.15 |
| 5-136 | 0.56 | 1.01 | 5-213 | 0.19 | 0.29 |
| 5-137 | 1.90 | 5.85 | 5-214 | 0.20 | 0.32 |
| 5-138 | 0.31 | 1.51 | 5-215 | 0.07 | 0.63 |
| 5-139 | 0.76 | 1.44 | 5-216 | 0.14 | 1.16 |
| 5-140 | 0.32 | 0.74 | 5-217 | 0.07 | 0.77 |
| 5-141 | 0.18 | 0.43 | 5-218 | 0.16 | 0.73 |
| 5-142 | 0.13 | 0.33 | 5-219 | 0.13 | 1.36 |
| 5-143 | 0.18 | 0.66 | 5-220 | 0.14 | 0.19 |
| 5-144 | 0.10 | 0.21 | 5-221 | 0.35 | 5.29 |
| 5-145 | 0.19 | 1.22 | 5-222 | 0.13 | 0.64 |

| Example | JAK1 IC$_{50}$ (nM) | JAK2 IC$_{50}$ (nM) | Example | JAK1 IC$_{50}$ (nM) | JAK2 IC$_{50}$ (nM) |
| --- | --- | --- | --- | --- | --- |
| 5-223 | 0.07 | 0.82 | 8-2 | 0.44 | 1.16 |
| 5-224 | 0.36 | 3.00 | 8-3 | 2.32 | 8.62 |
| 5-225 | 0.15 | 2.30 | 8-4 | 6.90 | 33.07 |
| 5-226 | 0.11 | 2.94 | 8-5 | 0.20 | 0.54 |
| 5-227 | 0.15 | 0.76 | 8-6 | 1.94 | 12.45 |
| 5-228 | 0.25 | 1.06 | 8-7 | 0.21 | 0.63 |
| 5-229 | 0.34 | 1.39 | 8-8 | 0.29 | 0.52 |
| 5-230 | 0.12 | 0.16 | 8-9 | 0.19 | 0.28 |
| 5-231 | 0.12 | 0.21 | 8-10 | 0.19 | 0.29 |
| 5-232 | 0.27 | 0.60 | 8-11 | 0.24 | 0.28 |
| 5-233 | 0.36 | 0.40 | 8-12 | 0.26 | 0.99 |
| 5-234 | 0.63 | 0.99 | 8-13 | 0.31 | 0.75 |
| 5-235 | 0.14 | 0.21 | 8-14 | 0.73 | 2.84 |
| 5-236 | 0.12 | 0.25 | 8-15 | 0.53 | 2.84 |
| 5-237 | 0.15 | 0.28 | 8-16 | 1.54 | 8.34 |
| 5-238 | 0.11 | 0.48 | 8-17 | 1.40 | 3.26 |
| 5-239 | 2.29 | 16.7 | 8-18 | 3.16 | 13.96 |
| 5-240 | 13.0 | 79.9 | 8-19 | 1.19 | 1.98 |
| 5-241 | 2.62 | 23.4 | 9-1 | 0.11 | 0.48 |
| 5-242 | 14.0 | 129.6 | 9-2 | 0.08 | 0.31 |
| 5-243 | 6.62 | 100.4 | 9-3 | 0.24 | 1.63 |
| 5-244 | 23.0 | 347.8 | 9-4 | 0.65 | 5.17 |
| 5-245 | 3.93 | 42.3 | 9-5 | 0.55 | 3.05 |
| 5-246 | 16.8 | 172.5 | 9-6 | 0.08 | 0.29 |
| 5-247 | 0.11 | 2.24 | 9-7 | 0.09 | 0.51 |
| 5-248 | 0.39 | 9.56 | 9-8 | 0.16 | 1.21 |
| 5-249 | 1.13 | 2.43 | 9-9 | 3.96 | 38.78 |
| 5-250 | 4.34 | 12.12 | 9-10 | 0.17 | 1.07 |
| 5-251 | 0.06 | 0.78 | 9-11 | 0.14 | 1.15 |
| 5-252 | 0.34 | 0.84 | 9-12 | 1.69 | 16.75 |
| 5-253 | 0.72 | 1.40 | 9-13 | 1.08 | 11.97 |
| 5-254 | 0.66 | 1.40 | 9-14 | 0.23 | 1.96 |
| 5-255 | 0.14 | 3.32 | 9-15 | 0.81 | 8.38 |
| 5-256 | 0.04 | 0.06 | 9-16 | 1.05 | 6.75 |
| 5-257 | 2.08 | 3.17 | 9-17 | 0.15 | 0.70 |
| 5-258 | 0.07 | 0.08 | 9-18 | 0.14 | 0.39 |
| 5-259 | 0.04 | 0.05 | 9-19 | 0.26 | 3.14 |
| 5-260 | 0.26 | 2.35 | 9-20 | 0.31 | 2.48 |
| 5-261 | 2.26 | 2.74 | 9-21 | 0.08 | 0.33 |
| 5-262 | 0.09 | 0.08 | 9-22 | 0.09 | 0.21 |
| 5-263 | 0.48 | 0.77 | 9-23 | 0.14 | 1.32 |
| 5-264 | 0.51 | 0.79 | 9-24 | 0.14 | 0.36 |
| 5-265 | 0.05 | 0.04 | 9-25 | 0.10 | 0.16 |
| 5-266 | 0.05 | 0.04 | 10-1 | 0.13 | 0.26 |
| 5-267 | 2.42 | 4.02 | 10-2 | 0.19 | 0.86 |
| 5-268 | 2.63 | 4.78 | 10-3 | 0.27 | 0.97 |
| 5-269 | 0.11 | 0.09 | 10-4 | 0.45 | 3.08 |
| 5-270 | 0.12 | 0.13 | 10-5 | 0.12 | 0.29 |
| 5-271 | 0.25 | 3.27 | 10-6 | 0.12 | 0.27 |
| 5-272 | 0.06 | 0.10 | 11-1 | 0.27 | 1.01 |
| 5-273 | 0.17 | 0.14 | 11-2 | 0.38 | 1.69 |
| 5-274 | 0.36 | 0.26 | 11-3 | 0.31 | 1.09 |
| 5-275 | 0.17 | 0.09 | 11-4 | 0.27 | 1.45 |
| 5-276 | 0.57 | 0.40 | 11-5 | 0.27 | 0.61 |
| 5-277 | 0.05 | 0.05 | 11-6 | 0.12 | 0.47 |
| 5-278 | 0.20 | 2.65 | 11-7 | 0.18 | 1.35 |
| 5-279 | 0.18 | 0.12 | 11-8 | 0.18 | 0.29 |
| 5-280 | 7.33 | 9.56 | 11-9 | 0.41 | 1.37 |
| 5-281 | 7.90 | 10.04 | 11-10 | 0.06 | 0.10 |
| 5-282 | 0.33 | 0.49 | 11-11 | 0.16 | 0.91 |
| 5-283 | 0.33 | 0.43 | 12 | 0.11 | 0.24 |
| 5-284 | 0.15 | 0.24 | 13-1 | 0.22 | 3.82 |
| 5-285 | 0.15 | 0.21 | 13-2 | 0.64 | 5.54 |
| 5-286 | 0.24 | 0.33 | 14-1 | 0.09 | 0.18 |
| 5-287 | 0.25 | 0.35 | 14-2 | 0.06 | 0.12 |
| 5-288 | 0.15 | 0.30 | 15-1 | 0.16 | 0.37 |
| 5-289 | 0.88 | 1.89 | 15-2 | 0.04 | 0.04 |
| 5-290 | 0.25 | 0.48 | 15-3 | 0.25 | 0.26 |
| 5-291 | 0.15 | 0.34 | 15-4 | 0.20 | 0.55 |
| 5-292 | 1.20 | 1.92 | 15-5 | 0.15 | 0.17 |
| 5-293 | 0.43 | 0.68 | 15-6 | 0.10 | 0.09 |
| 5-294 | 0.22 | 0.37 | 15-7 | 0.17 | 1.02 |
| 5-295 | 0.42 | 0.60 | 15-8 | 0.09 | 0.41 |
| 5-296 | 0.65 | 0.91 | 16-1 | 2.77 | 3.06 |
| 6 | 421.30 | >1496 | 16-2 | 1.14 | 4.81 |
| 7 | 0.09 | 1.90 | 16-3 | 1.15 | 3.82 |
| 8-1 | 0.17 | 0.38 | 16-4 | 2.01 | 2.01 |

-continued

| Example | JAK1 IC$_{50}$ (nM) | JAK2 IC$_{50}$ (nM) |
|---|---|---|
| 17 | 0.10 | 0.24 |
| 18-1 | 0.26 | 0.94 |
| 18-2 | 6.80 | 64 |
| 18-3 | 41.14 | 1292 |
| 18-4 | 6.33 | 101.90 |
| 18-5 | 4.14 | 84.56 |
| 18-6 | 0.09 | 1.75 |
| 18-7 | 2.98 | 19.82 |
| 18-8 | 0.03 | 2.53 |
| 18-9 | 1.14 | 102.10 |
| 18-10 | 73.97 | 1020 |
| 18-11 | 0.22 | 2.20 |
| 18-12 | 5.41 | 38.48 |
| 18-13 | 64.96 | >1496 |
| 18-14 | 1.71 | 32.35 |
| 18-15 | 151.20 | 1137 |
| 18-16 | 0.15 | 1.43 |
| 18-17 | 119.90 | 1099 |
| 18-18 | 7.27 | 54.70 |
| 18-19 | 0.37 | 36.64 |
| 18-20 | 52.18 | >1496 |
| 18-21 | 0.12 | 64.17 |
| 18-22 | 20.51 | >1496 |
| 18-23 | 124.8 | >1496 |
| 18-24 | 0.09 | 5.87 |
| 18-25 | 70.15 | >1496 |
| 18-26 | 2.48 | 54.73 |
| 18-27 | 2.23 | 9.07 |
| 18-28 | 0.05 | 0.11 |
| 18-29 | 0.10 | 0.13 |
| 18-30 | 2.62 | 3.54 |
| 18-31 | 1.81 | 16.95 |
| 18-32 | 0.04 | 0.09 |
| 18-33 | 48.51 | 591.8 |
| 18-34 | 1.07 | 12.09 |
| 18-35 | 0.21 | 0.21 |
| 18-36 | 0.83 | 6.85 |
| 18-37 | 0.23 | 4.43 |
| 18-38 | 16.14 | 211.1 |
| 18-39 | 1.37 | 1.78 |
| 19-1 | 0.08 | 1.94 |
| 19-2 | 0.10 | 2.07 |
| 19-3 | 0.04 | 0.06 |
| 20-1 | 0.30 | 0.71 |
| 20-2 | 0.43 | 0.62 |
| 20-3 | 0.65 | 0.83 |
| 20-4 | 0.35 | 0.88 |
| 20-5 | 0.13 | 0.19 |
| 20-6 | 0.13 | 0.17 |
| 20-7 | 0.09 | 0.36 |
| 20-8 | 0.15 | 0.16 |
| 20-9 | 0.14 | 0.17 |
| 20-10 | 0.21 | 0.31 |
| 20-11 | 0.23 | 0.35 |
| 20-12 | 0.25 | 0.45 |
| 20-13 | 0.22 | 0.26 |
| 20-14 | 0.28 | 0.51 |
| 20-15 | 0.19 | 0.51 |
| 20-16 | 0.10 | 0.15 |
| 21-1 | 0.08 | 0.73 |
| 21-2 | 0.04 | 0.04 |
| 21-3 | 0.07 | 0.12 |
| 21-4 | 0.09 | 0.19 |
| 21-5 | 0.09 | 1.32 |
| 21-6 | 0.12 | 2.25 |
| 21-7 | 0.41 | 0.90 |
| 21-8 | 0.38 | 1.03 |
| 21-9 | 1.11 | 1.96 |
| 21-10 | 0.97 | 1.95 |
| 21-11 | 0.43 | 0.38 |
| 21-12 | 0.26 | 0.18 |
| 21-13 | 0.27 | 0.20 |
| 21-14 | 0.33 | 0.32 |
| 21-15 | 0.77 | 0.65 |
| 21-16 | 0.71 | 0.64 |
| 21-17 | 0.63 | 0.58 |
| 21-18 | 0.55 | 0.50 |
| 21-19 | 0.45 | 0.50 |
| 21-20 | 0.18 | 0.17 |
| 22 | 3.78 | 23.3 |
| 23 | 0.23 | 2.50 |
| 24 | 0.34 | 1.13 |

The invention claimed is:

1. A compound of Formula I or a pharmaceutically acceptable salt, or a stereoisimer thereof:

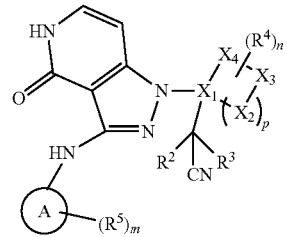

I

A is selected from phenyl, methyl, ethyl, cyclopropylmethyl, cyclopropyl, cyclobutyl, isoindolinyl, benzo[d]thiazolyl,

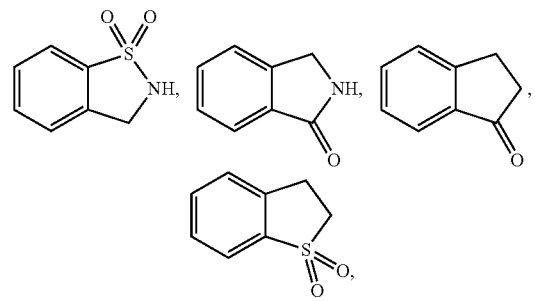

2,3-dihydro-1H-indenyl, quinolinyl, pyridinyl, and indolinyl;

$R^2$ and $R^3$ are each independently selected from hydrogen, $C_{1-4}$alkyl and hydroxy, wherein $R^2$ and $R^3$ may optionally, join together with the carbon they are attached to form a 3 to 6 membered ring;

$X_1$ is C;

$X_2$, $X_3$, and $X_4$ are each independently selected from O, N, S, and C and provided that the formed ring system contains 0, 1, 2, or 3 atoms selected from O, N and S;

n is 0, 1, 2, 3 or 4;

m is 0, 1, 2, 3 or 4;

p is 0, 1, 2, 3, or 4;

$R^4$ is selected from:
halogen,
oxo (=O),
$C_{1-10}$ alkyl(oxy)$_{0-1}$(carbonyl)$_{0-1}$C$_{0-10}$ alkyl,
$C_{1-10}$ heteroalkyl(oxy)$_{0-1}$(carbonyl)$_{0-1}$C$_{0-10}$ alkyl,
$C_{2-10}$ alkenyl(oxy)$_{0-1}$(carbonyl)$_{0-1}$C$_{0-10}$ alkyl,
aryl $C_{0-10}$ alkyl(oxy)$_{0-1}$(carbonyl)$_{0-1}$C$_{0-10}$ alkyl, $C_{3-12}$ cycloalkyl $C_{0-10}$ alkyl(oxy)$_{0-1}$(carbonyl)$_{0-1}$$C_{0-10}$ alkyl,
heteroaryl $C_{0-10}$ alkyl(oxy)$_{0-1}$(carbonyl)$_{0-1}$$C_{0-10}$ alkyl,
$(C_{3-12})$heterocycloalkyl $C_{0-10}$ alkyl(oxy)$_{0-1}$(carbonyl)$_{0-1}$ $C_{0-10}$ alkyl,
$C_{0-10}$ alkyl(oxy)$_{0-1}$(carbonyl)$_{0-1}$amino$C_{0-10}$ alkyl,
$C_{1-10}$ alkylamino(carbonyl)$_{0-1}$$C_{0-10}$alkyl,
$(C_{1-10})$heteroalkyl(oxy)$_{0-1}$(carbonyl)$_{0-1}$amino$C_{0-10}$ alkyl,
$(C_{1-10})$heteroalkylamino(carbonyl)$_{0-1}$$C_{0-10}$alkyl,
$C_{3-12}$ cycloalkyl $C_{0-10}$ alkylamino$C_{0-10}$ alkyl,
aryl $C_{0-10}$ alkylamino$C_{0-10}$ alkyl,
heteroaryl $C_{0-10}$ alkylamino$C_{0-10}$ alkyl,
$(C_{3-12})$heterocycloalkyl $C_{0-10}$ alkylamino$C_{0-10}$ alkyl,
$C_{1-10}$ alkylsulfonyl,
$C_{1-10}$ heteroalkylsulfonyl,
$(C_{3-12})$cycloalkyl$C_{0-10}$alkylsulfonyl,
$(C_{3-12})$cycloheteroalkyl$C_{0-10}$alkylsulfonyl,
heteroaryl$C_{0-10}$ alkylsulfonyl,
aryl$C_{0-10}$ alkylsulfonyl,
—SO$_2$NH$_2$,
—SO$_2$NH($C_{1-6}$alkyl),
—SO$_2$N($C_{1-6}$alkyl)$_2$,
$C_{0-10}$ alkylsulfamoyl,
$C_{1-10}$ heteroalkylsulfamoyl,
$(C_{3-12})$cycloalkyl$C_{0-10}$ alkylsulfamoyl,
$(C_{3-12})$cycloheteroalkyl$C_{0-10}$ alkylsulfamoyl,
heteroaryl$C_{0-10}$ alkylsulfamoyl,
aryl$C_{0-10}$ alkylsulfamoyl,
$C_{0-10}$ alkylsulfonimidoyl$C_{0-10}$ alkyl,
$C_{1-10}$ heteroalkylsulfonimidoyl$C_{0-10}$ alkyl,
$(C_{3-12})$cycloalkyl$C_{0-10}$ alkylsulfonimidoyl$C_{0-10}$ alkyl,
$(C_{3-12})$cycloheteroalkyl$C_{0-10}$alkylsulfonimidoyl$C_{0-10}$ alkyl,
heteroaryl$C_{0-10}$ alkylsulfonimidoyl$C_{0-10}$ alkyl,
aryl$C_{0-10}$ alkylsulfonimidoyl$C_{0-10}$ alkyl,
$(C_{1-10}$ alkyl)$_{1-2}$amino,
—CO$_2$($C_{0-10}$ alkyl),
—($C_{0-10}$ alkyl)CO$_2$H,
—SO$_2$CF$_3$,
—SO$_2$CF$_2$H,
—SO$_2$CH$_2$CF$_3$,
$C_{1-10}$ alkylsulfinyl,
$C_{1-4}$acylamino$C_{0-10}$ alkyl,
hydroxy,
—($C_{1-10}$ alkyl)OH,
$C_{1-10}$ alkoxy$C_{0-10}$ alkyl,
cyano,
($C_{1-6}$alkyl)cyano, and
$C_{1-6}$haloalkyl,
wherein two R$^4$ together with the ring atom to which each is attached optionally may form a saturated ring;
R$^5$ is selected from:
halogen,
oxo (=O),
$C_{1-10}$ alkyl(oxy)$_{0-1}$(carbonyl)$_{0-1}$$C_{0-10}$ alkyl,
$C_{1-10}$ heteroalkyl(oxy)$_{0-1}$(carbonyl)$_{0-1}$$C_{0-10}$ alkyl,
$C_{2-10}$ alkenyl(oxy)$_{0-1}$(carbonyl)$_{0-1}$$C_{0-10}$ alkyl,
aryl $C_{0-10}$ alkyl(oxy)$_{0-1}$(carbonyl)$_{0-1}$$C_{0-10}$ alkyl,
$C_{3-12}$ cycloalkyl $C_{0-10}$ alkyl(oxy)$_{0-1}$(carbonyl)$_{0-1}$$C_{0-10}$ alkyl,
heteroaryl $C_{0-10}$ alkyl(oxy)$_{0-1}$(carbonyl)$_{0-1}$$C_{0-10}$ alkyl,
$(C_{3-12})$heterocycloalkyl $C_{0-10}$ alkyl(oxy)$_{0-1}$(carbonyl)$_{0-1}$ $C_{0-10}$ alkyl,
$C_{0-10}$ alkylaminocarbonyl$C_{0-10}$alkyl,
$C_{0-10}$ alkyl(oxy)$_{0-1}$(carbonyl)$_{0-1}$ amino$C_{0-10}$ alkyl,
$(C_{1-10})$heteroalkyl(oxy)$_{0-1}$(carbonyl)$_{0-1}$ amino$C_{0-10}$ alkyl,
$C_{3-12}$ cycloalkyl $C_{0-10}$ alkylamino$C_{0-10}$ alkyl,
aryl $C_{0-10}$ alkylamino$C_{0-10}$ alkyl,
heteroaryl $C_{0-10}$ alkylamino$C_{0-10}$ alkyl,
$(C_{3-12})$heterocycloalkyl $C_{0-10}$ alkylamino$C_{0-10}$ alkyl,
$(C_{1-10}$ alkyl)$_{1-2}$ amino,
—SF$_5$,
$C_{0-10}$ alkylsulfonyl,
$C_{1-10}$ heteroalkylsulfonyl,
$(C_{3-12})$cycloalkyl$C_{0-10}$alkylsulfonyl,
$(C_{3-12})$cycloheteroalkyl$C_{0-10}$alkylsulfonyl,
heteroaryl$C_{0-10}$ alkylsulfonyl,
aryl$C_{0-10}$ alkylsulfonyl,
$C_{0-10}$ alkylsulfamoyl,
$C_{1-10}$ heteroalkylsulfamoyl,
$(C_{3-12})$cycloalkyl$C_{0-10}$ alkylsulfamoyl,
$(C_{3-12})$cycloheteroalkyl$C_{0-10}$ alkylsulfamoyl,
heteroaryl$C_{0-10}$ alkylsulfamoyl,
$C_{0-10}$ alkylsulfonimidoyl$C_{0-10}$ alkyl,
$C_{1-10}$ heteroalkylsulfonimidoyl$C_{0-10}$ alkyl,
$(C_{3-12})$cycloalkyl$C_{0-10}$ alkylsulfonimidoyl$C_{0-10}$ alkyl,
$(C_{3-12})$cycloheteroalkyl$C_{0-10}$alkylsulfonimidoyl$C_{0-10}$ alkyl,
heteroaryl$C_{0-10}$ alkylsulfonimidoyl$C_{0-10}$ alkyl,
aryl$C_{0-10}$ alkylsulfonimidoyl$C_{0-10}$ alkyl,
—SO$_2$NH$_2$,
—SO$_2$NH($C_{1-6}$alkyl),
—SO$_2$N($C_{1-6}$alkyl)$_2$,
aryl$C_{0-10}$ alkylsulfamoyl,
($C_{0-10}$ alkyl)$_{1-2}$ amino,
—CO$_2$($C_{0-10}$ alkyl),
—($C_{0-10}$ alkyl)CO$_2$H,
—SO$_2$CF$_3$,
—SO$_2$CF$_2$H,
—SO$_2$CH$_2$CF$_3$,
$C_{1-10}$ alkylsulfinyl,
$C_{1-4}$acylamino$C_{0-10}$ alkyl,
hydroxy,
—($C_{1-10}$ alkyl)OH,
$C_{1-10}$ alkoxy$C_{0-10}$ alkyl,
cyano,
($C_{1-6}$alkyl)cyano, and
$C_{1-6}$haloalkyl; and
wherein R$^4$ and R$^5$ are each optionally substituted with 1, 2, 3, or 4 R$^6$ substituents and R$^6$ is independently selected from:
halogen,
$C_{1-10}$ alkyl(oxy)$_{0-1}$(carbonyl)$_{0-1}$$C_{0-10}$ alkyl,
$C_{1-10}$ heteroalkyl(oxy)$_{0-1}$(carbonyl)$_{0-1}$$C_{0-10}$ alkyl,
$C_{2-10}$ alkenyl(oxy)$_{0-1}$(carbonyl)$_{0-1}$$C_{0-10}$ alkyl,
aryl $C_{0-10}$ alkyl(oxy)$_{0-1}$(carbonyl)$_{0-1}$$C_{0-10}$ alkyl,
$C_{3-12}$ cycloalkyl $C_{0-10}$ alkyl(oxy)$_{0-1}$(carbonyl)$_{0-1}$$C_{0-10}$ alkyl,
heteroaryl $C_{0-10}$ alkyl(oxy)$_{0-1}$(carbonyl)$_{0-1}$$C_{0-10}$ alkyl,
$(C_{3-12})$heterocycloalkyl $C_{0-10}$ alkyl(oxy)$_{0-1}$(carbonyl)$_{0-1}$ $C_{0-10}$ alkyl,
$C_{1-10}$ alkyl(carbonyl)$_{0-1}$ oxy$C_{0-10}$ alkyl,
$C_{2-10}$ alkenyl(carbonyl)$_{0-1}$ oxy$C_{0-10}$ alkyl,
$C_{1-10}$ heteroalkyl(carbonyl)$_{0-1}$ oxy$C_{0-10}$ alkyl,
aryl $C_{0-10}$ alkyl (carbonyl)$_{0-1}$ oxy$C_{0-10}$ alkyl,
$(C_{3-12})$cycloalkyl $C_{0-10}$ alkyl(carbonyl)$_{0-1}$ oxy$C_{0-10}$ alkyl,
heteroaryl$C_{0-10}$ alkyl(carbonyl)$_{0-1}$ oxy$C_{0-10}$ alkyl,
$(C_{3-12})$heterocycloalkyl $C_{0-10}$ alkyl(carbonyl)$_{0-1}$ oxy$C_{0-10}$ alkyl, ((C$_{0-10}$)alkyl)$_{1-2}$aminocarbonyloxy,
aryl (C$_{0-10}$)alkylaminocarbonyloxy,
—CO$_2$(C$_{0-10}$ alkyl),
—(C$_{0-10}$ alkyl)CO$_2$H,
oxo (=O),
C$_{0-10}$ alkylsulfonyl,
C$_{1-10}$ heteroalkylsulfonyl,
(C$_{3-12}$)cycloalkylsulfonyl,
(C$_{3-12}$)cycloheteroalkylsulfonyl,
heteroarylsulfonyl,
arylsulfonyl,
aminosulfonyl,
—SO$_2$NH$_2$,
—SO$_2$NH(C$_{1-6}$alkyl),
—SO$_2$N(C$_{1-6}$alkyl)$_2$,
—SO$_2$CF$_3$,
—SO$_2$CF$_2$H,
C$_{1-10}$ alkylsulfinyl,
amino,
(C$_{1-10}$ alkyl)$_{1-2}$amino,
-(oxy)$_{0-1}$(carbonyl)$_{0-1}$N(C$_{0-10}$ alkyl)$_{1-2}$
C$_{1-4}$acylaminoC$_{0-10}$ alkyl,
hydroxy,
(C$_{1-10}$ alkyl)OH,
C$_{1-10}$ alkoxyC$_{0-10}$ alkyl,
(C$_{1-10}$ alkyl)cyano,
cyano, and
C$_{1-6}$haloalkyl; and
R$^6$ is optionally substituted with 1, 2, or 3 R$^7$ substituents selected from hydrogen, hydroxy, (C$_{1-6}$)alkyl, C$_{1-10}$ alkoxyC$_{0-10}$ alkyl, (C$_{1-10}$ alkyl)OH, halogen, CO$_2$H, —(C$_{0-6}$)alkylCN, —O(C=O)C$_1$-C$_6$ alkyl, NO$_2$, trifluoromethoxy, trifluoroethoxy, trifluoromethyl, trifluoroethyl, —N=C(O)O(C$_{0-6}$)alkyl, C$_{1-10}$ alkylsulfonyl, oxo (O=), aminosulfonyl, —SO$_2$C$_{1-6}$alkyl, —SO$_2$CF$_3$, —SO$_2$CF$_2$H, —C$_{1-10}$ alkylsulfinyl, —O$_{(0-1)}$(C$_{1-10}$)halo, —SO$_2$NH$_2$, —SO$_2$NH(C$_{1-6}$alkyl), —SO$_2$N(C$_{1-6}$alkyl)$_2$, alkyl, amino(C$_{1-6}$alkyl)$_{0-2}$ and NH$_2$.

2. A compound according to claim 1, wherein R$^5$ is selected from: halogen, oxo (=O), C$_{1-10}$ alkyl(oxy)$_{0-1}$(carbonyl)$_{0-1}$C$_{0-10}$ alkyl, C$_{1-10}$ heteroalkyl(oxy)$_{0-1}$ (carbonyl)$_{0-1}$C$_{0-10}$ alkyl, aryl C$_{0-10}$ alkyl(oxy)$_{0-1}$(carbonyl)$_{0-1}$C$_{0-10}$ alkyl, C$_{3-12}$ cycloalkyl C$_{0-10}$ alkyl(oxy)$_{0-1}$(carbonyl)$_{0-1}$C$_{0-10}$ alkyl, heteroaryl C$_{0-10}$ alkyl(oxy)$_{0-1}$(carbonyl)$_{0-1}$C$_{0-10}$ alkyl, (C$_{3-12}$)heterocycloalkyl C$_{0-10}$ alkyl(oxy)$_{0-1}$(carbonyl)$_{0-1}$C$_{0-10}$ alkyl, C$_{0-10}$ alkylaminocarbonylC$_{0-10}$ alkyl, C$_{0-10}$ alkyl (oxy)$_{0-1}$(carbonyl)$_{0-1}$ aminoC$_{0-10}$ alkyl, (C$_{1-10}$)heteroalkyl (oxy)$_{0-1}$(carbonyl)$_{0-1}$ aminoC$_{0-10}$ alkyl, —SF$_5$, C$_{0-10}$ alkylsulfonyl, C$_{1-10}$ heteroalkylsulfonyl, (C$_{3-12}$)cycloalkylC$_{0-10}$ alkylsulfonyl, (C$_{3-12}$)cycloheteroalkylC$_{0-10}$alkylsulfonyl, C$_{0-10}$ alkylsulfamoyl, (C$_{3-12}$)cycloalkylC$_{0-10}$ alkylsulfamoyl, (C$_{3-12}$)cycloheteroalkylC$_{0-10}$ alkylsulfamoyl, heteroarylC$_{0-10}$ alkylsulfamoyl, C$_{0-10}$ alkylsulfonimidoylC$_{0-10}$ alkyl, C$_{1-10}$ heteroalkylsulfonimidoylC$_{0-10}$ alkyl, —SO$_2$NH$_2$, —SO$_2$NH(C$_{1-6}$alkyl), —SO$_2$N(C$_{1-6}$alkyl)$_2$, arylC$_{0-10}$ alkylsulfamoyl, (C$_{1-10}$ alkyl)$_{1-2}$amino, —SO$_2$CF$_3$, —SO$_2$CF$_2$H, —SO$_2$CH$_2$CF$_3$, hydroxy, —(C$_{1-10}$ alkyl)OH, C$_{1-10}$ alkoxyC$_{0-10}$ alkyl, cyano, (C$_{1-6}$alkyl)cyano, and C$_{1-6}$haloalkyl; wherein R$^5$ is optionally substituted with 0, 1, 2, 3, or 4 R$^6$ substituents.

3. A compound according to claim 2, wherein R$^4$ is selected from: halogen, oxo (=O), C$_{1-10}$ alkyl(oxy)$_{0-1}$(carbonyl)$_{0-1}$C$_{0-10}$ alkyl, C$_{1-10}$ heteroalkyl(oxy)$_{0-1}$ (carbonyl)$_{0-1}$C$_{0-10}$ alkyl, aryl C$_{0-10}$ alkyl(oxy)$_{0-1}$(carbonyl)$_{0-1}$C$_{0-10}$ alkyl, C$_{3-12}$ cycloalkyl C$_{0-10}$ alkyl(oxy)$_{0-1}$(carbonyl)$_{0-1}$C$_{0-10}$ alkyl, heteroaryl C$_{0-10}$ alkyl(oxy)$_{0-1}$(carbonyl)$_{0-1}$C$_{0-10}$ alkyl, (C$_{3-12}$)heterocycloalkyl C$_{0-10}$ alkyl(oxy)$_{0-1}$(carbonyl)$_{0-1}$C$_{0-10}$ alkyl, C$_{0-10}$ alkyl(oxy)$_{0-1}$ (carbonyl)$_{0-1}$ aminoC$_{0-10}$ alkyl, C$_{1-10}$ alkylamino(carbonyl)$_{0-1}$C$_{0-10}$alkyl, (C$_{1-10}$)heteroalkyl(oxy)$_{0-1}$(carbonyl)$_{0-1}$ aminoC$_{0-10}$alkyl, (C$_{1-10}$)heteroalkylamino(carbonyl)$_{0-1}$C$_{0-10}$alkyl, C$_{3-12}$ cycloalkyl C$_{0-10}$ alkylaminoC$_{0-10}$ alkyl, aryl C$_{0-10}$ alkylaminoC$_{0-10}$ alkyl, heteroaryl C$_{0-10}$ alkylaminoC$_{0-10}$ alkyl, (C$_{3-12}$)heterocycloalkyl C$_{0-10}$ alkylaminoC$_{0-10}$ alkyl, C$_{0-10}$ alkylsulfonyl, (C$_{3-12}$)cycloalkylC$_{0-10}$alkylsulfonyl, (C$_{3-12}$)cycloheteroalkylC$_{0-10}$alkylsulfonyl, —SO$_2$NH$_2$, —SO$_2$NH(C$_{1-6}$ alkyl), —SO$_2$N(C$_{1-6}$alkyl)$_2$, C$_{0-10}$ alkylsulfonimidoylC$_{0-10}$ alkyl, C$_{1-10}$ heteroalkylsulfonimidoylC$_{0-10}$ alkyl, (C$_{1-10}$ alkyl)$_{1-2}$amino, —CO$_2$(C$_{0-10}$ alkyl), —SO$_2$CF$_3$, —SO$_2$CF$_2$H, —SO$_2$CH$_2$CF$_3$, hydroxy, —(C$_{1-10}$ alkyl)OH, C$_{1-10}$ alkoxyC$_{0-10}$ alkyl, cyano, (C$_{1-6}$alkyl)cyano, and C$_{1-6}$haloalkyl, wherein R$^4$ is optionally substituted with 0, 1, 2, 3, or 4 R$^6$ substituents, and two R$^4$ together with the ring atom to which each is attached optionally may form a saturated ring.

4. A compound according to claim 3, wherein R$^4$ is selected from tert-butylcarbonyl, methoxycarbonyl, methylcarbonyl, cyclopropylmethyl, cyclopropylmethylcarbonyl, cyclopropylethylcarbonyl, cyclopropylcarbonyl, cyclobutylcarbonyl, cyclopentyloxycarbonyl, isopropyloxycarbonyl, phenylmethyl, phenylpropyl, phenylmethylcarbonyl, phenylethylcarbonyl, phenyloxycarbonyl, phenylcarbonyl, oxazolylmethyl, 1,3-oxazolylmethyl, indolylmethyl, 1-phenylethyl, pyridinylmethyl, cyclohexylcarbonyl, fluoro, 2,2,2-trifluoroethyl, ethyl, 2-hydoxyethyl, neopentylcarbonyl, neopentyloxycarbonyl, ethylcarbonyl, ethyloxycarbonyl, methoxymethylcarbonyl (methylamino)methylcarbonyl, 2,3-dihydro-1H-indenylcarbonyl, pyrrolidinylmethylcarbonyl, tetrahydro-2H-pyranylcarbonyl, tetrahydro-2H-thiopyranyloxycarbonyl, tetrahydro-2H-pyranyloxycarbonyl, 1-(pyridinyl)ethyloxycarbonyl, adamantylcarbonyl, tetrahydrofuranyloxycarbonyl, trifluoroethylsulfonyl, dimethylamino, tert-butyloxycarbonyl, methyl, tert-butylaminocarbonyl, aminocarbonyl, azetidinyl, cyclohexylamino, oxo, hydroxy, methylaminocarbonyl, cyclopropylsulfonyl, methoxy, phenylamino, pyridinyl, hydroxyisopropyl, hydroxyeth-2-yl, trifluoromethyl, 2-(methylthio)eth-2-ylcarbonyl, methylsulfonyl, ethylcarbonyl, methylamino, isopropyloxycarbonyl, and hydroxyisopropyl; wherein R$^4$ is optionally substituted with 0, 1, 2, 3, or 4 R$^6$ substituents, and wherein two R$^4$ together with the ring atom to which each is attached optionally may form a saturated ring.

5. A compound according to claim 4, wherein embodiment R$^5$ is selected from: methoxycarbonyl, tert-butylsulfonyl, tert-butylsulfamoyl, tert-butyl(methyl)sulfamoyl, tert-butyl(ethyl)sulfamoyl, pentafluorosulfanyl, methoxy, dimethyamino, oxo, amino, fluoro, isobutyl, isopropyl, sulfamoyl, dimethylsulfamoyl, methylsulfonyl, ethylsulfonyl, trifluoromethylsulfonyl, tert-butyloxycarbonyl(1-methyl) ethyl, diethylsulfamoyl, ethylsulfamoyl, pyrrolidinylsulfonyl, methyl, tert-butylaminomethyl, methylaminocarbonyl, methylaminomethyl, ethyl, (1-hydroxy)ethyl, piperidinylsulfonyl, piperidinyl, thiomorpholinylcarbonyl, thiazolidinylcarbonyl, thiomorpholinylmethyl, pyrrolidinylcarbonyl, piperidinylcarbonyl, ethylaminocarbonyl, morpholinylcarbonyl, tert-butyl, cyclopentylmethyl, cyclohexyl, cyclohexylsulfonyl, cyclohexylsulfamoyl, cyclopentyl, cyclopentylsulfonyl, benzyl, hydroxymethyl, 8-oxa-3-azabicyclo[3.2.1]octanyl, 8-oxa-3-azabicyclo[3.2.1]octane-3carbonyl, 3-oxa-8-azabicyclo[3.2.1]octan-8-ylcarbonyl, ethoxycarbonyl (dimethyleth-2-yl), hydroxy, trifluoromethyl, azetidinylsulfonyl, cyclopropylsulfonyl, cyclopropyl, chloro, ethylaminomethyl, pyrrolidinylmethyl, 1-pyrrolidin- 1-ylethyl, cyclopropylmethyl, pyrazolylmethyl, morpholinylsulfonyl, isopropylaminomethyl, pyrazolyl, pyrrolidinyl, piperadinyl, methylsulfonyl, isopropylsulfonyl, isopropylsulfamoyl, methylsulfamoyl, benzylsulfamoyl, cyclopropylmethyl, cyclobutyl, tert-butylsulfonyl, tert-butyloxycarbonyl, tert-butyloxycarbonylmethyl, methoxymethyl, 2-oxa-5-azabicyclo[2.2.1]heptane-5-carbonyl, methoxyeth-2-yl, triazolylmethyl, 1,2,3-triazolylmethyl, aminomethyl, ethylaminomethyl, aminocarbonyl, morpholinyl, isopropyl, isopropyl(methy)sulfamoyl, sulfonyl, cyano, 2,2,2-trifluoroethyl, ethylaminocarbonyl, tert-butylaminomethyl, isopropyloxycarbonyl(dimethyleth-2-yl), 1,1,1-trifluoro-3,3-dimethylbut-2-yl, (1,1,2-trimethylpropyl)sulfonyl, (1,1-dimethylpropyl)sulfonyl, isopropylsulfonimidoyl methylsulfonyl, ethylcarbonyl, 2,3-dihydro-1H-indenyl, ethylmethylsulfamoyl, neopentyl, methylaminomethyl dimethylamino, 2-(isopropylamino)propan-2-yl, 2,2-dimethylpropyl, hydroxymethyl, hydroxyeth-2-yl, tert-butyloxycarbonyl(2-methylprop-2-yl), methoxy, ethylaminocarbonyl, methylaminocarbonyl, and methoxymethyl; and wherein $R^5$ is optionally substituted with 0, 1, 2, 3, or 4 $R^6$ substituents.

6. A compound or a pharmaceutically acceptable salt, or a stereoisomer thereof selected from:

tert-butyl 3-(cyanomethyl)-3-(4-oxo-3-(phenylamino)-4,5-dihydro-1H-pyrazolo[4,3-c]pyridin-1-yl)azetidine-1-carboxylate;

tert-butyl 4-(cyanomethyl)-4-(4-oxo-3-(phenylamino)-4,5-dihydro-1H-pyrazolo[4,3-c]pyridin-1-yl)piperidine-1-carboxylate;

tert-butyl 4-(cyanomethyl)-4-[3-(ethylamino)-4-oxo-4,5-dihydro-1H-pyrazolo[4,3-c]pyridin-1-yl]piperidine-1-carboxylate;

tert-butyl 4-(cyanomethyl)-4-{3-[(cyclopropylmethyl)amino]-4-oxo-4,5-dihydro-1H-pyrazolo[4,3-c]pyridin-1-yl}piperidine-1-carboxylate;

tert-butyl 4-(cyanomethyl)-4-[3-(cyclobutylamino)-4-oxo-4,5-dihydro-1H-pyrazolo[4,3-c]pyridin-1-yl]piperidine-1-carboxylate;

tert-butyl 3-(cyanomethyl)-3-[3-(ethylamino)-4-oxo-4,5-dihydro-1H-pyrazolo[4,3-c]pyridin-1-yl]azetidine-1-carboxylate;

tert-butyl 4-(cyanomethyl)-4-[3-(methylamino)-4-oxo-4,5-dihydro-1H-pyrazolo[4,3-c]pyridin-1-yl]piperidine-1-carboxylate;

tert-butyl 3-(cyanomethyl)-3-[3-(cyclopropylamino)-4-oxo-4,5-dihydro-1H-pyrazolo[4,3-c]pyridin-1-yl]azetidine-1-carboxylate;

tert-butyl 3-(cyanomethyl)-3-(4-oxo-3-((2-(trifluoromethyl)pyridin-4-yl)amino)-4,5-dihydro-1H-pyrazolo[4,3-c]pyridin-1-yl)azetidine-1-carboxylate;

tert-butyl 3-(cyanomethyl)-3-(3((4(methoxycarbonyl)phenyl)amino)-4-oxo-4,5-dihydro-1H-pyrazolo[4,3-c]pyridin-1-yl)azetidine-1-carboxylate;

tert-butyl 3-(cyanomethyl)-3-(3-((4-fluorophenyl)amino)-4-oxo-4,5-dihydro-1H-pyrazolo[4,3-c]pyridin-1-yl)azetidine-1-carboxylate;

tert-butyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

tert-butyl 4-(cyanomethyl)-4-[4-oxo-3-({4-[2,2,2-trifluoro-hydroxyethyl]phenyl}amino)-4,5-dihydro-1H-pyrazolo[4,3-c]pyridin-1-yl]piperidine-1-carboxylate;

tert-butyl 4-(cyanomethyl)-4-{4-oxo-3-[(4-sulfamoylphenyl)amino]-4,5-dihydro-1H-pyrazolo[4,3-c]pyridin-1-yl}piperidine-1-carboxylate;

tert-butyl 4-(cyanomethyl)-4-(4-oxo-3-{[1-oxo-2-(2,2,2-trifluoroethyl)-2,3-dihydro-1H-isoindol-5-yl]amino}-4,5-dihydro-1H-pyrazolo[4,3-c]pyridin-1-yl)piperidine-1-carboxylate;

tert-butyl 4-(cyanomethyl)-3-fluoro-4-(3-{[4-(methylsulfonyl)phenyl]amino}-4-oxo-4,5-dihydro-1H-pyrazolo[4,3-c]pyridin-1-yl)piperidine-1-carboxylate;

tert-butyl 4-(cyanomethyl)-4-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}piperidine-1-carboxylate;

tert-butyl 4-(cyanomethyl)-4-{4-oxo-3-{[4-(pentafluorosulfanyl)phenyl]amino}-4,5-dihydro-1H-pyrazolo[4,3-c]pyridin-1-yl)piperidine-1-carboxylate;

tert-butyl 4-(cyanomethyl)-4-(4-oxo-3-{[4-(trifluoromethyl)phenyl]amino}-4,5-dihydro-1H-pyrazolo[4,3-c]pyridin-1-yl)piperidine-1-carboxylate;

tert-butyl 4-(cyanomethyl)-3-fluoro-4-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}piperidine-1-carboxylate;

tert-butyl 4-(cyanomethyl)-3-methyl-4-(3-{[4-(methylsulfonyl)phenyl]amino}-4-oxo-4,5-dihydro-1H-pyrazolo[4,3-c]pyridin-1-yl)piperidine-1-carboxylate;

tert-butyl 4-(cyanomethyl)-4-(4-oxo-3-((1-oxo-2,3-dihydro-1H-inden-5-yl)amino)-4,5-dihydro-1H-pyrazolo[4,3-c]pyridin-1-yl)piperidine-1- carboxylate;

tert-butyl 4-(cyanomethyl)-4-(3-{[3-(methylsulfonyl)phenyl]amino}-4-oxo-4,5-dihydro-1H-pyrazolo[4,3-c]pyridin-1-yl)piperidine-1-carboxylate;

tert-butyl 4-(cyanomethyl)-3-fluoro-4-(3-{[4-(methylsulfonyl)phenyl]amino}-4-oxo-4,5-dihydro-1H-pyrazolo[4,3-c]pyridin-1-yl)piperidine-1-carboxylate;

tert-butyl 4-(cyanomethyl)-4-(3-{[4-(dimethylsulfamoyl)phenyl]amino}-4-oxo-4,5-dihydro-1H-pyrazolo[4,3-c]pyridin-1-yl)-3-fluoropiperidine-1-carboxylate;

tert-butyl 4-(cyanomethyl)-3-fluoro-4-[4-oxo-3-(phenylamino)-4,5-dihydro-1H-pyrazolo[4,3-c]pyridin-1-yl]piperidine-1-carboxylate;

tert-butyl 4-(cyanomethyl)-3-fluoro-4-[4-oxo-3-({4-[2,2,2-trifluoro-1-hydroxyethyl]phenyl}amino)-4,5-dihydro-1H-pyrazolo[4,3-c]pyridin-1-yl]piperidine-1-carboxylate;

tert-butyl 4-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}-4-(cyanomethyl)-3-fluoropiperidine-1-carboxylate;

tert-butyl 4-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}-4-(cyanomethyl)piperidine-1-carboxylate;

tert-butyl 4-(cyanomethyl)-4-(3-{[1,1-dioxido-2-(2,2,2-trifluoroethyl)-2,3-dihydro-1,2-benzisothiazol-5-yl]amino}-4-oxo-4,5-dihydro-1H-pyrazolo[4,3-c]pyridin-1-yl)-3-fluoropiperidine-1-carboxylate;

tert-butyl 4-(cyanomethyl)-4-(3-((1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)piperidine-1-carboxylate;

2-(4-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-1-(2,2-difluoropropanoyl)piperidin-4-yl)acetonitrile;

2-(3-(4-oxo-3-(phenylamino)-4,5-dihydro-1H-pyrazolo[4,3-c]pyridin-1-yl)tetrahydro-2H-pyran-3-yl)acetonitrile;

4-((1-(3-(cyanomethyl)tetrahydro-2H-pyran-3-yl)-4-oxo-4,5-dihydro-1H-pyrazolo[4,3-c]pyridin-3-yl)amino)-N,N-dimethylbenzenesulfonamide;

2-(3-(3-((4-(methylsulfonyl)phenyl)amino)-4-oxo-4,5-dihydro-1H-pyrazolo[4,3-c]pyridin-1-yl)tetrahydro-2H-pyran-3-yl)acetonitrile;

methyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate;

tert-butyl 5-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-5-(cyanomethyl)tetrahydro-2H-pyran-2-carboxylate;

tert-butyl 5-(cyanomethyl)-5-(3-((4-(N,N-dimethylsulfamoyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)tetrahydro-2H-pyran-2-carboxylate;

tert-butyl 3-(cyanomethyl)-3-(3-{[4-(methylsulfonyl)phenyl]amino}-4-oxo-4,5-dihydro-1H-pyrazolo[4,3-c]pyridin-1-yl)azetidine-1-carboxylate;

tert-butyl 3-(cyanomethyl)-3-{3-[(2-fluoropyridin-4-yl)amino]-4-oxo-4,5-dihydro-1H-pyrazolo[4,3-c]pyridin-1-yl}azetidine-1-carboxylate;

tert-butyl 3-(cyanomethyl)-3-[4-oxo-3-({4-[(trifluoromethyl)sulfonyl]phenyl}amino)-4,5-dihydro-1H-pyrazolo[4,3-c]pyridin-1-yl]azetidine-1-carboxylate;

tert-butyl 4-(cyanomethyl)-4-{3-[(4-fluorophenyl)amino]-4-oxo-4,5-dihydro-1H-pyrazolo[4,3-c]pyridin-1-yl}piperidine-1-carboxylate;

tert-butyl 4-(cyanomethyl)-4-(3-((4-(N,N-dimethylsulfamoyl)-3-methylphenyl)amino)-4-oxo-4,5-dihydro-1H-pyrazolo[4,3-c]pyridin-1-yl)piperidine-1-carboxylate;

tert-butyl 5-(3-((4-1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate;

tert-butyl 5-(cyanomethyl)-5-(4-oxo-3-(phenylamino)-4,5-dihydro-1H-pyrazolo[4,3-c]pyridin-1-yl)tetrahydro-2H-pyran-2-carboxylate;

tert-butyl 5-(cyanomethyl)-5-(3-((2-methyl-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-2-carboxylate;

N-(tert-butyl)-4-((1-(4-(cyanomethyl)-1-(2,2-difluoropropanoyl)piperidin-4-yl)-4-oxo-4,5-dihydro-1H-pyrazolo[4,3-c]pyridin-3-yl)amino)benzenesulfonamide;

2-(1-(2,2-difluoropropanoyl)-4-(3-((4-(isopropylsulfonyl)phenyl)amino)-4-oxo-4,5-dihydro-1H-pyrazolo[4,3-c]pyridin-1-yl)piperidin-4-yl)acetonitrile;

N-(tert-butyl)-4-((1-(4-(cyanomethyl)-1-(2,2-difluoropropanoyl)piperidin-4-yl)-4-oxo-4,5-dihydro-1H-pyrazolo[4,3-c]pyridin-3-yl)amino)-N-methylbenzenesulfonamide;

2-(4-(3-((4-(tert-butylsulfonyl)phenyl)amino)-4-oxo-4,5-dihydro-1H-pyrazolo[4,3-c]pyridin-1-yl)-1-(2,2-difluoropropanoyl)piperidin-4-yl)acetonitrile;

tert-butyl 4-(3-(3,5-bis((1H-pyrazol-1-yl)methyl)phenylamino)-4-oxo-4,5-dihydro-1H-pyrazolo[4,3-c]pyridin-1-yl)-4-(cyanomethyl)piperidine-1-carboxylate;

tert-butyl 4-(cyanomethyl)-4-(3-(3,5-dimethylphenylamino)-4-oxo-4,5-dihydropyrazolo[4,3-c]pyridin-1-yl)piperidine-1-carboxylate;

tert-butyl 4-(3-(3,5-bis((1H-1,2,3-triazol-1-yl)methyl)phenylamino)-4-oxo-4,5-dihydropyrazolo[4,3-c]pyridin-1-yl)-4-(cyanomethyl)piperidine-1-carboxylate;

tert-butyl 4-(3-(3,5-bis((2H-1,2,3-triazol-2-yl)methyl)phenylamino)-4-oxo-4,5-dihydropyrazolo[4,3-c]pyridin-1-yl)-4-(cyanomethyl)piperidine-1-carboxylate;

tert-butyl 4-(3-((1H-1,2,3-triazol-1-yl)methyl)-5-((2H-1,2,3-triazol-2-yl)methyl)phenylamino)-4-oxo-4,5-dihydropyrazolo[4,3-c]pyridin-1-yl)-4-(cyanomethyl)piperidine-1-carboxylate;

tert-butyl 4-(3-(m-toluidino)-4-oxo-4,5-dihydropyrazolo[4,3-c]pyridin-1-yl)-4-(cyanomethyl)piperidine-1-carboxylate;

tert-butyl 4-(cyanomethyl)-4-(3-(isoindolin-5-ylamino)-4-oxo-4,5-dihydropyrazolo[4,3-c]pyridin-1-yl)piperidine-1-carboxylate;

1,1-dioxo-2,3-dihydro-1,2-benzothiazol-5-yl]amino}-4-oxo-1H,4H,5H-pyrazolo[4,3-c]pyridin-1-yl)piperidine-1-carboxylate;

tert-butyl 4-(cyanomethyl)-4-(3-{[2-(cyclopropylmethyl)-1,1-dioxo-2,3-dihydro-1,2-benzothiazol-5-yl]amino}-4-oxo-1H,4H,5H-pyrazolo[4,3-c]pyridin-1-yl)piperidine-1-carboxylate;

tert-butyl 4-(cyanomethyl)-4-{3-[(2-ethyl-1,1-dioxo-2,3-dihydro-1,2-benzothiazol-5-yl)amino]-4-oxo-1H,4H,5H-pyrazolo[4,3-c]pyridin-1-yl}piperidine-1-carboxylate;

methyl 4-(cyanomethyl)-4-(3-[(2-methyl-1,1-dioxo-2,3-dihydro-1,2-benzothiazol-5-yl)amino]-4-oxo-1H,4H,5H-pyrazolo[4,3-c]pyridin-1-yl]piperidine-1-carboxylate;

methyl 4-{3-[(2-tert-butyl-1,1-dioxo-2,3-dihydro-1,2-benzothiazol-5-yl)amino]-4-oxo-1H,4H,5H-pyrazolo[4,3-c]pyridin-1-yl}-4-(cyanomethyl)piperidine-1-carboxylate;

methyl 4-{3-[(2-ethyl-1,1-dioxo-2,3-dihydro-1,2-benzothiazol-5-yl)amino]-4-oxo-1H,4H,5H-pyrazolo[4,3-c]pyridin-1-yl}-4-(cyanomethyl)piperidine-1-carboxylate;

methyl 4-(cyanomethyl)-4-(3-{[2-(2-methylpropyl)-1,1-dioxo-2,3-dihydro-1,2-benzothiazol-5-yl]amino}-4-oxo-1H,4H,5H-pyrazolo[4,3-c]pyridin-1-yl)piperidine-1-carboxylate;

methyl 4-(cyanomethyl)-4-(3-{[2-(cyclopropylmethyl)-1,1-dioxo-2,3-dihydro-1,2-benzothiazol-5-yl]amino}-4-oxo-1H,4H,5H-pyrazolo[4,3-c]pyridin-1-yl)piperidine-1-carboxylate;

methyl 4-(cyanomethyl)-4-(3-{[2-(cyclopentylmethyl)-1,1-dioxo-2,3-dihydro-1,2-benzothiazol-5-yl]amino}-4-oxo-1H,4H,5H-pyrazolo[4,3-c]pyridin-1-yl)piperidine-1-carboxylate;

tert-butyl 4-(cyanomethyl)-4-[4-oxo-3-({4-[(trifluoromethyl)sulfonyl]phenyl}amino)-4,5-dihydro-1H-pyrazolo[4,3-c]pyridin-1-yl]piperidine-1-carboxylate;

tert-butyl 4-(cyanomethyl)-4-(3-{[4-(methylsulfonyl)phenyl]amino}-4-oxo-4,5-dihydro-1H-pyrazolo[4,3-c]pyridin-1-yl)piperidine-1-carboxylate;

tert-butyl 4-(cyanomethyl)-4-{3-[(2-fluoropyridin-4-yl)amino]-4-oxo-4,5-dihydro-1H-pyrazolo[4,3-c]pyridin-1-yl}piperidine-1-carboxylate;

4-(1-(1-(cyanomethyl)cyclohexyl)-4-oxo-4,5-dihydro-1H-pyrazolo[4,3-c]pyridin-3-ylamino)-N,N-dimethylbenzenesulfonamide;

2-(1-(3-((2-(tert-butyl)-1,1-dioxido-2,3-dihydrobenzo[d]
isothiazol-5-yl)amino)-4-oxo-4,5-dihydro-1H-pyrazolo[4,3-c]pyridin-1-yl)cyclohexyl)acetonitrile;
2-(1-(3-((2-methyl-1,1-dioxido-2,3-dihydrobenzo[d]isothiazol-5-yl)amino)-4-oxo-4,5-dihydro-1H-pyrazolo[4,3-c]pyridin-1-yl)cyclohexyl)acetonitrile;
tert-butyl 4-(cyanomethyl)-4-(3-((1,1-dioxido-2,3-dihydrobenzo[b]thiophen-5-yl)amino)-4-oxo-4,5-dihydro-1H-pyrazolo[4,3-c]pyridin-1-yl)piperidine-1-carboxylate;
2-(8-(4-oxo-3-((4-(trifluoromethyl)phenyl)amino)-4,5-dihydro-1H-pyrazolo[4,3-c]pyridin-1-yl)-1,4-dioxaspiro[4.5]decan-8-yl)acetonitrile;
4-({1-[1-(cyanomethyl)-2-fluorocyclohexyl]-4-oxo-4,5-dihydro-1H-pyrazolo[4,3-c]pyridin-3-yl}amino)-N,N-dimethylbenzenesulfonamide;
{2-fluoro-1-[4-oxo-3-({4-[2,2,2-trifluoro-1-hydroxy-1-methylethyl]phenyl}amino)-4,5-dihydro-1H-pyrazolo[4,3-c]pyridin-1-yl]cyclohexyl}acetonitrile
{2-fluoro-1-[3-({4-[(1-methylethyl)sulfonyl]phenyl}amino)-4-oxo-4,5-dihydro-1H-pyrazolo[4,3-c]pyridin-1-yl]cyclohexyl}acetonitrile;
2-(1-(3-((4-(1-amino-2,2,2-trifluoroethyl)phenyl)amino)-4-oxo-4,5-dihydro-1H-pyrazolo[4,3-c]pyridin-1-yl)cyclopentyl)acetonitrile;
tert-butyl 5-(3-((4-(N-(tert-butyl)-N-methylsulfamoyl)phenyl)amino)-4-oxo-4,5-dihydro-1H-pyrazolo[4,3-c]pyridin-1-yl)-5-(cyanomethyl)tetrahydro-2H-pyran-2-carboxylate;
tert-butyl 5-(cyanomethyl)-5-(3-((4-(N-isopropyl-N-methylsulfamoyl)phenyl)amino)-4-oxo-4,5-dihydro-1H-pyrazolo[4,3-c]pyridin-1-yl)tetrahydro-2H-pyran-2-carboxylate;
tert-butyl 5-(cyanomethyl)-5-(3-((4-(N-ethyl-N-methylsulfamoyl)phenyl)amino)-4-oxo-4,5-dihydro-1H-pyrazolo[4,3-c]pyridin-1-yl)tetrahydro-2H-pyran-2-carboxylate;
tert-butyl 5-(cyanomethyl)-5-(3-((1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)tetrahydro-2H-pyran-2-carboxylate;
tert-butyl 5-(cyanomethyl)-5-(3-((4-(N-methylsulfamoyl)phenyl)amino)-4-oxo-4,5-dihydro-1H-pyrazolo[4,3-c]pyridin-1-yl)tetrahydro-2H-pyran-2-carboxylate;
tert-butyl 5-(cyanomethyl)-5-(4-oxo-3-((1-oxo-2-(2,2,2-trifluoroethyl)isoindolin-5-yl)amino)-4,5-dihydro-1H-pyrazolo[4,3-c]pyridin-1-yl)tetrahydro-2H-pyran-2-carboxylate;
tert-butyl 5-(3-((4-((1H-1,2,3-triazol-1-yl)methyl)phenyl)amino)-4-oxo-4,5-dihydro-1H-pyrazolo[4,3-c]pyridin-1-yl)-5-(cyanomethyl)tetrahydro-2H-pyran-2-carboxylate;
tert-butyl 5-(3-((4-((2H-1,2,3-triazol-2-yl)methyl)phenyl)amino)-4-oxo-4,5-dihydro-1H-pyrazolo[4,3-c]pyridin-1-yl)-5-(cyanomethyl)tetrahydro-2H-pyran-2-carboxylate;
tert-butyl 5-(cyanomethyl)-5-(3-((4-(isopropylsulfonyl)phenyl)amino)-4-oxo-4,5-dihydro-1H-pyrazolo[4,3-c]pyridin-1-yl)tetrahydro-2H-pyran-2-carboxylate;
tert-butyl 5-(cyanomethyl)-5-(3-((4-(cyclopropylsulfonyl)phenyl)amino)-4-oxo-4,5-dihydro-1H-pyrazolo[4,3-c]pyridin-1-yl)tetrahydro-2H-pyran-2-carboxylate;
tert-butyl 5-(3-((2-(tert-butyl)-1-oxoisoindolin-5-yl)amino)-4-oxo-4,5-dihydro-1H-pyrazolo[4,3-c]pyridin-1-yl)-5-(cyanomethyl)tetrahydro-2H-pyran-2-carboxylate;
tert-butyl 5-(cyanomethyl)-5-(3-((2-cyclohexyl-1-oxoisoindolin-5-yl)amino)-4-oxo-4,5-dihydro-1H-pyrazolo[4,3-c]pyridin-1-yl)tetrahydro-2H-pyran-2-carboxylate;
tert-butyl 5-(cyanomethyl)-5-(3-((2-cyclopentyl-1-oxoisoindolin-5-yl)amino)-4-oxo-4,5-dihydro-1H-pyrazolo[4,3-c]pyridin-1-yl)tetrahydro-2H-pyran-2-carboxylate;
tert-butyl 5-(3-((4-(1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate;
[3-(3-{[4-(azetidin-1-ylsulfonyl)phenyl]amino}-4-oxo-4,5-dihydro-1H-pyrazolo[4,3-c]pyridin-1-yl)tetrahydro-2H-pyran-3-yl]acetonitrile;
{3-[3-({4-[(3-methylazetidin-1-yl)sulfonyl]phenyl}amino)-4-oxo-4,5-dihydro-1H-pyrazolo[4,3-c]pyridin-1-yl]tetrahydro-2H-pyran-3-yl}acetonitrile;
{3-[3-({4-[(2,2-dimethylpyrrolidin-1-yl)sulfonyl]phenyl}amino)-4-oxo-4,5-dihydro-1H-pyrazolo[4,3-c]pyridin-1-yl]tetrahydro-2H-pyran-3-yl}acetonitrile;
[3-{3-[(4-{[2-methylazetidin-1-yl]sulfonyl}phenyl)amino]-4-oxo-4,5-dihydro-1H-pyrazolo[4,3-c]pyridin-1-yl}tetrahydro-2H-pyran-3-yl]acetonitrile;
{3-[4-oxo-3-({4-[2,2,2-trifluoro-1-hydroxy-1-methylethyl]phenyl}amino)-4,5-dihydro-1H-pyrazolo[4,3-c]pyridin-1-yl]tetrahydro-2H-pyran-3-yl}acetonitrile;
ethyl 3-(4-((1-(3-(cyanomethyl)tetrahydro-2H-pyran-3-yl)-4-oxo-4,5-dihydro-1H-pyrazolo[4,3-c]pyridin-3-yl)amino)phenyl)-4,4,4-trifluoro-3-hydroxy-2,2-dimethylbutanoate;
2-(3-(3-((4-(3-hydroxy-3-(trifluoromethyl)pyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;
2-(3-(3-((4-(3-fluoropyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;
2-(3-(3-((4-(3-methoxypyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;
2-(3-(3-((4-(3-methoxypyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;
2-(3-(3-((3-methyl-4-(morpholine-4-carbonyl)phenyl)amino)-4-oxo-4,5-dihydro-1H-pyrazolo[4,3-c]pyridin-1-yl)tetrahydro-2H-pyran-3-yl)acetonitrile;
2-(3-(3-((1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)tetrahydro-2H-pyran-3-yl)acetonitrile;
2-(1-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)cyclopentyl)acetonitrile;
2-(1-(3-((4-(tert-butylsulfonyl)phenyl)amino)-4-oxo-4,5-dihydro-1H-pyrazolo[4,3-c]pyridin-1-yl)cyclopentyl)acetonitrile;
4-((1-(1-(cyanomethyl)cyclopentyl)-4-oxo-4,5-dihydro-1H-pyrazolo[4,3-c]pyridin-3-yl)amino)-N,N-dimethylbenzenesulfonamide;
4-((1-(1-(cyanomethyl)cyclopentyl)-4-oxo-4,5-dihydro-1H-pyrazolo[4,3-c]pyridin-3-yl)amino)benzonitrile;
2-(1-(4-oxo-3-((1-oxo-1,3-dihydroisobenzofuran-5-yl)amino)-4,5-dihydro-1H-pyrazolo[4,3-c]pyridin-1-yl)cyclopentyl)acetonitrile;

(1-{3-[(3,3-dimethyl-1-oxo-1,3-dihydro-2-benzofuran-5-yl)amino]-4-oxo-4,5-dihydro-1H-pyrazolo[4,3-c]pyridin-1-yl}cyclopentyl)acetonitrile;

tert-butyl 4-((1-(1-(cyanomethyl)cyclopentyl)-4-oxo-4,5-dihydro-1H-pyrazolo[4,3-c]pyridin-3-yl)amino)benzoate;

4-((1-(1-(cyanomethyl)cyclopentyl)-4-oxo-4,5-dihydro-1H-pyrazolo[4,3-c]pyridin-3-yl)amino)-N-methylbenzamide;

2-(1-(3-((2-isopropyl-1-oxoisoindolin-5-yl)amino)-4-oxo-4,5-dihydro-1H-pyrazolo[4,3-c]pyridin-1-yl)cyclopentyl)acetonitrile;

4-((1-(1-(cyanomethyl)cyclopentyl)-4-oxo-4,5-dihydro-1H-pyrazolo[4,3-c]pyridin-3-yl)amino)-N-isopropylbenzenesulfonamide;

4-((1-(1-(cyanomethyl)cyclopentyl)-4-oxo-4,5-dihydro-1H-pyrazolo[4,3-c]pyridin-3-yl)amino)-N-methylbenzenesulfonamide;

2-(1-(3-((4-(azetidin-1-ylsulfonyl)phenyl)amino)-4-oxo-4,5-dihydro-1H-pyrazolo[4,3-c]pyridin-1-yl)cyclopentyl)acetonitrile;

2-(1-(3-((4-(ethylsulfonyl)phenyl)amino)-4-oxo-4,5-dihydro-1H-pyrazolo[4,3-c]pyridin-1-yl)cyclopentyl)acetonitrile;

N-(tert-butyl)-4-((1-(1-(cyanomethyl)cyclopentyl)-4-oxo-4,5-dihydro-1H-pyrazolo[4,3-c]pyridin-3-yl)amino)-N-methylbenzenesulfonamide;

N-(tert-butyl)-4-((1-(1-(cyanomethyl)cyclopentyl)-4-oxo-4,5-dihydro-1H-pyrazolo[4,3-c]pyridin-3-yl)amino)-N-ethylbenzenesulfonamide;

4-((1-(1-(cyanomethyl)cyclopentyl)-4-oxo-4,5-dihydro-1H-pyrazolo[4,3-c]pyridin-3-yl)amino)-N,N-diethylbenzenesulfonamide;

tert-butyl 2-(4-((1-(1-(cyanomethyl)cyclopentyl)-4-oxo-4,5-dihydro-1H-pyrazolo[4,3-c]pyridin-3-yl)amino)-N-methylphenylsulfonamido)-2-methylpropanoate;

2-(1-(4-oxo-3-((1-oxo-2-(2,2,2-trifluoroethyl)isoindolin-5-yl)amino)-4,5-dihydro-1H-pyrazolo[4,3-c]pyridin-1-yl)cyclopentyl)acetonitrile;

ethyl 2-(4-((1-(1-(cyanomethyl)cyclopentyl)-4-oxo-4,5-dihydro-1H-pyrazolo[4,3-c]pyridin-3-yl)amino)-N-methylphenylsulfonamido)-2-methylpropanoate;

tert-butyl 2-(5-((1-(1-(cyanomethyl)cyclopentyl)-4-oxo-4,5-dihydro-1H-pyrazolo[4,3-c]pyridin-3-yl)amino)-1-oxoisoindolin-2-yl)-2-methylpropanoate;

methyl 4-(cyanomethyl)-4-(4-oxo-3-((4-(1,1,1-trifluoro-2-hydroxypropan-2-yl)phenyl)amino)-4,5-dihydro-1H-pyrazolo[4,3-c]pyridin-1-yl)piperidine-1-carboxylate;

methyl 4-(cyanomethyl)-4-(3-((1-hydroxy-1-(trifluoromethyl)-2,3-dihydro-1H-inden-5-yl)amino)-4-oxo-4,5-dihydro-1H-pyrazolo[4,3-c]pyridin-1-yl)piperidine-1-carboxylate;

methyl 4-(cyanomethyl)-4-(3-((4-cyanophenyl)amino)-4-oxo-4,5-dihydro-1H-pyrazolo[4,3-c]pyridin-1-yl)piperidine-1-carboxylate;

methyl 4-(cyanomethyl)-4-(3-((4-fluorophenyl)amino)-4-oxo-4,5-dihydro-1H-pyrazolo[4,3-c]pyridin-1-yl)piperidine-1-carboxylate;

methyl 4-(cyanomethyl)-4-(4-oxo-3-((4-(trifluoromethyl)phenyl)amino)-4,5-dihydro-1H-pyrazolo[4,3-c]pyridin-1-yl)piperidine-1-carboxylate;

methyl 4-(cyanomethyl)-4-(4-oxo-3-(quinolin-6-ylamino)-4,5-dihydro-1H-pyrazolo[4,3-c]pyridin-1-yl)piperidine-1-carboxylate;

methyl 4-(cyanomethyl)-4-(3-((4-(isopropylsulfonyl)phenyl)amino)-4-oxo-4,5-dihydro-1H-pyrazolo[4,3-c]pyridin-1-yl)piperidine-1-carboxylate;

methyl 4-(3-((4-(tert-butylsulfonyl)phenyl)amino)-4-oxo-4,5-dihydro-1H-pyrazolo[4,3-c]pyridin-1-yl)-4-(cyanomethyl)piperidine-1-carboxylate;

2-(2-fluoro-1-(3-((3-methyl-4-(morpholine-4-carbonyl)phenyl)amino)-4-oxo-4,5-dihydro-1H-pyrazolo[4,3-c]pyridin-1-yl)cyclohexyl)acetonitrile;

2-(2-fluoro-1-(3-((2-fluoropyridin-4-yl)amino)-4-oxo-4,5-dihydro-1H-pyrazolo[4,3-c]pyridin-1-yl)cyclohexyl)acetonitrile;

2-(1-(3-((4-(4,4-difluoropiperidine-1-carbonyl)-3-methylphenyl)amino)-4-oxo-4,5-dihydro-1H-pyrazolo[4,3-c]pyridin-1-yl)-2-fluorocyclohexyl)acetonitrile;

2-(2-fluoro-1-(3-((3-methyl-4-(thiomorpholine-4-carbonyl)phenyl)amino)-4-oxo-4,5-dihydro-1H-pyrazolo[4,3-c]pyridin-1-yl)cyclohexyl)acetonitrile;

tert-butyl 5-(cyanomethyl)-5-(3-((3-methyl-4-(thiazolidine-3-carbonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((3-methyl-4-(2-methylthiazolidine-3-carbonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((3-methyl-4-(2-methylthiomorpholine-4-carbonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(3-hydroxy-3-(trifluoromethyl)pyrrolidine-1-carbonyl)-3-methylphenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(1,1,1-trifluoro-2-hydroxy-4-isopropoxy-3,3-dimethyl-4-oxobutan-2-yl)phenyl)amino)-4,5-dihydro-1H-pyrazolo[4,3-c]pyridin-1-yl)tetrahydro-2H-pyran-2-carboxylate;

tert-butyl 5-(cyanomethyl)-5-(3-((1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(1,1,1-trifluoro-2-hydroxy-3,3-dimethylbutan-2-yl)phenyl)amino)-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(2,2,2-trifluoro-1-hydroxyethyl)phenyl)amino)-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(1,1,1-trifluoro-2-hydroxypropan-2-yl)phenyl)amino)-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(1,1,1-trifluoro-2-methoxypropan-2-yl)phenyl)amino)-4,5-dihydro-1H-pyrazolo[4,3-c]pyridin-1-yl)tetrahydro-2H-pyran-2-carboxylate;

{1-[3-({4-[1-(ethylamino)-2,2,2-trifluoroethyl]phenyl}amino)-4-oxo-4,5-dihydro-1H-pyrazolo[4,3-c]pyridin-1-yl]-2-fluorocyclohexyl}acetonitrile;

[2-fluoro-1-{3-[(4-{1-methyl-1-[(1-methylethyl)amino]ethyl}phenyl)amino]-4-oxo-4,5-dihydro-1H-pyrazolo[4,3-c]pyridin-1-yl}cyclohexyl]acetonitrile;

{1-[3-({4-[1-amino-2,2,2-trifluoroethyl]phenyl}amino)-4-oxo-4,5-dihydro-1H-pyrazolo[4,3-c]pyridin-1-yl]-2-fluorocyclohexyl}acetonitrile;

[3-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}tetrahydro-2H-pyran-3-yl]acetonitrile;

{3-[3-({4-[(1-methylethyl)sulfonyl]phenyl}amino)-4-oxo-4,5-dihydro-1H-pyrazolo[4,3-c]pyridin-1-yl]tetrahydro-2H-pyran-3-yl}acetonitrile;

4-({1-[3-(cyanomethyl)-4-fluorotetrahydro-2H-pyran-3-yl]-4-oxo-4,5-dihydro-1H-pyrazolo[4,3-c]pyridin-3-yl}amino)-N,N-dimethylbenzenesulfonamide;

N-tert-butyl-4-({1-[3-(cyanomethyl)tetrahydro-2H-pyran-3-yl]-4-oxo-4,5-dihydro-1H-pyrazolo[4,3-c]pyridin-3-yl}amino)-N-methylbenzenesulfonamide;

[3-(3-{[4-(tert-butylsulfonyl)phenyl]amino}-4-oxo-4,5-dihydro-1H-pyrazolo[4,3-c]pyridin-1-yl)tetrahydro-2H-pyran-3-yl]acetonitrile;

N-tert-butyl-4-({1-[3-(cyanomethyl)tetrahydro-2H-pyran-3-yl]-4-oxo-4,5-dihydro-1H-pyrazolo[4,3-c]pyridin-3-yl}amino)benzenesulfonamide;

tert-butyl[5-({1-[3-(cyanomethyl)tetrahydro-2H-pyran-3-yl]-4-oxo-4,5-dihydro-1H-pyrazolo[4,3-c]pyridin-3-yl}amino)-1,1-dioxido-1,2-benzisothiazol-2(3H)-yl]acetate;

tert-butyl 3-{[4-({1-[3-(cyanomethyl)tetrahydro-2H-pyran-3-yl]-4-oxo-4,5-dihydro-1H-pyrazolo[4,3-c]pyridin-3-yl}amino)phenyl]sulfonyl}-3-methylbutanoate;

{3-[3-({4-[1-amino-2,2,2-trifluoroethyl]phenyl}amino)-4-oxo-4,5-dihydro-1H-pyrazolo[4,3-c]pyridin-1-yl]tetrahydro-2H-pyran-3-yl}acetonitrile;

{3-[3-({4-[1-(tert-butylamino)-2,2,2-trifluoroethyl]phenyl}amino)-4-oxo-4,5-dihydro-1H-pyrazolo[4,3-c]pyridin-1-yl]tetrahydro-2H-pyran-3-yl}acetonitrile;

[3-(3-{[4-(cyclopentylsulfonyl)phenyl]amino}-4-oxo-4,5-dihydro-1H-pyrazolo[4,3-c]pyridin-1-yl)tetrahydro-2H-pyran-3-yl]acetonitrile;

{3-[4-oxo-3-({4-[(1,1,2-trimethylpropyl)sulfonyl]phenyl}amino)-4,5-dihydro-1H-pyrazolo[4,3-c]pyridin-1-yl]tetrahydro-2H-pyran-3-yl}acetonitrile;

[3-(3-{[4-(cyclohexylsulfonyl)phenyl]amino}-4-oxo-4,5-dihydro-1H-pyrazolo[4,3-c]pyridin-1-yl)tetrahydro-2H-pyran-3-yl]acetonitrile;

tert-butyl 5-(3-((4-(1-(tert-butylamino)-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate;

{3-[3-({4-[(1,1-dimethylpropyl)sulfonyl]phenyl}amino)-4-oxo-4,5-dihydro-1H-pyrazolo[4,3-c]pyridin-1-yl]tetrahydro-2H-pyran-3-yl}acetonitrile;

[3-{3-[(2-cyclopentyl-1-oxo-2,3-dihydro-1H-isoindol-5-yl)amino]-4-oxo-4,5-dihydro-1H-pyrazolo[4,3-c]pyridin-1-yl}tetrahydro-2H-pyran-3-yl]acetonitrile;

{3-[4-oxo-3-({4-[2,2,2-trifluoro-1-pyrrolidin-1-ylethyl]phenyl}amino)-4,5-dihydro-1H-pyrazolo[4,3-c]pyridin-1-yl]tetrahydro-2H-pyran-3-yl}acetonitrile;

{3-[4-oxo-3-({4-[1-pyrrolidin-1-ylethyl]phenyl}amino)-4,5-dihydro-1H-pyrazolo[4,3-c]pyridin-1-yl]tetrahydro-2H-pyran-3-yl}acetonitrile;

{3-[3-({4-[(2,2-dimethylcyclopentyl)sulfonyl]phenyl}amino)-4-oxo-4,5-dihydro-1H-pyrazolo[4,3-c]pyridin-1-yl]tetrahydro-2H-pyran-3-yl}acetonitrile;

tert-butyl 5-(cyanomethyl)-5-(3-((4-(morpholinosulfonyl)phenyl)amino)-4-oxo-4,5-dihydro-1H-pyrazolo[4,3-c]pyridin-1-yl)tetrahydro-2H-pyran-2-carboxylate;

[3-(3-{[4-(morpholin-4-ylsulfonyl)phenyl]amino}-4-oxo-4,5-dihydro-1H-pyrazolo[4,3-c]pyridin-1-yl)tetrahydro-2H-pyran-3-yl]acetonitrile;

[3-{4-oxo-3-[(4-{2,2,2-trifluoro-1-[(1-methylethyl)amino]ethyl}phenyl)amino]-4,5-dihydro-1H-pyrazolo[4,3-c]pyridin-1-yl}tetrahydro-2H-pyran-3-yl]acetonitrile;

tert-butyl 5-(cyanomethyl)-5-(3-((4-(1-(ethylamino)-2,2,2-trifluoroethyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(2,2,2-trifluoro-1-(isopropylamino)ethyl)phenyl)amino)-4,5-dihydro-1H-pyrazolo[4,3-c]pyridin-1-yl)tetrahydro-2H-pyran-2-carboxylate;

tert-butyl 5-(cyanomethyl)-5-(3-((4-(1-(pyrrolidin-1-yl)ethyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(1-(dimethylamino)-2,2,2-trifluoroethyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(4-oxo-3-(quinolin-6-ylamino)-4,5-dihydro-1H-pyrazolo[4,3-c]pyridin-1-yl)tetrahydro-2H-pyran-2-carboxylate;

tert-butyl 5-(cyanomethyl)-5-(3-((2-cyanoquinolin-6-yl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((2-methylquinolin-6-yl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(3,5-dimethyl-1H-pyrazol-1-yl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((3-methyl-4-(1H-pyrazol-1-yl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(2,2-dimethylmorpholine-4-carbonyl)-3-methylphenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(4-oxo-3-(quinolin-3-ylamino)-4,5-dihydro-1H-pyrazolo[4,3-c]pyridin-1-yl)tetrahydro-2H-pyran-2-carboxylate;

tert-butyl 5-(cyanomethyl)-5-(3-((2-(dimethylamino)quinolin-6-yl)amino)-4-oxo-4,5-dihydro-1H-pyrazolo[4,3-c]pyridin-1-yl)tetrahydro-2H-pyran-2-carboxylate;

tert-butyl 5-(3-((2-carbamoylquinolin-6-yl)amino)-4-oxo-4,5-dihydro-1H-pyrazolo[4,3-c]pyridin-1-yl)-5-(cyanomethyl)tetrahydro-2H-pyran-2-carboxylate;

2-(3-(4-oxo-3-((4-(1-(trifluoromethyl)cyclopropyl)phenyl)amino)-4,5-dihydro-1H-pyrazolo[4,3-c]pyridin-1-yl)tetrahydro-2H-pyran-3-yl)acetonitrile;

2-(3-(3-((2-(dimethylamino)quinolin-6-yl)amino)-4-oxo-4,5-dihydro-1H-pyrazolo[4,3-c]pyridin-1-yl)tetrahydro-2H-pyran-3-yl)acetonitrile;

2-(3-(3-((2-methylquinolin-6-yl)amino)-4-oxo-4,5-dihydro-1H-pyrazolo[4,3-c]pyridin-1-yl)tetrahydro-2H-pyran-3-yl)acetonitrile;

tert-butyl 5-(cyanomethyl)-5-(3-((2-morpholinoquinolin-6-yl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((2-(2-methylmorpholino)quinolin-6-yl)amino)-4-oxo-4,5-dihydro-1H-pyrazolo[4,3-c]pyridin-1-yl)tetrahydro-2H-pyran-2-carboxylate;

tert-butyl 5-(3-((2-(8-oxa-3-azabicyclo[3.2.1]octan-3-yl) quinolin-6-yl)amino)-4-oxo-4,5-dihydro-1H-pyrazolo [4,3-c]pyridin-1-yl)-5-(cyanomethyl)tetrahydro-2H-pyran-2-carboxylate;

tert-butyl 5-(cyanomethyl)-5-(4-oxo-3-((4-(propan-2-yl-sulfonimidoyl)phenyl)amino)-4,5-dihydro-1H-pyrazolo[4,3-c]pyridin-1-yl)tetrahydro-2H-pyran-2-carboxylate;

2-(3-(4-oxo-3-((4-(propan-2-ylsulfonimidoyl)phenyl) amino)-4,5-dihydro-1H-pyrazolo[4,3-c]pyridin-1-yl) tetrahydro-2H-pyran-3-yl)acetonitrile;

4-({1-[1-(cyanomethyl)-2-fluorocyclohexyl]-4-oxo-4,5-dihydro-1H-pyrazolo[4,3-c]pyridin-3-yl}amino)-N,N-dimethylbenzenesulfonamide;

tert-butyl 5-(3-((4-(tert-butylsulfonyl)phenyl)amino)-4-oxo-4,5-dihydro-1H-pyrazolo[4,3-c]pyridin-1-yl)-5-(cyanomethyl)tetrahydro-2H-pyran-2-carboxylate;

tert-butyl 5-(cyanomethyl)-5-(3-((4-(cyclopropylsulfo-nyl)phenyl)amino)-4-oxo-4,5-dihydro-1H-pyrazolo[4, 3-c]pyridin-1-yl)tetrahydro-2H-pyran-2-carboxylate;

tert-butyl 5-(cyanomethyl)-5-(3-((4-(isopropylsulfonyl) phenyl)amino)-4-oxo-4,5-dihydro-1H-pyrazolo[4,3-c] pyridin-1-yl)tetrahydro-2H-pyran-2-carboxylate;

tert-butyl 5-(cyanomethyl)-5-(3-((2-(dimethylcarbamoyl) quinolin-6-yl)amino)-4-oxo-4,5-dihydro-1H-pyrazolo [4,3-c]pyridin-1-yl)tetrahydro-2H-pyran-2-carboxylate;

4-({1-[3-(cyanomethyl)tetrahydrofuran-3-yl]-4-oxo-4,5-dihydro-1H-pyrazolo[4,3-c]pyridin-3-yl}amino)benzonitrile;

[3-{3-[(4-chlorophenyl)amino]-4-oxo-4,5-dihydro-1H-pyrazolo[4,3-c]pyridin-1-yl}tetrahydrofuran-3-yl]acetonitrile;

[3-{3-[(4-chloro-8-fluoroquinolin-6-yl)amino]-4-oxo-4, 5-dihydro-1H-pyrazolo[4,3-c]pyridin-1-yl}tetrahydrofuran-3-yl]acetonitrile;

[3-{3-[(4-fluoroquinolin-6-yl)amino]-4-oxo-4,5-dihydro-1H-pyrazolo[4,3-c]pyridin-1-yl}tetrahydrofuran-3-yl] acetonitrile;

2-(3-(3-((2-(tert-butyl)-1,1-dioxido-2,3-dihydrobenzo[d] isothiazol-5-yl)amino)-4-oxo-4,5-dihydro-1H-pyrazolo[4,3-c]pyridin-1-yl)tetrahydrofuran-3-yl)acetonitrile;

2-(3-(3-((4-(tert-butylsulfonyl)phenyl)amino)-4-oxo-4,5-dihydro-1H-pyrazolo[4,3-c]pyridin-1-yl)tetrahydrofuran-3-yl)acetonitrile;

2-(4-(3-((2-(tert-butyl)-1,1-dioxido-2,3-dihydrobenzo[d] isothiazol-5-yl)amino)-4-oxo-4,5-dihydro-1H-pyrazolo[4,3-c]pyridin-1-yl)tetrahydro-2H-pyran-4-yl)acetonitrile;

2-(4-(3-((4-(tert-butylsulfonyl)phenyl)amino)-4-oxo-4,5-dihydro-1H-pyrazolo[4,3-c]pyridin-1-yl)tetrahydro-2H-pyran-4-yl)acetonitrile;

N-(tert-butyl)-4-(((1-(4-(cyanomethyl)tetrahydro-2H-pyran-4-yl)-4-oxo-4,5-dihydro-1H-pyrazolo[4,3-c] pyridin-3-yl)amino)-N-methylbenzenesulfonamide;

4-(((1-(4-(cyanomethyl)tetrahydro-2H-pyran-4-yl)-4-oxo-4,5-dihydro-1H-pyrazolo[4,3-c]pyridin-3-yl)amino)-N,N-dimethylbenzenesulfonamide;

2-(4-(3-((2-(tert-butyl)-1,1-dioxido-2,3-dihydrobenzo[d] isothiazol-5-yl)amino)-4-oxo-4,5-dihydro-1H-pyrazolo[4,3-c]pyridin-1-yl)-3-fluorotetrahydro-2H-pyran-4-yl)acetonitrile;

2-(3-fluoro-4-(3-(3-methyl-4-(morpholine-4-carbonyl) phenylamino)-4-oxo-4,5-dihydropyrazolo[4,3-c]pyridin-1-yl)-tetrahydro-2H-pyran-4-yl)acetonitrile;

2-(4-(3-((2-(tert-butyl)-1-oxoisoindolin-5-yl)amino)-4-oxo-4,5-dihydro-1H-pyrazolo[4,3-c]pyridin-1-yl)-3-fluorotetrahydro-2H-pyran-4-yl)acetonitrile;

2-(3-fluoro-4-(3-(3-methyl-4-(thiomorpholine-4-carbonyl)phenylamino)-4-oxo-4,5-dihydropyrazolo[4,3-c] pyridin-1-yl)-tetrahydro-2H-pyran-4-yl)acetonitrile;

2-(3-fluoro-4-(4-oxo-3-((4-(2-(trifluoromethyl)piperidin-2-yl)phenyl)amino)-4,5-dihydro-1H-pyrazolo[4,3-c] pyridin-1-yl)tetrahydro-2H-pyran-4-yl)acetonitrile;

2-(4-(3-((4-(1-(tert-butylamino)-2,2,2-trifluoroethyl)phenyl)amino)-4-oxo-4,5-dihydro-1H-pyrazolo[4,3-c] pyridin-1-yl)-3-fluorotetrahydro-2H-pyran-4-yl)acetonitrile;

2-[4-(3-{[1,1-dioxo-2-(piperidin-4-yl)-3H-1,2-benzothiazol-5-yl]amino}-4-oxo-5H-pyrazolo[4,3-c]pyridin-1-yl)-3-fluorooxan-4-yl]acetonitrile;

tert-butyl 4-(cyanomethyl)-3-fluoro-4-{3-[(4-{1-methyl-1-[(1-methylethyl)amino]ethyl}phenyl)amino]-4-oxo-4,5-dihydro-1H-pyrazolo[4,3-c]pyridin-1-yl}piperidine-1-carboxylate;

tert-butyl 5-(cyanomethyl)-5-(3-((4-(2-(isopropylamino) propan-2-yl)phenyl)amino)-4-oxo-4,5-dihydro-1H-pyrazolo[4,3-c]pyridin-1-yl)tetrahydro-2H-pyran-2-carboxylate;

tert-butyl 4-(cyanomethyl)-3-fluoro-4-(3-{[4-(1-methoxyethyl)phenyl]amino}-4-oxo-4,5-dihydro-1H-pyrazolo[4,3-c]pyridin-1-yl)piperidine-1-carboxylate;

tert-butyl 4-(cyanomethyl)-4-{3-[(4-{1-methyl-1-[(1-methylethyl)amino]ethyl}phenyl)amino]-4-oxo-4,5-dihydro-1H-pyrazolo[4,3-c]pyridin-1-yl}piperidine-1-carboxylate;

2-(4-(3-((1,1-dioxido-2-(1-(2,2,2-trifluoroethyl)piperidin-4-yl)-2,3-dihydrobenzo[d]isothiazol-5-yl)amino)-4-oxo-4,5-dihydro-1H-pyrazolo[4,3-c]pyridin-1-yl)-3-fluorotetrahydro-2H-pyran-4-yl)acetonitrile;

tert-butyl 4-(cyanomethyl)-3-fluoro-4-(3-((3-methyl-4-(thiomorpholine-4-carbonyl)phenyl)amino)-4-oxo-4,5-dihydro-1H-pyrazolo[4,3-c]pyridin-1-yl)piperidine-1-carboxylate;

tert-butyl 4-(3-((4-(1-benzyl-3-(trifluoromethyl)pyrrolidin-3-yl)phenyl)amino)-4-oxo-4,5-dihydro-1H-pyrazolo[4,3-c]pyridin-1-yl)-4-(cyanomethyl)piperidine-1-carboxylate;

tert-butyl 4-(cyanomethyl)-4-(4-oxo-3-((4-(3-(trifluoromethyl)pyrrolidin-3-yl)phenyl)amino)-4,5-dihydro-1H-pyrazolo[4,3-c]pyridin-1-yl)piperidine-1-carboxylate;

tert-butyl 5-(cyanomethyl)-5-(4-oxo-3-((4-(3-(trifluoromethyl)pyrrolidin-3-yl)phenyl)amino)-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(2-(trifluoromethyl)piperidin-2-yl)phenyl)amino)-4,5-dihydro-1H-pyrazolo[4,3-c]pyridin-1-yl)tetrahydro-2H-pyran-2-carboxylate;

tert-butyl 4-(cyanomethyl)-4-(4-oxo-3-((4-(((2,2,2-trifluoroethyl)amino)methyl)phenyl)amino)-4,5-dihydro-1H-pyrazolo[4,3-c]pyridin-1-yl)piperidine-1-carboxylate;

tert-butyl 4-(cyanomethyl)-4-(3-((4-(N-isopropylsulfamoyl)phenyl)amino)-4-oxo-4,5-dihydro-1H-pyrazolo [4,3-c]pyridin-1-yl)piperidine-1-carboxylate;

tert-butyl 4-(3-((4-(N-benzylsulfamoyl)phenyl)amino)-4-oxo-4,5-dihydro-1H-pyrazolo[4,3-c]pyridin-1-yl)-4-(cyanomethyl)piperidine-1-carboxylate;

tert-butyl 4-(cyanomethyl)-4-(3-((4-(N-(cyclopropylmethyl)sulfamoyl)phenyl)amino)-4-oxo-4,5-dihydro-1H-pyrazolo[4,3-c]pyridin-1-yl)piperidine-1-carboxylate;

tert-butyl 4-(cyanomethyl)-4-(3-((4-(N-(2-methoxyethyl)sulfamoyl)phenyl)amino)-4-oxo-4,5-dihydro-1H-pyrazolo[4,3-c]pyridin-1-yl)piperidine-1-carboxylate;

tert-butyl 4-(cyanomethyl)-4-(3-((4-(N-cyclohexylsulfamoyl)phenyl)amino)-4-oxo-4,5-dihydro-1H-pyrazolo[4,3-c]pyridin-1-yl)piperidine-1-carboxylate;

tert-butyl 4-(cyanomethyl)-4-(4-oxo-3-((4-(piperidin-1-ylsulfonyl)phenyl)amino)-4,5-dihydro-1H-pyrazolo[4,3-c]pyridin-1-yl)piperidine-1- carboxylate;

tert-butyl 4-(cyanomethyl)-4-(3-((4-(morpholinosulfonyl)phenyl)amino)-4-oxo-4,5-dihydro-1H-pyrazolo[4,3-c]pyridin-1-yl)piperidine-1-carboxylate;

tert-butyl 4-(cyanomethyl)-4-(3-((3-fluoro-4-(N-isopropylsulfamoyl)phenyl)amino)-4-oxo-4,5-dihydro-1H-pyrazolo[4,3-c]pyridin-1-yl)piperidine-1-carboxylate;

tert-butyl 4-(cyanomethyl)-4-(3-((4-(N-(cyclopropylmethyl)sulfamoyl)-3-fluorophenyl)amino)-4-oxo-4,5-dihydro-1H-pyrazolo[4,3-c]pyridin-1-yl)piperidine-1-carboxylate;

(4-{3-[(4-fluorophenyl)amino]-4-oxo-4,5-dihydro-1H-pyrazolo[4,3-c]pyridin-1-yl}piperidin-4-yl)acetonitrile;

[1-(cyclopropylcarbonyl)-4-{3-[(4-fluorophenyl)amino]-4-oxo-4,5-dihydro-1H-pyrazolo[4,3-c]pyridin-1-yl}piperidin-4-yl]acetonitrile;

4-({1-[1-benzyl-4-(cyanomethyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(4-methylbenzyl)piperidin-4-yl]-4-oxo-4,5-dihydro-1H-pyrazolo[4,3-c]pyridin-3-yl}amino)-N,N-dimethylbenzenesulfonamide;

4-[(1-{4-(cyanomethyl)-1-[4-(trifluoromethyl)benzyl]piperidin-4-yl}-4-oxo-4,5-dihydro-1H-pyrazolo[4,3-c]pyridin-3-yl)amino]-N,N-dimethylbenzenesulfonamide;

4-[(1-{4-(cyanomethyl)-1-[4-(1-methylethyl)benzyl]piperidin-4-yl}-4-oxo-4,5-dihydro-1H-pyrazolo[4,3-c]pyridin-3-yl)amino]-N,N-dimethylbenzenesulfonamide;

4-[(1-{4-(cyanomethyl)-1-[4-(1-methylethyl)benzyl]piperidin-4-yl}-4-oxo-4,5-dihydro-1H-pyrazolo[4,3-c]pyridin-3-yl)amino]-N,N-dimethylbenzene sulfonamide;

4-[(1-{4-(cyanomethyl)-1-[4-(1methylethoxy)benzyl]piperidin-4-yl}-4-oxo-4,5-dihydro-1H-pyrazolo[4,3-c]pyridin-3-yl)amino]-N,N-dimethylbenzene sulfonamide;

4-({1-[4-(cyanomethyl)-1-(4-fluorobenzyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(3-fluorobenzyl)piperidin-4-yl]-4-oxo-4,5-dihydro-1H-pyrazolo[4,3-c]pyridin-3-yl}amino)-N,N-dimethylbenzene sulfonamide;

4-({1-[4-(cyanomethyl)-1-(2-fluorobenzyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(2,6-difluorobenzyl)piperidin-4-yl]-4-oxo-4,5-dihydro-1H-pyrazolo[4,3-c]pyridin-3-yl}amino)-N,N-dimethylbenzene sulfonamide;

4-({1-[4-(cyanomethyl)-1-(2,3,6-trifluorobenzyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(1,3-oxazol-2-ylmethyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(4-isoxazol-3-ylbenzyl)piperidin-4-yl]-4-oxo-4,5-dihydro-1H-pyrazolo[4,3-c]pyridin-3-yl}amino)-N,N-dimethylbenzenesulfonamide;

4-[(1-{4-(cyanomethyl)-1-[4-(2-oxopyrrolidin-1-yl)benzyl]piperidin-4-yl}-4-oxo-4,5-dihydro-1H-pyrazolo[4,3-c]pyridin-3- yl)amino]-N,N-dimethylbenzenesulfonamide;

4-({1-[4-(cyanomethyl)-1-(3-phenylpropyl)piperidin-4-yl]-4-oxo-4,5-dihydro-1H-pyrazolo[4,3-c]pyridin-3-yl}amino)-N,N-dimethylbenzene sulfonamide;

4-({1-[4-(cyanomethyl)-1-(1H-indol-4-ylmethyl)piperidin-4-yl]-4-oxo-4,5-dihydro-1H-pyrazolo[4,3-c]pyridin-3-yl}amino)-N,N-dimethylbenzenesulfonamide;

4-((1-(4-(cyanomethyl)-1-(1-(2,6-difluorophenyl)ethyl)piperidin-4-yl)-4-oxo-4,5-dihydro-1H-pyrazolo[4,3-c]pyridin-3-yl)amino)-N,N-dimethylbenzenesulfonamide;

4-((1-(4-(cyanomethyl)-1-phenethylpiperidin-4-yl)-4-oxo-4,5-dihydro-1H-pyrazolo[4,3-c]pyridin-3-yl)amino)-N,N-dimethylbenzenesulfonamide;

3-({1-[4-(cyanomethyl)-1-(pyridin-3-ylmethyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-propanoylpiperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(3,3,3-trifluoropropanoyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(methoxyacetyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(N,N-dimethylglycyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(2,2-dimethylpropanoyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(cyclopropylcarbonyl)piperidin-4-yl]-4-oxo-4,5-dihydro-1H-pyrazolo[4,3-c]pyridin-3-yl}amino)-N,N-dimethylbenzenesulfonamide;

4-[(1-{4-(cyanomethyl)-1-[(3,3-difluorocyclobutyl)carbonyl]piperidin-4-yl}-4-oxo-4,5-dihydro-1H-pyrazolo[4,3-c]pyridin-3-yl)amino]-N,N-dimethylbenzenesulfonamide;

4-({1-[4-(cyanomethyl)-1-(cyclohexylcarbonyl)piperidin-4-yl]-4-oxo-4,5-dihydro-1H-pyrazolo[4,3-c]pyridin-3-yl}amino)-N,N-dimethylbenzenesulfonamide;

4-[(1-{4-(cyanomethyl)-1-[tricyclo[3.3.1.1ature,7]dec-1-ylcarbonyl]piperidin-4-yl}-4-oxo-4,5-dihydro-1H-pyrazolo[4,3-c]pyridin-3-yl)amino]-N,N-dimethylbenzenesulfonamide;

4-({1-[4-(cyanomethyl)-1-(cyclopropylacetyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(3-cyclopropylpropanoyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(phenylcarbonyl)piperidin-4-yl]-4-oxo-4,5-dihydro-1H-pyrazolo[4,3-c]pyridin-3-yl}amino)-N,N-dimethylbenzenesulfonamide;

4-[(1-{1-[(4-chlorophenyl)carbonyl]-4-(cyanomethyl)piperidin-4-yl}-4-oxo-4,5-dihydro-1H-pyrazolo[4,3-c]pyridin-3-yl)amino]-N,N-dimethylbenzenesulfonamide;

4-[(1-{1-[(3-chlorophenyl)carbonyl]-4-(cyanomethyl)piperidin-4-yl}-4-oxo-4,5-dihydro-1H-pyrazolo[4,3-c]pyridin-3-yl)amino]-N,N-dimethylbenzenesulfonamide;

4-[(1-{1-[(2-chlorophenyl)carbonyl]-4-(cyanomethyl)piperidin-4-yl}-4-oxo-4,5-dihydro-1H-pyrazolo[4,3-c]pyridin-3-yl)amino]-N,N-dimethylbenzenesulfonamide;

4-({1-[4-(cyanomethyl)-1-{[4-(trifluoromethyl)phenyl]acetyl}piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(3-phenylpropanoyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(2,3-dihydro-1H-inden-2-ylcarbonyl)piperidin-4-yl]-4-oxo-4,5-dihydro-1H-pyrazolo[4,3-c]pyridin-3-yl}amino)-N,N-dimethylbenzenesulfonamide;

4-[(1-{4-(cyanomethyl)-1-[(2-oxopyrrolidin-1-yl)acetyl]piperidin-4-yl}-4-oxo-4,5-dihydro-1H-pyrazolo[4,3-c]pyridin-3-yl)amino]-N,N-dimethylbenzenesulfonamide;

4-({1-[4-(cyanomethyl)-1-(tetrahydro-2H-pyran-4-ylcarbonyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(4,4,4-trifluorobutanoyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(3-cyanopropanoyl)piperidin-4-yl]-4-oxo-4,5-dihydro-1H-pyrazolo[4,3-c]pyridin-3-yl}amino)-N,N-dimethylbenzenesulfonamide;

4-({1-[4-(cyanomethyl)-1-(3,3-dimethylbutanoyl)piperidin-4-yl]-4-oxo-4,5-dihydro-1H-pyrazolo[4,3-c]pyridin-3-yl}amino)-N,N-dimethylbenzenesulfonamide;

4-((1-(4-(cyanomethyl)-1-(2-(methylthio)propanoyl)piperidin-4-yl)-4-oxo-4,5-dihydro-1H-pyrazolo[4,3-c]pyridin-3-yl)amino)-N,N-dimethylbenzenesulfonamide;

4-((1-(1-(2-cyanoacetyl)-4-(cyanomethyl)piperidin-4-yl)-4-oxo-4,5-dihydro-1H-pyrazolo[4,3-c]pyridin-3-yl)amino)-N,N-dimethylbenzenesulfonamide;

methyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

phenyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

4-fluorophenyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

neopentyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

ethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

isopropyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

methyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

2-methylcyclopentyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

2-(methylthio)ethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

tetrahydro-2H-thiopyran-4-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

1-methoxypropan-2-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

tetrahydrofuran-3-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

tetrahydro-2H-pyran-4-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

1,1,1-trifluoropropan-2-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

1-(pyridin-2-yl)ethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

1-cyanoethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

tetrahydrofuran-3-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

2,2,2-trifluoroethyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

isopropyl-4-(cyanomethyl)-4-(3-(2-fluoropyridin-4-ylamino)-4-oxo-4,5-dihydropyrazolo[4,3-c]pyridin-1-yl)piperidine-1-carboxylate;

methyl 4-(cyanomethyl)-4-(3-(2-fluoropyridin-4-ylamino)-4-oxo-4,5-dihydropyrazolo[4,3-c]pyridin-1-yl)piperidine-1-carboxylate;

4-((1-(4-(cyanomethyl)-1-((2,2,2-trifluoroethyl)sulfonyl)piperidin-4-yl)-4-oxo-4,5-dihydro-1H-pyrazolo[4,3-c]pyridin-3-yl)amino)-N,N-dimethylbenzenesulfonamide;

4-((1-(4-(cyanomethyl)-1-(cyclopropylsulfonyl)piperidin-4-yl)-4-oxo-4,5-dihydro-1H-pyrazolo[4,3-c]pyridin-3-yl)amino)-N,N-dimethylbenzenesulfonamide;

2-(4-(3-((4-(methylsulfonyl)phenyl)amino)-4-oxo-4,5-dihydro-1H-pyrazolo[4,3-c]pyridin-1-yl)-1-(4-(trifluoromethyl)pyridin-2-yl)piperidin-4-yl)acetonitrile;

6-(4-(cyanomethyl)-4-(3-((4(methylsulfonyl)phenyl)amino)-4-oxo-4,5-dihydro-1H-pyrazolo[4,3-c]pyridin-1-yl)piperidin-1-yl)nicotinonitrile;

6-(4-(cyanomethyl)-4-(3-((4((difluoromethyl)sulfonyl)phenyl)amino)-4-oxo-4,5-dihydro-1H-pyrazolo[4,3-c]pyridin-1-yl)piperidin-1-yl)nicotinonitrile;

2-(4-(3-((4-(methylsulfonyl)phenyl)amino)-4-oxo-4,5-di-hydro-1H-pyrazolo[4,3-c]pyridin-1-yl)-1-(5(trifluo-romethyl)pyridin-2-yl)piperidin-4-yl)acetonitrile;

6-(4-(cyanomethyl)-4-(3-((3-methyl-4-(thiomorpholine-4-carbonyl)phenyl)amino)-4-oxo-4,5-dihydro-1H-pyrazolo[4,3-c]pyridin-1-yl)piperidin-1-yl)nicotinonitrile;

6-((3R,4R)-4-(cyanomethyl)-3-fluoro-4-(3-((3-methyl-4-(thiomorpholine-4-carbonyl)phenyl)amino)-4-oxo-4,5-dihydro-1H-pyrazolo[4,3-c]pyridin-1-yl)piperidin-1-yl)nicotinonitrile;

2-(1-(5-iodopyridin-2-yl)-4-(3-((4-(methylsulfonyl)phe-nyl)amino)-4-oxo-4,5-dihydro-1H-pyrazolo[4,3-c]pyridin-1-yl)piperidin-4-yl)acetonitrile;

2-(1-(5-bromopyridin-2-yl)-4-(3-((4-(methylsulfonyl)phenyl)amino)-4-oxo-4,5-dihydro-1H-pyrazolo[4,3-c]pyridin-1-yl)piperidin-4-yl)acetonitrile;

2-(4-(3-(3-methyl-4-(thiomorpholine-4-carbonyl)phe-nylamino)-4-oxo-4,5-dihydropyrazolo[4,3-c]pyridin-1-yl)-1-(4-(trifluoromethyl)pyridin-2-yl)piperidin-4-yl)acetonitrile;

(R or S)-2-(4-(4-oxo-3-(4-(2,2,2-trifluoro-1-hydroxy-ethyl)phenylamino)-4,5-dihydropyrazolo[4,3-c]pyri-din-1-yl)-1-(4-(trifluoromethyl)pyridin-2-yl)piperidin-4-yl)acetonitrile;

2-(4-(3-(4-(4,4-difluoropiperidine-1-carbonyl)-3-methyl-phenylamino)-4-oxo-4,5-dihydropyrazolo[4,3-c]pyri-din-1-yl)-1-(4-(trifluoromethyl)pyridin-2-yl)piperidin-4-yl)acetonitrile;

2-(1-(2,2-difluoropropanoyl)-4-(3-((4-(methylsulfonyl)phenyl)amino)-4-oxo-4,5-dihydro-1H-pyrazolo[4,3-c]pyridin-1-yl)piperidin-4-yl)acetonitrile;

2-(4-(3-fluoroazetidin-1-yl)-1-(4-oxo-3-((4-(trifluorom-ethyl)phenyl)amino)-4,5-dihydro-1H-pyrazolo[4,3-c]pyridin-1-yl)cyclohexyl)acetonitrile;

2-(1-(4-oxo-3-((4-(trifluoromethyl)phenyl)amino)-4,5-dihydro-1H-pyrazolo[4,3-c]pyridin-1-yl)-4-(phe-nylamino)cyclohexyl)acetonitrile;

2-(4-hydroxy-1-(4-oxo-3-((4-(trifluoromethyl)phenyl)amino)-4,5-dihydro-1H-pyrazolo[4,3-c]pyridin-1-yl)cyclohexyl)acetonitrile;

2-(1-(3-((4-chlorophenyl)amino)-4-oxo-4,5-dihydro-1H-pyrazolo[4,3-c]pyridin-1-yl)-4-(3-fluoroazetidin-1-yl)cyclohexyl)acetonitrile;

2-(1-(3-((4-chlorophenyl)amino)-4-oxo-4,5-dihydro-1H-pyrazolo[4,3-c]pyridin-1-yl)-4-(3-methoxyazetidin-1-yl)cyclohexyl)acetonitrile;

2-(1-(3-((4-chlorophenyl)amino)-4-oxo-4,5-dihydro-1H-pyrazolo[4,3-c]pyridin-1-yl)-4-((2,2,2-trifluoroethyl)amino)cyclohexyl)acetonitrile;

2-(1-(3-((4-chlorophenyl)amino)-4-oxo-4,5-dihydro-1H-pyrazolo[4,3-c]pyridin-1-yl)-4-hydroxycyclohexyl)ac-etonitrile;

2-(1-(3-((4-chlorophenyl)amino)-4-oxo-4,5-dihydro-1H-pyrazolo[4,3-c]pyridin-1-yl)-4-(phenylamino)cyclo-hexyl)acetonitrile;

2-(4-(3-methoxyazetidin-1-yl)-1-(4-oxo-3-((4-(trifluo-romethoxy)phenyl)amino)-4,5-dihydro-1H-pyrazolo[4,3-c]pyridin-1-yl)cyclohexyl)acetonitrile;

2-(1-(4-oxo-3-((4-(trifluoromethoxy)phenyl)amino)-4,5-dihydro-1H-pyrazolo[4,3-c]pyridin-1-yl)-4-(phe-nylamino)cyclohexyl)acetonitrile;

2-(4-(cyclohexylamino)-1-(4-oxo-3-((4-(trifluo-romethoxy)phenyl)amino)-4,5-dihydro-1H-pyrazolo[4,3-c]pyridin-1-yl)cyclohexyl)acetonitrile;

2-(1-(3-((4-chloro-3-fluorophenyl)amino)-4-oxo-4,5-di-hydro-1H-pyrazolo[4,3-c]pyridin-1-yl)-4-(cyclohexy-lamino)cyclohexyl)acetonitrile;

2-(1-(3-((4-chloro-3-fluorophenyl)amino)-4-oxo-4,5-di-hydro-1H-pyrazolo[4,3-c]pyridin-1-yl)-4-(3-methoxyazetidin-1-yl)cyclohexyl)acetonitrile;

2-(1-(3-((4-chloro-3-fluorophenyl)amino)-4-oxo-4,5-di-hydro-1H-pyrazolo[4,3-c]pyridin-1-yl)-4-(phe-nylamino)cyclohexyl)acetonitrile;

2-(1-(3-((4-((difluoromethyl)sulfonyl)phenyl)amino)-4-oxo-4,5-dihydro-1H-pyrazolo[4,3-c]pyridin-1-yl)-4-(3-fluoroazetidin-1-yl)cyclohexyl)acetonitrile;

4-((1-(1-(cyanomethyl)-4-(3-fluoroazetidin-1-yl)cyclo-hexyl)-4-oxo-4,5-dihydro-1H-pyrazolo[4,3-c]pyridin-3-yl)amino)-N,N-dimethylbenzenesulfonamide;

2-(4-(3-fluoroazetidin-1-yl)-1-(3-((2-methyl-1,1-dioxido-2,3-dihydrobenzo[d]isothiazol-6-yl)amino)-4-oxo-4,5-dihydro-1H-pyrazolo[4,3-c]pyridin-1-yl)cyclohexyl)acetonitrile;

2-(4-(dimethylamino)-1-(3-((2-methyl-1,1-dioxido-2,3-dihydrobenzo-[d]isothiazol-6-yl)amino)-4-oxo-4,5-di-hydro-1H-pyrazolo[4,3-c]pyridin-1-yl)cyclohexyl)ac-etonitrile;

2-(4-(3-fluoroazetidin-1-yl)-1-(3-((2-methyl-1,1-dioxido-2,3-dihydrobenzo[d]isothiazol-6-yl)amino)-4-oxo-4,5-dihydro-1H-pyrazolo[4,3-c]pyridin-1-yl)cyclohexyl)acetonitrile;

2-(1-(3-((2-(tert-butyl)-1,1-dioxido-2,3-dihydrobenzo[d]isothiazol-5-yl)amino)-4-oxo-4,5-dihydro-1H-pyra-zolo[4,3-c]pyridin-1-yl)-4-(dimethylamino)cyclo-hexyl)acetonitrile;

4-((1-(1-(cyanomethyl)-4-oxocyclohexyl)-4-oxo-4,5-di-hydro-1H-pyrazolo[4,3-c]pyridin-3-yl)amino)-N,N-di-methylbenzenesulfonamide;

N-(tert-butyl)-5-(3-((2-(tert-butyl)-1,1-dioxido-2,3-dihy-drobenzo[d]isothiazol-5-yl)amino)-4-oxo-4,5-dihydro-1H-pyrazolo[4,3-c]pyridin-1-yl)-5-(cyanomethyl)tet-rahydro-2H-pyran-2-carboxamide;

N-tert-butyl-5-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}-5-(cyanomethyl)-N-methyltetrahydro-2H-pyran-2-carboxamide;

isopropyl 5-(3-((2-(tert-butyl)-1,1-dioxido-2,3-dihyd-robenzo[d]isothiazol-5-yl)amino)-4-oxo-4,5-dihydro-1H-pyrazolo[4,3-c]pyridin-1-yl)-5-(cyanomethyl)tet-rahydro-2H-pyran-2-carboxylate;

2-(3-(3-((4-(4,4-difluoropiperidine-1-carbonyl)-3-meth-ylphenyl)amino)-4-oxo-4,5-dihydro-1H-pyrazolo[4,3-c]pyridin-1-yl)tetrahydro-2H-pyran-3-yl)acetonitrile;

2-(3-(3-((3-methyl-4-(2-methylpiperidine-1-carbonyl)phenyl)amino)-4-oxo-4,5-dihydro-1H-pyrazolo[4,3-c]pyridin-1-yl)tetrahydro-2H-pyran-3-yl)acetonitrile;

2-(3-(3-((3-methyl-4-(2-methylpiperidine-1-carbonyl)phenyl)amino)-4-oxo-4,5-dihydro-1H-pyrazolo[4,3-c]pyridin-1-yl)tetrahydro-2H-pyran-3-yl)acetonitrile;

2-(3-(3-((4-(4-hydroxy-4-methylpiperidine-1-carbonyl)-3-methylphenyl)amino)-4-oxo-4,5-dihydro-1H-pyra-zolo[4,3-c]pyridin-1-yl)tetrahydro-2H-pyran-3-yl)ac-etonitrile;

tert-butyl 5-(cyanomethyl)-5-(3-((3-methyl-4-(morpho-line-4-carbonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((3-methyl-4-(thiomor-pholine-4-carbonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((3-methyl-4-(pyrrolidine-1-carbonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((3-methyl-4-(3-methylmorpholine-4-carbonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((3-methyl-4-(2-methylmorpholine-4-carbonyl)phenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(2,6-dimethylmorpholine-4-carbonyl)-3-methylphenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((4-(ethyl(2,2,2-trifluoroethyl)carbamoyl)-3-methylphenyl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(3-((3-methyl-4-(methyl(2,2,2-trifluoroethyl)carbamoyl)phenyl)amino)-4-oxo-4,5-dihydro-1H-pyrazolo[4,3-c]pyridin-1-yl)tetrahydro-2H-pyran-2-carboxylate;

tert-butyl 5-(3-((4-(2-oxa-5-azabicyclo[2.2.1]heptane-5-carbonyl)-3-methylphenyl)amino)-4-oxo-4,5-dihydro-1H-pyrazolo[4,3-c]pyridin-1-yl)-5-(cyanomethyl)tetrahydro-2H-pyran-2-carboxylate;

tert-butyl 5-(cyanomethyl)-5-(3-((2-methylbenzo[d]thiazol-6-yl)amino)-4-oxo-4,5-dihydro-1H-pyrazolo[4,3-c]pyridin-1-yl)tetrahydro-2H-pyran-2-carboxylate;

[1-{3-[(3,3-dimethyl-2-oxo-2,3-dihydro-1H-indol-6-yl)amino]-4-oxo-4,5-dihydro-1H-pyrazolo[4,3-c]pyridin-1-yl}-2-fluorocyclohexyl]acetonitrile;

tert-butyl 5-(cyanomethyl)-5-(3-((3,3-dimethyl-2-oxoindolin-6-yl)amino)-4-oxo-4,5-dihydro-1H-pyrazolo[4,3-c]pyridin-1-yl)tetrahydro-2H-pyran-2-carboxylate;

[3-{3-[(3,3-dimethyl-2-oxo-2,3-dihydro-1H-indol-6-yl)amino]-4-oxo-4,5-dihydro-1H-pyrazolo[4,3-c]pyridin-1-yl}tetrahydro-2H-pyran-3-yl]acetonitrile;

[3-{3-[(2-methyl-1,3-benzothiazol-6-yl)amino]-4-oxo-4,5-dihydro-1H-pyrazolo[4,3-c]pyridin-1-yl}tetrahydro-2H-pyran-3-yl]acetonitrile;

tert-butyl 5-(cyanomethyl)-5-(3-((2-fluoropyridin-4-yl)amino)-4-oxo-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(2,2,2-trifluoro-1-methoxyethyl)phenyl)amino)-4,5-dihydro-1H-pyrazolo[4,3-c]pyridin-1-yl)tetrahydro-2H-pyran-2-carboxylate;

tert-butyl 5-(cyanomethyl)-5-(4-oxo-3-((4-(2,2,2-trifluoro-1-methoxyethyl)phenyl)amino)-4,5-dihydro-1H-pyrazolo[4,3-c]pyridin-1-yl)tetrahydro-2H-pyran-2-carboxylate;

tert-butyl 4-(cyanomethyl)-4-(3-((4-(4,4-difluoropiperidine-1-carbonyl)-3-methylphenyl)amino)-4-oxo-4,5-dihydro-1H-pyrazolo[4,3-c]pyridin-1-yl)piperidine-1-carboxylate;

tert-butyl-4-(3-((4-(8-oxa-3-azabicyclo[3.2.1]octane-3-carbonyl)-3-methylphenyl)amino)-4-oxo-4,5-dihydro-1H-pyrazolo[4,3-c]pyridin-1-yl)-4-(cyanomethyl)piperidine-1-carboxylate;

tert-butyl 4-(cyanomethyl)-4-{3-[(5-methyl-4-{3-oxa-8-azabicyclo[3.2.1]octan-8-ylcarbonyl}cyclohexa-1,3,5-trien-1-yl)amino]-4-oxo-5H-pyrazolo[4,3-c]pyridin-1-yl}piperidine-1-carboxylate;

tert-butyl-4-(cyanomethyl)-4-(3-(3-methyl-4-(thiomorpholine-4-carbonyl)phenylamino)-4-oxo-4,5-dihydropyrazolo[4,3-c]pyridin-1-yl)piperidine-1-carboxylate;

tert-butyl-4-(cyanomethyl)-4-(3-((1,1-dioxido-2-(1-(2,2,2-trifluoroethyl)piperidin-4-yl)-2,3-dihydrobenzo[d]isothiazol-5-yl)amino)-4-oxo-4,5-dihydro-1H-pyrazolo[4,3-c]pyridin-1-yl)piperidine-1-carboxylate;

tert-butyl 4-(cyanomethyl)-4-(4-oxo-3-(4-(2-(trifluoromethyl)piperidin-2-yl)phenylamino)-4,5-dihydropyrazolo[4,3-c]pyridin-1-yl)piperidine-1-carboxylate;

tert-butyl 4-(cyanomethyl)-4-(4-oxo-3-(4-(2-(trifluoromethyl)pyrrolidin-2-yl)phenylamino)-4,5-dihydropyrazolo[4,3-c]pyridin-1-yl)piperidine-1-carboxylate;

tert-butyl 4-(cyanomethyl)-4-(3-(3-methyl-4-(morpholine-4-carbonyl)phenylamino)-4-oxo-4,5-dihydropyrazolo[4,3-c]pyridin-1-yl)piperidine-1-carboxylate;

5-(3-((4-chlorophenyl)amino)-4-oxo-4,5-dihydro-1H-pyrazolo[4,3-c]pyridin-1-yl)-5-(cyanomethyl)-N-(methylsulfonyl)tetrahydro-2H-pyran-2-carboxamide;

5-(3-((4-chlorophenyl)amino)-4-oxo-4,5-dihydro-1H-pyrazolo[4,3-c]pyridin-1-yl)-5-(cyanomethyl)-N,N-dimethyltetrahydro-2H-pyran-2-carboxamide; and 2-(3-(3-((4-chlorophenyl)amino)-4-oxo-4,5-dihydro-1H-pyrazolo[4,3-c]pyridin-1-yl)-6-(2-hydroxypropan-2-yl)tetrahydro-2H-pyran-3-yl)acetonitrile.

7. A pharmaceutical composition comprising a compound of claim 1 or a pharmaceutically acceptable salt thereof and a pharmaceutically acceptable carrier.

8. A pharmaceutical composition comprising a compound of claim 6 or a pharmaceutically acceptable salt thereof and a pharmaceutically acceptable carrier.

9. A compound according to claim 6, or a pharmaceutically acceptable salt, selected from:

tert-butyl 4-(cyanomethyl)-4-[4-oxo-3-({4-[(1S)-2,2,2-trifluoro-1-hydroxyethyl]phenyl}amino)-4,5-dihydro-1H-pyrazolo[4,3-c]pyridin-1-yl]piperidine-1-carboxylate;

tert-butyl 4-(cyanomethyl)-4-[4-oxo-3-({4-[(1R)-2,2,2-trifluoro-1-hydroxyethyl]phenyl}amino)-4,5-dihydro-1H-pyrazolo[4,3-c]pyridin-1-yl]piperidine-1-carboxylate;

tert-butyl (3R,4R)-4-(cyanomethyl)-3-fluoro-4-{3-[(2-methyl-1,1-dioxido-2,3-dihydro-1,2-benzisothiazol-5-yl)amino]-4-oxo-4,5-dihydro-1H-pyrazolo[4,3-c]pyridin-1-yl}piperidine-1-carboxylate;

tert-butyl (3R,4S)-4-(cyanomethyl)-3-methyl-4-(3-{[4-(methylsulfonyl)phenyl]amino}-4-oxo-4,5-dihydro-1H-pyrazolo[4,3-c]pyridin-1-yl)piperidine-1-carboxylate;

tert-butyl (3R,4R)-4-(cyanomethyl)-3-methyl-4-(3-{[4-(methylsulfonyl)phenyl]amino}-4-oxo-4,5-dihydro-1H-pyrazolo[4,3-c]pyridin-1-yl)piperidine-1-carboxylate;

tert-butyl (3S,4R)-4-(cyanomethyl)-3-fluoro-4-(3-{[4-(methylsulfonyl)phenyl]amino}-4-oxo-4,5-dihydro-1H-pyrazolo[4,3-c]pyridin-1-yl)piperidine-1-carboxylate;

tert-butyl (3R,4S)-4-(cyanomethyl)-3-fluoro-4-(3-{[4-(methylsulfonyl)phenyl]amino}-4-oxo-4,5-dihydro-1H-pyrazolo[4,3-c]pyridin-1-yl)piperidine-1-carboxylate;

tert-butyl (3S,4S)-4-(cyanomethyl)-3-fluoro-4-(3-{[4-(methylsulfonyl)phenyl]amino}-4-oxo-4,5-dihydro-1H-pyrazolo[4,3-c]pyridin-1-yl)piperidine-1-carboxylate;

tert-butyl (3R,4R)-4-(cyanomethyl)-3-fluoro-4-(3-{[4-(methylsulfonyl)phenyl]amino}-4-oxo-4,5-dihydro-1H-pyrazolo[4,3-c]pyridin-1-yl)piperidine-1-carboxylate;

tert-butyl (3R,4R)-4-(cyanomethyl)-4-(3-{[4-(dimethylsulfamoyl)phenyl]amino}-4-oxo-4,5-dihydro-1H-pyrazolo[4,3-c]pyridin-1-yl)-3-fluoropiperidine-1-carboxylate;

tert-butyl (3R,4R)-4-(cyanomethyl)-3-fluoro-4-[4-oxo-3-(phenylamino)-4,5-dihydro-1H-pyrazolo[4,3-c]pyridin-1-yl]piperidine-1-carboxylate;

tert-butyl (3R,4R)-4-(cyanomethyl)-3-fluoro-4-[4-oxo-3-({4-[(1S)-2,2,2-trifluoro-1-hydroxyethyl]phenyl}amino)-4,5-dihydro-1H-pyrazolo[4,3-c]pyridin-1-yl]piperidine-1-carboxylate;

tert-butyl (3R,4R)-4-(cyanomethyl)-3-fluoro-4-[4-oxo-3-({4-[(1R)-2,2,2-trifluoro-1-hydroxyethyl]phenyl}amino)-4,5-dihydro-1H-pyrazolo[4,3-c]pyridin-1-yl]piperidine-1-carboxylate;

tert-butyl (3R,4R)-4-{3-[(2-tert-butyl-1,1-di oxido-2,3-dihydro-1,2-benzisothiazol-5-yl)amino]-4-oxo-4,5-dihydro-1H-pyrazolo[4,3-c]pyridin-1-yl}-4-(cyanomethyl)-3-fluoropiperidine-1-carboxylate;

tert-butyl (3R,4R)-4-(cyanomethyl)-4-(3-{[1,1-dioxido-2-(2,2,2-trifluoroethyl)-2,3-dihydro-1,2-benzisothiazol-5-yl]amino}-4-oxo-4,5-dihydro-1H-pyrazolo[4,3-c]pyridin-1-yl)-3-fluoropiperidine-1-carboxylate;

(S)-2-(3-(4-oxo-3-(phenylamino)-4,5-dihydro-1H-pyrazolo[4,3-c]pyridin-1-yl)tetrahydro-2H-pyran-3-yl)acetonitrile;

(S)-4-((1-(3-(cyanomethyl)tetrahydro-2H-pyran-3-yl)-4-oxo-4,5-dihydro-1H-pyrazolo[4,3-c]pyridin-3-yl)amino)-N,N-dimethylbenzenesulfonamide;

(R)-4-((1-(3-(cyanomethyl)tetrahydro-2H-pyran-3-yl)-4-oxo-4,5-dihydro-1H-pyrazolo[4,3-c]pyridin-3-yl)amino)-N,N-dimethylbenzenesulfonamide;

(R)-2-(3-(3-((4-(methylsulfonyl)phenyl)amino)-4-oxo-4,5-dihydro-1H-pyrazolo[4,3-c]pyridin-1-yl)tetrahydro-2H-pyran-3-yl)acetonitrile;

(S)-2-(3-(3-((4-(methylsulfonyl)phenyl)amino)-4-oxo-4,5-dihydro-1H-pyrazolo[4,3-c]pyridin-1-yl)tetrahydro-2H-pyran-3-yl)acetonitrile;

(2S,5S)-methyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate;

(2R,5R)-methyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate;

(2R,5S)-tert-butyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl -(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate;

(2R,5R)-tert-butyl 5-(cyanomethyl)-5-(3-((4-(methylsulfonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(3-((2-(tert-butyl)-1,1-dioxido-2,3-dihydro-1H-pyrazolo[4,3-c]pyridin-1-yl)-5-(cyanomethyl)tetrahydro-2H-pyran-2-carboxylate;

(2R,5R)-tert-butyl 5-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-5-(cyanomethyl)tetrahydro-2H-pyran-2-carboxylate;

(2S,5S)-tert-butyl 5-(cyanomethyl)-5-(3-((4-(N,N-dimethylsulfamoyl)phenyl)amino)-4-oxo-4,5-dihydro-1H-pyrazolo[4,3-c]pyridin-1-y l)tetrahydro-2H-pyran-2-carboxylate;

(2S,5S)-tert-butyl 5-(cyanomethyl)-5-(3-((1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)tetrahydro-2H-pyran-2-carboxylate;

(2R,5S)-tert-butyl 5-(3-((4-((R)-1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate;

(2S,5S)-tert-butyl 5-(3-((4-((R)-1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate;

(2R,5S)-tert-butyl 5-(3-((4-((S)-1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate;

(2S,5S)-tert-butyl 5-(3-((4-((S)-1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate;

(2S,5S)-tert-butyl-(cyanomethyl)-5-(4-oxo-3-(phenylamino)-4,5-dihydro-1H-pyrazolo[4,3-c]pyridin-1-yl)tetrahydro-2H-pyran-2-carboxylate;

(2S,5S)-tert-butyl5-(cyanomethyl)-5-(3-((2-methyl-1,1-dioxido-2,3-dihydrobenzo[d]isothiazol-5-yl)amino)-4-oxo-4,5-dihydro-1H-pyrazolo[4,3-c]pyridin-1-yl)tetrahydro-2H-pyran-2-carboxylate;

4-({1-[(1R,2R))-1-(cyanomethyl)-2-fluorocyclohexyl]-4-oxo-4,5-dihydro-1H-pyrazolo[4,3-c]pyridin-3-yl}amino)-N,N-dimethylbenzenesulfonamide;

{(1R,2R)-2-fluoro-1-[4-oxo-3-({4-[(1S)-2,2,2-trifluoro-1-hydroxy-1-methylethyl]phenyl}amino)-4,5-dihydro-1H-pyrazolo[4,3-c]pyridin-1-yl]cyclohexyl}acetonitrile;

{(1R,2R)-2-fluoro-1-[4-oxo-3-({4-[(1R)-2,2,2-trifluoro-1-hydroxy-1-methylethyl]phenyl}amino)-4,5-dihydro-1H-pyrazolo[4,3-c]pyridin-1-yl]cyclohexyl}acetonitrile;

{(1R,2R)-2-fluoro-1-[3-({4-[(1-methylethyl)sulfonyl]phenyl}amino)-4-oxo-4,5-dihydro-1H-pyrazolo[4,3-c]pyridin-1-yl]cyclohexyl}acetonitrile;

(R)-2-(1-(3-((4-(1-amino-2,2,2-trifluoroethyl)phenyl)amino)-4-oxo-4,5-dihydro-1H-pyrazolo[4,3-c]pyridin-1-yl)cyclopentyl)acetonitrile;

(S)-2-(1-(3-((4-(1-amino-2,2,2-trifluoroethyl)phenyl)amino)-4-oxo-4,5-dihydro-1H-pyrazolo[4,3-c]pyridin-1-yl)cyclopentyl)acetonitrile;

(2S,5S)-tert-butyl 5-(3-((4-(N-(tert-butyl)-N-methylsulfamoyl)phenyl)amino)-4-oxo-4,5-dihydro-1H-pyrazolo[4,3-c]pyridin-1-yl)-5-(cyanomethyl)tetrahydro-2H-pyran-2-carboxylate;

(2S,5S)-tert-butyl -(cyanomethyl)-5-(3-((4-(N-isopropyl-N-methylsulfamoyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl -(cyanomethyl)-5-(3-((4-(N-ethyl-N-methylsulfamoyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((1,1-dioxido-2-(2,2,2-trifluoroethyl)-2,3-dihydrobenzo[d]isothiazol-5-yl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((4-(N-methylsulfamoyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((1-oxo-2-(2,2,2-trifluoroethyl)isoindolin-5-yl)amino)-4,5-dihydro-1H-pyrazolo[4,3-c]pyridin-1-yl)tetrahydro-2H-pyran-2-carboxylate;

(2S,5S)-tert-butyl 5-(3-((4-((1H-1,2,3-triazol-1-yl)methyl)phenyl)amino)-4-oxo-4,5-dihydro-1H-pyrazolo[4,3-c]pyridin-1-yl)-5-(cyanomethyl)tetrahydro-2H-pyran-2-carboxylate;

(2S,5S)-tert-butyl 5-(3-((4-((2H-1,2,3-triazol-2-yl)methyl)phenyl)amino)-4-oxo-4,5-dihydro-1H-pyrazolo[4,3-c]pyridin-1-yl)-5-(cyanomethyl)tetrahydro-2H-pyran-2-carboxylate;

(2S,5S)-tert-butyl 5-(cyanomethyl)-5-(3-((4-(isopropylsulfonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((4-(cyclopropylsulfonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(3-((2-(tert-butyl)-1-oxoisoindolin-5-yl)amino)-4-oxo-4,5-dihydro-1H-pyrazolo[4,3-c]pyridin-1-yl)-5-(cyanomethyl)tetrahydro-2H-pyran-2-carboxylate;

(2S,5S)-tert-butyl 5-(cyanomethyl)-5-(3-((2-cyclohexyl-1-oxoisoindolin-5-yl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((2-cyclopentyl-1-oxoisoindolin-5-yl)amino)-4-oxo-4,5-dihydro-1H-pyrazolo[4,3-c]pyridin-1-yl)tetrahydro-2H-pyran-2-carboxylate;

(2S,5S)-tert-butyl 5-(3-((4-(1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate;

(2S,5S)-tert-butyl 5-(3-((4-(1-amino-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate;

[(3S)-3-(3-{[4-(azetidin-1-ylsulfonyl)phenyl]amino}-4-oxo-4,5-dihydro-1H-pyrazolo[4,3-c]pyridin-1-yl)tetrahydro-2H-pyran-3-yl]acetonitrile;

{(3S)-3-[3-({4-[(3-methylazetidin-1-yl)sulfonyl]phenyl}amino)-4-oxo-4,5-dihydro-1H-pyrazolo[4,3-c]pyridin-1-yl]tetrahydro-2H-pyran-3-yl}acetonitrile;

{(3S)-3-[3-({4-[(2,2-dimethylpyrrolidin-1-yl)sulfonyl]phenyl}amino)-4-oxo-4,5-dihydro-1H-pyrazolo[4,3-c]pyridin-1-yl]tetrahydro-2H-pyran-3-yl}acetonitrile;

[(3S)-3-{3-[(4-{[(2R)-2-methylazetidin-1-yl]sulfonyl}phenyl)amino]-4-oxo-4,5-dihydro-1H-pyrazolo[4,3-c]pyridin-1-yl}tetrahydro-2H-pyran-3-yl]acetonitrile;

[(3S)-3-{3-{[(4-[(2S)-2-methylazetidin-1-yl]sulfonyl}phenyl)amino]-4-oxo-4,5-dihydro-1H-pyrazolo[4,3-c]pyridin-1-yl}tetrahydro-2H-pyran-3-yl]acetonitrile;

{(3S)-3-[4-oxo-3-({4-[(1S)-2,2,2-trifluoro-1-hydroxy-1-methylethyl]phenyl}amino)-4,5-dihydro-1H-pyrazolo[4,3-c]pyridin-1-yl]tetrahydro-2H-pyran-3-yl}acetonitrile;

{(3S)-3-[4-oxo-3-({4-[(1R)-2,2,2-trifluoro-1-hydroxy-1-methylethyl]phenyl}amino)-4,5-dihydro-1H-pyrazolo[4,3-c]pyridin-1-yl]tetrahydro-2H-pyran-3-yl}acetonitrile;

(S)-ethyl 3-(4-((1-((3S)-3-(cyanomethyl)tetrahydro-2H-pyran-3-yl)-4-oxo-4,5-dihydro-1H-pyrazolo[4,3-c]pyridin-3-yl)amino)phenyl)-4,4,4-trifluoro-3-hydroxy-2,2-dimethylbutanoate;

(R)-ethyl 3-(4-((1-((3S)-3-(cyanomethyl)tetrahydro-2H-pyran-3-yl)-4-oxo-4,5-dihydro-1H-pyrazolo[4,3-c]pyridin-3-yl)amino)phenyl)-4,4,4-trifluoro-3-hydroxy-2,2-dimethylbutanoate;

2-((S)-3-(3-((4-((S)-3-hydroxy-3-(trifluoromethyl)pyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;

2-((S)-3-(3-((4-((R)-3-hydroxy-3-(trifluoromethyl)pyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;

2-((S)-3-(3-((4-((R)-3-fluoropyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;

2-((S)-3-(3-((4-((S)-3-methoxypyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;

2-((S)-3-(3-((4-((R)-3-methoxypyrrolidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;

(S)-2-(3-(3-((3-methyl-4-(morpholine-4-carbonyl)phenyl)amino)-4-oxo-4,5-dihydro-1H-pyrazolo[4,3-c]pyridin-1-yl)tetrahydro-2H-pyran-3-yl)acetonitrile;

2-((S)-3-(3-(((S)-1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)tetrahydro-2H-pyran-3-yl)acetonitrile;

2-((S)-3-(3-(((R)-1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)tetrahydro-2H-pyran-3-yl)acetonitrile;

(R)-methyl 4-(cyanomethyl)-4-(4-oxo-3-((4-(1,1,1-trifluoro-2-hydroxypropan-2-yl)phenyl)amino)-4,5-dihydro-1H-pyrazolo[4,3-c]pyridin-1-yl)piperidine-1-carboxylate;

(S)-methyl 4-(cyanomethyl)-4-(4-oxo-3-((4-(1,1,1-trifluoro-2-hydroxypropan-2-yl)phenyl)amino)-4,5-dihydro-1H-pyrazolo[4,3-c]pyridin-1-yl)piperidine-1-carboxylate;

(R)-methyl 4-(cyanomethyl)-4-(3-((1-hydroxy-1-(trifluoromethyl)-2,3-dihydro-1H-inden-5-yl)amino)-4-oxo-4,5-dihydro-1H-pyrazolo[4,3-c]pyridin-1-yl)piperidine-1-carboxylate;

(S)-methyl 4-(cyanomethyl)-4-(3-((1-hydroxy-1-(trifluoromethyl)-2,3-dihydro-1H-inden-5-yl)amino)-4-oxo-4,5-dihydro-1H-pyrazolo[4,3-c]pyridin-1-yl)piperidine-1-carboxylate;

2-((1R,2R)-2-fluoro-1-(3-((3-methyl-4-(morpholine-4-carbonyl)phenyl)amino)-4-oxo-4,5-dihydro-1H-pyrazolo[4,3-c]pyridin-1-yl)cyclohexyl)acetonitrile;

2-((1R,2R)-2-fluoro-1-(3-((2-fluoropyridin-4-yl)amino)-4-oxo-4,5-dihydro-1H-pyrazolo[4,3-c]pyridin-1-yl)cyclohexyl)acetonitrile;

2-((1R,2R)-1-(3-((4-(4,4-difluoropiperidine-1-carbonyl)-3-methylphenyl)amino)-4-oxo-4,5-dihydro-1H-pyrazolo[4,3-c]pyridin-1-yl)-2-fluorocyclohexyl)acetonitrile;

2-((1R,2R)-2-fluoro-1-(3-((3-methyl-4-(thiomorpholine-4-carbonyl)phenyl)amino)-4-oxo-4,5-dihydro-1H-pyrazolo[4,3-c]pyridin-1-yl)cyclohexyl)acetonitrile;

(2S,5S)-tert-butyl 5-(cyanomethyl)-5-(3-((3-methyl-4-(thiazolidine-3-carbonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((3-methyl-4-((R)-2-methylthiazolidine-3-carbonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((3-methyl-4-((S)-2-methylthiazolidine-3-carbonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((3-methyl-4-((S)-2-methylthiomorpholine-4-carbonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((3-methyl-4-((R)-2-methylthiomorpholine-4-carbonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((4-((S)-3-hydroxy-3-(trifluoromethyl)pyrrolidine-1-carbonyl)-3-methylphenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((4-((R)-3-hydroxy-3-(trifluoromethyl)pyrrolidine-1-carbonyl)-3-methylphenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((S)-1,1,1-trifluoro-2-hydroxy-4-isopropoxy-3,3-dimethyl-4-oxobutan-2-yl)phenyl)amino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((R)-1,1,1-trifluoro-2-hydroxy-4-isopropoxy-3,3-dimethyl-4-oxobutan-2-yl)phenyl)amino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-(((S)-1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-(((R)-1-hydroxy-2,2-dimethyl-1-(trifluoromethyl)-2,3-dihydro-1H-inden-5-yl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((S)-1,1,1-trifluoro-2-hydroxy-3,3-dimethylbutan-2-yl)phenyl)amino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((R)-1,1,1-trifluoro-2-hydroxy-3,3-dimethylbutan-2-yl)phenyl)amino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((S)-2,2,2-trifluoro-1-hydroxyethyl)phenyl)amino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((R)-2,2,2-trifluoro-1-hydroxyethyl)phenyl)amino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((S)-1,1,1-trifluoro-2-hydroxypropan-2-yl)phenyl)amino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((R)-1,1,1-trifluoro-2-hydroxypropan-2-yl)phenyl)amino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((S)-1,1,1-trifluoro-2-methoxypropan-2-yl)phenyl)amino)-4,5-dihydro-1H-pyrazolo[4,3-c]pyridin-1-yl)tetrahydro-2H-pyran-2-carboxylate;

{(1R,2R)-1-[3-({4-[(1R)-1-(ethylamino)-2,2,2-trifluoroethyl]phenyl}amino)-4-oxo-4,5-dihydro-1H-pyrazolo[4,3-c]pyridin-1-yl]-2-fluorocyclohexyl}acetonitrile;

{(1R,2R)-1-[3-({4-[(1S)-1-(ethylamino)-2,2,2-trifluoroethyl]phenyl}amino)-4-oxo-4,5-dihydro-1H-pyrazolo[4,3-c]pyridin-1-yl]-2-fluorocyclohexyl}acetonitrile;

[(1R,2R)-2-fluoro-1-{3-[(4-{1-methyl-1-[(1-methylethyl)amino]ethyl}phenyl)amino]-4-oxo-4,5-dihydro-1H-pyrazolo[4,3-c]pyridin-1-yl}cyclohexyl]acetonitrile;

{(1R,2R)-1-[3-({4-[(1R)-1-amino-2,2,2-trifluoroethyl]phenyl}amino)-4-oxo-4,5-dihydro-1H-pyrazolo[4,3-c]pyridin-1-yl]-2-fluorocyclohexyl}acetonitrile;

{(1R,2R)-1-[3-({4-[(1S)-1-amino-2,2,2-trifluoroethyl]phenyl}amino)-4-oxo-4,5-dihydro-1H-pyrazolo[4,3-c]pyridin-1-yl]-2-fluorocyclohexyl}acetonitrile;

[(3S)-3-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}tetrahydro-2H-pyran-3-yl]acetonitrile;

{(3S)-3-[3-({4-[(1-methylethyl)sulfonyl]phenyl}amino)-4-oxo-4,5-dihydro-1H-pyrazolo[4,3-c]pyridin-1-yl]tetrahydro-2H-pyran-3-yl}acetonitrile;

4-({1-[(3R,4S)-3-(cyanomethyl)-4-fluorotetrahydro-2H-pyran-3-yl]-4-oxo-4,5-dihydro-1H-pyrazolo[4,3-c]pyridin-3-yl}amino)-N,N-dimethylbenzenesulfonamide;

4-({1-[(3S,4R)-3-(cyanomethyl)-4-fluorotetrahydro-2H-pyran-3-yl]-4-oxo-4,5-dihydro-1H-pyrazolo[4,3-c]pyridin-3-yl}amino)-N,N-dimethylbenzenesulfonamide;

N-tert-butyl-4-({1-[(3S)-3-(cyanomethyl)tetrahydro-2H-pyran-3-yl]-4-oxo-4,5-dihydro-1H-pyrazolo[4,3-c]pyridin-3-yl}amino)-N-methylbenzenesulfonamide;

[(3S)-3-(3-{[4-(tert-butylsulfonyl)phenyl]amino}-4-oxo-4,5-dihydro-1H-pyrazolo[4,3-c]pyridin-1-yl)tetrahydro-2H-pyran-3-yl]acetonitrile;

N-tert-butyl-4-({1-[(3S)-3-(cyanomethyl)tetrahydro-2H-pyran-3-yl]-4-oxo-4,5-dihydro-1H-pyrazolo[4,3-c]pyridin-3-yl}amino)benzenesulfonamide;

tert-butyl [5-({1-[(3S)-3-(cyanomethyl)tetrahydro-2H-pyran-3-yl]-4-oxo-4,5-dihydro-1H-pyrazolo[4,3-c]pyridin-3-yl}amino)-1,1-dioxido-1,2-benzisothiazol-2(3H)-yl]acetate;

tert-butyl 3-{[4-({1-[(3S)-3-(cyanomethyl)tetrahydro-2H-pyran-3-yl]-4-oxo-4,5-dihydro-1H-pyrazolo[4,3-c]pyridin-3-yl}amino)phenyl]sulfonyl}-3-methylbutanoate;

{(3S)-3-[3-({4-[(1R)-1-amino-2,2,2-trifluoroethyl]phenyl}amino)-4-oxo-4,5-dihydro-1H-pyrazolo[4,3-c]pyridin-1-yl]tetrahydro-2H-pyran-3-yl}acetonitrile;

{(3S)-3-[3-({4-[(1S)-1-amino-2,2,2-trifluoroethyl]phenyl}amino)-4-oxo-4,5-dihydro-1H-pyrazolo[4,3-c]pyridin-1-yl]tetrahydro-2H-pyran-3-yl}acetonitrile;

{(3S)-3-(3-({[4-[(1R)-1-(tert-butylamino)-2,2,2-trifluoroethyl]phenyl}amino)-4-oxo-4,5-dihydro-1H-pyrazolo[4,3-c]pyridin-1-yl)tetrahydro-2H-pyran-3-yl}acetonitrile;

{(3S)-3-[3-({4-[(1S)-1-(tert-butylamino)-2,2,2-trifluoroethyl]phenyl}amino)-4-oxo-4,5-dihydro-1H-pyrazolo[4,3-c]pyridin-1-yl]tetrahydro-2H-pyran-3-yl}acetonitrile;

[(3S)-3-(3-{[4-(cyclopentylsulfonyl)phenyl]amino}-4-oxo-4,5-dihydro-1H-pyrazolo[4,3-c]pyridin-1-yl)tetrahydro-2H-pyran-3-yl]acetonitrile;

{(3S)-3-[4-oxo-3-({4-[(1,1,2-trimethylpropyl)sulfonyl]phenyl}amino)-4,5-dihydro-1H-pyrazolo[4,3-c]pyridin-1-yl]tetrahydro-2H-pyran-3-yl}acetonitrile;

[(3S)-3-(3-{[4-(cyclohexylsulfonyl)phenyl]amino}-4-oxo-4,5-dihydro-1H-pyrazolo[4,3-c]pyridin-1-yl)tetrahydro-2H-pyran-3-yl]acetonitrile;

(2S,5S)-tert-butyl 5-(3-((4-((R)-1-(tert-butylamino)-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate;

(2S,5S)-tert-butyl 5-(3-((4-((S)-1-(tert-butylamino)-2,2,2-trifluoroethyl)phenyl)amino)-4-oxo-4,5-dihydro-1H-pyrazolo[4,3-c]pyridin-1-yl)-5-(cyanomethyl)tetrahydro-2H-pyran-2-carboxylate;

{(3S)-3-[3-({4-[(1,1-dimethylpropyl)sulfonyl]phenyl}amino)-4-oxo-4,5-dihydro-1H-pyrazolo[4,3-c]pyridin-1-yl]tetrahydro-2H-pyran-3-yl}acetonitrile;

[(3S)-3-{3[(2-cyclopentyl-1-oxo-2,3-dihydro-1H-isoindol-5-yl)amino]-4-oxo-4,5-dihydro-1H-pyrazolo[4,3-c]pyridin-1-yl}tetrahydro-2H-pyran-3-yl]acetonitrile;

{(3S)-3-[4-oxo-3-({4-[(1R)-2,2,2-trifluoro-1-pyrrolidin-1-ylethyl]phenyl}amino)-4,5-dihydro-1H-pyrazolo[4,3-c]pyridin-1-yl]tetrahydro-2H-pyran-3-yl}acetonitrile;

{(3S)-3-[4-oxo-3-({4-[(1R)-2,2,2-trifluoro-1-pyrrolidin-1-ylethyl]phenyl}amino)-4,5-dihydro-1H-pyrazolo[4,3-c]pyridin-1-yl]tetrahydro-2H-pyran-3-yl}acetonitrile;

{(3S)-3-[4-oxo-3-({4-[(1S)-1-pyrrolidin-1-ylethyl]phenyl}amino)-4,5-dihydro-1H-pyrazolo[4,3-c]pyridin-1-yl]tetrahydro-2H-pyran-3-yl}acetonitrile;

{(3S)-3-[4-oxo-3-({4-[(1R)-1-pyrrolidin-1-ylethyl]phenyl}amino)-4,5-dihydro-1H-pyrazolo[4,3-c]pyridin-1-yl]tetrahydro-2H-pyran-3-yl}acetonitrile;

{(3S)-3-[3-({4-[(2,2-dimethylcyclopentyl)sulfonyl]phenyl}amino)-4-oxo-4,5-dihydro-1H-pyrazolo[4,3-c]pyridin-1-yl]tetrahydro-2H-pyran-3-yl}acetonitrile;

(2S,5S)-tert-butyl 5-(cyanomethyl)-5-(3-((4-(morpholinosulfonyl)phenyl)amino)-4-oxo-4,5-dihydro-1H-pyrazolo[4,3-c]pyridin-1-yl)tetrahydro-2H-pyran-2-carboxylate;

[(3S)-3-(3-{[4-(morpholin-4-ylsulfonyl)phenyl]amino}-4-oxo-4,5-dihydro-1H-pyrazolo[4,3-c]pyridin-1-yl)tetrahydro-2H-pyran-3-yl]acetonitrile;

[(3S)-3-{4-oxo-3-[(4-{(1R)-2,2,2-trifluoro-1-[(1-methylethyl)amino]ethyl}phenyl)amino]-4,5-dihydro-1H-pyrazolo[4,3-c]pyridin-1-yl}tetrahydro-2H-pyran-3-yl]acetonitrile;

[(3S)-3-{4-oxo-3-[(4-{(1S)-2,2,2-trifluoro-1-[(1-methylethyl)amino]ethyl}phenyl)amino]-4,5-dihydro-1H-pyrazolo[4,3-c]pyridin-1-yl}tetrahydro-2H-pyran-3-yl]acetonitrile;

(2S,5S)-tert-butyl 5-(cyanomethyl)-5-(3-((4-((R)-1-(ethylamino)-2,2,2-trifluoroethyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((4-((S)-1-(ethylamino)-2,2,2-trifluoroethyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((R)-2,2,2-trifluoro-1-(isopropylamino)ethyl)phenyl)amino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((S)-2,2,2-trifluoro-1-(isopropylamino)ethyl)phenyl)amino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((S)-1-(pyrrolidin-1-yl)ethyl)phenyl)amino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((R)-1-(pyrrolidin-1-yl)ethyl)phenyl)amino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((4-((R)-1-(dimethylamino)-2,2,2-trifluoroethyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((4-((S)-1-(dimethylamino)-2,2,2-trifluoroethyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-(quinolin-6-ylamino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((2-cyanoquinolin-6-yl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((2-methylquinolin-6-yl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((4-(3,5-dimethyl-1H-pyrazol-1-yl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((3-methyl-4-(1H-pyrazol-1-yl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((4-(2,2-dimethylmorpholine-4-carbonyl)-3-methylphenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-(quinolin-3-ylamino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((2-(dimethylamino)quinolin-6-yl)amino)-4-oxo-4,5-dihydro-1H-pyrazolo[4,3-c]pyridin-1-yl)tetrahydro-2H-pyran-2-carboxylate;

(2S,5S)-tert-butyl 5-(3-((2-carbamoylquinolin-6-yl)amino)-4-oxo-4,5-dihydro-1H-pyrazolo[4,3-c]pyridin-1-yl)-5-(cyanomethyl)tetrahydro-2H-pyran-2-carboxylate;

(S)-2-(3-(4-oxo-3-((4-(1-(trifluoromethyl)cyclopropyl)phenyl)amino)-4,5-dihydro-1H-pyrazolo[4,3-c]pyridin-1-yl)tetrahydro-2H-pyran-3-yl)acetonitrile;

(S)-2-(3-(3-((2-(dimethylamino)quinolin-6-yl)amino)-4-oxo-4,5-dihydro-1H-pyrazolo[4,3-c]pyridin-1-yl)tetrahydro-2H-pyran-3-yl)acetonitrile;

(S)-2-(3-(3-((2-methylquinolin-6-yl)amino)-4-oxo-4,5-dihydro-1H-pyrazolo[4,3-c]pyridin-1-yl)tetrahydro-2H-pyran-3-yl)acetonitrile;

(2S,5S)-tert-butyl 5-(cyanomethyl)-5-(3-((2-morpholinoquinolin-6-yl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((2-((S)-2-methylmorpholino)quinolin-6-yl)amino)-4-oxo-4,5-dihydro-1H-pyrazolo[4,3-c]pyridin-1-yl)tetrahydro-2H-pyran-2-carboxylate;

(2S,5S)-tert-butyl 5-(3-((2-(8-oxa-3-azabicyclo[3.2.1]octan-3-yl)quinolin-6-yl)amino)-4-oxo-4,5-dihydro-1H-pyrazolo[4,3-c]pyridin-1-yl)-5-(cyanomethyl)tetrahydro-2H-pyran-2-carboxylate;

(2S,5S)-tert-butyl 5-(cyanomethyl)-5-(4-oxo-3-((4-(propan-2-yl-(S)-sulfonimidoyl)phenyl)amino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-(propan-2-yl-(R)-sulfonimidoyl)phenyl)amino)-4,5-dihydro-1H-pyrazolo[4,3-c]pyridin-1-yl)tetrahydro-2H-pyran-2-carboxylate;

2-((3S)-3-(4-oxo-3-((4-(propan-2-yl-(S)-sulfonimidoyl)phenyl)amino)-4,5-dihydro-1H-pyrazolo[4,3-c]pyridin-1-yl)tetrahydro-2H-pyran-3-yl)acetonitrile;

2-((3S)-3-(4-oxo-3-((4-(propan-2-yl-(R)-sulfonimidoyl)phenyl)amino)-4,5-dihydro-1H-pyrazolo[4,3-c]pyridin-1-yl)tetrahydro-2H-pyran-3-yl)acetonitrile;

4-({1-[(1R,2R)-1-(cyanomethyl)-2-fluorocyclohexyl]-4-oxo-4,5-dihydro-1H-pyrazolo[4,3-c]pyridin-3-yl}amino)-N,N-dimethylbenzenesulfonamide;

(2S,5S)-tert-butyl 5-(3-((4-(tert-butylsulfonyl)phenyl)amino)-4-oxo-4,5-dihydro-1H-pyrazolo[4,3-c]pyridin-1-yl)-5-(cyanomethyl)tetrahydro-2H-pyran-2-carboxylate;

(2S,5S)-tert-butyl 5-(cyanomethyl)-5-(3-((4-(cyclopropylsulfonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((4-(isopropylsulfonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((2-(dimethylcarbamoyl)quinolin-6-yl)amino)-4-oxo-4,5-dihydro-1H-pyrazolo[4,3-c]pyridin-1-yl)tetrahydro-2H-pyran-2-carboxylate;

4-({1-[(3R)-3-(cyanomethyl)tetrahydrofuran-3-yl]-4-oxo-4,5-dihydro-1H-pyrazolo[4,3-c]pyridin-3-yl}amino)benzonitrile;

4-({1-[(3S)-3-(cyanomethyl)tetrahydrofuran-3-yl]-4-oxo-4,5-dihydro-1H-pyrazolo[4,3-c]pyridin-3-yl}amino)benzonitrile;

[(3R)-3-{3-[(4-chlorophenyl)amino]-4-oxo-4,5-dihydro-1H-pyrazolo[4,3-c]pyridin-1-yl}tetrahydrofuran-3-yl]acetonitrile;

[(3S)-3-{3-[(4-chlorophenyl)amino]-4-oxo-4,5-dihydro-1H-pyrazolo[4,3-c]pyridin-1-yl}tetrahydrofuran-3-yl]acetonitrile;

[(3R)-3-{3-[(4-chloro-8-fluoroquinolin-6-yl)amino]-4-oxo-4,5-dihydro-1H-pyrazolo[4,3-c]pyridin-1-yl}tetrahydrofuran-3-yl]acetonitrile;

[(3S)-3-{3-[(4-chloro-8-fluoroquinolin-6-yl)amino]-4-oxo-4,5-dihydro-1H-pyrazolo[4,3-c]pyridin-1-yl}tetrahydrofuran-3-yl]acetonitrile;

[(3R)-3-{3-[(4-fluoroquinolin-6-yl)amino]-4-oxo-4,5-dihydro-1H-pyrazolo[4,3-c]pyridin-1-yl}tetrahydrofuran-3-yl]acetonitrile;

[(3S)-3-{3-[(4-fluoroquinolin-6-yl)amino]-4-oxo-4,5-dihydro-1H-pyrazolo[4,3-c]pyridin-1-yl}tetrahydrofuran-3-yl]acetonitrile;

(S)-2-(3-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)tetrahydrofuran-3-yl)acetonitrile;

(R)-2-(3-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)tetrahydrofuran-3-yl)acetonitrile;

(S)-2-(3-(3-((4-(tert-butylsulfonyl)phenyl)amino)-4-oxo-4,5-dihydro-1H-pyrazolo[4,3-c]pyridin-1-yl)tetrahydrofuran-3-yl)acetonitrile;

(R)-2-(3-(3-((4-(tert-butylsulfonyl)phenyl)amino)-4-oxo-4,5-dihydro-1H-pyrazolo[4,3-c]pyridin-1-yl)tetrahydrofuran-3-yl)acetonitrile;

2-((3S,4S)-4-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-3-fluorotetrahydro-2H-pyran-4-yl)acetonitrile;

2-((3R,4R)-4-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-3-fluorotetrahydro-2H-pyran-4-yl)acetonitrile;

2-((3S,4S)-3-fluoro-4-(3-(3-methyl-4-(morpholine-4-carbonyl)phenylamino)-4-oxo-4,5-dihydropyrazolo[4,3-c]pyridin-1-yl)-tetrahydro-2H-pyran-4-yl)acetonitrile;

2-((3R,4R)-3-fluoro-4-(3-((3-methyl-4-(morpholine-4-carbonyl)phenyl)amino)-4-oxo-4,5-dihydro-1H-pyrazolo[4,3-c]pyridin-1-yl)tetrahydro-2H-pyran-4-yl)acetonitrile;

2-((3R,4R)-4-(3-((2-(tert-butyl)-1-oxoisoindolin-5-yl)amino)-4-oxo-4,5-dihydro-1H-pyrazolo[4,3-c]pyridin-1-yl)-3-fluorotetrahydro-2H-pyran-4-yl)acetonitrile;

2-((3S,4S)-4-(3-(2-tert-butyl-1-oxoisoindolin-5-ylamino)-4-oxo-4,5-dihydropyrazolo[4,3-c]pyridin-1-yl)-3-fluoro-tetrahydro-2H-pyran-4-yl)acetonitrile;

2-((3S,4S)-3-fluoro-4-(3-(3-methyl-4-(thiomorpholine-4-carbonyl)phenylamino)-4-oxo-4,5-dihydropyrazolo[4,3-c]pyridin-1-yl)-tetrahydro-2H-pyran-4-yl)acetonitrile;

2-((3R,4R)-3-fluoro-4-(3-((3-methyl-4-(thiomorpholine-4-carbonyl)phenyl)amino)-4-oxo-4,5-dihydro-1H-pyrazolo[4,3-c]pyridin-1-yl)tetrahydro-2H-pyran-4-yl)acetonitrile;

2-((3S,4S)-3-fluoro-4-(4-oxo-3-((4-((S)-2-(trifluoromethyl)piperidin-2-yl)phenyl)amino)-4,5-dihydro-1H-pyrazolo[4,3-c]pyridin-1-yl)tetrahydro-2H-pyran-4-yl)acetonitrile;

2-((3S,4S)-3-fluoro-4-(4-oxo-3-((4-((R)-2-(trifluoromethyl)piperidin-2-yl)phenyl)amino)-4,5-dihydro-1H-pyrazolo[4,3-c]pyridin-1-yl)tetrahydro-2H-pyran-4-yl)acetonitrile;

2-((3R,4R)-3-fluoro-4-(4-oxo-3-((4-((S)-2-(trifluoromethyl)piperidin-2-yl)phenyl)amino)-4,5-dihydro-1H-pyrazolo[4,3-c]pyridin-1-yl)tetrahydro-2H-pyran-4-yl)acetonitrile;

2-((3R,4R)-3-fluoro-4-(4-oxo-3-((4-((R)-2-(trifluoromethyl)piperidin-2-yl)phenyl)amino)-4,5-dihydro-1H-pyrazolo[4,3-c]pyridin-1-yl)tetrahydro-2H-pyran-4-yl)acetonitrile;

2-((3S,4S)-4-(3-((4-((R)-1-(tert-butylamino)-2,2,2-trifluoroethyl)phenyl)amino)-4-oxo-4,5-dihydro-1H-pyrazolo[4,3-c]pyridin-1-yl)-3-fluorotetrahydro-2H-pyran-4-yl)acetonitrile;

2-((3S,4S)-4-(3-((4-((S)-1-(tert-butylamino)-2,2,2-trifluoroethyl)phenyl)amino)-4-oxo-4,5-dihydro-1H-pyrazolo[4,3-c]pyridin-1-yl)-3-fluorotetrahydro-2H-pyran-4-yl)acetonitrile;

2-((3R,4R)-4-(3-((4-((R)-1-(tert-butylamino)-2,2,2-trifluoroethyl)phenyl)amino)-4-oxo-4,5-dihydro-1H-pyrazolo[4,3-c]pyridin-1-yl)-3-fluorotetrahydro-2H-pyran-4-yl)acetonitrile;

2-((3R,4R)-4-(3-((4-((S)-1-(tert-butylamino)-2,2,2-trifluoroethyl)phenyl)amino)-4-oxo-4,5-dihydro-1H-pyrazolo[4,3-c]pyridin-1-yl)-3-fluorotetrahydro-2H-pyran-4-yl)acetonitrile;

2-[(3S,4S)-4-(3-{[1,1-dioxo-2-(piperidin-4-yl)-3H-1,2-benzothiazol-5-yl]amino}-4-oxo-5H-pyrazolo[4,3-c]pyridin-1-yl)-3-fluorooxan-4-yl]acetonitrile;

2-((3R,4R)-4-(3-((1,1-dioxido-2-(piperidin-4-yl)-2,3-dihydrobenzo[d]isothiazol-5-yl)amino)-4-oxo-4,5-dihydro-1H-pyrazolo[4,3-c]pyridin-1-yl)-3-fluorotetrahydro-2H-pyran-4-yl)acetonitrile;

tert-butyl (3R,4R)-4-(cyanomethyl)-3-fluoro-4-{3-[(4-{1-methyl-1-[(1-methylethyl)amino]ethyl}phenyl)amino]-4-oxo-4,5-dihydro-1H-pyrazolo[4,3-c]pyridin-1-yl}piperidine-1-carboxylate;

(2S,5S)-tert-butyl 5-(cyanomethyl)-5-(3-((4-(2-(isopropylamino)propan-2-yl)phenyl)amino)-4-oxo-4,5-dihydro-1H-pyrazolo[4,3-c]pyridin-1-yl)tetrahydro-2H-pyran-2-carboxylate;

tert-butyl (3R,4R)-4-(cyanomethyl)-3-fluoro-4-(3-{[4-(1-methoxyethyl)phenyl]amino}-4-oxo-4,5-dihydro-1H-pyrazolo[4,3-c]pyridin-1-yl)piperidine-1-carboxylate;

2-((3R,4R)-4-(3-((1,1-dioxido-2-(1-(2,2,2-trifluoroethyl)piperidin-4-yl)-2,3-dihydrobenzo[d]isothiazol-5-yl)amino)-4-oxo-4,5-dihydro-1H-pyrazolo[4,3-c]pyridin-1-yl)-3-fluorotetrahydro-2H-pyran-4-yl)acetonitrile;

2-((3S,4S)-4-(3-((1,1-dioxido-2-(1-(2,2,2-trifluoroethyl)piperidin-4-yl)-2,3-dihydrobenzo[d]isothiazol-5-yl)amino)-4-oxo-4,5-dihydro-1H-pyrazolo[4,3-c]pyridin-1-yl)-3-fluorotetrahydro-2H-pyran-4-yl)acetonitrile;

(3R,4R)-tert-butyl 4-(cyanomethyl)-3-fluoro-4-(3-((3-methyl-4-(thiomorpholine-4-carbonyl)phenyl)amino)-4-oxo-4,5-dihydro-1H-pyrazolo[4,3-c]pyridin-1-yl)piperidine-1-carboxylate;

(R) tert-butyl 4-(3-((4-(1-benzyl-3-(trifluoromethyl)pyrrolidin-3-yl)phenyl)amino)-4-oxo-4,5-dihydro-1H-pyrazolo[4,3-c]pyridin-1-yl)-4-(cyanomethyl)piperidine-1-carboxylate;

(S) tert-butyl 4-(cyanomethyl)-4-(4-oxo-3-((4-(3-(trifluoromethyl)pyrrolidin-3-yl)phenyl)amino)-4,5-dihydro-1H-pyrazolo[4,3-c]pyridin-1-yl)piperidine-1-carboxylate;

(2S,5S)-tert-butyl 5-(cyanomethyl)-5-(4-oxo-3-((4-((R)-3-(trifluoromethyl)pyrrolidin-3-yl)phenyl)amino)-4,5-dihydro-1H-pyrazolo[4,3-c]pyridin-1-yl)tetrahydro-2H-pyran-2-carboxylate;

(trans)-2-methylcyclopentyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

(R)-tetrahydrofuran-3-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

(S)-tetrahydrofuran-3-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

(trans)-2-methylcyclopentyl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

(R)-tetrahydrofuran-3-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

(S)-tetrahydrofuran-3-yl 4-(cyanomethyl)-4-(3-((4-(N,N-dimethylsulfamoyl)phenyl)amino)-4-oxo-4,5-dihydro-1H-pyrazolo[4,3-c]pyridin-1-yl)piperidine-1-carboxylate;

(R)-2-(4-(4-oxo-3-(4-(2,2,2-trifluoro-1-hydroxyethyl)phenylamino)-4,5-dihydropyrazolo[4,3-c]pyridin-1-yl)-1-(4-(trifluoromethyl)pyridin-2-yl)piperidin-4-yl)acetonitrile;

(S)-2-(4-(4-oxo-3-(4-(2,2,2-trifluoro-1-hydroxyethyl)phenylamino)-4,5-dihydropyrazolo[4,3-c]pyridin-1-yl)-1-(4-(trifluoromethyl)pyridin-2-yl)piperidin-4-yl)acetonitrile;

(cis) 2-(4-(3-fluoroazetidin-1-yl)-1-(4-oxo-3-((4-(trifluoromethyl)phenyl)amino)-4,5-dihydro-1H-pyrazolo[4,3-c]pyridin-1-yl)cyclohexyl)acetonitrile;

(trans) 2-(4-(3-fluoroazetidin-1-yl)-1-(4-oxo-3-((4-(trifluoromethyl)phenyl)amino)-4,5-dihydro-1H-pyrazolo[4,3-c]pyridin-1-yl)cyclohexyl)acetonitrile;

cis 2-(1-(4-oxo-3-((4-(trifluoromethyl)phenyl)amino)-4,5-dihydro-1H-pyrazolo[4,3-c]pyridin-1-yl)-4-(phenylamino)cyclohexyl)acetonitrile;

trans 2-(1-(4-oxo-3-((4-(trifluoromethyl)phenyl)amino)-4,5-dihydro-1H-pyrazolo[4,3-c]pyridin-1-yl)-4-(phenylamino)cyclohexyl)acetonitrile;

(cis) 2-(4-hydroxy-1-(4-oxo-3-((4-(trifluoromethyl)phenyl)amino)-4,5-dihydro-1H-pyrazolo[4,3-c]pyridin-1-yl)cyclohexyl)acetonitrile;

(trans) 2-(4-hydroxy-1-(4-oxo-3-((4-(trifluoromethyl)phenyl)amino)-4,5-dihydro-1H-pyrazolo[4,3-c]pyridin-1-yl)cyclohexyl)acetonitrile;

trans 2-(1-(3-((4-chlorophenyl)amino)-4-oxo-4,5-dihydro-1H-pyrazolo[4,3-c]pyridin-1-yl)-4-(3-fluoroazetidin-1-yl)cyclohexyl)acetonitrile;

cis 2-(1-(3-((4-chlorophenyl)amino)-4-oxo-4,5-dihydro-1H-pyrazolo[4,3-c]pyridin-1-yl)-4-(3-fluoroazetidin-1-yl)cyclohexyl)acetonitrile;

trans 2-(1-(3-((4-chlorophenyl)amino)-4-oxo-4,5-dihydro-1H-pyrazolo[4,3-c]pyridin-1-yl)-4-(3-methoxyazetidin-1-yl)cyclohexyl)acetonitrile;

cis 2-(1-(3-((4-chlorophenyl)amino)-4-oxo-4,5-dihydro-1H-pyrazolo[4,3-c]pyridin-1-yl)-4-(3-methoxyazetidin-1-yl)cyclohexyl)acetonitrile;
cis 2-(1-(3-((4-chlorophenyl)amino)-4-oxo-4,5-dihydro-1H-pyrazolo[4,3-c]pyridin-1-yl)-4-((2,2,2-trifluoroethyl)amino)cyclohexyl)acetonitrile;
trans 2-(1-(3-((4-chlorophenyl)amino)-4-oxo-4,5-dihydro-1H-pyrazolo[4,3-c]pyridin-1-yl)-4-((2,2,2-trifluoroethyl)amino)cyclohexyl)acetonitrile;
cis 2-(1-(3-((4-chlorophenyl)amino)-4-oxo-4,5-dihydro-1H-pyrazolo[4,3-c]pyridin-1-yl)-4-hydroxycyclohexyl)acetonitrile;
trans 2-(1-(3-((4-chlorophenyl)amino)-4-oxo-4,5-dihydro-1H-pyrazolo[4,3-c]pyridin-1-yl)-4-hydroxycyclohexyl)acetonitrile;
cis 2-(1-(3-((4-chlorophenyl)amino)-4-oxo-4,5-dihydro-1H-pyrazolo[4,3-c]pyridin-1-yl)-4-(phenylamino)cyclohexyl)acetonitrile;
trans 2-(1-(3-((4-chlorophenyl)amino)-4-oxo-4,5-dihydro-1H-pyrazolo[4,3-c]pyridin-1-yl)-4-(phenylamino)cyclohexyl)acetonitrile;
cis 2-(4-(3-methoxyazetidin-1-yl)-1-(4-oxo-3-((4-(trifluoromethoxy)phenyl)amino)-4,5-dihydro-1H-pyrazolo[4,3-c]pyridin-1-yl)cyclohexyl)acetonitrile;
trans 2-(4-(3-methoxyazetidin-1-yl)-1-(4-oxo-3-((4-(trifluoromethoxy)phenyl)amino)-4,5-dihydro-1H-pyrazolo[4,3-c]pyridin-1-yl)cyclohexyl)acetonitrile;
cis 2-(1-(4-oxo-3-((4-(trifluoromethoxy)phenyl)amino)-4,5-dihydro-1H-pyrazolo[4,3-c]pyridin-1-yl)-4-(phenylamino)cyclohexyl)acetonitrile;
trans 2-(1-(4-oxo-3-((4-(trifluoromethoxy)phenyl)amino)-4,5-dihydro-1H-pyrazolo[4,3-c]pyridin-1-yl)-4-(phenylamino)cyclohexyl)acetonitrile;
trans 2-(4-(cyclohexylamino)-1-(4-oxo-3-((4-(trifluoromethoxy)phenyl)amino)-4,5-dihydro-1H-pyrazolo[4,3-c]pyridin-1-yl)cyclohexyl)acetonitrile;
cis 2-(4-(cyclohexylamino)-1-(4-oxo-3-((4-(trifluoromethoxy)phenyl)amino)-4,5-dihydro-1H-pyrazolo[4,3-c]pyridin-1-yl)cyclohexyl)acetonitrile;
trans 2-(1-(3-((4-chloro-3-fluorophenyl)amino)-4-oxo-4,5-dihydro-1H-pyrazolo[4,3-c]pyridin-1-yl)-4-(cyclohexylamino)cyclohexyl)acetonitrile;
cis 2-(1-(3-((4-chloro-3-fluorophenyl)amino)-4-oxo-4,5-dihydro-1H-pyrazolo[4,3-c]pyridin-1-yl)-4-(cyclohexylamino)cyclohexyl)acetonitrile;
cis 2-(1-(3-((4-chloro-3-fluorophenyl)amino)-4-oxo-4,5-dihydro-1H-pyrazolo[4,3-c]pyridin-1-yl)-4-(3-methoxyazetidin-1-yl)cyclohexyl)acetonitrile;
trans 2-(1-(3-((4-chloro-3-fluorophenyl)amino)-4-oxo-4,5-dihydro-1H-pyrazolo[4,3-c]pyridin-1-yl)-4-(3-methoxyazetidin-1-yl)cyclohexyl)acetonitrile;
cis 2-(1-(3-((4-chloro-3-fluorophenyl)amino)-4-oxo-4,5-dihydro-1H-pyrazolo[4,3-c]pyridin-1-yl)-4-(phenylamino)cyclohexyl)acetonitrile;
trans 2-(1-(3-((4-chloro-3-fluorophenyl)amino)-4-oxo-4,5-dihydro-1H-pyrazolo[4,3-c]pyridin-1-yl)-4-(phenylamino)cyclohexyl)acetonitrile;
cis 2-(1-(3-((4-((difluoromethyl)sulfonyl)phenyl)amino)-4-oxo-4,5-dihydro-1H-pyrazolo[4,3-c]pyridin-1-yl)-4-(3-fluoroazetidin-1-yl)cyclohexyl)acetonitrile;
trans 2-(1-(3-((4-((difluoromethyl)sulfonyl)phenyl)amino)-4-oxo-4,5-dihydro-1H-pyrazolo[4,3-c]pyridin-1-yl)-4-(3-fluoroazetidin-1-yl)cyclohexyl)acetonitrile;
trans 4-((1-(1-(cyanomethyl)-4-(3-fluoroazetidin-1-yl)cyclohexyl)-4-oxo-4,5-dihydro-1H-pyrazolo[4,3-c]pyridin-3-yl)amino)-N,N-dimethylbenzenesulfonamide;
cis 4-((1-(1-(cyanomethyl)-4-(3-fluoroazetidin-1-yl)cyclohexyl)-4-oxo-4,5-dihydro-1H-pyrazolo[4,3-c]pyridin-3-yl)amino)-N,N-dimethylbenzenesulfonamide;
cis 2-(4-(3-Fluoroazetidin-1-yl)-1-(3-((2-methyl-1,1-dioxido-2,3-dihydrobenzo[d]isothiazol-6-yl)amino)-4-oxo-4,5-dihydro-1H-pyrazolo[4,3-c]pyridin-1-yl)cyclohexyl)acetonitrile;
trans 2-(4-(3-Fluoroazetidin-1-yl)-1-(3-((2-methyl-1,1-dioxido-2,3-dihydrobenzo[d]isothiazol-6-yl)amino)-4-oxo-4,5-dihydro-1H-pyrazolo[4,3-c]pyridin-1-yl)cyclohexyl)acetonitrile;
cis 2-(4-(dimethylamino)-1-(3-((2-methyl-1,1-dioxido-2,3-dihydrobenzo-[d]isothiazol-6-yl)amino)-4-oxo-4,5-dihydro-1H-pyrazolo[4,3-c]pyridin-1-yl)cyclohexyl)acetonitrile;
trans 2-(4-(dimethylamino)-1-(3-((2-methyl-1,1-dioxido-2,3-dihydrobenzo-[d]isothiazol-6-yl)amino)-4-oxo-4,5-dihydro-1H-pyrazolo[4,3-c]pyridin-1-yl)cyclohexyl)acetonitrile;
trans 2-(4-(3-fluoroazetidin-1-yl)-1-(3-((2-methyl-1,1-dioxido-2,3-dihydrobenzo[d]isothiazol-6-yl)amino)-4-oxo-4,5-dihydro-1H-pyrazolo[4,3-c]pyridin-1-yl)cyclohexyl)acetonitrile;
cis 2-(4-(3-fluoroazetidin-1-yl)-1-(3-((2-methyl-1,1-dioxido-2,3-dihydrobenzo[d]isothiazol-6-yl)amino)-4-oxo-4,5-dihydro-1H-pyrazolo[4,3-c]pyridin-1-yl)cyclohexyl)acetonitrile;
trans 2-(1-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-4-(dimethylamino)cyclohexyl)acetonitrile;
cis 2-(1-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-4-(dimethylamino)cyclohexyl)acetonitrile;
(2S,5S)-N-(tert-butyl)-5-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-5-(cyanomethyl)tetrahydro-2H-pyran-2-carboxamide;
(2S,5S)-N-tert-butyl-5-{3-[(2-tert-butyl-1,1-dioxido-2,3-dihydro-1,2-benzisothiazol-5-yl)amino]-4-oxo-4,5-dihydro-1H-pyrazolo[4,3-c]pyridin-1-yl}-5-(cyanomethyl)-N-methyltetrahydro-2H-pyran-2-carboxamide;
(2S,5S)-isopropyl 5-(3-((2-(tert-butyl)-1,1-dioxido-2,3-dihydrobenzo[d]isothiazol-5-yl)amino)-4-oxo-4,5-dihydro-1H-pyrazolo[4,3-c]pyridin-1-yl)-5-(cyanomethyl)tetrahydro-2H-pyran-2-carboxylate;
(S)-2-(3-(3-((4-(4,4-difluoropiperidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;
2-((S)-3-(3-((3-methyl-4-((S)-2-methylpiperidine-1-carbonyl)phenyl)amino)-4-oxo-4,5-dihydro-1H-pyrazolo[4,3-c]pyridin-1-yl)tetrahydro-2H-pyran-3-yl)acetonitrile;
2-((S)-3-(3-((3-methyl-4-((R)-2-methylpiperidine-1-carbonyl)phenyl)amino)-4-oxo-4,5-dihydro-1H-pyrazolo[4,3-c]pyridin-1-yl)tetrahydro-2H-pyran-3-yl)acetonitrile;
(S)-2-(3-(3-((4-(4-hydroxy-4-methylpiperidine-1-carbonyl)-3-methylphenyl)amino)-4-oxo-4,5-dihydro-1H-pyrazolo[4,3-c]pyridin-1-yl)tetrahydro-2H-pyran-3-yl)acetonitrile;
(2S,5S)-tert-butyl 5-(cyanomethyl)-5-(3-((3-methyl-4-(morpholine-4-carbonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((3-methyl-4-(thiomorpholine-4-carbonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((3-methyl-4-(pyrrolidine-1-carbonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((3-methyl-4-((S)-3-methylmorpholine-4-carbonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((3-methyl-4-((R)-3-methylmorpholine-4-carbonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((3-methyl-4-((S)-2-methylmorpholine-4-carbonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((3-methyl-4-((R)-2-methylmorpholine-4-carbonyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((4-((2S,6S)-2,6-dimethylmorpholine-4-carbonyl)-3-methylphenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((4-((2R,6R)-2,6-dimethylmorpholine-4-carbonyl)-3-methylphenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(3-((3-methyl-4-(methyl(2,2,2-trifluoroethyl)carbamoyl)phenyl)amino)-4-oxo-4,5-dihydro-1H-pyrazolo[4,3-c]pyridin-1-yl)tetrahydro-2H-pyran-2-carboxylate;

(2S,5S)-tert-butyl 5-(3-((4-((1S,4S)-2-oxa-5-azabicyclo[2.2.1]heptane-5-carbonyl)-3-methylphenyl)amino)-4-oxo-4,5-dihydro-1H-pyrazolo[4,3-c]pyridin-1-yl)-5-(cyanomethyl)tetrahydro-2H-pyran-2-carboxylate;

(2S,5S)-tert-butyl 5-(cyanomethyl)-5-(3-((2-methylbenzo[d]thiazol-6-yl)amino)-4-oxo-4,5-dihydro-1H-pyrazolo[4,3-c]pyridin-1-yl)tetrahydro-2H-pyran-2-carboxylate;

[(1R,2R)-1-{3-[(3,3-dimethyl-2-oxo-2,3-dihydro-1H-indol-6-yl)amino]-4-oxo-4,5-dihydro-1H-pyrazolo[4,3-c]pyridin-1-yl}-2-fluorocyclohexyl]acetonitrile;

(2S,5S)-tert-butyl 5-(cyanomethyl)-5-(3-((3,3-dimethyl-2-oxoindolin-6-yl)amino)-4-oxo-4,5-dihydro-1H-pyrazolo[4,3-c]pyridin-1-yl)tetrahydro-2H-pyran-2-carboxylate;

[(3S)-3-{3-[(3,3-dimethyl-2-oxo-2,3-dihydro-1H-indol-6-yl)amino]-4-oxo-4,5-dihydro-1H-pyrazolo[4,3-c]pyridin-1-yl}tetrahydro-2H-pyran-3-yl]acetonitrile;

[(3S)-3-{3-[(2-methyl-1,3-benzothiazol-6-yl)amino]-4-oxo-4,5-dihydro-1H-pyrazolo[4,3-c]pyridin-1-yl}tetrahydro-2H-pyran-3-yl]acetonitrile;

(2S,5S)-tert-butyl 5-(cyanomethyl)-5-(3-((2-fluoropyridin-4-yl)amino)-4-oxo-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((R)-2,2,2-trifluoro-1-methoxyethyl)phenyl)amino)-4,5-dihydro-1H-pyrazolo[4,3-c]pyridin-1-yl)tetrahydro-2H-pyran-2-carboxylate;

(2S,5S)-tert-butyl 5-(cyanomethyl)-5-(4-oxo-3-((4-((S)-2,2,2-trifluoro-1-methoxyethyl)phenyl)amino)-4,5-dihydro-1H-pyrazolo[4,3-c]pyridin-1-yl)tetrahydro-2H-pyran-2-carboxylate;

tert-butyl 4-(cyanomethyl)-4-[4-oxo-3-({4-[(1R)-2,2,2-trifluoro-1-methoxyethyl]phenyl}amino)-4,5-dihydro-1H-pyrazolo[4,3-c]pyridin-1-yl]piperidine-1-carboxylate;

tert-butyl 4-(cyanomethyl)-4-[4-oxo-3-({4-[(1S)-2,2,2-trifluoro-1-methoxyethyl]phenyl}amino)-4,5-dihydro-1H-pyrazolo[4,3-c]pyridin-1-yl]piperidine-1-carboxylate;

(S)-tert-butyl 4-(cyanomethyl)-4-(4-oxo-3-(4-(2-(trifluoromethyl)piperidin-2-yl)phenylamino)-4,5-dihydropyrazolo[4,3-c]pyridin-1-yl)piperidine-1-carboxylate;

(R)-tert-butyl 4-(cyanomethyl)-4-(4-oxo-3-(4-(2-(trifluoromethyl)piperidin-2-yl)phenylamino)-4,5-dihydropyrazolo[4,3-c]pyridin-1-yl)piperidine-1-carboxylate;

(R)-tert-butyl 4-(cyanomethyl)-4-(4-oxo-3-(4-(2-(trifluoromethyl)pyrrolidin-2-yl)phenylamino)-4,5-dihydropyrazolo[4,3-c]pyridin-1-yl)piperidine-1-carboxylate;

(S)-tert-butyl 4-(cyanomethyl)-4-(4-oxo-3-(4-(2-(trifluoromethyl)pyrrolidin-2-yl)phenylamino)-4,5-dihydropyrazolo[4,3-c]pyridin-1-yl)piperidine-1-carboxylate;

(2S,5S)-5-(3-((4-chlorophenyl)amino)-4-oxo-4,5-dihydro-1H-pyrazolo[4,3-c]pyridin-1-yl)-5-(cyanomethyl)-N-(methylsulfonyl)tetrahydro-2H-pyran-2-carboxamide; or 2-((3S,6S)-3-(3-((4-chlorophenyl)amino)-4-oxo-4,5-dihydro-1H-pyrazolo[4,3-c]pyridin-1-yl)-6-(2-hydroxypropan-2-yl)tetrahydro-2H-pyran-3-yl)acetonitrile.

* * * * *